United States Patent [19]

Ishii et al.

[11] Patent Number: 5,116,404
[45] Date of Patent: May 26, 1992

[54] URACIL DERIVATIVES AND PESTICIDES CONTAINING THE SAME AS ACTIVE INGREDIENT

[75] Inventors: Shigeru Ishii, Funabashi; Kazunari Nakayama; Kazuo Yagi, both of Narashino; Jun Satow, Funabashi; Kenzou Fukuda, Funabashi; Kaoru Itoh, Funabashi; Toshiyuki Umehara, Kuki; Masaki Kudo; Yoichi Inoue, both of Urawa; Tsutomu Nawamaki, Yono; Shigeomi Watanabe, Omiya, all of Japan

[73] Assignee: Nissan Chemical Industries Ltd., Tokyo, Japan

[21] Appl. No.: 638,811

[22] Filed: Jan. 8, 1991

[30] Foreign Application Priority Data

Jan. 18, 1990 [JP] Japan ................................... 2-8826
Mar. 5, 1990 [JP] Japan ................................... 2-53450
Nov. 28, 1990 [JP] Japan ................................... 2-327671

[51] Int. Cl.⁵ .................... A01N 43/54; A01N 43/10; C07D 239/95; C07D 239/96
[52] U.S. Cl. .................................... 71/92; 71/90; 514/252; 514/264; 514/272; 514/274; 514/275; 544/229; 544/238; 544/295; 544/296; 544/309; 544/310; 544/311; 544/312; 544/313; 544/314; 544/317; 544/321; 544/323
[58] Field of Search ............... 544/229, 295, 296, 238, 544/309, 310, 311-314, 317, 321, 323; 514/269, 272, 274, 252, 275; 71/90, 92

[56] References Cited

U.S. PATENT DOCUMENTS

| 3,497,515 | 2/1970 | Loux .................................... 71/92 |
| 3,580,913 | 5/1971 | Lutz .................................... 71/92 |
| 3,869,457 | 3/1975 | Lutz et al. ............................ 71/92 |
| 4,746,352 | 5/1988 | Wenger et al. ...................... 71/90 |
| 4,760,163 | 7/1988 | Wenger et al. ...................... 71/90 |
| 4,812,164 | 3/1989 | Wenger et al. ...................... 544/309 |
| 4,859,229 | 8/1989 | Wenger et al. ...................... 71/92 |
| 4,927,451 | 5/1990 | Brouwer et al. .................... 544/314 |
| 4,941,909 | 7/1990 | Wenger et al. ...................... 544/309 |
| 4,979,982 | 12/1990 | Brouwer et al. .................... 544/314 |

FOREIGN PATENT DOCUMENTS 144541 10/1980 Fed. Rep. of Germany .

OTHER PUBLICATIONS

Synthesis of Aryl Substituted Dihydrouracils by: Treat B. Johnston & John E. Livak, J. Am. Chem.Soc., 58, 299, 1935.
Chemical Abstracts (vol. 52), 6364h (1958).

*Primary Examiner*—Cecilia Shen
*Attorney, Agent, or Firm*—Oblon, Spivak, McClelland, Maier & Neustadt

[57] ABSTRACT

The present invention provides novel uracil derivatives and pesticides which contain the novel uracil derivatives as an active ingredient, and exhibit preventing and controlling effects against harmful living things, especially agricultural insect pests, sanitary insect pests, stored product insect pests, house insect pests and veterinary insect pests at a very low drug-concentration.

13 Claims, No Drawings

URACIL DERIVATIVES AND PESTICIDES CONTAINING THE SAME AS ACTIVE INGREDIENT

BACKGROUND OF THE INVENTION

The present invention relates to novel uracil derivatives and pesticides which contains the said derivatives as active ingredient.

Disclosures about the uracil compounds have been made in several patents and prior art literatures. For example, 3,6-diphenyluracil and 3-phenyl-6-(3-bromo-4-methoxyphenyl)uracil are disclosed in Journal of American Chemical Society, Vol. 58, p. 299, 1935. Also, 3,6-diphenyluracil is disclosed in Chemical Abstract, Vol. 52, 6364h, 1958.

However, there is no disclosure of activity of the said compounds against living things in the said literatures.

In U.S. Pat. Nos. 3,580,913, 3,869,457 and 3,981,715, there are disclosed the uracil compounds having at 6-position of the uracil ring a trifluoromethyl group and at 3-position thereof a substituted or non-substituted phenyl group, but in these compounds the number of the substituents in the phenyl group is up to 2 and there is no disclosure of uracil compound having the phenyl group which has 3 or more substituents. Also, in these patents, there is no disclosure about preventing and controlling effects to insect pests of the said compounds.

In U.S. Pat. Nos. 4,746,352, 4,760,163, 4,859,229, and 4,812,164 and International Patent Publication Nos. WO 88-10254, WO 89-02891 and WO 89-03825, there are disclosed the uracil compounds in which the 6-position of the uracil ring is hydrogen atom, a $C_{1-4}$ alkyl group or a $C_{1-4}$ fluoroalkyl group and the 3-position thereof is a phenyl group which has three substituents at the 2-, 4- and 5-positions, but in these compounds the substituent at the 5-position of the phenyl group is defined to be the one linked by oxygen atom or a carbonyl group. Further, there is no disclosure about preventing and controlling effects to insect pests of the said compounds in these patents.

Warming-up of the earth and spread of heating systems have created an environment which encourages the activity of various species of insect pests or allows them to stay active all the year around. The thus widened scope of activity of insect pests is giving serious influence on the life of human beings. Thus, the development of a compound which shows high efficacy against various species of insect pests at an extremely low dosage (drug-concentration) and gives no baneful influence to mammals and other useful living things has been eagerly desired.

As a result of extensive and intensive researches for obtaining a compound which is satisfied with the above requests, it has been found that uracil derivatives obtained by reacting a compound represented by the formula:

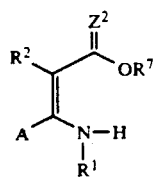

(XXXVI)

(wherein $R^1$, $R^2$, $Z^2$ and A are as defined in claim 1, and $R^7$ represents $C_{1-6}$ alkyl group, benzyl group or phenyl group) and a compound represented by the formula (IV) or (V):

(IV)

(V)

(wherein B and $Z^1$ are as defined in claim 1, and $R^8$ represents $C_{1-6}$ alkyl group, benzyl group or phenyl group) exhibit preventing and controlling effects (pesticidal effect) against various species of insect pests such as agricultural insect pests, sanitary insect pests, stored product insect pests, house insect pests and veterinary insect pests at a very low drug-concentration and are no fear of giving and damage to the mammals, fishes, crustaceans and useful insects. The present invention was attained on the basis of this finding.

SUMMARY OF THE INVENTION

In a first aspect of the present invention, there is provided uracil derivatives represented by the general formula (I):

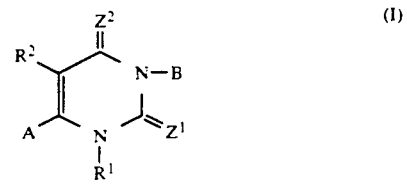

(I)

wherein $R^1$ represents hydrogen atom, $C_{1-4}$ alkyl group, $C_{2-4}$ alkenyl group, $C_{2-4}$ alkynyl group, $C_{1-4}$ haloalkyl group, $C_{2-4}$ alkoxyalkyl group, formyl group, $C_{2-6}$ alkylcarbonyl group, $C_{2-6}$ alkoxycarbonyl group, $C_{3-6}$ alkoxycarbonylalkyl group, $C_{2-6}$ cyanoalkyl group, benzyl group, phenyl group, —$SR^{12}$ group [wherein $R^{12}$ is $C_{2-6}$ alkoxycarbonyl group, $C_{1-6}$ alkylsulfonyl group, —$NR^{13}R^{14}$ group (wherein $R^{13}$ is $C_{1-6}$ alkyl group and $R^{14}$ is $C_{1-6}$ alkyl group, $C_{2-6}$ alkoxycarbonyl group, $C_{3-9}$ alkoxycarbonylalkyl group, $C_{1-6}$ alkylsulfonyl group, $C_{2-6}$ alkylcarbonyl group, $C_{3-9}$ dialkylaminocarbonyl group, $C_{2-6}$ dialkylaminosulfonyl group and phenyl group which may be substituted or non-substituted) and phenyl group which may be substituted or non-substituted (the substituent is selected from halogen atom, cyano group, nitro group, $C_{1-4}$ alkyl group, $C_{1-4}$ haloalkyl group, $C_{1-4}$ alkoxy group, $C_{2-6}$ alkoxycarbonyl group, $C_{1-4}$ haloalkoxy group, $C_{2-6}$ haloalkoxycarbonyl group, $C_{2-6}$ alkylcarbonyl group, $C_{2-6}$ haloalkylcarbonyl group, $C_{1-4}$ alkylsulfonyl group or $C_{1-4}$ haloalkyl sulfonyl group, and when the number of the substituents is not less than 2, the substituents may be same or different)], alkali metal or alkaline earth metal;

$R^2$ represents hydrogen atom, halogen atom, $C_{1-4}$ alkyl group, $C_{1-4}$ haloalkyl group, $C_{1-4}$ hydroxyalkyl group, $C_{2-4}$ alkoxyalkyl group, $C_{2-4}$ altylthioalkyl group, thiol group, $C_{1-4}$ alkylthio group, $C_{1-4}$ alkylsulfinyl group, $C_{1-4}$ alkylsulfonyl group, $C_{1-4}$ haloalkylthio group, $C_{1-4}$ haloalkylsulfinyl group, $C_{1-4}$ haloalkylsulfonyl group, hydroxyl group, $C_{1-4}$ alkoxy group, $C_{1-4}$ haloalkoxy group, formyl group, cyano group, nitro group or thiocyanate group;

$Z^1$ and $Z^2$ represent independently oxygen atom, sulfur atom or imino group;

A represents

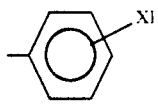

[wherein X is halogen atom, $C_{1-4}$ alkyl group, $C_{1-4}$ alkoxy group, $C_{1-4}$ alkylthio group, $C_{1-4}$ haloalkyl group, $C_{1-4}$ haloalkoxy group, $C_{1-4}$ haloalkylthio group, amino group, cyano group or nitro group, and l is an integer of 0 to 5 (when l is an integer of 2 to 5, the substituents X may be same or different)], or naphthyl group, furyl group, thienyl group, pyrrolyl group, pyrazolyl group, imidazolyl group, thiazolyl aromatic groups are the same as defined above), B is

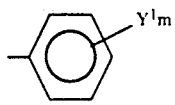

[wherein $Y^1$ is halogen atom, $C_{1-6}$ alkyl group, $C_{2-6}$ alkenyl group, $C_{2-6}$ alkynyl group, $C_{3-6}$ cycloalkyl group, $C_{1-6}$ haloalkyl group, $C_{2-6}$ haloalkenyl group, $C_{2-6}$ haloalkynyl group, $C_{3-6}$ halocycloalkyl group, $C_{2-6}$ cyanoalkyl group, $C_{1-6}$ hydroxyalkyl group, $C_{2-6}$ carboxyalkyl group, $C_{1-6}$ alkoxy group, $C_{2-6}$ alkenyloxy group, $C_{2-6}$ alkynyloxy group, $C_{3-6}$ cycloalkyloxy group, $C_{1-6}$ haloalkoxy group, $C_{2-6}$ haloalkenyloxy group, $C_{2-6}$ haloalkynyloxy group, $C_{3-6}$ halocycloalkoxy group, $C_{4-7}$ halocycloalkylalkoxy group, $C_{1-6}$ alkylthio group, $C_{2-6}$ alkenylthio group, $C_{2-6}$ alkynylthio group, $C_{3-6}$ cycloalkylthio group, $C_{1-6}$ haloalkylthio group, $C_{1-6}$ alkylsulfinyl group, $C_{2-6}$ alkenylsulfinyl group, $C_{2-6}$ alkynylsulfinyl group, $C_{3-6}$ cycloalkylsulfinyl group, $C_{1-6}$ haloalkylsulfinyl, $C_{1-6}$ alkylsulfonyl group, $C_{2-6}$ alkenylsulfonyl group, $C_{2-6}$ alkynylsulfonyl group, $C_{3-6}$ cycloalkylsulfonyl group, $C_{1-6}$ haloalkylsulfonyl group, $C_{2-6}$ alkoxyalkyl group, $C_{2-6}$ alkoxyalkoxy group, $C_{2-6}$ haloalkoxyalkyl group, $C_{2-6}$ haloalkoxyalkoxy group, $C_{2-6}$ alkylthioalkyl group, $C_{2-6}$ alkylthioalkoxy group, $C_{3-6}$ alkoxycarbonylalkyl group, $C_{3-6}$ alkylcarbonylalkyl group, $C_{2-6}$ alkoxycarbonyloxy group, $C_{2-6}$ alkylcarbonyl group, $C_{3-6}$ alkenylcarbonyl group, $C_{3-6}$ alkynylcarbonyl group, $C_{4-7}$ cycloalkylcarbonyl group, $C_{2-6}$ haloalkylcarbonyl group, isothiazolyl group, oxazolyl group, isoxazolyl group, oxadiazolyl group, thiadiazolyl group, triazolyl group, pyridyl group, pyridazyl group, pyrimidyl group or pyrazyl group which may be substituted or non-substituted (the substituent of the above aromatic group is selected from halogen atom, $C_{1-4}$ alkyl group, $C_{1-4}$ alkoxy group, $C_{1-4}$ alkylthio group, $C_{1-4}$ haloalkyl group, $C_{1-4}$ haloalkoxy group, $C_{1-4}$ haloalkylthio group, amino group, cyano group and nitro group, and when the number of the substituents is not less than 2, these substituents may be same or different), $C_{1-6}$ haloalkyl group containing one or more fluorine atom, halogen atom, cyano group, nitro group, $C_{1-6}$ alkylthio group, $C_{1-6}$ alkylsulfinyl group, $C_{1-6}$ alkylsulfonyl group, $C_{1-6}$ haloalkylthio group, $C_{1-6}$ haloalkylsulfinyl group, $C_{1-6}$ haloalkylsulfonyl group, $C_{1-6}$ alkoxy group, $C_{1-6}$ haloalkoxy group, or $C_{2-6}$ alkoxycarbonyl group; and when A is

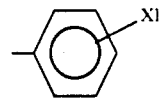

(where X and l are as defined above), or naphthyl group, furyl group, thienyl group, pyrrolyl group, pyrazolyl group, imidazolyl group, thiazolyl group, isothiazolyl group, oxazolyl group, isoxazolyl group, oxadiazolyl group, thiadiazolyl group, triazolyl group, pyridyl group, pyridazyl group, pyrimidyl group or pyrazyl group which may be substituted or non-substituted (the substituents of the above group, $C_{2-6}$ alkoxycarbonyl group, $C_{2-6}$ haloalkoxycarbonyl group, $C_{3-6}$ alkoxycarbonylalkoxy group, nitro group, cyano group, hydroxyl group, carboxyl group, thiocyanate group, isothiocyanate group, $C_{2-6}$ thiocyanatealkyl group, $C_{1-6}$ alkylsulfonyloxy group, $C_{2-6}$ alkylthiocarbonyl group, amino group ($-NR^3R^4$), aminocarbonyl group ($-CONR^3R^4$), aminocarbonyloxy group ($-O-CONR^3R^4$), amide group ($-NR^3COR^4$), alkoxycarbonylamino group ($-NR^3CO_2R^4$), aminosulfonyl group ($-SO_2NR^3R^4$), thioamide group ($-NR^3CSR^4$), methylenedioxy group, halomethylenedioxy group, ethylenedioxy group, haloethylenedioxy group, trimethylsilyl group or $-(W)_n-Ar$ group (wherein W is

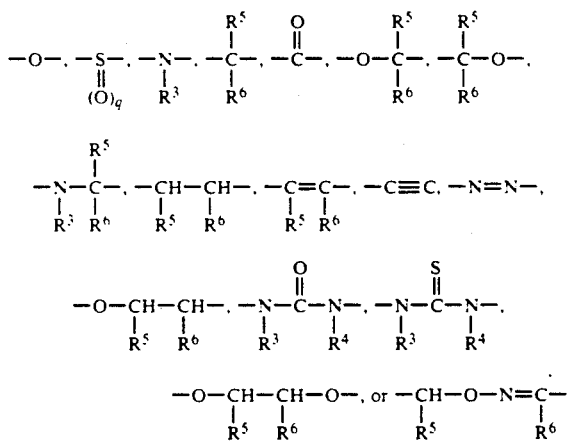

(in which $R^3$ and $R^4$ represent independently hydrogen atom, $C_{1-6}$ alkyl group, $C_{2-6}$ alkenyl group, $C_{2-6}$ alkynyl group, $C_{1-6}$ haloalkyl group, $C_{2-6}$ haloalkenyl group, $C_{2-6}$ haloalkynyl group, $C_{2-6}$ alkylcarbonyl group, $C_{2-6}$ alkoxycarbonyl group, phenyl group or benzyl group; $R^5$ and $R^6$ represent independently hydrogen atom, halogen atom, $C_{1-6}$ alkyl group, $C_{3-6}$ cycloalkyl group, cyano group or phenyl group; and q is an integer of 0 to 2); n is an integer of 0 or 1; and Ar is phenyl group, naphthyl group, furyl group, thienyl group, pyrrolyl group, pyrazolyl group, imidazolyl group, thiazolyl group, isothiazolyl group, oxazolyl group, isoxazolyl group, oxadiazolyl group, thiadiazolyl group, triazolyl group, pyridyl group, pyridazyl group, pyrimidyl group, pyrazyl group, quinolyl group or quinoxalyl group which may be substituted or non-substituted (the substituent of the above aromatic groups is selected from halogen atom, cyano group, nitro group, $C_{1-4}$ alkyl group, $C_{1-4}$ haloalkyl group, $C_{1-4}$ alkoxy group, $C_{1-4}$ haloalkoxy group, $C_{1-4}$ alkylthio group, $C_{1-4}$ haloalkylthio group, $C_{1-4}$ alkylsulfonyl group, $C_{1-4}$ haloalkylsulfonyl group, $C_{2-4}$ alkoxycarbonyl group, carboxyl group, amino group, $C_{1-4}$ monoalkylamino group, $C_{2-8}$ dialkylamino group, phenyl group, benzyl group, methylenedioxy group or halomethylenedioxy group, and when the number of the substituents is not less than 2, the substituents may be same or different)); and m is an integer of 0 to 5 (when it is 2 to 5, the substituents $Y^1$ may be same or different)], or naphtyl group, furyl group, thienyl group, pyrrolyl group, pyrazolyl group, imidazolyl group, thiazolyl group, isothiazolyl group, oxazolyl group, isoxazolyl group, thiadiazolyl group, oxadiazolyl group, triazolyl group, pyridyl group, pyridazyl group, pyrimizyl group, pyrazyl group, quinolyl group, quinoxalyl group, benzofuryl group, benzothienyl group, indolyl group, benzoxazolyl group or benzothiazolyl group which may be substituted or non-substituted (the substituent of the above aromatic groups is selected from halogen atom, cyano group, nitro group, $C_{1-4}$ alkyl group, $C_{1-4}$ haloalkyl group, $C_{1-4}$ alkoxy group, $C_{1-4}$ haloalkoxy group, $C_{1-4}$ alkylthio group, $C_{1-4}$ haloalkylthio group, $C_{1-4}$ alkylsulfonyl group, $C_{1-4}$ haloalkylsulfonyl group, $C_{2-4}$ alkoxycarbonyl group, carboxyl group, amino group, $C_{1-4}$ monoalkylamino group, $C_{2-8}$ dialkylamino group, phenyl group, phenoxy group or benzyl group, and when the number of the substituents is 2 or more, the substituents may be same or different), and when A is $C_{1-6}$ haloalkyl group containing one or more fluorine atoms, halogen atom, cyano group, nitro group, $C_{1-6}$ alkylthio group, $C_{1-6}$ alkylsulfinyl group, $C_{1-6}$ alkylsulfonyl group, $C_{1-6}$ haloalkylthio group, $C_{1-6}$ haloalkylsulfinyl group, $C_{1-6}$ haloalkylsulfonyl group, $C_{1-6}$ alkoxy group, $C_{1-6}$ haloalkoxy group or $C_{2-6}$ alkoxycarbonyl group, B is

[wherein $Y^2$ is halogen atom, $C_{1-4}$ alkyl group, $C_{1-4}$ alkoxy group, $C_{1-4}$ haloalkyl group, $C_{1-4}$ haloalkoxy group, $C_{1-4}$ alkylthio group, $C_{1-4}$ haloalkylthio group, $C_{1-4}$ alkylsulfinyl group, $C_{1-4}$ haloalkylsufinyl group, $C_{1-4}$ alkylsulfonyl group, $C_{1-4}$ haloalkylsulfonyl group, sulfonamide group, $C_{2-4}$ alkenyl group, $C_{2-4}$ haloalkenyl group, amino group, $C_{1-4}$ monoalkylamino group, $C_{2-8}$ dialkylamino group, $C_{2-6}$ alkoxyalkoxy group, $C_{2-6}$ alkoxycarbonyl group, cyano group or nitro group, and r is an integer of 3 to 5 (the substituents $Y^2$ may be same or different, and when r=3 with the substituents at the 2-, 4- and 5-positions, the substituent $Y^2$ at the 5-position is not $C_{1-4}$ alkoxy group, $C_{1-4}$ haloalkoxy group, $C_{2-6}$ alkoxyalkoxy group or $C_{2-6}$ alkoxycarbonyl group)], provided that A is not phenyl group and 3-bromo-4-methoxyphenyl group, when B is phenyl group.

In a second aspect of the present invention, there is provided pesticides comprising as an active ingredient a pesticidally effective amount of at least one of the uracil derivatives set forth in the first aspect.

In a third aspect of the present invention, there is provided a process for producing the uracil derivatives set forth in the first aspect, which comprises reacting compounds represented by the general formula (XXXVI):

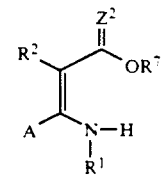

(wherein $R^1$, $R^2$, $Z^2$ and A are as defined above, and $R^7$ represents $C_{1-6}$ alkyl group, benzyl group or phenyl group) with compounds represented by the general formula (IV) or (V):

(wherein B and $Z^1$ are as defined above, and $R^8$ represents $C_{1-6}$ alkyl group, benzyl group or phenyl group).

DETAILED DESCRIPTION OF THE INVENTION

Uracil derivatives represented by the formula (I) according to the present invention are the compounds useful as active ingredient of pesticides.

The term "pesticides" used in the specification of the present invention means a composition having preventing and controlling effects to harmful living things, in particular, insecticidal, acaricidal, nematicidal and mollusicidal compositions and herbicidal composition.

Among the uracil derivatives represented by the formula (I), (1) compounds of the formula (I) wherein A is

[wherein X is halogen atom, $C_{1-4}$ alkyl group, $C_{1-4}$ alkoxy group, $C_{1-4}$ alkylthio group, $C_{1-4}$ haloalkyl group, $C_{1-4}$ haloalkoxy group, $C_{1-4}$ haloalkylthio group, amino group, cyano group or nitro group, and l is an integer of 0-5 (when l is an integer of 2 to 5, the substituents X may be same or different)], or naphthyl group, furyl group, thienyl group, pyrrolyl group, pyrazolyl group, imidazolyl group, thiazolyl group, isothiazolyl group, oxazolyl group, isoxazolyl group, oxadiazolyl group, thiadiazolyl group, triazolyl group, pyridyl group, pyridazyl group, pyrimidyl group or pyrazyl group which may be substituted or non-substituted (the substituent of the above aromatic group is selected from halogen atom, $C_{1-4}$ alkyl group, $C_{1-4}$ alkoxy group, $C_{1-4}$ alkylthio group, $C_{1-4}$ haloalkyl group, $C_{1-4}$ haloalkoxy group, $C_{1-4}$ haloalkylthio group, amino group, cyano group and nitro group, and when the number of the substituents is not less than 2, these substituents may be same or different), and B is

[wherein Y¹ is halogen atom, $C_{1-6}$ alkyl group, $C_{2-6}$ alkenyl group, $C_{2-6}$ alkynyl group, $C_{3-6}$ cycloalkyl group, $C_{1-6}$ haloalkyl group, $C_{2-6}$ haloalkenyl group, $C_{2-6}$ haloalkynyl group, $C_{3-6}$ halocycloalkyl group, $C_{2-6}$ cyanoalkyl group, $C_{1-6}$ hydroxyalkyl group, $C_{2-6}$ carboxyalkyl group, $C_{1-6}$ alkoxy group, $C_{2-6}$ alkenyloxy group, $C_{2-6}$ alkynyloxy group, $C_{3-6}$ cycloalkyloxy group, $C_{1-6}$ haloalkoxy group, $C_{2-6}$ haloalkenyloxy group, $C_{2-6}$ haloalkinyloxy group, $C_{3-6}$ halocycloalkoxy group, $C_{4-7}$ halocycloalkylalkoxy group, $C_{1-6}$ alkylthio group, $C_{2-6}$ alkenylthio group, $C_{2-6}$ alkynylthio group, $C_{3-6}$ cycloalkylthio group, $C_{1-6}$ haloalkylthio group, $C_{1-6}$ alkylsulfinyl group, $C_{2-6}$ alkenylsulfinyl group, $C_{2-6}$ alkynylsulfinyl group, $C_{3-6}$ cycloalkylsulfinyl group, $C_{1-6}$ haloalkylsulfinyl, $C_{1-6}$ alkylsulfonyl group, $C_{2-6}$ alkenylsulfonyl group, $C_{2-6}$ alkynylsulfonyl group, $C_{3-6}$ cycloalkylsulfonyl group, $C_{1-6}$ haloalkylsulfonyl group, $C_{2-6}$ alkoxyalkyl group, $C_{2-6}$ alkoxyalkoxy group, $C_{2-6}$ haloalkoxyalkyl group, $C_{2-6}$ haloalkoxyalkoxy group, $C_{2-6}$ alkylthioalkyl group, $C_{2-6}$ alkylthioalkoxy group, $C_{3-6}$ alkoxycarbonylalkyl group, $C_{3-6}$ alkylcarbonylalkyl group, $C_{2-6}$ alkoxycarbonyloxy group, $C_{2-6}$ alkylcarbonyl group, $C_{3-6}$ alkenylcarbonyl group, $C_{3-6}$ alkynylcarbonyl group, $C_{4-7}$ cycloalkylcarbonyl group, $C_{2-6}$ haloalkylcarbonyl group, $C_{2-6}$ alkoxycarbonyl group, $C_{2-6}$ haloalkoxycarbonyl group, $C_{3-6}$ alkoxycarbonylalkoxy group, nitro group, cyano group, hydroxyl group, carboxyl group, thiocyanate group, isothiocyanate group, $C_{2-6}$ thiocyanatealkyl group, $C_{1-6}$ alkylsulfonyloxy group, $C_{2-6}$ alkylthiocarbonyl group, amino group ($-NR^3R^4$), aminocarbonyl group ($-CONR^3R^4$), aminocarbonyloxy group ($-O-CONR^3R^4$), amide group ($-NR^3COR^4$), alkoxycarbonylamino group ($-NR^3CO_2R^4$), aminosulfonyl group ($-SO_2NR^3R^4$), thioamide group ($-NR^3CSR^4$), methylenedioxy group, halomethylenedioxy group, ethylenedioxy group, haloethylenedioxy group, trimethylsilyl group or $-(W)_n-Ar$ group (wherein W is

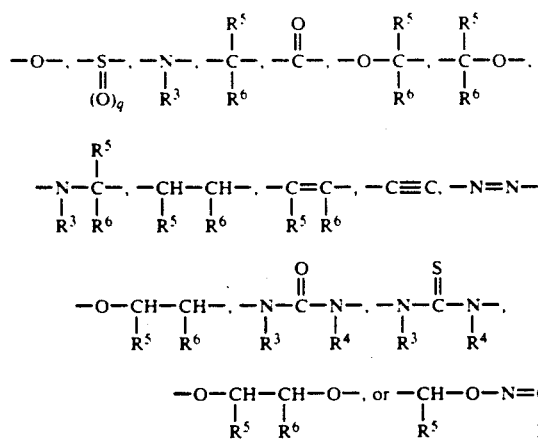

(in which $R^3$ and $R^4$ represent independently hydrogen atom, $C_{1-6}$ alkyl group, $C_{2-6}$ alkenyl group, $C_{2-6}$ alkynyl group, $C_{1-6}$ haloalkyl group, $C_{2-6}$ haloalkenyl group, $C_{2-6}$ haloalkynyl group, $C_{2-6}$ alkylcarbonyl group, $C_{2-6}$ alkoxycarbonyl group, phenyl group or benzyl group;

$R^5$ and $R^6$ represent independently hydrogen atom, halogen atom, $C_{1-6}$ alkyl group, $C_{3-6}$ cycloalkyl group, cyano group or phenyl group; and q is an integer of 0 to 2); n is an integer of 0 or 1; and Ar is phenyl group, naphthyl group, furyl group, thienyl group, pyrrolyl group, pyrazolyl group, imidazolyl group, thiazolyl group, isothiazolyl group, oxazolyl group, isoxazolyl group, oxadiazolyl group, thiadiazolyl group, triazolyl group, pyridyl group, pyridazyl group, pyrimidyl group, pyrazyl group, quinolyl group or quinoxalyl group which may be substituted or non-substituted (the substituent of the aromatic groups is selected from halogen atom, cyano group, nitro group, $C_{1-4}$ alkyl group, $C_{1-4}$ haloalkyl group, $C_{1-4}$ alkoxy group, $C_{1-4}$ haloalkoxy group, $C_{1-4}$ alkylthio group, $C_{1-4}$ haloalkylthio group, $C_{1-4}$ alkylsulfonyl group, $C_{1-4}$ haloalkylsulfonyl group, $C_{2-4}$ alkoxycarbonyl group, carboxyl group, amino group, $C_{1-4}$ monoalkylamino group, $C_{2-8}$ dialkylamino group, phenyl group, benzyl group, methylenedioxy group or halomethylenedioxy group, and when the number of the substituents is not less than 2, these substituents may be same or different)), and m is an integer of 0 to 5 (when it is 2 to 5, the substituents Y¹ may be same or different)], or naphtyl group, furyl group, thienyl group, pyrrolyl group, pyrazolyl group, imidazolyl group, thiazolyl group, isothiazolyl group, oxazolyl group, isoxazolyl group, thiadiazolyl group, oxadiazolyl group, triazolyl group, pyridyl group, pyridazyl group, pyrimizyl group, pyrazyl group, quinolyl group, quinoxalyl group, benzofuryl group, benzothienyl group, indolyl group, benzoxazolyl group or benzothiazolyl group which may be substituted or non-substituted (the substituent of the above aromatic groups is selected from halogen atom, cyano group, nitro group, $C_{1-4}$ alkyl group, $C_{1-4}$ haloalkyl group, $C_{1-4}$ alkoxy group, $C_{1-4}$ haloalkoxy group, $C_{1-4}$ alkylthio group, $C_{1-4}$ haloalkylthio group, $C_{1-4}$ alkylsulfonyl group, $C_{1-4}$ haloalkylsulfonyl group, $C_{2-4}$ alkoxycarbonyl group, carboxyl group, amino group, $C_{1-4}$ monoalkylamino group, $C_{2-8}$ dialkylamino group, phenyl group, phenoxy group or benzyl group, and when the number of the substituents is not less than 2, these substituents may be same or different), provided that A is not phenyl group and 3-bromo-4-methoxyphenyl group, when B is phenyl group, are preferred.

Further, (2) compounds of the formula (I) wherein A is

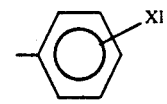

(wherein X and l as defined above), and B is

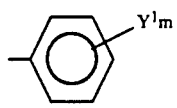

(wherein Y¹ and m are as defined above), provided that A is not phenyl group and 3-bromo-4-methoxyphenyl group, when B is phenyl group), are more preferred.

(3) Compounds of the formula (I) wherein A is naphthyl group furyl group, thienyl group, pyrrolyl group, pyrazolyl group. imidazolyl group. thiazolyl group. isothiazolyl group, oxazolyl group, isoxazolyl group. oxadiazolyl group. thiadiazolyl group. triazolyl group. pyridyl group. pyridazyl group. pyrimizyl group or pyrazyl group which may be substituted or non-substituted (the substituent is the same as defined above), and B is

(wherein $Y^1$ and m are as defined above) are more preferred.

Also, (4) compounds of the formula (I) wherein A is $C_{1-6}$ haloalkyl group containing one or more fluorine atoms, halogen atom, cyano group, nitro group, $C_{1-6}$ alkylthio group, $C_{1-6}$ alkylsulfinyl group, $C_{1-6}$ alkylsulfonyl group. $C_{1-6}$ haloalkylthio group, $C_{1-6}$ haloalkylsulfinyl group, $C_{1-6}$ haloalkylsulfonyl group, $C_{1-6}$ alkoxy group, $C_{1-6}$ haloalkoxy group, or $C_{2-6}$ alkoxycarbonyl group, and B is

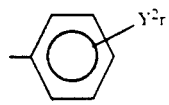

(wherein $Y^2$ is halogen atom, $C_{1-4}$ alkyl group, $C_{1-4}$ alkoxy group, $C_{1-4}$ haloalkyl group, $C_{1-4}$ haloalkoxy group, $C_{1-4}$ alkylthio group, $C_{1-4}$ haloalkylthio group, $C_{1-4}$ alkylsulfinyl group, $C_{1-4}$ haloalkylsufinyl group, $C_{1-4}$ alkylsulfonyl group, $C_{1-4}$ haloalkylsulfonyl group, sulfonamide group, $C_{2-4}$ alkenyl group, $C_{2-4}$ haloalkenyl group, amino group, $C_{1-4}$ monoalkylamino group, $C_{2-8}$ dialkylamino group, $C_{2-6}$ alkoxyalkoxy group, $C_{2-6}$ alkoxycarbonyl group, cyano group or nitro group, and r is an integer of 3 to 5 (the substituents $Y^2$ may be same or different, and when r=3 with the substituents at the 2-, 4- and 5-positions, the substituent $Y^2$ at the 5-position is not $C_{1-4}$ alkoxy group, $C_{1-4}$ haloalkoxy group, $C_{2-6}$ alkoxyalkoxy group or $C_{2-6}$ alkoxycarbonyl group), are more preferred.

Furthermore, among the above-mentioned preferred uracil derivatives, (i) compounds of the formula (I) wherein $R^1$ and $R^2$ each represents hydrogen atom, $Z^1$ and $Z^2$ each represents oxygen atom, A is 2-fluorophenyl group, 2-chlorophyl group, 2-chloro-6-fluorophenyl group or 2,6-difluorophenyl group, and B is

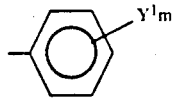

(where $Y^1$ and m represent the same as defined above); and (ii) compounds of the formula (I) wherein $R^1$ and $R^2$ each represents hydrogen atom, $Z^1$ and $Z^2$ each represents oxygen atom, A is trifluoromethyl group, pentafluoroethyl group or chlorodifluoromethyl group, and B is

(wherein $Y^2$ and r represent the same as defined above), are still more preferred.

The processes for the preparation of the compounds according to the present invention are described below.

As for the method for synthesis of the said uracil derivatives of the present invention, it is possible to synthesize the uracil skeleton by referring to, for example, the synthesis method shown in Comprehensive Heterocyclic Chemistry, Vol. 3, p. 57, 1984. The preparation processes, including the above method, will be described concretely below.

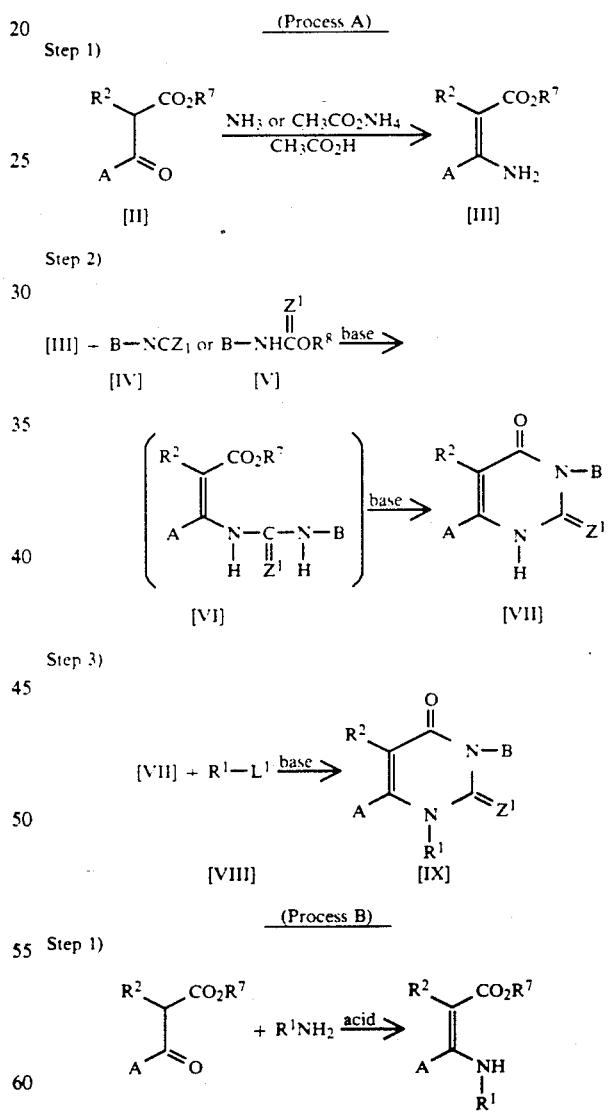

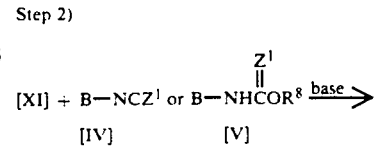

-continued
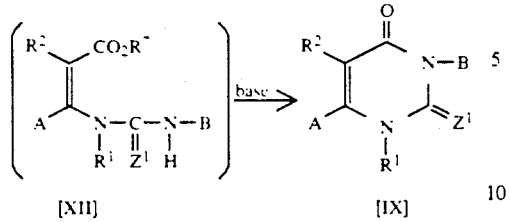
[XII] [IX]
(Process C)
Step 1)
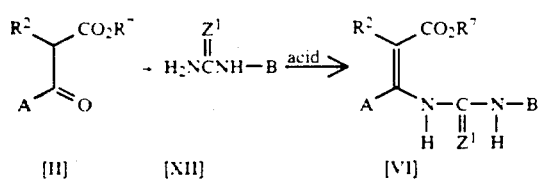
[II] [XII] [VI]
Step 2)
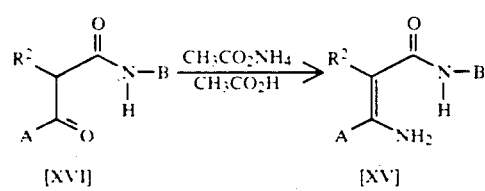
[VI] → [VII]
(Process D)
Step 1)
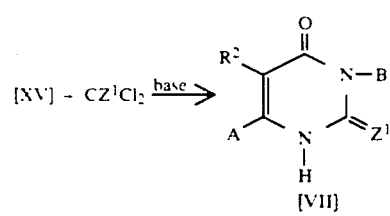
[XVI] [XV]
Step 2)
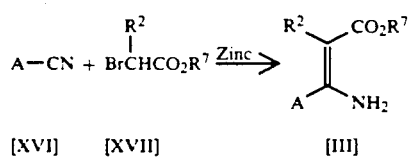
[XV] + CZ¹Cl₂ →ᵇᵃˢᵉ [VII]
(Process E)
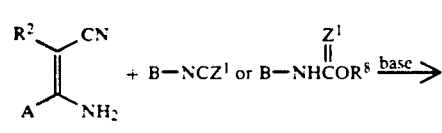
[XVI] [XVII] [III]
(Process F)
$$R^2\text{—}C(\text{CN})=C(A)\text{NH}_2 + B\text{—NCZ}^1 \text{ or } B\text{—NHCOR}^8 \xrightarrow{\text{base}}$$
[XVIII] [IV] [V]
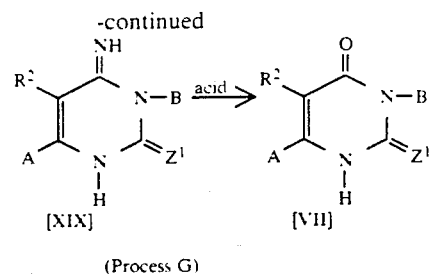
[XIX] [VII]
(Process G)
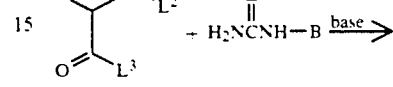
[XX] [XIII]
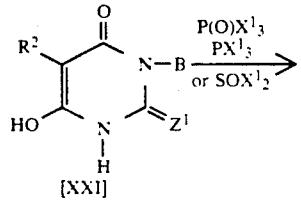
[XXI]
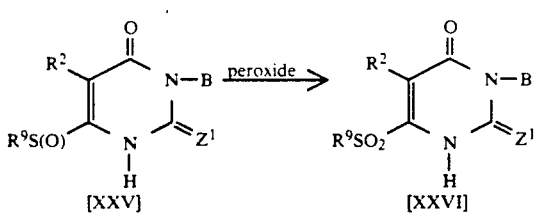
[XXII] [XXIII]
(Process H)
[XXII] + R⁹SM² ⟶
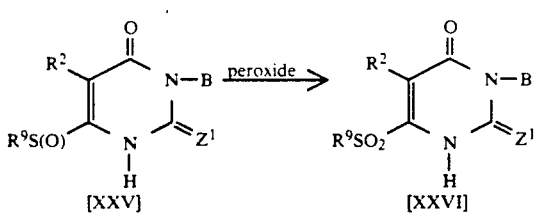
[XXIV]
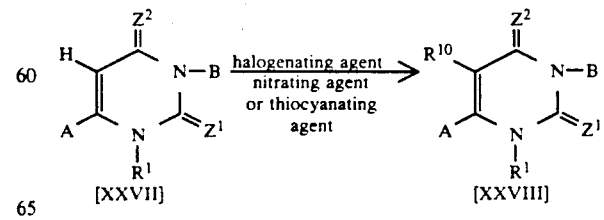
[XXV] [XXVI]
(Process I)
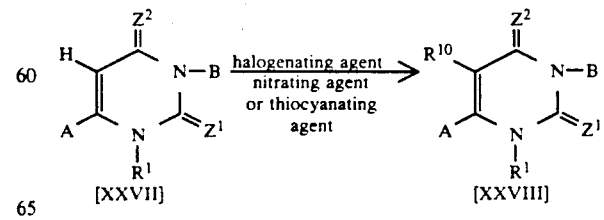
[XXVII] [XXVIII]
(Process J)
Step 1)

Step 2)

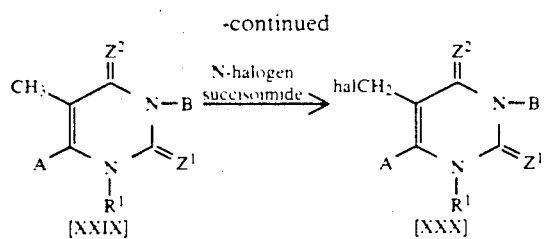

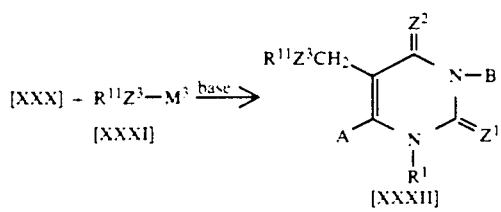

Step 3)

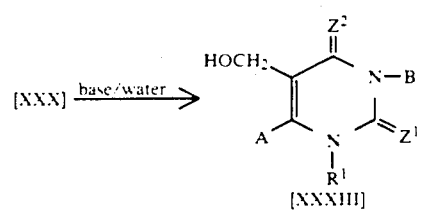

(Process K)

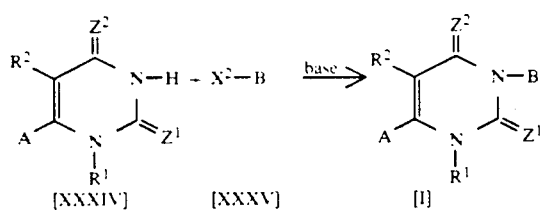

In the above-shown formulae (in Processes A-K), R¹, R², A, B, Z¹ and Z² are the same as defined above; R⁷ and R⁸ represent independently C₁₋₆ alkyl group, benzyl group or phenyl group; R⁹ represents C₁₋₆ alkyl group or C₁₋₆ haloalkyl group; R¹⁰ represents halogen atom, nitro group or thiocyanate group; R¹¹ represents C₁₋₄ alkyl group or C₁₋₄ haloalkyl group; L¹ represents halogen atom, methanesulfonate group, p-toluenesulfonate group or favorable elimination group such as C₁₋₄ alkylsulfate group; L² and L³ represent independently halogen atom, hydroxyl group or C₁₋₄ alkoxy group; X¹ represents chlorine atom or bromine atom; X² represents fluorine atom, chlorine atom, bromine atom or iodine atom; M¹ represents sodium atom, potassium atom or copper atom; M² and M³ represent independently sodium atom or potassium atom; Z³ represents oxygen atom or sulfur atom; and hal represents chlorine atom or bromine atom. The compounds of the formulae (VII), (IX), (XIX), (XXI), (XXII), (XXIII), (XXIV), (XXV), (XXVI), (XXVII), (XXVIII), (XXIX), (XXX), (XXXII) and (XXXIII) are the compounds of the present invention.

Process A is a method for synthesizing the compounds of the formula (I) wherein R² is hydrogen atom or C₁₋₄ alkyl group. The starting compound of the formula (II) can be synthesized by a known method by referring to, for example, Journal of Heterocyclic Chemistry, Vol. 9, p.513, 1972. In Step 1, the compound of the formula (II) is reacted with ammonia or ammonium acetate in a solvent such as ethanol in the presence of acetic acid, thereby obtaining a compound of the formula (III) in a high yield.

In Step 2, the obtained compound of the formula (III) and an iso(thio)cyanate of the formula (IV) or a (thio)-carbamic acid ester of the formula (V) are reacted in an inert solvent in the presence of a base, thereby obtaining a compound of the formula (VII) (a compound of the present invention) without isolating the intermediate (VI). The bases usable in the above reaction include alkali metal alkoxides such as sodium ethoxide, alkali metal hydroxides such as sodium hydroxide and potassium hydroxide; alkali metal carbonates such as sodium carbonate and potassium carbonate; and sodium hydride. As the solvent, there can be used lower alcohols such as methanol and ethanol; aromatic hydrocarbons such as benzene and toluene; ethers such as diethyl ether, tetrahydrofuran, 1,4-dioxane, 1,2-dimethoxyethane and 1,2-diethoxyethane; halogenated hydrocarbons such as dichloromethane and 1,2-dichloroethane; amides such as dimethylformamide and dimethylacetamide; acetonitrile; dimethyl sulfoxide and mixtures thereof. Generally, it is preferred to use sodium alkoxide ($R^7ONa$) as base in an alcohol ($R^7OH$) solvent which is the same as $R^7$ in the formula (III), or to use sodium hydride as base in such solvent as tetrahydrofuran, dimethylformamide or dimethyl sulfoxide. The reaction temperature is in the range from $-30°$ C. to the reflux temperature of the reaction mixture.

In Step 3, the compound of the formula (VII) and a compound of the formula (VIII) are reacted in an inert solvent in the presence of a base to form a compound of the formula (IX) of the present invention. When R¹ is C₁₋₄ alkyl group, C₂₋₄ alkenyl group, C₂₋₄ alkynyl group or C₂₋₄ alkoxyalkyl group, it is preferred to use a halide such as chloride and bromide as R¹-L¹ of the formula (VIII). When R¹ is C₁₋₄ alkyl group, use of dialkyl sulfate ($R^1_2SO_4$) is also favorable. Preferred examples of the base used in the above reaction are alkali metal alkoxides such as sodium ethoxide; alkali metal carbonates such as sodium carbonate and potassium carbonate; and sodium hydride. As the solvent, it is preferred to use water; lower alcohols such as ethanol; ethers such as 1,2-dimethoxyethane and tetrahydrofuran; dimethylformamide; and dimethyl sulfoxide.

The reaction temperature usable is from 0° C. to the reflux temperature of the reaction mixture, preferably 0° to 30° C. When R¹ is formyl, a halide of formic acid is preferably used as R¹-L¹, and When R¹ is C₂₋₆ alkylcarbonyl group, a halide or anhydride of C₂₋₆ alkanic acid is preferably used as R¹-L¹. When R¹ is C₂₋₆ alkoxycarbonyl group, C₂₋₆ alkyl chloroformate or bromoformate is preferably used as R¹-L¹. In the above reaction, sodium hydride is preferably used as base. However, in case of introducing C₂₋₆ alkylcarbonyl group by using an acid anhydride, the reaction can be carried out without using any base. Dimethylformamide or dimethyl sulfoxide is preferably used as solvent. Reaction temperature is in the range from 0° C. to the reflux temperature of the reaction mixture, preferably 0° to 30° C.

When Z¹ in the compound of the formula (VII) is sulfur atom, alkylation of the compound usually produces a mixture of N- and S-alkylation products. The desired N-C₁₋₄ alkyl, N-C₂₋₄ alkenyl, N-C₂₋₄ alkynyl or N-C₂₋₄ alkoxyalkyl compound can be easily isolated from the said mixture by an ordinary method such as column chromatography.

Process B is a method wherein various kinds of substituent other than hydrogen atom, can be introduced as $R^1$ before forming the uracil ring. In Step 1, a compound of the formula (II) and an amine of the formula (X) are reacted in the presence of an acid catalyst to form a compound of the formula (XI). Acetic acid or trifluoroacetic acid is preferably used as acid catalyst in this reaction.

In Step 2, a compound of the formula (XI) and an iso(thio)cyanate of the formula (IV) or a (thio)carbamic acid ester of the formula (V) are reacted in the presence of a base, thereby obtaining a compound of the formula (IX) of the present invention without isolating the intermediate of the formula (XII). The reaction conditions such as the kind of base, kind of solvent and reaction temperature used in this step are substantially the same as those used in Step 2 of Process A.

Process C is another method for synthesizing the intermediate (VI) in Step 2 of Process A. In Step 1, a compound of the formula (II) and a (thio)urea of the formula (XIII) are reacted in an inert solvent in the presence of an acid catalyst to form a compound of the formula (VI). In this reaction, strong mineral acids such as sulfuric acid and hydrochloric acid, organic acids such as p-toluenesulfonic acid and phosphoric acids such as orthophosphoric acid and polyphosphoric acid are preferably used as acid catalyst. As the solvent, aromatic hydrocarbons such as benzene and toluene, halogenated hydrocarbons such as carbon tetrachloride and chlorobenzene and ethers such as 1,2-dsimethoxyethane and 1,4-dioxane are preferably used. Reaction temperature is in the range from 20° C. to the reflux temperature of the reaction mixture, and it is preferred to carry out the reaction at the reflux temperature of the reaction mixture.

In Step 2, the compound of the formula (VI) is subjected to a cyclization reaction in an inert solvent in the presence of a base to form a compound of the formula (VII) which is a compound of the present invention. The reaction conditions, i.e. the kind of base, the kind of solvent used and reaction temperature used in this step are substantially the same as employed in Step 2 of Process A.

Process D is a method for synthesizing the compounds of the present invention represented by the formula (I) wherein $Z^1$ is sulfur atom. The starting compound of the formula (XIV) can be synthesized by a conventional method. In Step 1, similarly to Step 1 of Process A, a compound of the formula (XIV) is reacted with ammonium acetate in an inert solvent such as ethanol in the presence of acetic acid to form a compound of the formula (XV).

In Step 2, the compound of the formula (XV) is reacted with phosgene or thiophosgene in an inert solvent in the presence of a base to obtain a compound of the formula (VII) of the present invention. The base used in this reaction is preferably an organic base such as triethylamine and pyridine. As the solvent, aromatic hydrocarbons such as benzene and toluene and halogenated hydrocarbons such as dichloromethane and 1,2-dichloroethane are preferably used. Reaction temperature is in the range from 0° C. to reflux temperature of the reaction mixture, preferably 0° to 30° C. In the above reaction, 1,1'-thiocarbonyldiimidazole can be used in place of thiophosgene.

Process E is another method for synthesizing the intermediate (III) in Step 1 of Process A. This process comprises reacting a nitrile of the formula (XVI) with an alpha-bromoacetic ester of the formula (XVII) in an inert solvent in the presence of zinc to obtain a compound of the formula (III). The solvent used in this reaction is preferably selected from aromatic hydrocarbons such as benzene and toluene and ethers such as diethyl ether, tetrahydrofuran, 1,2-dimethoxyethane and 1,4-dioxane. Reaction temperature is in the range from 20° C. to the reflux temperature of the reaction mixture, and it is preferred to carry out the reaction at the reflux temperature of the reaction mixture.

Process F is a method for synthesizing the compounds of the present invention represented by the formula (I) wherein $Z^2$ is imino group or oxygen atom. The starting compound of the formula (XVIII) can be synthesized by a known method. This starting compound (XVIII) is reacted with a compound of the formula (IV) or (V) in an inert solvent in the presence of a base to obtain a compound of the formula (XIX) of the present invention. The reaction conditions such as kinds of base and solvent, and reaction temperature are substantially the same as used in Step 2 of Process A. By hydrolysis of the compound of the formula (XIX) under an acidic condition a compound of the formula (VII) of the present invention is obtained. The acid used in this hydrolysis reaction is preferably a mineral acid such as hydrochloric acid, sulfuric acid and nitric acid, more preferably a diluted aqueous solution thereof. Reaction temperature is in the range from 20° C. to the reflux temperature of the reaction mixture, and it is preferred to perform the reaction at the reflux temperature of the reaction mixture.

Process G is a method for synthesizing the compounds of the present invention of the formula (I) wherein A is halogen atom or cyano group. A malonic acid derivative of the formula (XX) and a (thio)urea of the formula (XIII) are reacted in an inert solvent in the presence of a base to form a compound of the formula (XXI). The bases usable in the above reaction include metal alkoxides such as sodium ethoxide, alkali methal hydroxides such as sodium hydroxide, alkali metal carbonates such as potassium carbonate, and sodium hydride. As the solvent, there can be used lower alcohols such as methanol and ethanol, aromatic hydrocarbons such as benzene and toluene, ethers such as diethyl ether, tetrahydrofuran and 1,4-dioxane, dimethylformamide and the like. Reaction temperature is in the range from 0° C. to the reflux temperature of the reaction mixture. When both of $L^2$ and $L^3$ in the compound of the formula (XX) are halogen atom, it is possible to obtain the compound of the formula (XXI) by conducting the reaction in a solvent such as dioxane without adding a base at a temperature in the range from 0° C. to the reflux temperature of the reaction mixture.

The compound of the formula (XXI) is reacted with phosphorus oxyhalide, phosphorus trihalide or thionyl halide to form a compound of the formula (XXII). In some cases, presence of a base facilitates the progress of the reaction. Examples of the said phosphorus oxyhalide are phosphorus oxychloride and phosphorus oxybromide. Examples of phosphorus trihalide are phosphorus trichloride and phosphorus tribromide, and examples of thionyl halide are thionyl chloride and thionyl bromide. The base used in the above reaction is preferably an organic base such as pyridine and triethylamine.

The compound of the formula (XXII) is reacted with a metallic cyanide in an inert solvent to form a compound of the formula (XXIII). Preferred examples of metallic cyanide used in the above reaction are sodium cyanide, potassium cyanide and copper cyanide. As the solvent, there can be used lower alcohols such as methanol and ethanol, aromatic hydrocarbons such as benzene and toluene, ethers such as diethyl ether, tetrahydrofuran and 1,4-dioxane, dimethylformamide and the like. Reaction temperature is in the range from 0° C. to the reflux temperature of the reaction mixture.

Process H is a method for synthesizing the compounds of the formula (I) wherein A is alkylthio group, alkylsulfinyl group or alkylsulfonyl group. A compound of the formula (XXII) and a metal salt of alkylmercaptan are reacted in an inert solvent to form a compound of the formula (XXIV). As the typical examples of metal in the metal salts of alkylmercaptan, sodium and potassium may be exemplified. As the solvent, ethers such as 1,2-dimethoxyethane and tetrahydrofuran are preferably used. Also, excess mercaptan can be used as solvent. Reaction temperature is in the range from 0° C. to the reflux temperature of the reaction mixture.

The compound of the formula (XXIV) is reacted with an equimolar amount of a peroxide in an inert solvent to obtain a compound of the formula (XXV), and the obtained compound of the formula (XXV) is further reacted with an equimolar amount of a peroxide to obtain a compound of the formula (XXVI). Also, by reacting the compound of the formula (XXIV) with twice as much molar amount of a peroxide, it is possible to obtain the compound of the formula (XXVI) without isolating the compound of the formula (XXV). As peroxide, there can be used hydrogen peroxide, peracetic acid, m-chloroperoxy benzoic acid and the like. As the solvent, there can be used alcohols such as methanol and ethanol, halogenated hydrocarbons such as dichloromethane, chloroform and carbon tetrachloride, water, acetic acid and the like. Reaction temperature is in the range from 0° C. to the reflux temperature of the reaction mixture, preferably 0° to 30° C.

Process I is a method for synthesizing a compound of the formula (XXVIII) of the present invention by converting hydrogen atom in an uracil derivative of the formula (XXVII) wherein $R^2$ is hydrogen atom, into halogen atom,m nitro group or thiocyanate group. As the halogenating agent used in this process, chlorine, sulfuryl chloride or N-chloroxuccinimide is preferably used for chlorination; bromine, sulfuryl bromide or N-bromosuccinimide for bromination; and iodine or iodine monochloride for iodination. As the solvent, acetic acid or halogenated hydrocarbons such as dichloromethane and carbon tetrachloride are preferably used. Reaction temperature is in the range from 0° C. to the reflux temperature of the reaction mixture, preferably 20° C. to the reflux temperature.

As the nitrating agent, nitric acid or a mixture of nitric acid and sulfuric acid is preferably used. As the solvent, it is preferred to use halogenated hydrocarbons such as dichloromethane and 1,2-dichloroethane or acetic acid. Solvent may not necessarily be used. Reaction temperature is in the range from 0° C. to the reflux temperature of the reaction mixture, preferably 0° to 50° C.

The thiocyanating agent used in the above process is preferably the one which is capable of generating thiocyanogen by using ammonium thiocyanate and bromine. As the solvent, halogenated hydrocarbons such as dichloromethane and carbon tetrachloride, ethers such as 1,2-dimethoxyethane and tetrahydrofuran, and acetic acid may be used. Reaction temperature is in the range from 0° C. to 50° C., preferably 0° to 30° C.

Process J is a method for synthesizing a compound of the formula (XXX) of the present invention by converting methyl group in an uracil derivative of the formula (XXIX) wherein $R^2$ is methyl group, into halomethyl group, and further synthesizing a compound of the formula (XXXII) or a compound of the formula (XXXIII) of the present invention by converting halomethyl group in the compound of the formula (XXX) into alkoxymethyl group, alkylthiomethyl group or hydroxymethyl group.

In Step 1, a compound of the formula (XXIX) is reacted with N-chlorosuccinimide or N-bromosuccinimide to obtain a 5-chloromethyl or 5-bromomethyl compound of the formula (XXX). As the solvent, halogenated hydrocarbons such as carbon tetrachloride are preferably used. Reaction temperature is in the range from 50° C. to the reflux temperature of the reaction mixture, and the reflux temperature of the reaction mixture is preferred. This reaction is accelerated by adding a radical initiator such as benzoyl peroxide or azobisisobutyronitrile, or by UV irradiation.

In Step 2, 5-halomethyl compound of the formula (XXX) is reacted with an alkali metal alkoxide or thioalkoxide of the formula (XXXI) to form a 5-alkoxymethyl or 5-alkylthiomethyl compound of the formula (XXXII). The alkali metal alkoxide or thioalkoxide of the formula (XXXI) used in the above reaction can be easily synthesized by reacting an alcohol or mercaptan with an alkali metal. Ethers such as 1,2-dimethoxyethane and tetrahydrofuran can be preferably used as solvent in the above reaction. Also, excess alcohol or mercaptan can be used as solvent. Reaction temperature is in the range from 0° C. to the reflux temperature of the reaction mixture, preferably 20° to 70° C.

In Step 3, 5-halomethyl compound of the formula (XXX) is hydrolyzed in the presence of a base to obtain a 5-hydroxymethyl compound of the formula (XXXIII). As the base used in the hydrolysis, alkali metal carbonates such as sodium carbonate or alkali metal hydrogencarbonates such as sodium hydrogencarbonate may be used. Reaction temperature is in the range from 0° C. to the reflux temperature of the reaction mixture, preferably 0° to 30° C.

Process K is a method of reacting an uracil compound of the formula (XXXIV) having hydrogen atom at the 3-position and a compound of the formula (XXXV) in an inert solvent in the presence of a base to obtain a compound of the formula (I). The halogenated aromatic compounds having electron withdrawing groups can be used as the compound of the formula (XXXV). The halogen may be fluorine, chlorine, bromine or iodine atom. As the base used in the above reaction alkali metal alkoxides such as sodium ethoxide, alkali metal hydroxides such as sodium hydroxide and potassium hydroxide, alkali metal carbonates such as sodium carbonate and potassium carbonate, and sodium hydride may be used. As the solvent, there can be used lower alcohols such as methanol and ethanol, aromatic hydrocarbons such as benzene and toluene, ethers such as diethyl ether, tetrahydrofuran, 1,4-dioxane and 1,2-dimethoxyethane, halogenated hydrocarbons such as dichloromethane and 1,2-dichloroethane, amides such as dimethylformamide and dimethylacetamide, acetonitrile, dimethyl sulfoxide and mixtures thereof. Generally, it is preferred to use sodium hydride as base and tetrahydrofuran, dimethylformamide or dimethyl sulfoxide as solvent. Reaction temperature is in the range from −30° C. to the reflux temperature of the reaction mixture.

In the above-described processes (Process A-Process K), no specific definition is given to molar ratio of the reactants, but usually it is advantageous to carry out the reactions by using the reactants at equimolar ratio or about equimolar ratio.

When it is necessary to purify the compounds of the present invention, such can be carried out by the suitable separating and purifying methods such as recrystallization and column chromatography.

Among the compounds of the present invention, those having asymmetric carbon atoms include the optically active compounds of both (+) and (−) forms.

Further, in case there exist the isomers of steric configuration in the compounds of the present invention, they include both cis and trans isomers.

Examples of the compounds included in the scope of the present invention are shown in Tables 1 to 5. It is to be understood that the compounds shown in these tables are illustrative ones and don't define the compounds provided by the present invention.

In Tables 1 to 5, Q1 to Q61 denote the groups represented by the following formulae:

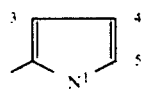 Q 1

 Q 2

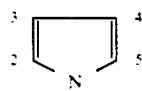 Q 3

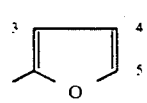 Q 4

 Q 5

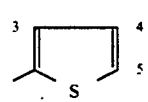 Q 6

 Q 7

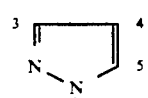 Q 8

-continued

 Q 9

 Q 10

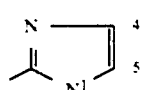 Q 11

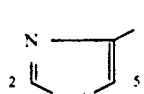 Q 12

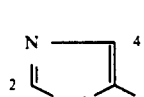 Q 13

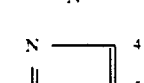 Q 14

 Q 15

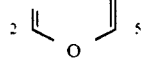 Q 16

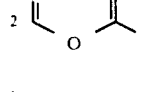 Q 17

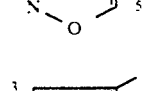 Q 18

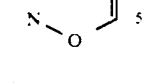 Q 19

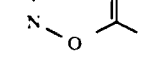 Q 20

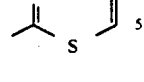 Q 21

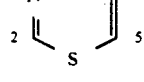 Q 22

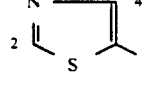 Q 23

-continued
 Q 24
 Q 25
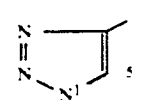 Q 26
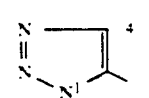 Q 27
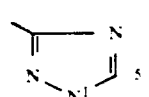 Q 28
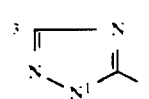 Q 29
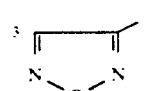 Q 30
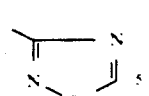 Q 31
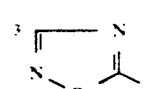 Q 32
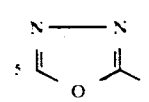 Q 33
 Q 34
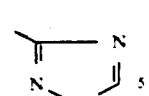 Q 35
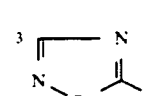 Q 36
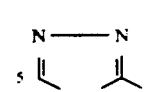 Q 37
 Q 38
-continued
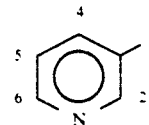 Q 39
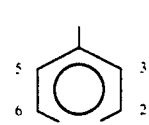 Q 40
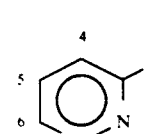 Q 41
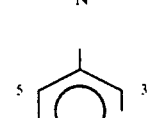 Q 42
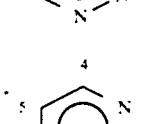 Q 43
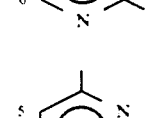 Q 44
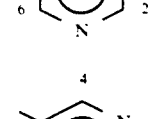 Q 45
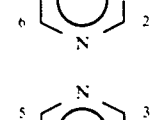 Q 46
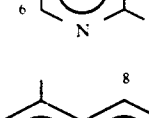 Q 47
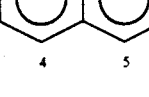 Q 48
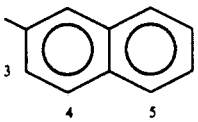 Q 49
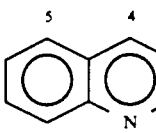

-continued

Q 50 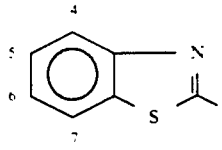

Q 51 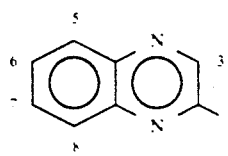

Q 52 

Q 53 

Q 54 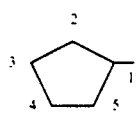

Q 55 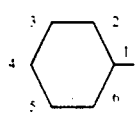

Q 56 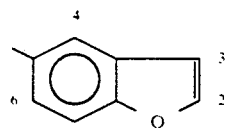

Q 57 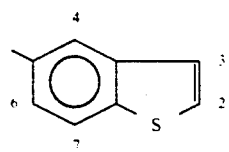

Q 58 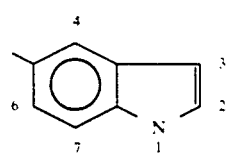

Q 59 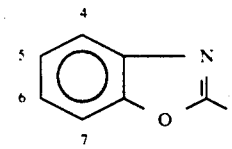

Q 60 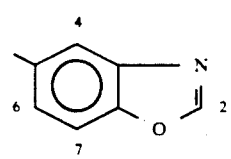

Q 61 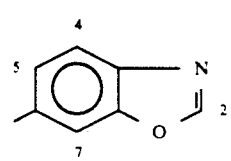

In use of the compounds of the present invention as an active ingredient of pesticides, they may be mixed with a suitable carrier or diluent selected from either solid carriers such as clay, talc, bentonite and diatomaceous earth or liquid carriers including water, alcohols such as methanol and ethanol, aromatic hydrocarbons such as benzene, toluene and xylene, chlorinated hydrocarbons, ethers, ketones, esters such as ethyl acetate, and acid amides such as dimethylformamide. Also, if necessary, they may be further added with a suitable adjuvant or adjuvants such as emulsifier, dispersant, suspension agent, penetrating agent, spreader, stabilizer, etc., and can be offered to practical use in various forms of formulation such as emulsifiable concentrate, oil solution, wettable powder, dust, granules, flowable, etc.

Also, the compounds of the present invention may be mixed with other herbicides, insecticides, fungicides, plant-growth regulating agent, synergists, etc., during formulation and application thereof, as occasion demands.

The dosage (drug-concentration) of the compounds of the present invention varies depending on the place of application, time (seasons) of application, method of application, diseases or insect pests to be applied, crops to be treated and other factors, but generally it is appropriate to apply the compound at a rate of about $0.005 \sim 50$ kg/ha calculated as the amount of active ingredient.

In the pesticides of the present invention, an amount of the active ingredient is 0.01 to 70 wt %. Concretely, the formulations and kinds of preparations thereof are set forth below.

|  | Active ingredient (wt %) | Carrier (wt %) | Surfactant (wt %) | Other components (adjuvants) (wt %) |
|---|---|---|---|---|
| Emulsifiable concentrates | 1 ~ 25 | 52 ~ 95 | 3 ~ 20 | 0 ~ 20 |
| Oil solutions | 1 ~ 30 | 57 ~ 99 | | |
| Flowables | 1 ~ 70 | 10 ~ 90 | 1 ~ 20 | 0 ~ 10 |
| Wettable powders | 1 ~ 70 | 15 ~ 93 | 3 ~ 10 | 0 ~ 5 |
| Dusts | 0.01 ~ 30 | 67 ~ 99.5 | | 0 ~ 3 |
| Granules | 0.01 ~ 30 | 67 ~ 99.5 | | 0.8 |

In application, emulsifiable concentrates, oil solutions, flowables and wettable powder are diluted with a predetermined amount of water and applied. Dusts and granules are directly applied without being diluted with water.

Each component of the above formulations is exemplified as follows.

Emulsifiable concentrates

Active ingredient: a compound of the present invention.

Carrier: xylene, dimethylformamide, methylnaphthalene, cyclohexanone, dichlorobenzene or isophorone.

Surfactant: Sorpol 2680, Sorpol 3005X or Sorpol 3353

Other components: piperonyl butoxide and/or benzotriazole.

Oil solutions

Active ingredient: a compound of the present invention.

Carrier: xylene, methylcellosolve or kerosense.

Flowables

Active ingredient: a compound of the present invention.

Carrier: water.

Surfactant: Lunox 1000OC, Sorpol 3353, Soprophor FL, Nippol, Agrisol S-710 or sodium ligninesulfonate.

Other components: Xanthan gum, formalin, ethylene glyxol and/or propylene glycol.

Wettable powders

Active ingredient: a compound of the present invention.

Carrier: calcium carbonate, kaolinite, Zeeklike D, Zeeklite PFP, diamtomaceous earth or talc.

Surfactant: Sorpol 5039, Lunox 1000C, calcium ligninesulfonate, sodium dodecylbenzenesulfonate, Sorpol 5050, Sorpol 005D or Sorpol 5029-0.

Other components: Carplex #80.

Dusts

Active ingredient: a compound of the present invention.

Carrier: calcium carbonate, kaolinite, Zeeklite D or talc.

Other components: diisopropyl phosphate and/or Carplex #80.

Granules (1)

Active ingredient: a compound of the present invention.

Carrier: calcium carbonate, kaolinite, bentonite or talc.

Other components: calcium ligninesulfonate and/or polyvinyl alcohol.

Granules (2)

Active ingredinent: a compound of the present invention.

Carrier: wheat flour, wheat bran, corn grits or Zeeklite D.

Other components: paraffin and/or soybean oil.

The compounds of the present invention are effective, with very low drug-concentration, on various kinds of insect pests; e.g., agricultural insect pests such as green rice leaf hopper (*Nephotettix cincticeps*), brown rice planthopper (*Nilaparvata lugens*), green peach aphid (*Myzus persicae*), twenty eight-spotted lady beetle (*Henosepilachna vigintioctopunctata*), diamondback moth (*Plutella xylostella*), common cutworm (*Spodoptera litura*) and; Tetranychidae such two-spotted spider mite (*Tetranychus urticae*), citrus red mite (*Panonychus citri*) and Kanzawa spider mite (*Tetranychus kanzawai*); sanitary insect pests such as house mosquito (*Culex pipiens palens*), housefly (*Musca domestics*), ant (*Formicidae*) and lice (*Anoplura*); stored product insect pests such as maize weevil (*Sitophilus oryzae*), red flour beetle (*Tribolium castaneum*) and almond moth (*Cadra cautella*); house insect pests such as termites; and verterinary insect pests such as acarids, fleas and lice.

In other words the compounds of the present invention can effectively control and prevent Dictyoptera, Isoptera, Hemiptera, Lepidoptera, Coleoptera, Hymenoptera, Diptera, ticks, acari and lice.

Further, some of the compounds of the present invention have a high herbicidal activity against various weeds, for example, those posing serious problems on farming, such as *Abutilon avicennae*, *Xanthium strumarium*, *Amaranthus retroflexus*, *Echinochloa*, *Digitaria adscendes*, *Setaria viridis*, *Sorghum bicolor*, etc. at a notably low drug-concentration and they cause no harm to the important crops such as rice, corn, wheat, soybean, cotton, beet, etc.

EXAMPLES

In the following, the processes for synthesizing the compounds of the present invention will be illustrated by the examples concretely. It is to be understood, however, that these examples are merely intended to be illustrative and not to be construed as limiting the scope of the invention.

SYNTHESIS EXAMPLE 1

3-(2-fluoro-4-chlorophenyl)-6-(2-fluorophenyl)-2,4(1H,3H)-pyrimidinedione (compound No. 1.3 of the present invention)

52.5 g of ethyl(2-fluorobenzoyl) acetate and 96.3 g of ammonium acetate were added to 250 ml of ethanol, followed by dropwise addition of 75.0 g of acetic acid to the solution with stirring at 10° C. The resulting solution was heated to room temperature and then stirred under reflux for 4 hours. After the reaction was completed, the solvent was distilled away under reduced pressure and the residue was dissolved in diethyl ether. This ether solution was washed with dilute hydrochloric acid, water and a saturated sodium chloride aqueous solution and then dried over anhydrous sodium sulfate. The solvent was distilled away to obtain 50.5 g of ethyl 3-amino-3-(2-fluorophenyl)-2-propenoate.

2.1 g of this ethyl 3-amino-3-(2-fluorophenyl)-2-propenoate was added dropwise to a solution of 0.5 g of sodium hydride (purity: 55%) in 20 ml of dimethylformamide with stirring at 0° C. The resulting solution was further stirred at room temperature for 15 minutes and then cooled to −30° C. and added dropwise with 20 ml of a toluene solution of 1.7 g of 2-fluoro-4-chlorophenyl isocyanate. The resultant solution was heated to room temperature and stirred at 80° C. for 30 minutes. Then the solvent was distilled away under reduced pressure and 100 ml of water was added to the residue to dissolve it. This aqueous solution was washed twice with diethyl ether and added to a mixed solution of 50 g of ice and 20 ml of concentrated hydrochloric acid. The precipitated crystals were filtered out and dried under the reduced pressure to obtain 3.0 g of a crude product. This crude product was washed with heated diisopropyl ether and then dried to obtain 2.4 g of the objective compound.

M.p. 186.0°~90.0° C.

$^1$H-NMR (DMSO d-6, TMS, δ ppm): 6.05 (1H,s), 7.10~8.05 (7H,m), 11.77 (1H,bs).

SYNTHESIS EXAMPLE 2

3-(4-trifluoromethoxyphenyl)-6-(2-chlorophenyl)-2,4-(1H,3H)-pyrimidinedione (compound No. 1.14 of the present invention)

2.0 g of sodium hydride (purity: 55%) was added to 100 ml of dimethylformamide, followed by dropwise addition of 7.9 g of ethyl 3-amino-3-(2-chlorophenyl)-2-propenoate to the solution with stirring at 0° C. The resulting solution was stirred at room temperature for 15 minutes and added with 8.7 g of ethyl 4-trifluoromethoxyphenylcarbamate. The solution was further stirred at 100° C. for 4 hours. Then the solvent was distilled away under reduced pressure and the residue was dissolved in 200 ml of water and washed twice with diethyl ether. This aqueous solution was added to a mixed solution of 100 g of ice and 50 ml of concentrated hydrochloric acid. The precipitated crystals were filtered out and dried under reduced pressure to obtain 10.7 g of a crude product. This crude product was washed with heated diisopropyl ether and dried to obtain 9.7 g of the objective compound.

M.p.: 254.0°~256.0° C.

$^1$H-NMR (CDCl$_3$+DMSO d-6, TMS, δ ppm): 5.67 (1H,s), 7.20~7.35 (8H,m), 11.60 (1H,bs).

SYNTHESIS EXAMPLE 3

1-ethoxymethyl-3-(4-trifluoromethoxyphenyl)-6-(2-chlorophenyl)-2,4(1H,3H)-pyrimidinedione (compound No. 1.41 of the present invention)

0.5 g of sodium hydride (purity: 55%) was added to 50 ml of dimethylformamide, and then 3.8 g of 3-(4-trifluoromethoxyphenyl)-6-(2-chlorophenyl)-2,4(1H,3H)-pyrimidinedione was added to the solution with stirring at 0° C. The resulting solution was stirred at room temperature for 15 minutes, then added dropwise with 1.3 g of chloromethylethyl ether and further stirred at room temperature for 3 hours. The reaction mixture was added into 200 ml of ice water and extracted with 200 ml of ethyl acetate. The organic layer was washed with water and dried, and then the solvent was distilled away under reduced pressure to obtain 3.8 g of a crude product. This crude product was recrystallized from diisopropyl ether to obtain 3.2 g of the objective compound.

M.p.: 168.5°~172.0° C.

$^1$H-NMR (CDCl$_3$, TMS, δ ppm): 1.07 (3H,t,J=6.0 Hz), 3.38 (2H,q,J=6.0 Hz), 4.59 (1H,d,J=10.0 Hz), 5.26 (1H,d,J=10.0 Hz), 5.70 (1H,s), 7.20~7.45 (8H,m).

SYNTHESIS EXAMPLE 4

3-(4-trifluoromethoxyphenyl)-5-bromo-6-(2-chlorophenyl)-2,4(1H,3H)-pyrimidinedione (compound No. 1.33 of the present invention)

3.8 g of 3-(4-trifluoromethoxyphenyl)-6-(2-chlorophenyl)-2,4(1H,3H)-pyrimidinedione was added to 75 ml of acetic acid, followed by dropwise addition of 1.7 g of bromine to the solution with stirring at room temperature. The reaction mixture was further stirred for 2 hours and then the solvent was distilled away under reduced pressure. The residue was dissolved in 200 ml of ethyl acetate, washed with an aqueous solution of sodium hydrogencarbonate and water, and dried over anhydrous sodium sulfate. Then the solvent was distilled away to obtain 4.5 g of a crude product. This crude crystal product was washed with heated diisopropyl ether and dried to obtain 4.1 g of the objective compound.

M.p.: 264.0°~268.5° C.

$^1$H-NMR (CDCl$_3$+DMSO d-6, TMS, δ ppm): 7.35~7.60 (8H,m).

SYNTHESIS EXAMPLE 5

3-(4-chlorophenyl)-6-(2-chlorophenyl)-(1H,3H)-pyrimidine-2-thion-4-one (compound No. 1.43 of the present invention)

2.3 g of ethyl 3-amino-3-(2-chlorophenyl)-2-propenoate was added dropwise to a solution of 0.5 g of sodium hydride (purity: 55%) in 20 ml of dimethylformamide with stirring at 0° C. The mixed solution was stirred at room temperature for 15 minutes, then cooled to 0° C. and added with 1.7 g of 4-chlorophenyl isothiocyanate. The resulting solution was heated to room temperature and further stirred at 100° C. for one hour. Then the solvent was distilled away under reduced pressure and the residue was dissolved by adding 100 ml of water. This aqueous solution was washed twice with diethyl ether and added to a mixed solution of 50 g of ice and 20 ml of concentrated hydrochloric acid. The aqueous mixture was extracted with 100 ml of ethyl acetate, washed with water and a saturated sodium chloride aqueous solution and dried over anhydrous sodium sulfate. Then the solvent was distilled away to obtain 2.1 g of a crude product. This crude product was washed with heated diisopropyl ether and dried to obtain 1.0 g of the objective compound.

M.p.: 245.0°~250.5° C.

$^1$H-NMR (CDCl$_3$+DMSO d-6, TMS, δ ppm): 5.94 (1H,s), 7.20~7.55 (8H,m).

SYNTHESIS EXAMPLE 6

3-(3,4-dichlorophenyl)-6-(2,6-difluorophenyl)-2,4(1H,3H)-pyrimidinedione (compound No. 1.166 of the present invention)

3.0 g of ethyl α-bromoacetate and a trace amount of iodine were added to a solution of 18.3 g of zinc in 250 ml of tetrahydrofuran under reflux and vigorously stirred to start the reaction. The reaction solution was cooled to room temperature and added with a 30 ml tetrahydrofuran solution of 13.9 g of 2,6-difluorobenzonitrile at one time. Then 17.8 g of ethyl α-bromoacetate was added dropwise at such a rate that slow refluxing would continue. The reaction solution was further refluxed for one hour, cooled, added into 350 ml of an aqueous solution of 50.0 g of ammonium chloride and extracted with 300 ml of diethyl ether. The obtained organic layer was washed with a sodium chloride aqueous solution and dried over anhydrous sodium sulfate. Then the solvent was distilled away under reduced pressure to obtain 16.5 g of ethyl 3-amino-3-(2,6-difluorophenyl)-2-propenoate.

1.12 g of the thus obtained substance was added dropwise to a solution of 0.24 g of sodium hydride (purity: 55%) in 20 ml of 1,4-dioxane with stirring at 0° C. The resulting solution was stirred at room temperature for one hour, cooled to 0° C. and added with 0.95 g of 3,4-dichlorophenyl isocyanate. After stirring at room temperature for 8 hours, the reaction solution was concentrated under reduced pressure and dissolved with 100 ml of water. After washing the solution with diethyl ether, an aqueous layer was added into a mixed solution of 20 ml of concentrated hydrochloric acid and 50 g of ice. The aqueous mixture was extracted with 100 ml of ethyl acetate, and the organic layer was washed with a sodium chloride aqueous solution and dried over anhydrous sodium sulfate. Then the solvent was distilled away under reduced pressure to obtain a crude product. This crude product was recrystallized from a mixed solvent of diisopropyl ether and isopropyl alcohol to obtain 0.20 g of the objective compound.

M.p.: 255.5°~256.5° C.

$^1$H-NMR (CDCl$_3$+DMSO d-6, TMS, δ ppm): 5.78 (1H,s), 6.90~7.75 (6H,m), 8.55 (1H,bs).

SYNTHESIS EXAMPLE 7

3-4-(3-chloro-5-trifluoromethyl-2-pyridyloxy)phenyl]-6-(2-chlorophenyl)-2,4(1H,3H)-pyrimidinedione (compound No. 1.66 of the present invention)

8.7 g of ethyl 3-amino-3-(2-chlorophenyl)-2-propenoate was added dropwise to a 40 ml dimethylformamide of 1.8 g of sodium hydride (purity: 55%) with stirring at 0° C. The solution was stirred at room temperature for 15 minutes, cooled to 0° C. and added dropwise with a 20 ml dimethylformamide solution of 7.2 g of ethyl 4-methoxymethoxyphenylcarbamate. After stirring the solution at 120° C. for 2 hours, the solvent was distilled away under reduced pressure. The residue was dissolved with 200 ml of water and washed with diethyl ether. The obtained aqueous layer was added into a mixed solution of 50 ml of concentrated hydrochloric acid and 150 g of ice. The precipitated crystals were filtered out and dried under reduced pressure to obtain 10.0 g of 3-(4-methoxymethoxyphenyl)-6-(2-chlorophenyl)-2,4(1H,3H)-pyrimidinedione.

7.0 g of the obtained 3-(4-methoxymethoxyphenyl)-6-(2-chlorophenyl)-2,4(1H,3H)-pyrimidinedione was dissolved in 100 ml of tetrahydrofuran and then added dropwise with 10 ml of concentrated hydrochloric acid with stirring at room temperature. The mixed solution was further stirred at room temperature for 12 hours and extracted with 200 ml of ethyl acetate. The organic layer was washed with a sodium chloride aqueous solution and dried over anhydrous sodium sulfate. Then the solvent was distilled away under reduced pressure to obtain 4.5 g of 3-(4-hydroxyphenyl)-6-(2-chlorophenyl)-2,4(1H,3H)-pyrimidinedione.

1.1 g of the obtained 3-(4-hydroxyphenyl)-6-(2-chlorophenyl)-2,4(1H,3H)-pyrimidinedione was added to a 10 ml dimethylformamide solution of 0.10 g of sodium hydride (purity: 55%) with stirring at room temperature. The mixed solution was stirred at room temperature for 15 minutes, added with 0.7 g of 2,3-dichloro-5-trifluoromethylpyridine, further stirred t 100° C. for 2 hours. The reaction mixture was added to 100 ml of water and extracted with 100 ml of ethyl acetate. The organic layer was washed with a sodium chloride aqueous solution and dried over anhydrous sodium sulfate. Then the solvent was distilled away under reduced pressure to obtain 0.8 g of the objective compound.

M.p.: 175.0° ~ 176.0° C.

$^1$H-NMR (DMSO d-6, TMS, δ ppm): 5.70 (1H,s), 7.32 (4H,s), 7.49 (4H,s), 7.49 (4H,s), 8.20 ~ 8.60 (3H,m).

SYNTHESIS EXAMPLE 8

3-(4-trifluoromethoxyphenyl)-5-fluoro-6-phenyl-2,4(1H,3H)-pyrimidinedione (compound No. 2.56 of the present invention)

6.0 g of ethyl a-fluorobenzoylacetate and 7.0 g of ammonium acetate were added to 50 ml of ethanol, followed by dropwise addition of 6.0 g of acetic acid to this solution with stirring at room temperature. The mixed solution was further stirred under reflux for 4 hours and added to a cooled aqueous solution of sodium hydrogencarbonte. This aqueous mixture was extracted with 200 ml of diethyl ether, and the organic layer was washed with a sodium chloride aqueous solution and dried over anhydrous sodium sulfate. Then the solvent was distilled away under reduced pressure to obtain 5.5 g of ethyl 2-fluoro-3-amino-3-phenyl-2-propenoate.

1.00 g of the thus obtained substance was added dropwise to a solution of 0.24 g of sodium hydride (purity: 55%) in 20 ml of dimethylformamide with stirring at 0° C. After stirring at room temperature for 15 minutes, the solution was cooled to 0° C. and added dropwise with 1.02 g of 4-trifluoromethoxyphenyl isocyanate. The mixed solution was heated to room temperature and further stirred at 80° C. for 2 hours. Then the reaction solution was concentrated under reduced pressure and dissolved in 100 ml of water. The resulting aqueous mixture was washed with diethyl ether and the obtained aqueous layer was added into a mixed solution of 20 ml of concentrated hydrochloric acid and 50 g of ice. The precipitated crystals were filtered out and dried under reduced pressure to obtain a crude product. The obtained product was washed with heated diisopropyl ether and dried to obtain 0.57 g of the objective compound.

M.p.: 295.0° ~ 303.0° C.

$^1$H-NMR (CDCl$_3$+DMSO d-6, TMS, δ ppm): 7.32 (4H,s), 7.45 ~ 7.85 (5H,m).

SYNTHESIS EXAMPLE 9

3-(4-trifluoromethoxyphenyl)-5-iodo-6-phenyl-2,4(1H,3H)-pyrimidinedione (compound No. 2.7 of the present invention)

0.45 g of 3-(4-trifluromethoxyphenyl-6-phenyl-2,4(1H,3H)-pyrimidinedione was added to 20 ml of chloroform, and to this solution was added dropwise 0.5 ml of iodine monochloride with stirring at room temperature. The mixed solution was further stirred at room temperature for one hour and then poured into ice water. This aqueous mixture was extracted with 50 ml of chloroform and the obtained organic layer was washed with a sodium thiosulfate aqueous solution and a sodium chloride aqueous solution and dried over anhydrous sodium sulfate. Then the solvent was distilled away under reduced pressure to obtain 0.53 g of a crude product (crystals). These crystals were washed with heated diisopropyl ether and dried to obtain 0.40 g of the objective compound.

M.p.: 294.0° ~ 298.0° C.

$^1$H-NMR (CDCl$_3$, TMS, δ ppm): 7.30 (5H,s), 7.50 (4H,s), 9.65 (1H,bs).

SYNTHESIS EXAMPLE 10

1-methyl-3-(2-fluoro-4-chlorophenyl)-6-(3-trifluoromethylphenyl)-2,4(1H,3H)-pyrimidinedione (compound No. 2.57 of the present invention)

1.00 g of 3-(2-fluoro-4-chlorophenyl)-6-(3-trifluoromethylphenyl)-2,4(1H,3H)-pyrimidinedione was dissolved in 10 ml of dimethylformamide, followed by addition of 0.48 g of anhydrous potassium carbonate and 0.48 g of methyl iodide, and stirring of the solution at room temperature for 4 hours. The resulting reaction solution was poured into water and the precipitated crystals were filtered out and dried to obtain 0.90 g of the objective compound.

M.p.: 139.0° ~ 142.0° C.

$^1$H-NMR (DMSO d-6, TMS, δ ppm): 3.20 (3H,s), 5.85 (1H,s), 7.12 ~ 7.40 (3H,m), 7.49 ~ 7.86 (4H,m).

SYNTHESIS EXAMPLE 11

3-(4-trifluoromethoxyphenyl)-5-cyano-6-phenyl-2,4(1H,3H)-pyrimidinedione (compound No. 2.5 of the present invention)

0.7 g of 3-(4-triluoromethoxyphenyl)-5-bromo-6-(2-chlorophenyl)-2,4(1H,3H)-pyrimidinedione and 0.6 g of cuprous cyanide were added to 30 ml of N-methyl-pyrrolidone and stirred at 200° C. for 8 hours. After cooling, the solution was added to 100 ml of water and extracted with 100 ml of ethyl acetate. The obtained organic layer was washed thrice with water and dried over anhydrous sodium sulfate. Then the solvent was distilled away under reduced pressure to obtain 0.62 g of a crude product. This crude product was purified by preparative thin-layer chromatography (developing solvent: a mixed solvent of chloroform and ethyl acetate) to obtain 0.20 g of the objective compound.

M.p.: 278.0°~282.0° C.

$^1$H-NMR (CDCl$_3$+DMSO d-6, TMS, δ ppm): 7.29 (5H,s), 7.40~7.70 (4H,m).

SYNTHESIS EXAMPLE 12

3-(4-trifluoromethoxyphenyl)-5-iodo-6-(2-pyridyl)-2,4(1H,3H)-pyrimidinedione (compound No. 3.4 of the present invention)

1.0 g of ethyl 3-amino-3-(2-pyridyl)-2-propenoate was added dropwise to a 20 ml dimethylformamide solution of 0.26 g of sodium hydride (purity: 55%) under stirring at 0° C. This solution was stirred at room temperature for 15 minutes and then added with 1.3 g of ethyl 4-trifluoromethoxyphenylcarbamate. The mixed solution was stirred at 100° C. for 3 hours and then the solvent was distilled away under reduced pressure. The residue was dissolved by adding 100 ml of water and washed with diethyl ether. The obtained aqueous layer was added into a mixed solution of 20 ml of concentrated hydrochloric acid and 50 g of ice. Then precipitated crystals were filtered out and dried under reduced pressure to obtain 1.0 g of 3-(4-trifluoromethoxyphenyl)-6-(2-pyridyl)-2,4(1H,3H)-pyrimidinedione.

1.0 g of the obtained 3-(4-trifluoromethoxyphenyl)-6-(2-pyridyl)-2,4(1H,3H)-pyrimidinedione was added to 20 ml of dichloromethane, and 0.7 g of iodine monochloride was added thereto with stirring at room temperature. The resulting solution was further stirred at room temperature for 3 hours, then poured into 100 ml of water and extracted with 100 ml of ethyl acetate. The obtained organic layer was washed with a sodium chloride aqueous solution and dried over anhydrous sodium sulfate. Then the solvent was distilled away under reduced pressure to obtain 0.60 g of the objective compound.

M.p.: 215.0°~217.0° C.

$^1$H-NMR (DMSO d-6, TMS, δ ppm): 7.20~7.95 (7H,s), 8.55~8.75 (1H,m).

SYNTHESIS EXAMPLE 13

3-(5-trifluoromethyl-2-pyridyl)-6-(2-chlorophenyl)-2,4(1H,3H)-pyrimidinedione (compound No. 4.4 of the present invention)

1.27 g of ethyl 3-amino-3-(2-chlorophenyl)-2-propenoate was added dropwise to a 20 ml of dimethylformamide solution of 0.26 g of sodium hydride (purity: 55%). The solution was stirred t room temperature for 15 minutes, then cooled to 0° C. and added with 1.24 g of methyl (5-trifluoromethyl-2-pyridyl)carbamate. The resulting solution was further stirred at 120° C. for 5 hours and then the solvent was distilled away under reduced pressure. The residue was dissolved with 100 ml of water and washed with diethyl ether. The obtained aqueous layer was added into a mixed solution of 20 ml of concentrated hydrochloric acid and 50 g of ice, and the precipitated crystals were filtered out and dried to obtain 0.21 g of the objective compound.

M.p.: 281.0°~283.0° C.

$^1$H-NMR (CDCl$_3$+DMSO d-6, TMS, δ ppm): 5.81 (1H,s), 7.40~7.60 (5H,m), 8.00~8.25 (1H,m), 8.75~8.90 (1H,m).

SYNTHESIS EXAMPLE 14

3-(2,6-dichloro-4-trifluoromethylphenyl)-6-trifluoromethyl-2,4(1H,3H)-pyrimidinedione (compound No. 5.8 of the present invention)

A 20 ml dimethylformamide solution of 2.7 g of ethyl 3-amino-4,4,4-trifluorocrotonate was added dropwise to a 20 ml dimethylformamide solution of 0.78 g of sodium hydride (purity: 55%) with stirring at 0° C. After heated to room temperature under stirring for 15 minutes, the mixed solution was cooled to −30° C. and then added dropwise with 20 ml of a dimethylformamide solution of 3.8 g of 2,6-dichloro-4-trifluoromethylphenyl isocyanate. The resulting solution was again heated to room temperature and stirred at 80° C. for 30 minutes. Then the solvent was distilled away under reduced pressure and the residue was dissolved by adding 100 ml of water. This aqueous solution was washed twice with diethyl ether, then added to a mixed solution of 50 g of ice and 20 ml of concentrated hydrochloric acid, and extracted with ethyl acetate. The obtained organic layer was washed with water and dried, and the solvent was distilled away under reduced pressure to obtain 3.75 g of a crude product. This crude product was recrystallized from a mixed solvent of diisopropyl ether and isopropyl alcohol to obtain 1.65 g of the objective compound.

M.p.: 248.0°~250.0° C.

$^1$H-NMR (CDCl$_3$+CD$_3$OD, TMS, δ ppm): 6.19 (1H,s), 7.71 (2H,s).

SYNTHESIS EXAMPLE 15

3-(2,3,4-trifluorophenyl)-6-trifluoromethyl-2,4(1H,3H)-pyrimidinedione (compound No. 5.1 of the present invention)

1.28 g of ethyl 3-amino-4,4,4-trifluorocrotonate was added to a 10 ml dimethylformamide solution of 0.33 g of sodium hydride (purity: 55%) under ice cooling and stirred at room temperature for 15 minutes, followed by addition of 1.31 g of ethyl 2,3,4-trifluorophenylcarbamate and was stirred at 90° C. for 4 hours. Then dimethylformamide was distilled away under reduced pressure and the residue was dissolved in 100 ml of water. This aqueous solution was washed with diethyl ether, then added to a mixed solution of 50 g of ice and 20 ml of concentrated hydrochloric acid and extracted with ethyl acetate. The obtained organic layer was washed with water and dried, and then the solvent was distilled away under reduced pressure to obtain 0.3 g of the objective compound.

M.p.: 137.0°~138.5° C.

$^1$H-NMR (CDCl$_3$+DMSO d-6, TMS, δ ppm): 6.10 (1H,s), 6.80~7.20 (2H,m).

SYNTHESIS EXAMPLE 16

3-(2,4,6-trichlorophenyl)-5-bromo-6-trifluoromethyl-2,4(1H,3H)-pyrimidinedione (compound No. 5.15 of the present invention)

3.6 g of 3-(2,4,6-trichlorophenyl)-6-trifluoromethyl-2,4(1H,3H)-pyrimidinedione and 4.1 g of sodium acetate were added to 30 ml of acetic acid, followed by dropwise addition of 6.4 g of bromine with stirring at room temperature. The resulting solution was stirred at 110° C. for 5 hours and then the solvent was distilled away under reduced pressure. The residue was extracted with 100 ml of ethyl acetate, and the obtained organic layer was washed with water and dried. Then the solvent was distilled away to obtain a crude product. This crude product was washed with isopropyl ether and dried to obtain 1.8 g of the objective compound.

M.p.: 219.0°~222.0° C.

$^1$H-NMR (CDCl$_3$+CD$_3$OD, TMS, δ ppm): 7.38 (2H,s).

SYNTHESIS EXAMPLE 17

1-ethoxymethyl-3-(2,4,6-trichlorophenyl)-6-trifluoromethyl-2,4(1H,3H)-pyrimidinedione (compound No. 5.20 of the present invention)

1.50 g of 3-(2,4,6-trichlorophenyl)-6-trifluoromethyl-2,4(1H,3H)-pyrimidinedione was added to a 10 ml tetrahydrofuran solution of 0.30 g of sodium hydride (purity: 55%) with stirring under ice cooling, and the mixed solution was stirred at room temperature for 15 minutes. Then, after adding 0.70 g of chloromethylethyl ether, the solution was further stirred at room temperature for 3 hours. Then ice was added to the solution to decompose excess sodium hydride. The resulting mixture was extracted with 100 ml of ethyl acetate, and the obtained organic layer was washed thrice with water and dried over magnesium sulfate. Then the solvent was distilled away under reduced pressure to obtain 1.2 g of the objective compound as a viscous oily substance.

$^1$H-NMR (CDCl$_3$, TMS, δ ppm): 1.18 (3H, t,J=6.0 Hz), 3.64 (2H,q,J=60 Hz), 5.38 (2H,s), 6.30 (1H,s), 7.37 (2H,s).

SYNTHESIS EXAMPLE 18

3-(2,4,6-trichlorophenyl)-6-chlorodifluoromethyl-2,4(1H,3H)-pyrimidinedione (compound No. 5.56 of the present invention)

1.0 g of ethyl 3-amino-4-chloro-4,4-difluorocrotonate was added dropwise to a 10 ml dimethylformamide solution of 0.24 g of sodium hydride (purity: 55%) with stirring at 0° C. The solution was stirred at room temperature for 15 minutes, then cooled to 0° C. and added with 0.8 g of 2,4,6-trichlorophenyl isocyanate. The resulting solution was heated to room temperature and further stirred at 100° C. for 2 hours. Then the solvent was distilled away under reduced pressure and the residue was dissolved in 100 ml of water and washed with diethyl ether. The aqueous layer was added into a mixed solution of 20 ml of concentrated hydrochloric acid and 50 g of ice, and the precipitated crystals were filtered out and dried under reduced pressure to obtain a crude product. This crude product was washed with a heated mixed solvent of diisopropyl ether and isopropyl alcohol, and dried to obtain 0.65 g of the objective compound.

M.p.: 268.0°~270.0° C.

$^1$H-NMR (CDCl$_3$+CD$_3$OD, δ ppm): 6.14 (1H,s), 7.48 (1H,s).

SYNTHESIS EXAMPLE 19

3-(2,4,6-trichlorophenyl)-6-trifluoromethyl-(1H,3H)-pyrimidine-2-thion-4-one (compound No. 5.75 of the present invention)

A 5 ml dimethylformamide solution of 3.7 g ethyl 3-amino-4,4,4-trifluorocrotonate was added dropwise to a 30 ml dimethylformamide solution of 1.0 g of sodium hydride (purity: 55%) with stirring at 5° C. The mixed solution was stirred at room temperature for 15 minutes, then cooled to 5° C. and added dropwise with a 10 ml dimethylformamide solution of 5.0 g of 2,4,6-trichlorophenyl isothiocyanate. The resulting solution was heated to room temperature and further stirred at 130° C. for 2 hours. Then the solvent was distilled away under reduced pressure and the residue was dissolved by adding 200 ml of water and washed with diethyl ether. The obtained aqueous layer was added into a mixed solution of 30 ml of concentrated hydrochloric acid and 100 g of ice and extracted with 200 ml of ethyl acetate. The obtained organic layer was washed with a sodium chloride aqueous solution and dried over anhydrous sodium sulfate. Then the solvent was distilled away under reduced pressure to obtain 2.8 g of a crude product. This product was purified by preparative thin-layer chromatography (developing solvent: a mixed solvent of chloroform and ethyl acetate) to obtain 0.43 g of the objective compound.

M.p. 208.0°~214.0° C.

$^1$H-NMR (CDCl$_3$+DMSO d-6, TMS, δ ppm): 6.39 (1H,s), 7.40 (2H,s), 9.60 (1H,bs).

SYNTHESIS EXAMPLE 20

3 (2,4-dinitro-6-trifluoromethylphenyl)-6-trifluoromethyl-2,4(1H,3H)-pyrimidinedione (compound No. 5.65 of this invention)

1.0 g of 6-trifluoromethyl-2,4(1H,3H)-pyrimidinedione was added to 10 ml of dimethylformamide, followed by addition of 0.65 g of sodium hydride (purity: 55%) with stirring at 0° C. The mixed solution was stirred at room temperature for 30 minutes, then cooled to 0° C. and added dropwise with a 5 ml dimethylformamide solution of 1.89 g of 2-chloro-3,5-dinitrobenzotrifluoride. After the solution was further stirred at room temperature for 3 hours, the solvent was distilled away under reduced pressure. After addition of cooled dilute hydrochloric acid thereto, the residue was extracted with 100 ml of ethyl acetate. The obtained organic layer was dried over anhydrous sodium sulfate and then the solvent was distilled away under reduced pressure to form a crude product. This crude product was recrystallized from a mixed solvent of chloroform and petroleum ether to obtain 0.77 g of the objective compound.

M.p.: 219.0°~220.5° C.

$^1$H-NMR (CDCl$_3$+CD$_3$OD, TMS, δ ppm): 6.10 (1H,s), 8.78 (1H,d,J=3.0 Hz), 9.08 (1H,d,J=3.0 Hz).

SYNTHESIS EXAMPLE 21

3-(2,4,6-trichlorophenyl)-6-bromo-2,4(1H,3H)-pyrimidinedione (compound No. 5.81 of the present invention)

1.7 g of malonic acid dichloride was added dropwise to a 50 ml 1,4-dioxane solution of 2.4 g of 2,4,6-trichlorophenylurea with stirring at 0° C. The solution was stirred at room temperature for 3 hours and then the solvent was distilled away under reduced pressure to obtain a crude product. This crude product was purified by silica gel column chromatography (developing solvent: chloroform) to obtain 2.35 g of 3-(2,4,6-trichlorophenyl)-6-hydroxy-2,4(1H,3H)-pyrimidinedione.

10 ml of phosphorus tribromide was added dropwise to 0.60 g of pyridine with stirring at 0° C. and, after stirring this solution at 0° C. for 15 minutes, 1.6 g of the obtained 3-(2,4,6-trichlorophenyl)-6-hydroxy-2,4(1H,3H)-pyrimidinedione was added thereto. The mixed solution was stirred at 80° C. for 3 hours, then added into ice water and extracted with 100 ml of ethyl acetate. The obtained organic layer was dried over anhydrous sodium sulfate and then the solvent was distilled away under reduced pressure to form a crude product. This crude product was recrystallized from a mixed solvent of hexane and isopropyl ether to obtain 0.62 g of the objective compound.

M.p.: 187.0° ~ 190.0° C.

$^1$H-NMR (CDCl$_3$+CD$_3$OD, TMS, δ ppm): 6.10 (1H,s), 7.45 (2H,s).

SYNTHESIS EXAMPLE 22

3-(2,6-dichloro-4-trifluoromethylphenyl)-6-methylthio-2,4(1H,3H)-pyrimidinedione (compound No. 5.87 of the present invention)

0.81 g of 3-(2,6-dichloro-4-trifluoromethylphenyl)-6-bromo 2,4(1H,3H)-pyrimidinedione was added to 5 ml of dimethylformamide, followed by addition of 0.35 g of sodium methyl mercaptide with stirring at room temperature. The solution was stirred at 80° C. for 2 hours, then cooled to room temperature, added to cooled dilute hydrochloric acid and extracted with 100 ml of ethyl acetate. The obtained organic layer was washed with dilute hydrochloric acid and water and dried over anhydrous sodium sulfate, and then the solvent was distilled away under reduced pressure to form a crude product. This crude product was recrystallized from a mixed solvent of hexane and isopropyl ether to obtain 0.33 g of the objective compound.

M.p.: 219.0° ~ 222.0° C.

$^1$H-NMR (CDCl$_3$, TMS, δ ppm): 2.48 (3H,s), 5.68 (1H,s), 7.76 (2H,s), 9.70 (1H,bs).

The properties of the compounds produced according to the above Synthesis Examples are shown in Table 6 ~ 10. (The representations given in these tables correspond to those in Tables 1 ~ 5).

The compound Nos. in Tables 6 ~ 10 will be referred to in the descriptions of Formulation Examples and Test Examples set forth below.

TABLE 1

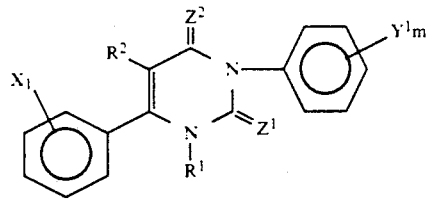

| R$^1$ | R$^2$ | X$_1$ | Y$^1_m$ | Z$^1$ | Z$^2$ |
|---|---|---|---|---|---|
| H | H | 2-F | 2-F | O | O |
| H | H | 2-F | 3-F | O | O |
| H | H | 2-F | 4-F | O | O |
| H | H | 2-F | 2-Cl | O | O |
| H | H | 2-F | 3-Cl | O | O |
| H | H | 2-F | 4-Cl | O | O |
| H | H | 2-F | 4-Br | O | O |
| H | H | 2-F | 4-I | O | O |
| H | H | 2-F | 4-CH$_3$ | O | O |
| H | H | 2-F | 4-CH(CH$_3$)$_2$ | O | O |
| H | H | 2-F | 4-CH$_2$CH$_2$CH$_2$CH$_3$ | O | O |
| H | H | 2-F | 4-C(CH$_3$)$_3$ | O | O |
| H | H | 2-F | 4-CH$_2$CH=CH$_2$ | O | O |
| H | H | 2-F | 4-CH$_2$CH=CHCH$_3$ | O | O |
| H | H | 2-F | 4-C≡CH | O | O |
| H | H | 2-F | 4-CH$_2$C≡CH | O | O |
| H | H | 2-F | 4-Q51 | O | O |
| H | H | 2-F | 4-Q52 | O | O |
| H | H | 2-F | 4-Q53 | O | O |
| H | H | 2-F | 4-Q54 | O | O |
| H | H | 2-F | 4-CHF$_2$ | O | O |
| H | H | 2-F | 4-CH$_2$Br | O | O |
| H | H | 2-F | 4-CH$_2$Cl | O | O |
| H | H | 2-F | 2-CF$_3$ | O | O |
| H | H | 2-F | 3-CF$_3$ | O | O |
| H | H | 2-F | 4-CF$_3$ | O | O |
| H | H | 2-F | 4-CH$_2$CH=CHCl | O | O |
| H | H | 2-F | 4-CH=C(Cl)CF$_3$ | O | O |
| H | H | 2-F | 4-CH$_2$C≡CBr | O | O |
| H | H | 2-F | 4-(Q54-1-Cl) | O | O |
| H | H | 2-F | 4-CH$_2$CN | O | O |
| H | H | 2-F | 4-CH$_2$CH(CH$_3$)CN | O | O |
| H | H | 2-F | 4-CH$_2$OH | O | O |
| H | H | 2-F | 4-CH$_2$CO$_2$H | O | O |

TABLE 1-continued

| | | | | | |
|---|---|---|---|---|---|
| H | H | 2-F | 4-OCH$_3$ | O | O |
| H | H | 2-F | 4-OCH$_2$CH$_3$ | O | O |
| H | H | 2-F | 4-OCH(CH$_3$)$_2$ | O | O |
| H | H | 2-F | 4-OC(CH$_3$)$_3$ | O | O |
| H | H | 2-F | 4-OCH$_2$CH=CH$_2$ | O | O |
| H | H | 2-F | 4-OCH$_2$C≡CH | O | O |
| H | H | 2-F | 4-O(Q53) | O | O |
| H | H | 2-F | 4-O(Q54) | O | O |
| H | H | 2-F | 4-O(Q54-2-CH(CH$_3$)$_2$-5-CH$_3$) | O | O |
| H | H | 2-F | 4-OCHF$_2$ | O | O |
| H | H | 2-F | 4-OCF$_2$Br | O | O |
| H | H | 2-F | 2-OCF$_3$ | O | O |
| H | H | 2-F | 3-OCF$_3$ | O | O |
| H | H | 2-F | 4-OCF$_3$ | O | O |
| H | H | 2-F | 4-OCH$_2$CF$_3$ | O | O |
| H | H | 2-F | 4-OCF$_2$CHF$_2$ | O | O |
| H | H | 2-F | 4-OCF$_2$CHCl$_2$ | O | O |
| H | H | 2-F | 4-OCF$_2$CHFCl | O | O |
| H | H | 2-F | 4-OCF$_2$CHFBr | O | O |
| H | H | 2-F | 4-OCF$_2$CF$_2$CF$_3$ | O | O |
| H | H | 2-F | 4-OCH$_2$CH=CHCl | O | O |
| H | H | 2-F | 4-OCH$_2$C≡CBr | O | O |
| H | H | 2-F | 4-O(Q51-2,2-Cl$_2$) | O | O |
| H | H | 2-F | 4-OCH$_2$(Q51-2,2-Cl$_2$) | O | O |
| H | H | 2-F | 4-SCH$_3$ | O | O |
| H | H | 2-F | 4-SCH$_2$CH=CH$_2$ | O | O |
| H | H | 2-F | 4-SCH$_2$C≡CH | O | O |
| H | H | 2-F | 4-S(Q54) | O | O |
| H | H | 2-F | 4-SCHF$_2$ | O | O |
| H | H | 2-F | 4-SCF$_3$ | O | O |
| H | H | 2-F | 4-SCF$_2$Cl | O | O |
| H | H | 2-F | 4-SOCH$_3$ | O | O |
| H | H | 2-F | 4-SOCH$_2$CH=CH$_2$ | O | O |
| H | H | 2-F | 4-SOCH$_2$C≡CH | O | O |
| H | H | 2-F | 4-SO(Q54) | O | O |
| H | H | 2-F | 4-SOCF$_3$ | O | O |
| H | H | 2-F | 4-SO$_2$CH$_3$ | O | O |
| H | H | 2-F | 4-SO$_2$CH$_2$CH=CH$_2$ | O | O |
| H | H | 2-F | 4-SO$_2$CH$_2$C≡CH | O | O |
| H | H | 2-F | 4-SO$_2$(Q54) | O | O |
| H | H | 2-F | 4-SO$_2$CF$_3$ | O | O |
| H | H | 2-F | 4-SO$_2$CF$_2$CHFCl | O | O |
| H | H | 2-F | 4-CH$_2$OCH$_3$ | O | O |
| H | H | 2-F | 4-OCH$_2$CH$_2$OCH$_3$ | O | O |
| H | H | 2-F | 4-CH$_2$OCH$_2$CF$_3$ | O | O |
| H | H | 2-F | 4-OCF$_2$CHFOCF$_3$ | O | O |
| H | H | 2-F | 4-CH$_2$SCH$_3$ | O | O |
| H | H | 2-F | 4-OCH$_2$CH$_2$SCH$_3$ | O | O |
| H | H | 2-F | 4-CH$_2$CO$_2$CH$_3$ | O | O |
| H | H | 2-F | 4-CH$_2$CO$_2$CH$_2$CF$_3$ | O | O |
| H | H | 2-F | 4-CH$_2$COCH$_3$ | O | O |
| H | H | 2-F | 4-OCO$_2$CH$_3$ | O | O |
| H | H | 2-F | 4-OCOCH$_3$ | O | O |
| H | H | 2-F | 4-COCH$_3$ | O | O |
| H | H | 2-F | 4-COCH$_2$CH=CH$_2$ | O | O |
| H | H | 2-F | 4-COCH$_2$C≡CH | O | O |
| H | H | 2-F | 4-CO(Q53) | O | O |
| H | H | 2-F | 4-COCF$_3$ | O | O |
| H | H | 2-F | 4-CO$_2$CH$_2$CH$_3$ | O | O |
| H | H | 2-F | 4-CO$_2$C(CH$_3$)$_3$ | O | O |
| H | H | 2-F | 4-CO$_2$CH$_2$CF$_3$ | O | O |
| H | H | 2-F | 4-CO$_2$CH(CH$_2$F)$_2$ | O | O |
| H | H | 2-F | 4-CO$_2$C(CH$_3$)(CF$_3$)$_2$ | O | O |
| H | H | 2-F | 4-OCH$_2$CO$_2$CH$_3$ | O | O |
| H | H | 2-F | 4-NO$_2$ | O | O |
| H | H | 2-F | 4-CN | O | O |
| H | H | 2-F | 4-OH | O | O |
| H | H | 2-F | 4-CO$_2$H | O | O |
| H | H | 2-F | 4-SCN | O | O |
| H | H | 2-F | 4-NCS | O | O |
| H | H | 2-F | 4-CH$_2$SCN | O | O |
| H | H | 2-F | 4-OSO$_2$CH$_3$ | O | O |
| H | H | 2-F | 4-CSCH$_3$ | O | O |
| H | H | 2-F | 4-NH$_2$ | O | O |
| H | H | 2-F | 4-N(CH$_3$)$_2$ | O | O |
| H | H | 2-F | 4-N(CH$_3$)CH$_2$CH$_3$ | O | O |
| H | H | 2-F | 4-N(CH$_3$)CH$_2$CH$_2$CH$_3$ | O | O |
| H | H | 2-F | 4-N(CH$_3$)CH$_2$CH=CHCl | O | O |
| H | H | 2-F | 4-N(CH$_3$)CH$_2$C≡CH | O | O |
| H | H | 2-F | 4-N(CH$_3$)CH$_2$C$_6$H$_5$ | O | O |
| H | H | 2-F | 4-CON(CH$_3$)$_2$ | O | O |
| H | H | 2-F | 4-OCON(CH$_3$)$_2$ | O | O |

TABLE 1-continued

| | | | | | |
|---|---|---|---|---|---|
| H | H | 2-F | 4-NHCOCH$_3$ | O | O |
| H | H | 2-F | 4-NHCO$_2$CH$_2$CH$_3$ | O | O |
| H | H | 2-F | 4-SO$_2$N(CH$_3$)$_2$ | O | O |
| H | H | 2-F | 4-NHCSCH$_3$ | O | O |
| H | H | 2-F | 4-Si(CH$_3$)$_3$ | O | O |
| H | H | 2-F | 3-OCH$_2$O-4 | O | O |
| H | H | 2-F | 3-OCF$_2$O-4 | O | O |
| H | H | 2-F | 3-OCH$_2$CH$_2$O-4 | O | O |
| H | H | 2-F | 3-OCF$_2$CF$_2$O-4 | O | O |
| H | H | 2-F | 3-OC(CH$_3$)$_2$CF$_2$O-4 | O | O |
| H | H | 2-F | 4-C$_6$H$_5$ | O | O |
| H | H | 2-F | 4-(C$_6$H$_4$-4-Cl) | O | O |
| H | H | 2-F | 4-OC$_6$H$_5$ | O | O |
| H | H | 2-F | 4-O(C$_6$H$_4$-2-C$_6$H$_5$) | O | O |
| H | H | 2-F | 4-O(C$_6$H$_4$-3-F) | O | O |
| H | H | 2-F | 4-O(C$_6$H$_4$-3-Br) | O | O |
| H | H | 2-F | 4-O(C$_6$H$_4$-4-Cl) | O | O |
| H | H | 2-F | 4-O(C$_6$H$_4$-4-Br) | O | O |
| H | H | 2-F | 4-O(C$_6$H$_4$-4-CF$_3$) | O | O |
| H | H | 2-F | 4-O(C$_6$H$_4$-4-CN) | O | O |
| H | H | 2-F | 4-O(C$_6$H$_4$-4-NO$_2$) | O | O |
| H | H | 2-F | 4-O(C$_6$H$_4$-4-OCHF$_2$) | O | O |
| H | H | 2-F | 4-O(C$_6$H$_4$-4-OCF$_3$) | O | O |
| H | H | 2-F | 4-O(C$_6$H$_4$-4-SO$_2$CF$_3$) | O | O |
| H | H | 2-F | 4-O(C$_6$H$_4$-4-SO$_2$C$_6$H$_5$) | O | O |
| H | H | 2-F | 4-O(C$_6$H$_3$-2,4-F$_2$) | O | O |
| H | H | 2-F | 4-O(C$_6$H$_3$-3,5-F$_2$) | O | O |
| H | H | 2-F | 4-O(C$_6$H$_3$-2,4-Cl$_2$) | O | O |
| H | H | 2-F | 4-O(C$_6$H$_3$-3,5-Cl$_2$) | O | O |
| H | H | 2-F | 4-O(C$_6$H$_3$-2,4-(CH$_3$)$_2$) | O | O |
| H | H | 2-F | 4-O(C$_6$H$_3$-2,6-(CH$_3$)$_2$) | O | O |
| H | H | 2-F | 4-O(C$_6$H$_3$-3-OCF$_2$CF$_2$O-4) | O | O |
| H | H | 2-F | 4-O(C$_6$H$_3$-2-F-4-Br) | O | O |
| H | H | 2-F | 4-O(C$_6$H$_3$-2-F-4-CF$_3$) | O | O |
| H | H | 2-F | 4-O(C$_6$H$_3$-2-Cl-4-CF$_3$) | O | O |
| H | H | 2-F | 4-O(C$_6$H$_2$-2,3,5-F$_3$) | O | O |
| H | H | 2-F | 4-O(C$_6$H$_2$-2,5-(CH$_3$)$_2$-4-Cl) | O | O |
| H | H | 2-F | 3-O(C$_6$H$_4$-4-CF$_3$) | O | O |
| H | H | 2-F | 3-O(C$_6$H$_3$-2-Cl-4-CF$_3$) | O | O |
| H | H | 2-F | 4-S(C$_6$H$_3$-2-Cl-4-CF$_3$) | O | O |
| H | H | 2-F | 4-SO$_2$C$_6$H$_5$ | O | O |
| H | H | 2-F | 4-NH(C$_6$H$_3$-3,5-Cl$_2$) | O | O |
| H | H | 2-F | 4-NH(C$_6$H$_3$-2-Cl-4-CF$_3$) | O | O |
| H | H | 2-F | 4-NH(C$_6$H$_4$-4-OCF$_3$) | O | O |
| H | H | 2-F | 4-NH(C$_6$H$_4$-4-CF$_3$) | O | O |
| H | H | 2-F | 4-N(CH$_2$CH$_2$CH$_3$)(C$_6$H$_4$-4-Cl) | O | O |
| H | H | 2-F | 4-CH$_2$C$_6$H$_5$ | O | O |
| H | H | 2-F | 4-CF$_2$(C$_6$H$_4$-4-Br) | O | O |
| H | H | 2-F | 4-COC$_6$H$_5$ | O | O |
| H | H | 2-F | 4-OCH$_2$(C$_6$H$_4$-4-Cl) | O | O |
| H | H | 2-F | 4-OCH$_2$(C$_6$H$_4$-4-CF$_3$) | O | O |
| H | H | 2-F | 4-OCH$_2$(C$_6$H$_3$-2,4-Cl$_2$) | O | O |
| H | H | 2-F | 4-CH$_2$OC$_6$H$_5$ | O | O |
| H | H | 2-F | 4-CH$_2$O(C$_6$H$_3$-2,4-Cl$_2$) | O | O |
| H | H | 2-F | 4-CH$_2$O(C$_6$H$_3$-2,6-(CH$_3$)$_2$) | O | O |
| H | H | 2-F | 4-NHCH$_2$C$_6$H$_5$ | O | O |
| H | H | 2-F | 4-CH$_2$CH$_2$C$_6$H$_5$ | O | O |
| H | H | 2-F | 4-CH=CH(C$_6$H$_4$-4-Cl) | O | O |
| H | H | 2-F | 4-C≡C(C$_6$H$_4$-CF$_3$) | O | O |
| H | H | 2-F | 4-N=NC$_6$H$_5$ | O | O |
| H | H | 2-F | 4-OCH$_2$CH$_2$C$_6$H$_5$ | O | O |
| H | H | 2-F | 4-NHCON(CH$_2$CH$_2$CH$_3$)(C$_6$H$_4$-4-Cl) | O | O |
| H | H | 2-F | 4-NHCSNHC$_6$H$_5$ | O | O |
| H | H | 2-F | 4-OCH$_2$CH$_2$O(C$_6$H$_3$-2-Cl-4-CF$_3$) | O | O |
| H | H | 2-F | 4-CH$_2$ON=(Q51)(C$_6$H$_4$-4-Cl) | O | O |
| H | H | 2-F | 4-OCH(CH(CH$_3$)$_2$)C$_6$H$_5$ | O | O |
| H | H | 2-F | 4-O(Q1-1-CH$_3$) | O | O |
| H | H | 2-F | 4-O(Q2-1-CH$_3$) | O | O |
| H | H | 2-F | 4-(Q3) | O | O |
| H | H | 2-F | 4-CH$_2$(Q4) | O | O |
| H | H | 2-F | 4-(Q5) | O | O |
| H | H | 2-F | 4-C≡C(Q6) | O | O |
| H | H | 2-F | 4-CH$_2$(Q7) | O | O |
| H | H | 2-F | 4-(Q8-3,5-(CF$_3$)$_2$) | O | O |
| H | H | 2-F | 4-(Q8-3-C$_6$H$_5$) | O | O |
| H | H | 2-F | 4-OCH$_2$(Q9-1-CH$_3$) | O | O |
| H | H | 2-F | 4-O(Q10-1-CH$_3$) | O | O |
| H | H | 2-F | 4-(Q11-1-C$_6$H$_5$) | O | O |
| H | H | 2-F | 4-(Q12-1-CH$_3$) | O | O |
| H | H | 2-F | 4-OCH$_2$(Q13-1-CH$_3$) | O | O |
| H | H | 2-F | 4-O(Q14-1-CH$_3$) | O | O |
| H | H | 2-F | 4-(Q15) | O | O |

TABLE 1-continued

| | | | | | |
|---|---|---|---|---|---|
| H | H | 2-F | 4-O(Q16) | O | O |
| H | H | 2-F | 4-O(Q17-5-CH₃) | O | O |
| H | H | 2-F | 4-O(Q18) | O | O |
| H | H | 2-F | 4-OCH₂(Q19) | O | O |
| H | H | 2-F | 4-OCH₂(Q20-4-Cl) | O | O |
| H | H | 2-F | 4-(Q21) | O | O |
| H | H | 2-F | 4-OCH₂(Q22) | O | O |
| H | H | 2-F | 4-(Q23) | O | O |
| H | H | 2-F | 4-OCH₂(Q24) | O | O |
| H | H | 2-F | 4-O(Q25-3-CH₃) | O | O |
| H | H | 2-F | 4-(Q26-1-CH₃) | O | O |
| H | H | 2-F | 4-OCH₂(Q27-1-CH₃) | O | O |
| H | H | 2-F | 4-OCH₂(Q28-1-CH₃) | O | O |
| H | H | 2-F | 4-O(Q29-1-CH₃) | O | O |
| H | H | 2-F | 4-NHCONH(Q30) | O | O |
| H | H | 2-F | 4-O(Q31) | O | O |
| H | H | 2-F | 4-OCH₂(Q32) | O | O |
| H | H | 2-F | 4-OCH₂(Q33) | O | O |
| H | H | 2-F | 4-O(Q34) | O | O |
| H | H | 2-F | 4-OCH₂(Q35) | O | O |
| H | H | 2-F | 4-O(Q36) | O | O |
| H | H | 2-F | 4-OCH₂(Q37-5-Cl) | O | O |
| H | H | 2-F | 3-O(Q38-5-CF₂CFCl₂) | O | O |
| H | H | 2-F | 3-O(Q38-3-Cl-5-CF₃) | O | O |
| H | H | 2-F | 4-O(Q38-3-Cl-5-CF₃) | O | O |
| H | H | 2-F | 4-O(Q38-3-Cl-5-CN) | O | O |
| H | H | 2-F | 4-O(Q38-3-Cl-5-CF₂CFCl₂) | O | O |
| H | H | 2-F | 4-O(Q38-5-CF₃-6-Cl) | O | O |
| H | H | 2-F | 4-NH(Q38-5-CF₃) | O | O |
| H | H | 2-F | 4-NH(Q38-3-Cl-5-CF₃) | O | O |
| H | H | 2-F | 4-(Q38-3-Cl-5-CF₃) | O | O |
| H | H | 2-F | 4-O(Q39-5-Br) | O | O |
| H | H | 2-F | 4-O(Q40-2,6-Cl₂) | O | O |
| H | H | 2-F | 4-O(Q41-6-Cl) | O | O |
| H | H | 2-F | 4-O(Q42) | O | O |
| H | H | 2-F | 4-O(Q43-5-Cl) | O | O |
| H | H | 2-F | 4-O(Q44) | O | O |
| H | H | 2-F | 4-O(Q45-4-CF₃-6-Cl) | O | O |
| H | H | 2-F | 4-O(Q46) | O | O |
| H | H | 2-F | 4-O(Q47) | O | O |
| H | H | 2-F | 4-O(Q47-4-Cl) | O | O |
| H | H | 2-F | 4-O(Q48) | O | O |
| H | H | 2-F | 4-O(Q49) | O | O |
| H | H | 2-F | 3-O(Q50-6-Cl) | O | O |
| H | H | 2-F | 3-O(Q50-6-CF₃) | O | O |
| H | H | 2-F | 3-O(Q50-6-F) | O | O |
| H | H | 2-F | 4-O(Q50-6-Cl) | O | O |
| H | H | 2-F | 4-O(Q50-6-CF₃) | O | O |
| H | H | 2-F | 2,4-F₂ | O | O |
| H | H | 2-F | 2,6-F₂ | O | O |
| H | H | 2-F | 3,5-F₂ | O | O |
| H | H | 2-F | 2,3-Cl₂ | O | O |
| H | H | 2-F | 2,4-Cl₂ | O | O |
| H | H | 2-F | 2,5-Cl₂ | O | O |
| H | H | 2-F | 2,6-Cl₂ | O | O |
| H | H | 2-F | 3,4-Cl₂ | O | O |
| H | H | 2-F | 3,5-Cl₂ | O | O |
| H | H | 2-F | 3,4-Br₂ | O | O |
| H | H | 2-F | 2,4-I₂ | O | O |
| H | H | 2-F | 2,4-(CH₃)₂ | O | O |
| H | H | 2-F | 3,4-(OCH₃)₂ | O | O |
| H | H | 2-F | 2-F-4-Cl | O | O |
| H | H | 2-F | 2-F-4-Br | O | O |
| H | H | 2-F | 2-F-4-OCH(CH₃)₂ | O | O |
| H | H | 2-F | 2-F-4-OCHF₂ | O | O |
| H | H | 2-F | 2-F-4-OCF₂CHF₂ | O | O |
| H | H | 2-F | 2-F-4-OCF₂CHFCF₃ | O | O |
| H | H | 2-F | 2-F-4-OCF₂CHFOCF₃ | O | O |
| H | H | 2-F | 2-F-4-SO₂CF₂CHFCl | O | O |
| H | H | 2-F | 2-F-4-O(C₆H₃-2-Cl-4-CF₃) | O | O |
| H | H | 2-F | 2-F-4-N-NC₆H₅ | O | O |
| H | H | 2-F | 2-F-4-NHCON(CH₂CH₂CH₃)(C₆H₄-4-Cl) | O | O |
| H | H | 2-F | 2-F-4-O(Q38-3-Cl-5-CF₃) | O | O |
| H | H | 2-F | 3-F-4-O(Q38-3-Cl-5-CF₃) | O | O |
| H | H | 2-F | 2-Cl-4-CF₃ | O | O |
| H | H | 2-F | 2-Cl-4-SCF₂CHF₂ | O | O |
| H | H | 2-F | 2-Cl-4-O(C₆H₃-2-Cl-4-CF₃) | O | O |
| H | H | 2-F | 2-Cl-4-O(Q38-3-Cl-5-CF₃) | O | O |
| H | H | 2-F | 2-Cl-5-O(Q50-6-CF₃) | O | O |
| H | H | 2-F | 2-Cl-5-S(Q50-6-CF₃) | O | O |
| H | H | 2-F | 3-Cl-4-CF₃ | O | O |
| H | H | 2-F | 3-Cl-4-OC(CH₃)₃ | O | O |

TABLE 1-continued

| | | | | | |
|---|---|---|---|---|---|
| H | H | 2-F | 3-Cl-4-OCF₃ | O | O |
| H | H | 2-F | 3-Cl-4-OCF₂CHF₂ | O | O |
| H | H | 2-F | 3-Cl-4-OCF₂CHFOCF₃ | O | O |
| H | H | 2-F | 3-Cl-4-SCF₂Cl | O | O |
| H | H | 2-F | 3-Cl-4-CO₂CH(CH(CH₃)₂)₂ | O | O |
| H | H | 2-F | 3-Cl-4-CO₂CH(CH₂F)₂ | O | O |
| H | H | 2-F | 3-Cl-4-CO₂C(CH₃)(CF₃)₂ | O | O |
| H | H | 2-F | 3-Cl-4-O(C₆H₄-4-Cl) | O | O |
| H | H | 2-F | 3-Cl-4-O(C₆H₄-4-NO₂) | O | O |
| H | H | 2-F | 3-Cl-4-O(C₆H₄-4-CF₃) | O | O |
| H | H | 2-F | 3-Cl-4-O(C₆H₃-2-Cl-4-CF₃) | O | O |
| H | H | 2-F | 3-Cl-4-O(C₆H₃-2-Cl-4-OCF₃) | O | O |
| H | H | 2-F | 3-Cl-4-CF₂(C₆H₄-4-Br) | O | O |
| H | H | 2-F | 3-Cl-4-CH=CH(C₆H₄-4-Cl) | O | O |
| H | H | 2-F | 3-Cl-4-O(Q38-5-CF₃) | O | O |
| H | H | 2-F | 3-Cl-4-O(Q38-5-CF₂CF₂CF₃) | O | O |
| H | H | 2-F | 3-Cl-4-O(Q38-3-Cl-5-CF₃) | O | O |
| H | H | 2-F | 3-Cl-4-O(Q38-5-CF₃-6-Cl) | O | O |
| H | H | 2-F | 3-Cl-4-NH(Q38-5-CF₃) | O | O |
| H | H | 2-F | 3-Cl-4-N(COC(CH₃)₃)(Q38-5-CF₃) | O | O |
| H | H | 2-F | 2-CH₃-4-N=NC₆H₅ | O | O |
| H | H | 2-F | 2-CH₃-4-O(Q38-3-Cl-5-CF₃) | O | O |
| H | H | 2-F | 3-CH₃-4-OCF₂CHF₂ | O | O |
| H | H | 2-F | 3-CH₃-4-O(C₆H₃-2-Cl-4-CF₃) | O | O |
| H | H | 2-F | 3-CH₃-4-O(Q38-3-Cl-5-CF₃) | O | O |
| H | H | 2-F | 3-Br-4-O(Q38-3-Cl-5-CF₃) | O | O |
| H | H | 2-F | 3-CF₃-4-Cl | O | O |
| H | H | 2-F | 3-CF₃-4-OCF₂CHF₂ | O | O |
| H | H | 2-F | 3-CF₃-4-OCF₂CHFBr | O | O |
| H | H | 2-F | 3-CF₃-4-OCF₂CHFCF₃ | O | O |
| H | H | 2-F | 3-CF₃-4-O(Q38-3-Cl-5-CF₃) | O | O |
| H | H | 2-F | 3-OCH₃-4-O(C₆H₃-2-Cl-4-CF₃) | O | O |
| H | H | 2-F | 3-CO₂CH₃-4-O(Q38-3-Cl-5-CF₃) | O | O |
| H | H | 2-F | 3-CO₂CH₂CH₃-4-O(Q38-3-Cl-5-CF₂CFCl₂) | O | O |
| H | H | 2-F | 2,3-F₂-4-OCF₃ | O | O |
| H | H | 2-F | 2,3-F₂-4-O(Q38-3-Cl-5-CF₃) | O | O |
| H | H | 2-F | 2,5-F₂-4-Cl | O | O |
| H | H | 2-F | 2,5-F₂-4-Br | O | O |
| H | H | 2-F | 2,5-F₂-4-OCF₃ | O | O |
| H | H | 2-F | 2,5-F₂-4-S(Q38-3-Cl-5-CF₃) | O | O |
| H | H | 2-F | 3,5-F₂-4-CF₃ | O | O |
| H | H | 2-F | 2,3-Cl₂-4-OCF₂CHFCl | O | O |
| H | H | 2-F | 2,3-Cl₂-4-O(C₆H₃-2-F-4-Br) | O | O |
| H | H | 2-F | 2,5-Cl₂-4-OCF₂CHF₂ | O | O |
| H | H | 2-F | 2,5-Cl₂-4-OCF₂CHFCF₃ | O | O |
| H | H | 2-F | 2,5-Cl₂-4-OCF₂CF₂CF₃ | O | O |
| H | H | 2-F | 2,5-Cl₂-4-O(C₆H₃-2-Cl-4-CF₃) | O | O |
| H | H | 2-F | 2,5-Cl₂-4-O(Q38-3-Cl-5-CF₃) | O | O |
| H | H | 2-F | 2,6-Cl₂-4-CF₃ | O | O |
| H | H | 2-F | 3,4,5-Cl₃ | O | O |
| H | H | 2-F | 3,5-Cl₂-4-OCH₂CH₂OCH₃ | O | O |
| H | H | 2-F | 3,5-Cl₂-4-OCH₂CH=CH₂ | O | O |
| H | H | 2-F | 3,5-Cl₂-4-OCH₂CH=CHCH₃ | O | O |
| H | H | 2-F | 3,5-Cl₂-4-OCF₂CHF₂ | O | O |
| H | H | 2-F | 3,5-Cl₂-4-OCH₂CF₃ | O | O |
| H | H | 2-F | 3,5-Cl₂-4-OCF₂CHFCl | O | O |
| H | H | 2-F | 3,5-Cl₂-4-OCF₂CHCl₂ | O | O |
| H | H | 2-F | 3,5-Cl₂-4-OCF₂CHFCF₃ | O | O |
| H | H | 2-F | 3,5-Cl₂-4-OCF₂CHFOCF₃ | O | O |
| H | H | 2-F | 3,5-Cl₂-4-OCF₂CF₂CF₃ | O | O |
| H | H | 2-F | 3,5-Cl₂-4-SCF₂CHF₂ | O | O |
| H | H | 2-F | 3,5-Cl₂-4-SCH₂CF₃ | O | O |
| H | H | 2-F | 3,5-Cl₂-4-N(CH₃)CH₂CH₂CH₃ | O | O |
| H | H | 2-F | 3,5-Cl₂-4-N(CH₃)CH₂C≡CH | O | O |
| H | H | 2-F | 3,5-Cl₂-4-N(CH₃)CH₂CH=CHCl | O | O |
| H | H | 2-F | 3,5-Cl₂-4-N(CH₃)CH₂C₆H₅ | O | O |
| H | H | 2-F | 3,5-Cl₂-4-O(C₆H₄-3-F) | O | O |
| H | H | 2-F | 3,5-Cl₂-4-O(C₆H₄-3-Br) | O | O |
| H | H | 2-F | 3,5-Cl₂-4-O(C₆H₄-4-Cl) | O | O |
| H | H | 2-F | 3,5-Cl₂-4-O(C₆H₄-4-CN) | O | O |
| H | H | 2-F | 3,5-Cl₂-4-O(C₆H₄-4-NO₂) | O | O |
| H | H | 2-F | 3,5-Cl₂-4-O(C₆H₄-4-SO₂CF₃) | O | O |
| H | H | 2-F | 3,5-Cl₂-4-O(C₆H₄-4-SO₂C₆H₅) | O | O |
| H | H | 2-F | 3,5-Cl₂-4-O(C₆H₃-2,4-F₂) | O | O |
| H | H | 2-F | 3,5-Cl₂-4-O(C₆H₃-2-Cl-4-CF₃) | O | O |
| H | H | 2-F | 3,5-Cl₂-4-O(C₆H₃-3-OCF₂CF₂O-4) | O | O |
| H | H | 2-F | 3,5-Cl₂-4-OCH₂(C₆H₄-4-Cl) | O | O |
| H | H | 2-F | 3,5-Cl₂-4-OCH₂(C₆H₄-4-CF₃) | O | O |
| H | H | 2-F | 3,5-Cl₂-4-OCH₂(C₆H₄-2-C₆H₅) | O | O |
| H | H | 2-F | 3,5-Cl₂-4-OCH₂(C₆H₃-2,4-Cl₂) | O | O |
| H | H | 2-F | 3,5-Cl₂-4-NH(C₆H₄-4-CF₃) | O | O |
| H | H | 2-F | 3,5-Cl₂-4-NH(C₆H₄-4-OCF₃) | O | O |

TABLE 1-continued

| | | | | | |
|---|---|---|---|---|---|
| H | H | 2-F | 3,5-Cl₂-4-(Q3) | O | O |
| H | H | 2-F | 3,5-Cl₂-4-(Q8-3-C₆H₅) | O | O |
| H | H | 2-F | 3,5-Cl₂-4-(Q38-3-Cl-5-CF₃) | O | O |
| H | H | 2-F | 3,5-Cl₂-4-(Q38-3-Cl-5-CF₃) | O | O |
| H | H | 2-F | 3,5-Cl₂-4-(Q38-3-Cl-5-CN) | O | O |
| H | H | 2-F | 3,5-Cl₂-4-OCH₂CH₂O(Q38-3-Cl-5-CF₃) | O | O |
| H | H | 2-F | 3,5-Cl₂-4-O(Q43-5-Cl) | O | O |
| H | H | 2-F | 3,5-Cl₂-4-O(Q45-2-CH₃) | O | O |
| H | H | 2-F | 3,5-Cl₂-4-(Q47-4-Cl) | O | O |
| H | H | 2-F | 3,5-Cl₂-4-O(Q50-6-Cl) | O | O |
| H | H | 2-F | 3,5-Cl₂-4-O(Q50-6-CF₃) | O | O |
| H | H | 2-F | 3,5-Cl₂-4-O(Q45-2-CH₃) | O | O |
| H | H | 2-F | 2,5-(CH₃)₂-4-O(C₆H₃-2-Cl-4-CF₃) | O | O |
| H | H | 2-F | 3,5-(CH₃)₂-4-OCF₂CHFCl | O | O |
| H | H | 2-F | 3,5-(CH₃)₂-4-O(C₆H₃-3,5-F₂) | O | O |
| H | H | 2-F | 3,5-(CH₃)₂-4-O(C₆H₂-2,3,5-F₃) | O | O |
| H | H | 2-F | 3,5-(CH₃)₂-4-N=NC₆H₅ | O | O |
| H | H | 2-F | 2-F-4,5-Cl₂ | O | O |
| H | H | 2-F | 2-F-3-CF₃-5-Cl | O | O |
| H | H | 2-F | 2-F-4-Br-5-CF₃ | O | O |
| H | H | 2-F | 2-F-4-Cl-5-OCH(CH₃)₂ | O | O |
| H | H | 2-F | 2-F-4-Br-5-OCF₃ | O | O |
| H | H | 2-F | 2-F-4-OCH₂CF₃-5-Cl | O | O |
| H | H | 2-F | 2-F-4-OCF₂CHF₂-5-Cl | O | O |
| H | H | 2-F | 2-F-4-O(C₆H₃-2-Cl-4-CF₃)-5-Cl | O | O |
| H | H | 2-F | 2-F-4-S(C₆H₃-2-Cl-4-CF₃)-5-Cl | O | O |
| H | H | 2-F | 2-Cl-3-CF₃-5-NO₂ | O | O |
| H | H | 2-F | 3-Cl-4-OCF₂CHF₂-5-CF₃ | O | O |
| H | H | 2-F | 3-Cl-4-OCF₂CHF₂-5-CH₂OCH₃ | O | O |
| H | H | 2-F | 3-Cl-4-OCF₂CHFCF₃-5-CF₃ | O | O |
| H | H | 2-F | 3-Cl-4-O(Q38-3-Cl-5-CF₃)-5-CO₂H | O | O |
| H | H | 2-F | 3-Cl-4-O(Q38-3-Cl-5-CF₃)-5-CO₂CH₃ | O | O |
| H | H | 2-F | 3-Cl-4-O(Q38-3-Cl-5-CF₃)-5-CH₂OCH₃ | O | O |
| H | H | 2-F | 2-CF₃-4,6-(NO₂)₂ | O | O |
| H | H | 2-F | 2-CF₃-4-OCF₂CHFCF₃-5-Cl | O | O |
| H | H | 2-F | 2-CF₃-4-OCH₂CH=CHCl-5-Br | O | O |
| H | H | 2-F | 2-CH₃-4-CH(CN)(C₆H₄-4-Cl)-5-Cl | O | O |
| H | H | 2-F | 2,3,4,5-F₄ | O | O |
| H | H | 2-F | 2,4-F₂-3,5-Cl₂ | O | O |
| H | H | 2-F | 2,6-F₂-3,5-Cl₂ | O | O |
| H | H | 2-F | 2,4-F₂-3-Cl-5-Br | O | O |
| H | H | 2-F | 2,4-Cl₂-3,5-F₂ | O | O |
| H | H | 2-F | 2,6-Cl₂-3,5-F₂ | O | O |
| H | H | 2-F | 2-F-3,5-Cl₂-4-OCH₃ | O | O |
| H | H | 2-F | 2,3,5-F₃-4-OCF₂CHFCF₃ | O | O |
| H | H | 2-F | 2-F-3,5-Cl₂-4-OCH₂CF₃ | O | O |
| H | H | 2-F | 2-F-3,5-Cl₂-4-OCF₂CHF₂ | O | O |
| H | H | 2-F | 2-F-3,5-Cl₂-4-OCF₂CHFOCF₃ | O | O |
| H | H | 2-F | 2-F-3,5-Cl₂-4-N(CH₃)CH₂CH₃ | O | O |
| H | H | 2-F | 2-F-3,5-Cl₂-4-N(CH₃)CH₂C₆H₅ | O | O |
| H | H | 2-F | 2-F-3,5-Cl₂-4-O(C₆H₃-2-Cl-4-CF₃) | O | O |
| H | H | 2-F | 2-F-3,5-Cl₂-4-O(Q38-3-Cl-5-CF₃) | O | O |
| H | H | 2-F | 2,5-(CH₃)₂-3-Cl-4-O(C₆H₃-2,4-(CH₃)₂) | O | O |
| H | H | 2-F | 2-CH₃-3,5-Cl₂-4-O(C₆H₃-2-CH₃-4-Cl) | O | O |
| H | H | 2-F | 2-CH₃-3-Cl-4-O(C₆H₄-4-F)-5-CH(OCH₃)₂ | O | O |
| H | H | 2-F | 2,3,4,5,6-F₆ | O | O |
| H | H | 2-F | 2,4,6-F₃-3,5-Cl₂ | O | O |
| H | H | 2-F | 3-Cl-4-F | O | O |
| H | H | 2-F | 4-OCH₂CH₂CH₂CH₃ | O | O |
| H | H | 2,6-F₂ | 2-F | O | O |
| H | H | 2,6-F₂ | 3-F | O | O |
| H | H | 2,6-F₂ | 4-F | O | O |
| H | H | 2,6-F₂ | 2-Cl | O | O |
| H | H | 2,6-F₂ | 3-Cl | O | O |
| H | H | 2,6-F₂ | 4-Cl | O | O |
| H | H | 2,6-F₂ | 4-Br | O | O |
| H | H | 2,6-F₂ | 4-I | O | O |
| H | H | 2,6-F₂ | 4-CH₃ | O | O |
| H | H | 2,6-F₂ | 4-CH(CH₃)₂ | O | O |
| H | H | 2,6-F₂ | 4-CH₂CH₂CH₂CH₃ | O | O |
| H | H | 2,6-F₂ | 4-C(CH₃)₃ | O | O |
| H | H | 2,6-F₂ | 4-CH₂CH=CH₂ | O | O |
| H | H | 2,6-F₂ | 4-CH₂CH=CHCH₃ | O | O |
| H | H | 2,6-F₂ | 4-C≡CH | O | O |
| H | H | 2,6-F₂ | 4-CH₂C≡CH | O | O |
| H | H | 2,6-F₂ | 4-Q51 | O | O |
| H | H | 2,6-F₂ | 4-Q52 | O | O |
| H | H | 2,6-F₂ | 4-Q53 | O | O |
| H | H | 2,6-F₂ | 4-Q54 | O | O |
| H | H | 2,6-F₂ | 4-CHF₂ | O | O |
| H | H | 2,6-F₂ | 4-CH₂Br | O | O |
| H | H | 2,6-F₂ | 4-CH₂Cl | O | O |

TABLE 1-continued

| | | | | | |
|---|---|---|---|---|---|
| H | H | 2,6-F$_2$ | 2-CF$_3$ | O | O |
| H | H | 2,6-F$_2$ | 3-CF$_3$ | O | O |
| H | H | 2,6-F$_2$ | 4-CF$_3$ | O | O |
| H | H | 2,6-F$_2$ | 4-CH$_2$CH=CHCl | O | O |
| H | H | 2,6-F$_2$ | 4-CH=C(Cl)CF$_3$ | O | O |
| H | H | 2,6-F$_2$ | 4-CH$_2$C≡CBr | O | O |
| H | H | 2,6-F$_2$ | 4-(Q54-1-Cl) | O | O |
| H | H | 2,6-F$_2$ | 4-CH$_2$CN | O | O |
| H | H | 2,6-F$_2$ | 4-CH$_2$CH(CH$_3$)CN | O | O |
| H | H | 2,6-F$_2$ | 4-CH$_2$OH | O | O |
| H | H | 2,6-F$_2$ | 4-CH$_2$CO$_2$H | O | O |
| H | H | 2,6-F$_2$ | 4-OCH$_3$ | O | O |
| H | H | 2,6-F$_2$ | 4-OCH$_2$CH$_3$ | O | O |
| H | H | 2,6-F$_2$ | 4-OCH(CH$_3$)$_2$ | O | O |
| H | H | 2,6-F$_2$ | 4-OC(CH$_3$)$_3$ | O | O |
| H | H | 2,6-F$_2$ | 4-OCH$_2$CH=CH$_2$ | O | O |
| H | H | 2,6-F$_2$ | 4-OCH$_2$C≡CH | O | O |
| H | H | 2,6-F$_2$ | 4-O(Q53) | O | O |
| H | H | 2,6-F$_2$ | 4-O(Q54) | O | O |
| H | H | 2,6-F$_2$ | 4-O(Q54-2-CH(CH$_3$)$_2$-5-CH$_3$) | O | O |
| H | H | 2,6-F$_2$ | 4-OCHF$_2$ | O | O |
| H | H | 2,6-F$_2$ | 4-OCF$_2$Br | O | O |
| H | H | 2,6-F$_2$ | 2-OCF$_3$ | O | O |
| H | H | 2,6-F$_2$ | 3-OCF$_3$ | O | O |
| H | H | 2,6-F$_2$ | 4-OCF$_3$ | O | O |
| H | H | 2,6-F$_2$ | 4-OCH$_2$CF$_3$ | O | O |
| H | H | 2,6-F$_2$ | 4-OCF$_2$CHF$_2$ | O | O |
| H | H | 2,6-F$_2$ | 4-OCF$_2$CHCl$_2$ | O | O |
| H | H | 2,6-F$_2$ | 4-OCF$_2$CHFCl | O | O |
| H | H | 2,6-F$_2$ | 4-OCF$_2$CHFBr | O | O |
| H | H | 2,6-F$_2$ | 4-OCF$_2$CF$_2$CF$_3$ | O | O |
| H | H | 2,6-F$_2$ | 4-OCH$_2$CH=CHCl | O | O |
| H | H | 2,6-F$_2$ | 4-OCH$_2$C≡CBr | O | O |
| H | H | 2,6-F$_2$ | 4-O(Q51-2,2-Cl$_2$) | O | O |
| H | H | 2,6-F$_2$ | 4-OCH$_2$(Q51-2,2-Cl$_2$) | O | O |
| H | H | 2,6-F$_2$ | 4-SCH$_3$ | O | O |
| H | H | 2,6-F$_2$ | 4-SCH$_2$CH=CH$_2$ | O | O |
| H | H | 2,6-F$_2$ | 4-SCH$_2$C≡CH | O | O |
| H | H | 2,6-F$_2$ | 4-S-(Q54) | O | O |
| H | H | 2,6-F$_2$ | 4-SCHF$_2$ | O | O |
| H | H | 2,6-F$_2$ | 4-SCF$_3$ | O | O |
| H | H | 2,6-F$_2$ | 4-SCF$_2$Cl | O | O |
| H | H | 2,6-F$_2$ | 4-SOCH$_3$ | O | O |
| H | H | 2,6-F$_2$ | 4-SOCH$_2$CH=CH$_2$ | O | O |
| H | H | 2,6-F$_2$ | 4-SOCH$_2$C≡CH | O | O |
| H | H | 2,6-F$_2$ | 4-SO(Q54) | O | O |
| H | H | 2,6-F$_2$ | 4-SOCF$_3$ | O | O |
| H | H | 2,6-F$_2$ | 4-SO$_2$CH$_3$ | O | O |
| H | H | 2,6-F$_2$ | 4-SO$_2$CH$_2$CH=CH$_2$ | O | O |
| H | H | 2,6-F$_2$ | 4-SO$_2$CH$_2$C≡CH | O | O |
| H | H | 2,6-F$_2$ | 4-SO$_2$(Q54) | O | O |
| H | H | 2,6-F$_2$ | 4-SO$_2$CF$_3$ | O | O |
| H | H | 2,6-F$_2$ | 4-SO$_2$CF$_2$CHFCl | O | O |
| H | H | 2,6-F$_2$ | 4-CH$_2$OCH$_3$ | O | O |
| H | H | 2,6-F$_2$ | 4-OCH$_2$CH$_2$OCH$_3$ | O | O |
| H | H | 2,6-F$_2$ | 4-CH$_2$OCH$_2$CF$_3$ | O | O |
| H | H | 2,6-F$_2$ | 4-OCF$_2$CHFOCF$_3$ | O | O |
| H | H | 2,6-F$_2$ | 4-CH$_2$SCH$_3$ | O | O |
| H | H | 2,6-F$_2$ | 4-OCH$_2$CH$_2$SCH$_3$ | O | O |
| H | H | 2,6-F$_2$ | 4-CH$_2$CO$_2$CH$_3$ | O | O |
| H | H | 2,6-F$_2$ | 4-CH$_2$CO$_2$CH$_2$CF$_3$ | O | O |
| H | H | 2,6-F$_2$ | 4-CH$_2$COCH$_3$ | O | O |
| H | H | 2,6-F$_2$ | 4-OCO$_2$CH$_3$ | O | O |
| H | H | 2,6-F$_2$ | 4-OCOCH$_3$ | O | O |
| H | H | 2,6-F$_2$ | 4-COCH$_3$ | O | O |
| H | H | 2,6-F$_2$ | 4-COCH$_2$CH=CH$_2$ | O | O |
| H | H | 2,6-F$_2$ | 4-COCH$_2$C≡CH | O | O |
| H | H | 2,6-F$_2$ | 4-CO(Q53) | O | O |
| H | H | 2,6-F$_2$ | 4-COCF$_3$ | O | O |
| H | H | 2,6-F$_2$ | 4-CO$_2$CH$_2$CH$_3$ | O | O |
| H | H | 2,6-F$_2$ | 4-CO$_2$C(CH$_3$)$_3$ | O | O |
| H | H | 2,6-F$_2$ | 4-CO$_2$CH$_2$CF$_3$ | O | O |
| H | H | 2,6-F$_2$ | 4-CO$_2$CH(CH$_2$F)$_2$ | O | O |
| H | H | 2,6-F$_2$ | 4-CO$_2$C(CH$_3$)(CF$_3$)$_2$ | O | O |
| H | H | 2,6-F$_2$ | 4-OCH$_2$CO$_2$CH$_3$ | O | O |
| H | H | 2,6-F$_2$ | 4-NO$_2$ | O | O |
| H | H | 2,6-F$_2$ | 4-CN | O | O |
| H | H | 2,6-F$_2$ | 4-OH | O | O |
| H | H | 2,6-F$_2$ | 4-CO$_2$H | O | O |
| H | H | 2,6-F$_2$ | 4-SCN | O | O |
| H | H | 2,6-F$_2$ | 4-NCS | O | O |
| H | H | 2,6-F$_2$ | 4-CH$_2$SCN | O | O |

TABLE 1-continued

| | | | | | |
|---|---|---|---|---|---|
| H | H | 2,6-F$_2$ | 4-OSO$_2$CH$_3$ | O | O |
| H | H | 2,6-F$_2$ | 4-CSCH$_3$ | O | O |
| H | H | 2,6-F$_2$ | 4-NH$_2$ | O | O |
| H | H | 2,6-F$_2$ | 4-N(CH$_3$)$_2$ | O | O |
| H | H | 2,6-F$_2$ | 4-N(CH$_3$)CH$_2$CH$_3$ | O | O |
| H | H | 2,6-F$_2$ | 4-N(CH$_3$)CH$_2$CH$_2$CH$_3$ | O | O |
| H | H | 2,6-F$_2$ | 4-N(CH$_3$)CH$_2$CH=CHCl | O | O |
| H | H | 2,6-F$_2$ | 4-N(CH$_3$)CH$_2$C≡CH | O | O |
| H | H | 2,6-F$_2$ | 4-N(CH$_3$)CH$_2$C$_6$H$_5$ | O | O |
| H | H | 2,6-F$_2$ | 4-CON(CH$_3$)$_2$ | O | O |
| H | H | 2,6-F$_2$ | 4-OCON(CH$_3$)$_2$ | O | O |
| H | H | 2,6-F$_2$ | 4-NHCOCH$_3$ | O | O |
| H | H | 2,6-F$_2$ | 4-NHCO$_2$CH$_2$CH$_3$ | O | O |
| H | H | 2,6-F$_2$ | 4-SO$_2$N(CH$_3$)$_2$ | O | O |
| H | H | 2,6-F$_2$ | 4-NHCSCH$_3$ | O | O |
| H | H | 2,6-F$_2$ | 4-Si(CH$_3$)$_3$ | O | O |
| H | H | 2,6-F$_2$ | 3-OCH$_2$O-4 | O | O |
| H | H | 2,6-F$_2$ | 3-OCF$_2$O-4 | O | O |
| H | H | 2,6-F$_2$ | 3-OCH$_2$CH$_2$O-4 | O | O |
| H | H | 2,6-F$_2$ | 3-OCF$_2$CF$_2$O-4 | O | O |
| H | H | 2,6-F$_2$ | 3-OC(CH$_3$)$_2$CF$_2$O-4 | O | O |
| H | H | 2,6-F$_2$ | 4-C$_6$H$_5$ | O | O |
| H | H | 2,6-F$_2$ | 4-(C$_6$H$_4$-4-Cl) | O | O |
| H | H | 2,6-F$_2$ | 4-OC$_6$H$_5$ | O | O |
| H | H | 2,6-F$_2$ | 4-O(C$_6$H$_4$-2-C$_6$H$_5$) | O | O |
| H | H | 2,6-F$_2$ | 4-O(C$_6$H$_4$-3-F) | O | O |
| H | H | 2,6-F$_2$ | 4-O(C$_6$H$_4$-3-Br) | O | O |
| H | H | 2,6-F$_2$ | 4-O(C$_6$H$_4$-4-Cl) | O | O |
| H | H | 2,6-F$_2$ | 4-O(C$_6$H$_4$-4-Br) | O | O |
| H | H | 2,6-F$_2$ | 4-O(C$_6$H$_4$-4-CF$_3$) | O | O |
| H | H | 2,6-F$_2$ | 4-O(C$_6$H$_4$-4-CN) | O | O |
| H | H | 2,6-F$_2$ | 4-O(C$_6$H$_4$-4-NO$_2$) | O | O |
| H | H | 2,6-F$_2$ | 4-O(C$_6$H$_4$-4-OCHF$_2$) | O | O |
| H | H | 2,6-F$_2$ | 4-O(C$_6$H$_4$-4-OCF$_3$) | O | O |
| H | H | 2,6-F$_2$ | 4-O(C$_6$H$_4$-4-SO$_2$CF$_3$) | O | O |
| H | H | 2,6-F$_2$ | 4-O(C$_6$H$_4$-4-SO$_2$C$_6$H$_5$) | O | O |
| H | H | 2,6-F$_2$ | 4-O(C$_6$H$_3$-2,4-F$_2$) | O | O |
| H | H | 2,6-F$_2$ | 4-O(C$_6$H$_3$-3,5-F$_2$) | O | O |
| H | H | 2,6-F$_2$ | 4-O(C$_6$H$_3$-2,4-Cl$_2$) | O | O |
| H | H | 2,6-F$_2$ | 4-O(C$_6$H$_3$-3,5-Cl$_2$) | O | O |
| H | H | 2,6-F$_2$ | 4-O(C$_6$H$_3$-2,4-(CH$_3$)$_2$) | O | O |
| H | H | 2,6-F$_2$ | 4-O(C$_6$H$_3$-2,6-(CH$_3$)$_2$) | O | O |
| H | H | 2,6-F$_2$ | 4-O(C$_6$H$_3$-3-OCF$_2$CF$_2$O-4) | O | O |
| H | H | 2,6-F$_2$ | 4-O(C$_6$H$_3$-2-F-4-Br) | O | O |
| H | H | 2,6-F$_2$ | 4-O(C$_6$H$_3$-2-F-4-CF$_3$) | O | O |
| H | H | 2,6-F$_2$ | 4-O(C$_6$H$_3$-2-Cl-4-CF$_3$) | O | O |
| H | H | 2,6-F$_2$ | 4-O(C$_6$H$_2$-2,3,5-F$_3$) | O | O |
| H | H | 2,6-F$_2$ | 4-O(C$_6$H$_2$-2,5-(CH$_3$)$_2$-4-Cl) | O | O |
| H | H | 2,6-F$_2$ | 3-O(C$_6$H$_4$-4-CF$_3$) | O | O |
| H | H | 2,6-F$_2$ | 3-O(C$_6$H$_3$-2-Cl-4-CF$_3$) | O | O |
| H | H | 2,6-F$_2$ | 4-S(C$_6$H$_3$-2-Cl-4-CF$_3$) | O | O |
| H | H | 2,6-F$_2$ | 4-SO$_2$C$_6$H$_5$ | O | O |
| H | H | 2,6-F$_2$ | 4-NH(C$_6$H$_3$-3,5-Cl$_2$) | O | O |
| H | H | 2,6-F$_2$ | 4-NH(C$_6$H$_3$-2-Cl-4-CF$_3$) | O | O |
| H | H | 2,6-F$_2$ | 4-NH(C$_6$H$_4$-4-OCF$_3$) | O | O |
| H | H | 2,6-F$_2$ | 4-NH(C$_6$H$_4$-4-CF$_3$) | O | O |
| H | H | 2,6-F$_2$ | 4-N(CH$_2$CH$_2$CH$_3$)(C$_6$H$_4$-4-Cl) | O | O |
| H | H | 2,6-F$_2$ | 4-CH$_2$C$_6$H$_5$ | O | O |
| H | H | 2,6-F$_2$ | 4-CF$_2$(C$_6$H$_4$-4-Br) | O | O |
| H | H | 2,6-F$_2$ | 4-COC$_6$H$_5$ | O | O |
| H | H | 2,6-F$_2$ | 4-OCH$_2$(C$_6$H$_4$-4-Cl) | O | O |
| H | H | 2,6-F$_2$ | 4-OCH$_2$(C$_6$H$_4$-4-CF$_3$) | O | O |
| H | H | 2,6-F$_2$ | 4-OCH$_2$(C$_6$H$_3$-2,4-Cl$_2$) | O | O |
| H | H | 2,6-F$_2$ | 4-CH$_2$OC$_6$H$_5$ | O | O |
| H | H | 2,6-F$_2$ | 4-CH$_2$O(C$_6$H$_3$-2,4-Cl$_2$) | O | O |
| H | H | 2,6-F$_2$ | 4-CH$_2$O(C$_6$H$_3$-2,6-(CH$_3$)$_2$) | O | O |
| H | H | 2,6-F$_2$ | 4-NHCH$_2$C$_6$H$_5$ | O | O |
| H | H | 2,6-F$_2$ | 4-CH$_2$CH$_2$C$_6$H$_5$ | O | O |
| H | H | 2,6-F$_2$ | 4-CH=CH(C$_6$H$_4$-4-Cl) | O | O |
| H | H | 2,6-F$_2$ | 4-C≡C(C$_6$H$_4$-CF$_3$) | O | O |
| H | H | 2,6-F$_2$ | 4-N=NC$_6$H$_5$ | O | O |
| H | H | 2,6-F$_2$ | 4-OCH$_2$CHC$_6$H$_5$ | O | O |
| H | H | 2,6-F$_2$ | 4-NHCON(CH$_2$CH$_2$CH$_3$)(C$_6$H$_4$-4-Cl) | O | O |
| H | H | 2,6-F$_2$ | 4-NHCSNHC$_6$H$_5$ | O | O |
| H | H | 2,6-F$_2$ | 4-OCH$_2$CH$_2$O(C$_6$H$_3$-2-Cl-4-CF$_3$) | O | O |
| H | H | 2,6-F$_2$ | 4-CH$_2$ON=(Q51)(C$_6$H$_4$-4-Cl) | O | O |
| H | H | 2,6-F$_2$ | 4-OCH(CH(CH$_3$)$_2$)C$_6$H$_5$ | O | O |
| H | H | 2,6-F$_2$ | 4-O(Q1-1-CH$_3$) | O | O |
| H | H | 2,6-F$_2$ | 4-O(Q2-1-CH$_3$) | O | O |
| H | H | 2,6-F$_2$ | 4-(Q3) | O | O |
| H | H | 2,6-F$_2$ | 4-CH$_2$(Q4) | O | O |
| H | H | 2,6-F$_2$ | 4-(Q5) | O | O |

TABLE 1-continued

| | | | | | |
|---|---|---|---|---|---|
| H | H | 2,6-F$_2$ | 4-C≡C(Q6) | O | O |
| H | H | 2,6-F$_2$ | 4-CH$_2$(Q7) | O | O |
| H | H | 2,6-F$_2$ | 4-(Q8-3,5-(CF$_3$)$_2$) | O | O |
| H | H | 2,6-F$_2$ | 4-(Q8-3-C$_6$H$_5$) | O | O |
| H | H | 2,6-F$_2$ | 4-OCH$_2$(Q9-1-CH$_3$) | O | O |
| H | H | 2,6-F$_2$ | 4-O(Q10-1-CH$_3$) | O | O |
| H | H | 2,6-F$_2$ | 4-(Q11-1-C$_6$H$_5$) | O | O |
| H | H | 2,6-F$_2$ | 4-(Q12-1-CH$_3$) | O | O |
| H | H | 2,6-F$_2$ | 4-OCH$_2$(Q13-1-CH$_3$) | O | O |
| H | H | 2,6-F$_2$ | 4-O(Q14-1-CH$_3$) | O | O |
| H | H | 2,6-F$_2$ | 4-(Q15) | O | O |
| H | H | 2,6-F$_2$ | 4-O(Q16) | O | O |
| H | H | 2,6-F$_2$ | 4-O(Q17-5-CH$_3$) | O | O |
| H | H | 2,6-F$_2$ | 4-O(Q18) | O | O |
| H | H | 2,6-F$_2$ | 4-OCH$_2$(Q19) | O | O |
| H | H | 2,6-F$_2$ | 4-OCH$_2$(Q20-4-Cl) | O | O |
| H | H | 2,6-F$_2$ | 4-(Q21) | O | O |
| H | H | 2,6-F$_2$ | 4-OCH$_2$(Q22) | O | O |
| H | H | 2,6-F$_2$ | 4-(Q23) | O | O |
| H | H | 2,6-F$_2$ | 4-OCH$_2$(Q24) | O | O |
| H | H | 2,6-F$_2$ | 4-O(Q25-3-CH$_3$) | O | O |
| H | H | 2,6-F$_2$ | 4-(Q26-1-CH$_3$) | O | O |
| H | H | 2,6-F$_2$ | 4-OCH$_2$(Q27-1-CH$_3$) | O | O |
| H | H | 2,6-F$_2$ | 4-OCH$_2$(Q28-1-CH$_3$) | O | O |
| H | H | 2,6-F$_2$ | 4-O(Q29-1-CH$_3$) | O | O |
| H | H | 2,6-F$_2$ | 4-NHCONH(Q30) | O | O |
| H | H | 2,6-F$_2$ | 4-O(Q31) | O | O |
| H | H | 2,6-F$_2$ | 4-OCH$_2$(Q32) | O | O |
| H | H | 2,6-F$_2$ | 4-OCH$_2$(Q33) | O | O |
| H | H | 2,6-F$_2$ | 4-O(Q34) | O | O |
| H | H | 2,6-F$_2$ | 4-OCH$_2$(Q35) | O | O |
| H | H | 2,6-F$_2$ | 4-O(Q36) | O | O |
| H | H | 2,6-F$_2$ | 4-OCH$_2$(Q37-5-Cl) | O | O |
| H | H | 2,6-F$_2$ | 3-O(Q38-5-CF$_2$CFCl$_2$) | O | O |
| H | H | 2,6-F$_2$ | 3-O(Q38-3-Cl-5-CF$_3$) | O | O |
| H | H | 2,6-F$_2$ | 4-O(Q38-3-Cl-5-CF$_3$) | O | O |
| H | H | 2,6-F$_2$ | 4-O(Q38-3-Cl-5-CN) | O | O |
| H | H | 2,6-F$_2$ | 4-O(Q38-3-Cl-5-CF$_2$CFCl$_2$) | O | O |
| H | H | 2,6-F$_2$ | 4-O(Q38-5-CF$_3$-6-Cl) | O | O |
| H | H | 2,6-F$_2$ | 4-NH(Q38-5-CF$_3$) | O | O |
| H | H | 2,6-F$_2$ | 4-NH(Q38-3-Cl-5-CF$_3$) | O | O |
| H | H | 2,6-F$_2$ | 4-(Q38-3-Cl-5-CF$_3$) | O | O |
| H | H | 2,6-F$_2$ | 4-O(Q39-5-Br) | O | O |
| H | H | 2,6-F$_2$ | 4-O(Q40-2,6-Cl$_2$) | O | O |
| H | H | 2,6-F$_2$ | 4-O(Q41-6-Cl) | O | O |
| H | H | 2,6-F$_2$ | 4-O(Q42) | O | O |
| H | H | 2,6-F$_2$ | 4-O(Q43-5-Cl) | O | O |
| H | H | 2,6-F$_2$ | 4-O(Q44) | O | O |
| H | H | 2,6-F$_2$ | 4-O(Q45-4-CF$_3$-6-Cl) | O | O |
| H | H | 2,6-F$_2$ | 4-O(Q46) | O | O |
| H | H | 2,6-F$_2$ | 4-O(Q47) | O | O |
| H | H | 2,6-F$_2$ | 4-O(Q47-4-Cl) | O | O |
| H | H | 2,6-F$_2$ | 4-O(Q48) | O | O |
| H | H | 2,6-F$_2$ | 4-O(Q49) | O | O |
| H | H | 2,6-F$_2$ | 3-O(Q50-6-Cl) | O | O |
| H | H | 2,6-F$_2$ | 3-O(Q50-6-CF$_3$) | O | O |
| H | H | 2,6-F$_2$ | 3-O(Q50-6-F) | O | O |
| H | H | 2,6-F$_2$ | 4-O(Q50-6-Cl) | O | O |
| H | H | 2,6-F$_2$ | 4-O(Q50-6-CF$_3$) | O | O |
| H | H | 2,6-F$_2$ | 2,4-F$_2$ | O | O |
| H | H | 2,6-F$_2$ | 2,6-F$_2$ | O | O |
| H | H | 2,6-F$_2$ | 3,5-F$_2$ | O | O |
| H | H | 2,6-F$_2$ | 2,3-Cl$_2$ | O | O |
| H | H | 2,6-F$_2$ | 2,4-Cl$_2$ | O | O |
| H | H | 2,6-F$_2$ | 2,5-Cl$_2$ | O | O |
| H | H | 2,6-F$_2$ | 2,6-Cl$_2$ | O | O |
| H | H | 2,6-F$_2$ | 3,4-Cl$_2$ | O | O |
| H | H | 2,6-F$_2$ | 3,5-Cl$_2$ | O | O |
| H | H | 2,6-F$_2$ | 3,4-Br$_2$ | O | O |
| H | H | 2,6-F$_2$ | 2,4-I$_2$ | O | O |
| H | H | 2,6-F$_2$ | 2,4-(CH$_3$)$_2$ | O | O |
| H | H | 2,6-F$_2$ | 3,4-(OCH$_3$)$_2$ | O | O |
| H | H | 2,6-F$_2$ | 2-F-4-Cl | O | O |
| H | H | 2,6-F$_2$ | 2-F-4-Br | O | O |
| H | H | 2,6-F$_2$ | 2-F-4-OCH(CH$_3$)$_2$ | O | O |
| H | H | 2,6-F$_2$ | 2-F-4-OCHF$_2$ | O | O |
| H | H | 2,6-F$_2$ | 2-F-4-OCF$_2$CHF$_2$ | O | O |
| H | H | 2,6-F$_2$ | 2-F-4-OCF$_2$CHFCF$_3$ | O | O |
| H | H | 2,6-F$_2$ | 2-F-4-OCF$_2$CHFOCF$_3$ | O | O |
| H | H | 2,6-F$_2$ | 2-F-4-SO$_2$CF$_2$CHFCl | O | O |
| H | H | 2,6-F$_2$ | 2-F-4-O(C$_6$H$_3$-2-Cl-4-CF$_3$) | O | O |
| H | H | 2,6-F$_2$ | 2-F-4-N-NC$_6$H$_5$ | O | O |

TABLE 1-continued

| | | | | | |
|---|---|---|---|---|---|
| H | H | 2,6-F₂ | 2-F-4-NHCON(CH₂CH₂CH₃)(C₆H₄-4-Cl) | O | O |
| H | H | 2,6-F₂ | 2-F-4-O(Q38-3-Cl-5-CF₃) | O | O |
| H | H | 2,6-F₂ | 3-F-4-O(Q38-3-Cl-5-CF₃) | O | O |
| H | H | 2,6-F₂ | 2-Cl-4-CF₃ | O | O |
| H | H | 2,6-F₂ | 2-Cl-4-SCF₂CHF₂ | O | O |
| H | H | 2,6-F₂ | 2-Cl-4-O(C₆H₃-2-Cl-4-CF₃) | O | O |
| H | H | 2,6-F₂ | 2-Cl-4-O(Q38-3-Cl-5-CF₃) | O | O |
| H | H | 2,6-F₂ | 2-Cl-5-O(Q50-6-CF₃) | O | O |
| H | H | 2,6-F₂ | 2-Cl-5-S(Q50-6-CF₃) | O | O |
| H | H | 2,6-F₂ | 3-Cl-4-CF₃ | O | O |
| H | H | 2,6-F₂ | 3-Cl-4-OC(CH₃)₃ | O | O |
| H | H | 2,6-F₂ | 3-Cl-4-OCF₃ | O | O |
| H | H | 2,6-F₂ | 3-Cl-4-OCF₂CHF₂ | O | O |
| H | H | 2,6-F₂ | 3-Cl-4-OCF₂CHFOCF₃ | O | O |
| H | H | 2,6-F₂ | 3-Cl-4-SCF₂Cl | O | O |
| H | H | 2,6-F₂ | 3-Cl-4-CO₂CH(CH(CH₃)₂)₂ | O | O |
| H | H | 2,6-F₂ | 3-Cl-4-CO₂CH(CH₂F)₂ | O | O |
| H | H | 2,6-F₂ | 3-Cl-4-CO₂C(CH₃)(CF₃)₂ | O | O |
| H | H | 2,6-F₂ | 3-Cl-4-O(C₆H₄-4-Cl) | O | O |
| H | H | 2,6-F₂ | 3-Cl-4-O(C₆H₄-4-NO₂) | O | O |
| H | H | 2,6-F₂ | 3-Cl-4-O(C₆H₄-4-CF₃) | O | O |
| H | H | 2,6-F₂ | 3-Cl-4-O(C₆H₃-2-Cl-4-CF₃) | O | O |
| H | H | 2,6-F₂ | 3-Cl-4-O(C₆H₃-2-Cl-4-OCF₃) | O | O |
| H | H | 2,6-F₂ | 3-Cl-4-CF₂(C₆H₄-4-Br) | O | O |
| H | H | 2,6-F₂ | 3-Cl-4-CH=CH(C₆H₄-4-Cl) | O | O |
| H | H | 2,6-F₂ | 3-Cl-4-O(Q38-5-CF₃) | O | O |
| H | H | 2,6-F₂ | 3-Cl-4-O(Q38-5-CF₂CF₂CF₃) | O | O |
| H | H | 2,6-F₂ | 3-Cl-4-O(Q38-3-Cl-5-CF₃) | O | O |
| H | H | 2,6-F₂ | 3-Cl-4-O(Q38-5-CF₃-6-Cl) | O | O |
| H | H | 2,6-F₂ | 3-Cl-4-NH(Q38-5-CF₃) | O | O |
| H | H | 2,6-F₂ | 3-Cl-4-N(COC(CH₃)₃)(Q38-5-CF₃) | O | O |
| H | H | 2,6-F₂ | 2-CH₃-4-N=NC₆H₅ | O | O |
| H | H | 2,6-F₂ | 2-CH₃-4-O(Q38-3-Cl-5-CF₃) | O | O |
| H | H | 2,6-F₂ | 3-CH₃-4-OCF₂CHF₂ | O | O |
| H | H | 2,6-F₂ | 3-CH₃-4-O(C₆H₃-2-Cl-4-CF₃) | O | O |
| H | H | 2,6-F₂ | 3-CH₃-4-O(Q38-3-Cl-5-CF₃) | O | O |
| H | H | 2,6-F₂ | 3-Br-4-O(Q38-3-Cl-5-CF₃) | O | O |
| H | H | 2,6-F₂ | 3-CF₃-4-Cl | O | O |
| H | H | 2,6-F₂ | 3-CF₃-4-OCF₂CHF₂ | O | O |
| H | H | 2,6-F₂ | 3-CF₃-4-OCF₂CHFBr | O | O |
| H | H | 2,6-F₂ | 3-CF₃-4-OCF₂CHFCF₃ | O | O |
| H | H | 2,6-F₂ | 3-CF₃-4-O(Q38-3-Cl-5-CF₃) | O | O |
| H | H | 2,6-F₂ | 3-OCH₃-4-O(C₆H₃-2-Cl-4-CF₃) | O | O |
| H | H | 2,6-F₂ | 3-CO₂CH₃-4-O(Q38-3-Cl-5-CF₃) | O | O |
| H | H | 2,6-F₂ | 3-CO₂CH₂CH₃-4-O(Q38-3-Cl-5-CF₂CFCl₂) | O | O |
| H | H | 2,6-F₂ | 2,3-F₂-4-OCF₃ | O | O |
| H | H | 2,6-F₂ | 2,3-F₂-4-O(Q38-3-Cl-5-CF₃) | O | O |
| H | H | 2,6-F₂ | 2,5-F₂-4-Cl | O | O |
| H | H | 2,6-F₂ | 2,5-F₂-4-Br | O | O |
| H | H | 2,6-F₂ | 2,5-F₂-4-OCF₃ | O | O |
| H | H | 2,6-F₂ | 2,5-F₂-4-S(Q38-3-Cl-5-CF₃) | O | O |
| H | H | 2,6-F₂ | 3,5-F₂-4-CF₃ | O | O |
| H | H | 2,6-F₂ | 2,3-Cl₂-4-OCF₂CHFCl | O | O |
| H | H | 2,6-F₂ | 2,3-Cl₂-4-O(C₆H₃-2-F-4-Br) | O | O |
| H | H | 2,6-F₂ | 2,5-Cl₂-4-OCF₂CHF₂ | O | O |
| H | H | 2,6-F₂ | 2,5-Cl₂-4-OCF₂CHFCF₃ | O | O |
| H | H | 2,6-F₂ | 2,5-Cl₂-4-OCF₂CF₂CF₃ | O | O |
| H | H | 2,6-F₂ | 2,5-Cl₂-4-O(C₆H₃-2-Cl-4-CF₃) | O | O |
| H | H | 2,6-F₂ | 2,5-Cl₂-4-O(Q38-3-Cl-5-CF₃) | O | O |
| H | H | 2,6-F₂ | 2,6-Cl₂-4-CF₃ | O | O |
| H | H | 2,6-F₂ | 3,4,5-Cl₃ | O | O |
| H | H | 2,6-F₂ | 3,5-Cl₂-4-OCH₂CH₂OCH₃ | O | O |
| H | H | 2,6-F₂ | 3,5-Cl₂-4-OCH₂CH=CH₂ | O | O |
| H | H | 2,6-F₂ | 3,5-Cl₂-4-OCH₂CH=CHCH₃ | O | O |
| H | H | 2,6-F₂ | 3,5-Cl₂-4-OCF₂CHF₂ | O | O |
| H | H | 2,6-F₂ | 3,5-Cl₂-4-OCH₂CF₃ | O | O |
| H | H | 2,6-F₂ | 3,5-Cl₂-4-OCF₂CHFCl | O | O |
| H | H | 2,6-F₂ | 3,5-Cl₂-4-OCF₂CHCl₂ | O | O |
| H | H | 2,6-F₂ | 3,5-Cl₂-4-OCF₂CHFCF₃ | O | O |
| H | H | 2,6-F₂ | 3,5-Cl₂-4-OCF₂CHFOCF₃ | O | O |
| H | H | 2,6-F₂ | 3,5-Cl₂-4-OCF₂CF₂CF₃ | O | O |
| H | H | 2,6-F₂ | 3,5-Cl₂-4-SCF₂CHF₂ | O | O |
| H | H | 2,6-F₂ | 3,5-Cl₂-4-SCH₂CF₂ | O | O |
| H | H | 2,6-F₂ | 3,5-Cl₂-4-N(CH₃)CH₂CH₂CH₃ | O | O |
| H | H | 2,6-F₂ | 3,5-Cl₂-4-N(CH₃)CH₂C≡CH | O | O |
| H | H | 2,6-F₂ | 3,5-Cl₂-4-N(CH₃)CH₂CH=CHCl | O | O |
| H | H | 2,6-F₂ | 3,5-Cl₂-4-N(CH₃)CH₂C₆H₅ | O | O |
| H | H | 2,6-F₂ | 3,5-Cl₂-4-O(C₆H₄-3-F) | O | O |
| H | H | 2,6-F₂ | 3,5-Cl₂-4-O(C₆H₄-3-Br) | O | O |
| H | H | 2,6-F₂ | 3,5-Cl₂-4-O(C₆H₄-4-Cl) | O | O |
| H | H | 2,6-F₂ | 3,5-Cl₂-4-O(C₆H₄-CN) | O | O |
| H | H | 2,6-F₂ | 3,5-Cl₂-4-O(C₆H₄-4-NO₂) | O | O |

TABLE 1-continued

| | | | | | |
|---|---|---|---|---|---|
| H | H | 2,6-F₂ | 3,5-Cl₂-4-O(C₆H₄-4-SO₂CF₃) | O | O |
| H | H | 2,6-F₂ | 3,5-Cl₂-4-O(C₆H₄-4-SO₂C₆H₅) | O | O |
| H | H | 2,6-F₂ | 3,5-Cl₂-4-O(C₆H₃-2,4-F₂) | O | O |
| H | H | 2,6-F₂ | 3,5-Cl₂-4-O(C₆H₃-2-Cl-4-CF₃) | O | O |
| H | H | 2,6-F₂ | 3,5-Cl₂-4-O(C₆H₃-3-OCF₂CF₂O-4) | O | O |
| H | H | 2,6-F₂ | 3,5-Cl₂-4-OCH₂(C₆H₄-4-Cl) | O | O |
| H | H | 2,6-F₂ | 3,5-Cl₂-4-OCH₂(C₆H₄-4-CF₃) | O | O |
| H | H | 2,6-F₂ | 3,5-Cl₂-4-OCH₂(C₆H₄-2-C₆H₅) | O | O |
| H | H | 2,6-F₂ | 3,5-Cl₂-4-OCH₂(C₆H₃-2,4-Cl₂) | O | O |
| H | H | 2,6-F₂ | 3,5-Cl₂-4-NH(C₆H₄-4-CF₃) | O | O |
| H | H | 2,6-F₂ | 3,5-Cl₂-4-NH(C₆H₄-4-OCF₃) | O | O |
| H | H | 2,6-F₂ | 3,5-Cl₂-4-(Q3) | O | O |
| H | H | 2,6-F₂ | 3,5-Cl₂-4-(Q6-3-C₆H₅) | O | O |
| H | H | 2,6-F₂ | 3,5-Cl₂-4-(Q38-3-Cl-5-CF₃) | O | O |
| H | H | 2,6-F₂ | 3,5-Cl₂-4-(Q38-3-Cl-5-CF₃) | O | O |
| H | H | 2,6-F₂ | 3,5-Cl₂-4-(Q38-3-Cl-5-CN) | O | O |
| H | H | 2,6-F₂ | 3,5-Cl₂-4-OCH₂CH₂O(Q38-3-Cl-5-CF₃) | O | O |
| H | H | 2,6-F₂ | 3,5-Cl₂-4-O(Q43-5-Cl) | O | O |
| H | H | 2,6-F₂ | 3,5-Cl₂-4-O(Q45-2-CH₃) | O | O |
| H | H | 2,6-F₂ | 3,5-Cl₂-4-(Q47-4-Cl) | O | O |
| H | H | 2,6-F₂ | 3,5-Cl₂-4-O(Q50-6-Cl) | O | O |
| H | H | 2,6-F₂ | 3,5-Cl₂-4-O(Q50-6-CF₃) | O | O |
| H | H | 2,6-F₂ | 3,5-Cl₂-4-O(Q45-2-CH₃) | O | O |
| H | H | 2,6-F₂ | 2,5-(CH₃)₂-4-O(C₆H₃-2-Cl-4-CF₃) | O | O |
| H | H | 2,6-F₂ | 3,5-(CH₃)₂-4-OCF₂CHFCl | O | O |
| H | H | 2,6-F₂ | 3,5-(CH₃)₂-4-O(C₆H₃-3,5-F₂) | O | O |
| H | H | 2,6-F₂ | 3,5-(CH₃)₂-4-O(C₆H₂-2,3,5-F₃) | O | O |
| H | H | 2,6-F₂ | 3,5-(CH₃)₂-4-N=NC₆H₅ | O | O |
| H | H | 2,6-F₂ | 2-F-4,5-Cl₂ | O | O |
| H | H | 2,6-F₂ | 2-F-3-CF₃-5-Cl | O | O |
| H | H | 2,6-F₂ | 2-F-4-Br-5-CF₃ | O | O |
| H | H | 2,6-F₂ | 2-F-4-Cl-5-OCH(CH₃)₂ | O | O |
| H | H | 2,6-F₂ | 2-F-4-Br-5-OCF₃ | O | O |
| H | H | 2,6-F₂ | 2-F-4-OCH₂CF₃-5-Cl | O | O |
| H | H | 2,6-F₂ | 2-F-4-OCF₂CHF₂-5-Cl | O | O |
| H | H | 2,6-F₂ | 2-4-F-O(C₆H₃-2-Cl-4-CF₃)-5-Cl | O | O |
| H | H | 2,6-F₂ | 2-F-4-S(C₆H₃-2-Cl-4-CF₃)-5-Cl | O | O |
| H | H | 2,6-F₂ | 2-Cl-3-CF₃5-NO₂ | O | O |
| H | H | 2,6-F₂ | 3-Cl-4-OCF₂CHF₂-5-CF₃ | O | O |
| H | H | 2,6-F₂ | 3-Cl-4-OCF₂CHF₂-5-CH₂OCH₃ | O | O |
| H | H | 2,6-F₂ | 3-Cl-4-OCF₂CHFCF₃-5-CF₃ | O | O |
| H | H | 2,6-F₂ | 3-Cl-4-O(Q38-3-Cl-5-CF₃)-5-CO₂H | O | O |
| H | H | 2,6-F₂ | 3-Cl-4-O(Q38-3-Cl-5-CF₃)-5-CO₂CH₃ | O | O |
| H | H | 2,6-F₂ | 3-Cl-4-O(Q38-3-Cl-5-CF₃)-5-CH₂OCH₃ | O | O |
| H | H | 2,6-F₂ | 2-CF₃-4,6-(NO₂)₂ | O | O |
| H | H | 2,6-F₂ | 2-CF₃-4-OCF₂CHFCF₃-5-Cl | O | O |
| H | H | 2,6-F₂ | 2-CF₃-4-OCH₂CH=CHCl-5-Br | O | O |
| H | H | 2,6-F₂ | 2-CH₃-4-CH(CN)(C₆H₄-4-Cl)-5-Cl | O | O |
| H | H | 2,6-F₂ | 2,3,4,5-F₄ | O | O |
| H | H | 2,6-F₂ | 2,4-F₂-3,5-Cl₂ | O | O |
| H | H | 2,6-F₂ | 2,6-F₂-3,5-Cl₂ | O | O |
| H | H | 2,6-F₂ | 2,4-F₂-3-Cl-5-Br | O | O |
| H | H | 2,6-F₂ | 2,4-Cl₂-3,5-F₂ | O | O |
| H | H | 2,6-F₂ | 2,6-Cl₂-3,5-F₂ | O | O |
| H | H | 2,6-F₂ | 2-F-3,5-Cl₂-4-OCH₃ | O | O |
| H | H | 2,6-F₂ | 2,3,5-F₃-4-OCF₂CHFCF₃ | O | O |
| H | H | 2,6-F₂ | 2-F-3,5-Cl₂-4-OCH₂CF₃ | O | O |
| H | H | 2,6-F₂ | 2-F-3,5-Cl₂-4-OCF₂CHF₂ | O | O |
| H | H | 2,6-F₂ | 2-F-3,5-Cl₂-4-OCF₂CHFOCF₃ | O | O |
| H | H | 2,6-F₂ | 2-F-3,5-Cl₂-4-N(CH₃)CH₂CH₃ | O | O |
| H | H | 2,6-F₂ | 2-F-3,5-Cl₂-4-N(CH₃)CH₂C₆H₅ | O | O |
| H | H | 2,6-F₂ | 2-F-3,5-Cl₂-4-O(C₆H₃-2-Cl-4-CF₃) | O | O |
| H | H | 2,6-F₂ | 2-F-3,5-Cl₂-4-O(Q38-3-Cl-5-CF₃) | O | O |
| H | H | 2,6-F₂ | 2,5-(CH₃)₂-3-Cl-4-O(C₆H₃-2,4-(CH₃)₂) | O | O |
| H | H | 2,6-F₂ | 2-CH₃-3,5-Cl₂-4-O(C₆H₃-2-CH₃-4-Cl) | O | O |
| H | H | 2,6-F₂ | 2-CH₃-3-Cl-4-O(C₆H₄-4-F)-5-CH(OCH₃)₂ | O | O |
| H | H | 2,6-F₂ | 2,3,4,5,6-F₅ | O | O |
| H | H | 2,6-F₂ | 2,4,6-F₃-3,5-Cl₂ | O | O |
| H | H | 2,6-F₂ | 3-Cl-4-F | O | O |
| H | H | 2,6-F₂ | 4-CH₂CH₂CH₂CH₃ | O | O |
| H | H | 2-Cl | 2-F | O | O |
| H | H | 2-Cl | 3-F | O | O |
| H | H | 2-Cl | 4-F | O | O |
| H | H | 2-Cl | 2-Cl | O | O |
| H | H | 2-Cl | 3-Cl | O | O |
| H | H | 2-Cl | 4-Cl | O | O |
| H | H | 2-Cl | 4-Br | O | O |
| H | H | 2-Cl | 4-I | O | O |
| H | H | 2-Cl | 4-CH₃ | O | O |

-continued

| | | | | | |
|---|---|---|---|---|---|
| H | H | 2-Cl | 4-CH(CH$_3$)$_2$ | O | O |
| H | H | 2-Cl | 4-CH$_2$CH$_2$CH$_2$CH$_3$ | O | O |
| H | H | 2-Cl | 4-C(CH$_3$)$_3$ | O | O |
| H | H | 2-Cl | 4-CH$_2$CH=CH$_2$ | O | O |
| H | H | 2-Cl | 4-CH$_2$CH=CHCH$_3$ | O | O |
| H | H | 2-Cl | 4-C≡CH | O | O |
| H | H | 2-Cl | 4-CH$_2$C≡CH | O | O |
| H | H | 2-Cl | 4-Q51 | O | O |
| H | H | 2-Cl | 4-Q52 | O | O |
| H | H | 2-Cl | 4-Q53 | O | O |
| H | H | 2-Cl | 4-Q54 | O | O |
| H | H | 2-Cl | 4-CHF$_2$ | O | O |
| H | H | 2-Cl | 4-CH$_2$Br | O | O |
| H | H | 2-Cl | 4-CH$_2$Cl | O | O |
| H | H | 2-Cl | 2-CF$_3$ | O | O |
| H | H | 2-Cl | 3-CF$_3$ | O | O |
| H | H | 2-Cl | 4-CH$_2$CH=CHCl | O | O |
| H | H | 2-Cl | 4-CH=C(Cl)CF$_3$ | O | O |
| H | H | 2-Cl | 4-CH$_2$C≡CBr | O | O |
| H | H | 2-Cl | 4-(Q54-1-Cl) | O | O |
| H | H | 2-Cl | 4-CH$_2$CN | O | O |
| H | H | 2-Cl | 4-CH$_2$CH(CH$_3$)CN | O | O |
| H | H | 2-Cl | 4-CH$_2$OH | O | O |
| H | H | 2-Cl | 4-CH$_2$CO$_2$H | O | O |
| H | H | 2-Cl | 4-OCH$_3$ | O | O |
| H | H | 2-Cl | 4-OCH$_2$CH$_3$ | O | O |
| H | H | 2-Cl | 4-OCH(CH$_3$)$_2$ | O | O |
| H | H | 2-Cl | 4-OC(CH$_3$)$_3$ | O | O |
| H | H | 2-Cl | 4-OCH$_2$CH=CH$_2$ | O | O |
| H | H | 2-Cl | 4-OCH$_2$C≡CH | O | O |
| H | H | 2-Cl | 4-O(Q53) | O | O |
| H | H | 2-Cl | 4-O(Q54) | O | O |
| H | H | 2-Cl | 4-O(Q54-2-CH(CH$_3$)$_2$-5-CH$_3$) | O | O |
| H | H | 2-Cl | 4-OCHF$_2$ | O | O |
| H | H | 2-Cl | 4-OCF$_2$Br | O | O |
| H | H | 2-Cl | 2-OCF$_3$ | O | O |
| H | H | 2-Cl | 3-OCF$_3$ | O | O |
| H | H | 2-Cl | 4-OCF$_3$ | O | O |
| H | H | 2-Cl | 4-OCH$_2$CF$_3$ | O | O |
| H | H | 2-Cl | 4-OCF$_2$CHF$_2$ | O | O |
| H | H | 2-Cl | 4-OCF$_2$CHCl$_2$ | O | O |
| H | H | 2-Cl | 4-OCF$_2$CHFCl | O | O |
| H | H | 2-Cl | 4-OCF$_2$CHFBr | O | O |
| H | H | 2-Cl | 4-OCF$_2$CF$_2$CF$_3$ | O | O |
| H | H | 2-Cl | 4-OCH$_2$CH=CHCl | O | O |
| H | H | 2-Cl | 4-OCH$_2$C≡CBr | O | O |
| H | H | 2-Cl | 4-O(Q51-2,2-Cl$_2$) | O | O |
| H | H | 2-Cl | 4-OCH$_2$(Q51-2,2-Cl$_2$) | O | O |
| H | H | 2-Cl | 4-SCH$_3$ | O | O |
| H | H | 2-Cl | 4-SCH$_2$CH=CH$_2$ | O | O |
| H | H | 2-Cl | 4-SCH$_2$C≡CH | O | O |
| H | H | 2-Cl | 4-S(Q54) | O | O |
| H | H | 2-Cl | 4-SCHF$_2$ | O | O |
| H | H | 2-Cl | 4-SCF$_3$ | O | O |
| H | H | 2-Cl | 4-SCF$_2$Cl | O | O |
| H | H | 2-Cl | 4-SOCH$_3$ | O | O |
| H | H | 2-Cl | 4-SOCH$_2$CH=CH$_2$ | O | O |
| H | H | 2-Cl | 4-SOCH$_2$C≡CH | O | O |
| H | H | 2-Cl | 4-SO(Q54) | O | O |
| H | H | 2-Cl | 4-SOCF$_3$ | O | O |
| H | H | 2-Cl | 4-SO$_2$CH$_3$ | O | O |
| H | H | 2-Cl | 4-SO$_2$CH$_2$CH=CH$_2$ | O | O |
| H | H | 2-Cl | 4-SO$_2$CH$_2$C≡CH | O | O |
| H | H | 2-Cl | 4-SO$_2$(Q54) | O | O |
| H | H | 2-Cl | 4-SO$_2$CF$_3$ | O | O |
| H | H | 2-Cl | 4-SO$_2$CF$_2$CHFCl | O | O |
| H | H | 2-Cl | 4-CH$_2$OCH$_3$ | O | O |
| H | H | 2-Cl | 4-OCH$_2$CH$_2$OCH$_3$ | O | O |
| H | H | 2-Cl | 4-CH$_2$OCH$_2$CF$_3$ | O | O |
| H | H | 2-Cl | 4-OCF$_2$CHFOCF$_3$ | O | O |
| H | H | 2-Cl | 4-CH$_2$SCH$_3$ | O | O |
| H | H | 2-Cl | 4-OCH$_2$CH$_2$SCH$_3$ | O | O |
| H | H | 2-Cl | 4-CH$_2$CO$_2$CH$_3$ | O | O |
| H | H | 2-Cl | 4-CH$_2$CO$_2$CH$_2$CF$_3$ | O | O |
| H | H | 2-Cl | 4-CH$_2$COCH$_3$ | O | O |
| H | H | 2-Cl | 4-OCO$_2$CH$_3$ | O | O |
| H | H | 2-Cl | 4-OCOCH$_3$ | O | O |
| H | H | 2-Cl | 4-COCH$_3$ | O | O |
| H | H | 2-Cl | 4-COCH$_2$CH=CH$_2$ | O | O |
| H | H | 2-Cl | 4-COCH$_2$C≡CH | O | O |
| H | H | 2-Cl | 4-CO(Q53) | O | O |
| H | H | 2-Cl | 4-COCF$_3$ | O | O |
| H | H | 2-Cl | 4-CO$_2$CH$_2$CH$_3$ | O | O |

-continued

| | | | | | |
|---|---|---|---|---|---|
| H | H | 2-Cl | 4-CO$_2$C(CH$_3$)$_3$ | O | O |
| H | H | 2-Cl | 4-CO$_2$CH$_2$CF$_3$ | O | O |
| H | H | 2-Cl | 4-CO$_2$CH(CH$_2$F)$_2$ | O | O |
| H | H | 2-Cl | 4-CO$_2$C(CH$_3$)(CF$_3$)$_2$ | O | O |
| H | H | 2-Cl | 4-OCH$_2$CO$_2$CH$_3$ | O | O |
| H | H | 2-Cl | 4-NO$_2$ | O | O |
| H | H | 2-Cl | 4-CN | O | O |
| H | H | 2-Cl | 4-OH | O | O |
| H | H | 2-Cl | 4-CO$_2$H | O | O |
| H | H | 2-Cl | 4-SCN | O | O |
| H | H | 2-Cl | 4-NCS | O | O |
| H | H | 2-Cl | 4-CH$_2$SCN | O | O |
| H | H | 2-Cl | 4-OSO$_2$CH$_3$ | O | O |
| H | H | 2-Cl | 4-CSCH$_3$ | O | O |
| H | H | 2-Cl | 4-NH$_2$ | O | O |
| H | H | 2-Cl | 4-N(CH$_3$)$_2$ | O | O |
| H | H | 2-Cl | 4-N(CH$_3$)CH$_2$CH$_3$ | O | O |
| H | H | 2-Cl | 4-N(CH$_3$)CH$_2$CH$_2$CH$_3$ | O | O |
| H | H | 2-Cl | 4-N(CH$_3$)CH$_2$CH=CHCl | O | O |
| H | H | 2-Cl | 4-N(CH$_3$)CH$_2$C≡CH | O | O |
| H | H | 2-Cl | 4-N(CH$_3$)CH$_2$C$_6$H$_5$ | O | O |
| H | H | 2-Cl | 4-CON(CH$_3$)$_2$ | O | O |
| H | H | 2-Cl | 4-OCON(CH$_3$)$_2$ | O | O |
| H | H | 2-Cl | 4-NHCOCH$_3$ | O | O |
| H | H | 2-Cl | 4-NHCO$_2$CH$_2$CH$_3$ | O | O |
| H | H | 2-Cl | 4-SO$_2$N(CH$_3$)$_2$ | O | O |
| H | H | 2-Cl | 4-NHCSCH$_3$ | O | O |
| H | H | 2-Cl | 4-Si(CH$_3$)$_3$ | O | O |
| H | H | 2-Cl | 3-OCH$_2$O-4 | O | O |
| H | H | 2-Cl | 3-OCF$_2$O-4 | O | O |
| H | H | 2-Cl | 3-OCH$_2$CH$_2$O-4 | O | O |
| H | H | 2-Cl | 3-OCF$_2$CF$_2$O-4 | O | O |
| H | H | 2-Cl | 3-OC(CH$_3$)$_2$CF$_2$O-4 | O | O |
| H | H | 2-Cl | 4-C$_6$H$_5$ | O | O |
| H | H | 2-Cl | 4-(C$_6$H$_4$-4-Cl) | O | O |
| H | H | 2-Cl | 4-OC$_6$H$_5$ | O | O |
| H | H | 2-Cl | 4-O(C$_6$H$_4$-2-C$_6$H$_5$) | O | O |
| H | H | 2-Cl | 4-O(C$_6$H$_4$-3-F) | O | O |
| H | H | 2-Cl | 4-O(C$_6$H$_4$-3-Br) | O | O |
| H | H | 2-Cl | 4-O(C$_6$H$_4$-4-Cl) | O | O |
| H | H | 2-Cl | 4-O(C$_6$H$_4$-4-Br) | O | O |
| H | H | 2-Cl | 4-O(C$_6$H$_4$-4-CF$_3$) | O | O |
| H | H | 2-Cl | 4-O(C$_6$H$_4$-4-CN) | O | O |
| H | H | 2-Cl | 4-O(C$_6$H$_4$-4-NO$_2$) | O | O |
| H | H | 2-Cl | 4-O(C$_6$H$_4$-4-OCHF$_2$) | O | O |
| H | H | 2-Cl | 4-O(C$_6$H$_4$-4-OCF$_3$) | O | O |
| H | H | 2-Cl | 4-O(C$_6$H$_4$-4-SO$_2$CF$_3$) | O | O |
| H | H | 2-Cl | 4-O(C$_6$H$_4$-4-SO$_2$C$_6$H$_5$) | O | O |
| H | H | 2-Cl | 4-O(C$_6$H$_3$-2,4-F$_2$) | O | O |
| H | H | 2-Cl | 4-O(C$_6$H$_3$-3,5-F$_2$) | O | O |
| H | H | 2-Cl | 4-O(C$_6$H$_3$-2,4-Cl$_2$) | O | O |
| H | H | 2-Cl | 4-O(C$_6$H$_3$-3,5-Cl$_2$) | O | O |
| H | H | 2-Cl | 4-O(C$_6$H$_3$-2,4-(CH$_3$)$_2$) | O | O |
| H | H | 2-Cl | 4-O(C$_6$H$_3$-2,6-(CH$_3$)$_2$) | O | O |
| H | H | 2-Cl | 4-O(C$_6$H$_3$-3-OCF$_2$CF$_2$O-4) | O | O |
| H | H | 2-Cl | 4-O(C$_6$H$_3$-2-F-4-Br) | O | O |
| H | H | 2-Cl | 4-O(C$_6$H$_3$-2-F-4-CF$_3$) | O | O |
| H | H | 2-Cl | 4-O(C$_6$H$_3$-2-Cl-4-CF$_3$) | O | O |
| H | H | 2-Cl | 4-O(C$_6$H$_2$-2,3,5-F$_3$) | O | O |
| H | H | 2-Cl | 4-O(C$_6$H$_2$-2,5-(CH$_3$)$_2$-4-Cl) | O | O |
| H | H | 2-Cl | 3-O(C$_6$H$_4$-4-CF$_3$) | O | O |
| H | H | 2-Cl | 3-O(C$_6$H$_3$-2-Cl-4-CF$_3$) | O | O |
| H | H | 2-Cl | 4-S(C$_6$H$_3$-2-Cl-4-CF$_3$) | O | O |
| H | H | 2-Cl | 4-SO$_2$C$_6$H$_5$ | O | O |
| H | H | 2-Cl | 4-NH(C$_6$H$_3$-3,5-Cl$_2$) | O | O |
| H | H | 2-Cl | 4-NH(C$_6$H$_3$-2-Cl-4-CF$_3$) | O | O |
| H | H | 2-Cl | 4-NH(C$_6$H$_4$-4-OCF$_3$) | O | O |
| H | H | 2-Cl | 4-NH(C$_6$H$_4$-4-CF$_3$) | O | O |
| H | H | 2-Cl | 4-N(CH$_2$CH$_2$CH$_3$)(C$_6$H$_4$-4-Cl) | O | O |
| H | H | 2-Cl | 4-CH$_2$C$_6$H$_5$ | O | O |
| H | H | 2-Cl | 4-CF$_2$(C$_6$H$_4$-4-Br) | O | O |
| H | H | 2-Cl | 4-COC$_6$H$_5$ | O | O |
| H | H | 2-Cl | 4-OCH$_2$(C$_6$H$_4$-4-Cl) | O | O |
| H | H | 2-Cl | 4-OCH$_2$(C$_6$H$_4$-4-CF$_3$) | O | O |
| H | H | 2-Cl | 4-OCH$_2$(C$_6$H$_3$-2,4-Cl$_2$) | O | O |
| H | H | 2-Cl | 4-CH$_2$OC$_6$H$_5$ | O | O |
| H | H | 2-Cl | 4-CH$_2$O(C$_6$H$_3$-2,4-Cl$_2$) | O | O |
| H | H | 2-Cl | 4-CH$_2$O(C$_6$H$_3$-2,6-(CH$_3$)$_2$) | O | O |
| H | H | 2-Cl | 4-NHCH$_2$C$_6$H$_5$ | O | O |
| H | H | 2-Cl | 4-CH$_2$CH$_2$C$_6$H$_5$ | O | O |
| H | H | 2-Cl | 4-CH=CH(C$_6$H$_4$-4-Cl) | O | O |
| H | H | 2-Cl | 4-C≡C(C$_6$H$_4$-4-CF$_3$) | O | O |
| H | H | 2-Cl | 4-N=NC$_6$H$_5$ | O | O |

-continued

| | | | | | |
|---|---|---|---|---|---|
| H | H | 2-Cl | 4-OCH$_2$CH$_2$C$_6$H$_5$ | O | O |
| H | H | 2-Cl | 4-NHCON(CH$_2$CH$_2$CH$_3$)(C$_6$H$_4$-4-Cl) | O | O |
| H | H | 2-Cl | 4-NHCSNHC$_6$H$_5$ | O | O |
| H | H | 2-Cl | 4-OCH$_2$CH$_2$O(C$_6$H$_3$-2-Cl-4-CF$_3$) | O | O |
| H | H | 2-Cl | 4-CH$_2$ON=C(Q51)(C$_6$H$_4$-4-Cl) | O | O |
| H | H | 2-Cl | 4-OCH(CH$_3$)$_2$C$_6$H$_5$ | O | O |
| H | H | 2-Cl | 4-O(Q1-1-CH$_3$) | O | O |
| H | H | 2-Cl | 4-O(Q2-1-CH$_3$) | O | O |
| H | H | 2-Cl | 4-(Q3) | O | O |
| H | H | 2-Cl | 4-CH$_2$(Q4) | O | O |
| H | H | 2-Cl | 4-(Q5) | O | O |
| H | H | 2-Cl | 4-C≡C(Q6) | O | O |
| H | H | 2-Cl | 4-CH$_2$(Q7) | O | O |
| H | H | 2-Cl | 4-(Q8-3,5-(CF$_3$)$_2$) | O | O |
| H | H | 2-Cl | 4-(Q8-3-C$_6$H$_5$) | O | O |
| H | H | 2-Cl | 4-OCH$_2$(Q9-1-CH$_3$) | O | O |
| H | H | 2-Cl | 4-O(Q10-1-CH$_3$) | O | O |
| H | H | 2-Cl | 4-(Q11-1-C$_6$H$_5$) | O | O |
| H | H | 2-Cl | 4-(Q12-1-CH$_3$) | O | O |
| H | H | 2-Cl | 4-OCH$_2$(Q13-1-CH$_3$) | O | O |
| H | H | 2-Cl | 4-O(Q14-1-CH$_3$) | O | O |
| H | H | 2-Cl | 4-(Q15) | O | O |
| H | H | 2-Cl | 4-O(Q16) | O | O |
| H | H | 2-Cl | 4-O(Q17-5-CH$_3$) | O | O |
| H | H | 2-Cl | 4-O(Q18) | O | O |
| H | H | 2-Cl | 4-OCH$_2$(Q19) | O | O |
| H | H | 2-Cl | 4-OCH$_2$(Q20-4-Cl) | O | O |
| H | H | 2-Cl | 4-(Q21) | O | O |
| H | H | 2-Cl | 4-OCH$_2$(Q22) | O | O |
| H | H | 2-Cl | 4-(Q23) | O | O |
| H | H | 2-Cl | 4-OCH$_2$(Q24) | O | O |
| H | H | 2-Cl | 4-O(Q25-3-CH$_3$) | O | O |
| H | H | 2-Cl | 4-(Q26-1-CH$_3$) | O | O |
| H | H | 2-Cl | 4-OCH$_2$(Q27-1-CH$_3$) | O | O |
| H | H | 2-Cl | 4-OCH$_2$(Q28-1-CH$_3$) | O | O |
| H | H | 2-Cl | 4-O(Q29-1-CH$_3$) | O | O |
| H | H | 2-Cl | 4-NHCONH(Q30) | O | O |
| H | H | 2-Cl | 4-O(Q31) | O | O |
| H | H | 2-Cl | 4-OCH$_2$(Q32) | O | O |
| H | H | 2-Cl | 4-OCH$_2$(Q33) | O | O |
| H | H | 2-Cl | 4-O(Q34) | O | O |
| H | H | 2-Cl | 4-OCH$_2$(Q35) | O | O |
| H | H | 2-Cl | 4-O(Q36) | O | O |
| H | H | 2-Cl | 4-OCH$_2$(Q37-5-Cl) | O | O |
| H | H | 2-Cl | 3-O(Q38-5-CF$_2$CFCl$_2$) | O | O |
| H | H | 2-Cl | 3-O(Q38-3-Cl-5-CF$_3$) | O | O |
| H | H | 2-Cl | 4-O(Q38-3-Cl-5-CF$_3$) | O | O |
| H | H | 2-Cl | 4-O(Q38-3-Cl-5-CN) | O | O |
| H | H | 2-Cl | 4-O(Q38-3-Cl-5-CF$_2$CFCl$_2$) | O | O |
| H | H | 2-Cl | 4-O(Q38-5-CF$_3$-6-Cl) | O | O |
| H | H | 2-Cl | 4-NH(Q38-5-CF$_3$) | O | O |
| H | H | 2-Cl | 4-NH(Q38-3-Cl-5-CF$_3$) | O | O |
| H | H | 2-Cl | 4-(Q38-3-Cl-5-CF$_3$) | O | O |
| H | H | 2-Cl | 4-O(Q39-5-Br) | O | O |
| H | H | 2-Cl | 4-O(Q40-2,6-Cl$_2$) | O | O |
| H | H | 2-Cl | 4-O(Q41-6-Cl) | O | O |
| H | H | 2-Cl | 4-O(Q42) | O | O |
| H | H | 2-Cl | 4-O(Q43-5-Cl) | O | O |
| H | H | 2-Cl | 4-O(Q44) | O | O |
| H | H | 2-Cl | 4-O(Q45-4-CF$_3$-6-Cl) | O | O |
| H | H | 2-Cl | 4-O(Q46) | O | O |
| H | H | 2-Cl | 4-O(Q47) | O | O |
| H | H | 2-Cl | 4-O(Q47)-4-Cl | O | O |
| H | H | 2-Cl | 4-O(Q48) | O | O |
| H | H | 2-Cl | 4-O(Q49) | O | O |
| H | H | 2-Cl | 3-O(Q50-6-Cl) | O | O |
| H | H | 2-Cl | 3-O(Q50-6-CF$_3$) | O | O |
| H | H | 2-Cl | 3-O(Q50-6-F) | O | O |
| H | H | 2-Cl | 4-O(Q50-6-Cl) | O | O |
| H | H | 2-Cl | 4-O(Q50-6-CF$_3$) | O | O |
| H | H | 2-Cl | 2,4-F$_2$ | O | O |
| H | H | 2-Cl | 2,6-F$_2$ | O | O |
| H | H | 2-Cl | 3,5-F$_2$ | O | O |
| H | H | 2-Cl | 2,3-Cl$_2$ | O | O |
| H | H | 2-Cl | 2,4-Cl$_2$ | O | O |
| H | H | 2-Cl | 2,5-Cl$_2$ | O | O |
| H | H | 2-Cl | 2,6-Cl$_2$ | O | O |
| H | H | 2-Cl | 3,4-Cl$_2$ | O | O |
| H | H | 2-Cl | 3,5-Cl$_2$ | O | O |
| H | H | 2-Cl | 3,4-Br$_2$ | O | O |
| H | H | 2-Cl | 2,4-I$_2$ | O | O |
| H | H | 2-Cl | 2,4-(CH$_3$)$_2$ | O | O |
| H | H | 2-Cl | 3,4-(OCH$_3$)$_2$ | O | O |

-continued

| | | | | | |
|---|---|---|---|---|---|
| H | H | 2-Cl | 2-F-4-Cl | O | O |
| H | H | 2-Cl | 2-F-4-Br | O | O |
| H | H | 2-Cl | 2-F-4-OCH(CH$_3$)$_2$ | O | O |
| H | H | 2-Cl | 2-F-4-OCHF$_2$ | O | O |
| H | H | 2-Cl | 2-F-4-OCF$_2$CHF$_2$ | O | O |
| H | H | 2-Cl | 2-F-4-OCF$_2$CHFCF$_3$ | O | O |
| H | H | 2-Cl | 2-F-4-OCF$_2$CHFOCF$_3$ | O | O |
| H | H | 2-Cl | 2-F-4-SO$_2$CF$_2$CHFCl | O | O |
| H | H | 2-Cl | 2-F-4-O(C$_6$H$_3$-2-Cl-4-CF$_3$) | O | O |
| H | H | 2-Cl | 2-F-4-N=NC$_6$H$_5$ | O | O |
| H | H | 2-Cl | 2-F-4-NHCON(CH$_2$CH$_2$CH$_3$)(C$_6$H$_4$-4-Cl) | O | O |
| H | H | 2-Cl | 2-F-4-O(Q38-3-Cl-5-CF$_3$) | O | O |
| H | H | 2-Cl | 3-F-4-O(Q38-3-Cl-5-CF$_3$) | O | O |
| H | H | 2-Cl | 2-Cl-4-CF$_3$ | O | O |
| H | H | 2-Cl | 2-Cl-4-SCF$_2$CHF$_2$ | O | O |
| H | H | 2-Cl | 2-Cl-4-O(C$_6$H$_3$-2-Cl-4-CF$_3$) | O | O |
| H | H | 2-Cl | 2-Cl-4-O(Q38-3-Cl-5-CF$_3$) | O | O |
| H | H | 2-Cl | 2-Cl-5-O(Q50-6-CF$_3$) | O | O |
| H | H | 2-Cl | 2-Cl-5-S(Q50-6-CF$_3$) | O | O |
| H | H | 2-Cl | 3-Cl-4-CF$_3$ | O | O |
| H | H | 2-Cl | 3-Cl-4-OC(CH$_3$)$_3$ | O | O |
| H | H | 2-Cl | 3-Cl-4-OCF$_3$ | O | O |
| H | H | 2-Cl | 3-Cl-4-OCF$_2$CHF$_2$ | O | O |
| H | H | 2-Cl | 3-Cl-4-OCF$_2$CHFOCF$_3$ | O | O |
| H | H | 2-Cl | 3-Cl-4-SCF$_2$Cl | O | O |
| H | H | 2-Cl | 3-Cl-4-CO$_2$CH(CH$_3$)$_2$)$_2$ | O | O |
| H | H | 2-Cl | 3-Cl-4-CO$_2$CH(CH$_2$F)$_2$ | O | O |
| H | H | 2-Cl | 3-Cl-4-CO$_2$C(CH$_3$)(CF$_3$)$_2$ | O | O |
| H | H | 2-Cl | 3-Cl-4-O(C$_6$H$_4$-4-Cl) | O | O |
| H | H | 2-Cl | 3-Cl-4-O(C$_6$H$_4$-4-NO$_2$) | O | O |
| H | H | 2-Cl | 3-Cl-4-O(C$_6$H$_4$-4-CF$_3$) | O | O |
| H | H | 2-Cl | 3-Cl-4-O(C$_6$H$_3$-2-Cl-4-CF$_3$) | O | O |
| H | H | 2-Cl | 3-Cl-4-O(C$_6$H$_3$-2-Cl-4-OCF$_3$) | O | O |
| H | H | 2-Cl | 3-Cl-4-CF$_2$(C$_6$H$_4$-4-Br) | O | O |
| H | H | 2-Cl | 3-Cl-4-CH=CH(C$_6$H$_4$-4-Cl) | O | O |
| H | H | 2-Cl | 3-Cl-4-O(Q38-5-CF$_3$) | O | O |
| H | H | 2-Cl | 3-Cl-4-O(Q38-5-CF$_2$CF$_2$CF$_3$) | O | O |
| H | H | 2-Cl | 3-Cl-4-O(Q38-3-Cl-5-CF$_3$) | O | O |
| H | H | 2-Cl | 3-Cl-4-O(Q38-5-CF$_3$-6-Cl) | O | O |
| H | H | 2-Cl | 3-Cl-4-NH(Q38-5-CF$_3$) | O | O |
| H | H | 2-Cl | 3-Cl-4-N(COC(CH$_3$)$_3$)(Q38-5-CF$_3$) | O | O |
| H | H | 2-Cl | 2-CH$_3$-4-N=NC$_6$H$_5$ | O | O |
| H | H | 2-Cl | 2-CH$_3$-4-O(Q38-3-Cl-5-CF$_3$) | O | O |
| H | H | 2-Cl | 3-CH$_3$-4-OCF$_2$CHF$_2$ | O | O |
| H | H | 2-Cl | 3-CH$_3$-4-O(C$_6$H$_3$-2-Cl-4-CF$_3$) | O | O |
| H | H | 2-Cl | 3-CH$_3$-4-O(Q38-3-Cl-5-CF$_3$) | O | O |
| H | H | 2-Cl | 3-Br-4-O(Q38-3-Cl-5-CF$_3$) | O | O |
| H | H | 2-Cl | 3-CF$_3$-4-Cl | O | O |
| H | H | 2-Cl | 3-CF$_3$-4-OCF$_2$CHF$_2$ | O | O |
| H | H | 2-Cl | 3-CF$_3$-4-OCF$_2$CHFBr | O | O |
| H | H | 2-Cl | 3-CF$_3$-4-OCF$_2$CHFCF$_3$ | O | O |
| H | H | 2-Cl | 3-CF$_3$-4-O(Q38-3-Cl-5-CF$_3$) | O | O |
| H | H | 2-Cl | 3-OCH$_3$-4-O(C$_6$H$_3$-2-Cl-4-CF$_3$) | O | O |
| H | H | 2-Cl | 3-CO$_2$CH$_3$-4-O(Q38-3-Cl-5-CF$_3$) | O | O |
| H | H | 2-Cl | 3-CO$_2$CH$_2$CH$_3$-4-O(Q38-3-Cl-5-CF$_2$CFCl$_2$) | O | O |
| H | H | 2-Cl | 2,3-F$_2$-4-OCF$_3$ | O | O |
| H | H | 2-Cl | 2,3-F$_2$-4-O(Q38-3-Cl-5-CF$_3$) | O | O |
| H | H | 2-Cl | 2,5-F$_2$-4-Cl | O | O |
| H | H | 2-Cl | 2,5-F$_2$-4-Br | O | O |
| H | H | 2-Cl | 2,5-F$_2$-4-OCF$_3$ | O | O |
| H | H | 2-Cl | 2,5-F$_2$-4-S(Q38-3-Cl-5-CF$_3$) | O | O |
| H | H | 2-Cl | 3,5-F$_2$-4-CF$_3$ | O | O |
| H | H | 2-Cl | 2,3-Cl$_2$-4-OCF$_2$CHFCl | O | O |
| H | H | 2-Cl | 2,3-Cl$_2$-4-O(C$_6$H$_3$-2-F-4-Br) | O | O |
| H | H | 2-Cl | 2,5-Cl$_2$-4-OCF$_2$CHF$_2$ | O | O |
| H | H | 2-Cl | 2,5-Cl$_2$-4-OCF$_2$CHFCF$_3$ | O | O |
| H | H | 2-Cl | 2,5-Cl$_2$-4-OCF$_2$CF$_2$CF$_3$ | O | O |
| H | H | 2-Cl | 2,5-Cl$_2$-4-O(C$_6$H$_3$-2-Cl-4-CF$_3$) | O | O |
| H | H | 2-Cl | 2,5-Cl$_2$-4-O(Q38-3-Cl-5-CF$_3$) | O | O |
| H | H | 2-Cl | 2,6-Cl$_2$-4-CF$_3$ | O | O |
| H | H | 2-Cl | 3,4,5-Cl$_3$ | O | O |
| H | H | 2-Cl | 3,5-Cl$_2$-4-OCH$_2$CH$_2$OCH$_3$ | O | O |
| H | H | 2-Cl | 3,5-Cl$_2$-4-OCH$_2$CH=CH$_2$ | O | O |
| H | H | 2-Cl | 3,5-Cl$_2$-4-OCH$_2$CH=CHCH$_3$ | O | O |
| H | H | 2-Cl | 3,5-Cl$_2$-4-OCF$_2$CHF$_2$ | O | O |
| H | H | 2-Cl | 3,5-Cl$_2$-4-OCH$_2$CF$_3$ | O | O |
| H | H | 2-Cl | 3,5-Cl$_2$-4-OCF$_2$CHFCl | O | O |
| H | H | 2-Cl | 3,5-Cl$_2$-4-OCF$_2$CHCl$_2$ | O | O |
| H | H | 2-Cl | 3,5-Cl$_2$-4-OCF$_2$CHFCF$_3$ | O | O |
| H | H | 2-Cl | 3,5-Cl$_2$-4-OCF$_2$CHFOCF$_3$ | O | O |
| H | H | 2-Cl | 3,5-Cl$_2$-4-OCF$_2$CF$_2$CF$_3$ | O | O |
| H | H | 2-Cl | 3,5-Cl$_2$-4-SCF$_2$CHF$_2$ | O | O |
| H | H | 2-Cl | 3,5-Cl$_2$-4-SCH$_2$CF$_3$ | O | O |

-continued

| | | | | | |
|---|---|---|---|---|---|
| H | H | 2-Cl | 3,5-Cl$_2$-4-N(CH$_3$)CH$_2$CH$_2$CH$_3$ | O | O |
| H | H | 2-Cl | 3,5-Cl$_2$-4-N(CH$_3$)CH$_2$C≡CH | O | O |
| H | H | 2-Cl | 3,5-Cl$_2$-4-N(CH$_3$)CH$_2$CH=CHCl | O | O |
| H | H | 2-Cl | 3,5-Cl$_2$-4-N(CH$_3$)CH$_2$C$_6$H$_5$ | O | O |
| H | H | 2-Cl | 3,5-Cl$_2$-4-O(C$_6$H$_4$-3-F) | O | O |
| H | H | 2-Cl | 3,5-Cl$_2$-4-O(C$_6$H$_4$-3-Br) | O | O |
| H | H | 2-Cl | 3,5-Cl$_2$-4-O(C$_6$H$_4$-4-Cl) | O | O |
| H | H | 2-Cl | 3,5-Cl$_2$-4-O(C$_6$H$_4$-4-CN) | O | O |
| H | H | 2-Cl | 3,5-Cl$_2$-4-O(C$_6$H$_4$-4-NO$_2$) | O | O |
| H | H | 2-Cl | 3,5-Cl$_2$-4-O(C$_6$H$_4$-4-SO$_2$CF$_3$) | O | O |
| H | H | 2-Cl | 3,5-Cl$_2$-4-O(C$_6$H$_4$-4-SO$_2$C$_6$H$_5$) | O | O |
| H | H | 2-Cl | 3,5-Cl$_2$-4-O(C$_6$H$_3$-2,4-F$_2$) | O | O |
| H | H | 2-Cl | 3,5-Cl$_2$-4-O(C$_6$H$_3$-2-Cl-4-CF$_3$) | O | O |
| H | H | 2-Cl | 3,5-Cl$_2$-4-O(C$_6$H$_3$-3-OCF$_2$CF$_2$O-4) | O | O |
| H | H | 2-Cl | 3,5-Cl$_2$-4-OCH$_2$(C$_6$H$_4$-4-Cl) | O | O |
| H | H | 2-Cl | 3,5-Cl$_2$-4-OCH$_2$(C$_6$H$_4$-4-CF$_3$ | O | O |
| H | H | 2-Cl | 3,5-Cl$_2$-4-OCH$_2$(C$_6$H$_4$-2-C$_6$H$_5$) | O | O |
| H | H | 2-Cl | 3,5-Cl$_2$-4-OCH$_2$(C$_6$H$_3$-2,4-Cl$_2$) | O | O |
| H | H | 2-Cl | 3,5-Cl$_2$-4-NH(C$_6$H$_4$-4-CF$_3$) | O | O |
| H | H | 2-Cl | 3,5-Cl$_2$-4-NH(C$_6$H$_4$-4-OCF$_3$) | O | O |
| H | H | 2-Cl | 3,5-Cl$_2$-4-(Q3) | O | O |
| H | H | 2-Cl | 3,5-Cl$_2$-4-(Q8-3-C$_6$H$_5$) | O | O |
| H | H | 2-Cl | 3,5-Cl$_2$-4-(Q38-3-Cl-5-CF$_3$) | O | O |
| H | H | 2-Cl | 3,5-Cl$_2$-4-O(Q38-3-Cl-5-CF$_3$) | O | O |
| H | H | 2-Cl | 3,5-Cl$_2$-4-O(Q38-3-Cl-5-CN) | O | O |
| H | H | 2-Cl | 3,5-Cl$_2$-4-OCH$_2$CH$_2$O(Q38-3-Cl-5-CF$_3$) | O | O |
| H | H | 2-Cl | 3,5-Cl$_2$-4-O(Q43-5-Cl) | O | O |
| H | H | 2-Cl | 3,5-Cl$_2$-4-O(Q45-2-CH$_3$) | O | O |
| H | H | 2-Cl | 3,5-Cl$_2$-4-(Q47-4-Cl) | O | O |
| H | H | 2-Cl | 3,5-Cl$_2$-4-O(Q50-6-Cl) | O | O |
| H | H | 2-Cl | 3,5-Cl$_2$-4-O(Q50-6-CF$_3$) | O | O |
| H | H | 2-Cl | 3,5-Cl$_2$-4-O(Q45-2-CH$_3$) | S | O |
| H | H | 2-Cl | 2,5-(CH$_3$)$_2$-4-O(C$_6$H$_3$-2-Cl-4-CF$_3$) | O | O |
| H | H | 2-Cl | 3,5-(CH$_3$)$_2$-4-OCF$_2$CHFCl | O | O |
| H | H | 2-Cl | 3,5-(CH$_3$)$_2$-4-O(C$_6$H$_3$-3,5-F$_2$) | O | O |
| H | H | 2-Cl | 3,5-(CH$_3$)$_2$-4-O(C$_6$H$_2$-2,3,5-F$_3$) | O | O |
| H | H | 2-Cl | 3,5-(CH$_3$)$_2$-4-N=NC$_6$H$_5$ | O | O |
| H | H | 2-Cl | 2-F-4,5-Cl$_2$ | O | O |
| H | H | 2-Cl | 2-F-3-CF$_3$-5-Cl | O | O |
| H | H | 2-Cl | 2-F-4-Br-5-CF$_3$ | O | O |
| H | H | 2-Cl | 2-F-4-Cl-5-OCH(CH$_3$)$_2$ | O | O |
| H | H | 2-Cl | 2-F-4-Br-5-OCF$_3$ | O | O |
| H | H | 2-Cl | 2-F-4-OCH$_2$CF$_3$-5-Cl | O | O |
| H | H | 2-Cl | 2-F-4-OCF$_2$CHF$_2$-5-Cl | O | O |
| H | H | 2-Cl | 2-F-4-O(C$_6$H$_3$-2-Cl-4-CF$_3$)-5-Cl | O | O |
| H | H | 2-Cl | 2-F-4-S(C$_6$H$_3$-2-Cl-4-CF$_3$)-5-Cl | O | O |
| H | H | 2-Cl | 2-Cl-3-CF$_3$-5-NO$_2$ | O | O |
| H | H | 2-Cl | 3-Cl-4-OCF$_2$CHF$_2$-5-CF$_3$ | O | O |
| H | H | 2-Cl | 3-Cl-4-OCF$_2$CHF$_2$-5-CH$_2$OCH$_3$ | O | O |
| H | H | 2-Cl | 3-Cl-4-OCF$_2$CHFCF$_3$-5-CF$_3$ | O | O |
| H | H | 2-Cl | 3-Cl-4-O(Q38-3-Cl-5-CF$_3$)-5-CO$_2$H | O | O |
| H | H | 2-Cl | 3-Cl-4-O(Q38-3-Cl-5-CF$_3$)-5-CO$_2$CH$_3$ | O | O |
| H | H | 2-Cl | 3-Cl-4-O(Q38-3-Cl-5-CF$_3$)-5-CH$_2$OCH$_3$ | O | O |
| H | H | 2-Cl | 2-CF$_3$-4,6-(NO$_2$)$_2$ | O | O |
| H | H | 2-Cl | 2-CF$_3$-4-OCF$_2$CHFCF$_3$-5-Cl | O | O |
| H | H | 2-Cl | 2-CF$_3$-4-OCH$_2$CH=CHCl-5-Br | O | O |
| H | H | 2-Cl | 2-CH$_3$-4-CH(CN)(C$_6$H$_4$-4-Cl)-5-Cl | O | O |
| H | H | 2-Cl | 2,3,4,5-F$_4$ | O | O |
| H | H | 2-Cl | 2,4-F$_2$-3,5-Cl$_2$ | O | O |
| H | H | 2-Cl | 2,6-F$_2$-3,5-Cl$_2$ | O | O |
| H | H | 2-Cl | 2,4-F$_2$-3-Cl-5-Br | O | O |
| H | H | 2-Cl | 2,4-Cl-3,5-F$_2$ | O | O |
| H | H | 2-Cl | 2,6-Cl-3,5-F$_2$ | O | O |
| H | H | 2-Cl | 2-F-3,5-Cl$_2$-4-OCH$_3$ | O | O |
| H | H | 2-Cl | 2,3,5-F$_3$-4-OCF$_2$CHFCF$_3$ | O | O |
| H | H | 2-Cl | 2-F-3,5-Cl$_2$-4-OCH$_2$CF$_3$ | O | O |
| H | H | 2-Cl | 2-F-3,5-Cl$_2$-4-OCF$_2$CHF$_2$ | O | O |
| H | H | 2-Cl | 2-F-3,5-Cl$_2$-4-OCF$_2$CHFOCF$_3$ | O | O |
| H | H | 2-Cl | 2-F-3,5-Cl$_2$-4-N(CH$_3$)CH$_2$CH$_3$ | O | O |
| H | H | 2-Cl | 2-F-3,5-Cl$_2$-4-N(CH$_3$)CH$_2$C$_6$H$_5$ | O | O |
| H | H | 2-Cl | 2-F-3,5-Cl$_2$-4-O(C$_6$H$_3$-2-Cl-4-CF$_3$) | O | O |
| H | H | 2-Cl | 2-F-3,5-Cl$_2$-4-O(Q38-3-Cl-5-CF$_3$) | O | O |
| H | H | 2-Cl | 2,5-(CH$_3$)$_2$-3-Cl-4-O(C$_6$H$_3$-2,4-(CH$_3$)$_2$) | O | O |
| H | H | 2-Cl | 2-CH$_3$-3,5-Cl$_2$-4-O(C$_6$H$_3$-2-CH$_3$-4-Cl) | O | O |
| H | H | 2-Cl | 2-CH$_3$-3-Cl-4-O(C$_6$H$_4$-4-F)-5-CH(OCH$_3$)$_2$ | O | O |
| H | H | 2-Cl | 2,3,4,5,6-F$_5$ | O | O |
| H | H | 2-Cl | 2,4-6-F$_3$-3,5-Cl$_2$ | O | O |
| H | H | 2-Cl | 3-Cl-4-F | O | O |
| H | H | 2-Cl | 4-CH$_2$CH$_2$CH$_2$CH$_3$ | O | O |
| H | H | 2-Br | 4-F | O | O |
| H | H | 2-Br | 2-Cl | O | O |
| H | H | 2-Br | 3-Cl | O | O |
| H | H | 2-Br | 4-Cl | O | O |

-continued

| | | | | | |
|---|---|---|---|---|---|
| H | H | 2-Br | 4-Br | O | O |
| H | H | 2-Br | 4-I | O | O |
| H | H | 2-Br | 4-CH$_3$ | O | O |
| H | H | 2-Br | 4-C(CH$_3$)$_3$ | O | O |
| H | H | 2-Br | 4-Q54 | O | O |
| H | H | 2-Br | 4-CF$_3$ | O | O |
| H | H | 2-Br | 4-CH$_2$CH=CHCl | O | O |
| H | H | 2-Br | 4-CH=C(Cl)CF$_3$ | O | O |
| H | H | 2-Br | 4-OCH$_3$ | O | O |
| H | H | 2-Br | 4-O(Q54-2-CH(CH$_3$)$_2$-5-CH$_3$) | O | O |
| H | H | 2-Br | 4-OCHF$_2$ | O | O |
| H | H | 2-Br | 4-OCF$_2$Br | O | O |
| H | H | 2-Br | 4-OCF$_3$ | O | O |
| H | H | 2-Br | 4-OCF$_2$CHF$_2$ | O | O |
| H | H | 2-Br | 4-OCF$_2$CHFBr | O | O |
| H | H | 2-Br | 4-OCF$_2$CF$_2$CF$_3$ | O | O |
| H | H | 2-Br | 4-O(Q51-2,2-Cl$_2$) | O | O |
| H | H | 2-Br | 4-OCH$_2$(Q51-2,2-Cl$_2$) | O | O |
| H | H | 2-Br | 4-SCH$_3$ | O | O |
| H | H | 2-Br | 4-SCF$_3$ | O | O |
| H | H | 2-Br | 4-SCF$_2$Cl | O | O |
| H | H | 2-Br | 4-SO$_2$CF$_3$ | O | O |
| H | H | 2-Br | 4-OCF$_2$CHFOCF$_3$ | O | O |
| H | H | 2-Br | 4-CO$_2$CH$_2$CF$_3$ | O | O |
| H | H | 2-Br | 4-NO$_2$ | O | O |
| H | H | 2-Br | 4-CN | O | O |
| H | H | 2-Br | 4-N(CH$_3$)CH$_2$CH$_2$CH$_3$ | O | O |
| H | H | 2-Br | 3-OCF$_2$O-4 | O | O |
| H | H | 2-Br | 3-OC(CH$_3$)$_2$CF$_2$O-4 | O | O |
| H | H | 2-Br | 4-(C$_6$H$_4$-4-Cl) | O | O |
| H | H | 2-Br | 4-O(C$_6$H$_4$-4-Cl) | O | O |
| H | H | 2-Br | 4-O(C$_6$H$_4$-4-CF$_3$) | O | O |
| H | H | 2-Br | 4-O(C$_6$H$_4$-4-CN) | O | O |
| H | H | 2-Br | 4-O(C$_6$H$_4$-4-NO$_2$) | O | O |
| H | H | 2-Br | 4-O(C$_6$H$_4$-4-OCF$_3$) | O | O |
| H | H | 2-Br | 4-O(C$_6$H$_3$-3,5-F$_2$) | O | O |
| H | H | 2-Br | 4-O(C$_6$H$_3$-2,4-Cl$_2$) | O | O |
| H | H | 2-Br | 4-O(C$_6$H$_3$-3,5-Cl$_2$) | O | O |
| H | H | 2-Br | 4-O(C$_6$H$_3$-3-OCF$_2$CF$_2$O-4) | O | O |
| H | H | 2-Br | 4-O(C$_6$H$_3$-2-Cl-4-CF$_3$) | O | O |
| H | H | 2-Br | 3-O(C$_6$H$_3$-2-Cl-4-CF$_3$) | O | O |
| H | H | 2-Br | 4-S(C$_6$H$_3$-2-Cl-4-CF$_3$) | O | O |
| H | H | 2-Br | 4-NH(C$_6$H$_3$-2-Cl-4-CF$_3$) | O | O |
| H | H | 2-Br | 4-N(CH$_2$CH$_2$CH$_3$)(C$_6$H$_4$-4-Cl) | O | O |
| H | H | 2-Br | 4-OCH$_2$(C$_6$H$_3$-2,4-Cl$_2$) | O | O |
| H | H | 2-Br | 4-CH$_2$ON=C(Q51)(C$_6$H$_4$-4-Cl) | O | O |
| H | H | 2-Br | 3-O(Q38-3-Cl-5-CF$_3$) | O | O |
| H | H | 2-Br | 4-O(Q38-3-Cl-5-CF$_3$) | O | O |
| H | H | 2-Br | 4-NH(Q38-3-Cl-5-CF$_3$) | O | O |
| H | H | 2-Br | 4-(Q38-3-Cl-5-CF$_3$) | O | O |
| H | H | 2-Br | 3-O(Q50-6-Cl) | O | O |
| H | H | 2-Br | 3-O(Q50-6-CF$_3$) | O | O |
| H | H | 2-Br | 4-O(Q50-6-CF$_3$) | O | O |
| H | H | 2-Br | 3,5-F$_2$ | O | O |
| H | H | 2-Br | 2,4-Cl$_2$ | O | O |
| H | H | 2-Br | 2,5-Cl$_2$ | O | O |
| H | H | 2-Br | 2,6-Cl$_2$ | O | O |
| H | H | 2-Br | 3,4-Cl$_2$ | O | O |
| H | H | 2-Br | 3,5-Cl$_2$ | O | O |
| H | H | 2-Br | 3,4-Br$_2$ | O | O |
| H | H | 2-Br | 2-F-4-Cl | O | O |
| H | H | 2-Br | 2-F-4-OCF$_2$CHF$_2$ | O | O |
| H | H | 2-Br | 2-F-4-O(C$_6$H$_3$-2-Cl-4-CF$_3$) | O | O |
| H | H | 2-Br | 2-F-4-N=NC$_6$H$_5$ | O | O |
| H | H | 2-Br | 2-F-4-NHCON(CH$_2$CH$_2$CH$_3$)(C$_6$H$_4$-4-Cl) | O | O |
| H | H | 2-Br | 2-F-4-O(Q38-3-Cl-5-CF$_3$) | O | O |
| H | H | 2-Br | 3-F-4-O(Q38-3-Cl-5-CF$_3$) | O | O |
| H | H | 2-Br | 2-Cl-4-CF$_3$ | O | O |
| H | H | 2-Br | 2-Cl-4-SCF$_2$CHF$_2$ | O | O |
| H | H | 2-Br | 2-Cl-4-O(C$_6$H$_3$-2-Cl-4-CF$_3$) | O | O |
| H | H | 2-Br | 2-Cl-4-O(Q38-3-Cl-5-CF$_3$) | O | O |
| H | H | 2-Br | 2-Cl-5-O(Q50-6-CF$_3$) | O | O |
| H | H | 2-Br | 2-Cl-5-S(Q50-6-CF$_3$) | O | O |
| H | H | 2-Br | 3-Cl-4-CF$_3$ | O | O |
| H | H | 2-Br | 3-Cl-4-OCF$_3$ | O | O |
| H | H | 2-Br | 3-Cl-4-OCF$_2$CHF$_2$ | O | O |
| H | H | 2-Br | 3-Cl-4-OCF$_2$CHFOCF$_3$ | O | O |
| H | H | 2-Br | 3-Cl-4-O(C$_6$H$_3$-2-Cl-4-CF$_3$) | O | O |
| H | H | 2-Br | 3-Cl-4-O(Q38-3-Cl-5-CF$_3$) | O | O |
| H | H | 2-Br | 2-CH$_3$-4-O(Q38-3-Cl-5-CF$_3$) | O | O |
| H | H | 2-Br | 3-CF$_3$-4-Cl | O | O |
| H | H | 2-Br | 3-CF$_3$-4-OCF$_2$CHF$_2$ | O | O |
| H | H | 2-Br | 3-CF$_3$-4-O(Q38-3-Cl-5-CF$_3$) | O | O |

-continued

| | | | | | |
|---|---|---|---|---|---|
| H | H | 2-Br | 2,3-F$_2$-4-OCF$_3$ | O | O |
| H | H | 2-Br | 2,3-F$_2$-4-O(Q38-3-Cl-5-CF$_3$) | O | O |
| H | H | 2-Br | 2,5-F$_2$-4-Cl | O | O |
| H | H | 2-Br | 2,5-F$_2$-4-OCF$_3$ | O | O |
| H | H | 2-Br | 3,5-F$_2$-4-CF$_3$ | O | O |
| H | H | 2-Br | 2,3-Cl$_2$-4-OCF$_2$CHFCl | O | O |
| H | H | 2-Br | 2,5-Cl$_2$-4-OCF$_2$CHF$_2$ | O | O |
| H | H | 2-Br | 2,5-Cl$_2$-4-O(C$_6$H$_3$-2-Cl-4-CF$_3$) | O | O |
| H | H | 2-Br | 2,5-Cl$_2$-4-O(Q38-3-Cl-5-CF$_3$) | O | O |
| H | H | 2-Br | 2,6-Cl$_2$-4-CF$_3$ | O | O |
| H | H | 2-Br | 3,4,5-Cl$_3$ | O | O |
| H | H | 2-Br | 3,5-Cl$_2$-4-OCF$_2$CHF$_2$ | O | O |
| H | H | 2-Br | 3,5-Cl$_2$-4-OCF$_2$CHFOCF$_3$ | O | O |
| H | H | 2-Br | 3,5-Cl$_2$-4-SCF$_2$CHF$_2$ | O | O |
| H | H | 2-Br | 3,5-Cl$_2$-4-N(CH$_3$)CH$_2$CH$_2$CH$_3$ | O | O |
| H | H | 2-Br | 3,5-Cl$_2$-4-O(C$_6$H$_4$-4-Cl) | O | O |
| H | H | 2-Br | 3,5-Cl$_2$-4-O(C$_6$H$_4$-4-CN) | O | O |
| H | H | 2-Br | 3,5-Cl$_2$-4-O(C$_6$H$_4$-4-NO$_2$) | O | O |
| H | H | 2-Br | 3,5-Cl$_2$-4-O(C$_6$H$_3$-2-Cl-4-CF$_3$) | O | O |
| H | H | 2-Br | 3,5-Cl$_2$-4-O(C$_6$H$_3$-3-OCF$_2$CF$_2$O-4) | O | O |
| H | H | 2-Br | 3,5-Cl$_2$-4-OCH$_2$(CH$_6$H$_4$-4-CF$_3$) | O | O |
| H | H | 2-Br | 3,5-Cl$_2$-4-NH(C$_6$H$_4$-4-CF$_3$) | O | O |
| H | H | 2-Br | 3,5-Cl$_2$-4-(Q38-3-Cl-5-CF$_3$) | O | O |
| H | H | 2-Br | 3,5-Cl$_2$-4-O(Q38-3-Cl-5-CF$_3$) | O | O |
| H | H | 2-Br | 3,5-Cl$_2$-4-O(Q50-6-CF$_3$) | O | O |
| H | H | 2-Br | 2-F-4,5-Cl$_2$ | O | O |
| H | H | 2-Br | 2-F-3-CF$_3$-5-Cl | O | O |
| H | H | 2-Br | 2-F-4-OCF$_2$CHF$_2$-5-Cl | O | O |
| H | H | 2-Br | 2-F-4-O(C$_6$H$_3$-2-Cl-4-CF$_3$)-5-Cl | O | O |
| H | H | 2-Br | 3-Cl-4-OCF$_2$CHF$_2$-5-CF$_3$ | O | O |
| H | H | 2-Br | 3-Cl-4-O(Q38-3-Cl-5-CF$_3$)-5-CH$_2$OCH$_3$ | O | O |
| H | H | 2-Br | 2-CF$_3$-4,6-(NO$_2$)$_2$. | O | O |
| H | H | 2-Br | 2,4-F$_2$-3,5-Cl$_2$ | O | O |
| H | H | 2-Br | 2,3,5-F$_3$-4-OCF$_2$CHFCF$_3$ | O | O |
| H | H | 2-Br | 2-F-3,5-Cl$_2$-4-OCF$_2$CHF$_2$ | O | O |
| H | H | 2-Br | 2-F-3,5-Cl$_2$-4-O(C$_6$H$_3$-2-Cl-4-CF$_3$) | O | O |
| H | H | 2-Br | 2-F-3,5-Cl$_2$-4-O(Q38-3-Cl-5-CF$_3$) | O | O |
| H | H | 2-Br | 2,3,4,5,6-F$_5$ | O | O |
| H | H | 2-Br | 2,4,6-F$_3$-3,5-Cl$_2$ | O | O |
| H | H | 2-CH$_3$ | 4-F | O | O |
| H | H | 2-CH$_3$ | 2-Cl | O | O |
| H | H | 2-CH$_3$ | 3-Cl | O | O |
| H | H | 2-CH$_3$ | 4-Cl | O | O |
| H | H | 2-CH$_3$ | 4-Br | O | O |
| H | H | 2-CH$_3$ | 4-I | O | O |
| H | H | 2-CH$_3$ | 4-CH$_3$ | O | O |
| H | H | 2-CH$_3$ | 4-C(CH$_3$)$_3$ | O | O |
| H | H | 2-CH$_3$ | 4-Q54 | O | O |
| H | H | 2-CH$_3$ | 4-CF$_3$ | O | O |
| H | H | 2-CH$_3$ | 4-CH$_2$CH=CHCl | O | O |
| H | H | 2-CH$_3$ | 4-CH=C(Cl)CF$_3$ | O | O |
| H | H | 2-CH$_3$ | 4-OCH$_3$ | O | O |
| H | H | 2-CH$_3$ | 4-O(Q54-2-CH(CH$_3$)$_2$-5-CH$_3$) | O | O |
| H | H | 2-CH$_3$ | 4-OCHF$_2$ | O | O |
| H | H | 2-CH$_3$ | 4-OCF$_2$Br | O | O |
| H | H | 2-CH$_3$ | 4-OCF$_3$ | O | O |
| H | H | 2-CH$_3$ | 4-OCF$_2$CHF$_2$ | O | O |
| H | H | 2-CH$_3$ | 4-OCF$_2$CHFBr | O | O |
| H | H | 2-CH$_3$ | 4-OCF$_2$CF$_2$CF$_3$ | O | O |
| H | H | 2-CH$_3$ | 4-O(Q51-2,2-Cl$_2$) | O | O |
| H | H | 2-CH$_3$ | 4-OCH$_2$(Q51-2,2-Cl$_2$) | O | O |
| H | H | 2-CH$_3$ | 4-SCH$_3$ | O | O |
| H | H | 2-CH$_3$ | 4-SCF$_3$ | O | O |
| H | H | 2-CH$_3$ | 4-SCF$_2$Cl | O | O |
| H | H | 2-CH$_3$ | 4-SO$_2$CF$_3$ | O | O |
| H | H | 2-CH$_3$ | 4-OCF$_2$CHFOCF$_3$ | O | O |
| H | H | 2-CH$_3$ | 4-CO$_2$CH$_2$CF$_3$ | O | O |
| H | H | 2-CH$_3$ | 4-NO$_2$ | O | O |
| H | H | 2-CH$_3$ | 4-CN | O | O |
| H | H | 2-CH$_3$ | 4-N(CH$_3$)CH$_2$CH$_2$CH$_3$ | O | O |
| H | H | 2-CH$_3$ | 3-OCF$_2$O-4 | O | O |
| H | H | 2-CH$_3$ | 3-OC(CH$_3$)$_2$CF$_2$O-4 | O | O |
| H | H | 2-CH$_3$ | 4-(C$_6$H$_4$-4-Cl) | O | O |
| H | H | 2-CH$_3$ | 4-O(C$_6$H$_4$-4-Cl) | O | O |
| H | H | 2-CH$_3$ | 4-O(C$_6$H$_4$-4-CF$_3$) | O | O |
| H | H | 2-CH$_3$ | 4-O(C$_6$H$_4$-4-CN) | O | O |
| H | H | 2-CH$_3$ | 4-O(C$_6$H$_4$-4-NO$_2$) | O | O |
| H | H | 2-CH$_3$ | 4-O(C$_6$H$_4$-4-OCF$_3$) | O | O |
| H | H | 2-CH$_3$ | 4-O(C$_6$H$_3$-3,5-F$_2$) | O | O |
| H | H | 2-CH$_3$ | 4-O(C$_6$H$_3$-2,4-Cl$_2$) | O | O |
| H | H | 2-CH$_3$ | 4-O(C$_6$H$_3$-3,5-Cl$_2$) | O | O |
| H | H | 2-CH$_3$ | 4-O(C$_6$H$_3$-3-OCF$_2$CF$_2$O-4) | O | O |
| H | H | 2-CH$_3$ | 4-O(C$_6$H$_3$-2-Cl-4-CF$_3$) | O | O |

-continued

| | | | | | |
|---|---|---|---|---|---|
| H | H | 2-CH$_3$ | 3-O(C$_6$H$_3$-2-Cl-4-CF$_3$) | O | O |
| H | H | 2-CH$_3$ | 4-S(C$_6$H$_3$-2-Cl-4-CF$_3$) | O | O |
| H | H | 2-CH$_3$ | 4-NH(C$_6$H$_3$-2-Cl-4-CF$_3$) | O | O |
| H | H | 2-CH$_3$ | 4-N(CH$_2$CH$_2$CH$_3$)(C$_6$H$_4$-4-Cl) | O | O |
| H | H | 2-CH$_3$ | 4-OCH$_2$(C$_6$H$_3$-2,4-Cl$_2$) | O | O |
| H | H | 2-CH$_3$ | 4-CH$_2$ON=C(Q51)(C$_6$H$_4$-4-Cl) | O | O |
| H | H | 2-CH$_3$ | 3-O(Q38-3-Cl-5-CF$_3$) | O | O |
| H | H | 2-CH$_3$ | 4-O(Q38-3-Cl-5-CF$_3$) | O | O |
| H | H | 2-CH$_3$ | 4-NH(Q38-3-Cl-5-CF$_3$) | O | O |
| H | H | 2-CH$_3$ | 4-(Q38-3-Cl-5-CF$_3$) | O | O |
| H | H | 2-CH$_3$ | 3-O(Q50-6-Cl) | O | O |
| H | H | 2-CH$_3$ | 3-O(Q50-6-CF$_3$) | O | O |
| H | H | 2-CH$_3$ | 4-O(Q50-6-CF$_3$) | O | O |
| H | H | 2-CH$_3$ | 3,5-F$_2$ | O | O |
| H | H | 2-CH$_3$ | 2,4-Cl$_2$ | O | O |
| H | H | 2-CH$_3$ | 2,5-Cl$_2$ | O | O |
| H | H | 2-CH$_3$ | 2,6-Cl$_2$ | O | O |
| H | H | 2-CH$_3$ | 3,4-Cl$_2$ | O | O |
| H | H | 2-CH$_3$ | 3,5-Cl$_2$ | O | O |
| H | H | 2-CH$_3$ | 3,4-Br$_2$ | O | O |
| H | H | 2-CH$_3$ | 2-F-4-Cl | O | O |
| H | H | 2-CH$_3$ | 2-F-4-OCF$_2$CHF$_2$ | O | O |
| H | H | 2-CH$_3$ | 2-F-4-O(C$_6$H$_3$-2-Cl-4-CF$_3$) | O | O |
| H | H | 2-CH$_3$ | 2-F-4-N=NC$_6$H$_5$ | O | O |
| H | H | 2-CH$_3$ | 2-F-4-NHCON(CH$_2$CH$_2$CH$_3$)(C$_6$H$_4$-4-Cl) | O | O |
| H | H | 2-CH$_3$ | 2-F-4-O(Q38-3-Cl-5-CF$_3$) | O | O |
| H | H | 2-CH$_3$ | 3-F-4-O(Q38-3-Cl-5-CF$_3$) | O | O |
| H | H | 2-CH$_3$ | 2-Cl-4-CF$_3$ | O | O |
| H | H | 2-CH$_3$ | 2-Cl-4-SCF$_2$CHF$_2$ | O | O |
| H | H | 2-CH$_3$ | 2-Cl-4-O(C$_6$H$_3$-2-Cl-4-CF$_3$) | O | O |
| H | H | 2-CH$_3$ | 2-Cl-4-O(Q38-3-Cl-5-CF$_3$) | O | O |
| H | H | 2-CH$_3$ | 2-Cl-5-O(Q50-6-CF$_3$) | O | O |
| H | H | 2-CH$_3$ | 2-Cl-5-S(Q50-6-CF$_3$) | O | O |
| H | H | 2-CH$_3$ | 3-Cl-4-CF$_3$ | O | O |
| H | H | 2-CH$_3$ | 3-Cl-4-OCF$_3$ | O | O |
| H | H | 2-CH$_3$ | 3-Cl-4-OCF$_2$CHF$_2$ | O | O |
| H | H | 2-CH$_3$ | 3-Cl-4-OCF$_2$CHFOCF$_3$ | O | O |
| H | H | 2-CH$_3$ | 3-Cl-4-O(C$_6$H$_3$-2-Cl-4-CF$_3$) | O | O |
| H | H | 2-CH$_3$ | 3-Cl-4-O(Q38-3-Cl-5-CF$_3$) | O | O |
| H | H | 2-CH$_3$ | 2-CH$_3$-4-O(Q38-3-Cl-5-CF$_3$) | O | O |
| H | H | 2-CH$_3$ | 3-CF$_3$-4-Cl | O | O |
| H | H | 2-CH$_3$ | 3-CF$_3$-4-OCF$_2$CHF$_2$ | O | O |
| H | H | 2-CH$_3$ | 3-CF$_3$-4-O(Q38-3-Cl-5-CF$_3$) | O | O |
| H | H | 2-CH$_3$ | 2,3-F$_2$-4-OCF$_3$ | O | O |
| H | H | 2-CH$_3$ | 2,3-F$_2$-4-O(Q38-3-Cl-5-CF$_3$) | O | O |
| H | H | 2-CH$_3$ | 2,5-F$_2$-4-Cl | O | O |
| H | H | 2-CH$_3$ | 2,5-F$_2$-4-OCF$_3$ | O | O |
| H | H | 2-CH$_3$ | 3,5-F$_2$-4-CF$_3$ | O | O |
| H | H | 2-CH$_3$ | 2,3-Cl$_2$-4-OCF$_2$CHFCl | O | O |
| H | H | 2-CH$_3$ | 2,5-Cl$_2$-4-OCF$_2$CHF$_2$ | O | O |
| H | H | 2-CH$_3$ | 2,5-Cl$_2$-4-O(C$_6$H$_3$-2-Cl-4-CF$_3$) | O | O |
| H | H | 2-CH$_3$ | 2,5-Cl$_2$-4-O(Q38-3-Cl-5-CF$_3$) | O | O |
| H | H | 2-CH$_3$ | 2,6-Cl$_2$-4-CF$_3$ | O | O |
| H | H | 2-CH$_3$ | 3,4,5-Cl$_3$ | O | O |
| H | H | 2-CH$_3$ | 3,5-Cl$_2$-4-OCF$_2$CHF$_2$ | O | O |
| H | H | 2-CH$_3$ | 3,5-Cl$_2$-4-OCF$_2$CHFOCF$_3$ | O | O |
| H | H | 2-CH$_3$ | 3,5-Cl$_2$-4-SCF$_2$CHF$_2$ | O | O |
| H | H | 2-CH$_3$ | 3,5-Cl$_2$-4-N(CH$_3$)CH$_2$CH$_3$ | O | O |
| H | H | 2-CH$_3$ | 3,5-Cl$_2$-4-O(C$_6$H$_4$-4-Cl) | O | O |
| H | H | 2-CH$_3$ | 3,5-Cl$_2$-4-O(C$_6$H$_4$-4-CN) | O | O |
| H | H | 2-CH$_3$ | 3,5-Cl$_2$-4-O(C$_6$H$_4$-4-NO$_2$) | O | O |
| H | H | 2-CH$_3$ | 3,5-Cl$_2$-4-O(C$_6$H$_3$-2-Cl-4-CF$_3$) | O | O |
| H | H | 2-CH$_3$ | 3,5-Cl$_2$-4-O(C$_6$H$_3$-3-OCF$_2$CF$_2$O-4) | O | O |
| H | H | 2-CH$_3$ | 3,5-Cl$_2$-4-OCH$_2$(C$_6$H$_4$-4-CF$_3$) | O | O |
| H | H | 2-CH$_3$ | 3,5-Cl$_2$-4-NH(C$_6$H$_4$-4-CF$_3$) | O | O |
| H | H | 2-CH$_3$ | 3,5-Cl$_2$-4-(Q38-3-Cl-5-CF$_3$) | O | O |
| H | H | 2-CH$_3$ | 3,5-Cl$_2$-4-O(Q38-3-Cl-5-CF$_3$) | O | O |
| H | H | 2-CH$_3$ | 3,5-Cl$_2$-4-O(Q50-6-CF$_3$) | O | O |
| H | H | 2-CH$_3$ | 2-F-4,5-Cl$_2$ | O | O |
| H | H | 2-CH$_3$ | 2-F-3-CF$_3$-5-Cl | O | O |
| H | H | 2-CH$_3$ | 2-F-4-OCF$_2$CHF$_2$-5-Cl | O | O |
| H | H | 2-CH$_3$ | 2-F-4-O(C$_6$H$_3$-2-Cl-4-CF$_3$)-5-Cl | O | O |
| H | H | 2-CH$_3$ | 3-Cl-4-OCF$_2$CHF$_2$-5-CF$_3$ | O | O |
| H | H | 2-CH$_3$ | 3-Cl-4-O(Q38-3-Cl-5-CF$_3$)-5-CH$_2$OCH$_3$ | O | O |
| H | H | 2-CH$_3$ | 2-CF$_3$-4,6-(NO$_2$)$_2$ | O | O |
| H | H | 2-CH$_3$ | 2,4-F$_2$-3,5-Cl$_2$ | O | O |
| H | H | 2-CH$_3$ | 2,3,5-F$_3$-4-OCF$_2$CHFCF$_3$ | O | O |
| H | H | 2-CH$_3$ | 2-F-3,5-Cl$_2$-4-OCF$_2$CHF$_2$ | O | O |
| H | H | 2-CH$_3$ | 2-F-3,5-Cl$_2$-4-O(C$_6$H$_3$-2-Cl-4-CF$_3$) | O | O |
| H | H | 2-CH$_3$ | 2-F-3,5-Cl$_2$-4-O(Q38-3-Cl-5-CF$_3$) | O | O |
| H | H | 2-CH$_3$ | 2,3,4,5,6-F$_5$ | O | O |
| H | H | 2-CH$_3$ | 2,4,6-F$_3$-3,5-Cl$_2$ | O | O |
| H | H | 2-OCH$_3$ | 4-F | O | O |

-continued

| | | | | | |
|---|---|---|---|---|---|
| H | H | 2-OCH₃ | 2-Cl | O | O |
| H | H | 2-OCH₃ | 3-Cl | O | O |
| H | H | 2-OCH₃ | 4-Cl | O | O |
| H | H | 2-OCH₃ | 4-Br | O | O |
| H | H | 2-OCH₃ | 4-I | O | O |
| H | H | 2-OCH₃ | 4-CH₃ | O | O |
| H | H | 2-OCH₃ | 4-C(C₃)₃ | O | O |
| H | H | 2-OCH₃ | 4-Q54 | O | O |
| H | H | 2-OCH₃ | 4-CF₃ | O | O |
| H | H | 2-OCH₃ | 4-CH₂CH=CHCl | O | O |
| H | H | 2-OCH₃ | 4-CH=C(Cl)CF₃ | O | O |
| H | H | 2-OCH₃ | 4-OCH₃ | O | O |
| H | H | 2-OCH₃ | 4-O(Q54-2-CH(CH₃)₂-5-CH₃) | O | O |
| H | H | 2-OCH₃ | 4-OCHF₂ | O | O |
| H | H | 2-OCH₃ | 4-OCF₂Br | O | O |
| H | H | 2-OCH₃ | 4-OCF₃ | O | O |
| H | H | 2-OCH₃ | 4-OCF₂CHF₂ | O | O |
| H | H | 2-OCH₃ | 4-OCF₂CHFBr | O | O |
| H | H | 2-OCH₃ | 4-OCF₂CF₂CF₃ | O | O |
| H | H | 2-OCH₃ | 4-O(Q51-2,2-Cl₂) | O | O |
| H | H | 2-OCH₃ | 4-OCH₂(Q51-2,2-Cl₂) | O | O |
| H | H | 2-OCH₃ | 4-SCH₃ | O | O |
| H | H | 2-OCH₃ | 4-SCF₃ | O | O |
| H | H | 2-OCH₃ | 4-SCF₂Cl | O | O |
| H | H | 2-OCH₃ | 4-SO₂CF₃ | O | O |
| H | H | 2-OCH₃ | 4-OCF₂CHFOCF₃ | O | O |
| H | H | 2-OCH₃ | 4-CO₂CH₂CF₃ | O | O |
| H | H | 2-OCH₃ | 4-NO₂ | O | O |
| H | H | 2-OCH₃ | 4-CN | O | O |
| H | H | 2-OCH₃ | 4-N(CH₃)CH₂CH₂CH₃ | O | O |
| H | H | 2-OCH₃ | 4-OCF₂O-4 | O | O |
| H | H | 2-OCH₃ | 3-OC(CH₃)₂CF₂O-4 | O | O |
| H | H | 2-OCH₃ | 4-(C₆H₄-4-Cl) | O | O |
| H | H | 2-OCH₃ | 4-O(C₆H₄-4-Cl) | O | O |
| H | H | 2-OCH₃ | 4-O(C₆H₄-4-CF₃) | O | O |
| H | H | 2-OCH₃ | 4-O(C₆H₄-4-CN) | O | O |
| H | H | 2-OCH₃ | 4-O(C₆H₄-4-NO₂) | O | O |
| H | H | 2-OCH₃ | 4-O(C₆H₄-4-OCF₃) | O | O |
| H | H | 2-OCH₃ | 4-O(C₆H₃-3,5-F₂) | O | O |
| H | H | 2-OCH₃ | 4-O(C₆H₃-2,4-Cl₂) | O | O |
| H | H | 2-OCH₃ | 4-O(C₆H₃-3,5-Cl₂) | O | O |
| H | H | 2-OCH₃ | 4-O(C₆H₃-3-OCF₂CF₂O-4) | O | O |
| H | H | 2-OCH₃ | 4-O(C₆H₃-2-Cl-4-CF₃) | O | O |
| H | H | 2-OCH₃ | 3-O(C₆H₃-2-Cl-4-CF₃) | O | O |
| H | H | 2-OCH₃ | 4-S(C₆H₃-2-Cl-4-CF₃) | O | O |
| H | H | 2-OCH₃ | 4-NH(C₆H₃-2-Cl-4-CF₃) | O | O |
| H | H | 2-OCH₃ | 4-N(CH₂CH₂CH₃)(C₆H₄-4-Cl) | O | O |
| H | H | 2-OCH₃ | 4-OCH₂(C₆H₃-2,4-Cl₂) | O | O |
| H | H | 2-OCH₃ | 4-CH₂ON=C(Q51)(C₆H₄-4-Cl) | O | O |
| H | H | 2-OCH₃ | 3-O(Q38-3-Cl-5-CF₃) | O | O |
| H | H | 2-OCH₃ | 4-O(Q38-3-Cl-5-CF₃) | O | O |
| H | H | 2-OCH₃ | 4-NH(Q38-3-Cl-5-CF₃) | O | O |
| H | H | 2-OCH₃ | 4-(Q38-3-Cl-5-CF₃) | O | O |
| H | H | 2-OCH₃ | 3-O(Q50-6-Cl) | O | O |
| H | H | 2-OCH₃ | 3-O(Q50-6-CF₃) | O | O |
| H | H | 2-OCH₃ | 4-O(Q50-6-CF₃) | O | O |
| H | H | 2-OCH₃ | 3,5-F₂ | O | O |
| H | H | 2-OCH₃ | 2,4-Cl₂ | O | O |
| H | H | 2-OCH₃ | 2,5-Cl₂ | O | O |
| H | H | 2-OCH₃ | 2,6-Cl₂ | O | O |
| H | H | 2-OCH₃ | 3,4-Cl₂ | O | O |
| H | H | 2-OCH₃ | 3,5-Cl₂ | O | O |
| H | H | 2-OCH₃ | 3,4-Br₂ | O | O |
| H | H | 2-OCH₃ | 2-F-4-Cl | O | O |
| H | H | 2-OCH₃ | 2-F-4-OCF₂CHF₂ | O | O |
| H | H | 2-OCH₃ | 2-F-4-O(C₆H₃-2-Cl-4-CF₃) | O | O |
| H | H | 2-OCH₃ | 2-F-4-N=NC₆H₅ | O | O |
| H | H | 2-OCH₃ | 2-F-4-NHCON(CH₂CH₂CH₃)(C₆H₄-4-Cl) | O | O |
| H | H | 2-OCH₃ | 2-F-4-O(Q38-3-Cl-5-CF₃) | O | O |
| H | H | 2-OCH₃ | 3-F-4-O(Q38-3-Cl-5-CF₃) | O | O |
| H | H | 2-OCH₃ | 2-Cl-4-CF₃ | O | O |
| H | H | 2-OCH₃ | 2-Cl-4-SCF₂CHF₂ | O | O |
| H | H | 2-OCH₃ | 2-Cl-4-O(C₆H₃-2-Cl-4-CF₃) | O | O |
| H | H | 2-OCH₃ | 2-Cl-4-O(Q38-3-Cl-5-CF₃) | O | O |
| H | H | 2-OCH₃ | 2-Cl-5-O(Q50-6-CF₃) | O | O |
| H | H | 2-OCH₃ | 2-Cl-5-S(Q50-6-CF₃) | O | O |
| H | H | 2-OCH₃ | 3-Cl-4-CF₃ | O | O |
| H | H | 2-OCH₃ | 3-Cl-4-OCF₃ | O | O |
| H | H | 2-OCH₃ | 3-Cl-4-OCF₂CHF₂ | O | O |
| H | H | 2-OCH₃ | 3-Cl-4-OCF₂CHFOCF₃ | O | O |
| H | H | 2-OCH₃ | 3-Cl-4-O(C₆H₃-2-Cl-4-CF₃) | O | O |
| H | H | 2-OCH₃ | 3-Cl-4-O(Q38-3-Cl-5-CF₃) | O | O |
| H | H | 2-OCH₃ | 2-CH₃-4-O(Q38-3-Cl-5-CF₃) | O | O |

-continued

| | | | | | |
|---|---|---|---|---|---|
| H | H | 2-OCH$_3$ | 3-CF$_3$-4-Cl | O | O |
| H | H | 2-OCH$_3$ | 3-CF$_3$-4-OCF$_2$CHF$_2$ | O | O |
| H | H | 2-OCH$_3$ | 3-CF$_3$-4-O(Q38-3-Cl-5-CF$_3$) | O | O |
| H | H | 2-OCH$_3$ | 2,3-F$_2$-4-OCF$_3$ | O | O |
| H | H | 2-OCH$_3$ | 2,3-F$_2$-4-O(Q38-3-Cl-5-CF$_3$) | O | O |
| H | H | 2-OCH$_3$ | 2,5-F$_2$-4-Cl | O | O |
| H | H | 2-OCH$_3$ | 2,5-F$_2$-4-OCF$_3$ | O | O |
| H | H | 2-OCH$_3$ | 3,5-F$_2$-4-CF$_3$ | O | O |
| H | H | 2-OCH$_3$ | 2,3-Cl$_2$-4-OCF$_2$CHFCl | O | O |
| H | H | 2-OCH$_3$ | 2,5-Cl$_2$-4-OCF$_2$CHF$_2$ | O | O |
| H | H | 2-OCH$_3$ | 2,5-Cl$_2$-4-O(C$_6$H$_3$-2-Cl-4-CF$_3$) | O | O |
| H | H | 2-OCH$_3$ | 2,5-Cl$_2$-4-O(Q38-3-Cl-5-CF$_3$) | O | O |
| H | H | 2-OCH$_3$ | 2,6-Cl$_2$-4-CF$_3$ | O | O |
| H | H | 2-OCH$_3$ | 3,4,5-Cl$_3$ | O | O |
| H | H | 2-OCH$_3$ | 3,5-Cl$_2$-4-OCF$_2$CHF$_2$ | O | O |
| H | H | 2-OCH$_3$ | 3,5-Cl$_2$-4-OCF$_2$CHFOCF$_3$ | O | O |
| H | H | 2-OCH$_3$ | 3,5-Cl$_2$-4-SCF$_2$CHF$_2$ | O | O |
| H | H | 2-OCH$_3$ | 3,5-Cl$_2$-4-N(CH$_3$)CH$_2$CH$_2$CH$_3$ | O | O |
| H | H | 2-OCH$_3$ | 3,5-Cl$_2$-4-O(C$_6$H$_4$-4-Cl) | O | O |
| H | H | 2-OCH$_3$ | 3,5-Cl$_2$-4-O(C$_6$H$_4$-4-CN) | O | O |
| H | H | 2-OCH$_3$ | 3,5-Cl$_2$-4-O(C$_6$H$_4$-4-NO$_2$) | O | O |
| H | H | 2-OCH$_3$ | 3,5-Cl$_2$-4-O(C$_6$H$_3$-2-Cl-4-CF$_3$) | O | O |
| H | H | 2-OCH$_3$ | 3,5-Cl$_2$-4-O(C$_6$H$_3$-3-OCF$_2$CF$_2$O-4) | O | O |
| H | H | 2-OCH$_3$ | 3,5-Cl$_2$-4-OCH$_2$(C$_6$H$_4$-4-CF$_3$) | O | O |
| H | H | 2-OCH$_3$ | 3,5-Cl$_2$-4-NH(C$_6$H$_4$-4-CF$_3$) | O | O |
| H | H | 2-OCH$_3$ | 3,5-Cl$_2$-4-(Q38-3-Cl-5-CF$_3$) | O | O |
| H | H | 2-OCH$_3$ | 3,5-Cl$_2$-4-O(Q38-3-Cl-5-CF$_3$) | O | O |
| H | H | 2-OCH$_3$ | 3,5-Cl$_2$-4-O(Q50-6-CF$_3$) | O | O |
| H | H | 2-OCH$_3$ | 2-F-4,5-Cl$_2$ | O | O |
| H | H | 2-OCH$_3$ | 2-F-3-CF$_3$-5-Cl | O | O |
| H | H | 2-OCH$_3$ | 2-F-4-OCF$_2$CHF$_2$-5-Cl | O | O |
| H | H | 2-OCH$_3$ | 2-F-4-O(C$_6$H$_3$-2-Cl-4-CF$_3$)-5-Cl | O | O |
| H | H | 2-OCH$_3$ | 3-Cl-4-OCF$_2$CHF$_2$-5-CF$_3$ | O | O |
| H | H | 2-OCH$_3$ | 3-Cl-4-O(Q38-3-Cl-5-CF$_3$)-5-CH$_2$OCH$_3$ | O | O |
| H | H | 2-OCH$_3$ | 2-CF$_3$-4,6-(NO$_2$)$_2$ | O | O |
| H | H | 2-OCH$_3$ | 2,4-F$_2$-3,5-Cl$_2$ | O | O |
| H | H | 2-OCH$_3$ | 2,3,5-F$_3$-4-OCF$_2$CHFCF$_3$ | O | O |
| H | H | 2-OCH$_3$ | 2-F-3,5-Cl$_2$-4-OCF$_2$CHF$_2$ | O | O |
| H | H | 2-OCH$_3$ | 2-F-3,5-Cl$_2$-4-O(C$_6$H$_3$-2-Cl-4-CF$_3$) | O | O |
| H | H | 2-OCH$_3$ | 2-F-3,5-Cl$_2$-4-O(Q38-3-Cl-5-CF$_3$) | O | O |
| H | H | 2-OCH$_3$ | 2,3,4,5,6-F$_5$ | O | O |
| H | H | 2-OCH$_3$ | 2,4,6-F$_3$-3,5-Cl$_2$ | O | O |
| H | H | 2-CF$_3$ | 4-F | O | O |
| H | H | 2-CF$_3$ | 2-Cl | O | O |
| H | H | 2-CF$_3$ | 3-Cl | O | O |
| H | H | 2-CF$_3$ | 4-Cl | O | O |
| H | H | 2-CF$_3$ | 4-Br | O | O |
| H | H | 2-CF$_3$ | 4-I | O | O |
| H | H | 2-CF$_3$ | 4-CH$_3$ | O | O |
| H | H | 2-CF$_3$ | 4-C(CH$_3$)$_3$ | O | O |
| H | H | 2-CF$_3$ | 4-Q54 | O | O |
| H | H | 2-CF$_3$ | 4-CF$_3$ | O | O |
| H | H | 2-CF$_3$ | 4-CH$_2$CH=CHCl | O | O |
| H | H | 2-CF$_3$ | 4-CH=C(Cl)CF$_3$ | O | O |
| H | H | 2-CF$_3$ | 4-OCH$_3$ | O | O |
| H | H | 2-CF$_3$ | 4-O(Q54-2-CH(CH$_3$)$_2$-5-CH$_3$) | O | O |
| H | H | 2-CF$_3$ | 4-OCHF$_2$ | O | O |
| H | H | 2-CF$_3$ | 4-OCF$_2$Br | O | O |
| H | H | 2-CF$_3$ | 4-OCF$_3$ | O | O |
| H | H | 2-CF$_3$ | 4-OCF$_2$CHF$_2$ | O | O |
| H | H | 2-CF$_3$ | 4-OCF$_2$CHFBr | O | O |
| H | H | 2-CF$_3$ | 4-OCF$_2$CF$_2$CF$_3$ | O | O |
| H | H | 2-CF$_3$ | 4-O(Q51-2,2-Cl$_2$) | O | O |
| H | H | 2-CF$_3$ | 4-OCH$_2$(Q51-2,2-Cl$_2$) | O | O |
| H | H | 2-CF$_3$ | 4-SCH$_3$ | O | O |
| H | H | 2-CF$_3$ | 4-SCF$_3$ | O | O |
| H | H | 2-CF$_3$ | 4-SCF$_2$Cl | O | O |
| H | H | 2-CF$_3$ | 4-SO$_2$CF$_3$ | O | O |
| H | H | 2-CF$_3$ | 4-OCF$_2$CHFOCF$_3$ | O | O |
| H | H | 2-CF$_3$ | 4-CO$_2$CH$_2$CF$_3$ | O | O |
| H | H | 2-CF$_3$ | 4-NO$_2$ | O | O |
| H | H | 2-CF$_3$ | 4-CN | O | O |
| H | H | 2-CF$_3$ | 4-N(CH$_3$)CH$_2$CH$_2$CH$_3$ | O | O |
| H | H | 2-CF$_3$ | 3-OCF$_2$O-4 | O | O |
| H | H | 2-CF$_3$ | 3-OC(CH$_3$)$_2$CF$_2$O-4 | O | O |
| H | H | 2-CF$_3$ | 4-(C$_6$H$_4$-4-Cl) | O | O |
| H | H | 2-CF$_3$ | 4-O(C$_6$H$_4$-4-Cl) | O | O |
| H | H | 2-CF$_3$ | 4-O(C$_6$H$_4$-4-CF$_3$) | O | O |
| H | H | 2-CF$_3$ | 4-O(C$_6$H$_4$-4-CN) | O | O |
| H | H | 2-CF$_3$ | 4-O(C$_6$H$_4$-4-NO$_2$) | O | O |

-continued

| | | | | | |
|---|---|---|---|---|---|
| H | H | 2-CF$_3$ | 4-O(C$_6$H$_4$-4-OCF$_3$) | O | O |
| H | H | 2-CF$_3$ | 4-O(C$_6$H$_3$-3,5-F$_2$) | O | O |
| H | H | 2-CF$_3$ | 4-O(C$_6$H$_3$-2,4-Cl$_2$) | O | O |
| H | H | 2-CF$_3$ | 4-O(C$_6$H$_3$-3,5-Cl$_2$) | O | O |
| H | H | 2-CF$_3$ | 4-O(C$_6$H$_3$-3-OCF$_2$CF$_2$O-4) | O | O |
| H | H | 2-CF$_3$ | 4-O(C$_6$H$_3$-2-Cl-4-CF$_3$) | O | O |
| H | H | 2-CF$_3$ | 3-O(C$_6$H$_3$-2-Cl-4-CF$_3$) | O | O |
| H | H | 2-CF$_3$ | 4-S(C$_6$H$_3$-2-Cl-4-CF$_3$) | O | O |
| H | H | 2-CF$_3$ | 4-NH(C$_6$H$_3$-2-Cl-4-CF$_3$) | O | O |
| H | H | 2-CF$_3$ | 4-N(CH$_2$CH$_2$CH$_3$)(C$_6$H$_4$-4-Cl) | O | O |
| H | H | 2-CF$_3$ | 4-OCH$_2$(C$_6$H$_3$-2,4-Cl$_2$) | O | O |
| H | H | 2-CF$_3$ | 4-CH$_2$ON=C(Q51)(C$_6$H$_4$-4-Cl) | O | O |
| H | H | 2-CF$_3$ | 3-O(Q38-3-Cl-5-CF$_3$) | O | O |
| H | H | 2-CF$_3$ | 4-O(Q38-3-Cl-5-CF$_3$) | O | O |
| H | H | 2-CF$_3$ | 4-NH(Q38-3-Cl-5-CF$_3$) | O | O |
| H | H | 2-CF$_3$ | 4-(Q38-3-Cl-5-CF$_3$) | O | O |
| H | H | 2-CF$_3$ | 3-O(Q50-6-Cl) | O | O |
| H | H | 2-CF$_3$ | 3-O(Q50-6-CF$_3$) | O | O |
| H | H | 2-CF$_3$ | 4-O(Q50-6-CF$_3$) | O | O |
| H | H | 2-CF$_3$ | 3,5-F$_2$ | O | O |
| H | H | 2-CF$_3$ | 2,4-Cl$_2$ | O | O |
| H | H | 2-CF$_3$ | 2,5-Cl$_2$ | O | O |
| H | H | 2-CF$_3$ | 2,6-Cl$_2$ | O | O |
| H | H | 2-CF$_3$ | 3,4-Cl$_2$ | O | O |
| H | H | 2-CF$_3$ | 3,5-Cl$_2$ | O | O |
| H | H | 2-CF$_3$ | 3,4-Br$_2$ | O | O |
| H | H | 2-CF$_3$ | 2-F-4-Cl | O | O |
| H | H | 2-CF$_3$ | 2-F-4-OCF$_2$CHF$_2$ | O | O |
| H | H | 2-CF$_3$ | 2-F-4-O(C$_6$H$_3$-2-Cl-4-CF$_3$) | O | O |
| H | H | 2-CF$_3$ | 2-F-4-N=NC$_6$H$_5$ | O | O |
| H | H | 2-CF$_3$ | 2-F-4-NHCON(CH$_2$CH$_2$CH$_3$)(C$_6$H$_4$-4-Cl) | O | O |
| H | H | 2-CF$_3$ | 2-F-4-O(Q38-3-Cl-5-CF$_3$) | O | O |
| H | H | 2-CF$_3$ | 3-F-4-O(Q38-3-Cl-5-CF$_3$) | O | O |
| H | H | 2-CF$_3$ | 2-Cl-4-CF$_3$ | O | O |
| H | H | 2-CF$_3$ | 2-Cl-4-SCF$_2$CHF$_2$ | O | O |
| H | H | 2-CF$_3$ | 2-Cl-4-O(C$_6$H$_3$-2-Cl-4-CF$_3$) | O | O |
| H | H | 2-CF$_3$ | 2-Cl-4-O(Q38-3-Cl-5-CF$_3$) | O | O |
| H | H | 2-CF$_3$ | 2-Cl-5-O(Q50-6-CF$_3$) | O | O |
| H | H | 2-CF$_3$ | 2-Cl-5-S(Q50-6-CF$_3$) | O | O |
| H | H | 2-CF$_3$ | 3-Cl-4-CF$_3$ | O | O |
| H | H | 2-CF$_3$ | 3-Cl-4-OCF$_3$ | O | O |
| H | H | 2-CF$_3$ | 3-Cl-4-OCF$_2$CHF$_2$ | O | O |
| H | H | 2-CF$_3$ | 3-Cl-4-OCF$_2$CHFOCF$_3$ | O | O |
| H | H | 2-CF$_3$ | 3-Cl-4-O(C$_6$H$_3$-2-Cl-4-CF$_3$) | O | O |
| H | H | 2-CF$_3$ | 3-Cl-4-O(Q38-3-Cl-5-CF$_3$) | O | O |
| H | H | 2-CF$_3$ | 2-CH$_3$-4-O(Q38-3-Cl-5-CF$_3$) | O | O |
| H | H | 2-CF$_3$ | 3-CF$_3$-4-Cl | O | O |
| H | H | 2-CF$_3$ | 3-CF$_3$-4-OCF$_2$CHF$_2$ | O | O |
| H | H | 2-CF$_3$ | 3-CF$_3$-4-O(Q38-3-Cl-5-CF$_3$) | O | O |
| H | H | 2-CF$_3$ | 2,3-F$_2$-4-OCF$_3$ | O | O |
| H | H | 2-CF$_3$ | 2,3-F$_2$-4-O(Q38-3-Cl-5-CF$_3$) | O | O |
| H | H | 2-CF$_3$ | 2,5-F$_2$-4-Cl | O | O |
| H | H | 2-CF$_3$ | 2,5-F$_2$-4-OCF$_3$ | O | O |
| H | H | 2-CF$_3$ | 3,5-F$_2$-4-CF$_3$ | O | O |
| H | H | 2-CF$_3$ | 2,3-Cl$_2$-4-OCF$_2$CHFCl | O | O |
| H | H | 2-CF$_3$ | 2,5-Cl$_2$-4-OCF$_2$CHF$_2$ | O | O |
| H | H | 2-CF$_3$ | 2,5-Cl$_2$-4-O(C$_6$H$_3$-2-Cl-4-CF$_3$) | O | O |
| H | H | 2-CF$_3$ | 2,5-Cl$_2$-4-O(Q38-3-Cl-5-CF$_3$) | O | O |
| H | H | 2-CF$_3$ | 2,6-Cl$_2$-4-CF$_3$ | O | O |
| H | H | 2-CF$_3$ | 3,4,5-Cl$_3$ | O | O |
| H | H | 2-CF$_3$ | 3,5-Cl$_2$-4-OCF$_2$CHF$_2$ | O | O |
| H | H | 2-CF$_3$ | 3,5-Cl$_2$-4-OCF$_2$CHFOCF$_3$ | O | O |
| H | H | 2-CF$_3$ | 3,5-Cl$_2$-4-SCF$_2$CHF$_2$ | O | O |
| H | H | 2-CF$_3$ | 3,5-Cl$_2$-4-N(CH$_3$)CH$_2$CH$_2$CH$_3$ | O | O |
| H | H | 2-CF$_3$ | 3,5-Cl$_2$-4-O(C$_6$H$_4$-4-Cl) | O | O |
| H | H | 2-CF$_3$ | 3,5-Cl$_2$-4-O(C$_6$H$_4$-4-CN) | O | O |
| H | H | 2-CF$_3$ | 3,5-Cl$_2$-4-O(C$_6$H$_4$-4-NO$_2$) | O | O |
| H | H | 2-CF$_3$ | 3,5-Cl$_2$-4-O(C$_6$H$_3$-2-Cl-4-CF$_3$) | O | O |
| H | H | 2-CF$_3$ | 3,5-Cl$_2$-4-O(C$_6$H$_3$-3-OCF$_2$CF$_2$O-4) | O | O |
| H | H | 2-CF$_3$ | 3,5-Cl$_2$-4-OCH$_2$(C$_6$H$_4$-4-CF$_3$) | O | O |
| H | H | 2-CF$_3$ | 3,5-Cl$_2$-4-NH(C$_6$H$_4$-4-CF$_3$) | O | O |
| H | H | 2-CF$_3$ | 3,5-Cl$_2$-4-(Q38-3-Cl-5-CF$_3$) | O | O |
| H | H | 2-CF$_3$ | 3,5-Cl$_2$-4-O(Q38-3-Cl-5-CF$_3$) | O | O |
| H | H | 2-CF$_3$ | 3,5-Cl$_2$-4-O(Q50-6-CF$_3$) | O | O |
| H | H | 2-CF$_3$ | 2-F-4,5-Cl$_2$ | O | O |
| H | H | 2-CF$_3$ | 2-F-3-CF$_3$-5-Cl | O | O |
| H | H | 2-CF$_3$ | 2-F-4-OCF$_2$CHF$_2$-5-Cl | O | O |
| H | H | 2-CF$_3$ | 2-F-4-O(C$_6$H$_3$-2-Cl-4-CF$_3$)-5-Cl | O | O |
| H | H | 2-CF$_3$ | 3-Cl-4-OCF$_2$CHF$_2$-5-CF$_3$ | O | O |
| H | H | 2-CF$_3$ | 3-Cl-4-O(Q38-3-Cl-5-CF$_3$)-5-CH$_2$OCH$_3$ | O | O |
| H | H | 2-CF$_3$ | 2-CF$_3$-4,6-(NO$_2$)$_2$ | O | O |
| H | H | 2-CF$_3$ | 2,4-F$_2$-3,5-Cl$_2$ | O | O |
| H | H | 2-CF$_3$ | 2,3,5-F$_3$-4-OCF$_2$CHFCF$_3$ | O | O |

-continued

| | | | | | | |
|---|---|---|---|---|---|---|
| H | H | 2-CF$_3$ | 2-F-3,5-Cl$_2$-4-OCF$_2$CHF$_2$ | | O | O |
| H | H | 2-CF$_3$ | 2-F-3,5-Cl$_2$-4-O(C$_6$H$_3$-2-Cl-4-CF$_3$) | | O | O |
| H | H | 2-CF$_3$ | 2-F-3,5-Cl$_2$-4-O(Q38-3-Cl-5-CF$_3$) | | O | O |
| H | H | 2-CF$_3$ | 2,3,4,5,6-F$_5$ | | O | O |
| H | H | 2-CF$_3$ | 2,4,6-F$_3$-3,5-Cl$_2$ | | O | O |
| H | H | 2-Cl-6-F | 4-F | | O | O |
| H | H | 2-Cl-6-F | 2-Cl | | O | O |
| H | H | 2-Cl-6-F | 3-Cl | | O | O |
| H | H | 2-Cl-6-F | 4-Cl | | O | O |
| H | H | 2-Cl-6-F | 4-Br | | O | O |
| H | H | 2-Cl-6-F | 4-I | | O | O |
| H | H | 2-Cl-6-F | 4-CH$_3$ | | O | O |
| H | H | 2-Cl-6-F | 4-C(CH$_3$)$_3$ | | O | O |
| H | H | 2-Cl-6-F | 4-Q54 | | O | O |
| H | H | 2-Cl-6-F | 4-CF$_3$ | | O | O |
| H | H | 2-Cl-6-F | 4-CH$_2$CH=CHCl | | O | O |
| H | H | 2-Cl-6-F | 4-CH=C(Cl)CF$_3$ | | O | O |
| H | H | 2-Cl-6-F | 4-OCH$_3$ | | O | O |
| H | H | 2-Cl-6-F | 4-O(Q54-2-CH(CH$_3$)$_2$-5-CH$_3$) | | O | O |
| H | H | 2-Cl-6-F | 4-OCHF$_2$ | | O | O |
| H | H | 2-Cl-6-F | 4-OCF$_2$Br | | O | O |
| H | H | 2-Cl-6-F | 4-OCF$_3$ | | O | O |
| H | H | 2-Cl-6-F | 4-OCF$_2$CHF$_2$ | | O | O |
| H | H | 2-Cl-6-F | 4-OCF$_2$CHFBr | | O | O |
| H | H | 2-Cl-6-F | 4-OCF$_2$CF$_2$CF$_3$ | | O | O |
| H | H | 2-Cl-6-F | 4-O(Q51-2,2-Cl$_2$) | | O | O |
| H | H | 2-Cl-6-F | 4-OCH$_2$(Q51-2,2-Cl$_2$) | | O | O |
| H | H | 2-Cl-6-F | 4-SCH$_3$ | | O | O |
| H | H | 2-Cl-6-F | 4-SCF$_3$ | | O | O |
| H | H | 2-Cl-6-F | 4-SCF$_2$Cl | | O | O |
| H | H | 2-Cl-6-F | 4-SO$_2$CF$_3$ | | O | O |
| H | H | 2-Cl-6-F | 4-OCF$_2$CHFOCF$_3$ | | O | O |
| H | H | 2-Cl-6-F | 4-CO$_2$CH$_2$CF$_3$ | | O | O |
| H | H | 2-Cl-6-F | 4-NO$_2$ | | O | O |
| H | H | 2-Cl-6-F | 4-CN | | O | O |
| H | H | 2-Cl-6-F | 4-N(CH$_3$)CH$_2$CH$_2$CH$_3$ | | O | O |
| H | H | 2-Cl-6-F | 3-OCF$_2$O-4 | | O | O |
| H | H | 2-Cl-6-F | 3-OC(CH$_3$)$_2$CF$_2$O-4 | | O | O |
| H | H | 2-Cl-6-F | 4-(C$_6$H$_4$-4-Cl) | | O | O |
| H | H | 2-Cl-6-F | 4-O(C$_6$H$_4$-4-Cl) | | O | O |
| H | H | 2-Cl-6-F | 4-O(C$_6$H$_4$-4-CF$_3$) | | O | O |
| H | H | 2-Cl-6-F | 4-O(C$_6$H$_4$-4-CN) | | O | O |
| H | H | 2-Cl-6-F | 4-O(C$_6$H$_4$-4-NO$_2$) | | O | O |
| H | H | 2-Cl-6-F | 4-O(C$_6$H$_4$-4-OCF$_3$) | | O | O |
| H | H | 2-Cl-6-F | 4-O(C$_6$H$_3$-3,5-F$_2$) | | O | O |
| H | H | 2-Cl-6-F | 4-O(C$_6$H$_3$-2,4-Cl$_2$) | | O | O |
| H | H | 2-Cl-6-F | 4-O(C$_6$H$_3$-3,5-Cl$_2$) | | O | O |
| H | H | 2-Cl-6-F | 4-O(C$_6$H$_3$-3-OCF$_2$CF$_2$O-4) | | O | O |
| H | H | 2-Cl-6-F | 4-O(C$_6$H$_3$-2-Cl-4-CF$_3$) | | O | O |
| H | H | 2-Cl-6-F | 3-O(C$_6$H$_3$-2-Cl-4-CF$_3$) | | O | O |
| H | H | 2-Cl-6-F | 4-S(C$_6$H$_3$-2-Cl-4-CF$_3$) | | O | O |
| H | H | 2-Cl-6-F | 4-NH(C$_6$H$_3$-2-Cl-4-CF$_3$) | | O | O |
| H | H | 2-Cl-6-F | 4-N(CH$_2$CH$_2$CH$_3$)(C$_6$H$_4$-4-Cl) | | O | O |
| H | H | 2-Cl-6-F | 4-OCH$_2$(C$_6$H$_3$-2,4-Cl$_2$) | | O | O |
| H | H | 2-Cl-6-F | 4-CH$_2$ON=C(Q51)(C$_6$H$_4$-4-Cl) | | O | O |
| H | H | 2-Cl-6-F | 3-O(Q38-3-Cl-5-CF$_3$) | | O | O |
| H | H | 2-Cl-6-F | 4-O(Q38-3-Cl-5-CF$_3$) | | O | O |
| H | H | 2-Cl-6-F | 4-NH(Q38-3-Cl-5-CF$_3$) | | O | O |
| H | H | 2-Cl-6-F | 4-(Q38-3-Cl-5-CF$_3$) | | O | O |
| H | H | 2-Cl-6-F | 3-O(Q50-6-Cl) | | O | O |
| H | H | 2-Cl-6-F | 3-O(Q50-6-CF$_3$) | | O | O |
| H | H | 2-Cl-6-F | 4-O(Q50-6-CF$_3$) | | O | O |
| H | H | 2-Cl-6-F | 3,5-F$_2$ | | O | O |
| H | H | 2-Cl-6-F | 2,4-Cl$_2$ | | O | O |
| H | H | 2-Cl-6-F | 2,5-Cl$_2$ | | O | O |
| H | H | 2-Cl-6-F | 2,6-Cl$_2$ | | O | O |
| H | H | 2-Cl-6-F | 3,4-Cl$_2$ | | O | O |
| H | H | 2-Cl-6-F | 3,5-Cl$_2$ | | O | O |
| H | H | 2-Cl-6-F | 3,4-Br$_2$ | | O | O |
| H | H | 2-Cl-6-F | 2-F-4-Cl | | O | O |
| H | H | 2-Cl-6-F | 2-F-4-OCF$_2$CHF$_2$ | | O | O |
| H | H | 2-Cl-6-F | 2-F-4-O(C$_6$H$_3$2-Cl-4-CF$_3$) | | O | O |
| H | H | 2-Cl-6-F | 2-F-4-N=NC$_6$H$_5$ | | O | O |
| H | H | 2-Cl-6-F | 2-F-4-NHCON(CH$_2$CH$_2$CH$_3$)(C$_6$H$_4$-4-Cl) | | O | O |
| H | H | 2-Cl-6-F | 2-F-4-O(Q38-3-Cl-5-CF$_3$) | | O | O |
| H | H | 2-Cl-6-F | 3-F-4-O(Q38-3-Cl-5-CF$_3$) | | O | O |
| H | H | 2-Cl-6-F | 2-Cl-4-CF$_3$ | | O | O |
| H | H | 2-Cl-6-F | 2-Cl-4-SCF$_2$CHF$_2$ | | O | O |
| H | H | 2-Cl-6-F | 2-Cl-4-O(C$_6$H$_3$-2-Cl-4-CF$_3$) | | O | O |
| H | H | 2-Cl-6-F | 2-Cl-4-O(Q38-3-Cl-5-CF$_3$) | | O | O |
| H | H | 2-Cl-6-F | 2-Cl-5-O(Q50-6-CF$_3$) | | O | O |
| H | H | 2-Cl-6-F | 2-Cl-5-S(Q50-6-CF$_3$) | | O | O |
| H | H | 2-Cl-6-F | 3-Cl-4-CF$_3$ | | O | O |

-continued

| | | | | | |
|---|---|---|---|---|---|
| H | H | 2-Cl-6-F | 3-Cl-4-OCF₃ | O | O |
| H | H | 2-Cl-6-F | 3-Cl-4-OCF₂CHF₂ | O | O |
| H | H | 2-Cl-6-F | 3-Cl-4-OCF₂CHFOCF₃ | O | O |
| H | H | 2-Cl-6-F | 3-Cl-4-O(C₆H₃-2-Cl-4-CF₃) | O | O |
| H | H | 2-Cl-6-F | 3-Cl-4-O(Q38-3-Cl-5-CF₃) | O | O |
| H | H | 2-Cl-6-F | 2-CH₃-4-O(Q38-3-Cl-5-CF₃) | O | O |
| H | H | 2-Cl-6-F | 3-CF₃-4-Cl | O | O |
| H | H | 2-Cl-6-F | 3-CF₃-4-OCF₂CHF₂ | O | O |
| H | H | 2-Cl-6-F | 3-CF₃-4-O(Q38-3-Cl-5-CF₃) | O | O |
| H | H | 2-Cl-6-F | 2,3-F₂-4-OCF₃ | O | O |
| H | H | 2-Cl-6-F | 2,3-F₂-4-O(Q38-3-Cl-5-CF₃) | O | O |
| H | H | 2-Cl-6-F | 2,5-F₂-4-Cl | O | O |
| H | H | 2-Cl-6-F | 2,5-F₂-4-OCF₃ | O | O |
| H | H | 2-Cl-6-F | 3,5-F₂-4-CF₃ | O | O |
| H | H | 2-Cl-6-F | 2,3-Cl₂-4-OCF₂CHFCl | O | O |
| H | H | 2-Cl-6-F | 2,5-Cl₂-4-OCF₂CHF₂ | O | O |
| H | H | 2-Cl-6-F | 2,5-Cl₂-4-O(C₆H₃-2-Cl-4-CF₃) | O | O |
| H | H | 2-Cl-6-F | 2,5-Cl₂-4-O(Q38-3-Cl-5-CF₃) | O | O |
| H | H | 2-Cl-6-F | 2,6-Cl₂-4-CF₃ | O | O |
| H | H | 2-Cl-6-F | 3,4,5-Cl₃ | O | O |
| H | H | 2-Cl-6-F | 3,5-Cl₂-4-OCF₂CHF₂ | O | O |
| H | H | 2-Cl-6-F | 3,5-Cl₂-4-OCF₂CHFOCF₃ | O | O |
| H | H | 2-Cl-6-F | 3,5-Cl₂-4-SCF₂CHF₂ | O | O |
| H | H | 2-Cl-6-F | 3,5-Cl₂-4-N(CH₃)CH₂CH₂CH₃ | O | O |
| H | H | 2-Cl-6-F | 3,5-Cl₂-4-O(C₆H₄-4-Cl) | O | O |
| H | H | 2-Cl-6-F | 3,5-Cl₂-4-O(C₆H₄-4-CN) | O | O |
| H | H | 2-Cl-6-F | 3,5-Cl₂-4-O(C₆H₄-4-NO₂) | O | O |
| H | H | 2-Cl-6-F | 3,5-Cl₂-4-O(C₆H₃-2-Cl-4-CF₃) | O | O |
| H | H | 2-Cl-6-F | 3,5-Cl₂-4-O(C₆H₃-3-OCF₂CF₂O-4) | O | O |
| H | H | 2-Cl-6-F | 3,5-Cl₂-4-OCH₂(C₆H₄-4-CF₃) | O | O |
| H | H | 2-Cl-6-F | 3,5-Cl₂-4-NH(C₆H₄-4-CF₃) | O | O |
| H | H | 2-Cl-6-F | 3,5-Cl₂-4-(Q38-3-Cl-5-CF₃) | O | O |
| H | H | 2-Cl-6-F | 3,5-Cl₂-4-O(Q38-3-Cl-5-CF₃) | O | O |
| H | H | 2-Cl-6-F | 3,5-Cl₂-4-O(Q50-6-CF₃) | O | O |
| H | H | 2-Cl-6-F | 2-F-4,5-Cl₂ | O | O |
| H | H | 2-Cl-6-F | 2-F-3-CF₃-5-Cl | O | O |
| H | H | 2-Cl-6-F | 2-F-4-OCF₂CHF₂-5-Cl | O | O |
| H | H | 2-Cl-6-F | 2-F-4-O(C₆H₃-2-Cl-4-CF₃)-5-Cl | O | O |
| H | H | 2-Cl-6-F | 3-Cl-4-OCF₂CHF₂-5-CF₃ | O | O |
| H | H | 2-Cl-6-F | 3-Cl-4-O(Q38-3-Cl-5-CF₃)-5-CH₂OCH₃ | O | O |
| H | H | 2-Cl-6-F | 2-CF₃-4,6-(NO₂)₂ | O | O |
| H | H | 2-Cl-6-F | 2,4-F₂-3,5-Cl₂ | O | O |
| H | H | 2-Cl-6-F | 2,3,5-F₃-4-OCF₂CHFCF₃ | O | O |
| H | H | 2-Cl-6-F | 2-F-3,5-Cl₂-4-OCF₂CHF₂ | O | O |
| H | H | 2-Cl-6-F | 2-F,3,5-Cl₂-4-O(C₆H₃-2-Cl-4-CF₃) | O | O |
| H | H | 2-Cl-6-F | 2-F-3,5-Cl₂-4-O(Q38-3-Cl-5-CF₃) | O | O |
| H | H | 2-Cl-6-F | 2,3,4,5,6-F₅ | O | O |
| H | H | 2-Cl-6-F | 2,4,6-F₃-3,5-Cl₂ | O | O |
| H | H | 2,6-Cl₂ | 4-F | O | O |
| H | H | 2,6-Cl₂ | 2-Cl | O | O |
| H | H | 2,6-Cl₂ | 3-Cl | O | O |
| H | H | 2,6-Cl₂ | 4-Cl | O | O |
| H | H | 2,6-Cl₂ | 4-Br | O | O |
| H | H | 2,6-Cl₂ | 4-I | O | O |
| H | H | 2,6-Cl₂ | 4-CH₃ | O | O |
| H | H | 2,6-Cl₂ | 4-C(CH₃)₃ | O | O |
| H | H | 2,6-Cl₂ | 4-Q54 | O | O |
| H | H | 2,6-Cl₂ | 4-CF₃ | O | O |
| H | H | 2,6-Cl₂ | 4-CH₂CH=CHCl | O | O |
| H | H | 2,6-Cl₂ | 4-CH=C(Cl)CF₃ | O | O |
| H | H | 2,6-Cl₂ | 4-OCH₃ | O | O |
| H | H | 2,6-Cl₂ | 4-O(Q54-2-CH(CH₃)₂-5-CH₃) | O | O |
| H | H | 2,6-Cl₂ | 4-OCHF₂ | O | O |
| H | H | 2,6-Cl₂ | 4-OCF₂Br | O | O |
| H | H | 2,6-Cl₂ | 4-OCF₃ | O | O |
| H | H | 2,6-Cl₂ | 4-OCF₂CHF₂ | O | O |
| H | H | 2,6-Cl₂ | 4-OCF₂CHFBr | O | O |
| H | H | 2,6-Cl₂ | 4-OCF₂CF₂CF₃ | O | O |
| H | H | 2,6-Cl₂ | 4-O(Q51-2,2-Cl₂) | O | O |
| H | H | 2,6-Cl₂ | 4-OCH₂(Q51-2,2-Cl₂) | O | O |
| H | H | 2,6-Cl₂ | 4-SCH₃ | O | O |
| H | H | 2,6-Cl₂ | 4-SCF₃ | O | O |
| H | H | 2,6-Cl₂ | 4-SCF₂Cl | O | O |
| H | H | 2,6-Cl₂ | 4-SO₂CF₃ | O | O |
| H | H | 2,6-Cl₂ | 4-OCF₂CHFOCF₃ | O | O |
| H | H | 2,6-Cl₂ | 4-CO₂CH₂CF₃ | O | O |
| H | H | 2,6-Cl₂ | 4-NO₂ | O | O |
| H | H | 2,6-Cl₂ | 4-CN | O | O |
| H | H | 2,6-Cl₂ | 4-N(CH₃)CH₂CH₂CH₃ | O | O |
| H | H | 2,6-Cl₂ | 3-OCF₂O-4 | O | O |
| H | H | 2,6-Cl₂ | 3-OC(CH₃)₂CF₂O-4 | O | O |
| H | H | 2,6-Cl₂ | 4-(C₆H₄-4-Cl) | O | O |
| H | H | 2,6-Cl₂ | 4-O(C₆H₄-4-Cl) | O | O |

-continued

| | | | | | |
|---|---|---|---|---|---|
| H | H | 2,6-Cl$_2$ | 4-O(C$_6$H$_4$-4-CF$_3$) | O | O |
| H | H | 2,6-Cl$_2$ | 4-O(C$_6$H$_4$-4-CN) | O | O |
| H | H | 2,6-Cl$_2$ | 4-O(C$_6$H$_4$-4-NO$_2$) | O | O |
| H | H | 2,6-Cl$_2$ | 4-O(C$_6$H$_4$-4-OCF$_3$) | O | O |
| H | H | 2,6-Cl$_2$ | 4-O(C$_6$H$_3$-3,5-F$_2$) | O | O |
| H | H | 2,6-Cl$_2$ | 4-O(C$_6$H$_3$-2,4-Cl$_2$) | O | O |
| H | H | 2,6-Cl$_2$ | 4-O(C$_6$H$_3$-3,5-Cl$_2$) | O | O |
| H | H | 2,6-Cl$_2$ | 4-O(C$_6$H$_3$-3-OCF$_2$CF$_2$O-4) | O | O |
| H | H | 2,6-Cl$_2$ | 4-O(C$_6$H$_3$-2-Cl-4-CF$_3$) | O | O |
| H | H | 2,6-Cl$_2$ | 3-O(C$_6$H$_3$-2-Cl-4-CF$_3$) | O | O |
| H | H | 2,6-Cl$_2$ | 4-S(C$_6$H$_3$-2-Cl-4-CF$_3$) | O | O |
| H | H | 2,6-Cl$_2$ | 4-NH(C$_6$H$_3$-2-Cl-4-CF$_3$) | O | O |
| H | H | 2,6-Cl$_2$ | 4-N(CH$_2$CH$_2$CH$_3$)(C$_6$H$_4$-4-Cl) | O | O |
| H | H | 2,6-Cl$_2$ | 4-OCH$_2$(C$_6$H$_3$-2,4-Cl$_2$) | O | O |
| H | H | 2,6-Cl$_2$ | 4-CH$_2$ON=C(Q51)(C$_6$H$_4$-4-Cl) | O | O |
| H | H | 2,6-Cl$_2$ | 3-O(Q38-3-Cl-5-CF$_3$) | O | O |
| H | H | 2,6-Cl$_2$ | 4-O(Q38-3-Cl-5-CF$_3$) | O | O |
| H | H | 2,6-Cl$_2$ | 4-NH(Q38-3-Cl-5-CF$_3$) | O | O |
| H | H | 2,6-Cl$_2$ | 4-(Q38-3-Cl-5-CF$_3$) | O | O |
| H | H | 2,6-Cl$_2$ | 3-O(Q50-6-Cl) | O | O |
| H | H | 2,6-Cl$_2$ | 3-O(Q50-6-CF$_3$) | O | O |
| H | H | 2,6-Cl$_2$ | 4-O(Q50-6-CF$_3$) | O | O |
| H | H | 2,6-Cl$_2$ | 3,5-F$_2$ | O | O |
| H | H | 2,6-Cl$_2$ | 2,4-Cl$_2$ | O | O |
| H | H | 2,6-Cl$_2$ | 2,5-Cl$_2$ | O | O |
| H | H | 2,6-Cl$_2$ | 2,6-Cl$_2$ | O | O |
| H | H | 2,6-Cl$_2$ | 3,4-Cl$_2$ | O | O |
| H | H | 2,6-Cl$_2$ | 3,5-Cl$_2$ | O | O |
| H | H | 2,6-Cl$_2$ | 3,4-Br$_2$ | O | O |
| H | H | 2,6-Cl$_2$ | 2-F-4-Cl | O | O |
| H | H | 2,6-Cl$_2$ | 2-F-4-OCF$_2$CHF$_2$ | O | O |
| H | H | 2,6-Cl$_2$ | 2-F-4-O(C$_6$H$_3$2-Cl-4-CF$_3$) | O | O |
| H | H | 2,6-Cl$_2$ | 2-F-4-N=NC$_6$H$_5$ | O | O |
| H | H | 2,6-Cl$_2$ | 2-F-4-NHCON(CH$_2$CH$_2$CH$_3$)(C$_6$H$_4$-4-Cl) | O | O |
| H | H | 2,6-Cl$_2$ | 2-F-4-O(Q38-3-Cl-5-CF$_3$) | O | O |
| H | H | 2,6-Cl$_2$ | 3-F-4-O(Q38-3-Cl-5-CF$_3$) | O | O |
| H | H | 2,6-Cl$_2$ | 2-Cl-4-CF$_3$ | O | O |
| H | H | 2,6-Cl$_2$ | 2-Cl-4-SCF$_2$CHF$_2$ | O | O |
| H | H | 2,6-Cl$_2$ | 2-Cl-4-O(C$_6$H$_3$-2-Cl-4-CF$_3$) | O | O |
| H | H | 2,6-Cl$_2$ | 2-Cl-4-O(Q38-3-Cl-5-CF$_3$) | O | O |
| H | H | 2,6-Cl$_2$ | 2-Cl-5-O(Q50-6-CF$_3$) | O | O |
| H | H | 2,6-Cl$_2$ | 2-Cl-5-S(Q50-6-CF$_3$) | O | O |
| H | H | 2,6-Cl$_2$ | 3-Cl-4-CF$_3$ | O | O |
| H | H | 2,6-Cl$_2$ | 3-Cl-4-OCF$_3$ | O | O |
| H | H | 2,6-Cl$_2$ | 3-Cl-4-OCF$_2$CHF$_2$ | O | O |
| H | H | 2,6-Cl$_2$ | 3-Cl-4-OCF$_2$CHFOCF$_3$ | O | O |
| H | H | 2,6-Cl$_2$ | 3-Cl-4-O(C$_6$H$_3$-2-Cl-4-CF$_3$) | O | O |
| H | H | 2,6-Cl$_2$ | 3-Cl-4-O(Q38-3-Cl-5-CF$_3$) | O | O |
| H | H | 2,6-Cl$_2$ | 2-CH$_3$-4-O(Q38-3-Cl-5-CF$_3$) | O | O |
| H | H | 2,6-Cl$_2$ | 3-CF$_3$-4-Cl | O | O |
| H | H | 2,6-Cl$_2$ | 3-CF$_3$-4-OCF$_2$CHF$_2$ | O | O |
| H | H | 2,6-Cl$_2$ | 3-CF$_3$-4-O(Q38-3-Cl-5-CF$_3$) | O | O |
| H | H | 2,6-Cl$_2$ | 2,3-F$_2$4-OCF$_3$ | O | O |
| H | H | 2,6-Cl$_2$ | 2,3-F$_2$-4-O(Q38-3-Cl-5-CF$_3$) | O | O |
| H | H | 2,6-Cl$_2$ | 2,5-F$_2$-4-Cl | O | O |
| H | H | 2,6-Cl$_2$ | 2,5-F$_2$-4-OCF$_3$ | O | O |
| H | H | 2,6-Cl$_2$ | 3,5-F$_2$-4-CF$_3$ | O | O |
| H | H | 2,6-Cl$_2$ | 2,3-Cl$_2$-4-OCF$_2$CHFCl | O | O |
| H | H | 2,6-Cl$_2$ | 2,5-Cl$_2$-4-OCF$_2$CHF$_2$ | O | O |
| H | H | 2,6-Cl$_2$ | 2,5-Cl$_2$-4-O(C$_6$H$_3$-2-Cl-4-CF$_3$) | O | O |
| H | H | 2,6-Cl$_2$ | 2,5-Cl$_2$-4-O(Q38-3-Cl-5-CF$_3$) | O | O |
| H | H | 2,6-Cl$_2$ | 2,6-Cl$_2$-4-CF$_3$ | O | O |
| H | H | 2,6-Cl$_2$ | 3,4,5-Cl$_3$ | O | O |
| H | H | 2,6-Cl$_2$ | 3,5-Cl$_2$-4-OCF$_2$CHF$_2$ | O | O |
| H | H | 2,6-Cl$_2$ | 3,5-Cl$_2$-4-OCF$_2$CHFOCF$_3$ | O | O |
| H | H | 2,6-Cl$_2$ | 3,5-Cl$_2$-4-SCF$_2$CHF$_2$ | O | O |
| H | H | 2,6-Cl$_2$ | 3,5-Cl$_2$-4-N(CH$_3$)CH$_2$CH$_2$CH$_3$ | O | O |
| H | H | 2,6-Cl$_2$ | 3,5-Cl$_2$-4-O(C$_6$H$_4$-4-Cl) | O | O |
| H | H | 2,6-Cl$_2$ | 3,5-Cl$_2$-4-O(C$_6$H$_4$-4-CN) | O | O |
| H | H | 2,6-Cl$_2$ | 3,5-Cl$_2$-4-O(C$_6$H$_4$-4-NO$_2$) | O | O |
| H | H | 2,6-Cl$_2$ | 3,5-Cl$_2$-4-O(C$_6$H$_3$-2-Cl-4-CF$_3$) | O | O |
| H | H | 2,6-Cl$_2$ | 3,5-Cl$_2$-4-O(C$_6$H$_3$-3-OCF$_2$CF$_2$O-4) | O | O |
| H | H | 2,6-Cl$_2$ | 3,5-Cl$_2$-4-OCH$_2$(C$_6$H$_4$-4-CF$_3$) | O | O |
| H | H | 2,6-Cl$_2$ | 3,5-Cl$_2$-4-NH(C$_6$H$_4$-4-CF$_3$) | O | O |
| H | H | 2,6-Cl$_2$ | 3,5-Cl$_2$-4-(Q38-3-Cl-5-CF$_3$) | O | O |
| H | H | 2,6-Cl$_2$ | 3,5-Cl$_2$-4-O(Q38-3-Cl-5-CF$_3$) | O | O |
| H | H | 2,6-Cl$_2$ | 3,5-Cl$_2$-4-O(Q50-6-CF$_3$) | O | O |
| H | H | 2,6-Cl$_2$ | 2-F-4,5-Cl$_2$ | O | O |
| H | H | 2,6-Cl$_2$ | 2-F-3-CF$_3$-5-Cl | O | O |
| H | H | 2,6-Cl$_2$ | 2-F-4-OCF$_2$CHF$_2$-5-Cl | O | O |
| H | H | 2,6-Cl$_2$ | 2-F-4-O(C$_6$H$_3$-2-Cl-4-CF$_3$)-5-Cl | O | O |
| H | H | 2,6-Cl$_2$ | 3-Cl-4-OCF$_2$CHF$_2$-5-CF$_3$ | O | O |
| H | H | 2,6-Cl$_2$ | 3-Cl-4-O(Q38-3-Cl-5-CF$_3$)-5-CH$_2$OCH$_3$ | O | O |

-continued

| | | | | | |
|---|---|---|---|---|---|
| H | H | 2,6-Cl$_2$ | 2-CF$_3$-4,6-(NO$_2$)$_2$ | O | O |
| H | H | 2,6-Cl$_2$ | 2,4-F$_2$-3,5-Cl$_2$ | O | O |
| H | H | 2,6-Cl$_2$ | 2,3,5-F$_3$-4-OCF$_2$CHFCF$_3$ | O | O |
| H | H | 2,6-Cl$_2$ | 2-F-3,5-Cl$_2$-4-OCF$_2$CHF$_2$ | O | O |
| H | H | 2,6-Cl$_2$ | 2-F-3,5-Cl$_2$-4-O(C$_6$H$_3$-2-Cl-4-CF$_3$) | O | O |
| H | H | 2,6-Cl$_2$ | 2-F-3,5-Cl$_2$-4-O(Q38-3-Cl-5-CF$_3$) | O | O |
| H | H | 2,6-Cl$_2$ | 2,3,4,5,6-F$_5$ | O | O |
| H | H | 2,6-Cl$_2$ | 2,4,6-F$_3$-3,5-Cl$_2$ | O | O |
| H | H | 2-I | 4-Cl | O | O |
| H | H | 2-I | 4-OCF$_3$ | O | O |
| H | H | 2-I | 3-OCF$_2$O-4 | O | O |
| H | H | 2-I | 4-O(C$_6$H$_3$-2-Cl-4-CF$_3$) | O | O |
| H | H | 2-I | 4-CH$_2$ON=C(Q51)(C$_6$H$_4$-4-Cl) | O | O |
| H | H | 2-I | 3-O(Q38-3-Cl-5-CF$_3$) | O | O |
| H | H | 2-I | 4-O(Q38-3-Cl-5-CF$_3$) | O | O |
| H | H | 2-I | 3-O(Q50-6-CF$_3$) | O | O |
| H | H | 2-I | 2,4-Cl$_2$ | O | O |
| H | H | 2-I | 3,4-Cl$_2$ | O | O |
| H | H | 2-I | 3,5-Cl$_2$ | O | O |
| H | H | 2-I | 2-F-4-OCF$_2$CHF$_2$ | O | O |
| H | H | 2-I | 2-Cl-4-O(Q38-3-Cl-5-CF$_3$) | O | O |
| H | H | 2-I | 2-Cl-5-O(Q50-6-CF$_3$) | O | O |
| H | H | 2-I | 3-Cl-4-OCF$_3$ | O | O |
| H | H | 2-I | 3-Cl-4-O(Q38-3-Cl-5-CF$_3$) | O | O |
| H | H | 2-I | 3,5-Cl$_2$-4-OCF$_2$CHF$_2$ | O | O |
| H | H | 2-I | 3,5-Cl$_2$-4-O(C$_6$H$_3$-2-Cl-4-CF$_3$) | O | O |
| H | H | 2-I | 3,5-Cl$_2$-4-O(Q38-3-Cl-5-CF$_3$) | O | O |
| H | H | 2-I | 3,5-Cl$_2$-4-O(Q50-6-CF$_3$) | O | O |
| H | H | 2-I | 2-F-4,5-Cl$_2$ | O | O |
| H | H | 2-I | 2-F-4-O(C$_6$H$_3$-2-Cl-4-CF$_3$)-5-Cl | O | O |
| H | H | 2-I | 3-Cl-4-OCF$_2$CHF$_2$-5-CF$_3$ | O | O |
| H | H | 2-I | 2,4-F$_2$-3,5-Cl$_2$ | O | O |
| H | H | 2-CH(CH$_3$)$_2$ | 4-Cl | O | O |
| H | H | 2-CH(CH$_3$)$_2$ | 4-OCF$_3$ | O | O |
| H | H | 2-CH(CH$_3$)$_2$ | 3-OCF$_2$O-4 | O | O |
| H | H | 2-CH(CH$_3$)$_2$ | 4-O(C$_6$H$_3$-2-Cl-4-CF$_3$) | O | O |
| H | H | 2-CH(CH$_3$)$_2$ | 4-CH$_2$ON=C(Q51)(C$_6$H$_4$-4-Cl) | O | O |
| H | H | 2-CH(CH$_3$)$_2$ | 3-O(Q38-3-Cl-5-CF$_3$) | O | O |
| H | H | 2-CH(CH$_3$)$_2$ | 4-O(Q38-3-Cl-5-CF$_3$) | O | O |
| H | H | 2-CH(CH$_3$)$_2$ | 3-O(Q50-6-CF$_3$) | O | O |
| H | H | 2-CH(CH$_3$)$_2$ | 2,4-Cl$_2$ | O | O |
| H | H | 2-CH(CH$_3$)$_2$ | 3,4-Cl$_2$ | O | O |
| H | H | 2-CH(CH$_3$)$_2$ | 3,5-Cl$_2$ | O | O |
| H | H | 2-CH(CH$_3$)$_2$ | 2-F-4-OCF$_2$CHF$_2$ | O | O |
| H | H | 2-CH(CH$_3$)$_2$ | 2-Cl-4-O(Q38-3-Cl-5-CF$_3$) | O | O |
| H | H | 2-CH(CH$_3$)$_2$ | 2-Cl-5-O(Q50-6-CF$_3$) | O | O |
| H | H | 2-CH(CH$_3$)$_2$ | 3-Cl-4-OCF$_3$ | O | O |
| H | H | 2-CH(CH$_3$)$_2$ | 3-Cl-4-O(Q38-3-Cl-5-CF$_3$) | O | O |
| H | H | 2-CH(CH$_3$)$_2$ | 3,5-Cl$_2$-4-OCF$_2$CHF$_2$ | O | O |
| H | H | 2-CH(CH$_3$)$_2$ | 3,5-Cl$_2$-4-O(C$_6$H$_3$-2-Cl-4-CF$_3$) | O | O |
| H | H | 2-CH(CH$_3$)$_2$ | 3,5-Cl$_2$-4-O(Q38-3-Cl-5-CF$_3$) | O | O |
| H | H | 2-CH(CH$_3$)$_2$ | 3,5-Cl$_2$-4-O(Q50-6-CF$_3$) | O | O |
| H | H | 2-CH(CH$_3$)$_2$ | 2-F-4,5-Cl$_2$ | O | O |
| H | H | 2-CH(CH$_3$)$_2$ | 2-F-4-O(C$_6$H$_3$-2-Cl-4-CF$_3$)-5-Cl | O | O |
| H | H | 2-CH(CH$_3$)$_2$ | 3-Cl-4-OCF$_2$CHF$_2$-5-CF$_3$ | O | O |
| H | H | 2-CH(CH$_3$)$_2$ | 2,4-F$_2$-3,5-Cl$_2$ | O | O |
| H | H | 2-CN | 4-Cl | O | O |
| H | H | 2-CN | 4-OCF$_3$ | O | O |
| H | H | 2-CN | 3-OCF$_2$O-4 | O | O |
| H | H | 2-CN | 4-O(C$_6$H$_3$-2-Cl-4-CF$_3$) | O | O |
| H | H | 2-CN | 4-CH$_2$ON=C(Q51)(C$_6$H$_4$-4-Cl) | O | O |
| H | H | 2-CN | 3-O(Q38-3-Cl-5-CF$_3$) | O | O |
| H | H | 2-CN | 4-O(Q38-3-Cl-5-CF$_3$) | O | O |
| H | H | 2-CN | 3-O(Q50-6-CF$_3$) | O | O |
| H | H | 2-CN | 2,4-Cl$_2$ | O | O |
| H | H | 2-CN | 3,4-Cl$_2$ | O | O |
| H | H | 2-CN | 3,5-Cl$_2$ | O | O |
| H | H | 2-CN | 2-F-4-OCF$_2$CHF$_2$ | O | O |
| H | H | 2-CN | 2-Cl-4-O(Q38-3-Cl-5-CF$_3$) | O | O |
| H | H | 2-CN | 2-Cl-5-O(Q50-6-CF$_3$) | O | O |
| H | H | 2-CN | 3-Cl-4-OCF$_3$ | O | O |
| H | H | 2-CN | 3-Cl-4-O(Q38-3-Cl-5-CF$_3$) | O | O |
| H | H | 2-CN | 3,5-Cl$_2$-4-OCF$_2$CHF$_2$ | O | O |
| H | H | 2-CN | 3,5-Cl$_2$-4-O(C$_6$H$_3$-2-Cl-4-CF$_3$) | O | O |
| H | H | 2-CN | 3,5-Cl$_2$-4-O(Q38-3-Cl-5-CF$_3$) | O | O |
| H | H | 2-CN | 3,5-Cl$_2$-4-O(Q50-6-CF$_3$) | O | O |
| H | H | 2-CN | 2-F-4,5-Cl$_2$ | O | O |
| H | H | 2-CN | 2-F-4-O(C$_6$H$_3$-2-Cl-4-CF$_3$)-5-Cl | O | O |
| H | H | 2-CN | 3-Cl-4-OCF$_2$CHF$_2$-5-CF$_3$ | O | O |
| H | H | 2-CN | 2,4-F$_2$-3,5-Cl$_2$ | O | O |
| H | H | 2-NO$_2$ | 4-Cl | O | O |
| H | H | 2-NO$_2$ | 4-OCF$_3$ | O | O |
| H | H | 2-NO$_2$ | 3-OCF$_2$O-4 | O | O |

-continued

| | | | | | |
|---|---|---|---|---|---|
| H | H | 2-NO$_2$ | 4-O(C$_6$H$_3$-2-Cl-4-CF$_3$) | O | O |
| H | H | 2-NO$_2$ | 4-CH$_2$ON=C(Q51)(C$_6$H$_4$-4-Cl) | O | O |
| H | H | 2-NO$_2$ | 3-O(Q38-3-Cl-5-CF$_3$) | O | O |
| H | H | 2-NO$_2$ | 4-O(Q38-3-Cl-5-CF$_3$) | O | O |
| H | H | 2-NO$_2$ | 3-O(Q50-6-CF$_3$) | O | O |
| H | H | 2-NO$_2$ | 2,4-Cl$_2$ | O | O |
| H | H | 2-NO$_2$ | 3,4-Cl$_2$ | O | O |
| H | H | 2-NO$_2$ | 3,5-Cl$_2$ | O | O |
| H | H | 2-NO$_2$ | 2-F-4-OCF$_2$CHF$_2$ | O | O |
| H | H | 2-NO$_2$ | 2-Cl-4-O(Q38-3-Cl-5-CF$_3$) | O | O |
| H | H | 2-NO$_2$ | 2-Cl-5-O(Q50-6-CF$_3$) | O | O |
| H | H | 2-NO$_2$ | 3-Cl-4-OCF$_3$ | O | O |
| H | H | 2-NO$_2$ | 3-Cl-4-O(Q38-3-Cl-5-CF$_3$) | O | O |
| H | H | 2-NO$_2$ | 3,5-Cl$_2$-4-OCF$_2$CHF$_2$ | O | O |
| H | H | 2-NO$_2$ | 3,5-Cl$_2$-4-O(C$_6$H$_3$-2-Cl-4-CF$_3$) | O | O |
| H | H | 2-NO$_2$ | 3,5-Cl$_2$-4-O(Q38-3-Cl-5-CF$_3$) | O | O |
| H | H | 2-NO$_2$ | 3,5-Cl$_2$-4-O(Q50-6-CF$_3$) | O | O |
| H | H | 2-NO$_2$ | 2-F-4,5-Cl$_2$ | O | O |
| H | H | 2-NO$_2$ | 2-F-4-O(C$_6$H$_3$-2-Cl-4-CF$_3$)-5-Cl | O | O |
| H | H | 2-NO$_2$ | 3-Cl-4-OCF$_2$CHF$_2$-5-CF$_3$ | O | O |
| H | H | 2-NO$_2$ | 2,4-F$_2$-3,5-Cl$_2$ | O | O |
| H | H | 2,4,6-F$_3$ | 4-Cl | O | O |
| H | H | 2,4,6-F$_3$ | 4-OCF$_3$ | O | O |
| H | H | 2,4,6-F$_3$ | 3-OCF$_2$O-4 | O | O |
| H | H | 2,4,6-F$_3$ | 4-O(C$_6$H$_3$-2-Cl-4-CF$_3$) | O | O |
| H | H | 2,4,6-F$_3$ | 4-CH$_2$ON=C(Q51)(C$_6$H$_4$-4-Cl) | O | O |
| H | H | 2,4,6-F$_3$ | 3-O(Q38-3-Cl-5-CF$_3$) | O | O |
| H | H | 2,4,6-F$_3$ | 4-O(Q38-3-Cl-5-CF$_3$) | O | O |
| H | H | 2,4,6-F$_3$ | 3-O(Q50-6-CF$_3$) | O | O |
| H | H | 2,4,6-F$_3$ | 2,4-Cl$_2$ | O | O |
| H | H | 2,4,6-F$_3$ | 3,4-Cl$_2$ | O | O |
| H | H | 2,4,6-F$_3$ | 3,5-Cl$_2$ | O | O |
| H | H | 2,4,6-F$_3$ | 2-F-4-OCF$_2$CHF$_2$ | O | O |
| H | H | 2,4,6-F$_3$ | 2-Cl-4-O(Q38-3-Cl-5-CF$_3$) | O | O |
| H | H | 2,4,6-F$_3$ | 2-Cl-5-O(Q50-6-CF$_3$) | O | O |
| H | H | 2,4,6-F$_3$ | 3-Cl-4-OCF$_3$ | O | O |
| H | H | 2,4,6-F$_3$ | 3-Cl-4-O(Q38-3-Cl-5-CF$_3$) | O | O |
| H | H | 2,4,6-F$_3$ | 3,5-Cl$_2$-4-OCF$_2$CHF$_2$ | O | O |
| H | H | 2,4,6-F$_3$ | 3,5-Cl$_2$-4-O(C$_6$H$_3$-2-Cl-4-CF$_3$) | O | O |
| H | H | 2,4,6-F$_3$ | 3,5-Cl$_2$-4-O(Q38-3-Cl-5-CF$_3$) | O | O |
| H | H | 2,4,6-F$_3$ | 3,5-Cl$_2$-4-O(Q50-6-CF$_3$) | O | O |
| H | H | 2,4,6-F$_3$ | 2-F-4,5-Cl$_2$ | O | O |
| H | H | 2,4,6-F$_3$ | 2-F-4-O(C$_6$H$_3$-2-Cl-4-CF$_3$)-5-Cl | O | O |
| H | H | 2,4,6-F$_3$ | 3-Cl-4-OCF$_2$CHF$_2$-5-CF$_3$ | O | O |
| H | H | 2,4,6-F$_3$ | 2,4-F$_2$-3,5-Cl$_2$ | O | O |
| H | H | 2,6-F$_2$-3-NH$_2$ | 4-Cl | O | O |
| H | H | 2,6-F$_2$-3-NH$_2$ | 4-OCF$_3$ | O | O |
| H | H | 2,6-F$_2$-3-NH$_2$ | 3-OCF$_2$O-4 | O | O |
| H | H | 2,6-F$_2$-3-NH$_2$ | 4-O(C$_6$H$_3$-2-Cl-4-CF$_3$) | O | O |
| H | H | 2,6-F$_2$-3-NH$_2$ | 4-CH$_2$ON=C(Q51)(C$_6$H$_4$-4-Cl) | O | O |
| H | H | 2,6-F$_2$-3-NH$_2$ | 3-O(Q38-3-Cl-5-CF$_3$) | O | O |
| H | H | 2,6-F$_2$-3-NH$_2$ | 4-O(Q38-3-Cl-5-CF$_3$) | O | O |
| H | H | 2,6-F$_2$-3-NH$_2$ | 3-O(Q50-6-CF$_3$) | O | O |
| H | H | 2,6-F$_2$-3-NH$_2$ | 2,4-Cl$_2$ | O | O |
| H | H | 2,6-F$_2$-3-NH$_2$ | 3,4-Cl$_2$ | O | O |
| H | H | 2,6-F$_2$-3-NH$_2$ | 3,5-Cl$_2$ | O | O |
| H | H | 2,6-F$_2$-3-NH$_2$ | 2-F-4-OCF$_2$CHF$_2$ | O | O |
| H | H | 2,6-F$_2$-3-NH$_2$ | 2-Cl-4-O(Q38-3-Cl-5-CF$_3$) | O | O |
| H | H | 2,6-F$_2$-3-NH$_2$ | 2-Cl-5-O(Q50-6-CF$_3$) | O | O |
| H | H | 2,6-F$_2$-3-NH$_2$ | 3-Cl-4-OCF$_3$ | O | O |
| H | H | 2,6-F$_2$-3-NH$_2$ | 3-Cl-4-O(Q38-3-Cl-5-CF$_3$) | O | O |
| H | H | 2,6-F$_2$-3-NH$_2$ | 3,5-Cl$_2$-4-OCF$_2$CHF$_2$ | O | O |
| H | H | 2,6-F$_2$-3-NH$_2$ | 3,5-Cl$_2$-4-O(C$_6$H$_3$-2-Cl-4-CF$_3$) | O | O |
| H | H | 2,6-F$_2$-3-NH$_2$ | 3,5-Cl$_2$-4-O(Q38-3-Cl-5-CF$_3$) | O | O |
| H | H | 2,6-F$_2$-3-NH$_2$ | 3,5-Cl$_2$-4-O(Q50-6-CF$_3$) | O | O |
| H | H | 2,6-F$_2$-3-NH$_2$ | 2-F-4,5-Cl$_2$ | O | O |
| H | H | 2,6-F$_2$-3-NH$_2$ | 2-F-4-O(C$_6$H$_3$-2-Cl-4-CF$_3$)-5-Cl | O | O |
| H | H | 2,6-F$_2$-3-NH$_2$ | 3-Cl-4-OCF$_2$CHF$_2$-5-CF$_3$ | O | O |
| H | H | 2,6-F$_2$-3-NH$_2$ | 2,4-F$_2$-3,5-Cl$_2$ | O | O |
| H | H | 2-OCH(CH$_3$)$_2$ | 4-Cl | O | O |
| H | H | 2-OCH(CH$_3$)$_2$ | 4-OCF$_3$ | O | O |
| H | H | 2-OCH(CH$_3$)$_2$ | 3-OCF$_2$O-4 | O | O |
| H | H | 2-OCH(CH$_3$)$_2$ | 4-O(C$_6$H$_3$-2-Cl-4-CF$_3$) | O | O |
| H | H | 2-OCH(CH$_3$)$_2$ | 4-S(C$_6$H$_3$-2-Cl-4-CF$_3$) | O | O |
| H | H | 2-OCH(CH$_3$)$_2$ | 4-CH$_2$ON=C(Q51)(C$_6$H$_4$-4-Cl) | O | O |
| H | H | 2-OCH(CH$_3$)$_2$ | 3-O(Q38-3-Cl-5-CF$_3$) | O | O |
| H | H | 2-OCH(CH$_3$)$_2$ | 4-O(Q38-3-Cl-5-CF$_3$) | O | O |
| H | H | 2-OCH(CH$_3$)$_2$ | 3-O(Q50-6-CF$_3$) | O | O |
| H | H | 2-OCH(CH$_3$)$_2$ | 3,4-Cl$_2$ | O | O |
| H | H | 2-OCH(CH$_3$)$_2$ | 2-F-4-OCF$_2$CHF$_2$ | O | O |
| H | H | 2-OCH(CH$_3$)$_2$ | 2-Cl-5-O(Q50-6-CF$_3$) | O | O |
| H | H | 2-OCH(CH$_3$)$_2$ | 3-Cl-4-OCF$_2$CHF$_2$ | O | O |
| H | H | 2-OCH(CH$_3$)$_2$ | 3-Cl-4-O(Q38-3-Cl-5-CF$_3$) | O | O |

-continued

| | | | | | |
|---|---|---|---|---|---|
| H | H | 2-OCH(CH₃)₂ | 3,5-Cl₂-4-OCF₂CHF₂ | O | O |
| H | H | 2-OCH(CH₃)₂ | 3,5-Cl₂-4-OCF₂CHFOCF₃ | O | O |
| H | H | 2-OCH(CH₃)₂ | 3,5-Cl₂-4-O(C₆H₃-2-Cl-4-CF₃) | O | O |
| H | H | 2-OCH(CH₃)₂ | 3,5-Cl₂-4-O(Q38-3-Cl-5-CF₃) | O | O |
| H | H | 2-OCH(CH₃)₂ | 3,5-Cl₂-4-O(Q50-6-CF₃) | O | O |
| H | H | 2-OCH(CH₃)₂ | 2,4-F₂-3,5-Cl₂ | O | O |
| H | H | 2-SCH₃ | 4-Cl | O | O |
| H | H | 2-SCH₃ | 4-OCF₃ | O | O |
| H | H | 2-SCH₃ | 3-OCF₂O-4 | O | O |
| H | H | 2-SCH₃ | 4-O(C₆H₃-2-Cl-4-CF₃) | O | O |
| H | H | 2-SCH₃ | 4-S(C₆H₃-2-Cl-4-CF₃) | O | O |
| H | H | 2-SCH₃ | 4-CH₂ON=C(Q51)(C₆H₄-4-Cl) | O | O |
| H | H | 2-SCH₃ | 3-O(Q38-3-Cl-5-CF₃) | O | O |
| H | H | 2-SCH₃ | 4-O(Q38-3-Cl-5-CF₃) | O | O |
| H | H | 2-SCH₃ | 3-O(Q50-6-CF₃) | O | O |
| H | H | 2-SCH₃ | 3,4-Cl₂ | O | O |
| H | H | 2-SCH₃ | 2-F-4-OCF₂CHF₂ | O | O |
| H | H | 2-SCH₃ | 2-Cl-5-O(Q50-6-CF₃) | O | O |
| H | H | 2-SCH₃ | 3-Cl-4-OCF₂CHF₂ | O | O |
| H | H | 2-SCH₃ | 3-Cl-4-O(Q38-3-Cl-5-CF₃) | O | O |
| H | H | 2-SCH₃ | 3,5-Cl₂-4-OCF₂CHF₂ | O | O |
| H | H | 2-SCH₃ | 3,5-Cl₂-4-OCF₂CHFOCF₃ | O | O |
| H | H | 2-SCH₃ | 3,5-Cl₂-4-O(C₆H₃-2-Cl-4-CF₃) | O | O |
| H | H | 2-SCH₃ | 3,5-Cl₂-4-O(Q38-3-Cl-5-CF₃) | O | O |
| H | H | 2-SCH₃ | 3,5-Cl₂-4-O(Q50-6-CF₃) | O | O |
| H | H | 2-SCH₃ | 2,4-F₂-3,5-Cl₂ | O | O |
| H | H | 2-CH₂Cl | 4-Cl | O | O |
| H | H | 2-CH₂Cl | 4-OCF₃ | O | O |
| H | H | 2-CH₂Cl | 3-OCF₂O-4 | O | O |
| H | H | 2-CH₂Cl | 4-O(C₆H₃-2-Cl-4-CF₃) | O | O |
| H | H | 2-CH₂Cl | 4-S(C₆H₃-2-Cl-4-CF₃) | O | O |
| H | H | 2-CH₂Cl | 4-CH₂ON=C(Q51)(C₆H₄-4-Cl) | O | O |
| H | H | 2-CH₂Cl | 3-O(Q38-3-Cl-5-CF₃) | O | O |
| H | H | 2-CH₂Cl | 4-O(Q38-3-Cl-5-CF₃) | O | O |
| H | H | 2-CH₂Cl | 3-O(Q50-6-CF₃) | O | O |
| H | H | 2-CH₂Cl | 3,4-Cl₂ | O | O |
| H | H | 2-CH₂Cl | 2-F-4-OCF₂CHF₂ | O | O |
| H | H | 2-CH₂Cl | 2-Cl-5-O(Q50-6-CF₃) | O | O |
| H | H | 2-CH₂Cl | 3-Cl-4-OCF₂CHF₂ | O | O |
| H | H | 2-CH₂Cl | 3-Cl-4-O(Q38-3-Cl-5-CF₃) | O | O |
| H | H | 2-CH₂Cl | 3,5-Cl₂-4-OCF₂CHF₂ | O | O |
| H | H | 2-CH₂Cl | 3,5-Cl₂-4-OCF₂CHFOCF₃ | O | O |
| H | H | 2-CH₂Cl | 3,5-Cl₂-4-O(C₆H₃-2-Cl-4-CF₃) | O | O |
| H | H | 2-CH₂Cl | 3,5-Cl₂-4-O(Q38-3-Cl-5-CF₃) | O | O |
| H | H | 2-CH₂Cl | 3,5-Cl₂-4-O(Q50-6-CF₃) | O | O |
| H | H | 2-CH₂Cl | 2,4-F₂-3,5-Cl₂ | O | O |
| H | H | 2-OCHF₂ | 4-Cl | O | O |
| H | H | 2-OCHF₂ | 4-OCF₃ | O | O |
| H | H | 2-OCHF₂ | 3-OCF₂O-4 | O | O |
| H | H | 2-OCHF₂ | 4-O(C₆H₃-2-Cl-4-CF₃) | O | O |
| H | H | 2-OCHF₂ | 4-S(C₆H₃-2-Cl-4-CF₃) | O | O |
| H | H | 2-OCHF₂ | 4-CH₂ON=C(Q51)(C₆H₄-4-Cl) | O | O |
| H | H | 2-OCHF₂ | 3-O(Q38-3-Cl-5-CF₃) | O | O |
| H | H | 2-OCHF₂ | 4-O(Q38-3-Cl-5-CF₃) | O | O |
| H | H | 2-OCHF₂ | 3-O(Q50-6-CF₃) | O | O |
| H | H | 2-OCHF₂ | 3,4-Cl₂ | O | O |
| H | H | 2-OCHF₂ | 2-F-4-OCF₂CHF₂ | O | O |
| H | H | 2-OCHF₂ | 2-Cl-5-O(Q50-6-CF₃) | O | O |
| H | H | 2-OCHF₂ | 3-Cl-4-OCF₂CHF₂ | O | O |
| H | H | 2-OCHF₂ | 3-Cl-4-O(Q38-3-Cl-5-CF₃) | O | O |
| H | H | 2-OCHF₂ | 3,5-Cl₂-4-OCF₂CHF₂ | O | O |
| H | H | 2-OCHF₂ | 3,5-Cl₂-4-OCF₂CHFOCF₃ | O | O |
| H | H | 2-OCHF₂ | 3,5-Cl₂-4-O(C₆H₃-2-Cl-4-CF₃) | O | O |
| H | H | 2-OCHF₂ | 3,5-Cl₂-4-O(Q38-3-Cl-5-CF₃) | O | O |
| H | H | 2-OCHF₂ | 3,5-Cl₂-4-O(Q50-6-CF₃) | O | O |
| H | H | 2-OCHF₂ | 2,4-F₂-3,5-Cl₂ | O | O |
| H | H | 2-OCF₃ | 4-Cl | O | O |
| H | H | 2-OCF₃ | 4-OCF₃ | O | O |
| H | H | 2-OCF₃ | 3-OCF₂O-4 | O | O |
| H | H | 2-OCF₃ | 4-O(C₆H₃-2-Cl-4-CF₃) | O | O |
| H | H | 2-OCF₃ | 4-S(C₆H₃-2-Cl-4-CF₃) | O | O |
| H | H | 2-OCF₃ | 4-CH₂ON=C(Q51)(C₆H₄-4-Cl) | O | O |
| H | H | 2-OCF₃ | 3-O(Q38-3-Cl-5-CF₃) | O | O |
| H | H | 2-OCF₃ | 4-O(Q38-3-Cl-5-CF₃) | O | O |
| H | H | 2-OCF₃ | 3-O(Q50-6-CF₃) | O | O |
| H | H | 2-OCF₃ | 3,4-Cl₂ | O | O |
| H | H | 2-OCF₃ | 2-F-4-OCF₂CHF₂ | O | O |
| H | H | 2-OCF₃ | 2-Cl-5-O(Q50-6-CF₃) | O | O |
| H | H | 2-OCF₃ | 3-Cl-4-OCF₂CHF₂ | O | O |
| H | H | 2-OCF₃ | 3-Cl-4-O(Q38-3-Cl-5-CF₃) | O | O |
| H | H | 2-OCF₃ | 3,5-Cl₂-4-OCF₂CHF₂ | O | O |
| H | H | 2-OCF₃ | 3,5-Cl₂-4-OCF₂CHFOCF₃ | O | O |
| H | H | 2-OCF₃ | 3,5-Cl₂-4-O(C₆H₃-2-Cl-4-CF₃) | O | O |

-continued

| | | | | | |
|---|---|---|---|---|---|
| H | H | 2-OCF₃ | 3,5-Cl₂-4-O(Q38-3-Cl-5-CF₃) | O | O |
| H | H | 2-OCF₃ | 3,5-Cl₂-4-O(Q50-6-CF₃) | O | O |
| H | H | 2-OCF₃ | 2,4-F₂-3,5-Cl₂ | O | O |
| H | H | 2-SCF₃ | 4-Cl | O | O |
| H | H | 2-SCF₃ | 4-OCF₃ | O | O |
| H | H | 2-SCF₃ | 3-OCF₂O-4 | O | O |
| H | H | 2-SCF₃ | 4-O(C₆H₃-2-Cl-4-CF₃) | O | O |
| H | H | 2-SCF₃ | 4-S(C₆H₃-2-Cl-4-CF₃) | O | O |
| H | H | 2-SCF₃ | 4-CH₂ON=C(Q51)(C₆H₄-4-Cl) | O | O |
| H | H | 2-SCF₃ | 3-O(Q38-3-Cl-5-CF₃) | O | O |
| H | H | 2-SCF₃ | 4-O(Q38-3-Cl-5-CF₃) | O | O |
| H | H | 2-SCF₃ | 3-O(Q50-6-CF₃) | O | O |
| H | H | 2-SCF₃ | 3,4-Cl₂ | O | O |
| H | H | 2-SCF₃ | 2-F-4-OCF₂CHF₂ | O | O |
| H | H | 2-SCF₃ | 2-Cl-5-O(Q50-6-CF₃) | O | O |
| H | H | 2-SCF₃ | 3-Cl-4-OCF₂CHF₂ | O | O |
| H | H | 2-SCF₃ | 3-Cl-4-O(Q38-3-Cl-5-CF₃) | O | O |
| H | H | 2-SCF₃ | 3,5-Cl₂-4-OCF₂CHF₂ | O | O |
| H | H | 2-SCF₃ | 3,5-Cl₂-4-OCF₂CHFOCF₃ | O | O |
| H | H | 2-SCF₃ | 3,5-Cl₂-4-O(C₆H₃-2-Cl-4-CF₃) | O | O |
| H | H | 2-SCF₃ | 3,5-Cl₂-4-O(Q38-3-Cl-5-CF₃) | O | O |
| H | H | 2-SCF₃ | 3,5-Cl₂-4-O(Q50-6-CF₃) | O | O |
| H | H | 2-SCF₃ | 2,4-F₂-3,5-Cl₂ | O | O |
| H | H | 2-SCF₂Br | 4-Cl | O | O |
| H | H | 2-SCF₂Br | 4-OCF₃ | O | O |
| H | H | 2-SCF₂Br | 3-OCF₂O-4 | O | O |
| H | H | 2-SCF₂Br | 4-O(C₆H₃-2-Cl-4-CF₃) | O | O |
| H | H | 2-SCF₂Br | 4-S(C₆H₃-2-Cl-4-CF₃) | O | O |
| H | H | 2-SCF₂Br | 4-CH₂ON=C(Q51)(C₆H₄-4-Cl) | O | O |
| H | H | 2-SCF₂Br | 3-O(Q38-3-Cl-5-CF₃) | O | O |
| H | H | 2-SCF₂Br | 4-O(Q38-3-Cl-5-CF₃) | O | O |
| H | H | 2-SCF₂Br | 3-O(Q50-6-CF₃) | O | O |
| H | H | 2-SCF₂Br | 3,4-Cl₂ | O | O |
| H | H | 2-SCF₂Br | 2-F-4-OCF₂CHF₂ | O | O |
| H | H | 2-SCF₂Br | 2-Cl-5-O(Q50-6-CF₃) | O | O |
| H | H | 2-SCF₂Br | 3-Cl-4-OCF₂CHF₂ | O | O |
| H | H | 2-SCF₂Br | 3-Cl-4-O(Q38-3-Cl-5-CF₃) | O | O |
| H | H | 2-SCF₂Br | 3,5-Cl₂-4-OCF₂CHF₂ | O | O |
| H | H | 2-SCF₂Br | 3,5-Cl₂-4-OCF₂CHFOCF₃ | O | O |
| H | H | 2-SCF₂Br | 3,5-Cl₂-4-O(C₆H₃-2-Cl-4-CF₃) | O | O |
| H | H | 2-SCF₂Br | 3,5-Cl₂-4-O(Q38-3-Cl-5-CF₃) | O | O |
| H | H | 2-SCF₂Br | 3,5-Cl₂-4-O(Q50-6-CF₃) | O | O |
| H | H | 2-SCF₂Br | 2,4-F₂-3,5-Cl₂ | O | O |
| H | H | 2-F-6-Br | 4-Cl | O | O |
| H | H | 2-F-6-Br | 4-OCF₃ | O | O |
| H | H | 2-F-6-Br | 3-OCF₂O-4 | O | O |
| H | H | 2-F-6-Br | 4-O(C₆H₃-2-Cl-4-CF₃) | O | O |
| H | H | 2-F-6-Br | 4-S(C₆H₃-2-Cl-4-CF₃) | O | O |
| H | H | 2-F-6-Br | 4-CH₂ON=C(Q51)(C₆H₄-4-Cl) | O | O |
| H | H | 2-F-6-Br | 3-O(Q38-3-Cl-5-CF₃) | O | O |
| H | H | 2-F-6-Br | 4-O(Q38-3-Cl-5-CF₃) | O | O |
| H | H | 2-F-6-Br | 3-O(Q50-6-CF₃) | O | O |
| H | H | 2-F-6-Br | 3,4-Cl₂ | O | O |
| H | H | 2-F-6-Br | 2-F-4-OCF₂CHF₂ | O | O |
| H | H | 2-F-6-Br | 2-Cl-5-O(Q50-6-CF₃) | O | O |
| H | H | 2-F-6-Br | 3-Cl-4-OCF₂CHF₂ | O | O |
| H | H | 2-F-6-Br | 3-Cl-4-O(Q38-3-Cl-5-CF₃) | O | O |
| H | H | 2-F-6-Br | 3,5-Cl₂-4-OCF₂CHF₂ | O | O |
| H | H | 2-F-6-Br | 3,5-Cl₂-4-OCF₂CHFOCF₃ | O | O |
| H | H | 2-F-6-Br | 3,5-Cl₂-4-O(C₆H₃-2-Cl-4-CF₃) | O | O |
| H | H | 2-F-6-Br | 3,5-Cl₂-4-O(Q38-3-Cl-5-CF₃) | O | O |
| H | H | 2-F-6-Br | 3,5-Cl₂-4-O(Q50-6-CF₃) | O | O |
| H | H | 2-F-6-Br | 2,4-F₂-3,5-Cl₂ | O | O |
| H | H | 2-F-6-CH₃ | 4-Cl | O | O |
| H | H | 2-F-6-CH₃ | 4-OCF₃ | O | O |
| H | H | 2-F-6-CH₃ | 3-OCF₂O-4 | O | O |
| H | H | 2-F-6-CH₃ | 4-O(C₆H₃-2-Cl-4-CF₃) | O | O |
| H | H | 2-F-6-CH₃ | 4-S(C₆H₃-2-Cl-4-CF₃) | O | O |
| H | H | 2-F-6-CH₃ | 4-CH₂ON=C(Q51)(C₆H₄-4-Cl) | O | O |
| H | H | 2-F-6-CH₃ | 3-O(Q38-3-Cl-5-CF₃) | O | O |
| H | H | 2-F-6-CH₃ | 4-O(Q38-3-Cl-5-CF₃) | O | O |
| H | H | 2-F-6-CH₃ | 3-O(Q50-6-CF₃) | O | O |
| H | H | 2-F-6-CH₃ | 3,4-Cl₂ | O | O |
| H | H | 2-F-6-CH₃ | 2-F-4-OCF₂CHF₂ | O | O |
| H | H | 2-F-6-CH₃ | 2-Cl-5-O(Q50-6-CF₃) | O | O |
| H | H | 2-F-6-CH₃ | 3-Cl-4-OCF₂CHF₂ | O | O |
| H | H | 2-F-6-CH₃ | 3-Cl-4-O(Q38-3-Cl-5-CF₃) | O | O |
| H | H | 2-F-6-CH₃ | 3,5-Cl₂-4-OCF₂CHF₂ | O | O |
| H | H | 2-F-6-CH₃ | 3,5-Cl₂-4-OCF₂CHFOCF₃ | O | O |
| H | H | 2-F-6-CH₃ | 3,5-Cl₂-4-O(C₆H₃-2-Cl-4-CF₃) | O | O |
| H | H | 2-F-6-CH₃ | 3,5-Cl₂-4-O(Q38-3-Cl-5-CF₃) | O | O |
| H | H | 2-F-6-CH₃ | 3,5-Cl₂-4-O(Q50-6-CF₃) | O | O |
| H | H | 2-F-6-CH₃ | 2,4-F₂-3,5-Cl₂ | O | O |

-continued

| | | | | | |
|---|---|---|---|---|---|
| H | H | 2-F-6-OCH₃ | 4-Cl | O | O |
| H | H | 2-F-6-OCH₃ | 4-OCF₃ | O | O |
| H | H | 2-F-6-OCH₃ | 3-OCF₂O-4 | O | O |
| H | H | 2-F-6-OCH₃ | 4-O(C₆H₃-2-Cl-4-CF₃) | O | O |
| H | H | 2-F-6-OCH₃ | 4-S(C₆H₃-2-Cl-4-CF₃) | O | O |
| H | H | 2-F-6-OCH₃ | 4-CH₂ON=C(Q51)(C₆H₄-4-Cl) | O | O |
| H | H | 2-F-6-OCH₃ | 3-O(Q38-3-Cl-5-CF₃) | O | O |
| H | H | 2-F-6-OCH₃ | 4-O(Q38-3-Cl-5-CF₃) | O | O |
| H | H | 2-F-6-OCH₃ | 3-O(Q50-6-CF₃) | O | O |
| H | H | 2-F-6-OCH₃ | 3,4-Cl₂ | O | O |
| H | H | 2-F-6-OCH₃ | 2-F-4-OCF₂CHF₂ | O | O |
| H | H | 2-F-6-OCH₃ | 2-Cl-5-O(Q50-6-CF₃) | O | O |
| H | H | 2-F-6-OCH₃ | 3-Cl-4-OCF₂CHF₂ | O | O |
| H | H | 2-F-6-OCH₃ | 3-Cl-4-O(Q38-3-Cl-5-CF₃) | O | O |
| H | H | 2-F-6-OCH₃ | 3,5-Cl₂-4-OCF₂CHF₂ | O | O |
| H | H | 2-F-6-OCH₃ | 3,5-Cl₂-4-OCF₂CHFOCF₃ | O | O |
| H | H | 2-F-6-OCH₃ | 3,5-Cl₂-4-O(C₆H₃-2-Cl-4-CF₃) | O | O |
| H | H | 2-F-6-OCH₃ | 3,5-Cl₂-4-O(Q38-3-Cl-5-CF₃) | O | O |
| H | H | 2-F-6-OCH₃ | 3,5-Cl₂-4-O(Q50-6-CF₃) | O | O |
| H | H | 2-F-6-OCH₃ | 2,4-F₂-3,5-Cl₂ | O | O |
| H | H | 2-F-6-CF₃ | 4-Cl | O | O |
| H | H | 2-F-6-CF₃ | 4-OCF₃ | O | O |
| H | H | 2-F-6-CF₃ | 3-OCF₂O-4 | O | O |
| H | H | 2-F-6-CF₃ | 4-O(C₆H₃-2-Cl-4-CF₃) | O | O |
| H | H | 2-F-6-CF₃ | 4-S(C₆H₃-2-Cl-4-CF₃) | O | O |
| H | H | 2-F-6-CF₃ | 4-CH₂ON=C(Q51)(C₆H₄-4-Cl) | O | O |
| H | H | 2-F-6-CF₃ | 3-O(Q38-3-Cl-5-CF₃) | O | O |
| H | H | 2-F-6-CF₃ | 4-O(Q38-3-Cl-5-CF₃) | O | O |
| H | H | 2-F-6-CF₃ | 3-O(Q50-6-CF₃) | O | O |
| H | H | 2-F-6-CF₃ | 3,4-Cl₂ | O | O |
| H | H | 2-F-6-CF₃ | 2-F-4-OCF₂CHF₂ | O | O |
| H | H | 2-F-6-CF₃ | 2-Cl-5-O(Q50-6-CF₃) | O | O |
| H | H | 2-F-6-CF₃ | 3-Cl-4-OCF₂CHF₂ | O | O |
| H | H | 2-F-6-CF₃ | 3-Cl-4-O(Q38-3-Cl-5-CF₃) | O | O |
| H | H | 2-F-6-CF₃ | 3,5-Cl₂-4-OCF₂CHF₂ | O | O |
| H | H | 2-F-6-CF₃ | 3,5-Cl₂-4-OCF₂CHFOCF₃ | O | O |
| H | H | 2-F-6-CF₃ | 3,5-Cl₂-4-O(C₆H₃-2-Cl-4-CF₃) | O | O |
| H | H | 2-F-6-CF₃ | 3,5-Cl₂-4-O(Q38-3-Cl-5-CF₃) | O | O |
| H | H | 2-F-6-CF₃ | 3,5-Cl₂-4-O(Q50-6-CF₃) | O | O |
| H | H | 2-F-6-CF₃ | 2,4-F₂-3,5-Cl₂ | O | O |
| H | H | 2,3,6-F₃ | 4-Cl | O | O |
| H | H | 2,3,6-F₃ | 4-OCF₃ | O | O |
| H | H | 2,3,6-F₃ | 3-OCF₂O-4 | O | O |
| H | H | 2,3,6-F₃ | 4-O(C₆H₃-2-Cl-4-CF₃) | O | O |
| H | H | 2,3,6-F₃ | 4-S(C₆H₃-2-Cl-4-CF₃) | O | O |
| H | H | 2,3,6-F₃ | 4-CH₂ON=C(Q51)(C₆H₄-4-Cl) | O | O |
| H | H | 2,3,6-F₃ | 3-O(Q38-3-Cl-5-CF₃) | O | O |
| H | H | 2,3,6-F₃ | 4-O(Q38-3-Cl-5-CF₃) | O | O |
| H | H | 2,3,6-F₃ | 3-O(Q50-6-CF₃) | O | O |
| H | H | 2,3,6-F₃ | 3,4-Cl₂ | O | O |
| H | H | 2,3,6-F₃ | 2-F-4-OCF₂CHF₂ | O | O |
| H | H | 2,3,6-F₃ | 2-Cl-5-O(Q50-6-CF₃) | O | O |
| H | H | 2,3,6-F₃ | 3-Cl-4-OCF₂CHF₂ | O | O |
| H | H | 2,3,6-F₃ | 3-Cl-4-O(Q38-3-Cl-5-CF₃) | O | O |
| H | H | 2,3,6-F₃ | 3,5-Cl₂-4-OCF₂CHF₂ | O | O |
| H | H | 2,3,6-F₃ | 3,5-Cl₂-4-OCF₂CHFOCF₃ | O | O |
| H | H | 2,3,6-F₃ | 3,5-Cl₂-4-O(C₆H₃-2-Cl-4-CF₃) | O | O |
| H | H | 2,3,6-F₃ | 3,5-Cl₂-4-O(Q38-3-Cl-5-CF₃) | O | O |
| H | H | 2,3,6-F₃ | 3,5-Cl₂-4-O(Q50-6-CF₃) | O | O |
| H | H | 2,3,6-F₃ | 2,4-F₂-3,5-Cl₂ | O | O |
| H | H | 2,4-F₂-6-Cl | 4-Cl | O | O |
| H | H | 2,4-F₂-6-Cl | 4-OCF₃ | O | O |
| H | H | 2,4-F₂-6-Cl | 3-OCF₂O-4 | O | O |
| H | H | 2,4-F₂-6-Cl | 4-O(C₆H₃-2-Cl-4-CF₃) | O | O |
| H | H | 2,4-F₂-6-Cl | 4-S(C₆H₃-2-Cl-4-CF₃) | O | O |
| H | H | 2,4-F₂-6-Cl | 4-CH₂ON=C(Q51)(C₆H₄-4-Cl) | O | O |
| H | H | 2,4-F₂-6-Cl | 3-O(Q38-3-Cl-5-CF₃) | O | O |
| H | H | 2,4-F₂-6-Cl | 4-O(Q38-3-Cl-5-CF₃) | O | O |
| H | H | 2,4-F₂-6-Cl | 3-O(Q50-6-CF₃) | O | O |
| H | H | 2,4-F₂-6-Cl | 3,4-Cl₂ | O | O |
| H | H | 2,4-F₂-6-Cl | 2-F-4-OCF₂CHF₂ | O | O |
| H | H | 2,4-F₂-6-Cl | 2-Cl-5-O(Q50-6-CF₃) | O | O |
| H | H | 2,4-F₂-6-Cl | 3-Cl-4-OCF₂CHF₂ | O | O |
| H | H | 2,4-F₂-6-Cl | 3-Cl-4-O(Q38-3-Cl-5-CF₃) | O | O |
| H | H | 2,4-F₂-6-Cl | 3,5-Cl₂-4-OCF₂CHF₂ | O | O |
| H | H | 2,4-F₂-6-Cl | 3,5-Cl₂-4-OCF₂CHFOCF₃ | O | O |
| H | H | 2,4-F₂-6-Cl | 3,5-Cl₂-4-O(C₆H₃-2-Cl-4-CF₃) | O | O |
| H | H | 2,4-F₂-6-Cl | 3,5-Cl₂-4-O(Q38-3-Cl-5-CF₃) | O | O |
| H | H | 2,4-F₂-6-Cl | 3,5-Cl₂-4-O(Q50-6-CF₃) | O | O |
| H | H | 2,4-F₂-6-Cl | 2,4-F₂-3,5-Cl₂ | O | O |
| H | H | 2,6-Cl₂-3-NH₂ | 4-Cl | O | O |
| H | H | 2,6-Cl₂-3-NH₂ | 4-OCF₃ | O | O |
| H | H | 2,6-Cl₂-3-NH₂ | 3-OCF₂O-4 | O | O |

-continued

| | | | | | |
|---|---|---|---|---|---|
| H | H | 2,6-Cl₂-3-NH₂ | 4-O(C₆H₃-2-Cl-4-CF₃) | O | O |
| H | H | 2,6-Cl₂-3-NH₂ | 4-S(C₆H₃-2-Cl-4-CF₃) | O | O |
| H | H | 2,6-Cl₂-3-NH₂ | 4-CH₂ON=C(Q51)(C₆H₄-4-Cl) | O | O |
| H | H | 2,6-Cl₂-3-NH₂ | 3-O(Q38-3-Cl-5-CF₃) | O | O |
| H | H | 2,6-Cl₂-3-NH₂ | 4-O(Q38-3-Cl-5-CF₃) | O | O |
| H | H | 2,6-Cl₂-3-NH₂ | 3-O(Q50-6-CF₃) | O | O |
| H | H | 2,6-Cl₂-3-NH₂ | 3,4-Cl₂ | O | O |
| H | H | 2,6-Cl₂-3-NH₂ | 2-F-4-OCF₂CHF₂ | O | O |
| H | H | 2,6-Cl₂-3-NH₂ | 2-Cl-5-O(Q50-6-CF₃) | O | O |
| H | H | 2,6-Cl₂-3-NH₂ | 3-Cl-4-OCF₂CHF₂ | O | O |
| H | H | 2,6-Cl₂-3-NH₂ | 3-Cl-4-O(Q38-3-Cl-5-CF₃) | O | O |
| H | H | 2,6-Cl₂-3-NH₂ | 3,5-Cl₂-4-OCF₂CHF₂ | O | O |
| H | H | 2,6-Cl₂-3-NH₂ | 3,5-Cl₂-4-OCF₂CHFOCF₃ | O | O |
| H | H | 2,6-Cl₂-3-NH₂ | 3,5-Cl₂-4-O(C₆H₃-2-Cl-4-CF₃) | O | O |
| H | H | 2,6-Cl₂-3-NH₂ | 3,5-Cl₂-4-O(Q38-3-Cl-5-CF₃) | O | O |
| H | H | 2,6-Cl₂-3-NH₂ | 3,5-Cl₂-4-O(Q50-6-CF₃) | O | O |
| H | H | 2,6-Cl₂-3-NH₂ | 2,4-F₂-3,5-Cl₂ | O | O |
| H | H | 2,3-F₂ | 4-Cl | O | O |
| H | H | 2,3-F₂ | 4-OCF₃ | O | O |
| H | H | 2,3-F₂ | 4-S(C₆H₃-2-Cl-4-CF₃) | O | O |
| H | H | 2,3-F₂ | 4-CH₂ON=C(Q51)(C₆H₄-4-Cl) | O | O |
| H | H | 2,3-F₂ | 3-O(Q50-6-CF₃) | O | O |
| H | H | 2,3-F₂ | 3,4-Cl₂ | O | O |
| H | H | 2,3-F₂ | 2-F-4-OCF₂CHF₂ | O | O |
| H | H | 2,3-F₂ | 3-Cl-4-O(Q38-3-Cl-5-CF₃) | O | O |
| H | H | 2,3-F₂ | 3,5-Cl₂-4-OCF₂CHF₂ | O | O |
| H | H | 2,3-F₂ | 3,5-Cl₂-4-O(C₆H₃-2-Cl-4-CF₃) | O | O |
| H | H | 2,3-F₂ | 3,5-Cl₂-4-O(Q38-3-Cl-5-CF₃) | O | O |
| H | H | 2,3-F₂ | 2,4-F₂-3,5-Cl₂ | O | O |
| H | H | 2,4-F₂ | 4-Cl | O | O |
| H | H | 2,4-F₂ | 4-OCF₃ | O | O |
| H | H | 2,4-F₂ | 4-S(C₆H₃-2-Cl-4-CF₃) | O | O |
| H | H | 2,4-F₂ | 4-CH₂ON=C(Q51)(C₆H₄-4-Cl) | O | O |
| H | H | 2,4-F₂ | 3-O(Q50-6-CF₃) | O | O |
| H | H | 2,4-F₂ | 3,4-Cl₂ | O | O |
| H | H | 2,4-F₂ | 2-F-4-OCF₂CHF₂ | O | O |
| H | H | 2,4-F₂ | 3-Cl-4-O(Q38-3-Cl-5-CF₃) | O | O |
| H | H | 2,4-F₂ | 3,5-Cl₂-4-OCF₂CHF₂ | O | O |
| H | H | 2,4-F₂ | 3,5-Cl₂-4-O(C₆H₃-2-Cl-4-CF₃) | O | O |
| H | H | 2,4-F₂ | 3,5-Cl₂-4-O(Q38-3-Cl-5-CF₃) | O | O |
| H | H | 2,4-F₂ | 2,4-F₂-3,5-Cl₂ | O | O |
| H | H | 2,5-F₂ | 4-Cl | O | O |
| H | H | 2,5-F₂ | 4-OCF₃ | O | O |
| H | H | 2,5-F₂ | 4-S(C₆H₃-2-Cl-4-CF₃) | O | O |
| H | H | 2,5-F₂ | 4-CH₂ON=C(Q51)(C₆H₄-4-Cl) | O | O |
| H | H | 2,5-F₂ | 3-O(Q50-6-CF₃) | O | O |
| H | H | 2,5-F₂ | 3,4-Cl₂ | O | O |
| H | H | 2,5-F₂ | 2-F-4-OCF₂CHF₂ | O | O |
| H | H | 2,5-F₂ | 3-Cl-4-O(Q38-3-Cl-5-CF₃) | O | O |
| H | H | 2,5-F₂ | 3,5-Cl₂-4-OCF₂CHF₂ | O | O |
| H | H | 2,5-F₂ | 3,5-Cl₂-4-O(C₆H₃-2-Cl-4-CF₃) | O | O |
| H | H | 2,5-F₂ | 3,5-Cl₂-4-O(Q38-3-Cl-5-CF₃) | O | O |
| H | H | 2,5-F₂ | 2,4-F₂-3,5-Cl₂ | O | O |
| H | H | 2-F-3-Cl | 4-Cl | O | O |
| H | H | 2-F-3-Cl | 4-OCF₃ | O | O |
| H | H | 2-F-3-Cl | 4-S(C₆H₃-2-Cl-4-CF₃) | O | O |
| H | H | 2-F-3-Cl | 4-CH₂ON=C(Q51)(C₆H₄-4-Cl) | O | O |
| H | H | 2-F-3-Cl | 3-O(Q50-6-CF₃) | O | O |
| H | H | 2-F-3-Cl | 3,4-Cl₂ | O | O |
| H | H | 2-F-3-Cl | 2-F-4-OCF₂CHF₂ | O | O |
| H | H | 2-F-3-Cl | 3-Cl-4-O(Q38-3-Cl-5-CF₃) | O | O |
| H | H | 2-F-3-Cl | 3,5-Cl₂-4-OCF₂CHF₂ | O | O |
| H | H | 2-F-3-Cl | 3,5-Cl₂-4-O(C₆H₃-2-Cl-4-CF₃) | O | O |
| H | H | 2-F-3-Cl | 3,5-Cl₂-4-O(Q38-3-Cl-5-CF₃) | O | O |
| H | H | 2-F-3-Cl | 2,4-F₂-3,5-Cl₂ | O | O |
| H | H | 2-F-4-Cl | 4-Cl | O | O |
| H | H | 2-F-4-Cl | 4-OCF₃ | O | O |
| H | H | 2-F-4-Cl | 4-S(C₆H₃-2-Cl-4-CF₃) | O | O |
| H | H | 2-F-4-Cl | 4-CH₂ON=C(Q51)(C₆H₄-4-Cl) | O | O |
| H | H | 2-F-4-Cl | 3-O(Q50-6-CF₃) | O | O |
| H | H | 2-F-4-Cl | 3,4-Cl₂ | O | O |
| H | H | 2-F-4-Cl | 2-F-4-OCF₂CHF₂ | O | O |
| H | H | 2-F-4-Cl | 3-Cl-4-O(Q38-3-Cl-5-CF₃) | O | O |
| H | H | 2-F-4-Cl | 3,5-Cl₂-4-OCF₂CHF₂ | O | O |
| H | H | 2-F-4-Cl | 3,5-Cl₂-4-O(C₆H₃-2-Cl-4-CF₃) | O | O |
| H | H | 2-F-4-Cl | 3,5-Cl₂-4-O(Q38-3-Cl-5-CF₃) | O | O |
| H | H | 2-F-4-Cl | 2,4-F₂-3,5-Cl₂ | O | O |
| H | H | 2-F-5-Cl | 4-Cl | O | O |
| H | H | 2-F-5-Cl | 4-OCF₃ | O | O |
| H | H | 2-F-5-Cl | 4-S(C₆H₃-2-Cl-4-CF₃) | O | O |

-continued

| | | | | | |
|---|---|---|---|---|---|
| H | H | 2-F-5-Cl | 4-CH₂ON=C(Q51)(C₆H₄-4-Cl) | O | O |
| H | H | 2-F-5-Cl | 3-O(Q50-6-CF₃) | O | O |
| H | H | 2-F-5-Cl | 3,4-Cl₂ | O | O |
| H | H | 2-F-5-Cl | 2-F-4-OCF₂CHF₂ | O | O |
| H | H | 2-F-5-Cl | 3-Cl-4-O(Q38-3-Cl-5-CF₃) | O | O |
| H | H | 2-F-5-Cl | 3,5-Cl₂-4-OCF₂CHF₂ | O | O |
| H | H | 2-F-5-Cl | 3,5-Cl₂-4-O(C₆H₃-2-Cl-4-CF₃) | O | O |
| H | H | 2-F-5-Cl | 3,5-Cl₂-4-O(Q38-3-Cl-5-CF₃) | O | O |
| H | H | 2-F-5-Cl | 2,4-F₂-3,5-Cl₂ | O | O |
| H | H | 2-F-6-I | 4-Cl | O | O |
| H | H | 2-F-6-I | 4-OCF₃ | O | O |
| H | H | 2-F-6-I | 4-S(C₆H₃-2-Cl-4-CF₃) | O | O |
| H | H | 2-F-6-I | 4-CH₂ON=C(Q51)(C₆H₄-4-Cl) | O | O |
| H | H | 2-F-6-I | 3-O(Q50-6-CF₃) | O | O |
| H | H | 2-F-6-I | 3,4-Cl₂ | O | O |
| H | H | 2-F-6-I | 2-F-4-OCF₂CHF₂ | O | O |
| H | H | 2-F-6-I | 3-Cl-4-O(Q38-3-Cl-5-CF₃) | O | O |
| H | H | 2-F-6-I | 3,5-Cl₂-4-OCF₂CHF₂ | O | O |
| H | H | 2-F-6-I | 3,5-Cl₂-4-O(C₆H₃-2-Cl-4-CF₃) | O | O |
| H | H | 2-F-6-I | 3,5-Cl₂-4-O(Q38-3-Cl-5-CF₃) | O | O |
| H | H | 2-F-6-I | 2,4-F₂-3,5-Cl₂ | O | O |
| H | H | 2-F-6-SCH₃ | 4-Cl | O | O |
| H | H | 2-F-6-SCH₃ | 4-OCF₃ | O | O |
| H | H | 2-F-6-SCH₃ | 4-S(C₆H₃-2-Cl-4-CF₃) | O | O |
| H | H | 2-F-6-SCH₃ | 4-CH₂ON=C(Q51)(C₆H₄-4-Cl) | O | O |
| H | H | 2-F-6-SCH₃ | 3-O(Q50-6-CF₃) | O | O |
| H | H | 2-F-6-SCH₃ | 3,4-Cl₂ | O | O |
| H | H | 2-F-6-SCH₃ | 2-F-4-OCF₂CHF₂ | O | O |
| H | H | 2-F-6-SCH₃ | 3-Cl-4-O(Q38-3-Cl-5-CF₃) | O | O |
| H | H | 2-F-6-SCH₃ | 3,5-Cl₂-4-OCF₂CHF₂ | O | O |
| H | H | 2-F-6-SCH₃ | 3,5-Cl₂-4-O(C₆H₃-2-Cl-4-CF₃) | O | O |
| H | H | 2-F-6-SCH₃ | 3,5-Cl₂-4-O(Q38-3-Cl-5-CF₃) | O | O |
| H | H | 2-F-6-SCH₃ | 2,4-F₂-3,5-Cl₂ | O | O |
| H | H | 2-F-3-CF₃ | 4-Cl | O | O |
| H | H | 2-F-3-CF₃ | 4-OCF₃ | O | O |
| H | H | 2-F-3-CF₃ | 4-S(C₆H₃-2-Cl-4-CF₃) | O | O |
| H | H | 2-F-3-CF₃ | 4-CH₂ON=C(Q51)(C₆H₄-4-Cl) | O | O |
| H | H | 2-F-3-CF₃ | 3-O(Q50-6-CF₃) | O | O |
| H | H | 2-F-3-CF₃ | 3,4-Cl₂ | O | O |
| H | H | 2-F-3-CF₃ | 2-F-4-OCF₂CHF₂ | O | O |
| H | H | 2-F-3-CF₃ | 3-Cl-4-O(Q38-3-Cl-5-CF₃) | O | O |
| H | H | 2-F-3-CF₃ | 3,5-Cl₂-4-OCF₂CHF₂ | O | O |
| H | H | 2-F-3-CF₃ | 3,5-Cl₂-4-O(C₆H₃-2-Cl-4-CF₃) | O | O |
| H | H | 2-F-3-CF₃ | 3,5-Cl₂-4-O(Q38-3-Cl-5-CF₃) | O | O |
| H | H | 2-F-3-CF₃ | 2,4-F₂-3,5-Cl₂ | O | O |
| H | H | 2-F-3-CF₃ | 2-F-4-Cl | O | O |
| H | H | 2-F-3-CF₃ | 2,4,6-Cl₃ | O | O |
| H | H | 2-F-3-CF₃ | 2,6-Cl₂-4-CF₃ | O | O |
| H | H | 2-F-3-CF₃ | 2-CF₃-4,6-(NO₂)₂ | O | O |
| H | H | 2-F-5-CF₃ | 4-Cl | O | O |
| H | H | 2-F-5-CF₃ | 4-OCF₃ | O | O |
| H | H | 2-F-5-CF₃ | 4-S(C₆H₃-2-Cl-4-CF₃) | O | O |
| H | H | 2-F-5-CF₃ | 4-CH₂ON=C(Q51)(C₆H₄-4-Cl) | O | O |
| H | H | 2-F-5-CF₃ | 3-O(Q50-6-CF₃) | O | O |
| H | H | 2-F-5-CF₃ | 3,4-Cl₂ | O | O |
| H | H | 2-F-5-CF₃ | 2-F-4-OCF₂CHF₂ | O | O |
| H | H | 2-F-5-CF₃ | 3-Cl-4-O(Q38-3-Cl-5-CF₃) | O | O |
| H | H | 2-F-5-CF₃ | 3,5-Cl₂-4-OCF₂CHF₂ | O | O |
| H | H | 2-F-5-CF₃ | 3,5-Cl₂-4-O(C₆H₃-2-Cl-4-CF₃) | O | O |
| H | H | 2-F-5-CF₃ | 3,5-Cl₂-4-O(Q38-3-Cl-5-CF₃) | O | O |
| H | H | 2-F-5-CF₃ | 2,4-F₂-3,5-Cl₂ | O | O |
| H | H | 2-F-5-CF₃ | 2-F-4-Cl | O | O |
| H | H | 2-F-5-CF₃ | 2,4,6-Cl₃ | O | O |
| H | H | 2-F-5-CF₃ | 2,6-Cl₂-4-CF₃ | O | O |
| H | H | 2-F-5-CF₃ | 2-CF₃-4,6-(NO₂)₂ | O | O |
| H | H | 2-Cl-3-CF₃ | 4-Cl | O | O |
| H | H | 2-Cl-3-CF₃ | 4-OCF₃ | O | O |
| H | H | 2-Cl-3-CF₃ | 4-S(C₆H₃-2-Cl-4-CF₃) | O | O |
| H | H | 2-Cl-3-CF₃ | 4-CH₂ON=C(Q51)(C₆H₄-4-Cl) | O | O |
| H | H | 2-Cl-3-CF₃ | 3-O(Q50-6-CF₃) | O | O |
| H | H | 2-Cl-3-CF₃ | 3,4-Cl₂ | O | O |
| H | H | 2-Cl-3-CF₃ | 2-F-4-OCF₂CHF₂ | O | O |
| H | H | 2-Cl-3-CF₃ | 3-Cl-4-O(Q38-3-Cl-5-CF₃) | O | O |
| H | H | 2-Cl-3-CF₃ | 3,5-Cl₂-4-OCF₂CHF₂ | O | O |
| H | H | 2-Cl-3-CF₃ | 3,5-Cl₂-4-O(C₆H₃-2-Cl-4-CF₃) | O | O |
| H | H | 2-Cl-3-CF₃ | 3,5-Cl₂-4-O(Q38-3-Cl-5-CF₃) | O | O |
| H | H | 2-Cl-3-CF₃ | 2,4-F₂-3,5-Cl₂ | O | O |
| H | H | 2-Cl-3-CF₃ | 2-F-4-Cl | O | O |
| H | H | 2-Cl-3-CF₃ | 2,4,6-Cl₃ | O | O |
| H | H | 2-Cl-3-CF₃ | 2,6-Cl₂-4-CF₃ | O | O |
| H | H | 2-Cl-3-CF₃ | 2-CF₃-4,6-(NO₂)₂ | O | O |
| H | H | 2-Cl-5-CF₃ | 4-Cl | O | O |
| H | H | 2-Cl-5-CF₃ | 4-OCF₃ | O | O |

-continued

| | | | | | |
|---|---|---|---|---|---|
| H | H | 2-Cl-5-CF₃ | 4-S(C₆H₃-2-Cl-4-CF₃) | O | O |
| H | H | 2-Cl-5-CF₃ | 4-CH₂ON=C(Q51)(C₆H₄-4-Cl) | O | O |
| H | H | 2-Cl-5-CF₃ | 3-O(Q50-6-CF₃) | O | O |
| H | H | 2-Cl-5-CF₃ | 3,4-Cl₂ | O | O |
| H | H | 2-Cl-5-CF₃ | 2-F-4-OCF₂CHF₂ | O | O |
| H | H | 2-Cl-5-CF₃ | 3-Cl-4-O(Q38-3-Cl-5-CF₃) | O | O |
| H | H | 2-Cl-5-CF₃ | 3,5-Cl₂-4-OCF₂CHF₂ | O | O |
| H | H | 2-Cl-5-CF₃ | 3,5-Cl₂-4-O(C₆H₃-2-Cl-4-CF₃) | O | O |
| H | H | 2-Cl-5-CF₃ | 3,5-Cl₂-4-O(Q38-3-Cl-5-CF₃) | O | O |
| H | H | 2-Cl-5-CF₃ | 2,4-F₂-3,5-Cl₂ | O | O |
| H | H | 2-Cl-5-CF₃ | 2-F-4-Cl | O | O |
| H | H | 2-Cl-5-CF₃ | 2,4,6-Cl₃ | O | O |
| H | H | 2-Cl-5-CF₃ | 2,6-Cl₂-4-CF₃ | O | O |
| H | H | 2-Cl-5-CF₃ | 2-CF₃-4,6-(NO₂)₂ | O | O |
| H | H | 2-F-4-CF₃ | 4-Cl | O | O |
| H | H | 2-F-4-CF₃ | 4-OCF₃ | O | O |
| H | H | 2-F-4-CF₃ | 4-S(C₆H₃-2-Cl-4-CF₃) | O | O |
| H | H | 2-F-4-CF₃ | 4-CH₂ON=C(Q51)(C₆H₄-4-Cl) | O | O |
| H | H | 2-F-4-CF₃ | 3-O(Q50-6-CF₃) | O | O |
| H | H | 2-F-4-CF₃ | 2-F-4-OCF₂CHF₂ | O | O |
| H | H | 2-F-4-CF₃ | 3,5-Cl₂-4-OCF₂CHF₂ | O | O |
| H | H | 2-F-4-CF₃ | 3,5-Cl₂-4-O(C₆H₃-2-Cl-4-CF₃) | O | O |
| H | H | 2-F-4-CF₃ | 3,5-Cl₂-4-O(Q38-3-Cl-5-CF₃) | O | O |
| H | H | 2-F-4-CF₃ | 2,4-F₂-3,5-Cl₂ | O | O |
| H | H | 2-F-6-OCF₃ | 4-Cl | O | O |
| H | H | 2-F-6-OCF₃ | 4-OCF₃ | O | O |
| H | H | 2-F-6-OCF₃ | 4-S(C₆H₃-2-Cl-4-CF₃) | O | O |
| H | H | 2-F-6-OCF₃ | 4-CH₂ON=C(Q51)(C₆H₄-4-Cl) | O | O |
| H | H | 2-F-6-OCF₃ | 3-O(Q50-6-CF₃) | O | O |
| H | H | 2-F-6-OCF₃ | 2-F-4-OCF₂CHF₂ | O | O |
| H | H | 2-F-6-OCF₃ | 3,5-Cl₂-4-OCF₂CHF₂ | O | O |
| H | H | 2-F-6-OCF₃ | 3,5-Cl₂-4-O(C₆H₃-2-Cl-4-CF₃) | O | O |
| H | H | 2-F-6-OCF₃ | 3,5-Cl₂-4-O(Q38-3-Cl-5-CF₃) | O | O |
| H | H | 2-F-6-OCF₃ | 2,4-F₂-3,5-Cl₂ | O | O |
| H | H | 2-F-6-SCF₃ | 4-Cl | O | O |
| H | H | 2-F-6-SCF₃ | 4-OCF₃ | O | O |
| H | H | 2-F-6-SCF₃ | 4-S(C₆H₃-2-Cl-4-CF₃) | O | O |
| H | H | 2-F-6-SCF₃ | 4-CH₂ON=C(Q51)(C₆H₄-4-Cl) | O | O |
| H | H | 2-F-6-SCF₃ | 3-O(Q50-6-CF₃) | O | O |
| H | H | 2-F-6-SCF₃ | 2-F-4-OCF₂CHF₂ | O | O |
| H | H | 2-F-6-SCF₃ | 3,5-Cl₂-4-OCF₂CHF₂ | O | O |
| H | H | 2-F-6-SCF₃ | 3,5-Cl₂-4-O(C₆H₃-2-Cl-4-CF₃) | O | O |
| H | H | 2-F-6-SCF₃ | 3,5-Cl₂-4-O(Q38-3-Cl-5-CF₃) | O | O |
| H | H | 2-F-6-SCF₃ | 2,4-F₂-3,5-Cl₂ | O | O |
| H | H | 2-F-6-CN | 4-Cl | O | O |
| H | H | 2-F-6-CN | 4-OCF₃ | O | O |
| H | H | 2-F-6-CN | 4-S(C₆H₃-2-Cl-4-CF₃) | O | O |
| H | H | 2-F-6-CN | 4-CH₂ON=C(Q51)(C₆H₄-4-Cl) | O | O |
| H | H | 2-F-6-CN | 3-O(Q50-6-CF₃) | O | O |
| H | H | 2-F-6-CN | 2-F-4-OCF₂CHF₂ | O | O |
| H | H | 2-F-6-CN | 3,5-Cl₂-4-OCF₂CHF₂ | O | O |
| H | H | 2-F-6-CN | 3,5-Cl₂-4-O(C₆H₃-2-Cl-4-CF₃) | O | O |
| H | H | 2-F-6-CN | 3,5-Cl₂-4-O(Q38-3-Cl-5-CF₃) | O | O |
| H | H | 2-F-6-CN | 2,4-F₂-3,5-Cl₂ | O | O |
| H | H | 2-F-6-NO₂ | 4-Cl | O | O |
| H | H | 2-F-6-NO₂ | 4-OCF₃ | O | O |
| H | H | 2-F-6-NO₂ | 4-S(C₆H₃-2-Cl-4-CF₃) | O | O |
| H | H | 2-F-6-NO₂ | 4-CH₂ON=C(Q51)(C₆H₄-4-Cl) | O | O |
| H | H | 2-F-6-NO₂ | 3-O(Q50-6-CF₃) | O | O |
| H | H | 2-F-6-NO₂ | 2-F-4-OCF₂CHF₂ | O | O |
| H | H | 2-F-6-NO₂ | 3,5-Cl₂-4-OCF₂CHF₂ | O | O |
| H | H | 2-F-6-NO₂ | 3,5-Cl₂-4-O(C₆H₃-2-Cl-4-CF₃) | O | O |
| H | H | 2-F-6-NO₂ | 3,5-Cl₂-4-O(Q38-3-Cl-5-CF₃) | O | O |
| H | H | 2-F-6-NO₂ | 2,4-F₂-3,5-Cl₂ | O | O |
| H | H | 2,3,5,-F₃ | 4-Cl | O | O |
| H | H | 2,3,5,-F₃ | 4-OCF₃ | O | O |
| H | H | 2,3,5,-F₃ | 4-S(C₆H₃-2-Cl-4-CF₃) | O | O |
| H | H | 2,3,5,-F₃ | 4-CH₂ON=C(Q51)(C₆H₄-4-Cl) | O | O |
| H | H | 2,3,5,-F₃ | 3-O(Q50-6-CF₃) | O | O |
| H | H | 2,3,5,-F₃ | 2-F-4-OCF₂CHF₂ | O | O |
| H | H | 2,3,5,-F₃ | 3,5-Cl₂-4-OCF₂CHF₂ | O | O |
| H | H | 2,3,5,-F₃ | 3,5-Cl₂-4-O(C₆H₃-2-Cl-4-CF₃) | O | O |
| H | H | 2,3,5,-F₃ | 3,5-Cl₂-4-O(Q38-3-Cl-5-CF₃) | O | O |
| H | H | 2,3,5,-F₃ | 2,4-F₂-3,5-Cl₂ | O | O |
| H | H | 2-F-4,6-Cl₂ | 4-Cl | O | O |
| H | H | 2-F-4,6-Cl₂ | 4-OCF₃ | O | O |
| H | H | 2-F-4,6-Cl₂ | 4-S(C₆H₃-2-Cl-4-CF₃) | O | O |
| H | H | 2-F-4,6-Cl₂ | 4-CH₂ON=C(Q51)(C₆H₄-4-Cl) | O | O |
| H | H | 2-F-4,6-Cl₂ | 3-O(Q50-6-CF₃) | O | O |
| H | H | 2-F-4,6-Cl₂ | 2-F-4-OCF₂CHF₂ | O | O |
| H | H | 2-F-4,6-Cl₂ | 3,5-Cl₂-4-OCF₂CHF₂ | O | O |
| H | H | 2-F-4,6-Cl₂ | 3,5-Cl₂-4-O(C₆H₃-2-Cl-4-CF₃) | O | O |
| H | H | 2-F-4,6-Cl₂ | 3,5-Cl₂-4-O(Q38-3-Cl-5-CF₃) | O | O |

-continued

| | | | | | |
|---|---|---|---|---|---|
| H | H | 2-F-4,6-Cl$_2$ | 2,4-F$_2$-3,5-Cl$_2$ | O | O |
| H | H | 2,3,5,6-F$_4$ | 4-Cl | O | O |
| H | H | 2,3,5,6-F$_4$ | 4-OCF$_3$ | O | O |
| H | H | 2,3,5,6-F$_4$ | 4-S(C$_6$H$_3$-2-Cl-4-CF$_3$) | O | O |
| H | H | 2,3,5,6-F$_4$ | 4-CH$_2$ON=C(Q51)(C$_6$H$_4$-4-Cl) | O | O |
| H | H | 2,3,5,6-F$_4$ | 3-O(Q50-6-CF$_3$) | O | O |
| H | H | 2,3,5,6-F$_4$ | 2-F-4-OCF$_2$CHF$_2$ | O | O |
| H | H | 2,3,5,6-F$_4$ | 3,5-Cl$_2$-4-OCF$_2$CHF$_2$ | O | O |
| H | H | 2,3,5,6-F$_4$ | 3,5-Cl$_2$-4-O(C$_6$H$_3$-2-Cl-4-CF$_3$) | O | O |
| H | H | 2,3,5,6-F$_4$ | 3,5-Cl$_2$-4-O(Q38-3-Cl-5-CF$_3$) | O | O |
| H | H | 2,3,5,6-F$_4$ | 2,4-F$_2$-3,5-Cl$_2$ | O | O |
| H | H | 2,3,4,5,6,-F$_5$ | 4-Cl | O | O |
| H | H | 2,3,4,5,6,-F$_5$ | 4-OCF$_3$ | O | O |
| H | H | 2,3,4,5,6,-F$_5$ | 4-S(C$_6$H$_3$-2-Cl-4-CF$_3$) | O | O |
| H | H | 2,3,4,5,6,-F$_5$ | 4-CH$_2$ON=C(Q51)(C$_6$H$_4$-4-Cl) | O | O |
| H | H | 2,3,4,5,6,-F$_5$ | 3-O(Q50-6-CF$_3$) | O | O |
| H | H | 2,3,4,5,6,-F$_5$ | 2-F-4-OCF$_2$CHF$_2$ | O | O |
| H | H | 2,3,4,5,6,-F$_5$ | 3,5-Cl$_2$-4-OCF$_2$CHF$_2$ | O | O |
| H | H | 2,3,4,5,6,-F$_5$ | 3,5-Cl$_2$-4-O(C$_6$H$_3$-2-Cl-4-CF$_3$) | O | O |
| H | H | 2,3,4,5,6,-F$_5$ | 3,5-Cl$_2$-4-O(Q38-3-Cl-5-CF$_3$) | O | O |
| H | H | 2,3,4,5,6,-F$_5$ | 2,4-F$_2$-3,5-Cl$_2$ | O | O |
| H | H | 2-Cl-3-F | 4-Cl | O | O |
| H | H | 2-Cl-3-F | 4-OCF$_3$ | O | O |
| H | H | 2-Cl-3-F | 4-S(C$_6$H$_3$-2-Cl-4-CF$_3$) | O | O |
| H | H | 2-Cl-3-F | 4-CH$_2$ON=C(Q51)(C$_6$H$_4$-4-Cl) | O | O |
| H | H | 2-Cl-3-F | 3-O(Q50-6-CF$_3$) | O | O |
| H | H | 2-Cl-3-F | 2-F-4-OCF$_2$CHF$_2$ | O | O |
| H | H | 2-Cl-3-F | 3,5-Cl$_2$-4-OCF$_2$CHF$_2$ | O | O |
| H | H | 2-Cl-3-F | 3,5-Cl$_2$-4-O(C$_6$H$_3$-2-Cl-4-CF$_3$) | O | O |
| H | H | 2-Cl-3-F | 3,5-Cl$_2$-4-O(Q38-3-Cl-5-CF$_3$) | O | O |
| H | H | 2-Cl-3-F | 2,4-F$_2$-3,5-Cl$_2$ | O | O |
| H | H | 2-Cl-4-F | 4-Cl | O | O |
| H | H | 2-Cl-4-F | 4-OCF$_3$ | O | O |
| H | H | 2-Cl-4-F | 4-S(C$_6$H$_3$-2-Cl-4-CF$_3$) | O | O |
| H | H | 2-Cl-4-F | 4-CH$_2$ON=C(Q51)(C$_6$H$_4$-4-Cl) | O | O |
| H | H | 2-Cl-4-F | 3-O(Q50-6-CF$_3$) | O | O |
| H | H | 2-Cl-4-F | 2-F-4-OCF$_2$CHF$_2$ | O | O |
| H | H | 2-Cl-4-F | 3,5-Cl$_2$-4-OCF$_2$CHF$_2$ | O | O |
| H | H | 2-Cl-4-F | 3,5-Cl$_2$-4-O(C$_6$H$_3$-2-Cl-4-CF$_3$) | O | O |
| H | H | 2-Cl-4-F | 3,5-Cl$_2$-4-O(Q38-3-Cl-5-CF$_3$) | O | O |
| H | H | 2-Cl-4-F | 2,4-F$_2$-3,5-Cl$_2$ | O | O |
| H | H | 2-Cl-5-F | 4-Cl | O | O |
| H | H | 2-Cl-5-F | 4-OCF$_3$ | O | O |
| H | H | 2-Cl-5-F | 4-S(C$_6$H$_3$-2-Cl-4-CF$_3$) | O | O |
| H | H | 2-Cl-5-F | 4-CH$_2$ON=C(Q51)(C$_6$H$_4$-4-Cl) | O | O |
| H | H | 2-Cl-5-F | 3-O(Q50-6-CF$_3$) | O | O |
| H | H | 2-Cl-5-F | 2-F-4-OCF$_2$CHF$_2$ | O | O |
| H | H | 2-Cl-5-F | 3,5-Cl$_2$-4-OCF$_2$CHF$_2$ | O | O |
| H | H | 2-Cl-5-F | 3,5-Cl$_2$-4-O(C$_6$H$_3$-2-Cl-4-CF$_3$) | O | O |
| H | H | 2-Cl-5-F | 3,5-Cl$_2$-4-O(Q38-3-Cl-5-CF$_3$) | O | O |
| H | H | 2-Cl-5-F | 2,4-F$_2$-3,5-Cl$_2$ | O | O |
| H | H | 2,3-Cl$_2$ | 4-Cl | O | O |
| H | H | 2,3-Cl$_2$ | 4-OCF$_3$ | O | O |
| H | H | 2,3-Cl$_2$ | 4-S(C$_6$H$_3$-2-Cl-4-CF$_3$) | O | O |
| H | H | 2,3-Cl$_2$ | 4-CH$_2$ON=C(Q51)(C$_6$H$_4$-4-Cl) | O | O |
| H | H | 2,3-Cl$_2$ | 3-O(Q50-6-CF$_3$) | O | O |
| H | H | 2,3-Cl$_2$ | 2-F-4-OCF$_2$CHF$_2$ | O | O |
| H | H | 2,3-Cl$_2$ | 3,5-Cl$_2$-4-OCF$_2$CHF$_2$ | O | O |
| H | H | 2,3-Cl$_2$ | 3,5-Cl$_2$-4-O(C$_6$H$_3$-2-Cl-4-CF$_3$) | O | O |
| H | H | 2,3-Cl$_2$ | 3,5-Cl$_2$-4-O(Q38-3-Cl-5-CF$_3$) | O | O |
| H | H | 2,3-Cl$_2$ | 2,4-F$_2$-3,5-Cl$_2$ | O | O |
| H | H | 2,4-Cl$_2$ | 4-Cl | O | O |
| H | H | 2,4-Cl$_2$ | 4-OCF$_3$ | O | O |
| H | H | 2,4-Cl$_2$ | 4-S(C$_6$H$_3$-2-Cl-4-CF$_3$) | O | O |
| H | H | 2,4-Cl$_2$ | 4-CH$_2$ON=C(Q51)(C$_6$H$_4$-4-Cl) | O | O |
| H | H | 2,4-Cl$_2$ | 3-O(Q50-6-CF$_3$) | O | O |
| H | H | 2,4-Cl$_2$ | 2-F-4-OCF$_2$CHF$_2$ | O | O |
| H | H | 2,4-Cl$_2$ | 3,5-Cl$_2$-4-OCF$_2$CHF$_2$ | O | O |
| H | H | 2,4-Cl$_2$ | 3,5-Cl$_2$-4-O(C$_6$H$_3$-2-Cl-4-CF$_3$) | O | O |
| H | H | 2,4-Cl$_2$ | 3,5-Cl$_2$-4-O(Q38-3-Cl-5-CF$_3$) | O | O |
| H | H | 2,4-Cl$_2$ | 2,4-F$_2$-3,5-Cl$_2$ | O | O |
| H | H | 2,5-Cl$_2$ | 4-Cl | O | O |
| H | H | 2,5-Cl$_2$ | 4-OCF$_3$ | O | O |
| H | H | 2,5-Cl$_2$ | 4-S(C$_6$H$_3$-2-Cl-4-CF$_3$) | O | O |
| H | H | 2,5-Cl$_2$ | 4-CH$_2$ON=C(Q51)(C$_6$H$_4$-4-Cl) | O | O |
| H | H | 2,5-Cl$_2$ | 3-O(Q50-6-CF$_3$) | O | O |
| H | H | 2,5-Cl$_2$ | 2-F-4-OCF$_2$CHF$_2$ | O | O |
| H | H | 2,5-Cl$_2$ | 3,5-Cl$_2$-4-OCF$_2$CHF$_2$ | O | O |
| H | H | 2,5-Cl$_2$ | 3,5-Cl$_2$-4-O(C$_6$H$_3$-2-Cl-4-CF$_3$) | O | O |
| H | H | 2,5-Cl$_2$ | 3,5-Cl$_2$-4-O(Q38-3-Cl-5-CF$_3$) | O | O |
| H | H | 2,5-Cl$_2$ | 2,4-F$_2$-3,5-Cl$_2$ | O | O |
| H | H | 2-Cl-6-Br | 4-Cl | O | O |
| H | H | 2-Cl-6-Br | 4-OCF$_3$ | O | O |

-continued

| | | | | | |
|---|---|---|---|---|---|
| H | H | 2-Cl-6-Br | 4-S(C$_6$H$_3$-2-Cl-4-CF$_3$) | O | O |
| H | H | 2-Cl-6-Br | 4-CH$_2$ON=C(Q51)(C$_6$H$_4$-4-Cl) | O | O |
| H | H | 2-Cl-6-Br | 3-O(Q50-6-CF$_3$) | O | O |
| H | H | 2-Cl-6-Br | 2-F-4-OCF$_2$CHF$_2$ | O | O |
| H | H | 2-Cl-6-Br | 3,5-Cl$_2$-4-OCF$_2$CHF$_2$ | O | O |
| H | H | 2-Cl-6-Br | 3,5-Cl$_2$-4-O(C$_6$H$_3$-2-Cl-4-CF$_3$) | O | O |
| H | H | 2-Cl-6-Br | 3,5-Cl$_2$-4-O(Q38-3-Cl-5-CF$_3$) | O | O |
| H | H | 2-Cl-6-Br | 2,4-F$_2$-3,5-Cl$_2$ | O | O |
| H | H | 2-Cl-6-I | 4-Cl | O | O |
| H | H | 2-Cl-6-I | 4-OCF$_3$ | O | O |
| H | H | 2-Cl-6-I | 4-S(C$_6$H$_3$-2-Cl-4-CF$_3$) | O | O |
| H | H | 2-Cl-6-I | 4-CH$_2$ON=C(Q51)(C$_6$H$_4$-4-Cl) | O | O |
| H | H | 2-Cl-6-I | 3-O(Q50-6-CF$_3$) | O | O |
| H | H | 2-Cl-6-I | 2-F-4-OCF$_2$CHF$_2$ | O | O |
| H | H | 2-Cl-6-I | 3,5-Cl$_2$-4-OCF$_2$CHF$_2$ | O | O |
| H | H | 2-Cl-6-I | 3,5-Cl$_2$-4-O(C$_6$H$_3$-2-Cl-4-CF$_3$) | O | O |
| H | H | 2-Cl-6-I | 3,5-Cl$_2$-4-O(Q38-3-Cl-5-CF$_3$) | O | O |
| H | H | 2-Cl-6-I | 2,4-F$_2$-3,5-Cl$_2$ | O | O |
| H | H | 2-Cl-6-CH$_3$ | 4-Cl | O | O |
| H | H | 2-Cl-6-CH$_3$ | 4-OCF$_3$ | O | O |
| H | H | 2-Cl-6-CH$_3$ | 4-S(C$_6$H$_3$-2-Cl-4-CF$_3$) | O | O |
| H | H | 2-Cl-6-CH$_3$ | 4-CH$_2$ON=C(Q51)(C$_6$H$_4$-4-Cl) | O | O |
| H | H | 2-Cl-6-CH$_3$ | 3-O(Q50-6-CF$_3$) | O | O |
| H | H | 2-Cl-6-CH$_3$ | 2-F-4-OCF$_2$CHF$_2$ | O | O |
| H | H | 2-Cl-6-CH$_3$ | 3,5-Cl$_2$-4-OCF$_2$CHF$_2$ | O | O |
| H | H | 2-Cl-6-CH$_3$ | 3,5-Cl$_2$-4-O(C$_6$H$_3$-2-Cl-4-CF$_3$) | O | O |
| H | H | 2-Cl-6-CH$_3$ | 3,5-Cl$_2$-4-O(Q38-3-Cl-5-CF$_3$) | O | O |
| H | H | 2-Cl-6-CH$_3$ | 2,4-F$_2$-3,5-Cl$_2$ | O | O |
| H | H | 2-Cl-6-OCH$_3$ | 4-Cl | O | O |
| H | H | 2-Cl-6-OCH$_3$ | 4-OCF$_3$ | O | O |
| H | H | 2-Cl-6-OCH$_3$ | 4-S(C$_6$H$_3$-2-Cl-4-CF$_3$) | O | O |
| H | H | 2-Cl-6-OCH$_3$ | 4-CH$_2$ON=C(Q51)(C$_6$H$_4$-4-Cl) | O | O |
| H | H | 2-Cl-6-OCH$_3$ | 3-O(Q50-6-CF$_3$) | O | O |
| H | H | 2-Cl-6-OCH$_3$ | 2-F-4-OCF$_2$CHF$_2$ | O | O |
| H | H | 2-Cl-6-OCH$_3$ | 3,5-Cl$_2$-4-OCF$_2$CHF$_2$ | O | O |
| H | H | 2-Cl-6-OCH$_3$ | 3,5-Cl$_2$-4-O(C$_6$H$_3$-2-Cl-4-CF$_3$) | O | O |
| H | H | 2-Cl-6-OCH$_3$ | 3,5-Cl$_2$-4-O(Q38-3-Cl-5-CF$_3$) | O | O |
| H | H | 2-Cl-6-OCH$_3$ | 2,4-F$_2$-3,5-Cl$_2$ | O | O |
| H | H | 2-Cl-6-SCH$_3$ | 4-Cl | O | O |
| H | H | 2-Cl-6-SCH$_3$ | 4-OCF$_3$ | O | O |
| H | H | 2-Cl-6-SCH$_3$ | 4-S(C$_6$H$_3$-2-Cl-4-CF$_3$) | O | O |
| H | H | 2-Cl-6-SCH$_3$ | 4-CH$_2$ON=C(Q51)(C$_6$H$_4$-4-Cl) | O | O |
| H | H | 2-Cl-6-SCH$_3$ | 3-O(Q50-6-CF$_3$) | O | O |
| H | H | 2-Cl-6-SCH$_3$ | 2-F-4-OCF$_2$CHF$_2$ | O | O |
| H | H | 2-Cl-6-SCH$_3$ | 3,5-Cl$_2$-4-OCF$_2$CHF$_2$ | O | O |
| H | H | 2-Cl-6-SCH$_3$ | 3,5-Cl$_2$-4-O(C$_6$H$_3$-2-Cl-4-CF$_3$) | O | O |
| H | H | 2-Cl-6-SCH$_3$ | 3,5-Cl$_2$-4-O(Q38-3-Cl-5-CF$_3$) | O | O |
| H | H | 2-Cl-6-SCH$_3$ | 2,4-F$_2$-3,5-Cl$_2$ | O | O |
| H | H | 2-Cl-6-CF$_3$ | 4-Cl | O | O |
| H | H | 2-Cl-6-CF$_3$ | 4-OCF$_3$ | O | O |
| H | H | 2-Cl-6-CF$_3$ | 4-S(C$_6$H$_3$-2-Cl-4-CF$_3$) | O | O |
| H | H | 2-Cl-6-CF$_3$ | 4-CH$_2$ON=C(Q51)(C$_6$H$_4$-4-Cl) | O | O |
| H | H | 2-Cl-6-CF$_3$ | 3-O(Q50-6-CF$_3$) | O | O |
| H | H | 2-Cl-6-CF$_3$ | 2-F-4-OCF$_2$CHF$_2$ | O | O |
| H | H | 2-Cl-6-CF$_3$ | 3,5-Cl$_2$-4-OCF$_2$CHF$_2$ | O | O |
| H | H | 2-Cl-6-CF$_3$ | 3,5-Cl$_2$-4-O(C$_6$H$_3$-2-Cl-4-CF$_3$) | O | O |
| H | H | 2-Cl-6-CF$_3$ | 3,5-Cl$_2$-4-O(Q38-3-Cl-5-CF$_3$) | O | O |
| H | H | 2-Cl-6-CF$_3$ | 2,4-F$_2$-3,5-Cl$_2$ | O | O |
| H | H | 2-Cl-6-CN | 4-Cl | O | O |
| H | H | 2-Cl-6-CN | 4-OCF$_3$ | O | O |
| H | H | 2-Cl-6-CN | 4-S(C$_6$H$_3$-2-Cl-4-CF$_3$) | O | O |
| H | H | 2-Cl-6-CN | 4-CH$_2$ON=C(Q51)(C$_6$H$_4$-4-Cl) | O | O |
| H | H | 2-Cl-6-CN | 3-O(Q50-6-CF$_3$) | O | O |
| H | H | 2-Cl-6-CN | 2-F-4-OCF$_2$CHF$_2$ | O | O |
| H | H | 2-Cl-6-CN | 3,5-Cl$_2$-4-OCF$_2$CHF$_2$ | O | O |
| H | H | 2-Cl-6-CN | 3,5-Cl$_2$-4-O(C$_6$H$_3$-2-Cl-4-CF$_3$) | O | O |
| H | H | 2-Cl-6-CN | 3,5-Cl$_2$-4-O(Q38-3-Cl-5-CF$_3$) | O | O |
| H | H | 2-Cl-6-CN | 2,4-F$_2$-3,5-Cl$_2$ | O | O |
| H | H | 2-Cl-6-NO$_2$ | 4-Cl | O | O |
| H | H | 2-Cl-6-NO$_2$ | 4-OCF$_3$ | O | O |
| H | H | 2-Cl-6-NO$_2$ | 4-S(C$_6$H$_3$-2-Cl-4-CF$_3$) | O | O |
| H | H | 2-Cl-6-NO$_2$ | 4-CH$_2$ON=C(Q51)(C$_6$H$_4$-4-Cl) | O | O |
| H | H | 2-Cl-6-NO$_2$ | 3-O(Q50-6-CF$_3$) | O | O |
| H | H | 2-Cl-6-NO$_2$ | 2-F-4-OCF$_2$CHF$_2$ | O | O |
| H | H | 2-Cl-6-NO$_2$ | 3,5-Cl$_2$-4-OCF$_2$CHF$_2$ | O | O |
| H | H | 2-Cl-6-NO$_2$ | 3,5-Cl$_2$-4-O(C$_6$H$_3$-2-Cl-4-CF$_3$) | O | O |
| H | H | 2-Cl-6-NO$_2$ | 3,5-Cl$_2$-4-O(Q38-3-Cl-5-CF$_3$) | O | O |
| H | H | 2-Cl-6-NO$_2$ | 2,4-F$_2$-3,5-Cl$_2$ | O | O |
| H | H | 2-Cl-3,4-F$_2$ | 4-Cl | O | O |
| H | H | 2-Cl-3,4-F$_2$ | 4-OCF$_3$ | O | O |
| H | H | 2-Cl-3,4-F$_2$ | 4-S(C$_6$H$_3$-2-Cl-4-CF$_3$) | O | O |
| H | H | 2-Cl-3,4-F$_2$ | 4-CH$_2$ON=C(Q51)(C$_6$H$_4$-4-Cl) | O | O |
| H | H | 2-Cl-3,4-F$_2$ | 3-O(Q50-6-CF$_3$) | O | O |

-continued

| | | | | | |
|---|---|---|---|---|---|
| H | H | 2-Cl-3,4-F$_2$ | 2-F-4-OCF$_2$CHF$_2$ | O | O |
| H | H | 2-Cl-3,4-F$_2$ | 3,5-Cl$_2$-4-OCF$_2$CHF$_2$ | O | O |
| H | H | 2-Cl-3,4-F$_2$ | 3,5-Cl$_2$-4-O(C$_6$H$_3$-2-Cl-4-CF$_3$) | O | O |
| H | H | 2-Cl-3,4-F$_2$ | 3,5-Cl$_2$-4-O(Q38-3-Cl-5-CF$_3$) | O | O |
| H | H | 2-Cl-3,4-F$_2$ | 2,4-F$_2$-3,5-Cl$_2$ | O | O |
| H | H | 2-Cl-3,5-F$_2$ | 4-Cl | O | O |
| H | H | 2-Cl-3,5-F$_2$ | 4-OCF$_3$ | O | O |
| H | H | 2-Cl-3,5-F$_2$ | 4-S(C$_6$H$_3$-2-Cl-4-CF$_3$) | O | O |
| H | H | 2-Cl-3,5-F$_2$ | 4-CH$_2$ON=C(Q51)(C$_6$H$_4$-4-Cl) | O | O |
| H | H | 2-Cl-3,5-F$_2$ | 3-O(Q50-6-CF$_3$) | O | O |
| H | H | 2-Cl-3,5-F$_2$ | 2-F-4-OCF$_2$CHF$_2$ | O | O |
| H | H | 2-Cl-3,5-F$_2$ | 3,5-Cl$_2$-4-OCF$_2$CHF$_2$ | O | O |
| H | H | 2-Cl-3,5-F$_2$ | 3,5-Cl$_2$-4-O(C$_6$H$_3$-2-Cl-4-CF$_3$) | O | O |
| H | H | 2-Cl-3,5-F$_2$ | 3,5-Cl$_2$-4-O(Q38-3-Cl-5-CF$_3$) | O | O |
| H | H | 2-Cl-3,5-F$_2$ | 2,4-F$_2$-3,5-Cl$_2$ | O | O |
| H | H | 2-Cl-4,5-F$_2$ | 4-Cl | O | O |
| H | H | 2-Cl-4,5-F$_2$ | 4-OCF$_3$ | O | O |
| H | H | 2-Cl-4,5-F$_2$ | 4-S(C$_6$H$_3$-2-Cl-4-CF$_3$) | O | O |
| H | H | 2-Cl-4,5-F$_2$ | 4-CH$_2$ON=C(Q51)(C$_6$H$_4$-4-Cl) | O | O |
| H | H | 2-Cl-4,5-F$_2$ | 3-O(Q50-6-CF$_3$) | O | O |
| H | H | 2-Cl-4,5-F$_2$ | 2-F-4-OCF$_2$CHF$_2$ | O | O |
| H | H | 2-Cl-4,5-F$_2$ | 3,5-Cl$_2$-4-OCF$_2$CHF$_2$ | O | O |
| H | H | 2-Cl-4,5-F$_2$ | 3,5-Cl$_2$-4-O(C$_6$H$_3$-2-Cl-4-CF$_3$) | O | O |
| H | H | 2-Cl-4,5-F$_2$ | 3,5-Cl$_2$-4-O(Q38-3-Cl-5-CF$_3$) | O | O |
| H | H | 2-Cl-4,5-F$_2$ | 2,4-F$_2$-3,5-Cl$_2$ | O | O |
| H | H | 2-Cl-4,5,6-F$_3$ | 4-Cl | O | O |
| H | H | 2-Cl-4,5,6-F$_3$ | 4-OCF$_3$ | O | O |
| H | H | 2-Cl-4,5,6-F$_3$ | 4-S(C$_6$H$_3$-2-Cl-4-CF$_3$) | O | O |
| H | H | 2-Cl-4,5,6-F$_3$ | 4-CH$_2$ON=C(Q51)(C$_6$H$_4$-4-Cl) | O | O |
| H | H | 2-Cl-4,5,6-F$_3$ | 3-O(Q50-6-CF$_3$) | O | O |
| H | H | 2-Cl-4,5,6-F$_3$ | 2-F-4-OCF$_2$CHF$_2$ | O | O |
| H | H | 2-Cl-4,5,6-F$_3$ | 3,5-Cl$_2$-4-OCF$_2$CHF$_2$ | O | O |
| H | H | 2-Cl-4,5,6-F$_3$ | 3,5-Cl$_2$-4-O(C$_6$H$_3$-2-Cl-4-CF$_3$) | O | O |
| H | H | 2-Cl-4,5,6-F$_3$ | 3,5-Cl$_2$-4-O(Q38-3-Cl-5-CF$_3$) | O | O |
| H | H | 2-Cl-4,5,6-F$_3$ | 2,4-F$_2$-3,5-Cl$_2$ | O | O |
| H | H | 2,4,6-Cl$_3$ | 4-Cl | O | O |
| H | H | 2,4,6-Cl$_3$ | 4-OCF$_3$ | O | O |
| H | H | 2,4,6-Cl$_3$ | 4-S(C$_6$H$_3$-2-Cl-4-CF$_3$) | O | O |
| H | H | 2,4,6-Cl$_3$ | 4-CH$_2$ON=C(Q51)(C$_6$H$_4$-4-Cl) | O | O |
| H | H | 2,4,6-Cl$_3$ | 3-O(Q50-6-CF$_3$) | O | O |
| H | H | 2,4,6-Cl$_3$ | 2-F-4-OCF$_2$CHF$_2$ | O | O |
| H | H | 2,4,6-Cl$_3$ | 3,5-Cl$_2$-4-OCF$_2$CHF$_2$ | O | O |
| H | H | 2,4,6-Cl$_3$ | 3,5-Cl$_2$-4-O(C$_6$H$_3$-2-Cl-4-CF$_3$) | O | O |
| H | H | 2,4,6-Cl$_3$ | 3,5-Cl$_2$-4-O(Q38-3-Cl-5-CF$_3$) | O | O |
| H | H | 2,4,6-Cl$_3$ | 2,4-F$_2$-3,5-Cl$_2$ | O | O |
| H | H | 2,6-(CH$_3$)$_2$ | 4-Cl | O | O |
| H | H | 2,6-(CH$_3$)$_2$ | 4-OCF$_3$ | O | O |
| H | H | 2,6-(CH$_3$)$_2$ | 4-S(C$_6$H$_3$-2-Cl-4-CF$_3$) | O | O |
| H | H | 2,6-(CH$_3$)$_2$ | 4-CH$_2$ON=C(Q51)(C$_6$H$_4$-4-Cl) | O | O |
| H | H | 2,6-(CH$_3$)$_2$ | 3-O(Q50-6-CF$_3$) | O | O |
| H | H | 2,6-(CH$_3$)$_2$ | 2-F-4-OCF$_2$CHF$_2$ | O | O |
| H | H | 2,6-(CH$_3$)$_2$ | 3,5-Cl$_2$-4-OCF$_2$CHF$_2$ | O | O |
| H | H | 2,6-(CH$_3$)$_2$ | 3,5-Cl$_2$-4-O(C$_6$H$_3$-2-Cl-4-CF$_3$) | O | O |
| H | H | 2,6-(CH$_3$)$_2$ | 3,5-Cl$_2$-4-O(Q38-3-Cl-5-CF$_3$) | O | O |
| H | H | 2,6-(CH$_3$)$_2$ | 2,4-F$_2$-3,5-Cl$_2$ | O | O |
| H | H | 2,6-(OCH$_3$)$_2$ | 4-Cl | O | O |
| H | H | 2,6-(OCH$_3$)$_2$ | 4-OCF$_3$ | O | O |
| H | H | 2,6-(OCH$_3$)$_2$ | 4-S(C$_6$H$_3$-2-Cl-4-CF$_3$) | O | O |
| H | H | 2,6-(OCH$_3$)$_2$ | 4-CH$_2$ON=C(Q51)(C$_6$H$_4$-4-Cl) | O | O |
| H | H | 2,6-(OCH$_3$)$_2$ | 3-O(Q50-6-CF$_3$) | O | O |
| H | H | 2,6-(OCH$_3$)$_2$ | 2-F-4-OCF$_2$CHF$_2$ | O | O |
| H | H | 2,6-(OCH$_3$)$_2$ | 3,5-Cl$_2$-4-OCF$_2$CHF$_2$ | O | O |
| H | H | 2,6-(OCH$_3$)$_2$ | 3,5-Cl$_2$-4-O(C$_6$H$_3$-2-Cl-4-CF$_3$) | O | O |
| H | H | 2,6-(OCH$_3$)$_2$ | 3,5-Cl$_2$-4-O(Q38-3-Cl-5-CF$_3$) | O | O |
| H | H | 2,6-(OCH$_3$)$_2$ | 2,4-F$_2$-3,5-Cl$_2$ | O | O |
| H | H | 2,6-Br$_2$ | 4-Cl | O | O |
| H | H | 2,6-Br$_2$ | 4-OCF$_3$ | O | O |
| H | H | 2,6-Br$_2$ | 4-S(C$_6$H$_3$-2-Cl-4-CF$_3$) | O | O |
| H | H | 2,6-Br$_2$ | 4-CH$_2$ON=C(Q51)(C$_6$H$_4$-4-Cl) | O | O |
| H | H | 2,6-Br$_2$ | 3-O(Q50-6-CF$_3$) | O | O |
| H | H | 2,6-Br$_2$ | 2-F-4-OCF$_2$CHF$_2$ | O | O |
| H | H | 2,6-Br$_2$ | 3,5-Cl$_2$-4-OCF$_2$CHF$_2$ | O | O |
| H | H | 2,6-Br$_2$ | 3,5-Cl$_2$-4-O(C$_6$H$_3$-2-Cl-4-CF$_3$) | O | O |
| H | H | 2,6-Br$_2$ | 3,5-Cl$_2$-4-O(Q38-3-Cl-5-CF$_3$) | O | O |
| H | H | 2,6-Br$_2$ | 2,4-F$_2$-3,5-Cl$_2$ | O | O |
| H | H | 2-CH$_3$-6-CN | 4-Cl | O | O |
| H | H | 2-CH$_3$-6-CN | 4-OCF$_3$ | O | O |
| H | H | 2-CH$_3$-6-CN | 4-S(C$_6$H$_3$-2-Cl-4-CF$_3$) | O | O |
| H | H | 2-CH$_3$-6-CN | 4-CH$_2$ON=C(Q51)(C$_6$H$_4$-4-Cl) | O | O |
| H | H | 2-CH$_3$-6-CN | 3-O(Q50-6-CF$_3$) | O | O |
| H | H | 2-CH$_3$-6-CN | 2-F-4-OCF$_2$CHF$_2$ | O | O |
| H | H | 2-CH$_3$-6-CN | 3,5-Cl$_2$-4-OCF$_2$CHF$_2$ | O | O |
| H | H | 2-CH$_3$-6-CN | 3,5-Cl$_2$-4-O(C$_6$H$_3$-2-Cl-4-CF$_3$) | O | O |

-continued

| | | | | | |
|---|---|---|---|---|---|
| H | H | 2-CH$_3$-6-CN | 3,5-Cl$_2$-4-O(Q38-3-Cl-5-CF$_3$) | O | O |
| H | H | 2-CH$_3$-6-CN | 2,4-F$_2$-3,5-Cl$_2$ | O | O |
| H | H | 2-OCH$_3$-6-NO$_2$ | 4-Cl | O | O |
| H | H | 2-OCH$_3$-6-NO$_2$ | 4-OCF$_3$ | O | O |
| H | H | 2-OCH$_3$-6-NO$_2$ | 4-S(C$_6$H$_3$-2-Cl-4-CF$_3$) | O | O |
| H | H | 2-OCH$_3$-6-NO$_2$ | 4-CH$_2$ON=C(Q51)(C$_6$H$_4$-4-Cl) | O | O |
| H | H | 2-OCH$_3$-6-NO$_2$ | 3-O(Q50-6-CF$_3$) | O | O |
| H | H | 2-OCH$_3$-6-NO$_2$ | 2-F-4-OCF$_2$CHF$_2$ | O | O |
| H | H | 2-OCH$_3$-6-NO$_2$ | 3,5-Cl$_2$-4-OCF$_2$CHF$_2$ | O | O |
| H | H | 2-OCH$_3$-6-NO$_2$ | 3,5-Cl$_2$-4-O(C$_6$H$_3$-2-Cl-4-CF$_3$) | O | O |
| H | H | 2-OCH$_3$-6-NO$_2$ | 3,5-Cl$_2$-4-O(Q38-3-Cl-5-CF$_3$) | O | O |
| H | H | 2-OCH$_3$-6-NO$_2$ | 2,4-F$_2$-3,5-Cl$_2$ | O | O |
| H | H | 2-CH$_2$CH$_2$CH$_3$ | 4-Cl | O | O |
| H | H | 2-CH$_2$CH$_2$CH$_3$ | 4-OCF$_3$ | O | O |
| H | H | 2-CH$_2$CH$_2$CH$_3$ | 4-S(C$_6$H$_3$-2-Cl-4-CF$_3$) | O | O |
| H | H | 2-CH$_2$CH$_2$CH$_3$ | 4-CH$_2$ON=C(Q51)(C$_6$H$_4$-4-Cl) | O | O |
| H | H | 2-CH$_2$CH$_2$CH$_3$ | 3-O(Q50-6-CF$_3$) | O | O |
| H | H | 2-CH$_2$CH$_2$CH$_3$ | 2-F-4-OCF$_2$CHF$_2$ | O | O |
| H | H | 2-CH$_2$CH$_2$CH$_3$ | 3,5-Cl$_2$-4-OCF$_2$CHF$_2$ | O | O |
| H | H | 2-CH$_2$CH$_2$CH$_3$ | 3,5-Cl$_2$-4-O(C$_6$H$_3$-2-Cl-4-CF$_3$) | O | O |
| H | H | 2-CH$_2$CH$_2$CH$_3$ | 3,5-Cl$_2$-4-O(Q38-3-Cl-5-CF$_3$) | O | O |
| H | H | 2-CH$_2$CH$_2$CH$_3$ | 2,4-F$_2$-3,5-Cl$_2$ | O | O |
| H | H | 2-OCH$_2$CH$_3$ | 4-Cl | O | O |
| H | H | 2-OCH$_2$CH$_3$ | 4-OCF$_3$ | O | O |
| H | H | 2-OCH$_2$CH$_3$ | 4-S(C$_6$H$_3$-2-Cl-4-CF$_3$) | O | O |
| H | H | 2-OCH$_2$CH$_3$ | 4-CH$_2$ON=C(Q51)(C$_6$H$_4$-4-Cl) | O | O |
| H | H | 2-OCH$_2$CH$_3$ | 3-O(Q50-6-CF$_3$) | O | O |
| H | H | 2-OCH$_2$CH$_3$ | 2-F-4-OCF$_2$CHF$_2$ | O | O |
| H | H | 2-OCH$_2$CH$_3$ | 3,5-Cl$_2$-4-OCF$_2$CHF$_2$ | O | O |
| H | H | 2-OCH$_2$CH$_3$ | 3,5-Cl$_2$-4-O(C$_6$H$_3$-2-Cl-4-CF$_3$) | O | O |
| H | H | 2-OCH$_2$CH$_3$ | 3,5-Cl$_2$-4-O(Q38-3-Cl-5-CF$_3$) | O | O |
| H | H | 2-OCH$_2$CH$_3$ | 2,4-F$_2$-3,5-Cl$_2$ | O | O |
| H | H | 2-OCH$_2$CF$_3$ | 4-Cl | O | O |
| H | H | 2-OCH$_2$CF$_3$ | 4-OCF$_3$ | O | O |
| H | H | 2-OCH$_2$CF$_3$ | 4-S(C$_6$H$_3$-2-Cl-4-CF$_3$) | O | O |
| H | H | 2-OCH$_2$CF$_3$ | 4-CH$_2$ON=C(Q51)(C$_6$H$_4$-4-Cl) | O | O |
| H | H | 2-OCH$_2$CF$_3$ | 3-O(Q50-6-CF$_3$) | O | O |
| H | H | 2-OCH$_2$CF$_3$ | 2-F-4-OCF$_2$CHF$_2$ | O | O |
| H | H | 2-OCH$_2$CF$_3$ | 3,5-Cl$_2$-4-OCF$_2$CHF$_2$ | O | O |
| H | H | 2-OCH$_2$CF$_3$ | 3,5-Cl$_2$-4-O(C$_6$H$_3$-2-Cl-4-CF$_3$) | O | O |
| H | H | 2-OCH$_2$CF$_3$ | 3,5-Cl$_2$-4-O(Q38-3-Cl-5-CF$_3$) | O | O |
| H | H | 2-OCH$_2$CF$_3$ | 2,4-F$_2$-3,5-Cl$_2$ | O | O |
| H | F | 2-F | 2-F-4-Cl | O | O |
| H | F | 2-F | 4-S(C$_6$H$_3$-2-Cl-4-CF$_3$) | O | O |
| H | F | 2-F | 3,5-Cl$_2$-4-O(Q38-3-Cl-5-CF$_3$) | O | O |
| H | F | 2,6-F$_2$ | 4-Cl | O | O |
| H | F | 2,6-F$_2$ | 4-CH$_2$ON=C(Q51)(C$_6$H$_4$-4-Cl) | O | O |
| H | F | 2,6-F$_2$ | 3-O(Q50-6-CF$_3$) | O | O |
| H | F | 2,6-F$_2$ | 3,5-Cl$_2$-4-OCF$_2$CHF$_2$ | O | O |
| H | F | 2,6-F$_2$ | 3,5-Cl$_2$-4-O(Q38-3-Cl-5-CF$_3$) | O | O |
| H | F | 2,6-F$_2$ | 2,4-F$_2$-3,5-Cl$_2$ | O | O |
| H | F | 2-Cl-6-F | 2-F-4-OCF$_2$CHF$_2$ | O | O |
| H | F | 2-Cl-6-F | 3,5-Cl$_2$-4-O(C$_6$H$_3$-2-Cl-4-CF$_3$) | O | O |
| H | F | 2-Cl | 4-OCF$_3$ | O | O |
| H | F | 2-Cl | 4-CH$_2$ON=C(Q51)(C$_6$H$_4$-4-Cl) | O | O |
| H | F | 2-Cl | 3,5-Cl$_2$-4-OCF$_2$CHF$_2$ | O | O |
| H | F | 2,6-Cl$_2$ | 3,5-Cl$_2$-4-O(Q38-3-Cl-5-CF$_3$) | O | O |
| H | F | 2-Br | 3,5-Cl$_2$-4-OCF$_2$CHF$_2$ | O | O |
| H | F | 2-CH$_3$ | 3,5-Cl$_2$-4-O(Q38-3-Cl-5-CF$_3$) | O | O |
| H | F | 2,6-(OCH$_3$)$_2$ | 2,4-F$_2$-3,5-Cl$_2$ | O | O |
| H | Cl | 2-F | 2-F-4-Cl | O | O |
| H | Cl | 2-F | 4-S(C$_6$H$_3$-2-Cl-4-CF$_3$) | O | O |
| H | Cl | 2-F | 3,5-Cl$_2$-4-O(Q38-3-Cl-5-CF$_3$) | O | O |
| H | Cl | 2,6-F$_2$ | 4-Cl | O | O |
| H | Cl | 2,6-F$_2$ | 4-CH$_2$ON=C(Q51)(C$_6$H$_4$-4-Cl) | O | O |
| H | Cl | 2,6-F$_2$ | 3-O(Q50-6-CF$_3$) | O | O |
| H | Cl | 2,6-F$_2$ | 3,5-Cl$_2$-4-OCF$_2$CHF$_2$ | O | O |
| H | Cl | 2,6-F$_2$ | 3,5-Cl$_2$-4-O(Q38-3-Cl-5-CF$_3$) | O | O |
| H | Cl | 2,6-F$_2$ | 2,4-F$_2$-3,5-Cl$_2$ | O | O |
| H | Cl | 2-Cl-6-F | 2-F-4-OCF$_2$CHF$_2$ | O | O |
| H | Cl | 2-Cl-6-F | 3,5-Cl$_2$-4-O(C$_6$H$_3$-2-Cl-4-CF$_3$) | O | O |
| H | Cl | 2-Cl | 4-OCF$_3$ | O | O |
| H | Cl | 2-Cl | 4-CH$_2$ON=C(Q51)(C$_6$H$_4$-4-Cl) | O | O |
| H | Cl | 2-Cl | 3,5-Cl$_2$-4-OCF$_2$CHF$_2$ | O | O |
| H | Cl | 2,6-Cl$_2$ | 3,5-Cl$_2$-4-O(Q38-3-Cl-5-CF$_3$) | O | O |
| H | Cl | 2-Br | 3,5-Cl$_2$-4-OCF$_2$CHF$_2$ | O | O |
| H | Cl | 2-CH$_3$ | 3,5-Cl$_2$-4-O(Q38-3-Cl-5-CF$_3$) | O | O |
| H | Cl | 2,6-(OCH$_3$)$_2$ | 2,4-F$_2$-3,5-Cl$_2$ | O | O |
| H | Br | 2-F | 2-F-4-Cl | O | O |
| H | Br | 2-F | 4-S(C$_6$H$_3$-2-Cl-4-CF$_3$) | O | O |
| H | Br | 2-F | 3,5-Cl$_2$-4-O(Q38-3-Cl-5-CF$_3$) | O | O |
| H | Br | 2,6-F$_2$ | 4-Cl | O | O |
| H | Br | 2,6-F$_2$ | 4-CH$_2$ON=C(Q51)(C$_6$H$_4$-4-Cl) | O | O |

-continued

| | | | | | |
|---|---|---|---|---|---|
| H | Br | 2,6-F$_2$ | 3-O(Q50-6-CF$_3$) | O | O |
| H | Br | 2,6-F$_2$ | 3,5-Cl$_2$-4-OCF$_2$CHF$_2$ | O | O |
| H | Br | 2,6-F$_2$ | 3,5-Cl$_2$-4-O(Q38-3-Cl-5-CF$_3$) | O | O |
| H | Br | 2,6-F$_2$ | 2,4-F$_2$-3,5-Cl$_2$ | O | O |
| H | Br | 2-Cl-6-F | 2-F-4-OCF$_2$CHF$_2$ | O | O |
| H | Br | 2-Cl-6-F | 3,5-Cl$_2$-4-O(C$_6$H$_3$-2-Cl-4-CF$_3$) | O | O |
| H | Br | 2-Cl | 4-OCF$_3$ | O | O |
| H | Br | 2-Cl | 4-CH$_2$ON=C(Q51)(C$_6$H$_4$-4-Cl) | O | O |
| H | Br | 2-Cl | 3,5-Cl$_2$-4-OCF$_2$CHF$_2$ | O | O |
| H | Br | 2,6-Cl$_2$ | 3,5-Cl$_2$-4-O(Q38-3-Cl-5-CF$_3$) | O | O |
| H | Br | 2-Br | 3,5-Cl$_2$-4-OCF$_2$CHF$_2$ | O | O |
| H | Br | 2-CH$_3$ | 3,5-Cl$_2$-4-O(Q38-3-Cl-5-CF$_3$) | O | O |
| H | Br | 2,6-(OCH$_3$)$_2$ | 2,4-F$_2$-3,5-Cl$_2$ | O | O |
| H | I | 2-F | 2-F-4-Cl | O | O |
| H | I | 2-F | 4-S(C$_6$H$_3$-2-Cl-4-CF$_3$) | O | O |
| H | I | 2-F | 3,5-Cl$_2$-4-O(Q38-3-Cl-5-CF$_3$) | O | O |
| H | I | 2,6-F$_2$ | 4-Cl | O | O |
| H | I | 2,6-F$_2$ | 4-CH$_2$ON=C(Q51)(C$_6$H$_4$-4-Cl) | O | O |
| H | I | 2,6-F$_2$ | 3-O(Q50-6-CF$_3$) | O | O |
| H | I | 2,6-F$_2$ | 3,5-Cl$_2$-4-OCF$_2$CHF$_2$ | O | O |
| H | I | 2,6-F$_2$ | 3,5-Cl$_2$-4-O(Q38-3-Cl-5-CF$_3$) | O | O |
| H | I | 2,6-F$_2$ | 2,4-F$_2$-3,5-Cl$_2$ | O | O |
| H | I | 2-Cl-6-F | 2-F-4-OCF$_2$CHF$_2$ | O | O |
| H | I | 2-Cl-6-F | 3,5-Cl$_2$-4-O(C$_6$H$_3$-2-Cl-4-CF$_3$) | O | O |
| H | I | 2-Cl | 4-OCF$_3$ | O | O |
| H | I | 2-Cl | 4-CH$_2$ON=C(Q51)(C$_6$H$_4$-4-Cl) | O | O |
| H | I | 2-Cl | 3,5-Cl$_2$-4-OCF$_2$CHF$_2$ | O | O |
| H | I | 2,6-Cl$_2$ | 3,5-Cl$_2$-4-O(Q38-3-Cl-5-CF$_3$) | O | O |
| H | I | 2-Br | 3,5-Cl$_2$-4-OCF$_2$CHF$_2$ | O | O |
| H | I | 2-CH$_3$ | 3,5-Cl$_2$-4-O(Q38-3-Cl-5-CF$_3$) | O | O |
| H | I | 2,6-(OCH$_3$)$_2$ | 2,4-F$_2$-3,5-Cl$_2$ | O | O |
| H | CH$_3$ | 2-F | 2-F-4-Cl | O | O |
| H | CH$_3$ | 2-F | 4-S(C$_6$H$_3$-2-Cl-4-CF$_3$) | O | O |
| H | CH$_3$ | 2-F | 3,5-Cl$_2$-4-O(Q38-3-Cl-5-CF$_3$) | O | O |
| H | CH$_3$ | 2,6-F$_2$ | 4-Cl | O | O |
| H | CH$_3$ | 2,6-F$_2$ | 4-CH$_2$ON=C(Q51)(C$_6$H$_4$-4-Cl) | O | O |
| H | CH$_3$ | 2,6-F$_2$ | 3-O(Q50-6-CF$_3$) | O | O |
| H | CH$_3$ | 2,6-F$_2$ | 3,5-Cl$_2$-4-OCF$_2$CHF$_2$ | O | O |
| H | CH$_3$ | 2,6-F$_2$ | 3,5-Cl$_2$-4-O(Q38-3-Cl-5-CF$_3$) | O | O |
| H | CH$_3$ | 2,6-F$_2$ | 2,4-F$_2$-3,5-Cl$_2$ | O | O |
| H | CH$_3$ | 2-Cl-6-F | 2-F-4-OCF$_2$CHF$_2$ | O | O |
| H | CH$_3$ | 2-Cl-6-F | 3,5-Cl$_2$-4-O(C$_6$H$_3$-2-Cl-4-CF$_3$) | O | O |
| H | CH$_3$ | 2-Cl | 4-OCF$_3$ | O | O |
| H | CH$_3$ | 2-Cl | 4-CH$_2$ON=C(Q51)(C$_6$H$_4$-4-Cl) | O | O |
| H | CH$_3$ | 2-Cl | 3,5-Cl$_2$-4-OCF$_2$CHF$_2$ | O | O |
| H | CH$_3$ | 2,6-Cl$_2$ | 3,5-Cl$_2$-4-O(Q38-3-Cl-5-CF$_3$) | O | O |
| H | CH$_3$ | 2-Br | 3,5-Cl$_2$-4-OCF$_2$CHF$_2$ | O | O |
| H | CH$_3$ | 2-CH$_3$ | 3,5-Cl$_2$-4-O(Q38-3-Cl-5-CF$_3$) | O | O |
| H | CH$_3$ | 2,6-(OCH$_3$)$_2$ | 2,4-F$_2$-3,5-Cl$_2$ | O | O |
| H | CH$_2$CH$_3$ | 2-F | 2-F-4-Cl | O | O |
| H | CH$_2$CH$_3$ | 2-F | 4-S(C$_6$H$_3$-2-Cl-4-CF$_3$) | O | O |
| H | CH$_2$CH$_3$ | 2-F | 3,5-Cl$_2$-4-O(Q38-3-Cl-5-CF$_3$) | O | O |
| H | CH$_2$CH$_3$ | 2,6-F$_2$ | 4-Cl | O | O |
| H | CH$_2$CH$_3$ | 2,6-F$_2$ | 4-CH$_2$ON=C(Q51)(C$_6$H$_4$-4-Cl) | O | O |
| H | CH$_2$CH$_3$ | 2,6-F$_2$ | 3-O(Q50-6-CF$_3$) | O | O |
| H | CH$_2$CH$_3$ | 2,6-F$_2$ | 3,5-Cl$_2$-4-OCF$_2$CHF$_2$ | O | O |
| H | CH$_2$CH$_3$ | 2,6-F$_2$ | 3,5-Cl$_2$-4-O(Q38-3-Cl-5-CF$_3$) | O | O |
| H | CH$_2$CH$_3$ | 2,6-F$_2$ | 2,4-F$_2$-3,5-Cl$_2$ | O | O |
| H | CH$_2$CH$_3$ | 2-Cl-6-F | 2-F-4-OCF$_2$CHF$_2$ | O | O |
| H | CH$_2$CH$_3$ | 2-Cl-6-F | 3,5-Cl$_2$-4-O(C$_6$H$_3$-2-Cl-4-CF$_3$) | O | O |
| H | CH$_2$CH$_3$ | 2-Cl | 4-OCF$_3$ | O | O |
| H | CH$_2$CH$_3$ | 2-Cl | 4-CH$_2$ON=C(Q51)(C$_6$H$_4$-4-Cl) | O | O |
| H | CH$_2$CH$_3$ | 2-Cl | 3,5-Cl$_2$-4-OCF$_2$CHF$_2$ | O | O |
| H | CH$_2$CH$_3$ | 2,6-Cl$_2$ | 3,5-Cl$_2$-4-O(Q38-3-Cl-5-CF$_3$) | O | O |
| H | CH$_2$CH$_3$ | 2-Br | 3,5-Cl$_2$-4-OCF$_2$CHF$_2$ | O | O |
| H | CH$_2$CH$_3$ | 2-CH$_3$ | 3,5-Cl$_2$-4-O(Q38-3-Cl-5-CF$_3$) | O | O |
| H | CH$_2$CH$_3$ | 2,6-(OCH$_3$)$_2$ | 2,4-F$_2$-3,5-Cl$_2$ | O | O |
| H | CH(CH$_3$)$_2$ | 2-F | 2-F-4-Cl | O | O |
| H | CH(CH$_3$)$_2$ | 2-F | 4-S(C$_6$H$_3$-2-Cl-4-CF$_3$) | O | O |
| H | CH(CH$_3$)$_2$ | 2-F | 3,5-Cl$_2$-4-O(Q38-3-Cl-5-CF$_3$) | O | O |
| H | CH(CH$_3$)$_2$ | 2,6-F$_2$ | 4-Cl | O | O |
| H | CH(CH$_3$)$_2$ | 2,6-F$_2$ | 4-CH$_2$ON=C(Q51)(C$_6$H$_4$-4-Cl) | O | O |
| H | CH(CH$_3$)$_2$ | 2,6-F$_2$ | 3-O(Q50-6-CF$_3$) | O | O |
| H | CH(CH$_3$)$_2$ | 2,6-F$_2$ | 3,5-Cl$_2$-4-OCF$_2$CHF$_2$ | O | O |
| H | CH(CH$_3$)$_2$ | 2,6-F$_2$ | 3,5-Cl$_2$-4-O(Q38-3-Cl-5-CF$_3$) | O | O |
| H | CH(CH$_3$)$_2$ | 2,6-F$_2$ | 2,4-F$_2$-3,5-Cl$_2$ | O | O |
| H | CH(CH$_3$)$_2$ | 2-Cl-6-F | 2-F-4-OCF$_2$CHF$_2$ | O | O |
| H | CH(CH$_3$)$_2$ | 2-Cl-6-F | 3,5-Cl$_2$-4-O(C$_6$H$_3$-2-Cl-4-CF$_3$) | O | O |
| H | CH(CH$_3$)$_2$ | 2-Cl | 4-OCF$_3$ | O | O |
| H | CH(CH$_3$)$_2$ | 2-Cl | 4-CH$_2$ON=C(Q51)(C$_6$H$_4$-4-Cl) | O | O |
| H | CH(CH$_3$)$_2$ | 2-Cl | 3,5-Cl$_2$-4-OCF$_2$CHF$_2$ | O | O |
| H | CH(CH$_3$)$_2$ | 2,6-Cl$_2$ | 3,5-Cl$_2$-4-O(Q38-3-Cl-5-CF$_3$) | O | O |
| H | CH(CH$_3$)$_2$ | 2-Br | 3,5-Cl$_2$-4-OCF$_2$CHF$_2$ | O | O |

-continued

| | | | | | |
|---|---|---|---|---|---|
| H | CH(CH₃)₂ | 2-CH₃ | 3,5-Cl₂-4-O(Q38-3-Cl-5-CF₃) | O | O |
| H | CH(CH₃)₂ | 2,6-(OCH₃)₂ | 2,4-F₂-3,5-Cl₂ | O | O |
| H | CH₂CH₂CH₂CH₃ | 2-F | 2-F-4-Cl | O | O |
| H | CH₂CH₂CH₂CH₃ | 2-F | 4-S(C₆H₃-2-Cl-4-CF₃) | O | O |
| H | CH₂CH₂CH₂CH₃ | 2-F | 3,5-Cl₂-4-O(Q38-3-Cl-5-CF₃) | O | O |
| H | CH₂CH₂CH₂CH₃ | 2,6-F₂ | 4-Cl | O | O |
| H | CH₂CH₂CH₂CH₃ | 2,6-F₂ | 4-CH₂ON=C(Q51)(C₆H₄-4-Cl) | O | O |
| H | CH₂CH₂CH₂CH₃ | 2,6-F₂ | 3-O(Q50-6-CF₃) | O | O |
| H | CH₂CH₂CH₂CH₃ | 2,6-F₂ | 3,5-Cl₂-4-OCF₂CHF₂ | O | O |
| H | CH₂CH₂CH₂CH₃ | 2,6-F₂ | 3,5-Cl₂-4-O(Q38-3-Cl-5-CF₃) | O | O |
| H | CH₂CH₂CH₂CH₃ | 2,6-F₂ | 2,4-F₂-3,5-Cl₂ | O | O |
| H | CH₂CH₂CH₂CH₃ | 2-Cl-6-F | 2-F-4-OCF₂CHF₂ | O | O |
| H | CH₂CH₂CH₂CH₃ | 2-Cl-6-F | 3,5-Cl₂-4-O(C₆H₃-2-Cl-4-CF₃) | O | O |
| H | CH₂CH₂CH₂CH₃ | 2-Cl | 4-OCF₃ | O | O |
| H | CH₂CH₂CH₂CH₃ | 2-Cl | 4-CH₂ON=C(Q51)(C₆H₄-4-Cl) | O | O |
| H | CH₂CH₂CH₂CH₃ | 2-Cl | 3,5-Cl₂-4-OCF₂CHF₂ | O | O |
| H | CH₂CH₂CH₂CH₃ | 2,6-Cl₂ | 3,5-Cl₂-4-O(Q38-3-Cl-5-CF₃) | O | O |
| H | CH₂CH₂CH₂CH₃ | 2-Br | 3,5-Cl₂-4-OCF₂CHF₂ | O | O |
| H | CH₂CH₂CH₂CH₃ | 2-CH₃ | 3,5-Cl₂-4-O(Q38-3-Cl-5-CF₃) | O | O |
| H | CH₂CH₂CH₂CH₃ | 2,6-(OCH₃)₂ | 2,4-F₂-3,5-Cl₂ | O | O |
| H | C(CH₃)₃ | 2-F | 2-F-4-Cl | O | O |
| H | C(CH₃)₃ | 2-F | 4-S(C₆H₃-2-Cl-4-CF₃) | O | O |
| H | C(CH₃)₃ | 2-F | 3,5-Cl₂-4-O(Q38-3-Cl-5-CF₃) | O | O |
| H | C(CH₃)₃ | 2,6-F₂ | 4-Cl | O | O |
| H | C(CH₃)₃ | 2,6-F₂ | 4-CH₂ON=C(Q51)(C₆H₄-4-Cl) | O | O |
| H | C(CH₃)₃ | 2,6-F₂ | 3-O(Q50-6-CF₃) | O | O |
| H | C(CH₃)₃ | 2,6-F₂ | 3,5-Cl₂-4-OCF₂CHF₂ | O | O |
| H | C(CH₃)₃ | 2,6-F₂ | 3,5-Cl₂-4-O(Q38-3-Cl-5-CF₃) | O | O |
| H | C(CH₃)₃ | 2,6-F₂ | 2,4-F₂-3,5-Cl₂ | O | O |
| H | C(CH₃)₃ | 2-Cl-6-F | 2-F-4-OCF₂CHF₂ | O | O |
| H | C(CH₃)₃ | 2-Cl-6-F | 3,5-Cl₂-4-O(C₆H₃-2-Cl-4-CF₃) | O | O |
| H | C(CH₃)₃ | 2-Cl | 4-OCF₃ | O | O |
| H | C(CH₃)₃ | 2-Cl | 4-CH₂ON=C(Q51)(C₆H₄-4-Cl) | O | O |
| H | C(CH₃)₃ | 2-Cl | 3,5-Cl₂-4-OCF₂CHF₂ | O | O |
| H | C(CH₃)₃ | 2,6-Cl₂ | 3,5-Cl₂-4-O(Q38-3-Cl-5-CF₃) | O | O |
| H | C(CH₃)₃ | 2-Br | 3,5-Cl₂-4-OCF₂CHF₂ | O | O |
| H | C(CH₃)₃ | 2-CH₃ | 3,5-Cl₂-4-O(Q38-3-Cl-5-CF₃) | O | O |
| H | C(CH₃)₃ | 2,6-(OCH₃)₂ | 2,4-F₂-3,5-Cl₂ | O | O |
| H | CF₃ | 2-F | 2-F-4-Cl | O | O |
| H | CF₃ | 2-F | 4-S(C₆H₃-2-Cl-4-CF₃) | O | O |
| H | CF₃ | 2-F | 3,5-Cl₂-4-O(Q38-3-Cl-5-CF₃) | O | O |
| H | CF₃ | 2,6-F₂ | 4-Cl | O | O |
| H | CF₃ | 2,6-F₂ | 4-CH₂ON=C(Q51)(C₆H₄-4-Cl) | O | O |
| H | CF₃ | 2,6-F₂ | 3-O(Q50-6-CF₃) | O | O |
| H | CF₃ | 2,6-F₂ | 3,5-Cl₂-4-OCF₂CHF₂ | O | O |
| H | CF₃ | 2,6-F₂ | 3,5-Cl₂-4-O(Q38-3-Cl-5-CF₃) | O | O |
| H | CF₃ | 2,6-F₂ | 2,4-F₂-3,5-Cl₂ | O | O |
| H | CF₃ | 2-Cl-6-F | 2-F-4-OCF₂CHF₂ | O | O |
| H | CF₃ | 2-Cl-6-F | 3,5-Cl₂-4-O(C₆H₃-2-Cl-4-CF₃) | O | O |
| H | CF₃ | 2-Cl | 4-OCF₃ | O | O |
| H | CF₃ | 2-Cl | 4-CH₂ON=C(Q51)(C₆H₄-4-Cl) | O | O |
| H | CF₃ | 2-Cl | 3,5-Cl₂-4-OCF₂CHF₂ | O | O |
| H | CF₃ | 2,6-Cl₂ | 3,5-Cl₂-4-O(Q38-3-Cl-5-CF₃) | O | O |
| H | CF₃ | 2-Br | 3,5-Cl₂-4-OCF₂CHF₂ | O | O |
| H | CF₃ | 2-CH₃ | 3,5-Cl₂-4-O(Q38-3-Cl-5-CF₃) | O | O |
| H | CF₃ | 2,6-(OCH₃)₂ | 2,4-F₂-3,5-Cl₂ | O | O |
| H | CH₂Cl | 2-F | 2-F-4-Cl | O | O |
| H | CH₂Cl | 2-F | 4-S(C₆H₃-2-Cl-4-CF₃) | O | O |
| H | CH₂Cl | 2-F | 3,5-Cl₂-4-O(Q38-3-Cl-5-CF₃) | O | O |
| H | CH₂Cl | 2,6-F₂ | 4-Cl | O | O |
| H | CH₂Cl | 2,6-F₂ | 4-CH₂ON=C(Q51)(C₆H₄-4-Cl) | O | O |
| H | CH₂Cl | 2,6-F₂ | 3-O(Q50-6-CF₃) | O | O |
| H | CH₂Cl | 2,6-F₂ | 3,5-Cl₂-4-OCF₂CHF₂ | O | O |
| H | CH₂Cl | 2,6-F₂ | 3,5-Cl₂-4-O(Q38-3-Cl-5-CF₃) | O | O |
| H | CH₂Cl | 2,6-F₂ | 2,4-F₂-3,5-Cl₂ | O | O |
| H | CH₂Cl | 2-Cl-6-F | 2-F-4-OCF₂CHF₂ | O | O |
| H | CH₂Cl | 2-Cl-6-F | 3,5-Cl₂-4-O(C₆H₃-2-Cl-4-CF₃) | O | O |
| H | CH₂Cl | 2-Cl | 4-OCF₃ | O | O |
| H | CH₂Cl | 2-Cl | 4-CH₂ON=C(Q51)(C₆H₄-4-Cl) | O | O |
| H | CH₂Cl | 2-Cl | 3,5-Cl₂-4-OCF₂CHF₂ | O | O |
| H | CH₂Cl | 2,6-Cl₂ | 3,5-Cl₂-4-O(Q38-3-Cl-5-CF₃) | O | O |
| H | CH₂Cl | 2-Br | 3,5-Cl₂-4-OCF₂CHF₂ | O | O |
| H | CH₂Cl | 2-CH₃ | 3,5-Cl₂-4-O(Q38-3-Cl-5-CF₃) | O | O |
| H | CH₂Cl | 2,6-(OCH₃)₂ | 2,4-F₂-3,5-Cl₂ | O | O |
| H | CH₂Br | 2-F | 2-F-4-Cl | O | O |
| H | CH₂Br | 2-F | 4-S(C₆H₃-2-Cl-4-CF₃) | O | O |
| H | CH₂Br | 2-F | 3,5-Cl₂-4-O(Q38-3-Cl-5-CF₃) | O | O |
| H | CH₂Br | 2,6-F₂ | 4-Cl | O | O |
| H | CH₂Br | 2,6-F₂ | 4-CH₂ON=C(Q51)(C₆H₄-4-Cl) | O | O |
| H | CH₂Br | 2,6-F₂ | 3-O(Q50-6-CF₃) | O | O |
| H | CH₂Br | 2,6-F₂ | 3,5-Cl₂-4-OCF₂CHF₂ | O | O |
| H | CH₂Br | 2,6-F₂ | 3,5-Cl₂-4-O(Q38-3-Cl-5-CF₃) | O | O |
| H | CH₂Br | 2,6-F₂ | 2,4-F₂-3,5-Cl₂ | O | O |

-continued

| | | | | | |
|---|---|---|---|---|---|
| H | CH$_2$Br | 2-Cl-6-F | 2-F-4-OCF$_2$CHF$_2$ | O | O |
| H | CH$_2$Br | 2-Cl-6-F | 3,5-Cl$_2$-4-O(C$_6$H$_3$-2-Cl-4-CF$_3$) | O | O |
| H | CH$_2$Br | 2-Cl | 4-OCF$_3$ | O | O |
| H | CH$_2$Br | 2-Cl | 4-CH$_2$ON=C(Q51)(C$_6$H$_4$-4-Cl) | O | O |
| H | CH$_2$Br | 2-Cl | 3,5-Cl$_2$-4-OCF$_2$CHF$_2$ | O | O |
| H | CH$_2$Br | 2,6-Cl$_2$ | 3,5-Cl$_2$-4-O(Q38-3-Cl-5-CF$_3$) | O | O |
| H | CH$_2$Br | 2-Br | 3,5-Cl$_2$-4-OCF$_2$CHF$_2$ | O | O |
| H | CH$_2$Br | 2-CH$_3$ | 3,5-Cl$_2$-4-O(Q38-3-Cl-5-CF$_3$) | O | O |
| H | CH$_2$Br | 2,6-(OCH$_3$)$_2$ | 2,4-F$_2$-3,5-Cl$_2$ | O | O |
| H | CH$_2$OH | 2-F | 2-F-4-Cl | O | O |
| H | CH$_2$OH | 2-F | 4-S(C$_6$H$_3$-2-Cl-4-CF$_3$) | O | O |
| H | CH$_2$OH | 2-F | 3,5-Cl$_2$-4-O(Q38-3-Cl-5-CF$_3$) | O | O |
| H | CH$_2$OH | 2,6-F$_2$ | 4-Cl | O | O |
| H | CH$_2$OH | 2,6-F$_2$ | 4-CH$_2$ON=C(Q51)(C$_6$H$_4$-4-Cl) | O | O |
| H | CH$_2$OH | 2,6-F$_2$ | 3-O(Q50-6-CF$_3$) | O | O |
| H | CH$_2$OH | 2,6-F$_2$ | 3,5-Cl$_2$-4-OCF$_2$CHF$_2$ | O | O |
| H | CH$_2$OH | 2,6-F$_2$ | 3,5-Cl$_2$-4-O(Q38-3-Cl-5-CF$_3$) | O | O |
| H | CH$_2$OH | 2,6-F$_2$ | 2,4-F$_2$-3,5-Cl$_2$ | O | O |
| H | CH$_2$OH | 2-Cl-6-F | 2-F-4-OCF$_2$CHF$_2$ | O | O |
| H | CH$_2$OH | 2-Cl-6-F | 3,5-Cl$_2$-4-O(C$_6$H$_3$-2-Cl-4-CF$_3$) | O | O |
| H | CH$_2$OH | 2-Cl | 4-OCF$_3$ | O | O |
| H | CH$_2$OH | 2-Cl | 4-CH$_2$ON=C(Q51)(C$_6$H$_4$-4-Cl) | O | O |
| H | CH$_2$OH | 2-Cl | 3,5-Cl$_2$-4-OCF$_2$CHF$_2$ | O | O |
| H | CH$_2$OH | 2,6-Cl$_2$ | 3,5-Cl$_2$-4-O(Q38-3-Cl-5-CF$_3$) | O | O |
| H | CH$_2$OH | 2-Br | 3,5-Cl$_2$-4-OCF$_2$CHF$_2$ | O | O |
| H | CH$_2$OH | 2-CH$_3$ | 3,5-Cl$_2$-4-O(Q38-3-Cl-5-CF$_3$) | O | O |
| H | CH$_2$OH | 2,6-(OCH$_3$)$_2$ | 2,4-F$_2$-3,5-Cl$_2$ | O | O |
| H | CH$_2$OCH$_3$ | 2-F | 2-F-4-Cl | O | O |
| H | CH$_2$OCH$_3$ | 2-F | 4-S(C$_6$H$_3$-2-Cl-4-CF$_3$) | O | O |
| H | CH$_2$OCH$_3$ | 2-F | 3,5-Cl$_2$-4-O(Q38-3-Cl-5-CF$_3$) | O | O |
| H | CH$_2$OCH$_3$ | 2,6-F$_2$ | 4-Cl | O | O |
| H | CH$_2$OCH$_3$ | 2,6-F$_2$ | 4-CH$_2$ON=C(Q51)(C$_6$H$_4$-4-Cl) | O | O |
| H | CH$_2$OCH$_3$ | 2,6-F$_2$ | 3-O(Q50-6-CF$_3$) | O | O |
| H | CH$_2$OCH$_3$ | 2,6-F$_2$ | 3,5-Cl$_2$-4-OCF$_2$CHF$_2$ | O | O |
| H | CH$_2$OCH$_3$ | 2,6-F$_2$ | 3,5-Cl$_2$-4-O(Q38-3-Cl-5-CF$_3$) | O | O |
| H | CH$_2$OCH$_3$ | 2,6-F$_2$ | 2,4-F$_2$-3,5-Cl$_2$ | O | O |
| H | CH$_2$OCH$_3$ | 2-Cl-6-F | 2-F-4-OCF$_2$CHF$_2$ | O | O |
| H | CH$_2$OCH$_3$ | 2-Cl-6-F | 3,5-Cl$_2$-4-O(C$_6$H$_3$-2-Cl-4-CF$_3$) | O | O |
| H | CH$_2$OCH$_3$ | 2-Cl | 4-OCF$_3$ | O | O |
| H | CH$_2$OCH$_3$ | 2-Cl | 4-CH$_2$ON=C(Q51)(C$_6$H$_4$-4-Cl) | O | O |
| H | CH$_2$OCH$_3$ | 2-Cl | 3,5-Cl$_2$-4-OCF$_2$CHF$_2$ | O | O |
| H | CH$_2$OCH$_3$ | 2,6-Cl$_2$ | 3,5-Cl$_2$-4-O(Q38-3-Cl-5-CF$_3$) | O | O |
| H | CH$_2$OCH$_3$ | 2-Br | 3,5-Cl$_2$-4-OCF$_2$CHF$_2$ | O | O |
| H | CH$_2$OCH$_3$ | 2-CH$_3$ | 3,5-Cl$_2$-4-O(Q38-3-Cl-5-CF$_3$) | O | O |
| H | CH$_2$OCH$_3$ | 2,6-(OCH$_3$)$_2$ | 2,4-F$_2$-3,5-Cl$_2$ | O | O |
| H | CH$_2$OCH(CH$_3$)$_2$ | 2-F | 2-F-4-Cl | O | O |
| H | CH$_2$OCH(CH$_3$)$_2$ | 2-F | 4-S(C$_6$H$_3$-2-Cl-4-CF$_3$) | O | O |
| H | CH$_2$OCH(CH$_3$)$_2$ | 2-F | 3,5-Cl$_2$-4-O(Q38-3-Cl-5-CF$_3$) | O | O |
| H | CH$_2$OCH(CH$_3$)$_2$ | 2,6-F$_2$ | 4-Cl | O | O |
| H | CH$_2$OCH(CH$_3$)$_2$ | 2,6-F$_2$ | 4-CH$_2$ON=C(Q51)(C$_6$H$_4$-4-Cl) | O | O |
| H | CH$_2$OCH(CH$_3$)$_2$ | 2,6-F$_2$ | 3-O(Q50-6-CF$_3$) | O | O |
| H | CH$_2$OCH(CH$_3$)$_2$ | 2,6-F$_2$ | 3,5-Cl$_2$-4-OCF$_2$CHF$_2$ | O | O |
| H | CH$_2$OCH(CH$_3$)$_2$ | 2,6-F$_2$ | 3,5-Cl$_2$-4-O(Q38-3-Cl-5-CF$_3$) | O | O |
| H | CH$_2$OCH(CH$_3$)$_2$ | 2,6-F$_2$ | 2,4-F$_2$-3,5-Cl$_2$ | O | O |
| H | CH$_2$OCH(CH$_3$)$_2$ | 2-Cl-6-F | 2-F-4-OCF$_2$CHF$_2$ | O | O |
| H | CH$_2$OCH(CH$_3$)$_2$ | 2-Cl-6-F | 3,5-Cl$_2$-4-O(C$_6$H$_3$-2-Cl-4-CF$_3$) | O | O |
| H | CH$_2$OCH(CH$_3$)$_2$ | 2-Cl | 4-OCF$_3$ | O | O |
| H | CH$_2$OCH(CH$_3$)$_2$ | 2-Cl | 4-CH$_2$ON=C(Q51)(C$_6$H$_4$-4-Cl) | O | O |
| H | CH$_2$OCH(CH$_3$)$_2$ | 2-Cl | 3,5-Cl$_2$-4-OCF$_2$CHF$_2$ | O | O |
| H | CH$_2$OCH(CH$_3$)$_2$ | 2,6-Cl$_2$ | 3,5-Cl$_2$-4-O(Q38-3-Cl-5-CF$_3$) | O | O |
| H | CH$_2$OCH(CH$_3$)$_2$ | 2-Br | 3,5-Cl$_2$-4-OCF$_2$CHF$_2$ | O | O |
| H | CH$_2$OCH(CH$_3$)$_2$ | 2-CH$_3$ | 3,5-Cl$_2$-4-O(Q38-3-Cl-5-CF$_3$) | O | O |
| H | CH$_2$OCH(CH$_3$)$_2$ | 2,6-(OCH$_3$)$_2$ | 2,4-F$_2$-3,5-Cl$_2$ | O | O |
| H | CH$_2$SCH$_3$ | 2-F | 2-F-4-Cl | O | O |
| H | CH$_2$SCH$_3$ | 2-F | 4-S(C$_6$H$_3$-2-Cl-4-CF$_3$) | O | O |
| H | CH$_2$SCH$_3$ | 2-F | 3,5-Cl$_2$-4-O(Q38-3-Cl-5-CF$_3$) | O | O |
| H | CH$_2$SCH$_3$ | 2,6-F$_2$ | 4-Cl | O | O |
| H | CH$_2$SCH$_3$ | 2,6-F$_2$ | 4-CH$_2$ON=C(Q51)(C$_6$H$_4$-4-Cl) | O | O |
| H | CH$_2$SCH$_2$ | 2,6-F$_2$ | 3-O(Q50-6-CF$_3$) | O | O |
| H | CH$_2$SCH$_2$ | 2,6-F$_2$ | 3,5-Cl$_2$-4-OCF$_2$CHF$_2$ | O | O |
| H | CH$_2$SCH$_2$ | 2,6-F$_2$ | 3,5-Cl$_2$-4-O(Q38-3-Cl-5-CF$_3$) | O | O |
| H | CH$_2$SCH$_2$ | 2,6-F$_2$ | 2,4-F$_2$-3,5-Cl$_2$ | O | O |
| H | CH$_2$SCH$_3$ | 2-Cl-6-F | 2-F-4-OCF$_2$CHF$_2$ | O | O |
| H | CH$_2$SCH$_3$ | 2-Cl-6-F | 3,5-Cl$_2$-4-O(C$_6$H$_3$-2-Cl-4-CF$_3$) | O | O |
| H | CH$_2$SCH$_3$ | 2-Cl | 4-OCF$_3$ | O | O |
| H | CH$_2$SCH$_3$ | 2-Cl | 4-CH$_2$ON=C(Q51)(C$_6$H$_4$-4-Cl) | O | O |
| H | CH$_2$SCH$_3$ | 2-Cl | 3,5-Cl$_2$-4-OCF$_2$CHF$_2$ | O | O |
| H | CH$_2$SCH$_3$ | 2,6-Cl$_2$ | 3,5-Cl$_2$-4-O(Q38-3-Cl-5-CF$_3$) | O | O |
| H | CH$_2$SCH$_3$ | 2-Br | 3,5-Cl$_2$-4-OCF$_2$CHF$_2$ | O | O |
| H | CH$_2$SCH$_3$ | 2-CH$_3$ | 3,5-Cl$_2$-4-O(Q38-3-Cl-5-CF$_3$) | O | O |

-continued

| | | | | | |
|---|---|---|---|---|---|
| H | CH₂SCH₃ | 2,6-(OCH₃)₂ | 2,4-F₂-3,5-Cl₂ | O | O |
| H | CN | 2-F | 2-F-4-Cl | O | O |
| H | CN | 2-F | 4-S(C₆H₃-2-Cl-4-CF₃) | O | O |
| H | CN | 2-F | 3,5-Cl₂-4-O(Q38-3-Cl-5-CF₃) | O | O |
| H | CN | 2,6-F₂ | 4-Cl | O | O |
| H | CN | 2,6-F₂ | 4-CH₂ON=C(Q51)(C₆H₄-4-Cl) | O | O |
| H | CN | 2,6-F₂ | 3-O(Q50-6-CF₃) | O | O |
| H | CN | 2,6-F₂ | 3,5-Cl₂-4-OCF₂CHF₂ | O | O |
| H | CN | 2,6-F₂ | 3,5-Cl₂-4-O(Q38-3-Cl-5-CF₃) | O | O |
| H | CN | 2,6-F₂ | 2,4-F₂-3,5-Cl₂ | O | O |
| H | CN | 2-Cl-6-F | 2-F-4-OCF₂CHF₂ | O | O |
| H | CN | 2-Cl-6-F | 3,5-Cl₂-4-O(C₆H₃-2-Cl-4-CF₃) | O | O |
| H | CN | 2-Cl | 4-OCF₃ | O | O |
| H | CN | 2-Cl | 4-CH₂ON=C(Q51)(C₆H₄-4-Cl) | O | O |
| H | CN | 2-Cl | 3,5-Cl₂-4-OCF₂CHF₂ | O | O |
| H | CN | 2,6-Cl₂ | 3,5-Cl₂-4-O(Q38-3-Cl-5-CF₃) | O | O |
| H | CN | 2-Br | 3,5-Cl₂-4-OCF₂CHF₂ | O | O |
| H | CN | 2-CH₃ | 3,5-Cl₂-4-O(Q38-3-Cl-5-CF₃) | O | O |
| H | CN | 2,6-(OCH₃)₂ | 2,4-F₂-3,5-Cl₂ | O | O |
| H | NO₂ | 2-F | 2-F-4-Cl | O | O |
| H | NO₂ | 2-F | 4-S(C₆H₃-2-Cl-4-CF₃) | O | O |
| H | NO₂ | 2-F | 3,5-Cl₂-4-O(Q38-3-Cl-5-CF₃) | O | O |
| H | NO₂ | 2,6-F₂ | 4-Cl | O | O |
| H | NO₂ | 2,6-F₂ | 4-CH₂ON=C(Q51)(C₆H₄-4-Cl) | O | O |
| H | NO₂ | 2,6-F₂ | 3-O(Q50-6-CF₃) | O | O |
| H | NO₂ | 2,6-F₂ | 3,5-Cl₂-4-OCF₂CHF₂ | O | O |
| H | NO₂ | 2,6-F₂ | 3,5-Cl₂-4-O(Q38-3-Cl-5-CF₃) | O | O |
| H | NO₂ | 2,6-F₂ | 2,4-F₂-3,5-Cl₂ | O | O |
| H | NO₂ | 2-Cl-6-F | 2-F-4-OCF₂CHF₂ | O | O |
| H | NO₂ | 2-Cl-6-F | 3,5-Cl₂-4-O(C₆H₃-2-Cl-4-CF₃) | O | O |
| H | NO₂ | 2-Cl | 4-OCF₃ | O | O |
| H | NO₂ | 2-Cl | 4-CH₂ON=C(Q51)(C₆H₄-4-Cl) | O | O |
| H | NO₂ | 2-Cl | 3,5-Cl₂-4-OCF₂CHF₂ | O | O |
| H | NO₂ | 2,6-Cl₂ | 3,5-Cl₂-4-O(Q38)-3-Cl-5-CF₃) | O | O |
| H | NO₂ | 2-Br | 3,5-Cl₂-4-OCF₂CHF₂ | O | O |
| H | NO₂ | 2-CH₃ | 3,5-Cl₂-4-O(Q38-3-Cl-5-CF₃) | O | O |
| H | NO₂ | 2,6-(OCH₃)₂ | 2,4-F₂3,5-Cl₂ | O | O |
| H | SCN | 2-F | 2-F-4-Cl | O | O |
| H | SCN | 2-F | 4-S(C₆H₃-2-Cl-4-CF₃) | O | O |
| H | SCN | 2-F | 3,5-Cl₂-4-O(Q38-3-Cl-5-CF₃) | O | O |
| H | SCN | 2,6-F₂ | 4-Cl | O | O |
| H | SCN | 2,6-F₂ | 4-CH₂ON=C(Q51)(C₆H₄-4-Cl) | O | O |
| H | SCN | 2,6-F₂ | 3-O(Q50-6-CF₃) | O | O |
| H | SCN | 2,6-F₂ | 3,5-Cl₂-4-OCF₂CHF₂ | O | O |
| H | SCN | 2,6-F₂ | 3,5-Cl₂-4-O(Q38-3-Cl-5-CF₃) | O | O |
| H | SCN | 2,6-F₂ | 2,4-F₂-3,5-Cl₂ | O | O |
| H | SCN | 2-Cl-6-F | 2-F-4-OCF₂CHF₂ | O | O |
| H | SCN | 2-Cl-6-F | 3,5-Cl₂-4-O(C₆H₃-2-Cl-4-CF₃) | O | O |
| H | SCN | 2-Cl | 4-OCF₃ | O | O |
| H | SCN | 2-Cl | 4-CH₂ON=C(Q51)(C₆H₄-4-Cl) | O | O |
| H | SCN | 2-Cl | 3,5-Cl₂-4-OCF₂CHF₂ | O | O |
| H | SCN | 2,6-Cl₂ | 3,5-Cl₂-4-O(Q38-3-Cl-5-CF₃) | O | O |
| H | SCN | 2-Br | 3,5-Cl₂-4-OCF₂CHF₂ | O | O |
| H | SCN | 2-CH₃ | 3,5-Cl₂-4-O(Q38-3-Cl-5-CF₃) | O | O |
| H | SCN | 2,6-(OCH₃)₂ | 2,4-F₂-3,5-Cl₂ | O | O |
| CH₃ | H | 2-F | 2-F-4-Cl | O | O |
| CH₃ | H | 2-F | 4-S(C₆H₃-2-Cl-4-CF₃) | O | O |
| CH₃ | H | 2-F | 3,5-Cl₂-4-O(Q38-3-Cl-5-CF₃) | O | O |
| CH₃ | H | 2,6-F₂ | 4-Cl | O | O |
| CH₃ | H | 2,6-F₂ | 4-CH₂ON=C(Q51)(C₆H₄-4-Cl) | O | O |
| CH₃ | H | 2,6-F₂ | 3-O(Q50-6-CF₃) | O | O |
| CH₃ | H | 2,6-F₂ | 3,5-Cl₂-4-OCF₂CHF₂ | O | O |
| CH₃ | H | 2,6-F₂ | 3,5-Cl₂-4-O(Q38-3-Cl-5-CF₃) | O | O |
| CH₃ | H | 2,6-F₂ | 2,4-F₂3,5-Cl₂ | O | O |
| CH₃ | H | 2-Cl-6-F | 2-F-4-OCF₂CHF₂ | O | O |
| CH₃ | H | 2-Cl-6-F | 3,5-Cl₂-4-O(C₆H₃-2-Cl-4-CF₃) | O | O |
| CH₃ | H | 2-Cl | 4-OCF₃ | O | O |
| CH₃ | H | 2-Cl | 4-CH₂ON=C(Q51)(C₆H₄-4-Cl) | O | O |
| CH₃ | H | 2-Cl | 3,5-Cl₂-4-OCF₂CHF₂ | O | O |
| CH₃ | H | 2,6-Cl₂ | 3,5-Cl₂-4-O(Q38-3-Cl-5-CF₃) | O | O |
| CH₃ | H | 2-Br | 3,5-Cl₂-4-OCF₂CHF₂ | O | O |
| CH₃ | H | 2-CH₃ | 3,5-Cl₂-4-O(Q38-3-Cl-5-CF₃) | O | O |
| CH₃ | H | 2,6-(OCH₃)₂ | 2,4-F₂3,5-Cl₂ | O | O |
| CH₂CH₃ | H | 2-F | 2-F-4-Cl | O | O |
| CH₂CH₃ | H | 2-F | 4-S(C₆H₃-2-Cl-4-CF₃) | O | O |
| CH₂CH₃ | H | 2-F | 3,5-Cl₂-4-O(Q38-3-Cl-5-CF₃) | O | O |
| CH₂CH₃ | H | 2,6-F₂ | 4-Cl | O | O |
| CH₂CH₃ | H | 2,6-F₂ | 4-CH₂ON=C(Q51)(C₆H₄-4-Cl) | O | O |
| CH₂CH₃ | H | 2,6-F₂ | 3-O(Q50-6-CF₃ | O | O |
| CH₂CH₃ | H | 2,6-F₂ | 3,5-Cl₂-4-OCF₂CHF₂ | O | O |
| CH₂CH₃ | H | 2,6-F₂ | 3,5-Cl₂-4-O(Q38-3-Cl-5-CF₃) | O | O |
| CH₂CH₃ | H | 2,6-F₂ | 2,4-F₂-3,5-Cl₂ | O | O |
| CH₂CH₃ | H | 2-Cl-6-F | 2-F-4-OCF₂CHF₂ | O | O |

-continued

| | | | | | | |
|---|---|---|---|---|---|---|
| CH$_2$CH$_3$ | H | 2-Cl-6-F | 3,5-Cl$_2$-4-O(C$_6$H$_3$-2-Cl-4-CF$_3$) | | O | O |
| CH$_2$CH$_3$ | H | 2-Cl | 4-OCF$_3$ | | O | O |
| CH$_2$CH$_3$ | H | 2-Cl | 4-CH$_2$ON=C(Q51)(C$_6$H$_4$-4-Cl) | | O | O |
| CH$_2$CH$_3$ | H | 2-Cl | 3,5-Cl$_2$-4-OCF$_2$CHF$_2$ | | O | O |
| CH$_2$CH$_3$ | H | 2,6-Cl$_2$ | 3,5-Cl$_2$-4-O(Q38-3-Cl-5-CF$_3$) | | O | O |
| CH$_2$CH$_3$ | H | 2-Br | 3,5-Cl$_2$-4-OCF$_2$CHF$_2$ | | O | O |
| CH$_2$CH$_3$ | H | 2-CH$_3$ | 3,5-Cl$_2$-4-O(Q38-3-Cl-5-CF$_3$) | | O | O |
| CH$_2$CH$_3$ | H | 2,6-C(OCH$_3$)$_2$ | 2,4-F$_2$-3,5-Cl$_2$ | | O | O |
| CH(CH$_3$)$_2$ | H | 2-F | 2-F-4-Cl | | O | O |
| CH(CH$_3$)$_2$ | H | 2-F | 4-S(C$_6$H$_3$-2-Cl-4-CF$_3$) | | O | O |
| CH(CH$_3$)$_2$ | H | 2-F | 3,5-Cl$_2$-4-O(Q38-3-Cl-5-CF$_3$) | | O | O |
| CH(CH$_3$)$_2$ | H | 2,6-F$_2$ | 4-Cl | | O | O |
| CH(CH$_3$)$_2$ | H | 2,6-F$_2$ | 4-CH$_2$ON=C(Q51)(C$_6$H$_4$-4-Cl) | | O | O |
| CH(CH$_3$)$_2$ | H | 2,6-F$_2$ | 3-O(Q50-6-CF$_3$) | | O | O |
| CH(CH$_3$)$_2$ | H | 2,6-F$_2$ | 3,5-Cl$_2$-4-OCF$_2$CHF$_2$ | | O | O |
| CH(CH$_3$)$_2$ | H | 2,6-F$_2$ | 3,5-Cl$_2$-4-O(Q38-3-Cl-5-CF$_3$) | | O | O |
| CH(CH$_3$)$_2$ | H | 2,6-F$_2$ | 2,4-F$_2$,3,5-Cl$_2$ | | O | O |
| CH(CH$_3$)$_2$ | H | 2-Cl-6-F | 2-F-4-OCF$_2$CHF$_2$ | | O | O |
| CH(CH$_3$)$_2$ | H | 2-Cl-6-F | 3,5-Cl$_2$-4-O(C$_6$H$_3$-2-Cl-4-CF$_3$) | | O | O |
| CH(CH$_3$)$_2$ | H | 2-Cl | 4-OCF$_3$ | | O | O |
| CH(CH$_3$)$_2$ | H | 2-Cl | 4-CH$_2$ON=C(Q51)(C$_6$H$_4$-4-Cl) | | O | O |
| CH(CH$_3$)$_2$ | H | 2-Cl | 3,5-Cl$_2$-4-OCF$_2$CHF$_2$ | | O | O |
| CH(CH$_3$)$_2$ | H | 2,6-Cl$_2$ | 3,5-Cl$_2$-4-O(Q38-3-Cl-5-CF$_3$) | | O | O |
| CH(CH$_3$)$_2$ | H | 2-Br | 3,5-Cl$_2$-4-OCF$_2$CHF$_2$ | | O | O |
| CH(CH$_3$)$_2$ | H | 2-CH$_3$ | 3,5-Cl$_2$-4-O(Q38-3-Cl-5-CF$_3$) | | O | O |
| CH(CH$_3$)$_2$ | H | 2,6-(OCH$_3$)$_2$ | 2,4-F$_2$-3,5-Cl$_2$ | | O | O |
| CH$_2$CH$_2$CH$_2$CH$_3$ | H | 2-F | 2-F-4-Cl | | O | O |
| CH$_2$CH$_2$CH$_2$CH$_3$ | H | 2-F | 4-S(C$_6$H$_3$-2-Cl-4-CF$_3$) | | O | O |
| CH$_2$CH$_2$CH$_2$CH$_3$ | H | 2-F | 3,5-Cl$_2$-4-O(Q38-3-Cl-5-CF$_3$) | | O | O |
| CH$_2$CH$_2$CH$_2$CH$_3$ | H | 2,6-F$_2$ | 4-Cl | | O | O |
| CH$_2$CH$_2$CH$_2$CH$_3$ | H | 2,6-F$_2$ | 4-CH$_2$ON=C(Q51)(C$_6$H$_4$-4-Cl) | | O | O |
| CH$_2$CH$_2$CH$_2$CH$_3$ | H | 2,6-F$_2$ | 3-O(Q50-6-CF$_3$) | | O | O |
| CH$_2$CH$_2$CH$_2$CH$_3$ | H | 2,6-F$_2$ | 3,5-Cl$_2$-4-OCF$_2$CHF$_2$ | | O | O |
| CH$_2$CH$_2$CH$_2$CH$_3$ | H | 2,6-F$_2$ | 3,5-Cl$_2$-4-O(Q38-3-Cl-5-CF$_3$) | | O | O |
| CH$_2$CH$_2$CH$_2$CH$_3$ | H | 2,6-F$_2$ | 2,4-F$_2$-3,5-Cl$_2$ | | O | O |
| CH$_2$CH$_2$CH$_2$CH$_3$ | H | 2-Cl-6-F | 2-F-4-OCF$_2$CHF$_2$ | | O | O |
| CH$_2$CH$_2$CH$_2$CH$_3$ | H | 2-Cl-6-F | 3,5-Cl$_2$-4-O(C$_6$H$_3$-2-Cl-4-CF$_3$) | | O | O |
| CH$_2$CH$_2$CH$_2$CH$_3$ | H | 2-Cl | 4-OCF$_3$ | | O | O |
| CH$_2$CH$_2$CH$_2$CH$_3$ | H | 2-Cl | 4-CH$_2$ON=C(Q51)(C$_6$H$_4$-4-Cl) | | O | O |
| CH$_2$CH$_2$CH$_2$CH$_3$ | H | 2-Cl | 3,5-Cl$_2$-4-OCF$_2$CHF$_2$ | | O | O |
| CH$_2$CH$_2$CH$_2$CH$_3$ | H | 2,6-Cl$_2$ | 3,5-Cl$_2$-4-O(Q38-3-Cl-5-CF$_3$) | | O | O |
| CH$_2$CH$_2$CH$_2$CH$_3$ | H | 2-Br | 3,5-Cl$_2$-4-OCF$_2$CHF$_2$ | | O | O |
| CH$_2$CH$_2$CH$_2$CH$_3$ | H | 2-CH$_3$ | 3,5-Cl$_2$-4-O(Q38-3-Cl-5-CF$_3$) | | O | O |
| CH$_2$CH$_2$CH$_2$CH$_3$ | H | 2,6-(OCH$_3$)$_2$ | 2,4-F$_2$-3,5-Cl$_2$ | | O | O |
| C(CH$_3$)$_3$ | H | 2-F | 2-F-4-Cl | | O | O |
| C(CH$_3$)$_3$ | H | 2-F | 4-S(C$_6$H$_3$-2-Cl-4-CF$_3$) | | O | O |
| C(CH$_3$)$_3$ | H | 2-F | 3,5-Cl$_2$-4-O(Q38-3-Cl-5-CF$_3$) | | O | O |
| C(CH$_3$)$_3$ | H | 2,6-F$_2$ | 4-Cl | | O | O |
| C(CH$_3$)$_3$ | H | 2,6-F$_2$ | 4-CH$_2$ON=C(Q51)(C$_6$H$_4$-4-Cl) | | O | O |
| C(CH$_3$)$_3$ | H | 2,6-F$_2$ | 3-O(Q50-6-CF$_3$) | | O | O |
| C(CH$_3$)$_3$ | H | 2,6-F$_2$ | 3,5-Cl$_2$-4-OCF$_2$CHF$_2$ | | O | O |
| C(CH$_3$)$_3$ | H | 2,6-F$_2$ | 3,5-Cl$_2$-4-O(Q38-3-Cl-5-CF$_3$) | | O | O |
| C(CH$_3$)$_3$ | H | 2,6-F$_2$ | 2,4-F$_2$-3,5-Cl$_2$ | | O | O |
| C(CH$_3$)$_3$ | H | 2-Cl-6-F | 2-F-4-OCF$_2$CHF$_2$ | | O | O |
| C(CH$_3$)$_3$ | H | 2-Cl-6-F | 3,5-Cl$_2$-4-O(C$_6$H$_3$-2-Cl-4-CF$_3$) | | O | O |
| C(CH$_3$)$_3$ | H | 2-Cl | 4-OCF$_3$ | | O | O |
| C(CH$_3$)$_3$ | H | 2-Cl | 4-CH$_2$ON=C(Q51)(C$_6$H$_4$-4-Cl) | | O | O |
| C(CH$_3$)$_3$ | H | 2-Cl | 3,5-C$_2$-4-OCF$_2$CHF$_2$ | | O | O |
| C(CH$_3$)$_3$ | H | 2,6-Cl$_2$ | 3,5-Cl$_2$-4-O(Q38-3-Cl-5-CF$_3$) | | O | O |
| C(CH$_3$)$_3$ | H | 2-Br | 3,5-Cl$_2$-4-OCF$_2$CHF$_2$ | | O | O |
| C(CH$_3$)$_3$ | H | 2-CH$_3$ | 3,5-Cl$_2$-4-O(Q38-3-Cl-5-CF$_3$) | | O | O |
| C(CH$_3$)$_3$ | H | 2,6-(OCH$_3$)$_2$ | 2,4-F$_2$-3,5-Cl$_2$ | | O | O |
| CH$_2$CH=CH$_2$ | H | 2-F | 2-F-4-Cl | | O | O |
| CH$_2$CH=CH$_2$ | H | 2-F | 4-S(C$_6$H$_3$-2-Cl-4-CF$_3$) | | O | O |
| CH$_2$CH=CH$_2$ | H | 2-F | 3,5-Cl$_2$-4-O(Q38-3-Cl-5-CF$_3$) | | O | O |
| CH$_2$CH=CH$_2$ | H | 2,6-F$_2$ | 4-Cl | | O | O |
| CH$_2$CH=CH$_2$ | H | 2,6-F$_2$ | 4-CH$_2$ON=C(Q51)(C$_6$H$_4$-4-Cl) | | O | O |
| CH$_2$CH=CH$_2$ | H | 2,6-F$_2$ | 3-O(Q50-6-CF$_3$) | | O | O |
| CH$_2$CH=CH$_2$ | H | 2,6-F$_2$ | 3,5-Cl$_2$-4-OCF$_2$CHF$_2$ | | O | O |
| CH$_2$CH=CH$_2$ | H | 2,6-F$_2$ | 3,5-Cl$_2$-4-O(Q38-3-Cl-5-CF$_3$) | | O | O |
| CH$_2$CH=CH$_2$ | H | 2,6-F$_2$ | 2,4-F$_2$3,5-Cl$_2$ | | O | O |
| CH$_2$CH=CH$_2$ | H | 2-Cl-6-F | 2-F-4-OCF$_2$CHF$_2$ | | O | O |
| CH$_2$CH=CH$_2$ | H | 2-Cl-6-F | 3,5-Cl$_2$-4-O(C$_6$H$_3$-2-Cl-4-CF$_3$) | | O | O |
| CH$_2$CH=CH$_2$ | H | 2-Cl | 4-OCF$_2$ | | O | O |
| CH$_2$CH=CH$_2$ | H | 2-Cl | 4-CH$_2$ON=C(Q51)(C$_6$H$_4$-4-Cl) | | O | O |
| CH$_2$CH=CH$_2$ | H | 2-Cl | 3,5-Cl$_2$-4-OCF$_2$CHF$_2$ | | O | O |
| CH$_2$CH=CH$_2$ | H | 2,6-Cl$_2$ | 3,5-Cl$_2$-4-O(Q38-3-Cl-5-CF$_3$) | | O | O |
| CH$_2$CH=CH$_2$ | H | 2-Br | 3,5-Cl$_2$-4-OCF$_2$CHF$_2$ | | O | O |
| CH$_2$CH=CH$_2$ | H | 2-CH$_3$ | 3,5-Cl$_2$-4-O(Q38-3-Cl-5-CF$_3$) | | O | O |
| CH$_2$CH=CH$_2$ | H | 2,6-(OCH$_3$)$_2$ | 2,4-F$_2$-3,5-Cl$_2$ | | O | O |
| CH$_2$C≡CH | H | 2-F | 2-F-4-Cl | | O | O |
| CH$_2$C≡CH | H | 2-F | 4-S(C$_6$H$_3$-2-Cl-4-CF$_3$) | | O | O |
| CH$_2$C≡CH | H | 2-F | 3,5-Cl$_2$-4-O(Q38-3-Cl-5-CF$_3$) | | O | O |

-continued

| | | | | | |
|---|---|---|---|---|---|
| CH₂C≡CH | H | 2,6-F₂ | 4-Cl | O | O |
| CH₂C≡CH | H | 2,6-F₂ | 4-CH₂ON=C(Q51)(C₆H₄-4-Cl) | O | O |
| CH₂C≡CH | H | 2,6-F₂ | 3-O(Q50-6-CF₃) | O | O |
| CH₂C≡CH | H | 2,6-F₂ | 3,5-Cl₂-4-OCF₂CHF₂ | O | O |
| CH₂C≡CH | H | 2,6-F₂ | 3,5-Cl₂-4-O(Q38-3-Cl-5-CF₃) | O | O |
| CH₂C≡CH | H | 2,6-F₂ | 2,4-F₂,3,5-Cl₂ | O | O |
| CH₂C≡CH | H | 2-Cl-6-F | 2-F-4-OCF₂CHF₂ | O | O |
| CH₂C≡CH | H | 2-Cl-6-F | 3,5-Cl₂-4-O(C₆H₃-2-Cl-4-CF₃) | O | O |
| CH₂C≡CH | H | 2-Cl | 4-OCF₃ | O | O |
| CH₂C≡CH | H | 2-Cl | 4-CH₂ON=C(Q51)(C₆H₄-4-Cl) | O | O |
| CH₂C≡CH | H | 2-Cl | 3,5-Cl₂-4-OCF₂CHF₂ | O | O |
| CH₂C≡CH | H | 2,6-Cl₂ | 3,5-Cl₂-4-O(Q38-3-Cl-5-CF₃) | O | O |
| CH₂C≡CH | H | 2-Br | 3,5-Cl₂-4-OCF₂CHF₂ | O | O |
| CH₂C≡CH | H | 2-CH₃ | 3,5-Cl₂-4-O(Q38-3-Cl-5-CF₃) | O | O |
| CH₂C≡CH | H | 2,6-(OCH₃)₂ | 2,4-F₂-3,5-Cl₂ | O | O |
| CHF₂ | H | 2-F | 2-F-4-Cl | O | O |
| CHF₂ | H | 2-F | 4-S(C₆H₃-2-Cl-4-CF₃) | O | O |
| CHF₂ | H | 2-F | 3,5-Cl₂-4-O(Q38-3-Cl-5-CF₃) | O | O |
| CHF₂ | H | 2,6-F₂ | 4-Cl | O | O |
| CHF₂ | H | 2,6-F₂ | 4-CH₂ON=C(Q51)(C₆H₄-4-Cl) | O | O |
| CHF₂ | H | 2,6-F₂ | 3-O(Q50-6-CF₃) | O | O |
| CHF₂ | H | 2,6-F₂ | 3,5-Cl₂-4-OCF₂CHF₂ | O | O |
| CHF₂ | H | 2,6-F₂ | 3,5-Cl₂-4-O(Q38-3-Cl-5-CF₃) | O | O |
| CHF₂ | H | 2,6-F₂ | 2,4-F₂,3,5-Cl₂ | O | O |
| CHF₂ | H | 2-Cl-6-F | 2-F-4-OCF₂CHF₂ | O | O |
| CHF₂ | H | 2-Cl-6-F | 3,5-Cl₂-4-O(C₆H₃-2-Cl-4-CF₃) | O | O |
| CHF₂ | H | 2-Cl | 4-OCF₃ | O | O |
| CHF₂ | H | 2-Cl | 4-CH₂ON=C(Q51)(C₆H₄-4-Cl) | O | O |
| CHF₂ | H | 2-Cl | 3,5-Cl₂-4-OCF₂CHF₂ | O | O |
| CHF₂ | H | 2,6-Cl₂ | 3,5-Cl₂-4-O(Q38-3-Cl-5-CF₃) | O | O |
| CHF₂ | H | 2-Br | 3,5-Cl₂-4-OCF₂CHF₂ | O | O |
| CHF₂ | H | 2-CH₃ | 3,5-Cl₂-4-O(Q38-3-Cl-5-CF₃) | O | O |
| CHF₂ | H | 2,6-(OCH₃)₂ | 2,4-F₂-3,5-Cl₂ | O | O |
| CF₂Br | H | 2-F | 2-F-4-Cl | O | O |
| CF₂Br | H | 2-F | 4-S(C₆H₃-2-Cl-4-CF₃) | O | O |
| CF₂Br | H | 2-F | 3,5-Cl₂-4-O(Q38-3-Cl-5-CF₃) | O | O |
| CF₂Br | H | 2,6-F₂ | 4-Cl | O | O |
| CF₂Br | H | 2,6-F₂ | 4-CH₂ON=C(Q51)(C₆H₄-4-Cl) | O | O |
| CF₂Br | H | 2,6-F₂ | 3-O(Q50-6-CF₃) | O | O |
| CF₂Br | H | 2,6-F₂ | 3,5-Cl₂-4-OCF₂CHF₂ | O | O |
| CF₂Br | H | 2,6-F₂ | 3,5-Cl₂-4-O(Q38-3-Cl-5-CF₃) | O | O |
| CF₂Br | H | 2,6-F₂ | 2,4-F₂,3,5-Cl₂ | O | O |
| CF₂Br | H | 2-Cl-6-F | 2-F-4-OCF₂CHF₂ | O | O |
| CF₂Br | H | 2-Cl-6-F | 3,5-Cl₂-4-O(C₆H₃-2-Cl-4-CF₃) | O | O |
| CF₂Br | H | 2-Cl | 4-OCF₂ | O | O |
| CF₂Br | H | 2-Cl | 4-CH₂ON=C(Q51)(C₆H₄-4-Cl) | O | O |
| CF₂Br | H | 2-Cl | 3,5-Cl₂-4-OCF₂CHF₂ | O | O |
| CF₂Br | H | 2,6-Cl₂ | 3,5-Cl₂-4-O(Q38-3-Cl-5-CF₃) | O | O |
| CF₂Br | H | 2-Br | 3,5-Cl₂-4-OCF₂CHF₂ | O | O |
| CF₂Br | H | 2-CH₃ | 3,5-Cl₂-4-O(Q38-3-Cl-5-CF₃) | O | O |
| CF₂Br | H | 2,6-(OCH₃)₂ | 2,4-F₂-3,5-Cl₂ | O | O |
| CF₃ | H | 2-F | 2-F-4-Cl | O | O |
| CF₃ | H | 2-F | 4-S(C₆H₃-2-Cl-4-CF₃) | O | O |
| CF₃ | H | 2-F | 3,5-Cl₂-4-O(Q38-3-Cl-5-CF₃) | O | O |
| CF₃ | H | 2,6-F₂ | 4-Cl | O | O |
| CF₃ | H | 2,6-F₂ | 4-CH₂ON=C(Q51)(C₆H₄-4-Cl) | O | O |
| CF₃ | H | 2,6-F₂ | 3-O(Q50-6-CF₃) | O | O |
| CF₃ | H | 2,6-F₂ | 3,5-Cl₂-4-OCF₂CHF₂ | O | O |
| CF₃ | H | 2,6-F₂ | 3,5-Cl₂-4-O(Q38-3-Cl-5-CF₃) | O | O |
| CF₃ | H | 2,6-F₂ | 2,4-F₂,3,5-Cl₂ | O | O |
| CF₃ | H | 2-Cl-6-F | 2-F-4-OCF₂CHF₂ | O | O |
| CF₃ | H | 2-Cl-6-F | 3,5-Cl₂-4-O(C₆H₃-2-Cl-4-CF₃) | O | O |
| CF₃ | H | 2-Cl | 4-OCF₂ | O | O |
| CF₃ | H | 2-Cl | 4-CH₂ON=C(Q51)(C₆H₄-4-Cl) | O | O |
| CF₃ | H | 2-Cl | 3,5-Cl₂-4-OCF₂CHF₂ | O | O |
| CF₃ | H | 2,6-Cl₂ | 3,5-Cl₂-4-O(Q38-3-Cl-5-CF₃) | O | O |
| CF₃ | H | 2-Br | 3,5-Cl₂-4-OCF₂CHF₂ | O | O |
| CF₃ | H | 2-CH₃ | 3,5-Cl₂-4-O(Q38-3-Cl-5-CF₃) | O | O |
| CF₃ | H | 2,6-(OCH₃)₂ | 2,4-F₂-3,5-Cl₂ | O | O |
| CH₂OCH₃ | H | 2-F | 2-F-4-Cl | O | O |
| CH₂OCH₃ | H | 2-F | 4-S(C₆H₃-2-Cl-4-CF₃) | O | O |
| CH₂OCH₃ | H | 2-F | 3,5-Cl₂-4-O(Q38-3-Cl-5-CF₃) | O | O |
| CH₂OCH₃ | H | 2,6-F₂ | 4-Cl | O | O |
| CH₂OCH₃ | H | 2,6-F₂ | 4-CH₂ON=C(Q51)(C₆H₄-4-Cl) | O | O |
| CH₂OCH₃ | H | 2,6-F₂ | 3-O(Q50-6-CF₃) | O | O |
| CH₂OCH₃ | H | 2,6-F₂ | 3,5-Cl₂-4-OCF₂CHF₂ | O | O |
| CH₂OCH₃ | H | 2,6-F₂ | 3,5-Cl₂-4-O(Q38-3-Cl-5-CF₃) | O | O |
| CH₂OCH₃ | H | 2,6-F₂ | 2,4-F₂,3,5-Cl₂ | O | O |
| CH₂OCH₃ | H | 2-Cl-6-F | 2-F-4-OCF₂CHF₂ | O | O |
| CH₂OCH₃ | H | 2-Cl-6-F | 3,5-Cl₂-4-O(C₆H₃-2-Cl-4-CF₃) | O | O |
| CH₂OCH₃ | H | 2-Cl | 4-OCF₂ | O | O |
| CH₂OCH₃ | H | 2-Cl | 4-CH₂ON=C(Q51)(C₆H₄-4-Cl) | O | O |
| CH₂OCH₃ | H | 2-Cl | 3,5-Cl₂-4-OCF₂CHF₂ | O | O |

-continued

| | | | | | |
|---|---|---|---|---|---|
| CH₂OCH₃ | H | 2,6-Cl₂ | 3,5-Cl₂-4-O(Q38-3-Cl-5-CF₃) | O | O |
| CH₂OCH₃ | H | 2-Br | 3,5-Cl₂-4-OCF₂CHF₂ | O | O |
| CH₂OCH₃ | H | 2-CH₃ | 3,5-Cl₂-4-O(Q38-3-Cl-5-CF₃) | O | O |
| CH₂OCH₃ | H | 2,6-(OCH₃)₂ | 2,4-F₂-3,5-Cl₂ | O | O |
| CH₂OCH₂CH₃ | H | 2-F | 2-F-4-Cl | O | O |
| CH₂OCH₂CH₃ | H | 2-F | 4-S(C₆H₃-2-Cl-4-CF₃) | O | O |
| CH₂OCH₂CH₃ | H | 2-F | 3,5-Cl₂-4-O(Q38-3-Cl-5-CF₃) | O | O |
| CH₂OCH₂CH₃ | H | 2,6-F₂ | 4-Cl | O | O |
| CH₂OCH₂CH₃ | H | 2,6-F₂ | 4-CH₂ON=C(Q51)(C₆H₄-4-Cl) | O | O |
| CH₂OCH₂CH₃ | H | 2,6-F₂ | 3-O(Q50-6-CF₃) | O | O |
| CH₂OCH₂CH₃ | H | 2,6-F₂ | 3,5-Cl₂-4-OCF₂CHF₂ | O | O |
| CH₂OCH₂CH₃ | H | 2,6-F₂ | 3,5-Cl₂-4-O(Q38-3-Cl-5-CF₃) | O | O |
| CH₂OCH₂CH₃ | H | 2,6-F₂ | 2,4-F₂,3,5-Cl₂ | O | O |
| CH₂OCH₂CH₃ | H | 2-Cl-6-F | 2-F-4-OCF₂CHF₂ | O | O |
| CH₂OCH₂CH₃ | H | 2-Cl-6-F | 3,5-Cl₂-4-O(C₆H₃-2-Cl-4-CF₃) | O | O |
| CH₂OCH₂CH₃ | H | 2-Cl | 4-OCF₂ | O | O |
| CH₂OCH₂CH₃ | H | 2-Cl | 4-CH₂ON=C(Q51)(C₆H₄-4-Cl) | O | O |
| CH₂OCH₂CH₃ | H | 2-Cl | 3,5-Cl₂-4-OCF₂CHF₂ | O | O |
| CH₂OCH₂CH₃ | H | 2,6-Cl₂ | 3,5-Cl₂-4-O(Q38-3-Cl-5-CF₃) | O | O |
| CH₂OCH₂CH₃ | H | 2-Br | 3,5-Cl₂-4-OCF₂CHF₂ | O | O |
| CH₂OCH₂CH₃ | H | 2-CH₃ | 3,5-Cl₂-4-O(Q38-3-Cl-5-CF₃) | O | O |
| CH₂OCH₂CH₃ | H | 2,6-(OCH₃)₂ | 2,4-F₂-3,5-Cl₂ | O | O |
| CH₂CH₂OCH₃ | H | 2-F | 2-F-4-Cl | O | O |
| CH₂CH₂OCH₃ | H | 2-F | 4-S(C₆H₃-2-Cl-4-CF₃) | O | O |
| CH₂CH₂OCH₃ | H | 2-F | 3,5-Cl₂-4-O(Q38-3-Cl-5-CF₃) | O | O |
| CH₂CH₂OCH₃ | H | 2,6-F₂ | 4-Cl | O | O |
| CH₂CH₂OCH₃ | H | 2,6-F₂ | 4-CH₂ON=C(Q51)(C₆H₄-4-Cl) | O | O |
| CH₂CH₂OCH₃ | H | 2,6-F₂ | 3-O(Q50-6-CF₃) | O | O |
| CH₂CH₂OCH₃ | H | 2,6-F₂ | 3,5-Cl₂-4-OCF₂CHF₂ | O | O |
| CH₂CH₂OCH₃ | H | 2,6-F₂ | 3,5-Cl₂-4-O(Q38-3-Cl-5-CF₃) | O | O |
| CH₂CH₂OCH₃ | H | 2,6-F₂ | 2,4-F₂,3,5-Cl₂ | O | O |
| CH₂CH₂OCH₃ | H | 2-Cl-6-F | 2-F-4-OCF₂CHF₂ | O | O |
| CH₂CH₂OCH₃ | H | 2-Cl-6-F | 3,5-Cl₂-4-O(C₆H₃-2-Cl-4-CF₃) | O | O |
| CH₂CH₂OCH₃ | H | 2-Cl | 4-OCF₂ | O | O |
| CH₂CH₂OCH₃ | H | 2-Cl | 4-CH₂ON=C(Q51)(C₆H₄-4-Cl) | O | O |
| CH₂CH₂OCH₃ | H | 2-Cl | 3,5-Cl₂-4-OCF₂CHF₂ | O | O |
| CH₂CH₂OCH₃ | H | 2,6-Cl₂ | 3,5-Cl₂-4-O(Q38-3-Cl-5-CF₃) | O | O |
| CH₂CH₂OCH₃ | H | 2-Br | 3,5-Cl₂-4-OCF₂CHF₂ | O | O |
| CH₂CH₂OCH₃ | H | 2-CH₃ | 3,5-Cl₂-4-O(Q38-3-Cl-5-CF₃) | O | O |
| CH₂CH₂OCH₃ | H | 2,6-(OCH₃)₂ | 2,4-F₂-3,5-Cl₂ | O | O |
| CHO | H | 2-F | 2-F-4-Cl | O | O |
| CHO | H | 2-F | 4-S(C₆H₃-2-Cl-4-CF₃) | O | O |
| CHO | H | 2-F | 3,5-Cl₂-4-O(Q38-3-Cl-5-CF₃) | O | O |
| CHO | H | 2,6-F₂ | 4-Cl | O | O |
| CHO | H | 2,6-F₂ | 4-CH₂ON=C(Q51)(C₆H₄-4-Cl) | O | O |
| CHO | H | 2,6-F₂ | 3-O(Q50-6-CF₃) | O | O |
| CHO | H | 2,6-F₂ | 3,5-Cl₂-4-OCF₂CHF₂ | O | O |
| CHO | H | 2,6-F₂ | 3,5-Cl₂-4-O(Q38-3-Cl-5-CF₃) | O | O |
| CHO | H | 2,6-F₂ | 2,4-F₂,3,5-Cl₂ | O | O |
| CHO | H | 2-Cl-6-F | 2-F-4-OCF₂CHF₂ | O | O |
| CHO | H | 2-Cl-6-F | 3,5-Cl₂-4-O(C₆H₃-2-Cl-4-CF₃) | O | O |
| CHO | H | 2-Cl | 4-OCF₂ | O | O |
| CHO | H | 2-Cl | 4-CH₂ON=C(Q51)(C₆H₄-4-Cl) | O | O |
| CHO | H | 2-Cl | 3,5-Cl₂-4-OCF₂CHF₂ | O | O |
| CHO | H | 2,6-Cl₂ | 3,5-Cl₂-4-O(Q38-3-Cl-5-CF₃) | O | O |
| CHO | H | 2-Br | 3,5-Cl₂-4-OCF₂CHF₂ | O | O |
| CHO | H | 2-CH₃ | 3,5-Cl₂-4-O(Q38-3-Cl-5-CF₃) | O | O |
| CHO | H | 2,6-(OCH₃)₂ | 2,4-F₂-3,5-Cl₂ | O | O |
| COCH₃ | H | 2-F | 2-F-4-Cl | O | O |
| COCH₃ | H | 2-F | 4-S(C₆H₃-2-Cl-4-CF₃) | O | O |
| COCH₃ | H | 2-F | 3,5-Cl₂-4-O(Q38-3-Cl-5-CF₃) | O | O |
| COCH₃ | H | 2,6-F₂ | 4-Cl | O | O |
| COCH₃ | H | 2,6-F₂ | 4-CH₂ON=C(Q51)(C₆H₄-4-Cl) | O | O |
| COCH₃ | H | 2,6-F₂ | 3-O(Q50-6-CF₃) | O | O |
| COCH₃ | H | 2,6-F₂ | 3,5-Cl₂-4-OCF₂CHF₂ | O | O |
| COCH₃ | H | 2,6-F₂ | 3,5-Cl₂-4-O(Q38-3-Cl-5-CF₃) | O | O |
| COCH₃ | H | 2,6-F₂ | 2,4-F₂,3,5-Cl₂ | O | O |
| COCH₃ | H | 2-Cl-6-F | 2-F-4-OCF₂CHF₂ | O | O |
| COCH₃ | H | 2-Cl-6-F | 3,5-Cl₂-4-O(C₆H₃-2-Cl-4-CF₃) | O | O |
| COCH₃ | H | 2-Cl | 4-OCF₂ | O | O |
| COCH₃ | H | 2-Cl | 4-CH₂ON=C(Q51)(C₆H₄-4-Cl) | O | O |
| COCH₃ | H | 2-Cl | 3,5-Cl₂-4-OCF₂CHF₂ | O | O |
| COCH₃ | H | 2,6-Cl₂ | 3,5-Cl₂-4-O(Q38-3-Cl-5-CF₃) | O | O |
| COCH₃ | H | 2-Br | 3,5-Cl₂-4-OCF₂CHF₂ | O | O |
| COCH₃ | H | 2-CH₃ | 3,5-Cl₂-4-O(Q38-3-Cl-5-CF₃) | O | O |
| COCH₃ | H | 2,6-(OCH₃)₂ | 2,4-F₂-3,5-Cl₂ | O | O |
| COCH(CH₃)₂ | H | 2-F | 2-F-4-Cl | O | O |
| COCH(CH₃)₂ | H | 2-F | 4-S(C₆H₃-2-Cl-4-CF₃) | O | O |
| COCH(CH₃)₂ | H | 2-F | 3,5-Cl₂-4-O(Q38-3-Cl-5-CF₃) | O | O |
| COCH(CH₃)₂ | H | 2,6-F₂ | 4-Cl | O | O |
| COCH(CH₃)₂ | H | 2,6-F₂ | 4-CH₂ON=C(Q51)(C₆H₄-4-Cl) | O | O |
| COCH(CH₃)₂ | H | 2,6-F₂ | 3-O(Q50-6-CF₃) | O | O |
| COCH(CH₃)₂ | H | 2,6-F₂ | 3,5-Cl₂-4-OCF₂CHF₂ | O | O |

| | | -continued | | | |
|---|---|---|---|---|---|
| COCH(CH₃)₂ | H | 2,6-F₂ | 3,5-Cl₂-4-O(Q38-3-Cl-5-CF₃) | O | O |
| COCH(CH₃)₂ | H | 2,6-F₂ | 2,4-F₂,3,5-Cl₂ | O | O |
| COCH(CH₃)₂ | H | 2-Cl-6-F | 2-F-4-OCF₂CHF₂ | O | O |
| COCH(CH₃)₂ | H | 2-Cl-6-F | 3,5-Cl₂-4-O(C₆H₃-2-Cl-4-CF₃) | O | O |
| COCH(CH₃)₂ | H | 2-Cl | 4-OCF₂ | O | O |
| COCH(CH₃)₂ | H | 2-Cl | 4-CH₂ON=C(Q51)(C₆H₄-4-Cl) | O | O |
| COCH(CH₃)₂ | H | 2-Cl | 3,5-Cl₂-4-OCF₂CHF₂ | O | O |
| COCH(CH₃)₂ | H | 2,6-Cl₂ | 3,5-Cl₂-4-O(Q38-3-Cl-5-CF₃) | O | O |
| COCH(CH₃)₂ | H | 2-Br | 3,5-Cl₂-4-OCF₂CHF₂ | O | O |
| COCH(CH₃)₂ | H | 2-CH₃ | 3,5-Cl₂-4-O(Q38-3-Cl-5-CF₃) | O | O |
| COCH(CH₃)₂ | H | 2,6-(OCH₃)₂ | 2,4-F₂-3,5-Cl₂ | O | O |
| CO₂CH₂CH₃ | H | 2-F | 2-F-4-Cl | O | O |
| CO₂CH₂CH₃ | H | 2-F | 4-S(C₆H₃-2-Cl-4-CF₃) | O | O |
| CO₂CH₂CH₃ | H | 2-F | 3,5-Cl₂-4-O(Q38-3-Cl-5-CF₃) | O | O |
| CO₂CH₂CH₃ | H | 2,6-F₂ | 4-Cl | O | O |
| CO₂CH₂CH₃ | H | 2,6-F₂ | 4-CH₂ON=C(Q51)(C₆H₄-4-Cl) | O | O |
| CO₂CH₂CH₃ | H | 2,6-F₂ | 3-O(Q50-6-CF₃) | O | O |
| CO₂CH₂CH₃ | H | 2,6-F₂ | 3,5-Cl₂-4-OCF₂CHF₂ | O | O |
| CO₂CH₂CH₃ | H | 2,6-F₂ | 3,5-Cl₂-4-O(Q38-3-Cl-5-CF₃) | O | O |
| CO₂CH₂CH₃ | H | 2,6-F₂ | 2,4-F₂,3,5-Cl₂ | O | O |
| CO₂CH₂CH₃ | H | 2-Cl-6-F | 2-F-4-OCF₂CHF₂ | O | O |
| CO₂CH₂CH₃ | H | 2-Cl-6-F | 3,5-Cl₂-4-O(C₆H₃-2-Cl-4-CF₃) | O | O |
| CO₂CH₂CH₃ | H | 2-Cl | 4-OCF₂ | O | O |
| CO₂CH₂CH₃ | H | 2-Cl | 4-CH₂ON=C(Q51)(C₆H₄-4-Cl) | O | O |
| CO₂CH₂CH₃ | H | 2-Cl | 3,5-Cl₂-4-OCF₂CHF₂ | O | O |
| CO₂CH₂CH₃ | H | 2,6-Cl₂ | 3,5-Cl₂-4-O(Q38-3-Cl-5-CF₃) | O | O |
| CO₂CH₂CH₃ | H | 2-Br | 3,5-Cl₂-4-OCF₂CHF₂ | O | O |
| CO₂CH₂CH₃ | H | 2-CH₃ | 3,5-Cl₂-4-O(Q38-3-Cl-5-CF₃) | O | O |
| CO₂CH₂CH₃ | H | 2,6-(OCH₃)₂ | 2,4-F₂-3,5-Cl₂ | O | O |
| CO₂C(CH₃)₃ | H | 2-F | 2-F-4-Cl | O | O |
| CO₂C(CH₃)₃ | H | 2-F | 4-S(C₆H₃-2-Cl-4-CF₃) | O | O |
| CO₂C(CH₃)₃ | H | 2-F | 3,5-Cl₂-4-O(Q38-3-Cl-5-CF₃) | O | O |
| CO₂C(CH₃)₃ | H | 2,6-F₂ | 4-Cl | O | O |
| CO₂C(CH₃)₃ | H | 2,6-F₂ | 4-CH₂ON=C(Q51)(C₆H₄-4-Cl) | O | O |
| CO₂C(CH₃)₃ | H | 2,6-F₂ | 3-O(Q50-6-CF₃) | O | O |
| CO₂C(CH₃)₃ | H | 2,6-F₂ | 3,5-Cl₂-4-OCF₂CHF₂ | O | O |
| CO₂C(CH₃)₃ | H | 2,6-F₂ | 3,5-Cl₂-4-O(Q38-3-Cl-5-CF₃) | O | O |
| CO₂C(CH₃)₃ | H | 2,6-F₂ | 2,4-F₂,3,5-Cl₂ | O | O |
| CO₂C(CH₃)₃ | H | 2-Cl-6-F | 2-F-4-OCF₂CHF₂ | O | O |
| CO₂C(CH₃)₃ | H | 2-Cl-6-F | 3,5-Cl₂-4-O(C₆H₃-2-Cl-4-CF₃) | O | O |
| CO₂C(CH₃)₃ | H | 2-Cl | 4-OCF₂ | O | O |
| CO₂C(CH₃)₃ | H | 2-Cl | 4-CH₂ON=C(Q51)(C₆H₄-4-Cl) | O | O |
| CO₂C(CH₃)₃ | H | 2-Cl | 3,5-Cl₂-4-OCF₂CHF₂ | O | O |
| CO₂C(CH₃)₃ | H | 2,6-Cl₂ | 3,5-Cl₂-4-O(Q38-3-Cl-5-CF₃) | O | O |
| CO₂C(CH₃)₃ | H | 2-Br | 3,5-Cl₂-4-OCF₂CHF₂ | O | O |
| CO₂C(CH₃)₃ | H | 2-CH₃ | 3,5-Cl₂-4-O(Q38-3-Cl-5-CF₃) | O | O |
| CO₂C(CH₃)₃ | H | 2,6-(OCH₃)₂ | 2,4-F₂-3,5-Cl₂ | O | O |
| Na | H | 2-F | 2-F-4-Cl | O | O |
| Na | H | 2-F | 4-S(C₆H₃-2-Cl-4-CF₃) | O | O |
| Na | H | 2-F | 3,5-Cl₂-4-O(Q38-3-Cl-5-CF₃) | O | O |
| Na | H | 2,6-F₂ | 4-Cl | O | O |
| Na | H | 2,6-F₂ | 4-CH₂ON=C(Q51)(C₆H₄-4-Cl) | O | O |
| Na | H | 2,6-F₂ | 3-O(Q50-6-CF₃) | O | O |
| Na | H | 2,6-F₂ | 3,5-Cl₂-4-OCF₂CHF₂ | O | O |
| Na | H | 2,6-F₂ | 3,5-Cl₂-4-O(Q38-3-Cl-5-CF₃) | O | O |
| Na | H | 2,6-F₂ | 2,4-F₂,3,5-Cl₂ | O | O |
| Na | H | 2-Cl-6-F | 2-F-4-OCF₂CHF₂ | O | O |
| Na | H | 2-Cl-6-F | 3,5-Cl₂-4-O(C₆H₃-2-Cl-4-CF₃) | O | O |
| Na | H | 2-Cl | 4-OCF₂ | O | O |
| Na | H | 2-Cl | 4-CH₂ON=C(Q51)(C₆H₄-4-Cl) | O | O |
| Na | H | 2-Cl | 3,5-Cl₂-4-OCF₂CHF₂ | O | O |
| Na | H | 2,6-Cl₂ | 3,5-Cl₂-4-O(Q38-3-Cl-5-CF₃) | O | O |
| Na | H | 2-Br | 3,5-Cl₂-4-OCF₂CHF₂ | O | O |
| Na | H | 2-CH₃ | 3,5-Cl₂-4-O(Q38-3-Cl-5-CF₃) | O | O |
| Na | H | 2,6-(OCH₃)₂ | 2,4-F₂-3,5-Cl₂ | O | O |
| K | H | 2-F | 2-F-4-Cl | O | O |
| K | H | 2-F | 4-S(C₆H₃-2-Cl-4-CF₃) | O | O |
| K | H | 2-F | 3,5-Cl₂-4-O(Q38-3-Cl-5-CF₃) | O | O |
| K | H | 2,6-F₂ | 4-Cl | O | O |
| K | H | 2,6-F₂ | 4-CH₂ON=C(Q51)(C₆H₄-4-Cl) | O | O |
| K | H | 2,6-F₂ | 3-O(Q50-6-CF₃) | O | O |
| K | H | 2,6-F₂ | 3,5-Cl₂-4-OCF₂CHF₂ | O | O |
| K | H | 2,6-F₂ | 3,5-Cl₂-4-O(Q38-3-Cl-5-CF₃) | O | O |
| K | H | 2,6-F₂ | 2,4-F₂,3,5-Cl₂ | O | O |
| K | H | 2-Cl-6-F | 2-F-4-OCF₂CHF₂ | O | O |
| K | H | 2-Cl-6-F | 3,5-Cl₂-4-O(C₆H₃-2-Cl-4-CF₃) | O | O |
| K | H | 2-Cl | 4-OCF₂ | O | O |
| K | H | 2-Cl | 4-CH₂ON=C(Q51)(C₆H₄-4-Cl) | O | O |
| K | H | 2-Cl | 3,5-Cl₂-4-OCF₂CHF₂ | O | O |
| K | H | 2,6-Cl₂ | 3,5-Cl₂-4-O(Q38-3-Cl-5-CF₃) | O | O |
| K | H | 2-Br | 3,5-Cl₂-4-OCF₂CHF₂ | O | O |
| K | H | 2-CH₃ | 3,5-Cl₂-4-O(Q38-3-Cl-5-CF₃) | O | O |
| K | H | 2,6-(OCH₃)₂ | 2,4-F₂-3,5-Cl₂ | O | O |

| | | | | | |
|---|---|---|---|---|---|
| Ca | H | 2-F | 2-F-4-Cl | O | O |
| Ca | H | 2-F | 4-S(C$_6$H$_3$-2-Cl-4-CF$_3$) | O | O |
| Ca | H | 2-F | 3,5-Cl$_2$-4-O(Q38-3-Cl-5-CF$_3$) | O | O |
| Ca | H | 2,6-F$_2$ | 4-Cl | O | O |
| Ca | H | 2,6-F$_2$ | 4-CH$_2$ON=C(Q51)(C$_6$H$_4$-4-Cl) | O | O |
| Ca | H | 2,6-F$_2$ | 3-O(Q50-6-CF$_3$) | O | O |
| Ca | H | 2,6-F$_2$ | 3,5-Cl$_2$-4-OCF$_2$CHF$_2$ | O | O |
| Ca | H | 2,6-F$_2$ | 3,5-Cl$_2$-4-O(Q38-3-Cl-5-CF$_3$) | O | O |
| Ca | H | 2,6-F$_2$ | 2,4-F$_2$,3,5-Cl$_2$ | O | O |
| Ca | H | 2-Cl-6-F | 2-F-4-OCF$_2$CHF$_2$ | O | O |
| Ca | H | 2-Cl-6-F | 3,5-Cl$_2$-4-O(C$_6$H$_3$-2-Cl-4-CF$_3$) | O | O |
| Ca | H | 2-Cl | 4-OCF$_2$ | O | O |
| Ca | H | 2-Cl | 4-CH$_2$ON=C(Q51)(C$_6$H$_4$-4-Cl) | O | O |
| Ca | H | 2-Cl | 3,5-Cl$_2$-4-OCF$_2$CHF$_2$ | O | O |
| Ca | H | 2,6-Cl$_2$ | 3,5-Cl$_2$-4-O(Q38-3-Cl-5-CF$_3$) | O | O |
| Ca | H | 2-Br | 3,5-Cl$_2$-4-OCF$_2$CHF$_2$ | O | O |
| Ca | H | 2-CH$_3$ | 3,5-Cl$_2$-4-O(Q38-3-Cl-5-CF$_3$) | O | O |
| Ca | H | 2,6-(OCH$_3$)$_2$ | 2,4-F$_2$-3,5-Cl$_2$ | O | O |
| H | H | 2-F | 2-F-4-Cl | S | O |
| H | H | 2-F | 4-S(C$_6$H$_3$-2-Cl-4-CF$_3$) | S | O |
| H | H | 2-F | 3,5-Cl$_2$-4-O(Q38-3-Cl-5-CF$_3$) | S | O |
| H | H | 2,6-F$_2$ | 4-Cl | S | O |
| H | H | 2,6-F$_2$ | 4-CH$_2$ON=C(Q51)(C$_6$H$_4$-4-Cl) | S | O |
| H | H | 2,6-F$_2$ | 3-O(Q50-6-CF$_3$) | S | O |
| H | H | 2,6-F$_2$ | 3,5-Cl$_2$-4-OCF$_2$CHF$_2$ | S | O |
| H | H | 2,6-F$_2$ | 3,5-Cl$_2$-4-O(Q38-3-Cl-5-CF$_3$) | S | O |
| H | H | 2,6-F$_2$ | 2,4-F$_2$,3,5-Cl$_2$ | S | O |
| H | H | 2-Cl-6-F | 2-F-4-OCF$_2$CHF$_2$ | S | O |
| H | H | 2-Cl-6-F | 3,5-Cl$_2$-4-O(C$_6$H$_3$-2-Cl-4-CF$_3$) | S | O |
| H | H | 2-Cl | 4-Cl | S | O |
| H | H | 2-Cl | 4-OCF$_2$ | S | O |
| H | H | 2-Cl | 4-CH$_2$ON=C(Q51)(C$_6$H$_4$-4-Cl) | S | O |
| H | H | 2-Cl | 3,5-Cl$_2$-4-OCF$_2$CHF$_2$ | S | O |
| H | H | 2,6-Cl$_2$ | 3,5-Cl$_2$-4-O(Q38-3-Cl-5-CF$_3$) | S | O |
| H | H | 2-Br | 3,5-Cl$_2$-4-OCF$_2$CHF$_2$ | S | O |
| H | H | 2-CH$_3$ | 3,5-Cl$_2$-4-O(Q38-3-Cl-5-CF$_3$) | S | O |
| H | H | 2,6-(OCH$_3$)$_2$ | 2,4-F$_2$-3,5-Cl$_2$ | S | O |
| CH$_3$ | Cl | 2-F | 2-F-4-Cl | O | O |
| CH$_3$ | Cl | 2,6-F$_2$ | 4-Cl | O | O |
| CH$_3$ | Cl | 2,6-F$_2$ | 4-CH$_2$ON=C(Q51)(C$_6$H$_4$-4-Cl) | O | O |
| CH$_3$ | Cl | 2,6-F$_2$ | 3-O(Q50-6-CF$_3$) | O | O |
| CH$_3$ | Cl | 2,6-F$_2$ | 3,5-Cl$_2$-4-OCF$_2$CHF$_2$ | O | O |
| CH$_3$ | Cl | 2,6-F$_2$ | 3,5-Cl$_2$-4-O(Q38-3-Cl-5-CF$_3$) | O | O |
| CH$_3$ | Cl | 2,6-F$_2$ | 2,4-F$_2$-3,5-Cl$_2$ | O | O |
| CH$_3$ | Cl | 2-Cl-6-F | 2-F-4-OCF$_2$CHF$_2$ | O | O |
| CH$_3$ | Cl | 2-Cl | 4-OCF$_2$ | O | O |
| CH$_3$ | Cl | 2-Cl | 3,5-Cl$_2$-4-O(C$_6$H$_3$-2-Cl-4-CF$_3$) | O | O |
| CHF$_2$ | Br | 2-F | 2-F-4-Cl | O | O |
| CHF$_2$ | Br | 2,6-F$_2$ | 4-Cl | O | O |
| CHF$_2$ | Br | 2,6-F$_2$ | 4-CH$_2$ON=C(Q51)(C$_6$H$_4$-4-Cl) | O | O |
| CHF$_2$ | Br | 2,6-F$_2$ | 3-O(Q50-6-CF$_3$) | O | O |
| CHF$_2$ | Br | 2,6-F$_2$ | 3,5-Cl$_2$-4-OCF$_2$CHF$_2$ | O | O |
| CHF$_2$ | Br | 2,6-F$_2$ | 3,5-Cl$_2$-4-O(Q38-3-Cl-5-CF$_3$) | O | O |
| CHF$_2$ | Br | 2,6-F$_2$ | 2,4-F$_2$-3,5-Cl$_2$ | O | O |
| CHF$_2$ | Br | 2-Cl-6-F | 2-F-4-OCF$_2$CHF$_2$ | O | O |
| CHF$_2$ | Br | 2-Cl | 4-OCF$_2$ | O | O |
| CHF$_2$ | Br | 2-Cl | 3,5-Cl$_2$-4-O(C$_6$H$_3$-2-Cl-4-CF$_3$) | O | O |
| CH$_2$OCH$_3$ | CH$_3$ | 2-F | 2-F-4-Cl | O | O |
| CH$_2$OCH$_3$ | CH$_3$ | 2,6-F$_2$ | 4-Cl | O | O |
| CH$_2$OCH$_3$ | CH$_3$ | 2,6-F$_2$ | 4-CH$_2$ON=C(Q51)(C$_6$H$_4$-4-Cl) | O | O |
| CH$_2$OCH$_3$ | CH$_3$ | 2,6-F$_2$ | 3-O(Q50-6-CF$_3$) | O | O |
| CH$_2$OCH$_3$ | CH$_3$ | 2,6-F$_2$ | 3,5-Cl$_2$-4-OCF$_2$CHF$_2$ | O | O |
| CH$_2$OCH$_3$ | CH$_3$ | 2,6-F$_2$ | 3,5-Cl$_2$-4-O(Q38-3-Cl-5-CF$_3$) | O | O |
| CH$_2$OCH$_3$ | CH$_3$ | 2,6-F$_2$ | 2,4-F$_2$-3,5-Cl$_2$ | O | O |
| CH$_2$OCH$_3$ | CH$_3$ | 2-Cl-6-F | 2-F-4-OCF$_2$CHF$_2$ | O | O |
| CH$_2$OCH$_3$ | CH$_3$ | 2-Cl | 4-OCF$_2$ | O | O |
| CH$_2$OCH$_3$ | CH$_3$ | 2-Cl | 3,5-Cl$_2$-4-O(C$_6$H$_3$-2-Cl-4-CF$_3$) | O | O |
| CH$_2$CH$_2$CH$_3$ | CF$_3$ | 2-F | 2-F-4-Cl | O | O |
| CH$_2$CH$_2$CH$_3$ | CF$_3$ | 2,6-F$_2$ | 4-Cl | O | O |
| CH$_2$CH$_2$CH$_3$ | CF$_3$ | 2,6-F$_2$ | 4-CH$_2$ON=C(Q51)(C$_6$H$_4$-4-Cl) | O | O |
| CH$_2$CH$_2$CH$_3$ | CF$_3$ | 2,6-F$_2$ | 3-O(Q50-6-CF$_3$) | O | O |
| CH$_2$CH$_2$CH$_3$ | CF$_3$ | 2,6-F$_2$ | 3,5-Cl$_2$-4-OCF$_2$CHF$_2$ | O | O |
| CH$_2$CH$_2$CH$_3$ | CF$_3$ | 2,6-F$_2$ | 3,5-Cl$_2$-4-O(Q38-3-Cl-5-CF$_3$) | O | O |
| CH$_2$CH$_2$CH$_3$ | CF$_3$ | 2,6-F$_2$ | 2,4-F$_2$-3,5-Cl$_2$ | O | O |
| CH$_2$CH$_2$CH$_3$ | CF$_3$ | 2-Cl-6-F | 2-F-4-OCF$_2$CHF$_2$ | O | O |
| CH$_2$CH$_2$CH$_3$ | CF$_3$ | 2-Cl | 4-OCF$_2$ | O | O |
| CH$_2$CH$_2$CH$_3$ | CF$_3$ | 2-Cl | 3,5-Cl$_2$-4-O(C$_6$H$_3$-2-Cl-4-CF$_3$) | O | O |
| CO$_2$CH$_3$ | NO$_2$ | 2-F | 2-F-4-Cl | O | O |
| CO$_2$CH$_3$ | NO$_2$ | 2,6-F$_2$ | 4-Cl | O | O |
| CO$_2$CH$_3$ | NO$_2$ | 2,6-F$_2$ | 4-CH$_2$ON=C(Q51)(C$_6$H$_4$-4-Cl) | O | O |
| CO$_2$CH$_3$ | NO$_2$ | 2,6-F$_2$ | 3-O(Q50-6-CF$_3$) | O | O |
| CO$_2$CH$_3$ | NO$_2$ | 2,6-F$_2$ | 3,5-Cl$_2$-4-OCF$_2$CHF$_2$ | O | O |
| CO$_2$CH$_3$ | NO$_2$ | 2,6-F$_2$ | 3,5-Cl$_2$-4-O(Q38-3-Cl-5-CF$_3$) | O | O |

-continued

| | | | | | |
|---|---|---|---|---|---|
| CO₂CH₃ | NO₂ | 2,6-F₂ | 2,4-F₂-3,5-Cl₂ | O | O |
| CO₂CH₃ | NO₂ | 2-Cl-6-F | 2-F-4-OCF₂CHF₂ | O | O |
| CO₂CH₃ | NO₂ | 2-Cl | 4-OCF₃ | O | O |
| CO₂CH₃ | NO₂ | 2-Cl | 3,5-Cl₂-4-O(C₆H₃-2-Cl-4-CF₃) | O | O |
| H | H | 2-Cl | 4-Cl | NH | O |
| H | H | 2-Cl | 4-OCF₃ | NH | O |
| H | H | 2-Cl | 3,4-Cl₂ | NH | O |
| H | H | 2-F | 4-Cl | NH | O |
| H | H | 2-F | 4-OCF₃ | NH | O |
| H | H | 2-F | 3,4-Cl₂ | NH | O |
| H | H | 2,6-F₂ | 4-Cl | NH | O |
| H | H | 2,6-F₂ | 4-OCF₃ | NH | O |
| H | H | 2,6-F₂ | 3,4-Cl₂ | NH | O |
| H | CN | 2-Cl | 4-Cl | NH | O |
| H | CN | 2-Cl | 4-OCF₃ | NH | O |
| H | CN | 2-Cl | 3,4-Cl₂ | NH | O |
| H | CN | 2-F | 4-Cl | NH | O |
| H | CN | 2-F | 4-OCF₃ | NH | O |
| H | CN | 2-F | 3,4-Cl₂ | NH | O |
| H | CN | 2,6-F₂ | 4-Cl | NH | O |
| H | CN | 2,6-F₂ | 4-OCF₃ | NH | O |
| H | CN | 2,6-F₂ | 3,4-Cl₂ | NH | O |
| H | F | 2-Cl | 4-Cl | NH | O |
| H | F | 2-Cl | 4-OCF₃ | NH | O |
| H | F | 2-Cl | 3,4-Cl₂ | NH | O |
| H | F | 2-F | 4-Cl | NH | O |
| H | F | 2-F | 4-OCF₃ | NH | O |
| H | F | 2-F | 3,4-Cl₂ | NH | O |
| H | F | 2,6-F₂ | 4-Cl | NH | O |
| H | H | 2,6-F₂ | 4-OCF₃ | NH | O |
| H | H | 2,6-F₂ | 3,4-Cl₂ | NH | O |
| H | SCH₃ | 2-Cl | 4-Cl | O | O |
| H | SCH₃ | 2-Cl | 4-OCF₃ | O | O |
| H | SCH₃ | 2-Cl | 3,4-Cl₂ | O | O |
| H | SCH₃ | 2-F | 4-Cl | O | O |
| H | SCH₃ | 2-F | 4-OCF₃ | O | O |
| H | SCH₃ | 2-F | 3,4-Cl₂ | O | O |
| H | SCH₃ | 2,6-F₂ | 4-Cl | O | O |
| H | SCH₃ | 2,6-F₂ | 4-OCF₃ | O | O |
| H | SCH₃ | 2,6-F₂ | 3,4-Cl₂ | O | O |
| H | SCF₃ | 2-Cl | 4-Cl | O | O |
| H | SCF₃ | 2-Cl | 4-OCF₃ | O | O |
| H | SCF₃ | 2-Cl | 3,4-Cl₂ | O | O |
| H | SCF₃ | 2-F | 4-Cl | O | O |
| H | SCF₃ | 2-F | 4-OCF₃ | O | O |
| H | SCF₃ | 2-F | 3,4-Cl₂ | O | O |
| H | SCF₃ | 2,6-F₂ | 4-Cl | O | O |
| H | SCF₃ | 2,6-F₂ | 4-OCF₃ | O | O |
| H | SCF₃ | 2,6-F₂ | 3,4-Cl₂ | O | O |
| H | OCH₃ | 2-Cl | 4-Cl | O | O |
| H | OCH₃ | 2-Cl | 4-OCF₃ | O | O |
| H | OCH₃ | 2-Cl | 3,4-Cl₂ | O | O |
| H | OCH₃ | 2-F | 4-Cl | O | O |
| H | OCH₃ | 2-F | 4-OCF₃ | O | O |
| H | OCH₃ | 2-F | 3,4-Cl₂ | O | O |
| H | OCH₃ | 2,6-F₂ | 4-Cl | O | O |
| H | OCH₃ | 2,6-F₂ | 4-OCF₃ | O | O |
| H | OCH₃ | 2,6-F₂ | 3,4-Cl₂ | O | O |
| H | CHO | 2-Cl | 4-Cl | O | O |
| H | CHO | 2-Cl | 4-OCF₃ | O | O |
| H | CHO | 2-Cl | 3,4-Cl₂ | O | O |
| H | CHO | 2-F | 4-Cl | O | O |
| H | CHO | 2-F | 4-OCF₃ | O | O |
| H | CHO | 2-F | 3,4-Cl₂ | O | O |
| H | CHO | 2,6-F₂ | 4-Cl | O | O |
| H | CHO | 2,6-F₂ | 4-OCF₃ | O | O |
| H | CHO | 2,6-F₂ | 3,4-Cl₂ | O | O |
| H | H | 2-Cl | 4-O(Q43-5-Cl) | O | O |
| H | H | 2-Cl | 4-O(Q43) | O | O |
| H | H | 2-Cl | 3-Cl-4-O(Q43) | O | O |
| H | H | 2-Cl | 3-Cl-4-O(Q38-5-CF₃) | O | O |
| H | H | 2-Cl | 3-Cl-4-O(Q38-5-CF₃6-Cl) | O | O |
| H | H | 2-Cl | 3-Cl-4-O(Q38-5-I) | O | O |
| H | H | 2-Cl | 3-Cl-4-O(Q38-5-Cl) | O | O |
| H | H | 2-Cl | 4-O(Q38-5-Br) | O | O |
| H | H | 2-Cl | 3-Cl-4-O(Q38-5-Br) | O | O |
| H | H | 2-Cl | 3-Cl-4-O(Q38-5,6-Cl₂) | O | O |
| H | H | 2-Cl | 3-Cl-4-O(Q38-5-Br-6-Cl) | O | O |
| H | H | 2-Cl | 4-O(Q38-5-CF₃-6-Cl) | O | O |
| H | H | 2-Cl | 3-Cl-4-O(Q43-5-Cl) | O | O |
| H | H | 2-Cl | 3-Cl-4-O(Q43-5-I) | O | O |
| H | H | 2-Cl | 4-O(Q43-5-I) | O | O |
| H | H | 2-Cl | 3-Cl-4-O(Q43-5-CF₃-6-Cl) | O | O |

-continued

| | | | | | |
|---|---|---|---|---|---|
| H | H | 2-Cl | 3-NO$_2$-4-O(Q43-5-Cl) | O | O |
| H | H | 2-NO$_2$ | 3-NO$_2$-4-O(Q38-5-CF$_3$) | O | O |
| H | H | 2-NO$_2$ | 3-NO$_2$-4-O(Q43-5-Cl) | O | O |
| H | H | 2-NO$_2$ | 3-NO$_2$-4-O(Q43-5-Br) | O | O |
| H | H | 2-NO$_2$ | 3-NO$_2$-4-O(Q43-5-I) | O | O |
| H | H | 2-NO$_2$ | 3-NO$_2$-4-O(Q41-6-Br) | O | O |
| H | H | 2-NO$_2$ | 4-O(Q43) | O | O |
| H | H | 2-NO$_2$ | 3-Cl-4-O(Q38) | O | O |
| H | H | 2-NO$_2$ | 3-CF$_3$-4-O(Q43-5-I) | O | O |
| H | H | 2-NO$_2$ | 3-Cl-4-O(Q43-5-CF$_3$-6-Cl) | O | O |
| H | H | 2-NO$_2$ | 3-Cl-4-O(Q38-5-CF$_3$) | O | O |
| H | H | 2-NO$_2$ | 3-Cl-4-O(Q43-5-I) | O | O |
| H | H | 2-Br | 3-Cl-4-(Q43-5-I) | O | O |
| H | H | 2-Br | 3-Cl-4-O(Q43-5-CF$_3$-6-Cl) | O | O |
| H | H | 2-CF$_3$ | 3-Cl-4-O(Q38-5-CF$_3$) | O | O |
| H | H | 2-CF$_3$ | 3-Cl-4-O(Q43-5-CF$_3$-6-Cl) | O | O |
| H | H | 2,6-Cl$_2$ | 3-O(Q50) | O | O |
| H | H | 2,6-Cl$_2$ | 4-O(Q50) | O | O |
| H | H | 2,6-Cl$_2$ | 3-S(Q50) | O | O |
| H | H | 2,6-Cl$_2$ | 4-S(Q50) | O | O |
| H | H | 2,6-Cl$_2$ | 4-O(Q50-6-Cl) | O | O |
| H | H | 2,6-Cl$_2$ | 3-Cl-4-O(Q43-5-I) | O | O |
| H | H | 2,6-(OCH$_3$)$_2$ | 3-O(Q50) | O | O |
| H | H | 2,6-(OCH$_3$)$_2$ | 4-O(Q50) | O | O |
| H | H | 2,6-(OCH$_3$)$_2$ | 4-O(Q50-6-Cl) | O | O |
| H | H | 2,6-(OCH$_3$)$_2$ | 3-Cl-4-O(Q50) | O | O |
| H | H | 2,6-(OCH$_3$)$_2$ | 3-Cl-4-S(Q50) | O | O |
| H | H | 2,6-(OCH$_3$)$_2$ | 3-Cl-4-O(Q43-5-I) | O | O |
| H | H | 2,6-F$_2$ | 3-Cl-4-O(Q50) | O | O |
| H | H | 2-Cl | 3-Cl-4-S(Q50) | O | O |
| H | H | 2-Br | 3-Cl-4-O(Q50) | O | O |
| H | H | 2-NO$_2$ | 4-O(Q50) | O | O |
| H | H | 2-CF$_3$ | 3-Cl-4-O(Q50) | O | O |
| H | H | 2-Cl-6-F | 4-O(Q50) | O | O |
| SC$_6$H$_5$ | H | 2-Cl | 4-OCF$_3$ | O | O |
| SC$_6$H$_5$ | H | 2-Cl | 3,4-Cl$_2$ | O | O |
| S(C$_6$H$_4$-2-CH$_3$) | H | 2-Cl | 4-OCF$_3$ | O | O |
| S(C$_6$H$_4$-2-CH$_3$) | H | 2-Cl | 3,4-Cl$_2$ | O | O |
| S(C$_6$H$_4$-3-CH$_3$) | H | 2-Cl | 4-OCF$_3$ | O | O |
| S(C$_6$H$_4$-3-CH$_3$) | H | 2-Cl | 3,4-Cl$_2$ | O | O |
| S(C$_6$H$_4$-4-CH$_3$) | H | 2-Cl | 4-OCF$_3$ | O | O |
| S(C$_6$H$_4$-4-CH$_3$) | H | 2-Cl | 3,4-Cl$_2$ | O | O |
| S(C$_6$H$_4$-4-Cl) | H | 2-Cl | 4-OCF$_3$ | O | O |
| S(C$_6$H$_4$-4-Cl) | H | 2-Cl | 3,4-Cl$_2$ | O | O |
| S(C$_6$H$_4$-4-Br) | H | 2-Cl | 4-OCF$_3$ | O | O |
| S(C$_6$H$_4$-4-Br) | H | 2-Cl | 3,4-Cl$_2$ | O | O |
| S(C$_6$H$_4$-2-CH(CH$_3$)$_2$) | H | 2-Cl | 4-OCF$_3$ | O | O |
| S(C$_6$H$_4$-2-CH(CH$_3$)$_2$) | H | 2-Cl | 3,4-Cl$_2$ | O | O |
| S(C$_6$H$_4$-4-C(CH$_3$)$_3$) | H | 2-Cl | 4-OCF$_3$ | O | O |
| S(C$_6$H$_4$-4-C(CH$_3$)$_3$) | H | 2-Cl | 3,4-Cl$_2$ | O | O |
| S(C$_6$H$_4$-2-NO$_2$) | H | 2-Cl | 4-OCF$_3$ | O | O |
| S(C$_6$H$_4$-2-NO$_2$) | H | 2-Cl | 3,4-Cl$_2$ | O | O |
| S(C$_6$H$_4$-2-CO$_2$CH$_3$) | H | 2-Cl | 4-OCF$_3$ | O | O |
| S(C$_6$H$_4$-2-CO$_2$CH$_3$) | H | 2-Cl | 3,4-Cl$_2$ | O | O |
| S(C$_6$H$_4$-2-CO$_2$CH$_2$CH$_3$) | H | 2-Cl | 4-OCF$_3$ | O | O |
| S(C$_6$H$_4$-2-CO$_2$CH$_2$CH$_3$) | H | 2-Cl | 3,4-Cl$_2$ | O | O |
| S(C$_6$H$_4$-2-CO$_2$CH$_2$CH$_2$CH$_3$) | H | 2-Cl | 4-OCF$_3$ | O | O |
| S(C$_6$H$_4$-2-CO$_2$CH$_2$CH$_2$CH$_3$) | H | 2-Cl | 3,4-Cl$_2$ | O | O |
| S(C$_6$H$_4$-2-CO$_2$CH(CH$_3$)CH$_2$CH$_3$) | H | 2-Cl | 4-OCF$_3$ | O | O |
| S(C$_6$H$_4$-2-CO$_2$CH(CH$_3$)CH$_2$CH$_3$) | H | 2-Cl | 3,4-Cl$_2$ | O | O |
| S(C$_6$H$_4$-2,4-(NO$_2$)$_2$) | H | 2-Cl | 4-OCF$_3$ | O | O |
| S(C$_6$H$_4$-2,4-(NO$_2$)$_2$) | H | 2-Cl | 3,4-Cl$_2$ | O | O |
| SCCl$_3$ | H | 2-Cl | 4-OCF$_3$ | O | O |
| SCCl$_3$ | H | 2-Cl | 3,4-Cl$_2$ | O | O |
| SCO$_2$CH$_2$CH$_2$CH$_3$ | H | 2-Cl | 4-OCF$_3$ | O | O |
| SCO$_2$CH$_2$CH$_2$CH$_3$ | H | 2-Cl | 3,4-Cl$_2$ | O | O |
| SN(CH(CH$_3$)$_2$)CH$_2$CH$_2$CO$_2$CH$_2$CH$_3$ | H | 2-Cl | 4-OCF$_3$ | O | O |
| SN(CH(CH$_3$)$_2$)CH$_2$CH$_2$CO$_2$CH$_2$CH$_3$ | H | 2-Cl | 3,4-Cl$_2$ | O | O |
| SN(CH$_2$CH$_2$CH$_3$)$_2$ | H | 2-Cl | 4-OCF$_3$ | O | O |
| SN(CH$_2$CH$_2$CH$_3$)$_2$ | H | 2-Cl | 3,4-Cl$_2$ | O | O |
| SN(CH$_3$)CO$_2$CH(CH$_3$)$_2$ | H | 2-Cl | 4-OCF$_3$ | O | O |
| SN(CH$_3$)CO$_2$CH(CH$_3$)$_2$ | H | 2-Cl | 3,4-Cl$_2$ | O | O |
| SN(CH$_3$)CO$_2$CH$_2$CH$_2$CH$_3$ | H | 2-Cl | 4-OCF$_3$ | O | O |
| SN(CH$_3$)CO$_2$CH$_2$CH$_2$CH$_3$ | H | 2-Cl | 3,4-Cl$_2$ | O | O |
| SN(CH$_2$CH$_2$CH$_3$)CO$_2$CH(CH$_3$)$_2$ | H | 2-Cl | 4-OCF$_3$ | O | O |
| SN(CH$_2$CH$_2$CH$_3$)CO$_2$CH(CH$_3$)$_2$ | H | 2-Cl | 3,4-Cl$_2$ | O | O |
| SN(CH(CH$_3$)$_2$)CO$_2$CH$_2$CH$_2$CH$_3$ | H | 2-Cl | 4-OCF$_3$ | O | O |
| SN(CH(CH$_3$)$_2$)CO$_2$CH$_2$CH$_2$CH$_3$ | H | 2-Cl | 3,4-Cl$_2$ | O | O |
| SN(CH$_2$CH$_2$CH$_2$CH$_3$)CO$_2$CH$_3$ | H | 2-Cl | 4-OCF$_3$ | O | O |
| SN(CH$_2$CH$_2$CH$_2$CH$_3$)CO$_2$CH$_3$ | H | 2-Cl | 3,4-Cl$_2$ | O | O |
| SN(C(CH$_3$)$_3$)CO$_2$CH$_2$CH$_3$ | H | 2-Cl | 4-OCF$_3$ | O | O |
| SN(C(CH$_3$)$_3$)CO$_2$CH$_2$CH$_3$ | H | 2-Cl | 3,4-Cl$_2$ | O | O |
| SN(CH$_2$CH$_2$CH$_3$)SO$_2$CH$_3$ | H | 2-Cl | 4-OCF$_3$ | O | O |

-continued

| | | | | | |
|---|---|---|---|---|---|
| SN(CH2CH2CH3)SO2CH3 | H | 2-Cl | 3,4-Cl2 | O | O |
| SC6H5 | H | 2,6-F2 | 4-OCF3 | O | O |
| SC6H5 | H | 2,6-F2 | 3,4-Cl2 | O | O |
| S(C6H5-2-CH3) | H | 2,6-F2 | 4-OCF3 | O | O |
| S(C6H5-2-CH3) | H | 2,6-F2 | 3,4-Cl2 | O | O |
| S(C6H5-3-CH3) | H | 2,6-F2 | 4-OCF3 | O | O |
| S(C6H5-3-CH3) | H | 2,6-F2 | 3,4-Cl2 | O | O |
| S(C6H5-4-CH3) | H | 2,6-F2 | 4-OCF3 | O | O |
| S(C6H5-4-CH3) | H | 2,6-F2 | 3,4-Cl2 | O | O |
| S(C6H5-4-Cl) | H | 2,6-F2 | 4-OCF3 | O | O |
| S(C6H5-4-Cl) | H | 2,6-F2 | 3,4-Cl2 | O | O |
| S(C6H5-4-Br) | H | 2,6-F2 | 4-OCF3 | O | O |
| S(C6H5-4-Br) | H | 2,6-F2 | 3,4-Cl2 | O | O |
| S(C6H5-2-CH(CH3)2) | H | 2,6-F2 | 4-OCF3 | O | O |
| S(C6H5-2-CH(CH3)2) | H | 2,6-F2 | 3,4-Cl2 | O | O |
| S(C6H5-4-C(CH3)3) | H | 2,6-F2 | 4-OCF3 | O | O |
| S(C6H5-4-C(CH3)3) | H | 2,6-F2 | 3,4-Cl2 | O | O |
| S(C6H5-2-NO2) | H | 2,6-F2 | 4-OCF3 | O | O |
| S(C6H5-2-NO2) | H | 2,6-F2 | 3,4-Cl2 | O | O |
| S(C6H5-2-CO2CH3) | H | 2,6-F2 | 4-OCF3 | O | O |
| S(C6H5-2-CO2CH3) | H | 2,6-F2 | 3,4-Cl2 | O | O |
| S(C6H5-2-CO2CH2CH3) | H | 2,6-F2 | 4-OCF3 | O | O |
| S(C6H5-2-CO2CH2CH3) | H | 2,6-F2 | 3,4-Cl2 | O | O |
| S(C6H5-2-CO2CH2CH2CH3) | H | 2,6-F2 | 4-OCF3 | O | O |
| S(C6H5-2-CO2CH2CH2CH3) | H | 2,6-F2 | 3,4-Cl2 | O | O |
| S(C6H5-2-CO2CH(CH3)CH2CH3) | H | 2,6-F2 | 4-OCF3 | O | O |
| S(C6H4-2-CO2CH(CH3)CH2CH3) | H | 2,6-F2 | 3,4-Cl2 | O | O |
| S(C6H4-2,4-(NO2)2) | H | 2,6-F2 | 4-OCF3 | O | O |
| S(C6H4-2,4-(NO2)2) | H | 2,6-F2 | 3,4-Cl2 | O | O |
| SCCl3 | H | 2,6-F2 | 4-OCF3 | O | O |
| SCCl3 | H | 2,6-F2 | 3,4-Cl2 | O | O |
| SCO2CH2CH2CH3 | H | 2,6-F2 | 4-OCF3 | O | O |
| SCO2CH2CH2CH3 | H | 2,6-F2 | 3,4-Cl2 | O | O |
| SN(CH(CH3)2)CH2CH2CO2CH2CH3 | H | 2,6-F2 | 4-OCF3 | O | O |
| SN(CH(CH3)2)CH2CH2CO2CH2CH3 | H | 2,6-F2 | 3,4-Cl2 | O | O |
| SN(CH2CH2CH2CH3)2 | H | 2,6-F2 | 4-OCF3 | O | O |
| SN(CH2CH2CH3)2 | H | 2,6-F2 | 3,4-Cl2 | O | O |
| SN(CH3)CO2CH(CH3)2 | H | 2,6-F2 | 4-OCF3 | O | O |
| SN(CH3)CO2CH(CH3)2 | H | 2,6-F2 | 3,4-Cl2 | O | O |
| SN(CH3)CO2CH2CH2CH3 | H | 2,6-F2 | 4-OCF3 | O | O |
| SN(CH3)CO2CH2CH2CH2CH3 | H | 2,6-F2 | 3,4-Cl2 | O | O |
| SN(CH2CH2CH3)CO2CH(CH3)2 | H | 2,6-F2 | 4-OCF3 | O | O |
| SN(CH2CH2CH3)CO2CH(CH3)2 | H | 2,6-F2 | 3,4-Cl2 | O | O |
| SN(CH(CH3)2)CO2CH2CH3 | H | 2,6-F2 | 4-OCF3 | O | O |
| SN(CH(CH3)2)CO2CH2CH2CH3 | H | 2,6-F2 | 3,4-Cl2 | O | O |
| SN(CH2CH2CH2CH3)CO2CH3 | H | 2,6-F2 | 4-OCF3 | O | O |
| SN(CH2CH2CH2CH3)CO2CH3 | H | 2,6-F2 | 3,4-Cl2 | O | O |
| SN(C(CH3)3)CO2CH2CH3 | H | 2,6-F2 | 4-OCF3 | O | O |
| SN(C(CH3)3)CO2CH2CH3 | H | 2,6-F2 | 3,4-Cl2 | O | O |
| SN(CH2CH2CH3)SO2CH3 | H | 2,6-F2 | 4-OCF3 | O | O |
| SN(CH2CH2CH3)SO2CH3 | H | 2,6-F2 | 3,4-Cl2 | O | O |
| SC6H5 | H | 2-F | 4-OCF3 | O | O |
| SC6H5 | H | 2-Cl-6-F | 3,4-Cl2 | O | O |
| S(C6H5-2-CH3) | H | 2-Cl-6-F | 4-OCF3 | O | O |
| S(C6H5-2-CH3) | H | 2-F | 3,4-Cl2 | O | O |
| S(C6H5-3-CH3) | H | 2-F | 4-OCF3 | O | O |
| S(C6H5-3-CH3) | H | 2-Cl-6-F | 3,4-Cl2 | O | O |
| S(C6H5-4-CH3) | H | 2-Cl-6-F | 4-OCF3 | O | O |
| S(C6H5-4-CH3) | H | 2-F | 3,4-Cl2 | O | O |
| S(C6H5-4-Cl) | H | 2-F | 4-OCF3 | O | O |
| S(C6H5-4-Cl) | H | 2-Cl-6-F | 3,4-Cl2 | O | O |
| S(C6H5-4-Br) | H | 2-Cl-6-F | 4-OCF3 | O | O |
| S(C6H5-4-Br) | H | 2-F | 3,4-Cl2 | O | O |
| S(C6H5-2-CH(CH3)2) | H | 2-F | 4-OCF3 | O | O |
| S(C6H5-2-CH(CH3)2) | H | 2-Cl-6-F | 3,4-Cl2 | O | O |
| S(C6H5-4-C(CH3)3) | H | 2-Cl-6-F | 4-OCF3 | O | O |
| S(C6H5-4-C(CH3)3) | H | 2-F | 3,4-Cl2 | O | O |
| S(C6H5-2-NO2) | H | 2-F | 4-OCF3 | O | O |
| S(C6H5-2-NO2) | H | 2-Cl-6-F | 3,4-Cl2 | O | O |
| S(C6H5-2-CO2CH3) | H | 2-Cl-6-F | 4-OCF3 | O | O |
| S(C6H5-2-CO2CH3) | H | 2-F | 3,4-Cl2 | O | O |
| S(C6H5-2-CO2CH2CH3) | H | 2-F | 4-OCF3 | O | O |
| S(C6H5-2-CO2CH2CH3) | H | 2-Cl-6-F | 3,4-Cl2 | O | O |
| S(C6H5-2-CO2CH2CH2CH3) | H | 2-Cl-6-F | 4-OCF3 | O | O |
| S(C6H5-2-CO2CH2CH2CH3) | H | 2-F | 3,4-Cl2 | O | O |
| S(C6H5-2-CO2CH(CH3)CH2CH3) | H | 2-F | 4-OCF3 | O | O |
| S(C6H4-2-CO2CH(CH3)CH2CH3) | H | 2-Cl-6-F | 3,4-Cl2 | O | O |
| S(C6H4-2,4-(NO2)2) | H | 2-Cl-6-F | 4-OCF3 | O | O |
| S(C6H4-2,4-(NO2)2) | H | 2-F | 3,4-Cl2 | O | O |
| SCCl3 | H | 2-F | 4-OCF3 | O | O |
| SCCl3 | H | 2-Cl-6-F | 3,4-Cl2 | O | O |
| SCO2CH2CH2CH3 | H | 2-Cl-6-F | 4-OCF3 | O | O |
| SCO2CH2CH2CH3 | H | 2-F | 3,4-Cl2 | O | O |

-continued

| | | | | | |
|---|---|---|---|---|---|
| SN(CH(CH₃)₂)CH₂CH₂CO₂CH₂CH₃ | H | 2-F | 4-OCF₃ | O | O |
| SN(CH(CH₃)₂)CH₂CH₂CO₂CH₂CH₃ | H | 2-Cl-6-F | 3,4-Cl₂ | O | O |
| SN(CH₂CH₂CH₂CH₃)₂ | H | 2-Cl-6-F | 4-OCF₃ | O | O |
| SN(CH₂CH₂CH₂CH₃)₂ | H | 2-F | 3,4-Cl₂ | O | O |
| SN(CH₃)CO₂CH(CH₃)₂ | H | 2-F | 4-OCF₃ | O | O |
| SN(CH₃)CO₂CH(CH₃)₂ | H | 2-Cl-6-F | 3,4-Cl₂ | O | O |
| SN(CH₃)CO₂CH₂CH₂CH₂CH₃ | H | 2-Cl-6-F | 4-OCF₃ | O | O |
| SN(CH₃)CO₂CH₂CH₂CH₃ | H | 2-F | 3,4-Cl₂ | O | O |
| SN(CH₂CH₂CH₃)CO₂CH(CH₃)₂ | H | 2-F | 4-OCF₃ | O | O |
| SN(CH₂CH₂CH₃)CO₂CH(CH₃)₂ | H | 2-Cl-6-F | 3,4-Cl₂ | O | O |
| SN(CH(CH₃)₂)CO₂CH₂CH₂CH₃ | H | 2-Cl-6-F | 4-OCF₃ | O | O |
| SN(CH(CH₃)₂)CO₂CH₂CH₂CH₃ | H | 2-F | 3,4-Cl₂ | O | O |
| SN(CH₂CH₂CH₂CH₃)CO₂CH₃ | H | 2-F | 4-OCF₃ | O | O |
| SN(CH₂CH₂CH₂CH₃)CO₂CH₃ | H | 2-Cl-6-F | 3,4-Cl₂ | O | O |
| SN(C(CH₃)₃)CO₂CH₂CH₃ | H | 2-Cl-6-F | 4-OCF₃ | O | O |
| SN(C(CH₃)₃)CO₂CH₂CH₃ | H | 2-F | 3,4-Cl₂ | O | O |
| SN(CH₂CH₂CH₃)SO₂CH₃ | H | 2-F | 4-OCF₃ | O | O |
| SN(CH₂CH₂CH₃)SO₂CH₃ | H | 2-Cl-6-F | 3,4-Cl₂ | O | O |

TABLE 2

| R¹ | R² | X₁ | Y$_m$¹ | Z¹ | Z² |
|---|---|---|---|---|---|
| H | H | H | 4-Cl | NH | O |
| H | H | H | 4-OCF₃ | NH | O |
| H | H | H | 2-F-4-Cl | NH | O |
| H | H | H | 3,4-Cl₂ | NH | O |
| H | CN | H | 4-Cl | NH | O |
| H | CN | H | 4-OCF₃ | NH | O |
| H | CN | H | 2-F-4-Cl | NH | O |
| H | CN | H | 3,4-Cl₂ | NH | O |
| H | F | H | 4-Cl | NH | O |
| H | F | H | 4-OCF₃ | NH | O |
| H | F | H | 2-F-4-Cl | NH | O |
| H | F | H | 3,4-Cl₂ | NH | O |
| H | H | H | 4-Cl | O | O |
| H | H | H | 4-CF₃ | O | O |
| H | H | H | 4-OCF₃ | O | O |
| H | H | H | 2-F-4-Cl | O | O |
| H | H | H | 3,4-Cl₂ | O | O |
| H | H | H | 2-F-4-O(C₆H₃-2-Cl-4-CF₃) | O | O |
| H | H | H | 3,5-Cl₂-4-OCF₂CHF₂ | O | O |
| H | F | H | 4-Cl | O | O |
| H | F | H | 4-CF₃ | O | O |
| H | F | H | 4-OCF₃ | O | O |
| H | F | H | 2-F-4-Cl | O | O |
| H | F | H | 3,4-Cl₂ | O | O |
| H | F | H | 2-F-4-O(C₆H₃-2-Cl-4-CF₃) | O | O |
| H | F | H | 3,5-Cl₂-4-OCF₂CHF₂ | O | O |
| H | Cl | H | 4-Cl | O | O |
| H | Cl | H | 4-CF₃ | O | O |
| H | Cl | H | 4-OCF₃ | O | O |
| H | Cl | H | 2-F-4-Cl | O | O |
| H | Cl | H | 3,4-Cl₂ | O | O |
| H | Cl | H | 2-F-4-O(C₆H₃-2-Cl-4-CF₃) | O | O |
| H | Cl | H | 3,5-Cl₂-4-OCF₂CHF₂ | O | O |
| H | Cl | H | 4-Cl | S | O |
| H | Cl | H | 4-CF₃ | S | O |
| H | Cl | H | 4-OCF₃ | S | O |
| H | Cl | H | 2-F-4-Cl | S | O |
| H | Cl | H | 3,4-Cl₂ | S | O |
| H | Cl | H | 2-F-4-O(C₆H₃-2-Cl-4-CF₃) | S | O |
| H | Cl | H | 3,5-Cl₂-4-OCF₂CHF₂ | S | O |
| H | Br | H | 4-Cl | O | O |
| H | Br | H | 4-CF₃ | O | O |
| H | Br | H | 4-OCF₃ | O | O |
| H | Br | H | 2-F-4-Cl | O | O |
| H | Br | H | 3,4-Cl₂ | O | O |
| H | Br | H | 2-F-4-O(C₆H₃-2-Cl-4-CF₃) | O | O |
| H | Br | H | 3,5-Cl₂-4-OCF₂CHF₂ | O | O |
| CH₂OCH₃ | Br | H | 4-Cl | O | O |
| CH₂OCH₃ | Br | H | 4-CF₃ | O | O |

TABLE 2-continued

| $R^1$ | $R^2$ | $X_1$ | $Y_m^1$ | $Z^1$ | $Z^2$ |
|---|---|---|---|---|---|
| CH$_2$OCH$_3$ | Br | H | 4-OCF$_3$ | O | O |
| CH$_2$OCH$_3$ | Br | H | 2-F-4-Cl | O | O |
| CH$_2$OCH$_3$ | Br | H | 3,4-Cl$_2$ | O | O |
| CH$_2$OCH$_3$ | Br | H | 2-F-4-O(C$_6$H$_3$-2-Cl-4-CF$_3$) | O | O |
| CH$_2$OCH$_3$ | Br | H | 3,5-Cl$_2$-4-OCF$_2$CHF$_2$ | O | O |
| H | I | H | 4-Cl | O | O |
| H | I | H | 4-CF$_3$ | O | O |
| H | I | H | 4-OCF$_3$ | O | O |
| H | I | H | 2-F-4-Cl | O | O |
| H | I | H | 3,4-Cl$_2$ | O | O |
| H | I | H | 2-F-4-O(C$_6$H$_3$-2-Cl-4-CF$_3$) | O | O |
| H | I | H | 3,5-Cl$_2$-4-OCF$_2$CHF$_2$ | O | O |
| CH$_3$ | I | H | 4-Cl | O | O |
| CH$_3$ | I | H | 4-CF$_3$ | O | O |
| CH$_3$ | I | H | 4-OCF$_3$ | O | O |
| CH$_3$ | I | H | 2-F-4-Cl | O | O |
| CH$_3$ | I | H | 3,4-Cl$_2$ | O | O |
| CH$_3$ | I | H | 2-F-4-O(C$_6$H$_3$-2-Cl-4-CF$_3$) | O | O |
| CH$_3$ | I | H | 3,5-Cl$_2$-4-OCF$_2$CHF$_2$ | O | O |
| H | CH$_3$ | H | 4-Cl | O | O |
| H | CH$_3$ | H | 4-CF$_3$ | O | O |
| H | CH$_3$ | H | 4-OCF$_3$ | O | O |
| H | CH$_3$ | H | 2-F-4-Cl | O | O |
| H | CH$_3$ | H | 3,4-Cl$_2$ | O | O |
| H | CH$_3$ | H | 2-F-4-O(C$_6$H$_3$-2-Cl-4-CF$_3$) | O | O |
| H | CH$_3$ | H | 3,5-Cl$_2$-4-OCF$_2$CHF$_2$ | O | O |
| H | CF$_3$ | H | 4-Cl | O | O |
| H | CF$_3$ | H | 4-CF$_3$ | O | O |
| H | CF$_3$ | H | 4-OCF$_3$ | O | O |
| H | CF$_3$ | H | 2-F-4-Cl | O | O |
| H | CF$_3$ | H | 3,4-Cl$_2$ | O | O |
| H | CF$_3$ | H | 2-F-4-O(C$_6$H$_3$-2-Cl-4-CF$_3$) | O | O |
| H | CF$_3$ | H | 3,5-Cl$_2$-4-OCF$_2$CHF$_2$ | O | O |
| H | NO$_2$ | H | 4-Cl | O | O |
| H | NO$_2$ | H | 4-CF$_3$ | O | O |
| H | NO$_2$ | H | 4-OCF$_3$ | O | O |
| H | NO$_2$ | H | 2-F-4-Cl | O | O |
| H | NO$_2$ | H | 3,4-Cl$_2$ | O | O |
| H | NO$_2$ | H | 2-F-4-O(C$_6$H$_3$-2-Cl-4-CF$_3$) | O | O |
| H | NO$_2$ | H | 3,5-Cl$_2$-4-OCF$_2$CHF$_2$ | O | O |
| H | CN | H | 4-Cl | O | O |
| H | CN | H | 4-CF$_3$ | O | O |
| H | CN | H | 4-OCF$_3$ | O | O |
| H | CN | H | 2-F-4-Cl | O | O |
| H | CN | H | 3,4-Cl$_2$ | O | O |
| H | CN | H | 2-F-4-O(C$_6$H$_3$-2-Cl-4-CF$_3$) | O | O |
| H | CN | H | 3,5-Cl$_2$-4-OCF$_2$CHF$_2$ | O | O |
| H | CN | H | 4-Cl | S | O |
| H | CN | H | 4-CF$_3$ | S | O |
| H | CN | H | 4-OCF$_3$ | S | O |
| H | CN | H | 2-F-4-Cl | S | O |
| H | CN | H | 3,4-Cl$_2$ | S | O |
| H | CN | H | 2-F-4-O(C$_6$H$_3$-2-Cl-4-CF$_3$) | S | O |
| H | CN | H | 3,5-Cl$_2$-4-OCF$_2$CHF$_2$ | S | O |
| H | SCH$_3$ | H | 4-Cl | O | O |
| H | SCH$_3$ | H | 4-CF$_3$ | O | O |
| H | SCH$_3$ | H | 4-OCF$_3$ | O | O |
| H | SCH$_3$ | H | 2-F-4-Cl | O | O |
| H | SCH$_3$ | H | 3,4-Cl$_2$ | O | O |
| H | SCH$_3$ | H | 2-F-4-O(C$_6$H$_3$-2-Cl-4-CF$_3$) | O | O |
| H | SCH$_3$ | H | 3,5-Cl$_2$-4-OCF$_2$CHF$_2$ | O | O |
| H | SO$_2$CH$_3$ | H | 4-Cl | O | O |
| H | SO$_2$CH$_3$ | H | 4-CF$_3$ | O | O |
| H | SO$_2$CH$_3$ | H | 4-OCF$_3$ | O | O |
| H | SO$_2$CH$_3$ | H | 2-F-4-Cl | O | O |
| H | SO$_2$CH$_3$ | H | 3,4-Cl$_2$ | O | O |
| H | SO$_2$CH$_3$ | H | 2-F-4-O(C$_6$H$_3$-2-Cl-4-CF$_3$) | O | O |
| H | SO$_2$CH$_3$ | H | 3,5-Cl$_2$-4-OCF$_2$CHF$_2$ | O | O |
| H | SCF$_3$ | H | 4-Cl | O | O |
| H | SCF$_3$ | H | 4-CF$_3$ | O | O |

TABLE 2-continued

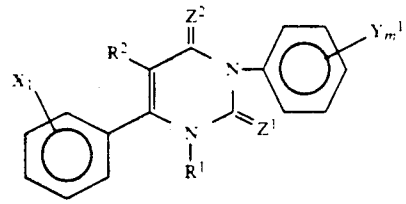

| R¹ | R² | X₁ | Y_m¹ | Z¹ | Z² |
|---|---|---|---|---|---|
| H | SCF₃ | H | 4-OCF₃ | O | O |
| H | SCF₃ | H | 2-F-4-Cl | O | O |
| H | SCF₃ | H | 3,4-Cl₂ | O | O |
| H | SCF₃ | H | 2-F-4-O(C₆H₃-2-Cl-4-CF₃) | O | O |
| H | SCF₃ | H | 3,5-Cl₂-4-OCF₂CHF₂ | O | O |
| H | OCH₃ | H | 4-Cl | O | O |
| H | OCH₃ | H | 4-CF₃ | O | O |
| H | OCH₃ | H | 4-OCF₃ | O | O |
| H | OCH₃ | H | 2-F-4-Cl | O | O |
| H | OCH₃ | H | 3,4-Cl₂ | O | O |
| H | OCH₃ | H | 2-F-4-O(C₆H₃-2-Cl-4-CF₃) | O | O |
| H | OCH₃ | H | 3,5-Cl₂-4-OCF₂CHF₂ | O | O |
| H | OCF₃ | H | 4-Cl | O | O |
| H | OCF₃ | H | 4-CF₃ | O | O |
| H | OCF₃ | H | 4-OCF₃ | O | O |
| H | OCF₃ | H | 2-F-4-Cl | O | O |
| H | OCF₃ | H | 3,4-Cl₂ | O | O |
| H | OCF₃ | H | 2-F-4-O(C₆H₃-2-Cl-4-CF₃) | O | O |
| H | OCF₃ | H | 3,5-Cl₂-4-OCF₂CHF₂ | O | O |
| H | CHO | H | 4-Cl | O | O |
| H | CHO | H | 4-CF₃ | O | O |
| H | CHO | H | 4-OCF₃ | O | O |
| H | CHO | H | 2-F-4-Cl | O | O |
| H | CHO | H | 3,4-Cl₂ | O | O |
| H | CHO | H | 2-F-4-O(C₆H₃-2-Cl-4-CF₃) | O | O |
| H | CHO | H | 3,5-Cl₂-4-OCF₂CHF₂ | O | O |
| H | H | 3-F | 4-Cl | O | O |
| H | H | 3-F | 4-CF₃ | O | O |
| H | H | 3-F | 4-OCF₃ | O | O |
| H | H | 3-F | 2-F-4-Cl | O | O |
| H | H | 3-F | 3,4-Cl₂ | O | O |
| H | H | 3-F | 2,4,5-Cl₃ | O | O |
| H | H | 3-F | 2,6-Cl₂-4-CF₃ | O | O |
| H | H | 3-Cl | 4-Cl | O | O |
| H | H | 3-Cl | 4-CF₃ | O | O |
| H | H | 3-Cl | 4-OCF₃ | O | O |
| H | H | 3-Cl | 2-F-4-Cl | O | O |
| H | H | 3-Cl | 3,4-Cl₂ | O | O |
| H | H | 3-Cl | 2,4,5-Cl₃ | O | O |
| H | H | 3-Cl | 2,6-Cl₂-4-CF₃ | O | O |
| H | H | 3-Br | 4-Cl | O | O |
| H | H | 3-Br | 4-CF₃ | O | O |
| H | H | 3-Br | 4-OCF₃ | O | O |
| H | H | 3-Br | 2-F-4-Cl | O | O |
| H | H | 3-Br | 3,4-Cl₂ | O | O |
| H | H | 3-Br | 2,4,5-Cl₃ | O | O |
| H | H | 3-Br | 2,6-Cl₂-4-CF₃ | O | O |
| H | H | 3-CF₃ | 2-F | O | O |
| H | H | 3-CF₃ | 4-F | O | O |
| H | H | 3-CF₃ | 2-Cl | O | O |
| H | H | 3-CF₃ | 3-Cl | O | O |
| H | H | 3-CF₃ | 4-Cl | O | O |
| H | H | 3-CF₃ | 4-Br | O | O |
| H | H | 3-CF₃ | 4-I | O | O |
| H | H | 3-CF₃ | 4-CH₃ | O | O |
| H | H | 3-CF₃ | 4-C(CH₃)₃ | O | O |
| H | H | 3-CF₃ | 2-CF₃ | O | O |
| H | H | 3-CF₃ | 3-CF₃ | O | O |
| H | H | 3-CF₃ | 4-CF₃ | O | O |
| H | H | 3-CF₃ | 4-OCH₃ | O | O |
| H | H | 3-CF₃ | 4-OCHF₂ | O | O |
| H | H | 3-CF₃ | 4-OCF₂Br | O | O |
| H | H | 3-CF₃ | 4-OCF₃ | O | O |
| H | H | 3-CF₃ | 4-SCH₃ | O | O |
| H | H | 3-CF₃ | 4-SO₂CH₃ | O | O |
| H | H | 3-CF₃ | 4-SCF₃ | O | O |
| H | H | 3-CF₃ | 4-SO₂CF₃ | O | O |
| H | H | 3-CF₃ | 4-COCH₃ | O | O |
| H | H | 3-CF₃ | 4-CO₂CH₂CH₃ | O | O |
| H | H | 3-CF₃ | 4-NO₂ | O | O |

TABLE 2-continued

| R¹ | R² | X₁ | Yₘ¹ | Z¹ | Z² |
|---|---|---|---|---|---|
| H | H | 3-CF₃ | 4-CN | O | O |
| H | H | 3-CF₃ | 3-OCF₂O-4 | O | O |
| H | H | 3-CF₃ | 4-O(C₆H₄-4-Cl) | O | O |
| H | H | 3-CF₃ | 4-O(Q39-5-CF₃) | O | O |
| H | H | 3-CF₃ | 2,4-F₂ | O | O |
| H | H | 3-CF₃ | 2,3-Cl₂ | O | O |
| H | H | 3-CF₃ | 2,4-Cl₂ | O | O |
| H | H | 3-CF₃ | 2,4-Cl₂ | S | O |
| H | H | 3-CF₃ | 2,5-Cl₂ | O | O |
| H | H | 3-CF₃ | 2,6-Cl₂ | O | O |
| H | H | 3-CF₃ | 3,4-Cl₂ | O | O |
| H | H | 3-CF₃ | 3,5-Cl₂ | O | O |
| H | H | 3-CF₃ | 3,4-Br₂ | O | O |
| H | H | 3-CF₃ | 2-F-4-Cl | O | O |
| H | H | 3-CF₃ | 2-F-4-Br | O | O |
| H | H | 3-CF₃ | 2-F-4-OCF₃ | O | O |
| H | H | 3-CF₃ | 2-Cl-4-CF₃ | O | O |
| H | H | 3-CF₃ | 3-Cl-4-CF₃ | O | O |
| H | H | 3-CF₃ | 2,4,5-F₃ | O | O |
| H | H | 3-CF₃ | 2,4,5-Cl₃ | O | O |
| H | H | 3-CF₃ | 2,4,6-Cl₃ | O | O |
| H | H | 3-CF₃ | 3,4,5-Cl₃ | O | O |
| H | H | 3-CF₃ | 2,5-F₂-4-Cl | O | O |
| H | H | 3-CF₃ | 2-F-4,5-Cl₂ | O | O |
| H | H | 3-CF₃ | 2,6-Cl₂-4-CF₃ | O | O |
| H | H | 3-CF₃ | 2,4-F₂-3,5-Cl₂ | O | O |
| H | H | 3-CF₃ | 2,3,4,5,6-F₅ | O | O |
| H | H | 3-CF₃ | 2,4-(NO₂)₂-6-CF₃ | O | O |
| H | H | 3-CF₃ | 2-F-4-O(C₆H₃-2-Cl-4-CF₃) | O | O |
| CH₃ | H | 3-CF₃ | 2-F | O | O |
| CH₃ | H | 3-CF₃ | 4-F | O | O |
| CH₃ | H | 3-CF₃ | 2-Cl | O | O |
| CH₃ | H | 3-CF₃ | 3-Cl | O | O |
| CH₃ | H | 3-CF₃ | 4-Cl | O | O |
| CH₃ | H | 3-CF₃ | 4-Br | O | O |
| CH₃ | H | 3-CF₃ | 4-I | O | O |
| CH₃ | H | 3-CF₃ | 4-CH₃ | O | O |
| CH₃ | H | 3-CF₃ | 4-C(CH₃)₃ | O | O |
| CH₃ | H | 3-CF₃ | 2-CF₃ | O | O |
| CH₃ | H | 3-CF₃ | 3-CF₃ | O | O |
| CH₃ | H | 3-CF₃ | 4-CF₃ | O | O |
| CH₃ | H | 3-CF₃ | 4-OCH₃ | O | O |
| CH₃ | H | 3-CF₃ | 4-OCHF₂ | O | O |
| CH₃ | H | 3-CF₃ | 4-OCF₂Br | O | O |
| CH₃ | H | 3-CF₃ | 4-OCF₃ | O | O |
| CH₃ | H | 3-CF₃ | 4-SCH₃ | O | O |
| CH₃ | H | 3-CF₃ | 4-SO₂CH₃ | O | O |
| CH₃ | H | 3-CF₃ | 4-SCF₃ | O | O |
| CH₃ | H | 3-CF₃ | 4-SO₂CF₃ | O | O |
| CH₃ | H | 3-CF₃ | 4-COCH₃ | O | O |
| CH₃ | H | 3-CF₃ | 4-CO₂CH₂CH₃ | O | O |
| CH₃ | H | 3-CF₃ | 4-NO₂ | O | O |
| CH₃ | H | 3-CF₃ | 4-CN | O | O |
| CH₃ | H | 3-CF₃ | 3-OCF₂O-4 | O | O |
| CH₃ | H | 3-CF₃ | 4-O(C₆H₄-4-Cl) | O | O |
| CH₃ | H | 3-CF₃ | 4-O(Q39-5-CF₃) | O | O |
| CH₃ | H | 3-CF₃ | 2,4-F₂ | O | O |
| CH₃ | H | 3-CF₃ | 2,3-Cl₂ | O | O |
| CH₃ | H | 3-CF₃ | 2,4-Cl₂ | O | O |
| CH₃ | H | 3-CF₃ | 2,4-Cl₂ | S | O |
| CH₃ | H | 3-CF₃ | 2,5-Cl₂ | O | O |
| CH₃ | H | 3-CF₃ | 2,6-Cl₂ | O | O |
| CH₃ | H | 3-CF₃ | 3,4-Cl₂ | O | O |
| CH₃ | H | 3-CF₃ | 3,5-Cl₂ | O | O |
| CH₃ | H | 3-CF₃ | 3,4-Br₂ | O | O |
| CH₃ | H | 3-CF₃ | 2-F-4-Cl | O | O |
| CH₃ | H | 3-CF₃ | 2-F-4-Br | O | O |
| CH₃ | H | 3-CF₃ | 2-F-4-OCF₃ | O | O |
| CH₃ | H | 3-CF₃ | 2-Cl-4-CF₃ | O | O |
| CH₃ | H | 3-CF₃ | 3-Cl-4-CF₃ | O | O |

TABLE 2-continued

| R¹ | R² | X₁ | Y_m¹ | Z¹ | Z² |
|---|---|---|---|---|---|
| CH₃ | H | 3-CF₃ | 2,4,5-F₃ | O | O |
| CH₃ | H | 3-CF₃ | 2,4,5-Cl₃ | O | O |
| CH₃ | H | 3-CF₃ | 2,4,6-Cl₃ | O | O |
| CH₃ | H | 3-CF₃ | 3,4,5-Cl₃ | O | O |
| CH₃ | H | 3-CF₃ | 2,5-F₂-4-Cl | O | O |
| CH₃ | H | 3-CF₃ | 2-F-4,5-Cl₂ | O | O |
| CH₃ | H | 3-CF₃ | 2,6-Cl₂-4-CF₃ | O | O |
| CH₃ | H | 3-CF₃ | 2,4-F₂-3,5-Cl₂ | O | O |
| CH₃ | H | 3-CF₃ | 2,3,4,5,6-F₅ | O | O |
| CH₃ | H | 3-CF₃ | 2,4-(NO₂)₂-6-CF₃ | O | O |
| CH₃ | H | 3-CF₃ | 2-F-4-O(C₆H₃-2-Cl-4-CF₃) | O | O |
| CH₂CH₃ | H | 3-CF₃ | 4-Cl | O | O |
| CH₂CH₃ | H | 3-CF₃ | 4-CF₃ | O | O |
| CH₂CH₃ | H | 3-CF₃ | 4-OCF₃ | O | O |
| CH₂CH₃ | H | 3-CF₃ | 2-F-4-Cl | O | O |
| CH₂CH₃ | H | 3-CF₃ | 3,4-Cl₂ | O | O |
| CH₂CH₃ | H | 3-CF₃ | 2,4,5-Cl₃ | O | O |
| CH₂CH₃ | H | 3-CF₃ | 2,6-Cl₂-4-CF₃ | O | O |
| CH₂OCH₃ | H | 3-CF₃ | 4-Cl | O | O |
| CH₂OCH₃ | H | 3-CF₃ | 4-CF₃ | O | O |
| CH₂OCH₃ | H | 3-CF₃ | 4-OCF₃ | O | O |
| CH₂OCH₃ | H | 3-CF₃ | 2-F-4-Cl | O | O |
| CH₂OCH₃ | H | 3-CF₃ | 3,4-Cl₂ | O | O |
| CH₂OCH₃ | H | 3-CF₃ | 2,4,5-Cl₃ | O | O |
| CH₂OCH₃ | H | 3-CF₃ | 2,6-Cl₂-4-CF₃ | O | O |
| CH₃ | Br | 3-CF₃ | 4-Cl | O | O |
| CH₃ | Br | 3-CF₃ | 4-CF₃ | O | O |
| CH₃ | Br | 3-CF₃ | 4-OCF₃ | O | O |
| CH₃ | Br | 3-CF₃ | 2-F-4-Cl | O | O |
| CH₃ | Br | 3-CF₃ | 3,4-Cl₂ | O | O |
| CH₃ | Br | 3-CF₃ | 2,4,5-Cl₃ | O | O |
| CH₃ | Br | 3-CF₃ | 2,6-Cl₂-4-CF₃ | O | O |
| CH₃ | CH₃ | 3-CF₃ | 4-Cl | O | O |
| CH₃ | CH₃ | 3-CF₃ | 4-CF₃ | O | O |
| CH₃ | CH₃ | 3-CF₃ | 4-OCF₃ | O | O |
| CH₃ | CH₃ | 3-CF₃ | 2-F-4-Cl | O | O |
| CH₃ | CH₃ | 3-CF₃ | 3,4-Cl₂ | O | O |
| CH₃ | CH₃ | 3-CF₃ | 2,4,5-Cl₃ | O | O |
| CH₃ | CH₃ | 3-CF₃ | 2,6-Cl₂-4-CF₃ | O | O |
| CH₃ | H | 3-CF₃ | 4-Cl | S | O |
| CH₃ | H | 3-CF₃ | 4-CF₃ | S | O |
| CH₃ | H | 3-CF₃ | 4-OCF₃ | S | O |
| CH₃ | H | 3-CF₃ | 2-F-4-Cl | S | O |
| CH₃ | H | 3-CF₃ | 3,4-Cl₂ | S | O |
| CH₃ | H | 3-CF₃ | 2,4,5-Cl₃ | S | O |
| CH₃ | H | 3-CF₃ | 2,6-Cl₂-4-CF₃ | S | O |
| H | H | 3-OCF₃ | 4-Cl | O | O |
| H | H | 3-OCF₃ | 4-CF₃ | O | O |
| H | H | 3-OCF₃ | 4-OCF₃ | O | O |
| H | H | 3-OCF₃ | 2-F-4-Cl | O | O |
| H | H | 3-OCF₃ | 3,4-Cl₂ | O | O |
| H | H | 3-OCF₃ | 2,4,5-Cl₃ | O | O |
| H | H | 3-OCF₃ | 2,6-Cl₂-4-CF₃ | O | O |
| H | H | 3-CN | 4-Cl | O | O |
| H | H | 3-CN | 4-CF₃ | O | O |
| H | H | 3-CN | 4-OCF₃ | O | O |
| H | H | 3-CN | 2-F-4-Cl | O | O |
| H | H | 3-CN | 3,4-Cl₂ | O | O |
| H | H | 3-CN | 2,4,5-Cl₃ | O | O |
| H | H | 3-CN | 2,6-Cl₂-4-CF₃ | O | O |
| CH₃ | H | 3-OCF₃ | 4-Cl | O | O |
| CH₃ | H | 3-OCF₃ | 4-CF₃ | O | O |
| CH₃ | H | 3-OCF₃ | 4-OCF₃ | O | O |
| CH₃ | H | 3-OCF₃ | 2-F-4-Cl | O | O |
| CH₃ | H | 3-OCF₃ | 3,4-Cl₂ | O | O |
| CH₃ | H | 3-OCF₃ | 2,4,5-Cl₃ | O | O |
| CH₃ | H | 3-OCF₃ | 2,6-Cl₂-4-CF₃ | O | O |
| CH₃ | H | 3-CN | 4-Cl | O | O |
| CH₃ | H | 3-CN | 4-CF₃ | O | O |
| CH₃ | H | 3-CN | 4-OCF₃ | O | O |

TABLE 2-continued

| R¹ | R² | X₁ | Y$_m$¹ | Z¹ | Z² |
|---|---|---|---|---|---|
| CH₃ | H | 3-CN | 2-F-4-Cl | O | O |
| CH₃ | H | 3-CN | 3,4-Cl₂ | O | O |
| CH₃ | H | 3-CN | 2,4,5-Cl₃ | O | O |
| CH₃ | H | 3-CN | 2,6-Cl₂-4-CF₃ | O | O |
| CH₃ | H | 3-Cl | 4-Cl | O | O |
| CH₃ | H | 3-Cl | 4-CF₃ | O | O |
| CH₃ | H | 3-Cl | 4-OCF₃ | O | O |
| CH₃ | H | 3-Cl | 2-F-4-Cl | O | O |
| CH₃ | H | 3-Cl | 3,4-Cl₂ | O | O |
| CH₃ | H | 3-Cl | 2,4,5-Cl₃ | O | O |
| CH₃ | H | 3-Cl | 2,6-Cl₂-4-CF₃ | O | O |
| CH₃ | H | 3-Br | 4-Cl | O | O |
| CH₃ | H | 3-Br | 4-CF₃ | O | O |
| CH₃ | H | 3-Br | 4-OCF₃ | O | O |
| CH₃ | H | 3-Br | 2-F-4-Cl | O | O |
| CH₃ | H | 3-Br | 3,4-Cl₂ | O | O |
| CH₃ | H | 3-Br | 2,4,5-Cl₃ | O | O |
| CH₃ | H | 3-Br | 2,6-Cl₂-4-CF₃ | O | O |
| CH₃ | H | 4-Cl | 4-Cl | O | O |
| CH₃ | H | 4-Cl | 4-CF₃ | O | O |
| CH₃ | H | 4-Cl | 4-OCF₃ | O | O |
| CH₃ | H | 4-Cl | 2-F-4-Cl | O | O |
| CH₃ | H | 4-Cl | 3,4-Cl₂ | O | O |
| CH₃ | H | 4-Cl | 2,4,5-Cl₃ | O | O |
| CH₃ | H | 4-Cl | 2,6-Cl₂-4-CF₃ | O | O |
| H | H | 4-Cl | 4-Cl | O | O |
| H | H | 4-Cl | 4-CF₃ | O | O |
| H | H | 4-Cl | 4-OCF₃ | O | O |
| H | H | 4-Cl | 2-F-4-Cl | O | O |
| H | H | 4-Cl | 3,4-Cl₂ | O | O |
| H | H | 4-Cl | 2,4,5-Cl₃ | O | O |
| H | H | 4-Cl | 2,6-Cl₂-4-CF₃ | O | O |
| H | H | 4-CF₃ | 4-Cl | O | O |
| H | H | 4-CF₃ | 4-CF₃ | O | O |
| H | H | 4-CF₃ | 4-OCF₃ | O | O |
| H | H | 4-CF₃ | 2-F-4-Cl | O | O |
| H | H | 4-CF₃ | 3,4-Cl₂ | O | O |
| H | H | 4-CF₃ | 2,4,5-Cl₃ | O | O |
| H | H | 4-CF₃ | 2,6-Cl₂-4-CF₃ | O | O |
| CH₃ | H | 4-CF₃ | 4-Cl | O | O |
| CH₃ | H | 4-CF₃ | 4-CF₃ | O | O |
| CH₃ | H | 4-CF₃ | 4-OCF₃ | O | O |
| CH₃ | H | 4-CF₃ | 2-F-4-Cl | O | O |
| CH₃ | H | 4-CF₃ | 3,4-Cl₂ | O | O |
| CH₃ | H | 4-CF₃ | 2,4,5-Cl₃ | O | O |
| CH₃ | H | 4-CF₃ | 2,6-Cl₂-4-CF₃ | O | O |
| CH₃ | H | 3,4-Cl₂ | 4-Cl | O | O |
| CH₃ | H | 3,4-Cl₂ | 4-CF₃ | O | O |
| CH₃ | H | 3,4-Cl₂ | 4-OCF₃ | O | O |
| CH₃ | H | 3,4-Cl₂ | 2-F-4-Cl | O | O |
| CH₃ | H | 3,4-Cl₂ | 3,4-Cl₂ | O | O |
| CH₃ | H | 3,4-Cl₂ | 2,4,5-Cl₃ | O | O |
| CH₃ | H | 3,4-Cl₂ | 2,6-Cl₂-4-CF₃ | O | O |
| H | H | 3,4-Cl₂ | 4-Cl | O | O |
| H | H | 3,4-Cl₂ | 4-CF₃ | O | O |
| H | H | 3,4-Cl₂ | 4-OCF₃ | O | O |
| H | H | 3,4-Cl₂ | 2-F-4-Cl | O | O |
| H | H | 3,4-Cl₂ | 3,4-Cl₂ | O | O |
| H | H | 3,4-Cl₂ | 2,4,5-Cl₃ | O | O |
| H | H | 3,4-Cl₂ | 2,6-Cl₂-4-CF₃ | O | O |
| H | H | 3,5-(CF₃)₂ | 4-Cl | O | O |
| H | H | 3,5-(CF₃)₂ | 4-CF₃ | O | O |
| H | H | 3,5-(CF₃)₂ | 4-OCF₃ | O | O |
| H | H | 3,5-(CF₃)₂ | 2-F-4-Cl | O | O |
| H | H | 3,5-(CF₃)₂ | 3,4-Cl₂ | O | O |
| H | H | 3,5-(CF₃)₂ | 2,4,5-Cl₃ | O | O |
| H | H | 3,5-(CF₃)₂ | 2,6-Cl₂-4-CF₃ | O | O |
| CH₃ | H | 3,5-(CF₃)₂ | 4-Cl | O | O |
| CH₃ | H | 3,5-(CF₃)₂ | 4-CF₃ | O | O |
| CH₃ | H | 3,5-(CF₃)₂ | 4-OCF₃ | O | O |

TABLE 2-continued

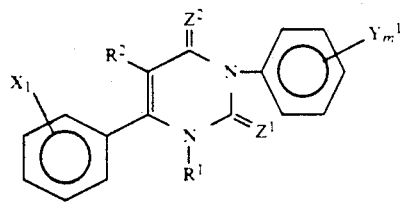

| R¹ | R² | X₁ | Y$_m$¹ | Z¹ | Z² |
|---|---|---|---|---|---|
| CH₃ | H | 3,5-(CF₃)₂ | 2-F-4-Cl | O | O |
| CH₃ | H | 3,5-(CF₃)₂ | 3,4-Cl₂ | O | O |
| CH₃ | H | 3,5-(CF₃)₂ | 2,4,5-Cl₃ | O | O |
| CH₃ | H | 3,5-(CF₃)₂ | 2,6-Cl₂-4-CF₃ | O | O |
| CH₃ | H | 3,4,5-Cl₃ | 4-Cl | O | O |
| CH₃ | H | 3,4,5-Cl₃ | 4-CF₃ | O | O |
| CH₃ | H | 3,4,5-Cl₃ | 4-OCF₃ | O | O |
| CH₃ | H | 3,4,5-Cl₃ | 2-F-4-Cl | O | O |
| CH₃ | H | 3,4,5-Cl₃ | 3,4-Cl₂ | O | O |
| CH₃ | H | 3,4,5-Cl₃ | 2,4,5-Cl₃ | O | O |
| CH₃ | H | 3,4,5-Cl₃ | 2,6-Cl₂-4-CF₃ | O | O |
| H | H | 3,4,5-Cl₃ | 4-Cl | O | O |
| H | H | 3,4,5-Cl₃ | 4-CF₃ | O | O |
| H | H | 3,4,5-Cl₃ | 4-OCF₃ | O | O |
| H | H | 3,4,5-Cl₃ | 2-F-4-Cl | O | O |
| H | H | 3,4,5-Cl₃ | 3,4-Cl₂ | O | O |
| H | H | 3,4,5-Cl₃ | 2,4,5-Cl₃ | O | O |
| H | H | 3,4,5-Cl₃ | 2,6-Cl₂-4-CF₃ | O | O |

TABLE 3

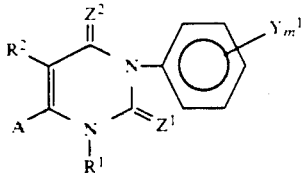 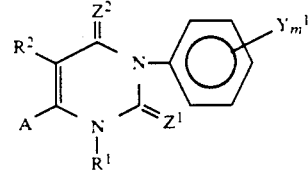

| R¹ | R² | A | Y$_m$¹ | Z¹ | Z² | R¹ | R² | A | Y$_m$¹ | Z¹ | Z² |
|---|---|---|---|---|---|---|---|---|---|---|---|
| H | H | Q1 | 4-Cl | O | O | H | H | Q19 | 4-OCF₃ | O | O |
| H | H | Q1 | 4-OCF₃ | O | O | H | H | Q20 | 4-Cl | O | O |
| H | H | Q2 | 4-Cl | O | O | H | H | Q20 | 4-OCF₃ | O | O |
| H | H | Q2 | 4-OCF₃ | O | O | H | H | Q21 | 4-Cl | O | O |
| H | H | Q3 | 4-Cl | O | O | H | H | Q21 | 4-OCF₃ | O | O |
| H | H | Q3 | 4-OCF₃ | O | O | H | H | Q22 | 4-Cl | O | O |
| H | H | Q4 | 4-Cl | O | O | H | H | Q22 | 4-OCF₃ | O | O |
| H | H | Q4 | 4-OCF₃ | O | O | H | H | Q23 | 4-Cl | O | O |
| H | H | Q5 | 4-Cl | O | O | H | H | Q23 | 4-OCF₃ | O | O |
| H | H | Q5 | 4-OCF₃ | O | O | H | H | Q24 | 4-Cl | O | O |
| H | H | Q6 | 4-Cl | O | O | H | H | Q24 | 4-OCF₃ | O | O |
| H | H | Q6 | 4-OCF₃ | O | O | H | H | Q25 | 4-Cl | O | O |
| H | H | Q7 | 4-Cl | O | O | H | H | Q25 | 4-OCF₃ | O | O |
| H | H | Q7 | 4-OCF₃ | O | O | H | H | Q26 | 4-Cl | O | O |
| H | H | Q8 | 4-Cl | O | O | H | H | Q26 | 4-OCF₃ | O | O |
| H | H | Q8 | 4-OCF₃ | O | O | H | H | Q27 | 4-Cl | O | O |
| H | H | Q9 | 4-Cl | O | O | H | H | Q27 | 4-OCF₃ | O | O |
| H | H | Q9 | 4-OCF₃ | O | O | H | H | Q28 | 4-Cl | O | O |
| H | H | Q10 | 4-Cl | O | O | H | H | Q28 | 4-OCF₃ | O | O |
| H | H | Q10 | 4-OCF₃ | O | O | H | H | Q29 | 4-Cl | O | O |
| H | H | Q11 | 4-Cl | O | O | H | H | Q29 | 4-OCF₃ | O | O |
| H | H | Q11 | 4-OCF₃ | O | O | H | H | Q30 | 4-Cl | O | O |
| H | H | Q12 | 4-Cl | O | O | H | H | Q30 | 4-OCF₃ | O | O |
| H | H | Q12 | 4-OCF₃ | O | O | H | H | Q31 | 4-Cl | O | O |
| H | H | Q13 | 4-Cl | O | O | H | H | Q31 | 4-OCF₃ | O | O |
| H | H | Q13 | 4-OCF₃ | O | O | H | H | Q32 | 4-Cl | O | O |
| H | H | Q14 | 4-Cl | O | O | H | H | Q32 | 4-OCF₃ | O | O |
| H | H | Q14 | 4-OCF₃ | O | O | H | H | Q33 | 4-Cl | O | O |
| H | H | Q15 | 4-Cl | O | O | H | H | Q33 | 4-OCF₃ | O | O |
| H | H | Q15 | 4-OCF₃ | O | O | H | H | Q34 | 4-Cl | O | O |
| H | H | Q16 | 4-Cl | O | O | H | H | Q34 | 4-OCF₃ | O | O |
| H | H | Q16 | 4-OCF₃ | O | O | H | H | Q35 | 4-Cl | O | O |
| H | H | Q17 | 4-Cl | O | O | H | H | Q35 | 4-OCF₃ | O | O |
| H | H | Q17 | 4-OCF₃ | O | O | H | H | Q36 | 4-Cl | O | O |
| H | H | Q18 | 4-Cl | O | O | H | H | Q36 | 4-OCF₃ | O | O |
| H | H | Q18 | 4-OCF₃ | O | O | H | H | Q37 | 4-Cl | O | O |
| H | H | Q19 | 4-Cl | O | O | H | H | Q37 | 4-OCF₃ | O | O |

TABLE 3-continued

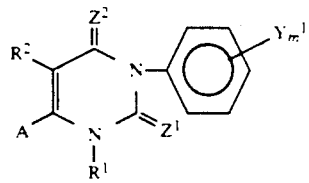 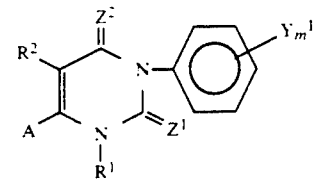

| R¹ | R² | A | $Y_m^1$ | Z¹ | Z² |
|---|---|---|---|---|---|
| H | H | Q40 | 4-Cl | O | O |
| H | H | Q40 | 4-OCF₃ | O | O |
| H | H | Q41 | 4-Cl | O | O |
| H | H | Q41 | 4-OCF₃ | O | O |
| H | H | Q42 | 4-Cl | O | O |
| H | H | Q42 | 4-OCF₃ | O | O |
| H | H | Q43 | 4-Cl | O | O |
| H | H | Q43 | 4-OCF₃ | O | O |
| H | H | Q44 | 4-Cl | O | O |
| H | H | Q44 | 4-OCF₃ | O | O |
| H | H | Q45 | 4-Cl | O | O |
| H | H | Q45 | 4-OCF₃ | O | O |
| H | H | Q46 | 4-Cl | O | O |
| H | H | Q46 | 4-OCF₃ | O | O |
| H | H | Q47 | 4-Cl | O | O |
| H | H | Q47 | 4-OCF₃ | O | O |
| H | H | Q48 | 4-Cl | O | O |
| H | H | Q48 | 4-OCF₃ | O | O |
| H | H | Q38 | 4-Cl | O | O |
| H | H | Q38 | 4-CF₃ | O | O |
| H | H | Q38 | 4-OCF₃ | O | O |
| H | H | Q38 | 3-OCF₂O-4 | O | O |
| H | H | Q38 | 4-O(C₆H₃-2-Cl-4-CF₃) | O | O |
| H | H | Q38 | 4-O(Q38-3-Cl-5-CF₃) | O | O |
| H | H | Q38 | 3,4-Cl₂ | O | O |
| H | H | Q38 | 2-F-4-Cl | O | O |
| H | H | Q38 | 2-F-4-OCF₂CHF₂ | O | O |
| H | H | Q38 | 3,5-Cl₂-4-OCF₂CHF₂ | O | O |
| H | H | Q38 | 2,4-F₂-3,5-Cl₂ | O | O |
| H | Br | Q38 | 4-Cl | O | O |
| H | Br | Q38 | 4-CF₃ | O | O |
| H | Br | Q38 | 4-OCF₃ | O | O |
| H | Br | Q38 | 3-OCF₂O-4 | O | O |
| H | Br | Q38 | 4-O(C₆H₃-2-Cl-4-CF₃) | O | O |
| H | Br | Q38 | 4-O(Q38-3-Cl-5-CF₃) | O | O |
| H | Br | Q38 | 3,4-Cl₂ | O | O |
| H | Br | Q38 | 2-F-4-Cl | O | O |
| H | Br | Q38 | 2-F-4-OCF₂CHF₂ | O | O |
| H | Br | Q38 | 3,5-Cl₂-4-OCF₂CHF₂ | O | O |
| H | Br | Q38 | 2,4-F₂-3,5-Cl₂ | O | O |
| H | I | Q38 | 4-Cl | O | O |
| H | I | Q38 | 4-OCF₃ | O | O |
| H | I | Q38 | 3-OCF₂O-4 | O | O |
| H | I | Q38 | 4-O(C₆H₃-2-Cl-4-CF₃) | O | O |
| H | I | Q38 | 4-O(Q38-3-Cl-5-CF₃) | O | O |
| H | I | Q38 | 3,4-Cl₂ | O | O |
| H | I | Q38 | 2-F-4-Cl | O | O |
| H | I | Q38 | 2-F-4-OCF₂CHF₂ | O | O |
| H | I | Q38 | 3,5-Cl₂-4-OCF₂CHF₂ | O | O |
| H | I | Q38 | 2,4-F₂-3,5-Cl₂ | O | O |
| H | Cl | Q38 | 4-Cl | O | O |
| H | Cl | Q38 | 4-CF₃ | O | O |
| H | Cl | Q38 | 4-OCF₃ | O | O |
| H | Cl | Q38 | 3-OCF₂O-4 | O | O |
| H | Cl | Q38 | 4-O(C₆H₃-2-Cl-4-CF₃) | O | O |
| H | Cl | Q38 | 4-O(Q38-3-Cl-5-CF₃) | O | O |
| H | Cl | Q38 | 3,4-Cl₂ | O | O |
| H | Cl | Q38 | 2-F-4-Cl | O | O |
| H | Cl | Q38 | 2-F-4-OCF₂CHF₂ | O | O |
| H | Cl | Q38 | 3,5-Cl₂-4-OCF₂CHF₂ | O | O |
| H | Cl | Q38 | 2,4-F₂-3,5-Cl₂ | O | O |
| H | CH₃ | Q38 | 4-Cl | O | O |
| H | CH₃ | Q38 | 4-OCF₃ | O | O |
| H | CH₃ | Q38 | 3-OCF₂O-4 | O | O |
| H | CH₃ | Q38 | 4-O(C₆H₃-2-Cl-4-CF₃) | O | O |
| H | CH₃ | Q38 | 4-O(Q38-3-Cl-5-CF₃) | O | O |
| H | CH₃ | Q38 | 3,4-Cl₂ | O | O |
| H | CH₃ | Q38 | 2-F-4-Cl | O | O |
| H | CH₃ | Q38 | 2-F-4-OCF₂CHF₂ | O | O |
| H | CH₃ | Q38 | 3,5-Cl₂-4-OCF₂CHF₂ | O | O |
| H | CH₃ | Q38 | 2,4-F₂-3,5-Cl₂ | O | O |
| H | CN | Q38 | 4-Cl | O | O |
| H | CN | Q38 | 4-CF₃ | O | O |
| H | CN | Q38 | 4-OCF₃ | O | O |
| H | CN | Q38 | 3-OCF₂O-4 | O | O |
| H | CN | Q38 | 4-O(C₆H₃-2-Cl-4-CF₃) | O | O |
| H | CN | Q38 | 4-O(Q38-3-Cl-5-CF₃) | O | O |
| H | CN | Q38 | 3,4-Cl₂ | O | O |
| H | CN | Q38 | 2-F-4-Cl | O | O |
| H | CN | Q38 | 2-F-4-OCF₂CHF₂ | O | O |
| H | CN | Q38 | 3,5-Cl₂-4-OCF₂CHF₂ | O | O |
| H | CN | Q38 | 2,4-F₂-3,5-Cl₂ | O | O |
| CH₃ | H | Q38 | 4-Cl | O | O |
| CH₃ | H | Q38 | 4-OCF₃ | O | O |
| CH₃ | H | Q38 | 3-OCF₂O-4 | O | O |
| CH₃ | H | Q38 | 4-O(C₆H₃-2-Cl-4-CF₃) | O | O |
| CH₃ | H | Q38 | 4-O(Q38-3-Cl-5-CF₃) | O | O |
| CH₃ | H | Q38 | 3,4-Cl₂ | O | O |
| CH₃ | H | Q38 | 2-F-4-Cl | O | O |
| CH₃ | H | Q38 | 2-F-4-OCF₂CHF₂ | O | O |
| CH₃ | H | Q38 | 3,5-Cl₂-4-OCF₂CHF₂ | O | O |
| CH₃ | H | Q38 | 2,4-F₂-3,5-Cl₂ | O | O |
| H | H | Q38 | 4-Cl | S | O |
| H | H | Q38 | 4-CF₃ | S | O |
| H | H | Q38 | 4-OCF₃ | S | O |
| H | H | Q38 | 3-OCF₂O-4 | S | O |
| H | H | Q38 | 4-O(C₆H₃-2-Cl-4-CF₃) | S | O |
| H | H | Q38 | 4-O(Q38-3-Cl-5-CF₃) | S | O |
| H | H | Q38 | 3,4-Cl₂ | S | O |
| H | H | Q38 | 2-F-4-Cl | S | O |
| H | H | Q38 | 2-F-4-OCF₂CHF₂ | S | O |
| H | H | Q38 | 3,5-Cl₂-4-OCF₂CHF₂ | S | O |
| H | H | Q38 | 2,4-F₂-3,5-Cl₂ | S | O |
| H | H | Q6-3-Cl | 4-Cl | O | O |
| H | H | Q6-3-Cl | 4-OCF₃ | O | O |
| H | H | Q6-3-Cl | 3-OCF₂O-4 | O | O |
| H | H | Q6-3-Cl | 4-O(C₆H₃-2-Cl-4-CF₃) | O | O |
| H | H | Q6-3-Cl | 4-O(Q38-3-Cl-5-CF₃) | O | O |
| H | H | Q6-3-Cl | 3,4-Cl₂ | O | O |
| H | H | Q6-3-Cl | 2-F-4-Cl | O | O |
| H | H | Q6-3-Cl | 2-F-4-OCF₂CHF₂ | O | O |
| H | H | Q6-3-Cl | 3,5-Cl₂-4-OCF₂CHF₂ | O | O |
| H | H | Q6-3-Cl | 2,4-F₂-3,5-Cl₂ | O | O |
| H | H | Q7-2-Cl | 4-Cl | O | O |
| H | H | Q7-2-Cl | 4-OCF₃ | O | O |
| H | H | Q7-2-Cl | 3-OCF₂O-4 | O | O |
| H | H | Q7-2-Cl | 4-O(C₆H₃-2-Cl-4-CF₃) | O | O |
| H | H | Q7-2-Cl | 4-O(Q38-3-Cl-5-CF₃) | O | O |
| H | H | Q7-2-Cl | 3,4-Cl₂ | O | O |
| H | H | Q7-2-Cl | 2-F-4-Cl | O | O |
| H | H | Q7-2-Cl | 2-F-4-OCF₂CHF₂ | O | O |
| H | H | Q7-2-Cl | 3,5-Cl₂-4-OCF₂CHF₂ | O | O |
| H | H | Q7-2-Cl | 2,4-F₂-3,5-Cl₂ | O | O |
| H | H | Q7-4-Cl | 4-Cl | O | O |
| H | H | Q7-4-Cl | 4-OCF₃ | O | O |
| H | H | Q7-4-Cl | 3-OCF₂O-4 | O | O |
| H | H | Q7-4-Cl | 4-O(C₆H₃-2-Cl-4-CF₃) | O | O |
| H | H | Q7-4-Cl | 4-O(Q38-3-Cl-5-CF₃) | O | O |
| H | H | Q7-4-Cl | 3,4-Cl₂ | O | O |
| H | H | Q7-4-Cl | 2-F-4-Cl | O | O |
| H | H | Q7-4-Cl | 2-F-4-OCF₂CHF₂ | O | O |
| H | H | Q7-4-Cl | 3,5-Cl₂-4-OCF₂CHF₂ | O | O |
| H | H | Q7-4-Cl | 2,4-F₂-3,5-Cl₂ | O | O |
| H | H | Q10-1-CH₃ | 4-Cl | O | O |
| H | H | Q10-1-CH₃ | 4-OCF₃ | O | O |
| H | H | Q10-1-CH₃ | 3-OCF₂O-4 | O | O |
| H | H | Q10-1-CH₃ | 4-O(C₆H₃-2-Cl-4-CF₃) | O | O |
| H | H | Q10-1-CH₃ | 4-O(Q38-3-Cl-5-CF₃) | O | O |
| H | H | Q10-1-CH₃ | 3,4-Cl₂ | O | O |
| H | H | Q10-1-CH₃ | 2-F-4-Cl | O | O |
| H | H | Q10-1-CH₃ | 2-F-4-OCF₂CHF₂ | O | O |
| H | H | Q10-1-CH₃ | 3,5-Cl₂-4-OCF₂CHF₂ | O | O |

TABLE 3-continued

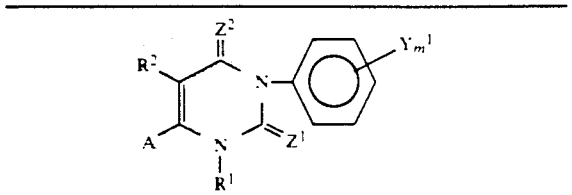

| R¹ | R² | A | $Y_m^1$ | Z¹ | Z² |
|---|---|---|---|---|---|
| H | H | Q10-1-CH₃ | 2,4-F₂-3,5-Cl₂ | O | O |
| H | H | Q27-1-CH₃ | 4-Cl | O | O |
| H | H | Q27-1-CH₃ | 4-OCF₃ | O | O |
| H | H | Q27-1-CH₃ | 3-OCF₂O-4 | O | O |
| H | H | Q27-1-CH₃ | 4-O(C₆H₃-2-Cl-4-CF₃) | O | O |
| H | H | Q27-1-CH₃ | 4-O(Q38-3-Cl-5-CF₃) | O | O |
| H | H | Q27-1-CH₃ | 3,4-Cl₂ | O | O |
| H | H | Q27-1-CH₃ | 2-F-4-Cl | O | O |
| H | H | Q27-1-CH₃ | 2-F-4-OCF₂CHF₂ | O | O |
| H | H | Q27-1-CH₃ | 3,5-Cl₂-4-OCF₂CHF₂ | O | O |
| H | H | Q27-1-CH₃ | 2,4-F₂-3,5-Cl₂ | O | O |
| H | H | Q38-3-F | 4-Cl | O | O |
| H | H | Q38-3-F | 4-OCF₃ | O | O |
| H | H | Q38-3-F | 3-OCF₂O-4 | O | O |
| H | H | Q38-3-F | 4-O(C₆H₃-2-Cl-4-CF₃) | O | O |
| H | H | Q38-3-F | 4-O(Q38-3-Cl-5-CF₃) | O | O |
| H | H | Q38-3-F | 3,4-Cl₂ | O | O |
| H | H | Q38-3-F | 2-F-4-Cl | O | O |
| H | H | Q38-3-F | 2-F-4-OCF₂CHF₂ | O | O |
| H | H | Q38-3-F | 3,5-Cl₂-4-OCF₂CHF₂ | O | O |
| H | H | Q38-3-F | 2,4-F₂-3,5-Cl₂ | O | O |
| H | H | Q38-3-Br | 4-Cl | O | O |
| H | H | Q38-3-Br | 4-OCF₃ | O | O |
| H | H | Q38-3-Br | 3-OCF₂O-4 | O | O |
| H | H | Q38-3-Br | 4-O(C₆H₃-2-Cl-4-CF₃) | O | O |
| H | H | Q38-3-Br | 4-O(Q38-3-Cl-5-CF₃) | O | O |
| H | H | Q38-3-Br | 3,4-Cl₂ | O | O |
| H | H | Q38-3-Br | 2-F-4-Cl | O | O |
| H | H | Q38-3-Br | 2-F-4-OCF₂CHF₂ | O | O |
| H | H | Q38-3-Br | 3,5-Cl₂-4-OCF₂CHF₂ | O | O |
| H | H | Q38-3-Br | 2,4-F₂-3,5-Cl₂ | O | O |
| H | H | Q38-3-CF₃ | 4-Cl | O | O |
| H | H | Q38-3-CF₃ | 4-OCF₃ | O | O |
| H | H | Q38-3-CF₃ | 3-OCF₂O-4 | O | O |
| H | H | Q38-3-CF₃ | 4-O(C₆H₃-2-Cl-4-CF₃) | O | O |
| H | H | Q38-3-CF₃ | 4-O(Q38-3-Cl-5-CF₃) | O | O |
| H | H | Q38-3-CF₃ | 3,4-Cl₂ | O | O |
| H | H | Q38-3-CF₃ | 2-F-4-Cl | O | O |
| H | H | Q38-3-CF₃ | 2-F-4-OCF₂CHF₂ | O | O |
| H | H | Q38-3-CF₃ | 3,5-Cl₂-4-OCF₂CHF₂ | O | O |
| H | H | Q38-3-CF₃ | 2,4-F₂-3,5-Cl₂ | O | O |
| H | H | Q38-3-CN | 4-Cl | O | O |
| H | H | Q38-3-CN | 4-OCF₃ | O | O |
| H | H | Q38-3-CN | 3-OCF₂O-4 | O | O |
| H | H | Q38-3-CN | 4-O(C₆H₃-2-Cl-4-CF₃) | O | O |
| H | H | Q38-3-CN | 4-O(Q38-3-Cl-5-CF₃) | O | O |
| H | H | Q38-3-CN | 3,4-Cl₂ | O | O |
| H | H | Q38-3-CN | 2-F-4-Cl | O | O |
| H | H | Q38-3-CN | 2-F-4-OCF₂CHF₂ | O | O |
| H | H | Q38-3-CN | 3,5-Cl₂-4-OCF₂CHF₂ | O | O |
| H | H | Q38-3-CN | 2,4-F₂-3,5-Cl₂ | O | O |
| H | H | Q38-3-NO₂ | 4-Cl | O | O |
| H | H | Q38-3-NO₂ | 4-OCF₃ | O | O |
| H | H | Q38-3-NO₂ | 3-OCF₂O-4 | O | O |
| H | H | Q38-3-NO₂ | 4-O(C₆H₃-2-Cl-4-CF₃) | O | O |
| H | H | Q38-3-NO₂ | 4-O(Q38-3-Cl-5-CF₃) | O | O |
| H | H | Q38-3-NO₂ | 3,4-Cl₂ | O | O |
| H | H | Q38-3-NO₂ | 2-F-4-Cl | O | O |
| H | H | Q38-3-NO₂ | 2-F-4-OCF₂CHF₂ | O | O |
| H | H | Q38-3-NO₂ | 3,5-Cl₂-4-OCF₂CHF₂ | O | O |
| H | H | Q38-3-NO₂ | 2,4-F₂-3,5-Cl₂ | O | O |
| H | H | Q39-2-Cl | 4-Cl | O | O |
| H | H | Q39-2-Cl | 4-OCF₃ | O | O |
| H | H | Q39-2-Cl | 3-OCF₂O-4 | O | O |
| H | H | Q39-2-Cl | 4-O(C₆H₃-2-Cl-4-CF₃) | O | O |
| H | H | Q39-2-Cl | 4-O(Q38-3-Cl-5-CF₃) | O | O |
| H | H | Q39-2-Cl | 3,4-Cl₂ | O | O |
| H | H | Q39-2-Cl | 2-F-4-Cl | O | O |
| H | H | Q39-2-Cl | 2-F-4-OCF₂CHF₂ | O | O |
| H | H | Q39-2-Cl | 3,5-Cl₂-4-OCF₂CHF₂ | O | O |
| H | H | Q39-2-Cl | 2,4-F₂-3,5-Cl₂ | O | O |
| H | H | Q39-4-Cl | 4-Cl | O | O |
| H | H | Q39-4-Cl | 4-OCF₃ | O | O |
| H | H | Q39-4-Cl | 3-OCF₂O-4 | O | O |
| H | H | Q39-4-Cl | 4-O(C₆H₃-2-Cl-4-CF₃) | O | O |
| H | H | Q39-4-Cl | 4-O(Q38-3-Cl-5-CF₃) | O | O |
| H | H | Q39-4-Cl | 3,4-Cl₂ | O | O |
| H | H | Q39-4-Cl | 2-F-4-Cl | O | O |
| H | H | Q39-4-Cl | 2-F-4-OCF₂CHF₂ | O | O |
| H | H | Q39-4-Cl | 3,5-Cl₂-4-OCF₂CHF₂ | O | O |
| H | H | Q39-4-Cl | 2,4-F₂-3,5-Cl₂ | O | O |
| H | H | Q39-2-OCH₃ | 4-Cl | O | O |
| H | H | Q39-2-OCH₃ | 4-OCF₃ | O | O |
| H | H | Q39-2-OCH₃ | 3-OCF₂O-4 | O | O |
| H | H | Q39-2-OCH₃ | 4-O(C₆H₃-2-Cl-4-CF₃) | O | O |
| H | H | Q39-2-OCH₃ | 4-O(Q38-3-Cl-5-CF₃) | O | O |
| H | H | Q39-2-OCH₃ | 3,4-Cl₂ | O | O |
| H | H | Q39-2-OCH₃ | 2-F-4-Cl | O | O |
| H | H | Q39-2-OCH₃ | 2-F-4-OCF₂CHF₂ | O | O |
| H | H | Q39-2-OCH₃ | 3,5-Cl₂-4-OCF₂CHF₂ | O | O |
| H | H | Q39-2-OCH₃ | 2,4-F₂-3,5-Cl₂ | O | O |
| H | H | Q39-2-SCH₃ | 4-Cl | O | O |
| H | H | Q39-2-SCH₃ | 4-OCF₃ | O | O |
| H | H | Q39-2-SCH₃ | 3-OCF₂O-4 | O | O |
| H | H | Q39-2-SCH₃ | 4-O(C₆H₃-2-Cl-4-CF₃) | O | O |
| H | H | Q39-2-SCH₃ | 4-O(Q38-3-Cl-5-CF₃) | O | O |
| H | H | Q39-2-SCH₃ | 3,4-Cl₂ | O | O |
| H | H | Q39-2-SCH₃ | 2-F-4-Cl | O | O |
| H | H | Q39-2-SCH₃ | 2-F-4-OCF₂CHF₂ | O | O |
| H | H | Q39-2-SCH₃ | 3,5-Cl₂-4-OCF₂CHF₂ | O | O |
| H | H | Q39-2-SCH₃ | 2,4-F₂-3,5-Cl₂ | O | O |
| H | H | Q39-2-OCF₃ | 4-Cl | O | O |
| H | H | Q39-2-OCF₃ | 4-OCF₃ | O | O |
| H | H | Q39-2-OCF₃ | 3-OCF₂O-4 | O | O |
| H | H | Q39-2-OCF₃ | 4-O(C₆H₃-2-Cl-4-CF₃) | O | O |
| H | H | Q39-2-OCF₃ | 4-O(Q38-3-Cl-5-CF₃) | O | O |
| H | H | Q39-2-OCF₃ | 3,4-Cl₂ | O | O |
| H | H | Q39-2-OCF₃ | 2-F-4-Cl | O | O |
| H | H | Q39-2-OCF₃ | 2-F-4-OCF₂CHF₂ | O | O |
| H | H | Q39-2-OCF₃ | 3,5-Cl₂-4-OCF₂CHF₂ | O | O |
| H | H | Q39-2-OCF₃ | 2,4-F₂-3,5-Cl₂ | O | O |
| H | H | Q38-3-F-6-Cl | 4-Cl | O | O |
| H | H | Q38-3-F-6-Cl | 4-OCF₃ | O | O |
| H | H | Q38-3-F-6-Cl | 3-OCF₂O-4 | O | O |
| H | H | Q38-3-F-6-Cl | 4-O(C₆H₃-2-Cl-4-CF₃) | O | O |
| H | H | Q38-3-F-6-Cl | 4-O(Q38-3-Cl-5-CF₃) | O | O |
| H | H | Q38-3-F-6-Cl | 3,4-Cl₂ | O | O |
| H | H | Q38-3-F-6-Cl | 2-F-4-Cl | O | O |
| H | H | Q38-3-F-6-Cl | 2-F-4-OCF₂CHF₂ | O | O |
| H | H | Q38-3-F-6-Cl | 3,5-Cl₂-4-OCF₂CHF₂ | O | O |
| H | H | Q38-3-F-6-Cl | 2,4-F₂-3,5-Cl₂ | O | O |
| H | H | Q38-3,6-Cl₂ | 4-Cl | O | O |
| H | H | Q38-3,6-Cl₂ | 4-OCF₃ | O | O |
| H | H | Q38-3,6-Cl₂ | 3-OCF₂O-4 | O | O |
| H | H | Q38-3,6-Cl₂ | 4-O(C₆H₃-2-Cl-4-CF₃) | O | O |
| H | H | Q38-3,6-Cl₂ | 4-O(Q38-3-Cl-5-CF₃) | O | O |
| H | H | Q38-3,6-Cl₂ | 3,4-Cl₂ | O | O |
| H | H | Q38-3,6-Cl₂ | 2-F-4-Cl | O | O |
| H | H | Q38-3,6-Cl₂ | 2-F-4-OCF₂CHF₂ | O | O |
| H | H | Q38-3,6-Cl₂ | 3,5-Cl₂-4-OCF₂CHF₂ | O | O |
| H | H | Q38-3,6-Cl₂ | 2,4-F₂-3,5-Cl₂ | O | O |
| H | H | Q39-2,6-Cl₂ | 4-Cl | O | O |
| H | H | Q39-2,6-Cl₂ | 4-OCF₃ | O | O |
| H | H | Q39-2,6-Cl₂ | 3-OCF₂O-4 | O | O |
| H | H | Q39-2,6-Cl₂ | 4-O(C₆H₃-2-Cl-4-CF₃) | O | O |
| H | H | Q39-2,6-Cl₂ | 4-O(Q38-3-Cl-5-CF₃) | O | O |
| H | H | Q39-2,6-Cl₂ | 3,4-Cl₂ | O | O |
| H | H | Q39-2,6-Cl₂ | 2-F-4-Cl | O | O |
| H | H | Q39-2,6-Cl₂ | 2-F-4-OCF₂CHF₂ | O | O |
| H | H | Q39-2,6-Cl₂ | 3,5-Cl₂-4-OCF₂CHF₂ | O | O |
| H | H | Q39-2,6-Cl₂ | 2,4-F₂-3,5-Cl₂ | O | O |
| H | H | Q38-3-Cl | 4-Cl | O | O |

TABLE 3-continued

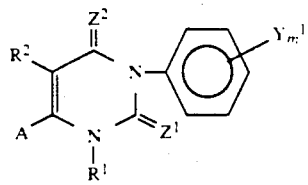

| R¹ | R² | A | $Y_m^1$ | Z¹ | Z² |
|---|---|---|---|---|---|
| H | H | Q38-3-Cl | 4-OCF₃ | O | O |
| H | H | Q38-3-Cl | 3-OCF₂O-4 | O | O |
| H | H | Q38-3-Cl | 4-O(C₆H₃-2-Cl-4-CF₃) | O | O |
| H | H | Q38-3-Cl | 4-O(Q38-3-Cl-5-CF₃) | O | O |
| H | H | Q38-3-Cl | 3,4-Cl₂ | O | O |
| H | H | Q38-3-Cl | 2-F-4-Cl | O | O |
| H | H | Q38-3-Cl | 2-F-4-OCF₂CHF₂ | O | O |
| H | H | Q38-3-Cl | 3,5-Cl₂-4-OCF₂CHF₂ | O | O |
| H | H | Q38-3-Cl | 2,4-F₂-3,5-Cl₂ | O | O |
| H | H | Q38-3-Cl | 4-F | O | O |
| H | H | Q38-3-Cl | 4-Br | O | O |
| H | H | Q38-3-Cl | 4-I | O | O |
| H | H | Q38-3-Cl | 4-CH₃ | O | O |
| H | H | Q38-3-Cl | 4-C(CH₃)₃ | O | O |
| H | H | Q38-3-Cl | 4-CF₃ | O | O |
| H | H | Q38-3-Cl | 4-OCH₃ | O | O |
| H | H | Q38-3-Cl | 4-OCHF₂ | O | O |
| H | H | Q38-3-Cl | 4-OCF₂Br | O | O |
| H | H | Q38-3-Cl | 4-OCF₂CHF₂ | O | O |
| H | H | Q38-3-Cl | 4-SCH₃ | O | O |
| H | H | Q38-3-Cl | 4-SCF₂Cl | O | O |
| H | H | Q38-3-Cl | 4-SCF₃ | O | O |
| H | H | Q38-3-Cl | 4-SOCH₃ | O | O |
| H | H | Q38-3-Cl | 4-SO₂CH₃ | O | O |
| H | H | Q38-3-Cl | 4-COCH₃ | O | O |
| H | H | Q38-3-Cl | 4-CO₂CH₃ | O | O |
| H | H | Q38-3-Cl | 4-CN | O | O |
| H | H | Q38-3-Cl | 4-NO₂ | O | O |
| H | H | Q38-3-Cl | 2,4-Cl₂ | O | O |
| H | H | Q38-3-Cl | 3,4-Cl₂ | O | O |
| H | H | Q38-3-Cl | 2,4,5-Cl₃ | O | O |
| H | H | Q38-3-Cl | 3,4,5-Cl₃ | O | O |
| H | H | Q38-3-Cl | 2-F-4,5-Cl₂ | O | O |
| H | H | Q38-3-Cl | 2,5-F₂-4-Cl | O | O |
| H | H | Q39-2-Cl | 4-F | O | O |
| H | H | Q39-2-Cl | 4-Br | O | O |
| H | H | Q39-2-Cl | 4-I | O | O |
| H | H | Q39-2-Cl | 4-CH₃ | O | O |
| H | H | Q39-2-Cl | 4-C(CH₃)₃ | O | O |
| H | H | Q39-2-Cl | 4-CF₃ | O | O |
| H | H | Q39-2-Cl | 4-OCH₃ | O | O |
| H | H | Q39-2-Cl | 4-OCHF₂ | O | O |
| H | H | Q39-2-Cl | 4-OCF₂Br | O | O |
| H | H | Q39-2-Cl | 4-OCF₂CHF₂ | O | O |
| H | H | Q39-2-Cl | 4-SCH₃ | O | O |
| H | H | Q39-2-Cl | 4-SCF₂Cl | O | O |
| H | H | Q39-2-Cl | 4-SCF₃ | O | O |
| H | H | Q39-2-Cl | 4-SOCH₃ | O | O |
| H | H | Q39-2-Cl | 4-SO₂CH₃ | O | O |
| H | H | Q39-2-Cl | 4-COCH₃ | O | O |
| H | H | Q39-2-Cl | 4-CO₂CH₃ | O | O |
| H | H | Q39-2-Cl | 4-CN | O | O |
| H | H | Q39-2-Cl | 4-NO₂ | O | O |
| H | H | Q39-2-Cl | 2,4-Cl₂ | O | O |
| H | H | Q39-2-Cl | 3,4-Cl₂ | O | O |
| H | H | Q39-2-Cl | 2,4,5-Cl₃ | O | O |
| H | H | Q39-2-Cl | 3,4,5-Cl₃ | O | O |
| H | H | Q39-2-Cl | 2-F-4,5-Cl₂ | O | O |
| H | H | Q39-2-Cl | 2,5-F₂-4-Cl | O | O |

TABLE 4

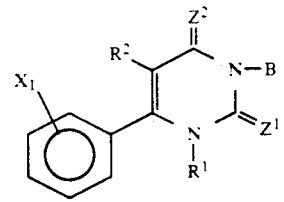

| R¹ | R² | X₁ | B | Z¹ | Z² |
|---|---|---|---|---|---|
| H | H | H | Q1 | O | O |
| H | H | 2-F | Q1 | O | O |
| H | H | 2-Cl | Q1 | O | O |
| H | H | 2,6-F₂ | Q1 | O | O |
| H | H | H | Q2 | O | O |
| H | H | 2-F | Q2 | O | O |
| H | H | 2-Cl | Q2 | O | O |
| H | H | 2,6-F₂ | Q2 | O | O |
| H | H | H | Q3 | O | O |
| H | H | 2-F | Q3 | O | O |
| H | H | 2-Cl | Q3 | O | O |
| H | H | 2,6-F₂ | Q3 | O | O |
| H | H | H | Q4 | O | O |
| H | H | 2-F | Q4 | O | O |
| H | H | 2-Cl | Q4 | O | O |
| H | H | 2,6-F₂ | Q4 | O | O |
| H | H | H | Q5 | O | O |
| H | H | 2-F | Q5 | O | O |
| H | H | 2-Cl | Q5 | O | O |
| H | H | 2,6-F₂ | Q5 | O | O |
| H | H | H | Q6 | O | O |
| H | H | 2-F | Q6 | O | O |
| H | H | 2-Cl | Q6 | O | O |
| H | H | 2,6-F₂ | Q6 | O | O |
| H | H | H | Q7 | O | O |
| H | H | 2-F | Q7 | O | O |
| H | H | 2-Cl | Q7 | O | O |
| H | H | 2,6-F₂ | Q7 | O | O |
| H | H | H | Q8 | O | O |
| H | H | 2-F | Q8 | O | O |
| H | H | 2-Cl | Q8 | O | O |
| H | H | 2,6-F₂ | Q8 | O | O |
| H | H | H | Q9 | O | O |
| H | H | 2-F | Q9 | O | O |
| H | H | 2-Cl | Q9 | O | O |
| H | H | 2,6-F₂ | Q9 | O | O |
| H | H | H | Q10 | O | O |
| H | H | 2-F | Q10 | O | O |
| H | H | 2-Cl | Q10 | O | O |
| H | H | 2,6-F₂ | Q10 | O | O |
| H | H | H | Q11 | O | O |
| H | H | 2-F | Q11 | O | O |
| H | H | 2-Cl | Q11 | O | O |
| H | H | 2,6-F₂ | Q11 | O | O |
| H | H | H | Q12 | O | O |
| H | H | 2-F | Q12 | O | O |
| H | H | 2-Cl | Q12 | O | O |
| H | H | 2,6-F₂ | Q12 | O | O |
| H | H | H | Q12 | S | O |
| H | H | 2-F | Q12 | S | O |
| H | H | 2-Cl | Q12 | S | O |
| H | H | 2,6-F₂ | Q12 | S | O |
| H | H | H | Q13 | O | O |
| H | H | 2-F | Q13 | O | O |
| H | H | 2-Cl | Q13 | O | O |
| H | H | 2,6-F₂ | Q13 | O | O |
| H | H | H | Q14 | O | O |
| H | H | 2-F | Q14 | O | O |
| H | H | 2-Cl | Q14 | O | O |
| H | H | 2,6-F₂ | Q14 | O | O |
| H | H | H | Q15 | O | O |
| H | H | 2-F | Q15 | O | O |
| H | H | 2-Cl | Q15 | O | O |
| H | H | 2,6-F₂ | Q15 | O | O |
| H | H | H | Q16 | O | O |
| H | H | 2-F | Q16 | O | O |
| H | H | 2-Cl | Q16 | O | O |
| H | H | 2,6-F₂ | Q16 | O | O |
| H | H | H | Q17 | O | O |
| H | H | 2-F | Q17 | O | O |

TABLE 4-continued

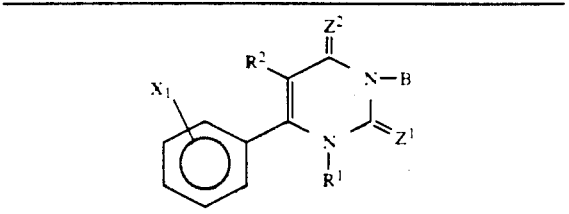

| R¹ | R² | X₁ | B | Z¹ | Z² |
|---|---|---|---|---|---|
| H | H | 2-Cl | Q17 | O | O |
| H | H | 2,6-F₂ | Q17 | O | O |
| H | H | H | Q18 | O | O |
| H | H | 2-F | Q18 | O | O |
| H | H | 2-Cl | Q18 | O | O |
| H | H | 2,6-F₂ | Q18 | O | O |
| H | H | H | Q19 | O | O |
| H | H | 2-F | Q19 | O | O |
| H | H | 2-Cl | Q19 | O | O |
| H | H | 2,6-F₂ | Q19 | O | O |
| H | H | H | Q20 | O | O |
| H | H | 2-F | Q20 | O | O |
| H | H | 2-Cl | Q20 | O | O |
| H | H | 2,6-F₂ | Q20 | O | O |
| H | H | H | Q21 | O | O |
| H | H | 2-F | Q21 | O | O |
| H | H | 2-Cl | Q21 | O | O |
| H | H | 2,6-F₂ | Q21 | O | O |
| H | H | H | Q22 | O | O |
| H | H | 2-F | Q22 | O | O |
| H | H | 2-Cl | Q22 | O | O |
| H | H | 2,6-F₂ | Q22 | O | O |
| H | H | H | Q23 | O | O |
| H | H | 2-F | Q23 | O | O |
| H | H | 2-Cl | Q23 | O | O |
| H | H | 2,6-F₂ | Q23 | O | O |
| H | H | H | Q24 | O | O |
| H | H | 2-F | Q24 | O | O |
| H | H | 2-Cl | Q24 | O | O |
| H | H | 2,6-F₂ | Q24 | O | O |
| H | H | H | Q25 | O | O |
| H | H | 2-F | Q25 | O | O |
| H | H | 2-Cl | Q25 | O | O |
| H | H | 2,6-F₂ | Q25 | O | O |
| H | H | H | Q26 | O | O |
| H | H | 2-F | Q26 | O | O |
| H | H | 2-Cl | Q26 | O | O |
| H | H | 2,6-F₂ | Q26 | O | O |
| H | H | H | Q27 | O | O |
| H | H | 2-F | Q27 | O | O |
| H | H | 2-Cl | Q27 | O | O |
| H | H | 2,6-F₂ | Q27 | O | O |
| H | H | H | Q28 | O | O |
| H | H | 2-F | Q28 | O | O |
| H | H | 2-Cl | Q28 | O | O |
| H | H | 2,6-F₂ | Q28 | O | O |
| H | H | H | Q29 | O | O |
| H | H | 2-F | Q29 | O | O |
| H | H | 2-Cl | Q29 | O | O |
| H | H | 2,6-F₂ | Q29 | O | O |
| H | H | H | Q30 | O | O |
| H | H | 2-F | Q30 | O | O |
| H | H | 2-Cl | Q30 | O | O |
| H | H | 2,6-F₂ | Q30 | O | O |
| H | H | H | Q31 | O | O |
| H | H | 2-F | Q31 | O | O |
| H | H | 2-Cl | Q31 | O | O |
| H | H | 2,6-F₂ | Q31 | O | O |
| H | H | H | Q32 | O | O |
| H | H | 2-F | Q32 | O | O |
| H | H | 2-Cl | Q32 | O | O |
| H | H | 2,6-F₂ | Q32 | O | O |
| H | H | H | Q33 | O | O |
| H | H | 2-F | Q33 | O | O |
| H | H | 2-Cl | Q33 | O | O |
| H | H | 2,6-F₂ | Q33 | O | O |
| H | H | H | Q34 | O | O |
| H | H | 2-F | Q34 | O | O |
| H | H | 2-Cl | Q34 | O | O |
| H | H | 2,6-F₂ | Q34 | O | O |
| H | H | H | Q35 | O | O |
| H | H | 2-F | Q35 | O | O |
| H | H | 2-Cl | Q35 | O | O |
| H | H | 2,6-F₂ | Q35 | O | O |
| H | H | H | Q36 | O | O |
| H | H | 2-F | Q36 | O | O |
| H | H | 2-Cl | Q36 | O | O |
| H | H | 2,6-F₂ | Q36 | O | O |
| H | H | H | Q37 | O | O |
| H | H | 2-F | Q37 | O | O |
| H | H | 2-Cl | Q37 | O | O |
| H | H | 2,6-F₂ | Q37 | O | O |
| H | H | H | Q38 | O | O |
| H | H | 2-F | Q38 | O | O |
| H | H | 2-Cl | Q38 | O | O |
| H | H | 2,6-F₂ | Q38 | O | O |
| H | H | H | Q39 | O | O |
| H | H | 2-F | Q39 | O | O |
| H | H | 2-Cl | Q39 | O | O |
| H | H | 2,6-F₂ | Q39 | O | O |
| H | H | H | Q40 | O | O |
| H | H | 2-F | Q40 | O | O |
| H | H | 2-Cl | Q40 | O | O |
| H | H | 2,6-F₂ | Q40 | O | O |
| H | H | H | Q41 | O | O |
| H | H | 2-F | Q41 | O | O |
| H | H | 2-Cl | Q41 | O | O |
| H | H | 2,6-F₂ | Q41 | O | O |
| H | H | H | Q41 | S | O |
| H | H | 2-F | Q41 | S | O |
| H | H | 2-Cl | Q41 | S | O |
| H | H | 2,6-F₂ | Q41 | S | O |
| H | H | H | Q42 | O | O |
| H | H | 2-F | Q42 | O | O |
| H | H | 2-Cl | Q42 | O | O |
| H | H | 2,6-F₂ | Q42 | O | O |
| H | H | H | Q43 | O | O |
| H | H | 2-F | Q43 | O | O |
| H | H | 2-Cl | Q43 | O | O |
| H | H | 2,6-F₂ | Q43 | O | O |
| H | H | H | Q44 | O | O |
| H | H | 2-F | Q44 | O | O |
| H | H | 2-Cl | Q44 | O | O |
| H | H | 2,6-F₂ | Q44 | O | O |
| H | H | H | Q45 | O | O |
| H | H | 2-F | Q45 | O | O |
| H | H | 2-Cl | Q45 | O | O |
| H | H | 2,6-F₂ | Q45 | O | O |
| H | H | H | Q46 | O | O |
| H | H | 2-F | Q46 | O | O |
| H | H | 2-Cl | Q46 | O | O |
| H | H | 2,6-F₂ | Q46 | O | O |
| H | H | H | Q47 | O | O |
| H | H | 2-F | Q47 | O | O |
| H | H | 2-Cl | Q47 | O | O |
| H | H | 2,6-F₂ | Q47 | O | O |
| H | H | H | Q48 | O | O |
| H | H | 2-F | Q48 | O | O |
| H | H | 2-Cl | Q48 | O | O |
| H | H | 2,6-F₂ | Q48 | O | O |
| H | H | H | Q49 | O | O |
| H | H | 2-F | Q49 | O | O |
| H | H | 2-Cl | Q49 | O | O |
| H | H | 2,6-F₂ | Q49 | O | O |
| H | H | H | Q50 | O | O |
| H | H | 2-F | Q50 | O | O |
| H | H | 2-Cl | Q50 | O | O |
| H | H | 2,6-F₂ | Q50 | O | O |
| H | H | H | Q55 | O | O |
| H | H | 2-F | Q55 | O | O |

TABLE 4-continued

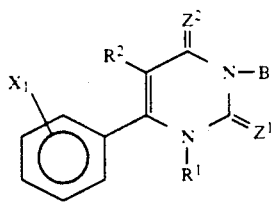 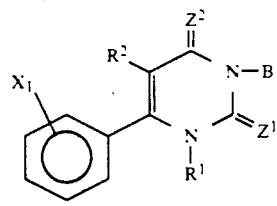

| R¹ | R² | X₁ | B | Z¹ | Z² | R¹ | R² | X₁ | B | Z¹ | Z² |
|---|---|---|---|---|---|---|---|---|---|---|---|
| H | H | 2-Cl | Q55 | O | O | H | H | H | Q37-5-CF₃ | O | O |
| H | H | 2,6-F₂ | Q55 | O | O | H | H | 2-F | Q37-5-CF₃ | O | O |
| H | H | H | Q56 | O | O | H | H | 2-Cl | Q37-5-CF₃ | O | O |
| H | H | 2-F | Q56 | O | O | H | H | 2,6-F₂ | Q37-5-CF₃ | O | O |
| H | H | 2-Cl | Q56 | O | O | H | H | H | Q37-5-OCF₃ | O | O |
| H | H | 2,6-F₂ | Q56 | O | O | H | H | 2-F | Q37-5-OCF₃ | O | O |
| H | H | H | Q57 | O | O | H | H | 2-Cl | Q37-5-OCF₃ | O | O |
| H | H | 2-F | Q57 | O | O | H | H | 2,6-F₂ | Q37-5-OCF₃ | O | O |
| H | H | 2-Cl | Q57 | O | O | H | Br | H | Q37-5-OCF₃ | O | O |
| H | H | 2,6-F₂ | Q57 | O | O | H | Br | 2-F | Q37-5-OCF₃ | O | O |
| H | H | H | Q58 | O | O | H | Br | 2-Cl | Q37-5-OCF₃ | O | O |
| H | H | 2-F | Q58 | O | O | H | Br | 2,6-F₂ | Q37-5-OCF₃ | O | O |
| H | H | 2-Cl | Q58 | O | O | H | H | H | Q37-5-SCF₃ | O | O |
| H | H | 2,6-F₂ | Q58 | O | O | H | H | 2-F | Q37-5-SCF₃ | O | O |
| H | H | H | Q59 | O | O | H | H | 2-Cl | Q37-5-SCF₃ | O | O |
| H | H | 2-F | Q59 | O | O | H | H | 2,6-F₂ | Q37-5-SCF₃ | O | O |
| H | H | 2-Cl | Q59 | O | O | H | H | H | Q38-5-Cl | O | O |
| H | H | 2,6-F₂ | Q59 | O | O | H | H | 2-F | Q38-5-Cl | O | O |
| H | H | H | Q60 | O | O | H | H | 2-Cl | Q38-5-Cl | O | O |
| H | H | 2-F | Q60 | O | O | H | H | 2,6-F₂ | Q38-5-Cl | O | O |
| H | H | 2-Cl | Q60 | O | O | CH₃ | H | H | Q38-5-Cl | O | O |
| H | H | 2,6-F₂ | Q60 | O | O | CH₃ | H | 2-F | Q38-5-Cl | O | O |
| H | H | H | Q61 | O | O | CH₃ | H | 2-Cl | Q38-5-Cl | O | O |
| H | H | 2-F | Q61 | O | O | CH₃ | H | 2,6-F₂ | Q38-5-Cl | O | O |
| H | H | 2-Cl | Q61 | O | O | H | H | H | Q38-5-Br | O | O |
| H | H | 2,6-F₂ | Q61 | O | O | H | H | 2-F | Q38-5-Br | O | O |
| H | H | H | Q6-5-CF₃ | O | O | H | H | 2-Cl | Q38-5-Br | O | O |
| H | H | 2-F | Q6-5-CF₃ | O | O | H | H | 2,6-F₂ | Q38-5-Br | O | O |
| H | H | 2-Cl | Q6-5-CF₃ | O | O | H | H | H | Q38-5-CF₃ | O | O |
| H | H | 2,6-F₂ | Q6-5-CF₃ | O | O | H | H | 2-F | Q38-5-CF₃ | O | O |
| H | H | H | Q6-4-CH₃-5-C₆H₅ | O | O | H | H | 2-Cl | Q38-5-CF₃ | O | O |
| H | H | 2-F | Q6-4-CH₃-5-C₆H₅ | O | O | H | H | 2,6-F₂ | Q38-5-CF₃ | O | O |
| H | H | 2-Cl | Q6-4-CH₃-5-C₆H₅ | O | O | H | Br | H | Q38-5-CF₃ | O | O |
| H | H | 2,6-F₂ | Q6-4-CH₃-5-C₆H₅ | O | O | H | Br | 2-F | Q38-5-CF₃ | O | O |
| CH₂OCH₃ | H | H | Q6-4-CH₃-5-C₆H₅ | O | O | H | Br | 2-Cl | Q38-5-CF₃ | O | O |
| CH₂OCH₃ | H | 2-F | Q6-4-CH₃-5-C₆H₅ | O | O | H | Br | 2,6-F₂ | Q38-5-CF₃ | O | O |
| CH₂OCH₃ | H | 2-Cl | Q6-4-CH₃-5-C₆H₅ | O | O | H | CN | H | Q38-5-CF₃ | O | O |
| CH₂OCH₃ | H | 2,6-F₂ | Q6-4-CH₃-5-C₆H₅ | O | O | H | CN | 2-F | Q38-5-CF₃ | O | O |
| H | H | H | Q7-5-Cl | O | O | H | CN | 2-Cl | Q38-5-CF₃ | O | O |
| H | H | 2-F | Q7-5-Cl | O | O | H | CN | 2,6-F₂ | Q38-5-CF₃ | O | O |
| H | H | 2-Cl | Q7-5-Cl | O | O | H | H | H | Q38-6-OCH₃ | O | O |
| H | H | 2,6-F₂ | Q7-5-Cl | O | O | H | H | 2-F | Q38-6-OCH₃ | O | O |
| H | H | H | Q17-5-C₆H₅ | O | O | H | H | 2-Cl | Q38-6-OCH₃ | O | O |
| H | H | 2-F | Q17-5-C₆H₅ | O | O | H | H | 2,6-F₂ | Q38-6-OCH₃ | O | O |
| H | H | 2-Cl | Q17-5-C₆H₅ | O | O | H | H | H | Q38-5-CO₂CH₃ | O | O |
| H | H | 2,6-F₂ | Q17-5-C₆H₅ | O | O | H | H | 2-F | Q38-5-CO₂CH₃ | O | O |
| H | Cl | H | Q17-5-C₆H₅ | O | O | H | H | 2-Cl | Q38-5-CO₂CH₃ | O | O |
| H | Cl | 2-F | Q17-5-C₆H₅ | O | O | H | H | 2,6-F₂ | Q38-5-CO₂CH₃ | O | O |
| H | Cl | 2-Cl | Q17-5-C₆H₅ | O | O | H | H | H | Q38-4,6-(CH₃)₂-5-C₆H₅ | O | O |
| H | Cl | 2,6-F₂ | Q17-5-C₆H₅ | O | O | H | H | 2-F | Q38-4,6-(CH₃)₂-5-C₆H₅ | O | O |
| H | H | H | Q9-1-C₆H₅ | O | O | H | H | 2-Cl | Q38-4,6-(CH₃)₂-5-C₆H₅ | O | O |
| H | H | 2-F | Q9-1-C₆H₅ | O | O | H | H | 2,6-F₂ | Q38-4,6-(CH₃)₂-5-C₆H₅ | O | O |
| H | H | 2-Cl | Q9-1-C₆H₅ | O | O | H | I | H | Q38-4,6-(CH₃)₂-5-C₆H₅ | O | O |
| H | H | 2,6-F₂ | Q9-1-C₆H₅ | O | O | H | I | 2-F | Q38-4,6-(CH₃)₂-5-C₆H₅ | O | O |
| H | H | H | Q20-4-CF₃ | O | O | H | I | 2-Cl | Q38-4,6-(CH₃)₂-5-C₆H₅ | O | O |
| H | H | 2-F | Q20-4-CF₃ | O | O | H | I | 2,6-F₂ | Q38-4,6-(CH₃)₂-5-C₆H₅ | O | O |
| H | H | 2-Cl | Q20-4-CF₃ | O | O | H | H | H | Q39-6-SCF₃ | O | O |
| H | H | 2,6-F₂ | Q20-4-CF₃ | O | O | H | H | 2-F | Q39-6-SCF₃ | O | O |
| H | H | H | Q37-5-Cl | O | O | H | H | 2-Cl | Q39-6-SCF₃ | O | O |
| H | H | 2-F | Q37-5-Cl | O | O | H | H | 2,6-F₂ | Q39-6-SCF₃ | O | O |
| H | H | 2-Cl | Q37-5-Cl | O | O | H | H | H | Q39-6-SO₂CF₃ | O | O |
| H | H | 2,6-F₂ | Q37-5-Cl | O | O | H | H | 2-F | Q39-6-SO₂CF₃ | O | O |
| H | H | H | Q37-5-Cl | S | O | H | H | 2-Cl | Q39-6-SO₂CF₃ | O | O |
| H | H | 2-F | Q37-5-Cl | S | O | H | H | 2,6-F₂ | Q39-6-SO₂CF₃ | O | O |
| H | H | 2-Cl | Q37-5-Cl | S | O | H | H | H | Q39-2,6-Cl₂ | O | O |
| H | H | 2,6-F₂ | Q37-5-Cl | S | O | H | H | 2-F | Q39-2,6-Cl₂ | O | O |
| H | H | H | Q37-5-CH₃ | O | O | H | H | 2-Cl | Q39-2,6-Cl₂ | O | O |
| H | H | 2-F | Q37-5-CH₃ | O | O | H | H | 2,6-F₂ | Q39-2,6-Cl₂ | O | O |
| H | H | 2-Cl | Q37-5-CH₃ | O | O | H | H | H | Q39-2,6-Cl₂ | S | O |
| H | H | 2,6-F₂ | Q37-5-CH₃ | O | O | H | H | 2-F | Q39-2,6-Cl₂ | S | O |

TABLE 4-continued

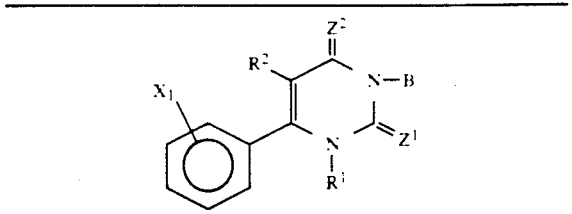

| R¹ | R² | X₁ | B | Z¹ | Z² |
|---|---|---|---|---|---|
| H | H | 2-Cl | Q39-2,6-Cl₂ | S | O |
| H | H | 2,6-F₂ | Q39-2,6-Cl₂ | S | O |
| H | Br | H | Q39-2,6-Cl₂ | O | O |
| H | Br | 2-F | Q39-2,6-Cl₂ | O | O |
| H | Br | 2-Cl | Q39-2,6-Cl₂ | O | O |
| H | Br | 2,6-F₂ | Q39-2,6-Cl₂ | O | O |
| H | H | H | Q39-4,6-Cl₂ | O | O |
| H | H | 2-F | Q39-4,6-Cl₂ | O | O |
| H | H | 2-Cl | Q39-4,6-Cl₂ | O | O |
| H | H | 2,6-F₂ | Q39-4,6-Cl₂ | O | O |
| H | H | H | Q39-6-OC₆H₅ | O | O |
| H | H | 2-F | Q39-6-OC₆H₅ | O | O |
| H | H | 2-Cl | Q39-6-OC₆H₅ | O | O |
| H | H | 2,6-F₂ | Q39-6-OC₆H₅ | O | O |
| H | NO₂ | H | Q39-6-OC₆H₅ | O | O |
| H | NO₂ | 2-F | Q39-6-OC₆H₅ | O | O |
| H | NO₂ | 2-Cl | Q39-6-OC₆H₅ | O | O |
| H | NO₂ | 2,6-F₂ | Q39-6-OC₆H₅ | O | O |
| H | H | H | Q46-5-C₆H₅-6-CH₃ | O | O |
| H | H | 2-F | Q46-5-C₆H₅-6-CH₃ | O | O |
| H | H | 2-Cl | Q46-5-C₆H₅-6-CH₃ | O | O |
| H | H | 2,6-F₂ | Q46-5-C₆H₅-6-CH₃ | O | O |
| H | H | H | Q59-2-CF₃ | O | O |
| H | H | 2-F | Q59-2-CF₃ | O | O |
| H | H | 2-Cl | Q59-2-CF₃ | O | O |
| H | H | 2,6-F₂ | Q59-2-CF₃ | O | O |
| H | Cl | H | Q59-2-CF₃ | O | O |
| H | Cl | 2-F | Q59-2-CF₃ | O | O |
| H | Cl | 2-Cl | Q59-2-CF₃ | O | O |
| H | Cl | 2,6-F₂ | Q59-2-CF₃ | O | O |
| H | H | H | Q60-2-CF₃ | O | O |

TABLE 4-continued

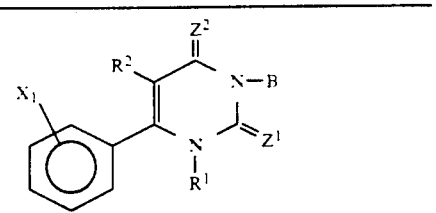

| R¹ | R² | X₁ | B | Z¹ | Z² |
|---|---|---|---|---|---|
| H | H | 2-F | Q60-2-CF₃ | O | O |
| H | H | 2-Cl | Q60-2-CF₃ | O | O |
| H | H | 2,6-F₂ | Q60-2-CF₃ | O | O |
| H | H | H | Q61-6-Cl | O | O |
| H | H | 2-F | Q61-6-Cl | O | O |
| H | H | 2-Cl | Q61-6-Cl | O | O |
| H | H | 2,6-F₂ | Q61-6-Cl | O | O |
| H | H | H | Q61-6-CF₃ | O | O |
| H | H | 2-F | Q61-6-CF₃ | O | O |
| H | H | 2-Cl | Q61-6-CF₃ | O | O |
| H | H | 2,6-F₂ | Q61-6-CF₃ | O | O |
| CH₃ | H | H | Q61-6-CF₃ | O | O |
| CH₃ | H | 2-F | Q61-6-CF₃ | O | O |
| CH₃ | H | 2-Cl | Q61-6-CF₃ | O | O |
| CH₃ | H | 2,6-F₂ | Q61-6-CF₃ | O | O |
| H | H | H | Q61-6-OCF₃ | O | O |
| H | H | 2-F | Q61-6-OCF₃ | O | O |
| H | H | 2-Cl | Q61-6-OCF₃ | O | O |
| H | H | 2,6-F₂ | Q61-6-OCF₃ | O | O |
| H | Br | H | Q61-6-OCF₃ | O | O |
| H | Br | 2-F | Q61-6-OCF₃ | O | O |
| H | Br | 2-Cl | Q61-6-OCF₃ | O | O |
| H | Br | 2,6-F₂ | Q61-6-OCF₃ | O | O |
| H | H | H | Q61-6-OC₆H₅ | O | O |
| H | H | 2-F | Q61-6-OC₆H₅ | O | O |
| H | H | 2-Cl | Q61-6-OC₆H₅ | O | O |
| H | H | 2,6-F₂ | Q61-6-OC₆H₅ | O | O |
| H | H | H | Q61-6-OC₆H₅ | S | O |
| H | H | 2-F | Q61-6-OC₆H₅ | S | O |
| H | H | 2-Cl | Q61-6-OC₆H₅ | S | O |
| H | H | 2,6-F₂ | Q61-6-OC₆H₅ | S | O |

TABLE 5

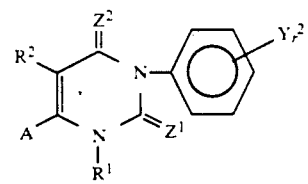

| R¹ | R² | A | Y_r² | Z¹ | Z² |
|---|---|---|---|---|---|
| H | H | CF₃ | 2,3,4-F₃ | O | O |
| H | H | CF₃ | 2,3,4-Cl₃ | O | O |
| H | H | CF₃ | 2,3-Cl₂-4-CF₃ | O | O |
| H | H | CF₃ | 2,3-Cl₂-4-OCF₃ | O | O |
| H | H | CF₃ | 2,4-Cl₂-3-CF₃ | O | O |
| H | H | CF₃ | 2,3-Br₂-4-CF₃ | O | O |
| H | H | CF₃ | 2,3,5-Cl₃ | O | O |
| H | H | CF₃ | 2,3,6-Cl₃ | O | O |
| H | H | CF₃ | 2,4,5-F₃ | O | O |
| H | H | CF₃ | 2,5-F₂-4-CF₃ | O | O |
| H | H | CF₃ | 2,4,5-Cl₃ | O | O |
| H | H | CF₃ | 2-Cl-4-CF₃-5-F | O | O |
| H | H | CF₃ | 2,5-Cl₂-4-CF₃ | O | O |
| H | H | CF₃ | 2-Cl-4-CF₃-5-Br | O | O |
| H | H | CF₃ | 2,5-Cl₂-4-NO₂ | O | O |
| H | H | CF₃ | 2-CF₃-4-NO₂-5-Cl | O | O |
| H | H | CF₃ | 2-CF₃-4-NO₂-5-CH₃ | O | O |
| H | H | CF₃ | 2-NO₂-4,5-Cl₂ | O | O |
| H | H | CF₃ | 2-NO₂-4-CF₃-5-Cl | O | O |
| H | H | CF₃ | 2,4,6-F₃ | O | O |
| H | H | CF₃ | 2-F-4-Cl-6-Br | O | O |
| H | H | CF₃ | 2,6-F₂-4-CF₃ | O | O |
| H | H | CF₃ | 2-F-4-CF₃-6-Cl | O | O |
| H | H | CF₃ | 2-F-4-CF₃-6-Br | O | O |

TABLE 5-continued

| | | | | | |
|---|---|---|---|---|---|
| H | H | CF$_3$ | 2-F-4-CF$_3$-6-OCH$_3$ | O | O |
| H | H | CF$_3$ | 2,6-F$_2$-4-OCF$_3$ | O | O |
| H | H | CF$_3$ | 2,4,6-Cl$_3$ | O | O |
| H | H | CF$_3$ | 2-Br-4-F-6-Cl | O | O |
| H | H | CF$_3$ | 2,6-Cl$_2$-4-Br | O | O |
| H | H | CF$_3$ | 2,6-Cl$_2$-4-I | O | O |
| H | H | CF$_3$ | 2,4-Br$_2$-6-Cl | O | O |
| H | H | CF$_3$ | 2,4-Cl$_2$-6-CF$_3$ | O | O |
| H | H | CF$_3$ | 2,4-Cl$_2$-6-SCF$_3$ | O | O |
| H | H | CF$_3$ | 2,6-Cl$_2$-4-C(CH$_3$)$_3$ | O | O |
| H | H | CF$_3$ | 2,6-Cl$_2$-4-OCH$_3$ | O | O |
| H | H | CF$_3$ | 2,6-Cl$_2$-4-CF$_3$ | O | O |
| H | H | CF$_3$ | 2,6-Cl$_2$-4-CHF$_2$ | O | O |
| H | H | CF$_3$ | 2,6-Cl$_2$-4-CF(CH$_3$)$_2$ | O | O |
| H | H | CF$_3$ | 2,6-Cl$_2$-4-OCF$_3$ | O | O |
| H | H | CF$_3$ | 2,6-Cl$_2$-4-OCHF$_2$ | O | O |
| H | H | CF$_3$ | 2,6-Cl$_2$-4-OCH$_2$CF$_3$ | O | O |
| H | H | CF$_3$ | 2,6-Cl$_2$-4-OCF$_2$CHF$_2$ | O | O |
| H | H | CF$_3$ | 2,6-Cl$_2$-4-OCF$_2$CHCl$_2$ | O | O |
| H | H | CF$_3$ | 2,6-Cl$_2$-4-OCF$_2$CHFCl | O | O |
| H | H | CF$_3$ | 2,6-Cl$_2$-4-SCH$_3$ | O | O |
| H | H | CF$_3$ | 2,6-Cl$_2$-4-SCF$_3$ | O | O |
| H | H | CF$_3$ | 2,6-Cl$_2$-4-SCHF$_2$ | O | O |
| H | H | CF$_3$ | 2,6-Cl$_2$-4-SCFCl$_2$ | O | O |
| H | H | CF$_3$ | 2,6-Cl$_2$-4-SCH$_2$CF$_3$ | O | O |
| H | H | CF$_3$ | 2,6-Cl$_2$-4-SCF$_2$CHF$_2$ | O | O |
| H | H | CF$_3$ | 2,6-Cl$_2$-4-SCF$_2$CHFCl | O | O |
| H | H | CF$_3$ | 2,6-Cl$_2$-4-SOCH$_3$ | O | O |
| H | H | CF$_3$ | 2,6-Cl$_2$-4-SOCF$_3$ | O | O |
| H | H | CF$_3$ | 2,6-Cl$_2$-4-SO$_2$CH$_3$ | O | O |
| H | H | CF$_3$ | 2,6-Cl$_2$-4-SO$_2$CF$_3$ | O | O |
| H | H | CF$_3$ | 2,6-Cl$_2$-4-SO$_2$NH$_2$ | O | O |
| H | H | CF$_3$ | 2,6-Cl$_2$-4-CH$_2$CH=CH$_2$ | O | O |
| H | H | CF$_3$ | 2,6-Cl$_2$-4-CH=CCl(CF$_3$) | O | O |
| H | H | CF$_3$ | 2,6-Cl$_2$-4-NH$_2$ | O | O |
| H | H | CF$_3$ | 2,6-Cl$_2$-4-OCH$_2$CH$_2$OCH$_3$ | O | O |
| H | H | CF$_3$ | 2,6-Cl$_2$-4-CO$_2$CH$_3$ | O | O |
| H | H | CF$_3$ | 2,6-Cl$_2$-4-CN | O | O |
| H | H | CF$_3$ | 2,6-Cl$_2$-4-NO$_2$ | O | O |
| H | H | CF$_3$ | 2-Br-4-CF$_3$-6-Cl | O | O |
| H | H | CF$_3$ | 2-Cl-4-CF$_3$-6-I | O | O |
| H | H | CF$_3$ | 2-Cl-4-CF$_3$-6-OCH$_3$ | O | O |
| H | H | CF$_3$ | 2-Cl-4,6-(CF$_3$)$_2$ | O | O |
| H | H | CF$_3$ | 2-Cl-4-CF$_3$-6-OCF$_3$ | O | O |
| H | H | CF$_3$ | 2-Cl-4-CF$_3$-6-NO$_2$ | O | O |
| H | H | CF$_3$ | 2-Cl-4,6-(OCF$_3$)$_2$ | O | O |
| H | H | CF$_3$ | 2-Cl-4-SCF$_3$-6-CF$_3$ | O | O |
| H | H | CF$_3$ | 2-Cl-4-NO$_2$-6-CF$_3$ | O | O |
| H | H | CF$_3$ | 2,6-Br$_2$-4-Cl | O | O |
| H | H | CF$_3$ | 2,6-Br$_2$-4-CF$_3$ | O | O |
| H | H | CF$_3$ | 2,4-Br$_2$-6-OCF$_3$ | O | O |
| H | H | CF$_3$ | 2,6-Br$_2$-4-OCF$_3$ | O | O |
| H | H | CF$_3$ | 2-Br-4-CF$_3$-6-NO$_2$ | O | O |
| H | H | CF$_3$ | 2,6-(CH$_3$)$_2$-4-Cl | O | O |
| H | H | CF$_3$ | 2,6-(CH$_3$)$_2$-4-CF$_3$ | O | O |
| H | H | CF$_3$ | 2,4-(NO$_2$)$_2$-6-CF$_3$ | O | O |
| H | H | CF$_3$ | 2,4-(CF$_3$)$_2$-6-NO$_2$ | O | O |
| H | H | CF$_3$ | 2,6-(CF$_3$)$_2$-4-NO$_2$ | O | O |
| H | H | CF$_3$ | 2,6-(NO$_2$)$_2$-4-CF$_3$ | O | O |
| H | H | CF$_3$ | 3,5-F$_2$-4-CF$_3$ | O | O |
| H | H | CF$_3$ | 3,4,5-Cl$_3$ | O | O |
| H | H | CF$_3$ | 3,5-Cl$_2$-4-CF$_3$ | O | O |
| H | H | CF$_3$ | 3,5-Cl$_2$-4-OCF$_2$CHF$_2$ | O | O |
| H | H | CF$_3$ | 3,5-Cl$_2$-4-SCF$_2$CHFCl | O | O |
| H | H | CF$_3$ | 2,3,4,5-F$_4$ | O | O |
| H | H | CF$_3$ | 2,4-F$_2$-3,5-Cl$_2$ | O | O |
| H | H | CF$_3$ | 2,3,4,5-Cl$_4$ | O | O |
| H | H | CF$_3$ | 2,3,5-Cl$_3$-4-CF$_3$ | O | O |
| H | H | CF$_3$ | 2,3,4,6-F$_4$ | O | O |
| H | H | CF$_3$ | 2,3,5-F$_3$-4-CF$_3$ | O | O |
| H | H | CF$_3$ | 2,3,4,6-Cl$_4$ | O | O |
| H | H | CF$_3$ | 2,3,6-Cl$_3$-4-Br | O | O |
| H | H | CF$_3$ | 2,3,6-Cl$_3$-4-CF$_3$ | O | O |
| H | H | CF$_3$ | 2,3,6-Cl$_3$-4-OCF$_3$ | O | O |
| H | H | CF$_3$ | 2,3,6-Cl$_3$-4-SCF$_3$ | O | O |
| H | H | CF$_3$ | 2,3-Cl$_2$-4,6-Br$_2$ | O | O |
| H | H | CF$_3$ | 2,6-Cl$_2$-3-CH$_3$-4-CF$_3$ | O | O |
| H | H | CF$_3$ | 2,6-Cl$_2$-3-CH$_2$CH$_3$-4-CF$_3$ | O | O |
| H | H | CF$_3$ | 2,6-Cl$_2$-3-OCH$_3$-4-CF$_3$ | O | O |
| H | H | CF$_3$ | 2,6-Cl$_2$-3-NHCH$_3$-4-CF$_3$ | O | O |
| H | H | CF$_3$ | 2,6-Br$_2$-3,4-Cl$_2$ | O | O |
| H | H | CF$_3$ | 2,4-Br$_2$-3,6-Cl$_2$ | O | O |

TABLE 5-continued

| | | | | | |
|---|---|---|---|---|---|
| H | H | CF$_3$ | 2,6-Br$_2$-3-Cl-4-CH$_3$ | O | O |
| H | H | CF$_3$ | 2,3,6-Br$_3$-4-CF$_3$ | O | O |
| H | H | CF$_3$ | 2-CF$_3$-3-F-4,6-Cl$_2$ | O | O |
| H | H | CF$_3$ | 2-CF$_3$-3-Cl-4,6-(NO$_2$)$_2$ | O | O |
| H | H | CF$_3$ | 2-CF$_3$-3-OCH$_2$CH$_3$-4,6-(NO$_2$)$_2$ | O | O |
| H | H | CF$_3$ | 2,6-(NO$_2$)$_2$-3-Cl-4-CF$_3$ | O | O |
| H | H | CF$_3$ | 2,3,5,6-Cl$_4$ | O | O |
| H | H | CF$_3$ | 2,3,4,5,6-F$_5$ | O | O |
| H | H | CF$_3$ | 2,3,5,6-F$_4$-4-CF$_3$ | O | O |
| H | H | CF$_3$ | 2,3,5,6-F$_4$-4-CN | O | O |
| H | H | CF$_3$ | 2,3,5,6-F$_4$-4-Cl | O | O |
| H | H | CF$_3$ | 2,3,5-F$_3$-4-CF$_3$-6-Cl | O | O |
| H | H | CF$_3$ | 2,3,5-F$_3$-4-CF$_3$-6-OCF$_3$ | O | O |
| H | H | CF$_3$ | 2,4,6-F$_3$-3,5-Cl$_2$ | O | O |
| H | H | CF$_3$ | 2,3,4,5,6-Cl$_5$ | O | O |
| H | H | CF$_3$ | 2,3,5,6-Cl$_4$-4-CF$_3$ | O | O |
| H | H | CF$_3$ | 2,3,5,6-Cl$_4$-4-NO$_2$ | O | O |
| H | H | CF$_2$CF$_3$ | 2,3,4-F$_3$ | O | O |
| H | H | CF$_2$CF$_3$ | 2,3,4-Cl$_3$ | O | O |
| H | H | CF$_2$CF$_3$ | 2,3-Cl$_2$-4-CF$_3$ | O | O |
| H | H | CF$_2$CF$_3$ | 2,3-Cl$_2$-4-OCF$_3$ | O | O |
| H | H | CF$_2$CF$_3$ | 2,4-Cl$_2$-3-CF$_3$ | O | O |
| H | H | CF$_2$CF$_3$ | 2,3-Br$_2$-4-CF$_3$ | O | O |
| H | H | CF$_2$CF$_3$ | 2,3,5-Cl$_3$ | O | O |
| H | H | CF$_2$CF$_3$ | 2,3,6-Cl$_3$ | O | O |
| H | H | CF$_2$CF$_3$ | 2,4,5-F$_3$ | O | O |
| H | H | CF$_2$CF$_3$ | 2,5-F$_2$-4-CF$_3$ | O | O |
| H | H | CF$_2$CF$_3$ | 2,4,5-Cl$_3$ | O | O |
| H | H | CF$_2$CF$_3$ | 2-Cl-4-CF$_3$-5-F | O | O |
| H | H | CF$_2$CF$_3$ | 2,5-Cl$_2$-4-CF$_3$ | O | O |
| H | H | CF$_2$CF$_3$ | 2-Cl-4-CF$_3$-5-Br | O | O |
| H | H | CF$_2$CF$_3$ | 2,5-Cl$_2$-4-NO$_2$ | O | O |
| H | H | CF$_2$CF$_3$ | 2-CF$_3$-4-NO$_2$-5-Cl | O | O |
| H | H | CF$_2$CF$_3$ | 2-CF$_3$-4-NO$_2$-5-CH$_3$ | O | O |
| H | H | CF$_2$CF$_3$ | 2-NO$_2$-4,5-Cl$_2$ | O | O |
| H | H | CF$_2$CF$_3$ | 2-NO$_2$-4-CF$_3$-5-Cl | O | O |
| H | H | CF$_2$CF$_3$ | 2,4,6-F$_3$ | O | O |
| H | H | CF$_2$CF$_3$ | 2-F-4-Cl-6-Br | O | O |
| H | H | CF$_2$CF$_3$ | 2,6-F$_2$-4-CF$_3$ | O | O |
| H | H | CF$_2$CF$_3$ | 2-F-4-CF$_3$-6-Cl | O | O |
| H | H | CF$_2$CF$_3$ | 2-F-4-CF$_3$-6-Br | O | O |
| H | H | CF$_2$CF$_3$ | 2-F-4-CF$_3$-6-OCH$_3$ | O | O |
| H | H | CF$_2$CF$_3$ | 2,6-F$_2$-4-OCF$_3$ | O | O |
| H | H | CF$_2$CF$_3$ | 2,4,6-Cl$_3$ | O | O |
| H | H | CF$_2$CF$_3$ | 2-Br-4-F-6-Cl | O | O |
| H | H | CF$_2$CF$_3$ | 2,6-Cl$_2$-4-Br | O | O |
| H | H | CF$_2$CF$_3$ | 2,6-Cl$_2$-4-I | O | O |
| H | H | CF$_2$CF$_3$ | 2,4-Br$_2$-6-Cl | O | O |
| H | H | CF$_2$CF$_3$ | 2,4-Cl$_2$-6-CF$_3$ | O | O |
| H | H | CF$_2$CF$_3$ | 2,4-Cl$_2$-6-SCF$_3$ | O | O |
| H | H | CF$_2$CF$_3$ | 2,6-Cl$_2$-4-C(CH$_3$)$_3$ | O | O |
| H | H | CF$_2$CF$_3$ | 2,6-Cl$_2$-4-OCH$_3$ | O | O |
| H | H | CF$_2$CF$_3$ | 2,6-Cl$_2$-4-CF$_3$ | O | O |
| H | H | CF$_2$CF$_3$ | 2,6-Cl$_2$-4-CHF$_2$ | O | O |
| H | H | CF$_2$CF$_3$ | 2,6-Cl$_2$-4-CF(CH$_3$)$_2$ | O | O |
| H | H | CF$_2$CF$_3$ | 2,6-Cl$_2$-4-OCF$_3$ | O | O |
| H | H | CF$_2$CF$_3$ | 2,6-Cl$_2$-4-OCHF$_2$ | O | O |
| H | H | CF$_2$CF$_3$ | 2,6-Cl$_2$-4-OCH$_2$CF$_3$ | O | O |
| H | H | CF$_2$CF$_3$ | 2,6-Cl$_2$-4-OCF$_2$CHF$_2$ | O | O |
| H | H | CF$_2$CF$_3$ | 2,6-Cl$_2$-4-OCF$_2$CHCl$_2$ | O | O |
| H | H | CF$_2$CF$_3$ | 2,6-Cl$_2$-4-OCF$_2$CHFCl | O | O |
| H | H | CF$_2$CF$_3$ | 2,6-Cl$_2$-4-SCH$_3$ | O | O |
| H | H | CF$_2$CF$_3$ | 2,6-Cl$_2$-4-SCF$_3$ | O | O |
| H | H | CF$_2$CF$_3$ | 2,6-Cl$_2$-4-SCHF$_2$ | O | O |
| H | H | CF$_2$CF$_3$ | 2,6-Cl$_2$-4-SCFCl$_2$ | O | O |
| H | H | CF$_2$CF$_3$ | 2,6-Cl$_2$-4-SCH$_2$CF$_3$ | O | O |
| H | H | CF$_2$CF$_3$ | 2,6-Cl$_2$-4-SCF$_2$CHF$_2$ | O | O |
| H | H | CF$_2$CF$_3$ | 2,6-Cl$_2$-4-SCF$_2$CHFCl | O | O |
| H | H | CF$_2$CF$_3$ | 2,6-Cl$_2$-4-SOCH$_3$ | O | O |
| H | H | CF$_2$CF$_3$ | 2,6-Cl$_2$-4-SOCF$_3$ | O | O |
| H | H | CF$_2$CF$_3$ | 2,6-Cl$_2$-4-SO$_2$CH$_3$ | O | O |
| H | H | CF$_2$CF$_3$ | 2,6-Cl$_2$-4-SO$_2$CF$_3$ | O | O |
| H | H | CF$_2$CF$_3$ | 2,6-Cl$_2$-4-SO$_2$NH$_2$ | O | O |
| H | H | CF$_2$CF$_3$ | 2,6-Cl$_2$-4-CH$_2$CH=CH$_2$ | O | O |
| H | H | CF$_2$CF$_3$ | 2,6-Cl$_2$-4-CH=CCl(CF$_3$) | O | O |
| H | H | CF$_2$CF$_3$ | 2,6-Cl$_2$-4-NH$_2$ | O | O |
| H | H | CF$_2$CF$_3$ | 2,6-Cl$_2$-4-OCH$_2$CH$_2$OCH$_3$ | O | O |
| H | H | CF$_2$CF$_3$ | 2,6-Cl$_2$-4-CO$_2$CH$_3$ | O | O |
| H | H | CF$_2$CF$_3$ | 2,6-Cl$_2$-4-CN | O | O |
| H | H | CF$_2$CF$_3$ | 2,6-Cl$_2$-4-NO$_2$ | O | O |
| H | H | CF$_2$CF$_3$ | 2-Br-4-CF$_3$-6-Br | O | O |
| H | H | CF$_2$CF$_3$ | 2-Cl-4-CF$_3$-6-I | O | O |

TABLE 5-continued

| | | | | | |
|---|---|---|---|---|---|
| H | H | CF$_2$CF$_3$ | 2-Cl-4-CF$_3$-6-OCH$_3$ | O | O |
| H | H | CF$_2$CF$_3$ | 2-Cl-4,6-(CF$_3$)$_2$ | O | O |
| H | H | CF$_2$CF$_3$ | 2-Cl-4-CF$_3$-6-OCF$_3$ | O | O |
| H | H | CF$_2$CF$_3$ | 2-Cl-4-CF$_3$-6-NO$_2$ | O | O |
| H | H | CF$_2$CF$_3$ | 2-Cl-4,6-(OCF$_3$)$_2$ | O | O |
| H | H | CF$_2$CF$_3$ | 2-Cl-4-SCF$_3$-6-CF$_3$ | O | O |
| H | H | CF$_2$CF$_3$ | 2-Cl-4-NO$_2$-6-CF$_3$ | O | O |
| H | H | CF$_2$CF$_3$ | 2,6-Br$_2$-4-Cl | O | O |
| H | H | CF$_2$CF$_3$ | 2,6-Br$_2$-4-CF$_3$ | O | O |
| H | H | CF$_2$CF$_3$ | 2,4-Br$_2$-6-OCF$_3$ | O | O |
| H | H | CF$_2$CF$_3$ | 2,6-Br$_2$-4-OCF$_3$ | O | O |
| H | H | CF$_2$CF$_3$ | 2-Br-4-CF$_3$-6-NO$_2$ | O | O |
| H | H | CF$_2$CF$_3$ | 2,6-(CH$_3$)$_2$-4-Cl | O | O |
| H | H | CF$_2$CF$_3$ | 2,6-(CH$_3$)$_2$-4-CF$_3$ | O | O |
| H | H | CF$_2$CF$_3$ | 2,4-(NO$_2$)$_2$-6-CF$_3$ | O | O |
| H | H | CF$_2$CF$_3$ | 2,4-(CF$_3$)$_2$-6-NO$_2$ | O | O |
| H | H | CF$_2$CF$_3$ | 2,6-(CF$_3$)$_2$-4-NO$_2$ | O | O |
| H | H | CF$_2$CF$_3$ | 2,6-(NO$_2$)$_2$-4-CF$_3$ | O | O |
| H | H | CF$_2$CF$_3$ | 3,5-F$_2$-4-CF$_3$ | O | O |
| H | H | CF$_2$CF$_3$ | 3,4,5-Cl$_3$ | O | O |
| H | H | CF$_2$CF$_3$ | 3,5-Cl$_2$-4-CF$_3$ | O | O |
| H | H | CF$_2$CF$_3$ | 3,5-Cl$_2$-4-OCF$_2$CHF$_2$ | O | O |
| H | H | CF$_2$CF$_3$ | 3,5-Cl$_2$-4-SCF$_2$CHFCl | O | O |
| H | H | CF$_2$CF$_3$ | 2,3,4,5-F$_4$ | O | O |
| H | H | CF$_2$CF$_3$ | 2,4-F$_2$-3,5-Cl$_2$ | O | O |
| H | H | CF$_2$CF$_3$ | 2,3,4,5-Cl$_4$ | O | O |
| H | H | CF$_2$CF$_3$ | 2,3,5-Cl$_3$-4-CF$_3$ | O | O |
| H | H | CF$_2$CF$_3$ | 2,3,4,6-F$_4$ | O | O |
| H | H | CF$_2$CF$_3$ | 2,3,5-F$_3$-4-CF$_3$ | O | O |
| H | H | CF$_2$CF$_3$ | 2,3,4,6-Cl$_4$ | O | O |
| H | H | CF$_2$CF$_3$ | 2,3,6-Cl$_3$-4-Br | O | O |
| H | H | CF$_2$CF$_3$ | 2,3,6-Cl$_3$-4-CF$_3$ | O | O |
| H | H | CF$_2$CF$_3$ | 2,3,6-Cl$_3$-4-OCF$_3$ | O | O |
| H | H | CF$_2$CF$_3$ | 2,3,6-Cl$_3$-4-SCF$_3$ | O | O |
| H | H | CF$_2$CF$_3$ | 2,3-Cl$_2$-4,6-Br$_2$ | O | O |
| H | H | CF$_2$CF$_3$ | 2,6-Cl$_2$-3-CH$_3$-4-CF$_3$ | O | O |
| H | H | CF$_2$CF$_3$ | 2,6-Cl$_2$-3-CH$_2$CH$_3$-4-CF$_3$ | O | O |
| H | H | CF$_2$CF$_3$ | 2,6-Cl$_2$-3-OCH$_3$-4-CF$_3$ | O | O |
| H | H | CF$_2$CF$_3$ | 2,6-Cl$_2$-3-NHCH$_3$-4-CF$_3$ | O | O |
| H | H | CF$_2$CF$_3$ | 2,6-Br$_2$-3,4-Cl$_2$ | O | O |
| H | H | CF$_2$CF$_3$ | 2,4-Br$_2$-3,6-Cl$_2$ | O | O |
| H | H | CF$_2$CF$_3$ | 2,6-Br$_2$-3-Cl-4-CH$_3$ | O | O |
| H | H | CF$_2$CF$_3$ | 2,3,6-Br$_3$-4-CF$_3$ | O | O |
| H | H | CF$_2$CF$_3$ | 2-CF$_3$-3-F-4,6-Cl$_2$ | O | O |
| H | H | CF$_2$CF$_3$ | 2-CF$_3$-3-Cl-4,6-(NO$_2$)$_2$ | O | O |
| H | H | CF$_2$CF$_3$ | 2-CF$_3$-3-OCH$_2$CH$_3$-4,6-(NO$_2$)$_2$ | O | O |
| H | H | CF$_2$CF$_3$ | 2,6-(NO$_2$)$_2$-3-Cl-4-CF$_3$ | O | O |
| H | H | CF$_2$CF$_3$ | 2,3,5,6-Cl$_4$ | O | O |
| H | H | CF$_2$CF$_3$ | 2,3,4,5,6-F$_5$ | O | O |
| H | H | CF$_2$CF$_3$ | 2,3,5,6-F$_4$-4-CF$_3$ | O | O |
| H | H | CF$_2$CF$_3$ | 2,3,5,6-F$_4$-4-CN | O | O |
| H | H | CF$_2$CF$_3$ | 2,3,5,6-F$_4$-4-Cl | O | O |
| H | H | CF$_2$CF$_3$ | 2,3,5-F$_3$-4-CF$_3$-6-Cl | O | O |
| H | H | CF$_2$CF$_3$ | 2,3,5-F$_3$-4-CF$_3$-6-OCF$_3$ | O | O |
| H | H | CF$_2$CF$_3$ | 2,4,6-F$_3$-3,5-Cl$_2$ | O | O |
| H | H | CF$_2$CF$_3$ | 2,3,4,5,6-Cl$_5$ | O | O |
| H | H | CF$_2$CF$_3$ | 2,3,5,6-Cl$_4$-4-CF$_3$ | O | O |
| H | H | CF$_2$CF$_3$ | 2,3,5,6-Cl$_4$-4-NO$_2$ | O | O |
| H | H | CF$_2$Cl | 2,3,4-F$_3$ | O | O |
| H | H | CF$_2$Cl | 2,3,4-Cl$_3$ | O | O |
| H | H | CF$_2$Cl | 2,3-Cl$_2$-4-CF$_3$ | O | O |
| H | H | CF$_2$Cl | 2,3,5-Cl$_3$ | O | O |
| H | H | CF$_2$Cl | 2,3,6-Cl$_3$ | O | O |
| H | H | CF$_2$Cl | 2,4,5-Cl$_3$ | O | O |
| H | H | CF$_2$Cl | 2,5-Cl$_2$-4-CF$_3$ | O | O |
| H | H | CF$_2$Cl | 2-CF$_3$-4-NO$_2$-5-Cl | O | O |
| H | H | CF$_2$Cl | 2,4,6-F$_3$ | O | O |
| H | H | CF$_2$Cl | 2,6-F$_2$-4-CF$_3$ | O | O |
| H | H | CF$_2$Cl | 2-F-4-CF$_3$-6-Cl | O | O |
| H | H | CF$_2$Cl | 2,4,6-Cl$_3$ | O | O |
| H | H | CF$_2$Cl | 2,6-Cl$_2$-4-Br | O | O |
| H | H | CF$_2$Cl | 2,4-Cl$_2$-6-CF$_3$ | O | O |
| H | H | CF$_2$Cl | 2,6-Cl$_2$-4-CF$_3$ | O | O |
| H | H | CF$_2$Cl | 2,6-Cl$_2$-4-CHF$_2$ | O | O |
| H | H | CF$_2$Cl | 2,6-Cl$_2$-4-OCF$_3$ | O | O |
| H | H | CF$_2$Cl | 2,6-Cl$_2$-4-OCF$_2$CHF$_2$ | O | O |
| H | H | CF$_2$Cl | 2,6-Cl$_2$-4-SCF$_3$ | O | O |
| H | H | CF$_2$Cl | 2,6-Cl$_2$-4-SO$_2$CH$_3$ | O | O |
| H | H | CF$_2$Cl | 2,6-Cl$_2$-4-SO$_2$CF$_3$ | O | O |
| H | H | CF$_2$Cl | 2,6-Cl$_2$-4-CO$_2$CH$_3$ | O | O |
| H | H | CF$_2$Cl | 2,6-Cl$_2$-4-CN | O | O |
| H | H | CF$_2$Cl | 2,6-Cl$_2$-4-NO$_2$ | O | O |

TABLE 5-continued

| | | | | | |
|---|---|---|---|---|---|
| H | H | $CF_2Cl$ | 2-Br-4-$CF_3$-6-Cl | O | O |
| H | H | $CF_2Cl$ | 2-Cl-4,6-$(CF_3)_2$ | O | O |
| H | H | $CF_2Cl$ | 2-Cl-4-$CF_3$-6-$NO_2$ | O | O |
| H | H | $CF_2Cl$ | 2-Cl-4-$NO_2$-6-$CF_3$ | O | O |
| H | H | $CF_2Cl$ | 2,6-$Br_2$-4-$CF_3$ | O | O |
| H | H | $CF_2Cl$ | 2,4-$(NO_2)_2$-6-$CF_3$ | O | O |
| H | H | $CF_2Cl$ | 2,6-$(NO_2)_2$-4-$CF_3$ | O | O |
| H | H | $CF_2Cl$ | 3,4,5-$Cl_3$ | O | O |
| H | H | $CF_2Cl$ | 3,5-$Cl_2$-4-$CF_3$ | O | O |
| H | H | $CF_2Cl$ | 3,5-$Cl_2$-4-$OCF_2CHF_2$ | O | O |
| H | H | $CF_2Cl$ | 2,3,4,5-$F_4$ | O | O |
| H | H | $CF_2Cl$ | 2,4-$F_2$-3,5-$Cl_2$ | O | O |
| H | H | $CF_2Cl$ | 2,3,4,5-$Cl_4$ | O | O |
| H | H | $CF_2Cl$ | 2,3,5-$Cl_3$-4-$CF_3$ | O | O |
| H | H | $CF_2Cl$ | 2,3,4,6-$F_4$ | O | O |
| H | H | $CF_2Cl$ | 2,3,4,6-$Cl_4$ | O | O |
| H | H | $CF_2Cl$ | 2,3,6-$Cl_3$-4-$CF_3$ | O | O |
| H | H | $CF_2Cl$ | 2,3,6-$Cl_3$-4-$OCF_3$ | O | O |
| H | H | $CF_2Cl$ | 2,6-$Cl_2$-3-$CH_3$-4-$CF_3$ | O | O |
| H | H | $CF_2Cl$ | 2,6-$Cl_2$-3-$OCH_3$-4-$CF_3$ | O | O |
| H | H | $CF_2Cl$ | 2,3,6-$Br_3$-4-$CF_3$ | O | O |
| H | H | $CF_2Cl$ | 2-$CF_3$-3-Cl-4,6-$(NO_2)_2$ | O | O |
| H | H | $CF_2Cl$ | 2-$CF_3$-3-$OCH_2CH_3$-4,6-$(NO_2)_2$ | O | O |
| H | H | $CF_2Cl$ | 2,6-$(NO_2)_2$-3-Cl-4-$CF_3$ | O | O |
| H | H | $CF_2Cl$ | 2,3,5,6-$Cl_4$ | O | O |
| H | H | $CF_2Cl$ | 2,3,4,5,6-$F_5$ | O | O |
| H | H | $CF_2Cl$ | 2,3,5,6-$F_4$-4-$CF_3$ | O | O |
| H | H | $CF_2Cl$ | 2,3,5,6-$F_4$-4-CN | O | O |
| H | H | $CF_2Cl$ | 2,4,6-$F_3$-3,5-$Cl_2$ | O | O |
| H | H | $CF_2Cl$ | 2,3,4,5,6-$Cl_5$ | O | O |
| H | H | $CF_2Cl$ | 2,3,5,6-$Cl_4$-4-$CF_3$ | O | O |
| H | H | $CF_2Cl$ | 2,3,5,6-$Cl_4$-4-$NO_2$ | O | O |
| H | H | $CH_2CF_3$ | 2,3,4-$F_3$ | O | O |
| H | H | $CH_2CF_3$ | 2,3,4-$Cl_3$ | O | O |
| H | H | $CH_2CF_3$ | 2,3-$Cl_2$-4-$CF_3$ | O | O |
| H | H | $CH_2CF_3$ | 2,3,5-$Cl_3$ | O | O |
| H | H | $CH_2CF_3$ | 2,3,6-$Cl_3$ | O | O |
| H | H | $CH_2CF_3$ | 2,4,5-$Cl_3$ | O | O |
| H | H | $CH_2CF_3$ | 2,5-$Cl_2$-4-$CF_3$ | O | O |
| H | H | $CH_2CF_3$ | 2-$CF_3$-4-$NO_2$-5-Cl | O | O |
| H | H | $CH_2CF_3$ | 2,4,6-$F_3$ | O | O |
| H | H | $CH_2CF_3$ | 2,6-$F_2$-4-$CF_3$ | O | O |
| H | H | $CH_2CF_3$ | 2-F-4-$CF_3$-6-Cl | O | O |
| H | H | $CH_2CF_3$ | 2,4,6-$Cl_3$ | O | O |
| H | H | $CH_2CF_3$ | 2,6-$Cl_2$-4-Br | O | O |
| H | H | $CH_2CF_3$ | 2,4-$Cl_2$-6-$CF_3$ | O | O |
| H | H | $CH_2CF_3$ | 2,6-$Cl_2$-4-$CF_3$ | O | O |
| H | H | $CH_2CF_3$ | 2,6-$Cl_2$-4-$CHF_2$ | O | O |
| H | H | $CH_2CF_3$ | 2,6-$Cl_2$-4-$OCF_3$ | O | O |
| H | H | $CH_2CF_3$ | 2,6-$Cl_2$-4-$OCF_2CHF_2$ | O | O |
| H | H | $CH_2CF_3$ | 2,6-$Cl_2$-4-$SCF_3$ | O | O |
| H | H | $CH_2CF_3$ | 2,6-$Cl_2$-4-$SO_2CH_3$ | O | O |
| H | H | $CH_2CF_3$ | 2,6-$Cl_2$-4-$SO_2CF_3$ | O | O |
| H | H | $CH_2CF_3$ | 2,6-$Cl_2$-4-$CO_2CH_3$ | O | O |
| H | H | $CH_2CF_3$ | 2,6-$Cl_2$-4-CN | O | O |
| H | H | $CH_2CF_3$ | 2,6-$Cl_2$-4-$NO_2$ | O | O |
| H | H | $CH_2CF_3$ | 2-Br-4-$CF_3$-6-Cl | O | O |
| H | H | $CH_2CF_3$ | 2-Cl-4,6-$(CF_3)_2$ | O | O |
| H | H | $CH_2CF_3$ | 2-Cl-4-$CF_3$-6-$NO_2$ | O | O |
| H | H | $CH_2CF_3$ | 2-Cl-4-$NO_2$-6-$CF_3$ | O | O |
| H | H | $CH_2CF_3$ | 2,6-$Br_2$-4-$CF_3$ | O | O |
| H | H | $CH_2CF_3$ | 2,4-$(NO_2)_2$-6-$CF_3$ | O | O |
| H | H | $CH_2CF_3$ | 2,6-$(NO_2)_2$-4-$CF_3$ | O | O |
| H | H | $CH_2CF_3$ | 3,4,5-$Cl_3$ | O | O |
| H | H | $CH_2CF_3$ | 3,5-$Cl_2$-4-$CF_3$ | O | O |
| H | H | $CH_2CF_3$ | 3,5-$Cl_2$-4-$OCF_2CHF_2$ | O | O |
| H | H | $CH_2CF_3$ | 2,3,4,5-$F_4$ | O | O |
| H | H | $CH_2CF_3$ | 2,4-$F_2$-3,5-$Cl_2$ | O | O |
| H | H | $CH_2CF_3$ | 2,3,4,5-$Cl_4$ | O | O |
| H | H | $CH_2CF_3$ | 2,3,5-$Cl_3$-4-$CF_3$ | O | O |
| H | H | $CH_2CF_3$ | 2,3,4,6-$F_4$ | O | O |
| H | H | $CH_2CF_3$ | 2,3,4,6-$Cl_4$ | O | O |
| H | H | $CH_2CF_3$ | 2,3,6-$Cl_3$-4-$CF_3$ | O | O |
| H | H | $CH_2CF_3$ | 2,3,6-$Cl_3$-4-$OCF_3$ | O | O |
| H | H | $CH_2CF_3$ | 2,6-$Cl_2$-3-$CH_3$-4-$CF_3$ | O | O |
| H | H | $CH_2CF_3$ | 2,6-$Cl_2$-3-$OCH_3$-4-$CF_3$ | O | O |
| H | H | $CH_2CF_3$ | 2,3,6-$Br_3$-4-$CF_3$ | O | O |
| H | H | $CH_2CF_3$ | 2-$CF_3$-3-Cl-4,6-$(NO_2)_2$ | O | O |
| H | H | $CH_2CF_3$ | 2-$CF_3$-3-$OCH_2CH_3$-4,6-$(NO_2)_2$ | O | O |
| H | H | $CH_2CF_3$ | 2,6-$(NO_2)_2$-3-Cl-4-$CF_3$ | O | O |
| H | H | $CH_2CF_3$ | 2,3,5,6-$Cl_4$ | O | O |
| H | H | $CH_2CF_3$ | 2,3,4,5,6-$F_5$ | O | O |

TABLE 5-continued

| | | | | | |
|---|---|---|---|---|---|
| H | H | CH₂CF₃ | 2,3,5,6-F₄-4-CF₃ | O | O |
| H | H | CH₂CF₃ | 2,3,5,6-F₄-4-CN | O | O |
| H | H | CH₂CF₃ | 2,4,6-F₃-3,5-Cl₂ | O | O |
| H | H | CH₂CF₃ | 2,3,4,5,6-Cl₅ | O | O |
| H | H | CH₂CF₃ | 2,3,5,6-Cl₄-4-CF₃ | O | O |
| H | H | CH₂CF₃ | 2,3,5,6-Cl₄-4-NO₂ | O | O |
| H | H | CF₂CF₂CF₃ | 2,3,4-F₃ | O | O |
| H | H | CF₂CF₂CF₃ | 2,3,4-Cl₃ | O | O |
| H | H | CF₂CF₂CF₃ | 2,3-Cl₂-4-CF₃ | O | O |
| H | H | CF₂CF₂CF₃ | 2,3,5-Cl₃ | O | O |
| H | H | CF₂CF₂CF₃ | 2,3,6-Cl₃ | O | O |
| H | H | CF₂CF₂CF₃ | 2,4,5-Cl₃ | O | O |
| H | H | CF₂CF₂CF₃ | 2,5-Cl₂-4-CF₃ | O | O |
| H | H | CF₂CF₂CF₃ | 2-CF₃-4-NO₂-5-Cl | O | O |
| H | H | CF₂CF₂CF₃ | 2,4,6-F₃ | O | O |
| H | H | CF₂CF₂CF₃ | 2,6-F₂-4-CF₃ | O | O |
| H | H | CF₂CF₂CF₃ | 2-F-4-CF₃-6-Cl | O | O |
| H | H | CF₂CF₂CF₃ | 2,4,6-Cl₃ | O | O |
| H | H | CF₂CF₂CF₃ | 2,6-Cl₂-4-Br | O | O |
| H | H | CF₂CF₂CF₃ | 2,4-Cl₂-6-CF₃ | O | O |
| H | H | CF₂CF₂CF₃ | 2,6-Cl₂-4-CF₃ | O | O |
| H | H | CF₂CF₂CF₃ | 2,6-Cl₂-4-CHF₂ | O | O |
| H | H | CF₂CF₂CF₃ | 2,6-Cl₂-4-OCF₃ | O | O |
| H | H | CF₂CF₂CF₃ | 2,6-Cl₂-4-OCF₂CHF₂ | O | O |
| H | H | CF₂CF₂CF₃ | 2,6-Cl₂-4-SCF₃ | O | O |
| H | H | CF₂CF₂CF₃ | 2,6-Cl₂-4-SO₂CH₃ | O | O |
| H | H | CF₂CF₂CF₃ | 2,6-Cl₂-4-SO₂CF₃ | O | O |
| H | H | CF₂CF₂CF₃ | 2,6-Cl₂-4-CO₂CH₃ | O | O |
| H | H | CF₂CF₂CF₃ | 2,6-Cl₂-4-CN | O | O |
| H | H | CF₂CF₂CF₃ | 2,6-Cl₂-4-NO₂ | O | O |
| H | H | CF₂CF₂CF₃ | 2-Br-4-CF₃-6-Cl | O | O |
| H | H | CF₂CF₂CF₃ | 2-Cl-4,6-(CF₃)₂ | O | O |
| H | H | CF₂CF₂CF₃ | 2-Cl-4-CF₃-6-NO₂ | O | O |
| H | H | CF₂CF₂CF₃ | 2-Cl-4-NO₂-6-CF₃ | O | O |
| H | H | CF₂CF₂CF₃ | 2,6-Br₂-4-CF₃ | O | O |
| H | H | CF₂CF₂CF₃ | 2,4-(NO₂)₂-6-CF₃ | O | O |
| H | H | CF₂CF₂CF₃ | 2,6-(NO₂)₂-4-CF₃ | O | O |
| H | H | CF₂CF₂CF₃ | 3,4,5-Cl₃ | O | O |
| H | H | CF₂CF₂CF₃ | 3,5-Cl₂-4-CF₃ | O | O |
| H | H | CF₂CF₂CF₃ | 3,5-Cl₂-4-OCF₂CHF₂ | O | O |
| H | H | CF₂CF₂CF₃ | 2,3,4,5-F₄ | O | O |
| H | H | CF₂CF₂CF₃ | 2,4-F₂-3,5-Cl₂ | O | O |
| H | H | CF₂CF₂CF₃ | 2,3,4,5-Cl₄ | O | O |
| H | H | CF₂CF₂CF₃ | 2,3,5-Cl₃-4-CF₃ | O | O |
| H | H | CF₂CF₂CF₃ | 2,3,4,6-F₄ | O | O |
| H | H | CF₂CF₂CF₃ | 2,3,4,6-Cl₄ | O | O |
| H | H | CF₂CF₂CF₃ | 2,3,6-Cl₃-4-CF₃ | O | O |
| H | H | CF₂CF₂CF₃ | 2,3,6-Cl₃-4-OCF₃ | O | O |
| H | H | CF₂CF₂CF₃ | 2,6-Cl₂-3-CH₃-4-CF₃ | O | O |
| H | H | CF₂CF₂CF₃ | 2,6-Cl₂-3-OCH₃-4-CF₃ | O | O |
| H | H | CF₂CF₂CF₃ | 2,3,6-Br₃-4-CF₃ | O | O |
| H | H | CF₂CF₂CF₃ | 2-CF₃-3-Cl-4,6-(NO₂)₂ | O | O |
| H | H | CF₂CF₂CF₃ | 2-CF₃-3-OCH₂CH₃-4,6-(NO₂)₂ | O | O |
| H | H | CF₂CF₂CF₃ | 2,6-(NO₂)₂-3-Cl-4-CF₃ | O | O |
| H | H | CF₂CF₂CF₃ | 2,3,5,6-Cl₄ | O | O |
| H | H | CF₂CF₂CF₃ | 2,3,4,5,6-F₅ | O | O |
| H | H | CF₂CF₂CF₃ | 2,3,5,6-F₄-4-CF₃ | O | O |
| H | H | CF₂CF₂CF₃ | 2,3,5,6-F₄-4-CN | O | O |
| H | H | CF₂CF₂CF₃ | 2,4,6-F₃-3,5-Cl₂ | O | O |
| H | H | CF₂CF₂CF₃ | 2,3,4,5,6-Cl₅ | O | O |
| H | H | CF₂CF₂CF₃ | 2,3,5,6-Cl₄-4-CF₃ | O | O |
| H | H | CF₂CF₂CF₃ | 2,3,5,6-Cl₄-4-NO₂ | O | O |
| H | H | CF(CF₃)₂ | 2,3,4-F₃ | O | O |
| H | H | CF(CF₃)₂ | 2,3,4-Cl₃ | O | O |
| H | H | CF(CF₃)₂ | 2,3-Cl₂-4-CF₃ | O | O |
| H | H | CF(CF₃)₂ | 2,3,5-Cl₃ | O | O |
| H | H | CF(CF₃)₂ | 2,3,6-Cl₃ | O | O |
| H | H | CF(CF₃)₂ | 2,4,5-Cl₃ | O | O |
| H | H | CF(CF₃)₂ | 2,5-Cl₂-4-CF₃ | O | O |
| H | H | CF(CF₃)₂ | 2-CF₃-4-NO₂-5-Cl | O | O |
| H | H | CF(CF₃)₂ | 2,4,6-F₃ | O | O |
| H | H | CF(CF₃)₂ | 2,6-F₂-4-CF₃ | O | O |
| H | H | CF(CF₃)₂ | 2-F-4-CF₃-6-Cl | O | O |
| H | H | CF(CF₃)₂ | 2,4,6-Cl₃ | O | O |
| H | H | CF(CF₃)₂ | 2,6-Cl₂-4-Br | O | O |
| H | H | CF(CF₃)₂ | 2,4-Cl₂-6-CF₃ | O | O |
| H | H | CF(CF₃)₂ | 2,6-Cl₂-4-CF₃ | O | O |
| H | H | CF(CF₃)₂ | 2,6-Cl₂-4-CHF₂ | O | O |
| H | H | CF(CF₃)₂ | 2,6-Cl₂-4-OCF₃ | O | O |
| H | H | CF(CF₃)₂ | 2,6-Cl₂-4-OCF₂CHF₂ | O | O |
| H | H | CF(CF₃)₂ | 2,6-Cl₂-4-SCF₃ | O | O |
| H | H | CF(CF₃)₂ | 2,6-Cl₂-4-SO₂CH₃ | O | O |

TABLE 5-continued

| | | | | | |
|---|---|---|---|---|---|
| H | H | CF(CF₃)₂ | 2,6-Cl₂-4-SO₂CF₃ | O | O |
| H | H | CF(CF₃)₂ | 2,6-Cl₂-4-CO₂CH₃ | O | O |
| H | H | CF(CF₃)₂ | 2,6-Cl₂-4-CN | O | O |
| H | H | CF(CF₃)₂ | 2,6-Cl₂-4-NO₂ | O | O |
| H | H | CF(CF₃)₂ | 2-Br-4-CF₃-6-Cl | O | O |
| H | H | CF(CF₃)₂ | 2-Cl-4,6-(CF₃)₂ | O | O |
| H | H | CF(CF₃)₂ | 2-Cl-4-CF₃-6-NO₂ | O | O |
| H | H | CF(CF₃)₂ | 2-Cl-4-NO₂-6-CF₃ | O | O |
| H | H | CF(CF₃)₂ | 2,6-Br₂-4-CF₃ | O | O |
| H | H | CF(CF₃)₂ | 2,4-(NO₂)₂-6-CF₃ | O | O |
| H | H | CF(CF₃)₂ | 2,6-(NO₂)₂-4-CF₃ | O | O |
| H | H | CF(CF₃)₂ | 3,4,5-Cl₃ | O | O |
| H | H | CF(CF₃)₂ | 3,5-Cl₂-4-CF₃ | O | O |
| H | H | CF(CF₃)₂ | 3,5-Cl₂-4-OCF₂CHF₂ | O | O |
| H | H | CF(CF₃)₂ | 2,3,4,5-F₄ | O | O |
| H | H | CF(CF₃)₂ | 2,4-F₂-3,5-Cl₂ | O | O |
| H | H | CF(CF₃)₂ | 2,3,4,5-Cl₄ | O | O |
| H | H | CF(CF₃)₂ | 2,3,5-Cl₃-4-CF₃ | O | O |
| H | H | CF(CF₃)₂ | 2,3,4,6-F₄ | O | O |
| H | H | CF(CF₃)₂ | 2,3,4,6-Cl₄ | O | O |
| H | H | CF(CF₃)₂ | 2,3,6-Cl₃-4-CF₃ | O | O |
| H | H | CF(CF₃)₂ | 2,3,6-Cl₃-4-OCF₃ | O | O |
| H | H | CF(CF₃)₂ | 2,6-Cl₂-3-CH₃-4-CF₃ | O | O |
| H | H | CF(CF₃)₂ | 2,6-Cl₂-3-OCH₃-4-CF₃ | O | O |
| H | H | CF(CF₃)₂ | 2,3,6-Br₃-4-CF₃ | O | O |
| H | H | CF(CF₃)₂ | 2-CF₃-3-Cl-4,6-(NO₂)₂ | O | O |
| H | H | CF(CF₃)₂ | 2-CF₃-3-OCH₂CH₃-4,6-(NO₂)₂ | O | O |
| H | H | CF(CF₃)₂ | 2,6-(NO₂)₂-3-Cl-4-CF₃ | O | O |
| H | H | CF(CF₃)₂ | 2,3,5,6-Cl₄ | O | O |
| H | H | CF(CF₃)₂ | 2,3,4,5,6-F₅ | O | O |
| H | H | CF(CF₃)₂ | 2,3,5,6-F₄-4-CF₃ | O | O |
| H | H | CF(CF₃)₂ | 2,3,5,6-F₄-4-CN | O | O |
| H | H | CF(CF₃)₂ | 2,4,6-F₃-3,5-Cl₂ | O | O |
| H | H | CF(CF₃)₂ | 2,3,4,5,6-Cl₅ | O | O |
| H | H | CF(CF₃)₂ | 2,3,5,6-Cl₄-4-CF₃ | O | O |
| H | H | CF(CF₃)₂ | 2,3,5,6-Cl₄-4-NO₂ | O | O |
| H | H | (CF₂)₃CF₃ | 2,3,4-F₃ | O | O |
| H | H | (CF₂)₃CF₃ | 2,3,4-Cl₃ | O | O |
| H | H | (CF₂)₃CF₃ | 2,3-Cl₂-4-CF₃ | O | O |
| H | H | (CF₂)₃CF₃ | 2,3,5-Cl₃ | O | O |
| H | H | (CF₂)₃CF₃ | 2,3,6-Cl₃ | O | O |
| H | H | (CF₂)₃CF₃ | 2,4,5-Cl₃ | O | O |
| H | H | (CF₂)₃CF₃ | 2,5-Cl₂-4-CF₃ | O | O |
| H | H | (CF₂)₃CF₃ | 2-CF₃-4-NO₂-5-Cl | O | O |
| H | H | (CF₂)₃CF₃ | 2,4,6-F₃ | O | O |
| H | H | (CF₂)₃CF₃ | 2,6-F₂-4-CF₃ | O | O |
| H | H | (CF₂)₃CF₃ | 2-F-4-CF₃-6-Cl | O | O |
| H | H | (CF₂)₃CF₃ | 2,4,6-Cl₃ | O | O |
| H | H | (CF₂)₃CF₃ | 2,6-Cl₂-4-Br | O | O |
| H | H | (CF₂)₃CF₃ | 2,4-Cl₂-6-CF₃ | O | O |
| H | H | (CF₂)₃CF₃ | 2,6-Cl₂-4-CF₃ | O | O |
| H | H | (CF₂)₃CF₃ | 2,6-Cl₂-4-CHF₂ | O | O |
| H | H | (CF₂)₃CF₃ | 2,6-Cl₂-4-OCF₃ | O | O |
| H | H | (CF₂)₃CF₃ | 2,6-Cl₂-4-OCF₂CHF₂ | O | O |
| H | H | (CF₂)₃CF₃ | 2,6-Cl₂-4-SCF₃ | O | O |
| H | H | (CF₂)₃CF₃ | 2,6-Cl₂-4-SO₂CH₃ | O | O |
| H | H | (CF₂)₃CF₃ | 2,6-Cl₂-4-SO₂CF₃ | O | O |
| H | H | (CF₂)₃CF₃ | 2,6-Cl₂-4-CO₂CH₃ | O | O |
| H | H | (CF₂)₃CF₃ | 2,6-Cl₂-4-CN | O | O |
| H | H | (CF₂)₃CF₃ | 2,6-Cl₂-4-NO₂ | O | O |
| H | H | (CF₂)₃CF₃ | 2-Br-4-CF₃-6-Cl | O | O |
| H | H | (CF₂)₃CF₃ | 2-Cl-4,6-(CF₃)₂ | O | O |
| H | H | (CF₂)₃CF₃ | 2-Cl-4-CF₃-6-NO₂ | O | O |
| H | H | (CF₂)₃CF₃ | 2-Cl-4-NO₂-6-CF₃ | O | O |
| H | H | (CF₂)₃CF₃ | 2,6-Br₂-4-CF₃ | O | O |
| H | H | (CF₂)₃CF₃ | 2,4-(NO₂)₂-6-CF₃ | O | O |
| H | H | (CF₂)₃CF₃ | 2,6-(NO₂)₂-4-CF₃ | O | O |
| H | H | (CF₂)₃CF₃ | 3,4,5-Cl₃ | O | O |
| H | H | (CF₂)₃CF₃ | 3,5-Cl₂-4-CF₃ | O | O |
| H | H | (CF₂)₃CF₃ | 3,5-Cl₂-4-OCF₂CHF₂ | O | O |
| H | H | (CF₂)₃CF₃ | 2,3,4,5-F₄ | O | O |
| H | H | (CF₂)₃CF₃ | 2,4-F₂-3,5-Cl₂ | O | O |
| H | H | (CF₂)₃CF₃ | 2,3,4,5-Cl₄ | O | O |
| H | H | (CF₂)₃CF₃ | 2,3,5-Cl₃-4-CF₃ | O | O |
| H | H | (CF₂)₃CF₃ | 2,3,4,6-F₄ | O | O |
| H | H | (CF₂)₃CF₃ | 2,3,4,6-Cl₄ | O | O |
| H | H | (CF₂)₃CF₃ | 2,3,6-Cl₃-4-CF₃ | O | O |
| H | H | (CF₂)₃CF₃ | 2,3,6-Cl₃-4-OCF₃ | O | O |
| H | H | (CF₂)₃CF₃ | 2,6-Cl₂-3-CH₃-4-CF₃ | O | O |
| H | H | (CF₂)₃CF₃ | 2,6-Cl₂-3-OCH₃-4-CF₃ | O | O |
| H | H | (CF₂)₃CF₃ | 2,3,6-Br₃-4-CF₃ | O | O |
| H | H | (CF₂)₃CF₃ | 2-CF₃-3-Cl-4,6-(NO₂)₂ | O | O |

TABLE 5-continued

| | | | | | |
|---|---|---|---|---|---|
| H | H | (CF₂)₃CF₃ | 2-CF₃-3-OCH₂CH₃-4,6-(NO₂)₂ | O | O |
| H | H | (CF₂)₃CF₃ | 2,6-(NO₂)₂-3-Cl-4-CF₃ | O | O |
| H | H | (CF₂)₃CF₃ | 2,3,5,6-Cl₄ | O | O |
| H | H | (CF₂)₃CF₃ | 2,3,4,5,6-F₅ | O | O |
| H | H | (CF₂)₃CF₃ | 2,3,5,6-F₄-4-CF₃ | O | O |
| H | H | (CF₂)₃CF₃ | 2,3,5,6-F₄-4-CN | O | O |
| H | H | (CF₂)₃CF₃ | 2,4,6-F₃-3,5-Cl₂ | O | O |
| H | H | (CF₂)₃CF₃ | 2,3,4,5,6-Cl₅ | O | O |
| H | H | (CF₂)₃CF₃ | 2,3,5,6-Cl₄-4-CF₃ | O | O |
| H | H | (CF₂)₃CF₃ | 2,3,5,6-Cl₄-4-NO₂ | O | O |
| H | H | (CF₂)₅CF₃ | 2,3,4-F₃ | O | O |
| H | H | (CF₂)₅CF₃ | 2,3,4-Cl₃ | O | O |
| H | H | (CF₂)₅CF₃ | 2,3-Cl₂-4-CF₃ | O | O |
| H | H | (CF₂)₅CF₃ | 2,3,5-Cl₃ | O | O |
| H | H | (CF₂)₅CF₃ | 2,3,6-Cl₃ | O | O |
| H | H | (CF₂)₅CF₃ | 2,4,5-Cl₃ | O | O |
| H | H | (CF₂)₅CF₃ | 2,5-Cl₂-4-CF₃ | O | O |
| H | H | (CF₂)₅CF₃ | 2-CF₃-4-NO₂-5-Cl | O | O |
| H | H | (CF₂)₅CF₃ | 2,4,6-F₃ | O | O |
| H | H | (CF₂)₅CF₃ | 2,6-F₂-4-CF₃ | O | O |
| H | H | (CF₂)₅CF₃ | 2-F-4-CF₃-6-Cl | O | O |
| H | H | (CF₂)₅CF₃ | 2,4,6-Cl₃ | O | O |
| H | H | (CF₂)₅CF₃ | 2,6-Cl₂-4-Br | O | O |
| H | H | (CF₂)₅CF₃ | 2,4-Cl₂-6-CF₃ | O | O |
| H | H | (CF₂)₅CF₃ | 2,6-Cl₂-4-CF₃ | O | O |
| H | H | (CF₂)₅CF₃ | 2,6-Cl₂-4-CHF₂ | O | O |
| H | H | (CF₂)₅CF₃ | 2,6-Cl₂-4-OCF₃ | O | O |
| H | H | (CF₂)₅CF₃ | 2,6-Cl₂-4-OCF₂CHF₂ | O | O |
| H | H | (CF₂)₅CF₃ | 2,6-Cl₂-4-SCF₃ | O | O |
| H | H | (CF₂)₅CF₃ | 2,6-Cl₂-4-SO₂CH₃ | O | O |
| H | H | (CF₂)₅CF₃ | 2,6-Cl₂-4-SO₂CF₃ | O | O |
| H | H | (CF₂)₅CF₃ | 2,6-Cl₂-4-CO₂CH₃ | O | O |
| H | H | (CF₂)₅CF₃ | 2,6-Cl₂-4-CN | O | O |
| H | H | (CF₂)₅CF₃ | 2,6-Cl₂-4-NO₂ | O | O |
| H | H | (CF₂)₅CF₃ | 2-Br-4-CF₃-6-Cl | O | O |
| H | H | (CF₂)₅CF₃ | 2-Cl-4,6-(CF₃)₂ | O | O |
| H | H | (CF₂)₅CF₃ | 2-Cl-4-CF₃-6-NO₂ | O | O |
| H | H | (CF₂)₅CF₃ | 2-Cl-4-NO₂-6-CF₃ | O | O |
| H | H | (CF₂)₅CF₃ | 2,6-Br₂-4-CF₃ | O | O |
| H | H | (CF₂)₅CF₃ | 2,4-(NO₂)₂-6-CF₃ | O | O |
| H | H | (CF₂)₅CF₃ | 2,6-(NO₂)₂-4-CF₃ | O | O |
| H | H | (CF₂)₅CF₃ | 3,4,5-Cl₃ | O | O |
| H | H | (CF₂)₅CF₃ | 3,5-Cl₂-4-CF₃ | O | O |
| H | H | (CF₂)₅CF₃ | 3,5-Cl₂-4-OCF₂CHF₂ | O | O |
| H | H | (CF₂)₅CF₃ | 2,3,4,5-F₄ | O | O |
| H | H | (CF₂)₅CF₃ | 2,4-F₂-3,5-Cl₂ | O | O |
| H | H | (CF₂)₅CF₃ | 2,3,4,5-Cl₄ | O | O |
| H | H | (CF₂)₅CF₃ | 2,3,5-Cl₃-4-CF₃ | O | O |
| H | H | (CF₂)₅CF₃ | 2,3,4,6-F₄ | O | O |
| H | H | (CF₂)₅CF₃ | 2,3,4,6-Cl₄ | O | O |
| H | H | (CF₂)₅CF₃ | 2,3,6-Cl₃-4-CF₃ | O | O |
| H | H | (CF₂)₅CF₃ | 2,3,6-Cl₃-4-OCF₃ | O | O |
| H | H | (CF₂)₅CF₃ | 2,6-Cl₂-3-CH₃-4-CF₃ | O | O |
| H | H | (CF₂)₅CF₃ | 2,6-Cl₂-3-OCH₃-4-CF₃ | O | O |
| H | H | (CF₂)₅CF₃ | 2,3,6-Br₃-4-CF₃ | O | O |
| H | H | (CF₂)₅CF₃ | 2-CF₃-3-Cl-4,6-(NO₂)₂ | O | O |
| H | H | (CF₂)₅CF₃ | 2-CF₃-3-OCH₂CH₃-4,6-(NO₂)₂ | O | O |
| H | H | (CF₂)₅CF₃ | 2,6-(NO₂)₂-3-Cl-4-CF₃ | O | O |
| H | H | (CF₂)₅CF₃ | 2,3,5,6-Cl₄ | O | O |
| H | H | (CF₂)₅CF₃ | 2,3,4,5,6-F₅ | O | O |
| H | H | (CF₂)₅CF₃ | 2,3,5,6-F₄-4-CF₃ | O | O |
| H | H | (CF₂)₅CF₃ | 2,3,5,6-F₄-4-CN | O | O |
| H | H | (CF₂)₅CF₃ | 2,4,6-F₃-3,5-Cl₂ | O | O |
| H | H | (CF₂)₅CF₃ | 2,3,4,5,6-Cl₅ | O | O |
| H | H | (CF₂)₅CF₃ | 2,3,5,6-Cl₄-4-CF₃ | O | O |
| H | H | (CF₂)₅CF₃ | 2,3,5,6-Cl₄-4-NO₂ | O | O |
| H | H | CHF₂ | 2,3,4-F₃ | O | O |
| H | H | CHF₂ | 2,3,4-Cl₃ | O | O |
| H | H | CHF₂ | 2,3,5-Cl₃ | O | O |
| H | H | CHF₂ | 2,3,6-Cl₃ | O | O |
| H | H | CHF₂ | 2,4,5-Cl₃ | O | O |
| H | H | CHF₂ | 2,5-Cl₂-4-CF₃ | O | O |
| H | H | CHF₂ | 2-CF₃-4-NO₂-5-Cl | O | O |
| H | H | CHF₂ | 2,4,6-Cl₃ | O | O |
| H | H | CHF₂ | 2,6-Cl₂-4-Br | O | O |
| H | H | CHF₂ | 2,4-Cl₂-6-CF₃ | O | O |
| H | H | CHF₂ | 2,6-Cl₂-4-CF₃ | O | O |
| H | H | CHF₂ | 2,6-Cl₂-4-CHF₂ | O | O |
| H | H | CHF₂ | 2,6-Cl₂-4-CN | O | O |
| H | H | CHF₂ | 2,6-Cl₂-4-NO₂ | O | O |
| H | H | CHF₂ | 2-Br-4-CF₃-6-Cl | O | O |
| H | H | CHF₂ | 2-Cl-4-CF₃-6-NO₂ | O | O |

TABLE 5-continued

| | | | | | |
|---|---|---|---|---|---|
| H | H | CHF$_2$ | 2-Cl-4-NO$_2$-6-CF$_3$ | O | O |
| H | H | CHF$_2$ | 2,6-Br$_2$-4-CF$_3$ | O | O |
| H | H | CHF$_2$ | 2,4-(NO$_2$)$_2$-6-CF$_3$ | O | O |
| H | H | CHF$_2$ | 2,6-(NO$_2$)$_2$-4-CF$_3$ | O | O |
| H | H | CHF$_2$ | 3,4,5-Cl$_3$ | O | O |
| H | H | CHF$_2$ | 3,5-Cl$_2$-4-CF$_3$ | O | O |
| H | H | CHF$_2$ | 2,4-F$_2$-3,5-Cl$_2$ | O | O |
| H | H | CHF$_2$ | 2,3,4,5-Cl$_4$ | O | O |
| H | H | CHF$_2$ | 2,3,5-Cl$_3$-4-CF$_3$ | O | O |
| H | H | CHF$_2$ | 2,3,4,6-Cl$_4$ | O | O |
| H | H | CHF$_2$ | 2,3,6-Cl$_3$-4-CF$_3$ | O | O |
| H | H | CHF$_2$ | 2,3,6-Cl$_3$-4-OCF$_3$ | O | O |
| H | H | CHF$_2$ | 2,6-Cl$_2$-3-OCH$_3$-4-CF$_3$ | O | O |
| H | H | CHF$_2$ | 2-CF$_3$-3-Cl-4,6-(NO$_2$)$_2$ | O | O |
| H | H | CHF$_2$ | 2-CF$_3$-3-OCH$_2$CH$_3$-4,6-(NO$_2$)$_2$ | O | O |
| H | H | CHF$_2$ | 2,6-(NO$_2$)$_2$-3-Cl-4-CF$_3$ | O | O |
| H | H | CHF$_2$ | 2,3,5,6-Cl$_4$ | O | O |
| H | H | CHF$_2$ | 2,3,4,5,6-F$_5$ | O | O |
| H | H | CHF$_2$ | 2,3,5,6-F$_4$-4-CN | O | O |
| H | H | CHF$_2$ | 2,3,5,6-Cl$_4$-4-CF$_3$ | O | O |
| H | H | CHF$_2$ | 2,3,5,6-Cl$_4$-4-NO$_2$ | O | O |
| H | H | CF$_2$Br | 2,3,4-F$_3$ | O | O |
| H | H | CF$_2$Br | 2,3,4-Cl$_3$ | O | O |
| H | H | CF$_2$Br | 2,3,5-Cl$_3$ | O | O |
| H | H | CF$_2$Br | 2,3,6-Cl$_3$ | O | O |
| H | H | CF$_2$Br | 2,4,5-Cl$_3$ | O | O |
| H | H | CF$_2$Br | 2,5-Cl$_2$-4-CF$_3$ | O | O |
| H | H | CF$_2$Br | 2-CF$_3$-4-NO$_2$-5-Cl | O | O |
| H | H | CF$_2$Br | 2,4,6-Cl$_3$ | O | O |
| H | H | CF$_2$Br | 2,6-Cl$_2$-4-Br | O | O |
| H | H | CF$_2$Br | 2,4-Cl$_2$-6-CF$_3$ | O | O |
| H | H | CF$_2$Br | 2,6-Cl$_2$-4-CF$_3$ | O | O |
| H | H | CF$_2$Br | 2,6-Cl$_2$-4-CHF$_2$ | O | O |
| H | H | CF$_2$Br | 2,6-Cl$_2$-4-CN | O | O |
| H | H | CF$_2$Br | 2,6-Cl$_2$-4-NO$_2$ | O | O |
| H | H | CF$_2$Br | 2-Br-4-CF$_3$-6-Cl | O | O |
| H | H | CF$_2$Br | 2-Cl-4-CF$_3$-6-NO$_2$ | O | O |
| H | H | CF$_2$Br | 2-Cl-4-NO$_2$-6-CF$_3$ | O | O |
| H | H | CF$_2$Br | 2,6-Br$_2$-4-CF$_3$ | O | O |
| H | H | CF$_2$Br | 2,4-(NO$_2$)$_2$-6-CF$_3$ | O | O |
| H | H | CF$_2$Br | 2,6-(NO$_2$)$_2$-4-CF$_3$ | O | O |
| H | H | CF$_2$Br | 3,4,5-Cl$_3$ | O | O |
| H | H | CF$_2$Br | 3,5-Cl$_2$-4-CF$_3$ | O | O |
| H | H | CF$_2$Br | 2,4-F$_2$-3,5-Cl$_2$ | O | O |
| H | H | CF$_2$Br | 2,3,4,5-Cl$_4$ | O | O |
| H | H | CF$_2$Br | 2,3,5-Cl$_3$-4-CF$_3$ | O | O |
| H | H | CF$_2$Br | 2,3,4,6-Cl$_4$ | O | O |
| H | H | CF$_2$Br | 2,3,6-Cl$_3$-4-CF$_3$ | O | O |
| H | H | CF$_2$Br | 2,3,6-Cl$_3$-4-OCF$_3$ | O | O |
| H | H | CF$_2$Br | 2,6-Cl$_2$-3-OCH$_3$-4-CF$_3$ | O | O |
| H | H | CF$_2$Br | 2-CF$_3$-3-Cl-4,6-(NO$_2$)$_2$ | O | O |
| H | H | CF$_2$Br | 2-CF$_3$-3-OCH$_2$CH$_3$-4,6-(NO$_2$)$_2$ | O | O |
| H | H | CF$_2$Br | 2,6-(NO$_2$)$_2$-3-Cl-4-CF$_3$ | O | O |
| H | H | CF$_2$Br | 2,3,5,6-Cl$_4$ | O | O |
| H | H | CF$_2$Br | 2,3,4,5,6-F$_5$ | O | O |
| H | H | CF$_2$Br | 2,3,5,6-F$_4$-4-CN | O | O |
| H | H | CF$_2$Br | 2,3,5,6-Cl$_4$-4-CF$_3$ | O | O |
| H | H | CF$_2$Br | 2,3,5,6-Cl$_4$-4-NO$_2$ | O | O |
| H | H | C(CF$_3$)$_3$ | 2,3,4-F$_3$ | O | O |
| H | H | C(CF$_3$)$_3$ | 2,3,4-Cl$_3$ | O | O |
| H | H | C(CF$_3$)$_3$ | 2,3,5-Cl$_3$ | O | O |
| H | H | C(CF$_3$)$_3$ | 2,3,6-Cl$_3$ | O | O |
| H | H | C(CF$_3$)$_3$ | 2,4,5-Cl$_3$ | O | O |
| H | H | C(CF$_3$)$_3$ | 2,5-Cl$_2$-4-CF$_3$ | O | O |
| H | H | C(CF$_3$)$_3$ | 2-CF$_3$-4-NO$_2$-5-Cl | O | O |
| H | H | C(CF$_3$)$_3$ | 2,4,6-Cl$_3$ | O | O |
| H | H | C(CF$_3$)$_3$ | 2,6-Cl$_2$-4-Br | O | O |
| H | H | C(CF$_3$)$_3$ | 2,4-Cl$_2$-6-CF$_3$ | O | O |
| H | H | C(CF$_3$)$_3$ | 2,6-Cl$_2$-4-CF$_3$ | O | O |
| H | H | C(CF$_3$)$_3$ | 2,6-Cl$_2$-4-CHF$_2$ | O | O |
| H | H | C(CF$_3$)$_3$ | 2,6-Cl$_2$-4-CN | O | O |
| H | H | C(CF$_3$)$_3$ | 2,6-Cl$_2$-4-NO$_2$ | O | O |
| H | H | C(CF$_3$)$_3$ | 2-Br-4-CF$_3$-6-Cl | O | O |
| H | H | C(CF$_3$)$_3$ | 2-Cl-4-CF$_3$-6-NO$_2$ | O | O |
| H | H | C(CF$_3$)$_3$ | 2-Cl-4-NO$_2$-6-CF$_3$ | O | O |
| H | H | C(CF$_3$)$_3$ | 2,6-Br$_2$-4-CF$_3$ | O | O |
| H | H | C(CF$_3$)$_3$ | 2,4-(NO$_2$)$_2$-6-CF$_3$ | O | O |
| H | H | C(CF$_3$)$_3$ | 2,6-(NO$_2$)$_2$-4-CF$_3$ | O | O |
| H | H | C(CF$_3$)$_3$ | 3,4,5-Cl$_3$ | O | O |

-continued

| | | | | | |
|---|---|---|---|---|---|
| H | H | C(CF$_3$)$_3$ | 3,5-Cl$_2$-4-CF$_3$ | O | O |
| H | H | C(CF$_3$)$_3$ | 2,4-F$_2$-3,5-Cl$_2$ | O | O |
| H | H | C(CF$_3$)$_3$ | 2,3,4,5-Cl$_4$ | O | O |
| H | H | C(CF$_3$)$_3$ | 2,3,5-Cl$_3$-4-CF$_3$ | O | O |
| H | H | C(CF$_3$)$_3$ | 2,3,4,6-Cl$_4$ | O | O |
| H | H | C(CF$_3$)$_3$ | 2,3,6-Cl$_3$-4-CF$_3$ | O | O |
| H | H | C(CF$_3$)$_3$ | 2,3,6-Cl$_3$-4-OCF$_3$ | O | O |
| H | H | C(CF$_3$)$_3$ | 2,6-Cl$_2$-3-OCH$_3$-4-CF$_3$ | O | O |
| H | H | C(CF$_3$)$_3$ | 2-CF$_3$-3-Cl-4,6-(NO$_2$)$_2$ | O | O |
| H | H | C(CF$_3$)$_3$ | 2-CF$_3$-3-OCH$_2$CH$_3$-4,6-(NO$_2$)$_2$ | O | O |
| H | H | C(CF$_3$)$_3$ | 2,6-(NO$_2$)$_2$-3-Cl-4-CF$_3$ | O | O |
| H | H | C(CF$_3$)$_3$ | 2,3,5,6-Cl$_4$ | O | O |
| H | H | C(CF$_3$)$_3$ | 2,3,4,5,6-F$_5$ | O | O |
| H | H | C(CF$_3$)$_3$ | 2,3,5,6-F$_4$-4-CN | O | O |
| H | H | C(CF$_3$)$_3$ | 2,3,5,6-Cl$_4$-4-CF$_3$ | O | O |
| H | H | C(CF$_3$)$_3$ | 2,3,5,6-Cl$_4$-4-NO$_2$ | O | O |
| H | H | (CF$_2$)$_4$CF$_3$ | 2,3,4-F$_3$ | O | O |
| H | H | (CF$_2$)$_4$CF$_3$ | 2,3,4-Cl$_3$ | O | O |
| H | H | (CF$_2$)$_4$CF$_3$ | 2,3,5-Cl$_3$ | O | O |
| H | H | (CF$_2$)$_4$CF$_3$ | 2,3,6-Cl$_3$ | O | O |
| H | H | (CF$_2$)$_4$CF$_3$ | 2,4,5-Cl$_3$ | O | O |
| H | H | (CF$_2$)$_4$CF$_3$ | 2,5-Cl$_2$-4-CF$_3$ | O | O |
| H | H | (CF$_2$)$_4$CF$_3$ | 2-CF$_3$-4-NO$_2$-5-Cl | O | O |
| H | H | (CF$_2$)$_4$CF$_3$ | 2,4,6-Cl$_3$ | O | O |
| H | H | (CF$_2$)$_4$CF$_3$ | 2,6-Cl$_2$-4-Br | O | O |
| H | H | (CF$_2$)$_4$CF$_3$ | 2,4-Cl$_2$-6-CF$_3$ | O | O |
| H | H | (CF$_2$)$_4$CF$_3$ | 2,6-Cl$_2$-4-CF$_3$ | O | O |
| H | H | (CF$_2$)$_4$CF$_3$ | 2,6-Cl$_2$-4-CHF$_2$ | O | O |
| H | H | (CF$_2$)$_4$CF$_3$ | 2,6-Cl$_2$-4-CN | O | O |
| H | H | (CF$_2$)$_4$CF$_3$ | 2,6-Cl$_2$-4-NO$_2$ | O | O |
| H | H | (CF$_2$)$_4$CF$_3$ | 2-Br-4-CF$_3$-6-Cl | O | O |
| H | H | (CF$_2$)$_4$CF$_3$ | 2-Cl-4-CF$_3$-6-NO$_2$ | O | O |
| H | H | (CF$_2$)$_4$CF$_3$ | 2-Cl-4-NO$_2$-6-CF$_3$ | O | O |
| H | H | (CF$_2$)$_4$CF$_3$ | 2,6-Br$_2$-4-CF$_3$ | O | O |
| H | H | (CF$_2$)$_4$CF$_3$ | 2,4-(NO$_2$)$_2$-6-CF$_3$ | O | O |
| H | H | (CF$_2$)$_4$CF$_3$ | 2,6-(NO$_2$)$_2$-4-CF$_3$ | O | O |
| H | H | (CF$_2$)$_4$CF$_3$ | 3,4,5-Cl$_3$ | O | O |
| H | H | (CF$_2$)$_4$CF$_3$ | 3,5-Cl$_2$-4-CF$_3$ | O | O |
| H | H | (CF$_2$)$_4$CF$_3$ | 2,4-F$_2$-3,5-Cl$_2$ | O | O |
| H | H | (CF$_2$)$_4$CF$_3$ | 2,3,4,5-Cl$_4$ | O | O |
| H | H | (CF$_2$)$_4$CF$_3$ | 2,3,5-Cl$_3$-4-CF$_3$ | O | O |
| H | H | (CF$_2$)$_4$CF$_3$ | 2,3,4,6-Cl$_4$ | O | O |
| H | H | (CF$_2$)$_4$CF$_3$ | 2,3,6-Cl$_3$-4-CF$_3$ | O | O |
| H | H | (CF$_2$)$_4$CF$_3$ | 2,3,6-Cl$_3$-4-OCF$_3$ | O | O |
| H | H | (CF$_2$)$_4$CF$_3$ | 2,6-Cl$_2$-3-OCH$_3$-4-CF$_3$ | O | O |
| H | H | (CF$_2$)$_4$CF$_3$ | 2-CF$_3$-3-Cl-4,6-(NO$_2$)$_2$ | O | O |
| H | H | (CF$_2$)$_4$CF$_3$ | 2-CF$_3$-3-OCH$_2$CH$_3$-4,6-(NO$_2$)$_2$ | O | O |
| H | H | (CF$_2$)$_4$CF$_3$ | 2,6-(NO$_2$)$_2$-3-Cl-4-CF$_3$ | O | O |
| H | H | (CF$_2$)$_4$CF$_3$ | 2,3,5,6-Cl$_4$ | O | O |
| H | H | (CF$_2$)$_4$CF$_3$ | 2,3,4,5,6-F$_5$ | O | O |
| H | H | (CF$_2$)$_4$CF$_3$ | 2,3,5,6-F$_4$-4-CN | O | O |
| H | H | (CF$_2$)$_4$CF$_3$ | 2,3,5,6-Cl$_4$-4-CF$_3$ | O | O |
| H | H | (CF$_2$)$_4$CF$_3$ | 2,3,5,6-Cl$_4$-4-NO$_2$ | O | O |
| H | Cl | CF$_3$ | 2,3,4-F$_3$ | O | O |
| H | Cl | CF$_3$ | 2,3,4-Cl$_3$ | O | O |
| H | Cl | CF$_3$ | 2,3-Cl$_2$-4-CF$_3$ | O | O |
| H | Cl | CF$_3$ | 2,3,5-Cl$_3$ | O | O |
| H | Cl | CF$_3$ | 2,3,6-Cl$_3$ | O | O |
| H | Cl | CF$_3$ | 2,4,5-Cl$_3$ | O | O |
| H | Cl | CF$_3$ | 2,5-Cl$_2$-4-CF$_3$ | O | O |
| H | Cl | CF$_3$ | 2-CF$_3$-4-NO$_2$-5-Cl | O | O |
| H | Cl | CF$_3$ | 2,4,6-F$_3$ | O | O |
| H | Cl | CF$_3$ | 2,6-F$_2$-4-CF$_3$ | O | O |
| H | Cl | CF$_3$ | 2-F-4-CF$_3$-6-Cl | O | O |
| H | Cl | CF$_3$ | 2,4,6-Cl$_3$ | O | O |
| H | Cl | CF$_3$ | 2,6-Cl$_2$-4-Br | O | O |
| H | Cl | CF$_3$ | 2,4-Cl$_2$-6-CF$_3$ | O | O |
| H | Cl | CF$_3$ | 2,6-Cl$_2$-4-CF$_3$ | O | O |
| H | Cl | CF$_3$ | 2,6-Cl$_2$-4-CHF$_2$ | O | O |
| H | Cl | CF$_3$ | 2,6-Cl$_2$-4-OCF$_3$ | O | O |
| H | Cl | CF$_3$ | 2,6-Cl$_2$-4-OCF$_2$CHF$_2$ | O | O |
| H | Cl | CF$_3$ | 2,6-Cl$_2$-4-SCF$_3$ | O | O |
| H | Cl | CF$_3$ | 2,6-Cl$_2$-4-SO$_2$CH$_3$ | O | O |
| H | Cl | CF$_3$ | 2,6-Cl$_2$-4-SO$_2$CF$_3$ | O | O |
| H | Cl | CF$_3$ | 2,6-Cl$_2$-4-CO$_2$CH$_3$ | O | O |
| H | Cl | CF$_3$ | 2,6-Cl$_2$-4-CN | O | O |
| H | Cl | CF$_3$ | 2,6-Cl$_2$-4-NO$_2$ | O | O |
| H | Cl | CF$_3$ | 2-Br-4-CF$_3$-6-Cl | O | O |
| H | Cl | CF$_3$ | 2-Cl-4-CF$_3$-6-NO$_2$ | O | O |
| H | Cl | CF$_3$ | 2-Cl-4-NO$_2$-6-CF$_3$ | O | O |
| H | Cl | CF$_3$ | 2,6-Br$_2$-4-CF$_3$ | O | O |
| H | Cl | CF$_3$ | 2,4-(NO$_2$)$_2$-6-CF$_3$ | O | O |
| H | Cl | CF$_3$ | 2,6-(NO$_2$)$_2$-4-CF$_3$ | O | O |

-continued

| | | | | | |
|---|---|---|---|---|---|
| H | Cl | CF$_3$ | 3,4,5-Cl$_3$ | O | O |
| H | Cl | CF$_3$ | 3,5-Cl$_2$-4-CF$_3$ | O | O |
| H | Cl | CF$_3$ | 3,5-Cl$_2$-4-OCF$_2$CHF$_2$ | O | O |
| H | Cl | CF$_3$ | 2,3,4,5-F$_4$ | O | O |
| H | Cl | CF$_3$ | 2,4-F$_2$-3,5-Cl$_2$ | O | O |
| H | Cl | CF$_3$ | 2,3,4,5-Cl$_4$ | O | O |
| H | Cl | CF$_3$ | 2,3,5-Cl$_3$-4-CF$_3$ | O | O |
| H | Cl | CF$_3$ | 2,3,4,6-F$_4$ | O | O |
| H | Cl | CF$_3$ | 2,3,4,6-Cl$_4$ | O | O |
| H | Cl | CF$_3$ | 2,3,6-Cl$_3$-4-CF$_3$ | O | O |
| H | Cl | CF$_3$ | 2,3,6-Cl$_3$-4-OCF$_3$ | O | O |
| H | Cl | CF$_3$ | 3,5-Cl$_2$-3-CH$_3$-4-CF$_3$ | O | O |
| H | Cl | CF$_3$ | 3,5-Cl$_2$-3-OCH$_3$-4-CF$_3$ | O | O |
| H | Cl | CF$_3$ | 2-CF$_3$-3-Cl-4,6-(NO$_2$)$_2$ | O | O |
| H | Cl | CF$_3$ | 2-CF$_3$-3-OCH$_2$CH$_3$-4,6-(NO$_2$)$_2$ | O | O |
| H | Cl | CF$_3$ | 2,6-(NO$_2$)$_2$-3-Cl-4-CF$_3$ | O | O |
| H | Cl | CF$_3$ | 2,3,5,6-Cl$_4$ | O | O |
| H | Cl | CF$_3$ | 2,3,4,5,6-F$_5$ | O | O |
| H | Cl | CF$_3$ | 2,3,5,6-F$_4$-4-CF$_3$ | O | O |
| H | Cl | CF$_3$ | 2,3,5,6-F$_4$-4-CN | O | O |
| H | Cl | CF$_3$ | 2,4,6-F$_3$-3,5-Cl$_2$ | O | O |
| H | Cl | CF$_3$ | 2,3,5,6-Cl$_4$-4-CF$_3$ | O | O |
| H | Br | CF$_3$ | 2,3,4-F$_3$ | O | O |
| H | Br | CF$_3$ | 2,3,4-Cl$_3$ | O | O |
| H | Br | CF$_3$ | 2,3-Cl$_2$-4-CF$_3$ | O | O |
| H | Br | CF$_3$ | 2,3,5-Cl$_3$ | O | O |
| H | Br | CF$_3$ | 2,3,6-Cl$_3$ | O | O |
| H | Br | CF$_3$ | 2,4,5-Cl$_3$ | O | O |
| H | Br | CF$_3$ | 2,5-Cl$_2$-4-CF$_3$ | O | O |
| H | Br | CF$_3$ | 2-CF$_3$-4-NO$_2$-5-Cl | O | O |
| H | Br | CF$_3$ | 2,4,6-F$_3$ | O | O |
| H | Br | CF$_3$ | 2,5-F$_2$-4-CF$_3$ | O | O |
| H | Br | CF$_3$ | 2-Cl-4-CF$_3$-6-F | O | O |
| H | Br | CF$_3$ | 2,4,6-Cl$_3$ | O | O |
| H | Br | CF$_3$ | 2,6-Cl$_2$-4-Br | O | O |
| H | Br | CF$_3$ | 2,4-Cl$_2$-6-CF$_3$ | O | O |
| H | Br | CF$_3$ | 2,6-Cl$_2$-4-CF$_3$ | O | O |
| H | Br | CF$_3$ | 2,6-Cl$_2$-4-CHF$_2$ | O | O |
| H | Br | CF$_3$ | 2,6-Cl$_2$-4-OCF$_3$ | O | O |
| H | Br | CF$_3$ | 2,6-Cl$_2$-4-OCF$_2$CHF$_2$ | O | O |
| H | Br | CF$_3$ | 2,6-Cl$_2$-4-SCF$_3$ | O | O |
| H | Br | CF$_3$ | 2,6-Cl$_2$-4-SO$_2$CH$_3$ | O | O |
| H | Br | CF$_3$ | 2,6-Cl$_2$-4-SO$_2$CF$_3$ | O | O |
| H | Br | CF$_3$ | 2,6-Cl$_2$-4-CO$_2$CH$_3$ | O | O |
| H | Br | CF$_3$ | 2,6-Cl$_2$-4-CN | O | O |
| H | Br | CF$_3$ | 2,6-Cl$_2$-4-NO$_2$ | O | O |
| H | Br | CF$_3$ | 2-Br-4-CF$_3$-6-Cl | O | O |
| H | Br | CF$_3$ | 2-Cl-4-CF$_3$-6-NO$_2$ | O | O |
| H | Br | CF$_3$ | 2-Cl-4-NO$_2$-6-CF$_3$ | O | O |
| H | Br | CF$_3$ | 2,6-Br$_2$-4-CF$_3$ | O | O |
| H | Br | CF$_3$ | 2,4-(NO$_2$)$_2$-6-CF$_3$ | O | O |
| H | Br | CF$_3$ | 2,6-(NO$_2$)$_2$-4-CF$_3$ | O | O |
| H | Br | CF$_3$ | 3,4,5-Cl$_3$ | O | O |
| H | Br | CF$_3$ | 3,5-Cl$_2$-4-CF$_3$ | O | O |
| H | Br | CF$_3$ | 3,5-Cl$_2$-4-OCF$_2$CHF$_2$ | O | O |
| H | Br | CF$_3$ | 2,3,4,5-F$_4$ | O | O |
| H | Br | CF$_3$ | 2,4-F$_2$-3,5-Cl$_2$ | O | O |
| H | Br | CF$_3$ | 2,3,4,5-Cl$_4$ | O | O |
| H | Br | CF$_3$ | 2,3,5-Cl$_3$-4-CF$_3$ | O | O |
| H | Br | CF$_3$ | 2,3,4,6-F$_4$ | O | O |
| H | Br | CF$_3$ | 2,3,4,6-Cl$_4$ | O | O |
| H | Br | CF$_3$ | 2,3,6-Cl$_3$-4-CF$_3$ | O | O |
| H | Br | CF$_3$ | 2,3,6-Cl$_3$-4-OCF$_3$ | O | O |
| H | Br | CF$_3$ | 3,5-Cl$_2$-3-CH$_3$-4-CF$_3$ | O | O |
| H | Br | CF$_3$ | 3,5-Cl$_2$-3-OCH$_3$-4-CF$_3$ | O | O |
| H | Br | CF$_3$ | 2-CF$_3$-3-Cl-4,6-(NO$_2$)$_2$ | O | O |
| H | Br | CF$_3$ | 2-CF$_3$-3-OCH$_2$CH$_3$-4,6-(NO$_2$)$_2$ | O | O |
| H | Br | CF$_3$ | 2,6-(NO$_2$)$_2$-3-Cl-4-CF$_3$ | O | O |
| H | Br | CF$_3$ | 2,3,5,6-Cl$_4$ | O | O |
| H | Br | CF$_3$ | 2,3,4,5,6-F$_5$ | O | O |
| H | Br | CF$_3$ | 2,3,5,6-F$_4$-4-CF$_3$ | O | O |
| H | Br | CF$_3$ | 2,3,5,6-F$_4$-4-CN | O | O |
| H | Br | CF$_3$ | 2,4,6-F$_3$-3,5-Cl$_2$ | O | O |
| H | Br | CF$_3$ | 2,3,5,6-Cl$_4$-4-CF$_3$ | O | O |
| H | CH$_3$ | CF$_3$ | 2,3,4-F$_3$ | O | O |
| H | CH$_3$ | CF$_3$ | 2,3,4-Cl$_3$ | O | O |
| H | CH$_3$ | CF$_3$ | 2,3-Cl$_2$-4-CF$_3$ | O | O |
| H | CH$_3$ | CF$_3$ | 2,3,5-Cl$_3$ | O | O |
| H | CH$_3$ | CF$_3$ | 2,3,6-Cl$_3$ | O | O |
| H | CH$_3$ | CF$_3$ | 2,4,5-Cl$_3$ | O | O |
| H | CH$_3$ | CF$_3$ | 2,5-Cl$_2$-4-CF$_3$ | O | O |
| H | CH$_3$ | CF$_3$ | 2-CF$_3$-4-NO$_2$-5-Cl | O | O |
| H | CH$_3$ | CF$_3$ | 2,4,6-F$_3$ | O | O |

-continued

| | | | | | |
|---|---|---|---|---|---|
| H | CH₃ | CF₃ | 2,5-F₂-4-CF₃ | O | O |
| H | CH₃ | CF₃ | 2-Cl-4-CF₃-6-F | O | O |
| H | CH₃ | CF₃ | 2,4,6-Cl₃ | O | O |
| H | CH₃ | CF₃ | 2,6-Cl₂-4-Br | O | O |
| H | CH₃ | CF₃ | 2,4-Cl₂-6-CF₃ | O | O |
| H | CH₃ | CF₃ | 2,6-Cl₂-4-CF₃ | O | O |
| H | CH₃ | CF₃ | 2,6-Cl₂-4-CHF₂ | O | O |
| H | CH₃ | CF₃ | 2,6-Cl₂-4-OCF₃ | O | O |
| H | CH₃ | CF₃ | 2,6-Cl₂-4-OCF₂CHF₂ | O | O |
| H | CH₃ | CF₃ | 2,6-Cl₂-4-SCF₃ | O | O |
| H | CH₃ | CF₃ | 2,6-Cl₂-4-SO₂CH₃ | O | O |
| H | CH₃ | CF₃ | 2,6-Cl₂-4-SO₂CF₃ | O | O |
| H | CH₃ | CF₃ | 2,6-Cl₂-4-CO₂CH₃ | O | O |
| H | CH₃ | CF₃ | 2,6-Cl₂-4-CN | O | O |
| H | CH₃ | CF₃ | 2,6-Cl₂-4-NO₂ | O | O |
| H | CH₃ | CF₃ | 2-Br-4-CF₃-6-Cl | O | O |
| H | CH₃ | CF₃ | 2-Cl-4-CF₃-6-NO₂ | O | O |
| H | CH₃ | CF₃ | 2-Cl-4-NO₂-6-CF₃ | O | O |
| H | CH₃ | CF₃ | 2,6-Br₂-4-CF₃ | O | O |
| H | CH₃ | CF₃ | 2,4-(NO₂)₂-6-CF₃ | O | O |
| H | CH₃ | CF₃ | 2,6-(NO₂)₂-4-CF₃ | O | O |
| H | CH₃ | CF₃ | 3,4,5-Cl₃ | O | O |
| H | CH₃ | CF₃ | 3,5-Cl₂-4-CF₃ | O | O |
| H | CH₃ | CF₃ | 3,5-Cl₂-4-OCF₂CHF₂ | O | O |
| H | CH₃ | CF₃ | 2,3,4,5-F₄ | O | O |
| H | CH₃ | CF₃ | 2,4-F₂-3,5-Cl₂ | O | O |
| H | CH₃ | CF₃ | 2,3,4,5-Cl₄ | O | O |
| H | CH₃ | CF₃ | 2,3,5-Cl₃-4-CF₃ | O | O |
| H | CH₃ | CF₃ | 2,3,4,6-F₄ | O | O |
| H | CH₃ | CF₃ | 2,3,4,6-Cl₄ | O | O |
| H | CH₃ | CF₃ | 2,3,6-Cl₃-4-CF₃ | O | O |
| H | CH₃ | CF₃ | 2,3,6-Cl₃-4-OCF₃ | O | O |
| H | CH₃ | CF₃ | 3,5-Cl₂-3-CH₃-4-CF₃ | O | O |
| H | CH₃ | CF₃ | 3,5-Cl₂-3-OCH₃-4-CF₃ | O | O |
| H | CH₃ | CF₃ | 2-CF₃-3-Cl-4,6-(NO₂)₂ | O | O |
| H | CH₃ | CF₃ | 2-CF₃-3-OCH₂CH₃-4,6-(NO₂)₂ | O | O |
| H | CH₃ | CF₃ | 2,6-(NO₂)₂-3-Cl-4-CF₃ | O | O |
| H | CH₃ | CF₃ | 2,3,5,6-Cl₄ | O | O |
| H | CH₃ | CF₃ | 2,3,4,5,6-F₅ | O | O |
| H | CH₃ | CF₃ | 2,3,5,6-F₄-4-CF₃ | O | O |
| H | CH₃ | CF₃ | 2,3,5,6-F₄-4-CN | O | O |
| H | CH₃ | CF₃ | 2,4,6-F₃-3,5-Cl₂ | O | O |
| H | CH₃ | CF₃ | 2,3,5,6-Cl₄-4-CF₃ | O | O |
| H | CN | CF₃ | 2,3,4-F₃ | O | O |
| H | CN | CF₃ | 2,3,4-Cl₃ | O | O |
| H | CN | CF₃ | 2,3-Cl₂-4-CF₃ | O | O |
| H | CN | CF₃ | 2,3,5-Cl₃ | O | O |
| H | CN | CF₃ | 2,3,6-Cl₃ | O | O |
| H | CN | CF₃ | 2,4,5-Cl₃ | O | O |
| H | CN | CF₃ | 2,5-Cl₂-4-CF₃ | O | O |
| H | CN | CF₃ | 2-CF₃-4-NO₂-5-Cl | O | O |
| H | CN | CF₃ | 2,4,6-F₃ | O | O |
| H | CN | CF₃ | 2,5-F₂-4-CF₃ | O | O |
| H | CN | CF₃ | 2-Cl-4-CF₃-6-F | O | O |
| H | CN | CF₃ | 2,4,6-Cl₃ | O | O |
| H | CN | CF₃ | 2,6-Cl₂-4-Br | O | O |
| H | CN | CF₃ | 2,4-Cl₂-6-CF₃ | O | O |
| H | CN | CF₃ | 2,6-Cl₂-4-CF₃ | O | O |
| H | CN | CF₃ | 2,6-Cl₂-4-CHF₂ | O | O |
| H | CN | CF₃ | 2,6-Cl₂-4-OCF₃ | O | O |
| H | CN | CF₃ | 2,6-Cl₂-4-OCF₂CHF₂ | O | O |
| H | CN | CF₃ | 2,6-Cl₂-4-SCF₃ | O | O |
| H | CN | CF₃ | 2,6-Cl₂-4-SO₂CH₃ | O | O |
| H | CN | CF₃ | 2,6-Cl₂-4-SO₂CF₃ | O | O |
| H | CN | CF₃ | 2,6-Cl₂-4-CO₂CH₃ | O | O |
| H | CN | CF₃ | 2,6-Cl₂-4-CN | O | O |
| H | CN | CF₃ | 2,6-Cl₂-4-NO₂ | O | O |
| H | CN | CF₃ | 2-Br-4-CF₃-6-Cl | O | O |
| H | CN | CF₃ | 2-Cl-4-CF₃-6-NO₂ | O | O |
| H | CN | CF₃ | 2-Cl-4-NO₂-6-CF₃ | O | O |
| H | CN | CF₃ | 2,6-Br₂-4-CF₃ | O | O |
| H | CN | CF₃ | 2,4-(NO₂)₂-6-CF₃ | O | O |
| H | CN | CF₃ | 2,6-(NO₂)₂-4-CF₃ | O | O |
| H | CN | CF₃ | 3,4,5-Cl₃ | O | O |
| H | CN | CF₃ | 3,5-Cl₂-4-CF₃ | O | O |
| H | CN | CF₃ | 3,5-Cl₂-4-OCF₂CHF₂ | O | O |
| H | CN | CF₃ | 2,3,4,5-F₄ | O | O |
| H | CN | CF₃ | 2,4-F₂-3,5-Cl₂ | O | O |
| H | CN | CF₃ | 2,3,4,5-Cl₄ | O | O |
| H | CN | CF₃ | 2,3,5-Cl₃-4-CF₃ | O | O |
| H | CN | CF₃ | 2,3,4,6-F₄ | O | O |
| H | CN | CF₃ | 2,3,4,6-Cl₄ | O | O |
| H | CN | CF₃ | 2,3,6-Cl₃-4-CF₃ | O | O |

-continued

| | | | | | |
|---|---|---|---|---|---|
| H | CN | CF$_3$ | 2,3,6-Cl$_3$-4-OCF$_3$ | O | O |
| H | CN | CF$_3$ | 3,5-Cl$_2$-3-CH$_3$-4-CF$_3$ | O | O |
| H | CN | CF$_3$ | 3,5-Cl$_2$-3-OCH$_3$-4-CF$_3$ | O | O |
| H | CN | CF$_3$ | 2-CF$_3$-3-Cl-4,6-(NO$_2$)$_2$ | O | O |
| H | CN | CF$_3$ | 2-CF$_3$-3-OCH$_2$CH$_3$-4,6-(NO$_2$)$_2$ | O | O |
| H | CN | CF$_3$ | 2,6-(NO$_2$)$_2$-3-Cl-4-CF$_3$ | O | O |
| H | CN | CF$_3$ | 2,3,5,6-Cl$_4$ | O | O |
| H | CN | CF$_3$ | 2,3,4,5,6-F$_5$ | O | O |
| H | CN | CF$_3$ | 2,3,5,6-F$_4$-4-CF$_3$ | O | O |
| H | CN | CF$_3$ | 2,3,5,6-F$_4$-4-CN | O | O |
| H | CN | CF$_3$ | 2,4,6-F$_3$-3,5-Cl$_2$ | O | O |
| H | CN | CF$_3$ | 2,3,5,6-Cl$_4$-4-CF$_3$ | O | O |
| H | NO$_2$ | CF$_3$ | 2,3,4-F$_3$ | O | O |
| H | NO$_2$ | CF$_3$ | 2,3,4-Cl$_3$ | O | O |
| H | NO$_2$ | CF$_3$ | 2,3-Cl$_2$-4-CF$_3$ | O | O |
| H | NO$_2$ | CF$_3$ | 2,3,5-Cl$_3$ | O | O |
| H | NO$_2$ | CF$_3$ | 2,3,6-Cl$_3$ | O | O |
| H | NO$_2$ | CF$_3$ | 2,4,5-Cl$_3$ | O | O |
| H | NO$_2$ | CF$_3$ | 2,5-Cl$_2$-4-CF$_3$ | O | O |
| H | NO$_2$ | CF$_3$ | 2-CF$_3$-4-NO$_2$-5-Cl | O | O |
| H | NO$_2$ | CF$_3$ | 2,4,6-F$_3$ | O | O |
| H | NO$_2$ | CF$_3$ | 2,5-F$_2$-4-CF$_3$ | O | O |
| H | NO$_2$ | CF$_3$ | 2-Cl-4-CF$_3$-6-F | O | O |
| H | NO$_2$ | CF$_3$ | 2,4,6-Cl$_3$ | O | O |
| H | NO$_2$ | CF$_3$ | 2,6-Cl$_2$-4-Br | O | O |
| H | NO$_2$ | CF$_3$ | 2,4-Cl$_2$-6-CF$_3$ | O | O |
| H | NO$_2$ | CF$_3$ | 2,6-Cl$_2$-4-CF$_3$ | O | O |
| H | NO$_2$ | CF$_3$ | 2,6-Cl$_2$-4-CHF$_2$ | O | O |
| H | NO$_2$ | CF$_3$ | 2,6-Cl$_2$-4-OCF$_3$ | O | O |
| H | NO$_2$ | CF$_3$ | 2,6-Cl$_2$-4-OCF$_2$CHF$_2$ | O | O |
| H | NO$_2$ | CF$_3$ | 2,6-Cl$_2$-4-SCF$_3$ | O | O |
| H | NO$_2$ | CF$_3$ | 2,6-Cl$_2$-4-SO$_2$CH$_3$ | O | O |
| H | NO$_2$ | CF$_3$ | 2,6-Cl$_2$-4-SO$_2$CF$_3$ | O | O |
| H | NO$_2$ | CF$_3$ | 2,6-Cl$_2$-4-CO$_2$CH$_3$ | O | O |
| H | NO$_2$ | CF$_3$ | 2,6-Cl$_2$-4-CN | O | O |
| H | NO$_2$ | CF$_3$ | 2,6-Cl$_2$-4-NO$_2$ | O | O |
| H | NO$_2$ | CF$_3$ | 2-Br-4-CF$_3$-6-Cl | O | O |
| H | NO$_2$ | CF$_3$ | 2-Cl-4-CF$_3$-6-NO$_2$ | O | O |
| H | NO$_2$ | CF$_3$ | 2-Cl-4-NO$_2$-6-CF$_3$ | O | O |
| H | NO$_2$ | CF$_3$ | 2,6-Br$_2$-4-CF$_3$ | O | O |
| H | NO$_2$ | CF$_3$ | 2,4-(NO$_2$)$_2$-6-CF$_3$ | O | O |
| H | NO$_2$ | CF$_3$ | 2,6-(NO$_2$)$_2$-4-CF$_3$ | O | O |
| H | NO$_2$ | CF$_3$ | 3,4,5-Cl$_3$ | O | O |
| H | NO$_2$ | CF$_3$ | 3,5-Cl$_2$-4-CF$_3$ | O | O |
| H | NO$_2$ | CF$_3$ | 3,5-Cl$_2$-4-OCF$_2$CHF$_2$ | O | O |
| H | NO$_2$ | CF$_3$ | 2,3,4,5-F$_4$ | O | O |
| H | NO$_2$ | CF$_3$ | 2,4-F$_2$-3,5-Cl$_2$ | O | O |
| H | NO$_2$ | CF$_3$ | 2,3,4,5-Cl$_4$ | O | O |
| H | NO$_2$ | CF$_3$ | 2,3,5-Cl$_3$-4-CF$_3$ | O | O |
| H | NO$_2$ | CF$_3$ | 2,3,4,6-F$_4$ | O | O |
| H | NO$_2$ | CF$_3$ | 2,3,4,6-Cl$_4$ | O | O |
| H | NO$_2$ | CF$_3$ | 2,3,6-Cl$_3$-4-CF$_3$ | O | O |
| H | NO$_2$ | CF$_3$ | 2,3,6-Cl$_3$-4-OCF$_3$ | O | O |
| H | NO$_2$ | CF$_3$ | 3,5-Cl$_2$-3-CH$_3$-4-CF$_3$ | O | O |
| H | NO$_2$ | CF$_3$ | 3,5-Cl$_2$-3-OCH$_3$-4-CF$_3$ | O | O |
| H | NO$_2$ | CF$_3$ | 2-CF$_3$-3-Cl-4,6-(NO$_2$)$_2$ | O | O |
| H | NO$_2$ | CF$_3$ | 2-CF$_3$-3-OCH$_2$CH$_3$-4,6-(NO$_2$)$_2$ | O | O |
| H | NO$_2$ | CF$_3$ | 2,6-(NO$_2$)$_2$-3-Cl-4-CF$_3$ | O | O |
| H | NO$_2$ | CF$_3$ | 2,3,5,6-Cl$_4$ | O | O |
| H | NO$_2$ | CF$_3$ | 2,3,4,5,6-F$_5$ | O | O |
| H | NO$_2$ | CF$_3$ | 2,3,5,6-F$_4$-4-CF$_3$ | O | O |
| H | NO$_2$ | CF$_3$ | 2,3,5,6-F$_4$-4-CN | O | O |
| H | NO$_2$ | CF$_3$ | 2,4,6-F$_3$-3,5-Cl$_2$ | O | O |
| H | NO$_2$ | CF$_3$ | 2,3,5,6-Cl$_4$-4-CF$_3$ | O | O |
| H | F | CF$_3$ | 2,3,4-Cl$_3$ | O | O |
| H | F | CF$_3$ | 2,3,5-Cl$_3$ | O | O |
| H | F | CF$_3$ | 2,3,6-Cl$_3$ | O | O |
| H | F | CF$_3$ | 2,4,5-Cl$_3$ | O | O |
| H | F | CF$_3$ | 2,5-Cl$_2$-4-CF$_3$ | O | O |
| H | F | CF$_3$ | 2-CF$_3$-4-NO$_2$-5-Cl | O | O |
| H | F | CF$_3$ | 2,4,6-Cl$_3$ | O | O |
| H | F | CF$_3$ | 2,6-Cl$_2$-4-CF$_3$ | O | O |
| H | F | CF$_3$ | 2,6-Cl$_2$-4-CHF$_2$ | O | O |
| H | F | CF$_3$ | 2,6-Cl$_2$-4-OCF$_3$ | O | O |
| H | F | CF$_3$ | 2,6-Cl$_2$-4-CN | O | O |
| H | F | CF$_3$ | 2,6-Cl$_2$-4-NO$_2$ | O | O |
| H | F | CF$_3$ | 2-Br-4-CF$_3$-6-Cl | O | O |
| H | F | CF$_3$ | 2-Cl-4-CF$_3$-6-NO$_2$ | O | O |
| H | F | CF$_3$ | 2-Cl-4-NO$_2$-6-CF$_3$ | O | O |
| H | F | CF$_3$ | 2,4-(NO$_2$)$_2$-6-CF$_3$ | O | O |
| H | F | CF$_3$ | 2,6-(NO$_2$)$_2$-4-CF$_3$ | O | O |
| H | F | CF$_3$ | 3,4,5-Cl$_3$ | O | O |
| H | F | CF$_3$ | 2,4-F$_2$-3,5-Cl$_2$ | O | O |

-continued

| | | | | | |
|---|---|---|---|---|---|
| H | F | CF$_3$ | 2,3,4,5-Cl$_4$ | O | O |
| H | F | CF$_3$ | 2,3,4,6-Cl$_4$ | O | O |
| H | F | CF$_3$ | 2,3,6-Cl$_3$-4-CF$_3$ | O | O |
| H | F | CF$_3$ | 2,3,5,6-Cl$_4$ | O | O |
| H | F | CF$_3$ | 2,3,4,5,6-F$_5$ | O | O |
| H | F | CF$_3$ | 2,3,5,6-F$_4$-4-CN | O | O |
| H | F | CF$_3$ | 2,3,5,6-Cl$_4$-4-CF$_3$ | O | O |
| H | I | CF$_3$ | 2,3,4-Cl$_3$ | O | O |
| H | I | CF$_3$ | 2,3,5-Cl$_3$ | O | O |
| H | I | CF$_3$ | 2,3,6-Cl$_3$ | O | O |
| H | I | CF$_3$ | 2,4,5-Cl$_3$ | O | O |
| H | I | CF$_3$ | 2,5-Cl$_2$-4-CF$_3$ | O | O |
| H | I | CF$_3$ | 2-CF$_3$-4-NO$_2$-5-Cl | O | O |
| H | I | CF$_3$ | 2,4,6-Cl$_3$ | O | O |
| H | I | CF$_3$ | 2,6-Cl$_2$-4-CF$_3$ | O | O |
| H | I | CF$_3$ | 2,6-Cl$_2$-4-CHF$_2$ | O | O |
| H | I | CF$_3$ | 2,6-Cl$_2$-4-OCF$_3$ | O | O |
| H | I | CF$_3$ | 2,6-Cl$_2$-4-CN | O | O |
| H | I | CF$_3$ | 2,6-Cl$_2$-4-NO$_2$ | O | O |
| H | I | CF$_3$ | 2-Br-4-CF$_3$-6-Cl | O | O |
| H | I | CF$_3$ | 2-Cl-4-CF$_3$-6-NO$_2$ | O | O |
| H | I | CF$_3$ | 2-Cl-4-NO$_2$-6-CF$_3$ | O | O |
| H | I | CF$_3$ | 2,4-(NO$_2$)$_2$-6-CF$_3$ | O | O |
| H | I | CF$_3$ | 2,6-(NO$_2$)$_2$-4-CF$_3$ | O | O |
| H | I | CF$_3$ | 3,4,5-Cl$_3$ | O | O |
| H | I | CF$_3$ | 2,4-F$_2$-3,5-Cl$_2$ | O | O |
| H | I | CF$_3$ | 2,3,4,5-Cl$_4$ | O | O |
| H | I | CF$_3$ | 2,3,4,6-Cl$_4$ | O | O |
| H | I | CF$_3$ | 2,3,6-Cl$_3$-4-CF$_3$ | O | O |
| H | I | CF$_3$ | 2,3,5,6-Cl$_4$ | O | O |
| H | I | CF$_3$ | 2,3,4,5,6-F$_5$ | O | O |
| H | I | CF$_3$ | 2,3,5,6-F$_4$-4-CN | O | O |
| H | I | CF$_3$ | 2,3,5,6-Cl$_4$-4-CF$_3$ | O | O |
| H | CF$_3$ | CF$_3$ | 2,3,4-Cl$_3$ | O | O |
| H | CF$_3$ | CF$_3$ | 2,3,5-Cl$_3$ | O | O |
| H | CF$_3$ | CF$_3$ | 2,3,6-Cl$_3$ | O | O |
| H | CF$_3$ | CF$_3$ | 2,4,5-Cl$_3$ | O | O |
| H | CF$_3$ | CF$_3$ | 2,5-Cl$_2$-4-CF$_3$ | O | O |
| H | CF$_3$ | CF$_3$ | 2-CF$_3$-4-NO$_2$-5-Cl | O | O |
| H | CF$_3$ | CF$_3$ | 2,4,6-Cl$_3$ | O | O |
| H | CF$_3$ | CF$_3$ | 2,6-Cl$_2$-4-CF$_3$ | O | O |
| H | CF$_3$ | CF$_3$ | 2,6-Cl$_2$-4-CHF$_2$ | O | O |
| H | CF$_3$ | CF$_3$ | 2,6-Cl$_2$-4-OCF$_3$ | O | O |
| H | CF$_3$ | CF$_3$ | 2,6-Cl$_2$-4-CN | O | O |
| H | CF$_3$ | CF$_3$ | 2,6-Cl$_2$-4-NO$_2$ | O | O |
| H | CF$_3$ | CF$_3$ | 2-Br-4-CF$_3$-6-Cl | O | O |
| H | CF$_3$ | CF$_3$ | 2-Cl-4-CF$_3$-6-NO$_2$ | O | O |
| H | CF$_3$ | CF$_3$ | 2-Cl-4-NO$_2$-6-CF$_3$ | O | O |
| H | CF$_3$ | CF$_3$ | 2,4-(NO$_2$)$_2$-6-CF$_3$ | O | O |
| H | CF$_3$ | CF$_3$ | 2,6-(NO$_2$)$_2$-4-CF$_3$ | O | O |
| H | CF$_3$ | CF$_3$ | 3,4,5-Cl$_3$ | O | O |
| H | CF$_3$ | CF$_3$ | 2,4-F$_2$-3,5-Cl$_2$ | O | O |
| H | CF$_3$ | CF$_3$ | 2,3,4,5-Cl$_4$ | O | O |
| H | CF$_3$ | CF$_3$ | 2,3,4,6-Cl$_4$ | O | O |
| H | CF$_3$ | CF$_3$ | 2,3,6-Cl$_3$-4-CF$_3$ | O | O |
| H | CF$_3$ | CF$_3$ | 2,3,5,6-Cl$_4$ | O | O |
| H | CF$_3$ | CF$_3$ | 2,3,4,5,6-F$_5$ | O | O |
| H | CF$_3$ | CF$_3$ | 2,3,5,6-F$_4$-4-CN | O | O |
| H | CF$_3$ | CF$_3$ | 2,3,5,6-Cl$_4$-4-CF$_3$ | O | O |
| H | CH$_2$OCH$_3$ | CF$_3$ | 2,4,5-Cl$_3$ | O | O |
| H | CH$_2$OCH$_3$ | CF$_3$ | 2,5-Cl$_2$-4-CF$_3$ | O | O |
| H | CH$_2$OCH$_3$ | CF$_3$ | 2-CF$_3$-4-NO$_2$-5-Cl | O | O |
| H | CH$_2$OCH$_3$ | CF$_3$ | 2,4,6-Cl$_3$ | O | O |
| H | CH$_2$OCH$_3$ | CF$_3$ | 2,6-Cl$_2$-4-CF$_3$ | O | O |
| H | CH$_2$OCH$_3$ | CF$_3$ | 2,6-Cl$_2$-4-NO$_2$ | O | O |
| H | CH$_2$OCH$_3$ | CF$_3$ | 2-Cl-4-CF$_3$-6-NO$_2$ | O | O |
| H | CH$_2$OCH$_3$ | CF$_3$ | 2-Cl-4-NO$_2$-6-CF$_3$ | O | O |
| H | CH$_2$OCH$_3$ | CF$_3$ | 2,4-(NO$_2$)$_2$-6-CF$_3$ | O | O |
| H | CH$_2$OCH$_3$ | CF$_3$ | 2,6-(NO$_2$)$_2$-4-CF$_3$ | O | O |
| H | CH$_2$OCH$_3$ | CF$_3$ | 2,3,4,6-Cl$_4$ | O | O |
| H | CH$_2$OCH$_3$ | CF$_3$ | 2,3,6-Cl$_3$-4-CF$_3$ | O | O |
| H | CH$_2$OCH$_3$ | CF$_3$ | 2,3,4,5,6-F$_5$ | O | O |
| H | CH$_2$OCH$_3$ | CF$_3$ | 2,3,5,6-F$_4$-4-CN | O | O |
| H | CH$_2$OCH$_3$ | CF$_3$ | 2,3,5,6-Cl$_4$-4-CF$_3$ | O | O |
| H | CH$_2$CH$_3$ | CF$_3$ | 2,4,5-Cl$_3$ | O | O |
| H | CH$_2$CH$_3$ | CF$_3$ | 2,4,6-Cl$_3$ | O | O |
| H | CH$_2$CH$_3$ | CF$_3$ | 2,6-Cl$_2$-4-CF$_3$ | O | O |
| H | CH$_2$CH$_3$ | CF$_3$ | 2,6-Cl$_2$-4-NO$_2$ | O | O |
| H | CH$_2$CH$_3$ | CF$_3$ | 2-Cl-4-NO$_2$-6-CF$_3$ | O | O |
| H | CH$_2$CH$_3$ | CF$_3$ | 2,4-(NO$_2$)$_2$-6-CF$_3$ | O | O |
| H | CH$_2$CH$_3$ | CF$_3$ | 2,6-(NO$_2$)$_2$-4-CF$_3$ | O | O |
| H | CH$_2$CH$_3$ | CF$_3$ | 2,3,4,6-Cl$_4$ | O | O |
| H | CH$_2$CH$_3$ | CF$_3$ | 2,3,6-Cl$_3$-4-CF$_3$ | O | O |

-continued

| | | | | | |
|---|---|---|---|---|---|
| H | CH₂CH₃ | CF₃ | 2,3,4,5,6-F₅ | O | O |
| H | CH₂CH₃ | CF₃ | 2,3,5,6-F₄-4-CN | O | O |
| H | CH₂CH₃ | CF₃ | 2,3,5,6-Cl₄-4-CF₃ | O | O |
| H | CH₂Cl | CF₃ | 2,4,6-Cl₃ | O | O |
| H | CH₂Cl | CF₃ | 2,6-Cl₂-4-CF₃ | O | O |
| H | CH₂Cl | CF₃ | 2-Cl-4-NO₂-6-CF₃ | O | O |
| H | CH₂Cl | CF₃ | 2,4-(NO₂)₂-6-CF₃ | O | O |
| H | CH₂Cl | CF₃ | 2,6-(NO₂)₂-4-CF₃ | O | O |
| H | CH₂Cl | CF₃ | 2,3,4,6-Cl₄ | O | O |
| H | CH₂Cl | CF₃ | 2,3,4,5,6-F₅ | O | O |
| H | CH₂Cl | CF₃ | 2,3,5,6-F₄-4-CN | O | O |
| H | CH(CH₃)₂ | CF₃ | 2,4,6-Cl₃ | O | O |
| H | CH(CH₃)₂ | CF₃ | 2,6-Cl₂-4-CF₃ | O | O |
| H | CH(CH₃)₂ | CF₃ | 2-Cl-4-NO₂-6-CF₃ | O | O |
| H | CH(CH₃)₂ | CF₃ | 2,4-(NO₂)₂-6-CF₃ | O | O |
| H | CH(CH₃)₂ | CF₃ | 2,3,4,5,6-F₅ | O | O |
| H | (CH₂)₃CH₃ | CF₃ | 2,4,6-Cl₃ | O | O |
| H | (CH₂)₃CH₃ | CF₃ | 2,6-Cl₂-4-CF₃ | O | O |
| H | (CH₂)₃CH₃ | CF₃ | 2-Cl-4-NO₂-6-CF₃ | O | O |
| H | (CH₂)₃CH₃ | CF₃ | 2,4-(NO₂)₂-6-CF₃ | O | O |
| H | (CH₂)₃CH₃ | CF₃ | 2,3,4,5,6-F₅ | O | O |
| H | C(CH₃)₃ | CF₃ | 2,4,6-Cl₃ | O | O |
| H | C(CH₃)₃ | CF₃ | 2,6-Cl₂-4-CF₃ | O | O |
| H | C(CH₃)₃ | CF₃ | 2-Cl-4-NO₂-6-CF₃ | O | O |
| H | C(CH₃)₃ | CF₃ | 2,4-(NO₂)₂-6-CF₃ | O | O |
| H | C(CH₃)₃ | CF₃ | 2,3,4,5,6-F₅ | O | O |
| H | CH₂OH | CF₃ | 2,6-Cl₂-4-CF₃ | O | O |
| H | CH₂OCH₂CH₃ | CF₃ | 2,6-Cl₂-4-CF₃ | O | O |
| H | CH₂SCH₃ | CF₃ | 2,6-Cl₂-4-CF₃ | O | O |
| H | SCN | CF₃ | 2,6-Cl₂-4-CF₃ | O | O |
| CH₃ | H | CF₃ | 2,3,4-F₃ | O | O |
| CH₃ | H | CF₃ | 2,3,4-Cl₃ | O | O |
| CH₃ | H | CF₃ | 2,3-Cl₂-4-CF₃ | O | O |
| CH₃ | H | CF₃ | 2,3,5-Cl₃ | O | O |
| CH₃ | H | CF₃ | 2,3,6-Cl₃ | O | O |
| CH₃ | H | CF₃ | 2,4,5-Cl₃ | O | O |
| CH₃ | H | CF₃ | 2,5-Cl₂-4-CF₃ | O | O |
| CH₃ | H | CF₃ | 2-CF₃-4-NO₂-5-Cl | O | O |
| CH₃ | H | CF₃ | 2,4,6-F₃ | O | O |
| CH₃ | H | CF₃ | 2,6-F₂-4-CF₃ | O | O |
| CH₃ | H | CF₃ | 2-Cl-4-CF₃-6-F | O | O |
| CH₃ | H | CF₃ | 2,4,6-Cl₃ | O | O |
| CH₃ | H | CF₃ | 2,6-Cl₂-4-Br | O | O |
| CH₃ | H | CF₃ | 2,4-Cl₂-6-CF₃ | O | O |
| CH₃ | H | CF₃ | 2,6-Cl₂-4-CF₃ | O | O |
| CH₃ | H | CF₃ | 2,6-Cl₂-4-CHF₂ | O | O |
| CH₃ | H | CF₃ | 2,6-Cl₂-4-OCF₃ | O | O |
| CH₃ | H | CF₃ | 2,6-Cl₂-4-OCF₂CHF₂ | O | O |
| CH₃ | H | CF₃ | 2,6-Cl₂-4-SCF₃ | O | O |
| CH₃ | H | CF₃ | 2,6-Cl₂-4-SO₂CH₃ | O | O |
| CH₃ | H | CF₃ | 2,6-Cl₂-4-SO₂CF₃ | O | O |
| CH₃ | H | CF₃ | 2,6-Cl₂-4-CO₂CH₃ | O | O |
| CH₃ | H | CF₃ | 2,6-Cl₂-4-CN | O | O |
| CH₃ | H | CF₃ | 2,6-Cl₂-4-NO₂ | O | O |
| CH₃ | H | CF₃ | 2-Br-4-CF₃-6-Cl | O | O |
| CH₃ | H | CF₃ | 2-Cl-4-CF₃-6-NO₂ | O | O |
| CH₃ | H | CF₃ | 2-Cl-4-NO₂-6-CF₃ | O | O |
| CH₃ | H | CF₃ | 2,6-Br₂-4-CF₃ | O | O |
| CH₃ | H | CF₃ | 2,4-(NO₂)₂-6-CF₃ | O | O |
| CH₃ | H | CF₃ | 2,6-(NO₂)₂-4-CF₃ | O | O |
| CH₃ | H | CF₃ | 3,4,5-Cl₃ | O | O |
| CH₃ | H | CF₃ | 3,5-Cl₂-4-CF₃ | O | O |
| CH₃ | H | CF₃ | 3,5-Cl₂-4-OCF₂CHF₂ | O | O |
| CH₃ | H | CF₃ | 2,3,4,5-F₄ | O | O |
| CH₃ | H | CF₃ | 2,4-F₂-3,5-Cl₂ | O | O |
| CH₃ | H | CF₃ | 2,3,4,5-Cl₄ | O | O |
| CH₃ | H | CF₃ | 2,3,5-Cl₃-4-CF₃ | O | O |
| CH₃ | H | CF₃ | 2,3,4,6-F₄ | O | O |
| CH₃ | H | CF₃ | 2,3,4,6-Cl₄ | O | O |
| CH₃ | H | CF₃ | 2,3,6-Cl₃-4-CF₃ | O | O |
| CH₃ | H | CF₃ | 2,3,6-Cl₃-4-OCF₃ | O | O |
| CH₃ | H | CF₃ | 3,5-Cl₂-3-CH₃-4-CF₃ | O | O |
| CH₃ | H | CF₃ | 3,5-Cl₂-3-OCH₃-4-CF₃ | O | O |
| CH₃ | H | CF₃ | 2-CF₃-3-Cl-4,6-(NO₂)₂ | O | O |
| CH₃ | H | CF₃ | 2-CF₃-3-OCH₂CH₃-4,6-(NO₂)₂ | O | O |
| CH₃ | H | CF₃ | 2,6-(NO₂)₂-3-Cl-4-CF₃ | O | O |
| CH₃ | H | CF₃ | 2,3,5,6-Cl₄ | O | O |
| CH₃ | H | CF₃ | 2,3,4,5,6-F₅ | O | O |
| CH₃ | H | CF₃ | 2,3,5,6-F₄-4-CF₃ | O | O |
| CH₃ | H | CF₃ | 2,3,5,6-F₄-4-CN | O | O |
| CH₃ | H | CF₃ | 2,4,6-F₃-3,5-Cl₂ | O | O |
| CH₃ | H | CF₃ | 2,3,5,6-Cl₄-4-CF₃ | O | O |
| CH₂CH₃ | H | CF₃ | 2,3,4-F₃ | O | O |

-continued

| | | | | | |
|---|---|---|---|---|---|
| CH₂CH₃ | H | CF₃ | 2,3,4-Cl₃ | O | O |
| CH₂CH₃ | H | CF₃ | 2,3-Cl₂-4-CF₃ | O | O |
| CH₂CH₃ | H | CF₃ | 2,3,5-Cl₃ | O | O |
| CH₂CH₃ | H | CF₃ | 2,3,6-Cl₃ | O | O |
| CH₂CH₃ | H | CF₃ | 2,4,5-Cl₃ | O | O |
| CH₂CH₃ | H | CF₃ | 2,5-Cl₂-4-CF₃ | O | O |
| CH₂CH₃ | H | CF₃ | 2-CF₃-4-NO₂-5-Cl | O | O |
| CH₂CH₃ | H | CF₃ | 2,4,6-F₃ | O | O |
| CH₂CH₃ | H | CF₃ | 2,5-F₂-4-CF₃ | O | O |
| CH₂CH₃ | H | CF₃ | 2-Cl-4-CF₃-6-F | O | O |
| CH₂CH₃ | H | CF₃ | 2,4,6-Cl₃ | O | O |
| CH₂CH₃ | H | CF₃ | 2,6-Cl₂-4-Br | O | O |
| CH₂CH₃ | H | CF₃ | 2,4-Cl₂-6-CF₃ | O | O |
| CH₂CH₃ | H | CF₃ | 2,6-Cl₂-4-CF₃ | O | O |
| CH₂CH₃ | H | CF₃ | 2,6-Cl₂-4-CHF₂ | O | O |
| CH₂CH₃ | H | CF₃ | 2,6-Cl₂-4-OCF₃ | O | O |
| CH₂CH₃ | H | CF₃ | 2,6-Cl₂-4-OCF₂CHF₂ | O | O |
| CH₂CH₃ | H | CF₃ | 2,6-Cl₂-4-SCF₃ | O | O |
| CH₂CH₃ | H | CF₃ | 2,6-Cl₂-4-SO₂CH₃ | O | O |
| CH₂CH₃ | H | CF₃ | 2,6-Cl₂-4-SO₂CF₃ | O | O |
| CH₂CH₃ | H | CF₃ | 2,6-Cl₂-4-CO₂CH₃ | O | O |
| CH₂CH₃ | H | CF₃ | 2,6-Cl₂-4-CN | O | O |
| CH₂CH₃ | H | CF₃ | 2,6-Cl₂-4-NO₂ | O | O |
| CH₂CH₃ | H | CF₃ | 2-Br-4-CF₃-6-Cl | O | O |
| CH₂CH₃ | H | CF₃ | 2-Cl-4-CF₃-6-NO₂ | O | O |
| CH₂CH₃ | H | CF₃ | 2-Cl-4-NO₂-6-CF₃ | O | O |
| CH₂CH₃ | H | CF₃ | 2,6-Br₂-4-CF₃ | O | O |
| CH₂CH₃ | H | CF₃ | 2,4-(NO₂)₂-6-CF₃ | O | O |
| CH₂CH₃ | H | CF₃ | 2,6-(NO₂)₂-4-CF₃ | O | O |
| CH₂CH₃ | H | CF₃ | 3,4,5-Cl₃ | O | O |
| CH₂CH₃ | H | CF₃ | 3,5-Cl₂-4-CF₃ | O | O |
| CH₂CH₃ | H | CF₃ | 3,5-Cl₂-4-OCF₂CHF₂ | O | O |
| CH₂CH₃ | H | CF₃ | 2,3,4,5-F₄ | O | O |
| CH₂CH₃ | H | CF₃ | 2,4-F₂-3,5-Cl₂ | O | O |
| CH₂CH₃ | H | CF₃ | 2,3,4,5-Cl₄ | O | O |
| CH₂CH₃ | H | CF₃ | 2,3,5-Cl₃-4-CF₃ | O | O |
| CH₂CH₃ | H | CF₃ | 2,3,4,6-F₄ | O | O |
| CH₂CH₃ | H | CF₃ | 2,3,4,6-Cl₄ | O | O |
| CH₂CH₃ | H | CF₃ | 2,3,6-Cl₃-4-CF₃ | O | O |
| CH₂CH₃ | H | CF₃ | 2,3,6-Cl₃-4-OCF₃ | O | O |
| CH₂CH₃ | H | CF₃ | 3,5-Cl₂-3-CH₃-4-CF₃ | O | O |
| CH₂CH₃ | H | CF₃ | 3,5-Cl₂-3-OCH₃-4-CF₃ | O | O |
| CH₂CH₃ | H | CF₃ | 2-CF₃-3-Cl-4,6-(NO₂)₂ | O | O |
| CH₂CH₃ | H | CF₃ | 2-CF₃-3-OCH₂CH₃-4,6-(NO₂)₂ | O | O |
| CH₂CH₃ | H | CF₃ | 2,6-(NO₂)₂-3-Cl-4-CF₃ | O | O |
| CH₂CH₃ | H | CF₃ | 2,3,5,6-Cl₄ | O | O |
| CH₂CH₃ | H | CF₃ | 2,3,4,5,6-F₅ | O | O |
| CH₂CH₃ | H | CF₃ | 2,3,5,6-F₄-4-CF₃ | O | O |
| CH₂CH₃ | H | CF₃ | 2,3,5,6-F₄-4-CN | O | O |
| CH₂CH₃ | H | CF₃ | 2,4,6-F₃-3,5-Cl₂ | O | O |
| CH₂CH₃ | H | CF₃ | 2,3,5,6-Cl₄-4-CF₃ | O | O |
| CH₂CH=CH₂ | H | CF₃ | 2,3,4-F₃ | O | O |
| CH₂CH=CH₂ | H | CF₃ | 2,3,4-Cl₃ | O | O |
| CH₂CH=CH₂ | H | CF₃ | 2,3-Cl₂-4-CF₃ | O | O |
| CH₂CH=CH₂ | H | CF₃ | 2,3,5-Cl₃ | O | O |
| CH₂CH=CH₂ | H | CF₃ | 2,3,6-Cl₃ | O | O |
| CH₂CH=CH₂ | H | CF₃ | 2,4,5-Cl₃ | O | O |
| CH₂CH=CH₂ | H | CF₃ | 2,5-Cl₂-4-CF₃ | O | O |
| CH₂CH=CH₂ | H | CF₃ | 2-CF₃-4-NO₂-5-Cl | O | O |
| CH₂CH=CH₂ | H | CF₃ | 2,4,6-F₃ | O | O |
| CH₂CH=CH₂ | H | CF₃ | 2,5-F₂-4-CF₃ | O | O |
| CH₂CH=CH₂ | H | CF₃ | 2-Cl-4-CF₃-6-F | O | O |
| CH₂CH=CH₂ | H | CF₃ | 2,4,6-Cl₃ | O | O |
| CH₂CH=CH₂ | H | CF₃ | 2,6-Cl₂-4-Br | O | O |
| CH₂CH=CH₂ | H | CF₃ | 2,4-Cl₂-6-CF₃ | O | O |
| CH₂CH=CH₂ | H | CF₃ | 2,6-Cl₂-4-CF₃ | O | O |
| CH₂CH=CH₂ | H | CF₃ | 2,6-Cl₂-4-CHF₂ | O | O |
| CH₂CH=CH₂ | H | CF₃ | 2,6-Cl₂-4-OCF₃ | O | O |
| CH₂CH=CH₂ | H | CF₃ | 2,6-Cl₂-4-OCF₂CHF₂ | O | O |
| CH₂CH=CH₂ | H | CF₃ | 2,6-Cl₂-4-SCF₃ | O | O |
| CH₂CH=CH₂ | H | CF₃ | 2,6-Cl₂-4-SO₂CH₃ | O | O |
| CH₂CH=CH₂ | H | CF₃ | 2,6-Cl₂-4-SO₂CF₃ | O | O |
| CH₂CH=CH₂ | H | CF₃ | 2,6-Cl₂-4-CO₂CH₃ | O | O |
| CH₂CH=CH₂ | H | CF₃ | 2,6-Cl₂-4-CN | O | O |
| CH₂CH=CH₂ | H | CF₃ | 2,6-Cl₂-4-NO₂ | O | O |
| CH₂CH=CH₂ | H | CF₃ | 2-Br-4-CF₃-6-Cl | O | O |
| CH₂CH=CH₂ | H | CF₃ | 2-Cl-4-CF₃-6-NO₂ | O | O |
| CH₂CH=CH₂ | H | CF₃ | 2-Cl-4-NO₂-6-CF₃ | O | O |
| CH₂CH=CH₂ | H | CF₃ | 2,6-Br₂-4-CF₃ | O | O |
| CH₂CH=CH₂ | H | CF₃ | 2,4-(NO₂)₂-6-CF₃ | O | O |

-continued

| | | | | | |
|---|---|---|---|---|---|
| CH₂CH=CH₂ | H | CF₃ | 2,6-(NO₂)₂-4-CF₃ | O | O |
| CH₂CH=CH₂ | H | CF₃ | 3,4,5-Cl₃ | O | O |
| CH₂CH=CH₂ | H | CF₃ | 3,5-Cl₂-4-CF₃ | O | O |
| CH₂CH=CH₂ | H | CF₃ | 3,5-Cl₂-4-OCF₂CHF₂ | O | O |
| CH₂CH=CH₂ | H | CF₃ | 2,3,4,5-F₄ | O | O |
| CH₂CH=CH₂ | H | CF₃ | 2,4-F₂-3,5-Cl₂ | O | O |
| CH₂CH=CH₂ | H | CF₃ | 2,3,4,5-Cl₄ | O | O |
| CH₂CH=CH₂ | H | CF₃ | 2,3,5-Cl₃-4-CF₃ | O | O |
| CH₂CH=CH₂ | H | CF₃ | 2,3,4,6-F₄ | O | O |
| CH₂CH=CH₂ | H | CF₃ | 2,3,4,6-Cl₄ | O | O |
| CH₂CH=CH₂ | H | CF₃ | 2,3,6-Cl₃-4-CF₃ | O | O |
| CH₂CH=CH₂ | H | CF₃ | 2,3,6-Cl₃-4-OCF₃ | O | O |
| CH₂CH=CH₂ | H | CF₃ | 3,5-Cl₂-3-CH₃-4-CF₃ | O | O |
| CH₂CH=CH₂ | H | CF₃ | 3,5-Cl₂-3-OCH₃-4-CF₃ | O | O |
| CH₂CH=CH₂ | H | CF₃ | 2-CF₃-3-Cl-4,6-(NO₂)₂ | O | O |
| CH₂CH=CH₂ | H | CF₃ | 2-CF₃-3-OCH₂CH₃-4,6-(NO₂)₂ | O | O |
| CH₂CH=CH₂ | H | CF₃ | 2,6-(NO₂)₂-3-Cl-4-CF₃ | O | O |
| CH₂CH=CH₂ | H | CF₃ | 2,3,5,6-Cl₄ | O | O |
| CH₂CH=CH₂ | H | CF₃ | 2,3,4,5,6-F₅ | O | O |
| CH₂CH=CH₂ | H | CF₃ | 2,3,5,6-F₄-4-CF₃ | O | O |
| CH₂CH=CH₂ | H | CF₃ | 2,3,5,6-F₄-4-CN | O | O |
| CH₂CH=CH₂ | H | CF₃ | 2,4,6-F₃-3,5-Cl₂ | O | O |
| CH₂CH=CH₂ | H | CF₃ | 2,3,5,6-Cl₄-4-CF₃ | O | O |
| CH₂OCH₂CH₃ | H | CF₃ | 2,3,4-F₃ | O | O |
| CH₂OCH₂CH₃ | H | CF₃ | 2,3,4-Cl₃ | O | O |
| CH₂OCH₂CH₃ | H | CF₃ | 2,3-Cl₂-4-CF₃ | O | O |
| CH₂OCH₂CH₃ | H | CF₃ | 2,3,5-Cl₃ | O | O |
| CH₂OCH₂CH₃ | H | CF₃ | 2,3,6-Cl₃ | O | O |
| CH₂OCH₂CH₃ | H | CF₃ | 2,4,5-Cl₃ | O | O |
| CH₂OCH₂CH₃ | H | CF₃ | 2,5-Cl₂-4-CF₃ | O | O |
| CH₂OCH₂CH₃ | H | CF₃ | 2-CF₃-4-NO₂-5-Cl | O | O |
| CH₂OCH₂CH₃ | H | CF₃ | 2,4,6-F₃ | O | O |
| CH₂OCH₂CH₃ | H | CF₃ | 2,5-F₂-4-CF₃ | O | O |
| CH₂OCH₂CH₃ | H | CF₃ | 2-Cl-4-CF₃-6-F | O | O |
| CH₂OCH₂CH₃ | H | CF₃ | 2,4,6-Cl₃ | O | O |
| CH₂OCH₂CH₃ | H | CF₃ | 2,6-Cl₂-4-Br | O | O |
| CH₂OCH₂CH₃ | H | CF₃ | 2,4-Cl₂-6-CF₃ | O | O |
| CH₂OCH₂CH₃ | H | CF₃ | 2,6-Cl₂-4-CF₃ | O | O |
| CH₂OCH₂CH₃ | H | CF₃ | 2,6-Cl₂-4-CHF₂ | O | O |
| CH₂OCH₂CH₃ | H | CF₃ | 2,6-Cl₂-4-OCF₃ | O | O |
| CH₂OCH₂CH₃ | H | CF₃ | 2,6-Cl₂-4-OCF₂CHF₂ | O | O |
| CH₂OCH₂CH₃ | H | CF₃ | 2,6-Cl₂-4-SCF₃ | O | O |
| CH₂OCH₂CH₃ | H | CF₃ | 2,6-Cl₂-4-SO₂CH₃ | O | O |
| CH₂OCH₂CH₃ | H | CF₃ | 2,6-Cl₂-4-SO₂CF₃ | O | O |
| CH₂OCH₂CH₃ | H | CF₃ | 2,6-Cl₂-4-CO₂CH₃ | O | O |
| CH₂OCH₂CH₃ | H | CF₃ | 2,6-Cl₂-4-CN | O | O |
| CH₂OCH₂CH₃ | H | CF₃ | 2,6-Cl₂-4-NO₂ | O | O |
| CH₂OCH₂CH₃ | H | CF₃ | 2-Br-4-CF₃-6-Cl | O | O |
| CH₂OCH₂CH₃ | H | CF₃ | 2-Cl-4-CF₃-6-NO₂ | O | O |
| CH₂OCH₂CH₃ | H | CF₃ | 2-Cl-4-NO₂-6-CF₃ | O | O |
| CH₂OCH₂CH₃ | H | CF₃ | 2,6-Br₂-4-CF₃ | O | O |
| CH₂OCH₂CH₃ | H | CF₃ | 2,4-(NO₂)₂-6-CF₃ | O | O |
| CH₂OCH₂CH₃ | H | CF₃ | 2,6-(NO₂)₂-4-CF₃ | O | O |
| CH₂OCH₂CH₃ | H | CF₃ | 3,4,5-Cl₃ | O | O |
| CH₂OCH₂CH₃ | H | CF₃ | 3,5-Cl₂-4-CF₃ | O | O |
| CH₂OCH₂CH₃ | H | CF₃ | 3,5-Cl₂-4-OCF₂CHF₂ | O | O |
| CH₂OCH₂CH₃ | H | CF₃ | 2,3,4,5-F₄ | O | O |
| CH₂OCH₂CH₃ | H | CF₃ | 2,4-F₂-3,5-Cl₂ | O | O |
| CH₂OCH₂CH₃ | H | CF₃ | 2,3,4,5-Cl₄ | O | O |
| CH₂OCH₂CH₃ | H | CF₃ | 2,3,5-Cl₃-4-CF₃ | O | O |
| CH₂OCH₂CH₃ | H | CF₃ | 2,3,4,6-F₄ | O | O |
| CH₂OCH₂CH₃ | H | CF₃ | 2,3,4,6-Cl₄ | O | O |
| CH₂OCH₂CH₃ | H | CF₃ | 2,3,6-Cl₃-4-CF₃ | O | O |
| CH₂OCH₂CH₃ | H | CF₃ | 2,3,6-Cl₃-4-OCF₃ | O | O |
| CH₂OCH₂CH₃ | H | CF₃ | 3,5-Cl₂-3-CH₃-4-CF₃ | O | O |
| CH₂OCH₂CH₃ | H | CF₃ | 3,5-Cl₂-3-OCH₃-4-CF₃ | O | O |
| CH₂OCH₂CH₃ | H | CF₃ | 2-CF₃-3-Cl-4,6-(NO₂)₂ | O | O |
| CH₂OCH₂CH₃ | H | CF₃ | 2-CF₃-3-OCH₂CH₃-4,6-(NO₂)₂ | O | O |
| CH₂OCH₂CH₃ | H | CF₃ | 2,6-(NO₂)₂-3-Cl-4-CF₃ | O | O |
| CH₂OCH₂CH₃ | H | CF₃ | 2,3,5,6-Cl₄ | O | O |
| CH₂OCH₂CH₃ | H | CF₃ | 2,3,4,5,6-F₅ | O | O |
| CH₂OCH₂CH₃ | H | CF₃ | 2,3,5,6-F₄-4-CF₃ | O | O |
| CH₂OCH₂CH₃ | H | CF₃ | 2,3,5,6-F₄-4-CN | O | O |
| CH₂OCH₂CH₃ | H | CF₃ | 2,4,6-F₃-3,5-Cl₂ | O | O |
| CH₂OCH₂CH₃ | H | CF₃ | 2,3,5,6-Cl₄-4-CF₃ | O | O |
| CHF₂ | H | CF₃ | 2,3,4-F₃ | O | O |
| CHF₂ | H | CF₃ | 2,3,4-Cl₃ | O | O |
| CHF₂ | H | CF₃ | 2,3-Cl₂-4-CF₃ | O | O |
| CHF₂ | H | CF₃ | 2,3,5-Cl₃ | O | O |
| CHF₂ | H | CF₃ | 2,3,6-Cl₃ | O | O |
| CHF₂ | H | CF₃ | 2,4,5-Cl₃ | O | O |
| CHF₂ | H | CF₃ | 2,5-Cl₂-4-CF₃ | O | O |
| CHF₂ | H | CF₃ | 2-CF₃-4-NO₂-5-Cl | O | O |

-continued

| | | | | | |
|---|---|---|---|---|---|
| CHF$_2$ | H | CF$_3$ | 2,4,6-F$_3$ | O | O |
| CHF$_2$ | H | CF$_3$ | 2,5-F$_2$-4-CF$_3$ | O | O |
| CHF$_2$ | H | CF$_3$ | 2-Cl-4-CF$_3$-6-F | O | O |
| CHF$_2$ | H | CF$_3$ | 2,4,6-Cl$_3$ | O | O |
| CHF$_2$ | H | CF$_3$ | 2,6-Cl$_2$-4-Br | O | O |
| CHF$_2$ | H | CF$_3$ | 2,4-Cl$_2$-6-CF$_3$ | O | O |
| CHF$_2$ | H | CF$_3$ | 2,6-Cl$_2$-4-CF$_3$ | O | O |
| CHF$_2$ | H | CF$_3$ | 2,6-Cl$_2$-4-CHF$_2$ | O | O |
| CHF$_2$ | H | CF$_3$ | 2,6-Cl$_2$-4-OCF$_3$ | O | O |
| CHF$_2$ | H | CF$_3$ | 2,6-Cl$_2$-4-OCF$_2$CHF$_2$ | O | O |
| CHF$_2$ | H | CF$_3$ | 2,6-Cl$_2$-4-SCF$_3$ | O | O |
| CHF$_2$ | H | CF$_3$ | 2,6-Cl$_2$-4-SO$_2$CH$_3$ | O | O |
| CHF$_2$ | H | CF$_3$ | 2,6-Cl$_2$-4-SO$_2$CF$_3$ | O | O |
| CHF$_2$ | H | CF$_3$ | 2,6-Cl$_2$-4-CO$_2$CH$_3$ | O | O |
| CHF$_2$ | H | CF$_3$ | 2,6-Cl$_2$-4-CN | O | O |
| CHF$_2$ | H | CF$_3$ | 2,6-Cl$_2$-4-NO$_2$ | O | O |
| CHF$_2$ | H | CF$_3$ | 2-Br-4-CF$_3$-6-Cl | O | O |
| CHF$_2$ | H | CF$_3$ | 2-Cl-4-CF$_3$-6-NO$_2$ | O | O |
| CHF$_2$ | H | CF$_3$ | 2-Cl-4-NO$_2$-6-CF$_3$ | O | O |
| CHF$_2$ | H | CF$_3$ | 2,6-Br$_2$-4-CF$_3$ | O | O |
| CHF$_2$ | H | CF$_3$ | 2,4-(NO$_2$)$_2$-6-CF$_3$ | O | O |
| CHF$_2$ | H | CF$_3$ | 2,6-(NO$_2$)$_2$-4-CF$_3$ | O | O |
| CHF$_2$ | H | CF$_3$ | 3,4,5-Cl$_3$ | O | O |
| CHF$_2$ | H | CF$_3$ | 3,5-Cl$_2$-4-CF$_3$ | O | O |
| CHF$_2$ | H | CF$_3$ | 3,5-Cl$_2$-4-OCF$_2$CHF$_2$ | O | O |
| CHF$_2$ | H | CF$_3$ | 2,3,4,5-F$_4$ | O | O |
| CHF$_2$ | H | CF$_3$ | 2,4-F$_2$-3,5-Cl$_2$ | O | O |
| CHF$_2$ | H | CF$_3$ | 2,3,4,5-Cl$_4$ | O | O |
| CHF$_2$ | H | CF$_3$ | 2,3,5-Cl$_3$-4-CF$_3$ | O | O |
| CHF$_2$ | H | CF$_3$ | 2,3,4,6-F$_4$ | O | O |
| CHF$_2$ | H | CF$_3$ | 2,3,4,6-Cl$_4$ | O | O |
| CHF$_2$ | H | CF$_3$ | 2,3,6-Cl$_3$-4-CF$_3$ | O | O |
| CHF$_2$ | H | CF$_3$ | 2,3,6-Cl$_3$-4-OCF$_3$ | O | O |
| CHF$_2$ | H | CF$_3$ | 3,5-Cl$_2$-3-CH$_3$-4-CF$_3$ | O | O |
| CHF$_2$ | H | CF$_3$ | 3,5-Cl$_2$-3-OCH$_3$-4-CF$_3$ | O | O |
| CHF$_2$ | H | CF$_3$ | 2-CF$_3$-3-Cl-4,6-(NO$_2$)$_2$ | O | O |
| CHF$_2$ | H | CF$_3$ | 2-CF$_3$-3-OCH$_2$CH$_3$-4,6-(NO$_2$)$_2$ | O | O |
| CHF$_2$ | H | CF$_3$ | 2,6-(NO$_2$)$_2$-3-Cl-4-CF$_3$ | O | O |
| CHF$_2$ | H | CF$_3$ | 2,3,5,6-Cl$_4$ | O | O |
| CHF$_2$ | H | CF$_3$ | 2,3,4,5,6-F$_5$ | O | O |
| CHF$_2$ | H | CF$_3$ | 2,3,5,6-F$_4$-4-CF$_3$ | O | O |
| CHF$_2$ | H | CF$_3$ | 2,3,5,6-F$_4$-4-CN | O | O |
| CHF$_2$ | H | CF$_3$ | 2,4,6-F$_3$-3,5-Cl$_2$ | O | O |
| CHF$_2$ | H | CF$_3$ | 2,3,5,6-Cl$_4$-4-CF$_3$ | O | O |
| COCH$_3$ | H | CF$_3$ | 2,3,4-F$_3$ | O | O |
| COCH$_3$ | H | CF$_3$ | 2,3,4-Cl$_3$ | O | O |
| COCH$_3$ | H | CF$_3$ | 2,3-Cl$_2$-4-CF$_3$ | O | O |
| COCH$_3$ | H | CF$_3$ | 2,3,5-Cl$_3$ | O | O |
| COCH$_3$ | H | CF$_3$ | 2,3,6-Cl$_3$ | O | O |
| COCH$_3$ | H | CF$_3$ | 2,4,5-Cl$_3$ | O | O |
| COCH$_3$ | H | CF$_3$ | 2,5-Cl$_2$-4-CF$_3$ | O | O |
| COCH$_3$ | H | CF$_3$ | 2-CF$_3$-4-NO$_2$-5-Cl | O | O |
| COCH$_3$ | H | CF$_3$ | 2,4,6-F$_3$ | O | O |
| COCH$_3$ | H | CF$_3$ | 2,5-F$_2$-4-CF$_3$ | O | O |
| COCH$_3$ | H | CF$_3$ | 2-Cl-4-CF$_3$-6-F | O | O |
| COCH$_3$ | H | CF$_3$ | 2,4,6-Cl$_3$ | O | O |
| COCH$_3$ | H | CF$_3$ | 2,6-Cl$_2$-4-Br | O | O |
| COCH$_3$ | H | CF$_3$ | 2,4-Cl$_2$-6-CF$_3$ | O | O |
| COCH$_3$ | H | CF$_3$ | 2,6-Cl$_2$-4-CF$_3$ | O | O |
| COCH$_3$ | H | CF$_3$ | 2,6-Cl$_2$-4-CHF$_2$ | O | O |
| COCH$_3$ | H | CF$_3$ | 2,6-Cl$_2$-4-OCF$_3$ | O | O |
| COCH$_3$ | H | CF$_3$ | 2,6-Cl$_2$-4-OCF$_2$CHF$_2$ | O | O |
| COCH$_3$ | H | CF$_3$ | 2,6-Cl$_2$-4-SCF$_3$ | O | O |
| COCH$_3$ | H | CF$_3$ | 2,6-Cl$_2$-4-SO$_2$CH$_3$ | O | O |
| COCH$_3$ | H | CF$_3$ | 2,6-Cl$_2$-4-SO$_2$CF$_3$ | O | O |
| COCH$_3$ | H | CF$_3$ | 2,6-Cl$_2$-4-CO$_2$CH$_3$ | O | O |
| COCH$_3$ | H | CF$_3$ | 2,6-Cl$_2$-4-CN | O | O |
| COCH$_3$ | H | CF$_3$ | 2,6-Cl$_2$-4-NO$_2$ | O | O |
| COCH$_3$ | H | CF$_3$ | 2-Br-4-CF$_3$-6-Cl | O | O |
| COCH$_3$ | H | CF$_3$ | 2-Cl-4-CF$_3$-6-NO$_2$ | O | O |
| COCH$_3$ | H | CF$_3$ | 2-Cl-4-NO$_2$-6-CF$_3$ | O | O |
| COCH$_3$ | H | CF$_3$ | 2,6-Br$_2$-4-CF$_3$ | O | O |
| COCH$_3$ | H | CF$_3$ | 2,4-(NO$_2$)$_2$-6-CF$_3$ | O | O |
| COCH$_3$ | H | CF$_3$ | 2,6-(NO$_2$)$_2$-4-CF$_3$ | O | O |
| COCH$_3$ | H | CF$_3$ | 3,4,5-Cl$_3$ | O | O |
| COCH$_3$ | H | CF$_3$ | 3,5-Cl$_2$-4-CF$_3$ | O | O |
| COCH$_3$ | H | CF$_3$ | 3,5-Cl$_2$-4-OCF$_2$CHF$_2$ | O | O |
| COCH$_3$ | H | CF$_3$ | 2,3,4,5-F$_4$ | O | O |
| COCH$_3$ | H | CF$_3$ | 2,4-F$_2$-3,5-Cl$_2$ | O | O |
| COCH$_3$ | H | CF$_3$ | 2,3,4,5-Cl$_4$ | O | O |
| COCH$_3$ | H | CF$_3$ | 2,3,5-Cl$_3$-4-CF$_3$ | O | O |
| COCH$_3$ | H | CF$_3$ | 2,3,4,6-F$_4$ | O | O |
| COCH$_3$ | H | CF$_3$ | 2,3,4,6-Cl$_4$ | O | O |

-continued

| | | | | | |
|---|---|---|---|---|---|
| COCH$_3$ | H | CF$_3$ | 2,3,6-Cl$_3$-4-CF$_3$ | O | O |
| COCH$_3$ | H | CF$_3$ | 2,3,6-Cl$_3$-4-OCF$_3$ | O | O |
| COCH$_3$ | H | CF$_3$ | 3,5-Cl$_2$-3-CH$_3$-4-CF$_3$ | O | O |
| COCH$_3$ | H | CF$_3$ | 3,5-Cl$_2$-3-OCH$_3$-4-CF$_3$ | O | O |
| COCH$_3$ | H | CF$_3$ | 2-CF$_3$-3-Cl-4,6-(NO$_2$)$_2$ | O | O |
| COCH$_3$ | H | CF$_3$ | 2-CF$_3$-3-OCH$_2$CH$_3$-4,6-(NO$_2$)$_2$ | O | O |
| COCH$_3$ | H | CF$_3$ | 2,6-(NO$_2$)$_2$-3-Cl-4-CF$_3$ | O | O |
| COCH$_3$ | H | CF$_3$ | 2,3,5,6-Cl$_4$ | O | O |
| COCH$_3$ | H | CF$_3$ | 2,3,4,5,6-F$_5$ | O | O |
| COCH$_3$ | H | CF$_3$ | 2,3,5,6-F$_4$-4-CF$_3$ | O | O |
| COCH$_3$ | H | CF$_3$ | 2,3,5,6-F$_4$-4-CN | O | O |
| COCH$_3$ | H | CF$_3$ | 2,4,6-F$_3$-3,5-Cl$_2$ | O | O |
| COCH$_3$ | H | CF$_3$ | 2,3,5,6-Cl$_4$-4-CF$_3$ | O | O |
| CO$_2$CH$_2$CH$_3$ | H | CF$_3$ | 2,3,4-F$_3$ | O | O |
| CO$_2$CH$_2$CH$_3$ | H | CF$_3$ | 2,3,4-Cl$_3$ | O | O |
| CO$_2$CH$_2$CH$_3$ | H | CF$_3$ | 2,3-Cl$_2$-4-CF$_3$ | O | O |
| CO$_2$CH$_2$CH$_3$ | H | CF$_3$ | 2,3,5-Cl$_3$ | O | O |
| CO$_2$CH$_2$CH$_3$ | H | CF$_3$ | 2,3,6-Cl$_3$ | O | O |
| CO$_2$CH$_2$CH$_3$ | H | CF$_3$ | 2,4,5-Cl$_3$ | O | O |
| CO$_2$CH$_2$CH$_3$ | H | CF$_3$ | 2,5-Cl$_2$-4-CF$_3$ | O | O |
| CO$_2$CH$_2$CH$_3$ | H | CF$_3$ | 2-CF$_3$-4-NO$_2$-5-Cl | O | O |
| CO$_2$CH$_2$CH$_3$ | H | CF$_3$ | 2,4,6-F$_3$ | O | O |
| CO$_2$CH$_2$CH$_3$ | H | CF$_3$ | 2,5-F$_2$-4-CF$_3$ | O | O |
| CO$_2$CH$_2$CH$_3$ | H | CF$_3$ | 2-Cl-4-CF$_3$-6-F | O | O |
| CO$_2$CH$_2$CH$_3$ | H | CF$_3$ | 2,4,6-Cl$_3$ | O | O |
| CO$_2$CH$_2$CH$_3$ | H | CF$_3$ | 2,6-Cl$_2$-4-Br | O | O |
| CO$_2$CH$_2$CH$_3$ | H | CF$_3$ | 2,4-Cl$_2$-6-CF$_3$ | O | O |
| CO$_2$CH$_2$CH$_3$ | H | CF$_3$ | 2,6-Cl$_2$-4-CF$_3$ | O | O |
| CO$_2$CH$_2$CH$_3$ | H | CF$_3$ | 2,6-Cl$_2$-4-CHF$_2$ | O | O |
| CO$_2$CH$_2$CH$_3$ | H | CF$_3$ | 2,6-Cl$_2$-4-OCF$_3$ | O | O |
| CO$_2$CH$_2$CH$_3$ | H | CF$_3$ | 2,6-Cl$_2$-4-OCF$_2$CHF$_2$ | O | O |
| CO$_2$CH$_2$CH$_3$ | H | CF$_3$ | 2,6-Cl$_2$-4-SCF$_3$ | O | O |
| CO$_2$CH$_2$CH$_3$ | H | CF$_3$ | 2,6-Cl$_2$-4-SO$_2$CH$_3$ | O | O |
| CO$_2$CH$_2$CH$_3$ | H | CF$_3$ | 2,6-Cl$_2$-4-SO$_2$CF$_3$ | O | O |
| CO$_2$CH$_2$CH$_3$ | H | CF$_3$ | 2,6-Cl$_2$-4-CO$_2$CH$_3$ | O | O |
| CO$_2$CH$_2$CH$_3$ | H | CF$_3$ | 2,6-Cl$_2$-4-CN | O | O |
| CO$_2$CH$_2$CH$_3$ | H | CF$_3$ | 2,6-Cl$_2$-4-NO$_2$ | O | O |
| CO$_2$CH$_2$CH$_3$ | H | CF$_3$ | 2-Br-4-CF$_3$-6-Cl | O | O |
| CO$_2$CH$_2$CH$_3$ | H | CF$_3$ | 2-Cl-4-CF$_3$-6-NO$_2$ | O | O |
| CO$_2$CH$_2$CH$_3$ | H | CF$_3$ | 2-Cl-4-NO$_2$-6-CF$_3$ | O | O |
| CO$_2$CH$_2$CH$_3$ | H | CF$_3$ | 2,6-Br$_2$-4-CF$_3$ | O | O |
| CO$_2$CH$_2$CH$_3$ | H | CF$_3$ | 2,4-(NO$_2$)$_2$-6-CF$_3$ | O | O |
| CO$_2$CH$_2$CH$_3$ | H | CF$_3$ | 2,6-(NO$_2$)$_2$-4-CF$_3$ | O | O |
| CO$_2$CH$_2$CH$_3$ | H | CF$_3$ | 3,4,5-Cl$_3$ | O | O |
| CO$_2$CH$_2$CH$_3$ | H | CF$_3$ | 3,5-Cl$_2$-4-CF$_3$ | O | O |
| CO$_2$CH$_2$CH$_3$ | H | CF$_3$ | 3,5-Cl$_2$-4-OCF$_2$CHF$_2$ | O | O |
| CO$_2$CH$_2$CH$_3$ | H | CF$_3$ | 2,3,4,5-F$_4$ | O | O |
| CO$_2$CH$_2$CH$_3$ | H | CF$_3$ | 2,4-F$_2$-3,5-Cl$_2$ | O | O |
| CO$_2$CH$_2$CH$_3$ | H | CF$_3$ | 2,3,4,5-Cl$_4$ | O | O |
| CO$_2$CH$_2$CH$_3$ | H | CF$_3$ | 2,3,5-Cl$_3$-4-CF$_3$ | O | O |
| CO$_2$CH$_2$CH$_3$ | H | CF$_3$ | 2,3,4,6-F$_4$ | O | O |
| CO$_2$CH$_2$CH$_3$ | H | CF$_3$ | 2,3,4,6-Cl$_4$ | O | O |
| CO$_2$CH$_2$CH$_3$ | H | CF$_3$ | 2,3,6-Cl$_3$-4-CF$_3$ | O | O |
| CO$_2$CH$_2$CH$_3$ | H | CF$_3$ | 2,3,6-Cl$_3$-4-OCF$_3$ | O | O |
| CO$_2$CH$_2$CH$_3$ | H | CF$_3$ | 3,5-Cl$_2$-3-CH$_3$-4-CF$_3$ | O | O |
| CO$_2$CH$_2$CH$_3$ | H | CF$_3$ | 3,5-Cl$_2$-3-OCH$_3$-4-CF$_3$ | O | O |
| CO$_2$CH$_2$CH$_3$ | H | CF$_3$ | 2-CF$_3$-3-Cl-4,6-(NO$_2$)$_2$ | O | O |
| CO$_2$CH$_2$CH$_3$ | H | CF$_3$ | 2-CF$_3$-3-OCH$_2$CH$_3$-4,6-(NO$_2$)$_2$ | O | O |
| CO$_2$CH$_2$CH$_3$ | H | CF$_3$ | 2,6-(NO$_2$)$_2$-3-Cl-4-CF$_3$ | O | O |
| CO$_2$CH$_2$CH$_3$ | H | CF$_3$ | 2,3,5,6-Cl$_4$ | O | O |
| CO$_2$CH$_2$CH$_3$ | H | CF$_3$ | 2,3,4,5,6-F$_5$ | O | O |
| CO$_2$CH$_2$CH$_3$ | H | CF$_3$ | 2,3,5,6-F$_4$-4-CF$_3$ | O | O |
| CO$_2$CH$_2$CH$_3$ | H | CF$_3$ | 2,3,5,6-F$_4$-4-CN | O | O |
| CO$_2$CH$_2$CH$_3$ | H | CF$_3$ | 2,4,6-F$_3$-3,5-Cl$_2$ | O | O |
| CO$_2$CH$_2$CH$_3$ | H | CF$_3$ | 2,3,5,6-Cl$_4$-4-CF$_3$ | O | O |
| CH(CH$_3$)$_2$ | H | CF$_3$ | 2,5-Cl$_2$-4-CF$_3$ | O | O |
| CH(CH$_3$)$_2$ | H | CF$_3$ | 2,4,6-Cl$_3$ | O | O |
| CH(CH$_3$)$_2$ | H | CF$_3$ | 2,6-Cl$_2$-4-CF$_3$ | O | O |
| CH(CH$_3$)$_2$ | H | CF$_3$ | 2,6-Cl$_2$-4-CHF$_2$ | O | O |
| CH(CH$_3$)$_2$ | H | CF$_3$ | 2,6-Cl$_2$-4-CN | O | O |
| CH(CH$_3$)$_2$ | H | CF$_3$ | 2,6-Cl$_2$-4-NO$_2$ | O | O |
| CH(CH$_3$)$_2$ | H | CF$_3$ | 2-Br-4-CF$_3$-6-Cl | O | O |
| CH(CH$_3$)$_2$ | H | CF$_3$ | 2-Cl-4-CF$_3$-6-NO$_2$ | O | O |
| CH(CH$_3$)$_2$ | H | CF$_3$ | 2-Cl-4-NO$_2$-6-CF$_3$ | O | O |
| CH(CH$_3$)$_2$ | H | CF$_3$ | 2,4-(NO$_2$)$_2$-6-CF$_3$ | O | O |
| CH(CH$_3$)$_2$ | H | CF$_3$ | 2,6-(NO$_2$)$_2$-4-CF$_3$ | O | O |
| CH(CH$_3$)$_2$ | H | CF$_3$ | 2,3,4,6-Cl$_4$ | O | O |
| CH(CH$_3$)$_2$ | H | CF$_3$ | 2,3,6-Cl$_3$-4-CF$_3$ | O | O |
| CH(CH$_3$)$_2$ | H | CF$_3$ | 2,3,4,5,6-F$_5$ | O | O |
| CH(CH$_3$)$_2$ | H | CF$_3$ | 2,3,4,6-F$_4$-4-CN | O | O |
| CH(CH$_3$)$_2$ | H | CF$_3$ | 2,3,4,6-Cl$_4$-4-CF$_3$ | O | O |
| CH$_2$CH$_2$CH$_3$ | H | CF$_3$ | 2,5-Cl$_2$-4-CF$_3$ | O | O |
| CH$_2$CH$_2$CH$_3$ | H | CF$_3$ | 2,4,6-Cl$_3$ | O | O |

-continued

| | | | | | |
|---|---|---|---|---|---|
| CH₂CH₂CH₃ | H | CF₃ | 2,6-Cl₂-4-CF₃ | O | O |
| CH₂CH₂CH₃ | H | CF₃ | 2,6-Cl₂-4-CHF₂ | O | O |
| CH₂CH₂CH₃ | H | CF₃ | 2,6-Cl₂-4-CN | O | O |
| CH₂CH₂CH₃ | H | CF₃ | 2,6-Cl₂-4-NO₂ | O | O |
| CH₂CH₂CH₃ | H | CF₃ | 2-Br-4-CF₃-6-Cl | O | O |
| CH₂CH₂CH₃ | H | CF₃ | 2-Cl-4-CF₃-6-NO₂ | O | O |
| CH₂CH₂CH₃ | H | CF₃ | 2-Cl-4-NO₂-6-CF₃ | O | O |
| CH₂CH₂CH₃ | H | CF₃ | 2,4-(NO₂)₂-6-CF₃ | O | O |
| CH₂CH₂CH₃ | H | CF₃ | 2,6-(NO₂)₂-4-CF₃ | O | O |
| CH₂CH₂CH₃ | H | CF₃ | 2,3,4,6-Cl₄ | O | O |
| CH₂CH₂CH₃ | H | CF₃ | 2,3,6-Cl₃-4-CF₃ | O | O |
| CH₂CH₂CH₃ | H | CF₃ | 2,3,4,5,6-F₅ | O | O |
| CH₂CH₂CH₃ | H | CF₃ | 2,3,4,6-F₄-4-CN | O | O |
| CH₂CH₂CH₃ | H | CF₃ | 2,3,4,6-Cl₄-4-CF₃ | O | O |
| (CH₂)₃CH₃ | H | CF₃ | 2,5-Cl₂-4-CF₃ | O | O |
| (CH₂)₃CH₃ | H | CF₃ | 2,4,6-Cl₃ | O | O |
| (CH₂)₃CH₃ | H | CF₃ | 2,6-Cl₂-4-CF₃ | O | O |
| (CH₂)₃CH₃ | H | CF₃ | 2,6-Cl₂-4-CHF₂ | O | O |
| (CH₂)₃CH₃ | H | CF₃ | 2,6-Cl₂-4-CN | O | O |
| (CH₂)₃CH₃ | H | CF₃ | 2,6-Cl₂-4-NO₂ | O | O |
| (CH₂)₃CH₃ | H | CF₃ | 2-Br-4-CF₃-6-Cl | O | O |
| (CH₂)₃CH₃ | H | CF₃ | 2-Cl-4-CF₃-6-NO₂ | O | O |
| (CH₂)₃CH₃ | H | CF₃ | 2-Cl-4-NO₂-6-CF₃ | O | O |
| (CH₂)₃CH₃ | H | CF₃ | 2,4-(NO₂)₂-6-CF₃ | O | O |
| (CH₂)₃CH₃ | H | CF₃ | 2,6-(NO₂)₂-4-CF₃ | O | O |
| (CH₂)₃CH₃ | H | CF₃ | 2,3,4,6-Cl₄ | O | O |
| (CH₂)₃CH₃ | H | CF₃ | 2,3,6-Cl₃-4-CF₃ | O | O |
| (CH₂)₃CH₃ | H | CF₃ | 2,3,4,5,6-F₅ | O | O |
| (CH₂)₃CH₃ | H | CF₃ | 2,3,4,6-F₄-4-CN | O | O |
| (CH₂)₃CH₃ | H | CF₃ | 2,3,4,6-Cl₄-4-CF₃ | O | O |
| C(CH₃)₃ | H | CF₃ | 2,5-Cl₂-4-CF₃ | O | O |
| C(CH₃)₃ | H | CF₃ | 2,4,6-Cl₃ | O | O |
| C(CH₃)₃ | H | CF₃ | 2,6-Cl₂-4-CF₃ | O | O |
| C(CH₃)₃ | H | CF₃ | 2,6-Cl₂-4-CHF₂ | O | O |
| C(CH₃)₃ | H | CF₃ | 2,6-Cl₂-4-CN | O | O |
| C(CH₃)₃ | H | CF₃ | 2,6-Cl₂-4-NO₂ | O | O |
| C(CH₃)₃ | H | CF₃ | 2-Br-4-CF₃-6-Cl | O | O |
| C(CH₃)₃ | H | CF₃ | 2-Cl-4-CF₃-6-NO₂ | O | O |
| C(CH₃)₃ | H | CF₃ | 2-Cl-4-NO₂-6-CF₃ | O | O |
| C(CH₃)₃ | H | CF₃ | 2,4-(NO₂)₂-6-CF₃ | O | O |
| C(CH₃)₃ | H | CF₃ | 2,6-(NO₂)₂-4-CF₃ | O | O |
| C(CH₃)₃ | H | CF₃ | 2,3,4,6-Cl₄ | O | O |
| C(CH₃)₃ | H | CF₃ | 2,3,6-Cl₃-4-CF₃ | O | O |
| C(CH₃)₃ | H | CF₃ | 2,3,4,5,6-F₅ | O | O |
| C(CH₃)₃ | H | CF₃ | 2,3,4,6-F₄-4-CN | O | O |
| C(CH₃)₃ | H | CF₃ | 2,3,4,6-Cl₄-4-CF₃ | O | O |
| CF₂Br | H | CF₃ | 2,5-Cl₂-4-CF₃ | O | O |
| CF₂Br | H | CF₃ | 2,4,6-Cl₃ | O | O |
| CF₂Br | H | CF₃ | 2,6-Cl₂-4-CF₃ | O | O |
| CF₂Br | H | CF₃ | 2,6-Cl₂-4-CHF₂ | O | O |
| CF₂Br | H | CF₃ | 2,6-Cl₂-4-CN | O | O |
| CF₂Br | H | CF₃ | 2,6-Cl₂-4-NO₂ | O | O |
| CF₂Br | H | CF₃ | 2-Br-4-CF₃-6-Cl | O | O |
| CF₂Br | H | CF₃ | 2-Cl-4-CF₃-6-NO₂ | O | O |
| CF₂Br | H | CF₃ | 2-Cl-4-NO₂-6-CF₃ | O | O |
| CF₂Br | H | CF₃ | 2,4-(NO₂)₂-6-CF₃ | O | O |
| CF₂Br | H | CF₃ | 2,6-(NO₂)₂-4-CF₃ | O | O |
| CF₂Br | H | CF₃ | 2,3,4,6-Cl₄ | O | O |
| CF₂Br | H | CF₃ | 2,3,6-Cl₃-4-CF₃ | O | O |
| CF₂Br | H | CF₃ | 2,3,4,5,6-F₅ | O | O |
| CF₂Br | H | CF₃ | 2,3,4,6-F₄-4-CN | O | O |
| CF₂Br | H | CF₃ | 2,3,4,6-Cl₄-4-CF₃ | O | O |
| CF₃ | H | CF₃ | 2,5-Cl₂-4-CF₃ | O | O |
| CF₃ | H | CF₃ | 2,4,6-Cl₃ | O | O |
| CF₃ | H | CF₃ | 2,6-Cl₂-4-CF₃ | O | O |
| CF₃ | H | CF₃ | 2,6-Cl₂-4-CHF₂ | O | O |
| CF₃ | H | CF₃ | 2,6-Cl₂-4-CN | O | O |
| CF₃ | H | CF₃ | 2,6-Cl₂-4-NO₂ | O | O |
| CF₃ | H | CF₃ | 2-Br-4-CF₃-6-Cl | O | O |
| CF₃ | H | CF₃ | 2-Cl-4-CF₃-6-NO₂ | O | O |
| CF₃ | H | CF₃ | 2-Cl-4-NO₂-6-CF₃ | O | O |
| CF₃ | H | CF₃ | 2,4-(NO₂)₂-6-CF₃ | O | O |
| CF₃ | H | CF₃ | 2,6-(NO₂)₂-4-CF₃ | O | O |
| CF₃ | H | CF₃ | 2,3,4,6-Cl₄ | O | O |
| CF₃ | H | CF₃ | 2,3,6-Cl₃-4-CF₃ | O | O |
| CF₃ | H | CF₃ | 2,3,4,5,6-F₅ | O | O |
| CF₃ | H | CF₃ | 2,3,4,6-F₄-4-CN | O | O |
| CF₃ | H | CF₃ | 2,3,4,6-Cl₄-4-CF₃ | O | O |
| CH₂OCH₃ | H | CF₃ | 2,5-Cl₂-4-CF₃ | O | O |
| CH₂OCH₃ | H | CF₃ | 2,4,6-Cl₃ | O | O |
| CH₂OCH₃ | H | CF₃ | 2,6-Cl₂-4-CF₃ | O | O |
| CH₂OCH₃ | H | CF₃ | 2,6-Cl₂-4-CHF₂ | O | O |
| CH₂OCH₃ | H | CF₃ | 2,6-Cl₂-4-CN | O | O |

-continued

| | | | | | |
|---|---|---|---|---|---|
| CH₂OCH₃ | H | CF₃ | 2,6-Cl₂-4-NO₂ | O | O |
| CH₂OCH₃ | H | CF₃ | 2-Br-4-CF₃-6-Cl | O | O |
| CH₂OCH₃ | H | CF₃ | 2-Cl-4-CF₃-6-NO₂ | O | O |
| CH₂OCH₃ | H | CF₃ | 2-Cl-4-NO₂-6-CF₃ | O | O |
| CH₂OCH₃ | H | CF₃ | 2,4-(NO₂)₂-6-CF₃ | O | O |
| CH₂OCH₃ | H | CF₃ | 2,6-(NO₂)₂-4-CF₃ | O | O |
| CH₂OCH₃ | H | CF₃ | 2,3,4,6-Cl₄ | O | O |
| CH₂OCH₃ | H | CF₃ | 2,3,6-Cl₃-4-CF₃ | O | O |
| CH₂OCH₃ | H | CF₃ | 2,3,4,5,6-F₅ | O | O |
| CH₂OCH₃ | H | CF₃ | 2,3,4,6-F₄-4-CN | O | O |
| CH₂OCH₃ | H | CF₃ | 2,3,4,6-Cl₄-4-CF₃ | O | O |
| CH₂CH₂OCH₃ | H | CF₃ | 2,5-Cl₂-4-CF₃ | O | O |
| CH₂CH₂OCH₃ | H | CF₃ | 2,4,6-Cl₃ | O | O |
| CH₂CH₂OCH₃ | H | CF₃ | 2,6-Cl₂-4-CF₃ | O | O |
| CH₂CH₂OCH₃ | H | CF₃ | 2,6-Cl₂-4-CHF₂ | O | O |
| CH₂CH₂OCH₃ | H | CF₃ | 2,6-Cl₂-4-CN | O | O |
| CH₂CH₂OCH₃ | H | CF₃ | 2,6-Cl₂-4-NO₂ | O | O |
| CH₂CH₂OCH₃ | H | CF₃ | 2-Br-4-CF₃-6-Cl | O | O |
| CH₂CH₂OCH₃ | H | CF₃ | 2-Cl-4-CF₃-6-NO₂ | O | O |
| CH₂CH₂OCH₃ | H | CF₃ | 2-Cl-4-NO₂-6-CF₃ | O | O |
| CH₂CH₂OCH₃ | H | CF₃ | 2,4-(NO₂)₂-6-CF₃ | O | O |
| CH₂CH₂OCH₃ | H | CF₃ | 2,6-(NO₂)₂-4-CF₃ | O | O |
| CH₂CH₂OCH₃ | H | CF₃ | 2,3,4,6-Cl₄ | O | O |
| CH₂CH₂OCH₃ | H | CF₃ | 2,3,6-Cl₃-4-CF₃ | O | O |
| CH₂CH₂OCH₃ | H | CF₃ | 2,3,4,5,6-F₅ | O | O |
| CH₂CH₂OCH₃ | H | CF₃ | 2,3,4,6-F₄-4-CN | O | O |
| CH₂CH₂OCH₃ | H | CF₃ | 2,3,4,6-Cl₄-4-CF₃ | O | O |
| CHO | H | CF₃ | 2,5-Cl₂-4-CF₃ | O | O |
| CHO | H | CF₃ | 2,4,6-Cl₃ | O | O |
| CHO | H | CF₃ | 2,6-Cl₂-4-CF₃ | O | O |
| CHO | H | CF₃ | 2,6-Cl₂-4-CHF₂ | O | O |
| CHO | H | CF₃ | 2,6-Cl₂-4-CN | O | O |
| CHO | H | CF₃ | 2,6-Cl₂-4-NO₂ | O | O |
| CHO | H | CF₃ | 2-Br-4-CF₃-6-Cl | O | O |
| CHO | H | CF₃ | 2-Cl-4-CF₃-6-NO₂ | O | O |
| CHO | H | CF₃ | 2-Cl-4-NO₂-6-CF₃ | O | O |
| CHO | H | CF₃ | 2,4-(NO₂)₂-6-CF₃ | O | O |
| CHO | H | CF₃ | 2,6-(NO₂)₂-4-CF₃ | O | O |
| CHO | H | CF₃ | 2,3,4,6-Cl₄ | O | O |
| CHO | H | CF₃ | 2,3,6-Cl₃-4-CF₃ | O | O |
| CHO | H | CF₃ | 2,3,4,5,6-F₅ | O | O |
| CHO | H | CF₃ | 2,3,4,6-F₄-4-CN | O | O |
| CHO | H | CF₃ | 2,3,4,6-Cl₄-4-CF₃ | O | O |
| COCH(CH₃)₂ | H | CF₃ | 2,5-Cl₂-4-CF₃ | O | O |
| COCH(CH₃)₂ | H | CF₃ | 2,4,6-Cl₃ | O | O |
| COCH(CH₃)₂ | H | CF₃ | 2,6-Cl₂-4-CF₃ | O | O |
| COCH(CH₃)₂ | H | CF₃ | 2,6-Cl₂-4-CHF₂ | | |
| COCH(CH₃)₂ | H | CF₃ | 2,6-Cl₂-4-CN | O | O |
| COCH(CH₃)₂ | H | CF₃ | 2,6-Cl₂-4-NO₂ | O | O |
| COCH(CH₃)₂ | H | CF₃ | 2-Br-4-CF₃-6-Cl | O | O |
| COCH(CH₃)₂ | H | CF₃ | 2-Cl-4-CF₃-6-NO₂ | O | O |
| COCH(CH₃)₂ | H | CF₃ | 2-Cl-4-NO₂-6-CF₃ | O | O |
| COCH(CH₃)₂ | H | CF₃ | 2,4-(NO₂)₂-6-CF₃ | O | O |
| COCH(CH₃)₂ | H | CF₃ | 2,6-(NO₂)₂-4-CF₃ | O | O |
| COCH(CH₃)₂ | H | CF₃ | 2,3,4,6-Cl₄ | O | O |
| COCH(CH₃)₂ | H | CF₃ | 2,3,6-Cl₃-4-CF₃ | O | O |
| COCH(CH₃)₂ | H | CF₃ | 2,3,4,5,6-F₅ | O | O |
| COCH(CH₃)₂ | H | CF₃ | 2,3,4,6-F₄-4-CN | O | O |
| COCH(CH₃)₂ | H | CF₃ | 2,3,4,6-Cl₄-4-CF₃ | O | O |
| CO₂CH₃ | H | CF₃ | 2,5-Cl₂-4-CF₃ | O | O |
| CO₂CH₃ | H | CF₃ | 2,4,6-Cl₃ | O | O |
| CO₂CH₃ | H | CF₃ | 2,6-Cl₂-4-CF₃ | O | O |
| CO₂CH₃ | H | CF₃ | 2,6-Cl₂-4-CHF₂ | O | O |
| CO₂CH₃ | H | CF₃ | 2,6-Cl₂-4-CN | O | O |
| CO₂CH₃ | H | CF₃ | 2,6-Cl₂-4-NO₂ | O | O |
| CO₂CH₃ | H | CF₃ | 2-Br-4-CF₃-6-Cl | O | O |
| CO₂CH₃ | H | CF₃ | 2-Cl-4-CF₃-6-NO₂ | O | O |
| CO₂CH₃ | H | CF₃ | 2-Cl-4-NO₂-6-CF₃ | O | O |
| CO₂CH₃ | H | CF₃ | 2,4-(NO₂)₂-6-CF₃ | O | O |
| CO₂CH₃ | H | CF₃ | 2,6-(NO₂)₂-4-CF₃ | O | O |
| CO₂CH₃ | H | CF₃ | 2,3,4,6-Cl₄ | O | O |
| CO₂CH₃ | H | CF₃ | 2,3,6-Cl₃-4-CF₃ | O | O |
| CO₂CH₃ | H | CF₃ | 2,3,4,5,6-F₅ | O | O |
| CO₂CH₃ | H | CF₃ | 2,3,4,6-F₄-4-CN | O | O |
| CO₂CH₃ | H | CF₃ | 2,3,4,6-Cl₄-4-CF₃ | O | O |
| CO₂C(CH₃)₃ | H | CF₃ | 2,5-Cl₂-4-CF₃ | O | O |
| CO₂C(CH₃)₃ | H | CF₃ | 2,4,6-Cl₃ | O | O |
| CO₂C(CH₃)₃ | H | CF₃ | 2,6-Cl₂-4-CF₃ | O | O |
| CO₂C(CH₃)₃ | H | CF₃ | 2,6-Cl₂-4-CHF₂ | O | O |
| CO₂C(CH₃)₃ | H | CF₃ | 2,6-Cl₂-4-CN | O | O |
| CO₂C(CH₃)₃ | H | CF₃ | 2,6-Cl₂-4-NO₂ | O | O |
| CO₂C(CH₃)₃ | H | CF₃ | 2-Br-4-CF₃-6-Cl | O | O |
| CO₂C(CH₃)₃ | H | CF₃ | 2-Cl-4-CF₃-6-NO₂ | O | O |

-continued

| | | | | | |
|---|---|---|---|---|---|
| CO₂C(CH₃)₃ | H | CF₃ | 2-Cl-4-NO₂-6-CF₃ | O | O |
| CO₂C(CH₃)₃ | H | CF₃ | 2,4-(NO₂)₂-6-CF₃ | O | O |
| CO₂C(CH₃)₃ | H | CF₃ | 2,6-(NO₂)₂-4-CF₃ | O | O |
| CO₂C(CH₃)₃ | H | CF₃ | 2,3,4,6-Cl₄ | O | O |
| CO₂C(CH₃)₃ | H | CF₃ | 2,3,6-Cl₃-4-CF₃ | O | O |
| CO₂C(CH₃)₃ | H | CF₃ | 2,3,4,5,6-F₅ | O | O |
| CO₂C(CH₃)₃ | H | CF₃ | 2,3,4,6-F₄-4-CN | O | O |
| CO₂C(CH₃)₃ | H | CF₃ | 2,3,4,6-Cl₄-4-CF₃ | O | O |
| CH₂CO₂CH₃ | H | CF₃ | 2,5-Cl₂-4-CF₃ | O | O |
| CH₂CO₂CH₃ | H | CF₃ | 2,4,6-Cl₃ | O | O |
| CH₂CO₂CH₃ | H | CF₃ | 2,6-Cl₂-4-CF₃ | O | O |
| CH₂CO₂CH₃ | H | CF₃ | 2,6-Cl₂-4-CHF₂ | O | O |
| CH₂CO₂CH₃ | H | CF₃ | 2,6-Cl₂-4-CN | O | O |
| CH₂CO₂CH₃ | H | CF₃ | 2,6-Cl₂-4-NO₂ | O | O |
| CH₂CO₂CH₃ | H | CF₃ | 2-Br-4-CF₃-6-Cl | O | O |
| CH₂CO₂CH₃ | H | CF₃ | 2-Cl-4-CF₃-6-NO₂ | O | O |
| CH₂CO₂CH₃ | H | CF₃ | 2-Cl-4-NO₂-6-CF₃ | O | O |
| CH₂CO₂CH₃ | H | CF₃ | 2,4-(NO₂)₂-6-CF₃ | O | O |
| CH₂CO₂CH₃ | H | CF₃ | 2,6-(NO₂)₂-4-CF₃ | O | O |
| CH₂CO₂CH₃ | H | CF₃ | 2,3,4,6-Cl₄ | O | O |
| CH₂CO₂CH₃ | H | CF₃ | 2,3,6-Cl₃-4-CF₃ | O | O |
| CH₂CO₂CH₃ | H | CF₃ | 2,3,4,5,6-F₅ | O | O |
| CH₂CO₂CH₃ | H | CF₃ | 2,3,4,6-F₄-4-CN | O | O |
| CH₂CO₂CH₃ | H | CF₃ | 2,3,4,6-Cl₄-4-CF₃ | O | O |
| CH₂CN | H | CF₃ | 2,5-Cl₂-4-CF₃ | O | O |
| CH₂CN | H | CF₃ | 2,4,6-Cl₃ | O | O |
| CH₂CN | H | CF₃ | 2,6-Cl₂-4-CF₃ | O | O |
| CH₂CN | H | CF₃ | 2,6-Cl₂-4-CHF₂ | O | O |
| CH₂CN | H | CF₃ | 2,6-Cl₂-4-CN | O | O |
| CH₂CN | H | CF₃ | 2,6-Cl₂-4-NO₂ | O | O |
| CH₂CN | H | CF₃ | 2-Br-4-CF₃-6-Cl | O | O |
| CH₂CN | H | CF₃ | 2-Cl-4-CF₃-6-NO₂ | O | O |
| CH₂CN | H | CF₃ | 2-Cl-4-NO₂-6-CF₃ | O | O |
| CH₂CN | H | CF₃ | 2,4-(NO₂)₂-6-CF₃ | O | O |
| CH₂CN | H | CF₃ | 2,6-(NO₂)₂-4-CF₃ | O | O |
| CH₂CN | H | CF₃ | 2,3,4,6-Cl₄ | O | O |
| CH₂CN | H | CF₃ | 2,3,6-Cl₃-4-CF₃ | O | O |
| CH₂CN | H | CF₃ | 2,3,4,5,6-F₅ | O | O |
| CH₂CN | H | CF₃ | 2,3,4,6-F₄-4-CN | O | O |
| CH₂CN | H | CF₃ | 2,3,4,6-Cl₄-4-CF₃ | O | O |
| CH₂C₆H₅ | H | CF₃ | 2,5-Cl₂-4-CF₃ | O | O |
| CH₂C₆H₅ | H | CF₃ | 2,4,6-Cl₃ | O | O |
| CH₂C₆H₅ | H | CF₃ | 2,6-Cl₂-4-CF₃ | O | O |
| CH₂C₆H₅ | H | CF₃ | 2,6-Cl₂-4-CHF₂ | O | O |
| CH₂C₆H₅ | H | CF₃ | 2,6-Cl₂-4-CN | O | O |
| CH₂C₆H₅ | H | CF₃ | 2,6-Cl₂-4-NO₂ | O | O |
| CH₂C₆H₅ | H | CF₃ | 2-Br-4-CF₃-6-Cl | O | O |
| CH₂C₆H₅ | H | CF₃ | 2-Cl-4-CF₃-6-NO₂ | O | O |
| CH₂C₆H₅ | H | CF₃ | 2-Cl-4-NO₂-6-CF₃ | O | O |
| CH₂C₆H₅ | H | CF₃ | 2,4-(NO₂)₂-6-CF₃ | O | O |
| CH₂C₆H₅ | H | CF₃ | 2,6-(NO₂)₂-4-CF₃ | O | O |
| CH₂C₆H₅ | H | CF₃ | 2,3,4,6-Cl₄ | O | O |
| CH₂C₆H₅ | H | CF₃ | 2,3,6-Cl₃-4-CF₃ | O | O |
| CH₂C₆H₅ | H | CF₃ | 2,3,4,5,6-F₅ | O | O |
| CH₂C₆H₅ | H | CF₃ | 2,3,4,6-F₄-4-CN | O | O |
| CH₂C₆H₅ | H | CF₃ | 2,3,4,6-Cl₄-4-CF₃ | O | O |
| C₆H₅ | H | CF₃ | 2,5-Cl₂-4-CF₃ | O | O |
| C₆H₅ | H | CF₃ | 2,4,6-Cl₃ | O | O |
| C₆H₅ | H | CF₃ | 2,6-Cl₂-4-CF₃ | O | O |
| C₆H₅ | H | CF₃ | 2,6-Cl₂-4-CHF₂ | O | O |
| C₆H₅ | H | CF₃ | 2,6-Cl₂-4-CN | O | O |
| C₆H₅ | H | CF₃ | 2,6-Cl₂-4-NO₂ | O | O |
| C₆H₅ | H | CF₃ | 2-Br-4-CF₃-6-Cl | O | O |
| C₆H₅ | H | CF₃ | 2-Cl-4-CF₃-6-NO₂ | O | O |
| C₆H₅ | H | CF₃ | 2-Cl-4-NO₂-6-CF₃ | O | O |
| C₆H₅ | H | CF₃ | 2,4-(NO₂)₂-6-CF₃ | O | O |
| C₆H₅ | H | CF₃ | 2,6-(NO₂)₂-4-CF₃ | O | O |
| C₆H₅ | H | CF₃ | 2,3,4,6-Cl₄ | O | O |
| C₆H₅ | H | CF₃ | 2,3,6-Cl₃-4-CF₃ | O | O |
| C₆H₅ | H | CF₃ | 2,3,4,5,6-F₅ | O | O |
| C₆H₅ | H | CF₃ | 2,3,4,6-F₄-4-CN | O | O |
| C₆H₅ | H | CF₃ | 2,3,4,6-Cl₄-4-CF₃ | O | O |
| Na | H | CF₃ | 2,5-Cl₂-4-CF₃ | O | O |
| Na | H | CF₃ | 2,4,6-Cl₃ | O | O |
| Na | H | CF₃ | 2,6-Cl₂-4-CF₃ | O | O |
| Na | H | CF₃ | 2,6-Cl₂-4-CHF₂ | O | O |
| Na | H | CF₃ | 2,6-Cl₂-4-CN | O | O |
| Na | H | CF₃ | 2,6-Cl₂-4-NO₂ | O | O |
| Na | H | CF₃ | 2-Br-4-CF₃-6-Cl | O | O |
| Na | H | CF₃ | 2-Cl-4-CF₃-6-NO₂ | O | O |
| Na | H | CF₃ | 2-Cl-4-NO₂-6-CF₃ | O | O |
| Na | H | CF₃ | 2,4-(NO₂)₂-6-CF₃ | O | O |
| Na | H | CF₃ | 2,6-(NO₂)₂-4-CF₃ | O | O |

-continued

| | | | | | |
|---|---|---|---|---|---|
| Na | H | CF$_3$ | 2,3,4,6-Cl$_4$ | O | O |
| Na | H | CF$_3$ | 2,3,6-Cl$_3$-4-CF$_3$ | O | O |
| Na | H | CF$_3$ | 2,3,4,5,6-F$_5$ | O | O |
| Na | H | CF$_3$ | 2,3,4,6-F$_4$-4-CN | O | O |
| Na | H | CF$_3$ | 2,3,4,6-Cl$_4$-4-CF$_3$ | O | O |
| K | H | CF$_3$ | 2,5-Cl$_2$-4-CF$_3$ | O | O |
| K | H | CF$_3$ | 2,4,6-Cl$_3$ | O | O |
| K | H | CF$_3$ | 2,6-Cl$_2$-4-CF$_3$ | O | O |
| K | H | CF$_3$ | 2,6-Cl$_2$-4-CHF$_2$ | O | O |
| K | H | CF$_3$ | 2,6-Cl$_2$-4-CN | O | O |
| K | H | CF$_3$ | 2,6-Cl$_2$-4-NO$_2$ | O | O |
| K | H | CF$_3$ | 2-Br-4-CF$_3$-6-Cl | O | O |
| K | H | CF$_3$ | 2-Cl-4-CF$_3$-6-NO$_2$ | O | O |
| K | H | CF$_3$ | 2-Cl-4-NO$_2$-6-CF$_3$ | O | O |
| K | H | CF$_3$ | 2,4-(NO$_2$)$_2$-6-CF$_3$ | O | O |
| K | H | CF$_3$ | 2,6-(NO$_2$)$_2$-4-CF$_3$ | O | O |
| K | H | CF$_3$ | 2,3,4,6-Cl$_4$ | O | O |
| K | H | CF$_3$ | 2,3,6-Cl$_3$-4-CF$_3$ | O | O |
| K | H | CF$_3$ | 2,3,4,5,6-F$_5$ | O | O |
| K | H | CF$_3$ | 2,3,4,6-F$_4$-4-CN | O | O |
| K | H | CF$_3$ | 2,3,4,6-Cl$_4$-4-CF$_3$ | O | O |
| Ca | H | CF$_3$ | 2,5-Cl$_2$-4-CF$_3$ | O | O |
| Ca | H | CF$_3$ | 2,4,6-Cl$_3$ | O | O |
| Ca | H | CF$_3$ | 2,6-Cl$_2$-4-CF$_3$ | O | O |
| Ca | H | CF$_3$ | 2,6-Cl$_2$-4-CHF$_2$ | O | O |
| Ca | H | CF$_3$ | 2,6-Cl$_2$-4-CN | O | O |
| Ca | H | CF$_3$ | 2,6-Cl$_2$-4-NO$_2$ | O | O |
| Ca | H | CF$_3$ | 2-Br-4-CF$_3$-6-Cl | O | O |
| Ca | H | CF$_3$ | 2-Cl-4-CF$_3$-6-NO$_2$ | O | O |
| Ca | H | CF$_3$ | 2-Cl-4-NO$_2$-6-CF$_3$ | O | O |
| Ca | H | CF$_3$ | 2,4-(NO$_2$)$_2$-6-CF$_3$ | O | O |
| Ca | H | CF$_3$ | 2,6-(NO$_2$)$_2$-4-CF$_3$ | O | O |
| Ca | H | CF$_3$ | 2,3,4,6-Cl$_4$ | O | O |
| Ca | H | CF$_3$ | 2,3,6-Cl$_3$-4-CF$_3$ | O | O |
| Ca | H | CF$_3$ | 2,3,4,5,6-F$_5$ | O | O |
| Ca | H | CF$_3$ | 2,3,4,6-F$_4$-4-CN | O | O |
| Ca | H | CF$_3$ | 2,3,4,6-Cl$_4$-4-CF$_3$ | O | O |
| H | H | CF$_3$ | 2,5-Cl$_2$-4-CF$_3$ | S | O |
| H | H | CF$_3$ | 2,4,6-Cl$_3$ | S | O |
| H | H | CF$_3$ | 2,6-Cl$_2$-4-CF$_3$ | S | O |
| H | H | CF$_3$ | 2,6-Cl$_2$-4-CHF$_2$ | S | O |
| H | H | CF$_3$ | 2,6-Cl$_2$-4-CN | S | O |
| H | H | CF$_3$ | 2,6-Cl$_2$-4-NO$_2$ | S | O |
| H | H | CF$_3$ | 2-Br-4-CF$_3$-6-Cl | S | O |
| H | H | CF$_3$ | 2-Cl-4-CF$_3$-6-NO$_2$ | S | O |
| H | H | CF$_3$ | 2-Cl-4-NO$_2$-6-CF$_3$ | S | O |
| H | H | CF$_3$ | 2,4-(NO$_2$)$_2$-6-CF$_3$ | S | O |
| H | H | CF$_3$ | 2,6-(NO$_2$)$_2$-4-CF$_3$ | S | O |
| H | H | CF$_3$ | 2,3,4,6-Cl$_4$ | S | O |
| H | H | CF$_3$ | 2,3,6-Cl$_3$-4-CF$_3$ | S | O |
| H | H | CF$_3$ | 2,3,4,5,6-F$_5$ | S | O |
| H | H | CF$_3$ | 2,3,4,6-F$_4$-4-CN | S | O |
| H | H | CF$_3$ | 2,3,4,6-Cl$_4$-4-CF$_3$ | S | O |
| CH$_2$C≡CH | H | CF$_3$ | 2,5-Cl$_2$-4-CF$_3$ | O | O |
| CH$_2$C≡CH | H | CF$_3$ | 2,4,6-Cl$_3$ | O | O |
| CH$_2$C≡CH | H | CF$_3$ | 2,6-Cl$_2$-4-CF$_3$ | O | O |
| CH$_2$C≡CH | H | CF$_3$ | 2,6-Cl$_2$-4-CHF$_2$ | O | O |
| CH$_2$C≡CH | H | CF$_3$ | 2,6-Cl$_2$-4-CN | O | O |
| CH$_2$C≡CH | H | CF$_3$ | 2,6-Cl$_2$-4-NO$_2$ | O | O |
| CH$_2$C≡CH | H | CF$_3$ | 2-Br-4-CF$_3$-6-Cl | O | O |
| CH$_2$C≡CH | H | CF$_3$ | 2-Cl-4-CF$_3$-6-NO$_2$ | O | O |
| CH$_2$C≡CH | H | CF$_3$ | 2-Cl-4-NO$_2$-6-CF$_3$ | O | O |
| CH$_2$C≡CH | H | CF$_3$ | 2,4-(NO$_2$)$_2$-6-CF$_3$ | O | O |
| CH$_2$C≡CH | H | CF$_3$ | 2,6-(NO$_2$)$_2$-4-CF$_3$ | O | O |
| CH$_2$C≡CH | H | CF$_3$ | 2,3,4,6-Cl$_4$ | O | O |
| CH$_2$C≡CH | H | CF$_3$ | 2,3,6-Cl$_3$-4-CF$_3$ | O | O |
| CH$_2$C≡CH | H | CF$_3$ | 2,3,4,5,6-F$_5$ | O | O |
| CH$_2$C≡CH | H | CF$_3$ | 2,3,4,6-F$_4$-4-CN | O | O |
| CH$_2$C≡CH | H | CF$_3$ | 2,3,4,6-Cl$_4$-4-CF$_3$ | O | O |
| CH$_3$ | H | CF$_2$CF$_3$ | 2,5-Cl$_2$-4-CF$_3$ | O | O |
| CH$_3$ | H | CF$_2$CF$_3$ | 2,4,6-Cl$_3$ | O | O |
| CH$_3$ | H | CF$_2$CF$_3$ | 2,6-Cl$_2$-4-CF$_3$ | O | O |
| CH$_3$ | H | CF$_2$CF$_3$ | 2,6-Cl$_2$-4-NO$_2$ | O | O |
| CH$_3$ | H | CF$_2$CF$_3$ | 2-Br-4-CF$_3$-6-Cl | O | O |
| CH$_3$ | H | CF$_2$CF$_3$ | 2-Cl-4-CF$_3$-6-NO$_2$ | O | O |
| CH$_3$ | H | CF$_2$CF$_3$ | 2,4-(NO$_2$)$_2$-6-CF$_3$ | O | O |
| CH$_3$ | H | CF$_2$CF$_3$ | 2,6-(NO$_2$)$_2$-4-CF$_3$ | O | O |
| CH$_3$ | H | CF$_2$CF$_3$ | 2,3,6-Cl$_3$-4-CF$_3$ | O | O |
| CH$_3$ | H | CF$_2$CF$_3$ | 2,3,4,5,6-F$_5$ | O | O |
| CH$_3$ | H | CF$_2$CF$_3$ | 2,3,4,6-F$_4$-4-CN | O | O |
| CH$_2$OCH$_2$CH$_3$ | H | CF$_2$CF$_3$ | 2,5-Cl$_2$-4-CF$_3$ | O | O |
| CH$_2$OCH$_2$CH$_3$ | H | CF$_2$CF$_3$ | 2,4,6-Cl$_3$ | O | O |
| CH$_2$OCH$_2$CH$_3$ | H | CF$_2$CF$_3$ | 2,6-Cl$_2$-4-CF$_3$ | O | O |

| | | | | | |
|---|---|---|---|---|---|
| CH₂OCH₂CH₃ | H | CF₂CF₃ | 2,6-Cl₂-4-NO₂ | O | O |
| CH₂OCH₂CH₃ | H | CF₂CF₃ | 2-Br-4-CF₃-6-Cl | O | O |
| CH₂OCH₂CH₃ | H | CF₂CF₃ | 2-Cl-4-CF₃-6-NO₂ | O | O |
| CH₂OCH₂CH₃ | H | CF₂CF₃ | 2,4-(NO₂)₂-6-CF₃ | O | O |
| CH₂OCH₂CH₃ | H | CF₂CF₃ | 2,6-(NO₂)₂-4-CF₃ | O | O |
| CH₂OCH₂CH₃ | H | CF₂CF₃ | 2,3,6-Cl₃-4-CF₃ | O | O |
| CH₂OCH₂CH₃ | H | CF₂CF₃ | 2,3,4,5,6-F₅ | O | O |
| CH₂OCH₂CH₃ | H | CF₂CF₃ | 2,3,4,6-F₄-4-CN | O | O |
| COCH₃ | H | CF₂CF₃ | 2,5-Cl₂-4-CF₃ | O | O |
| COCH₃ | H | CF₂CF₃ | 2,4,6-Cl₃ | O | O |
| COCH₃ | H | CF₂CF₃ | 2,6-Cl₂-4-CF₃ | O | O |
| COCH₃ | H | CF₂CF₃ | 2,6-Cl₂-4-NO₂ | O | O |
| COCH₃ | H | CF₂CF₃ | 2-Br-4-CF₃-6-Cl | O | O |
| COCH₃ | H | CF₂CF₃ | 2-Cl-4-CF₃-6-NO₂ | O | O |
| COCH₃ | H | CF₂CF₃ | 2,4-(NO₂)₂-6-CF₃ | O | O |
| COCH₃ | H | CF₂CF₃ | 2,6-(NO₂)₂-4-CF₃ | O | O |
| COCH₃ | H | CF₂CF₃ | 2,3,6-Cl₃-4-CF₃ | O | O |
| COCH₃ | H | CF₂CF₃ | 2,3,4,5,6-F₅ | O | O |
| COCH₃ | H | CF₂CF₃ | 2,3,4,6-F₄-4-CN | O | O |
| H | Br | CF₂CF₃ | 2,5-Cl₂-4-CF₃ | O | O |
| H | Br | CF₂CF₃ | 2,4,6-Cl₃ | O | O |
| H | Br | CF₂CF₃ | 2,6-Cl₂-4-CF₃ | O | O |
| H | Br | CF₂CF₃ | 2,6-Cl₂-4-NO₂ | O | O |
| H | Br | CF₂CF₃ | 2-Br-4-CF₃-6-Cl | O | O |
| H | Br | CF₂CF₃ | 2-Cl-4-CF₃-6-NO₂ | O | O |
| H | Br | CF₂CF₃ | 2,4-(NO₂)₂-6-CF₃ | O | O |
| H | Br | CF₂CF₃ | 2,6-(NO₂)₂-4-CF₃ | O | O |
| H | Br | CF₂CF₃ | 2,3,6-Cl₃-4-CF₃ | O | O |
| H | Br | CF₂CF₃ | 2,3,4,5,6-F₅ | O | O |
| H | Br | CF₂CF₃ | 2,3,4,6-F₄-4-CN | O | O |
| H | CN | CF₂CF₃ | 2,5-Cl₂-4-CF₃ | O | O |
| H | CN | CF₂CF₃ | 2,4,6-Cl₃ | O | O |
| H | CN | CF₂CF₃ | 2,6-Cl₂-4-CF₃ | O | O |
| H | CN | CF₂CF₃ | 2,6-Cl₂-4-NO₂ | O | O |
| H | CN | CF₂CF₃ | 2-Br-4-CF₃-6-Cl | O | O |
| H | CN | CF₂CF₃ | 2-Cl-4-CF₃-6-NO₂ | O | O |
| H | CN | CF₂CF₃ | 2,4-(NO₂)₂-6-CF₃ | O | O |
| H | CN | CF₂CF₃ | 2,6-(NO₂)₂-4-CF₃ | O | O |
| H | CN | CF₂CF₃ | 2,3,6-Cl₃-4-CF₃ | O | O |
| H | CN | CF₂CF₃ | 2,3,4,5,6-F₅ | O | O |
| H | CN | CF₂CF₃ | 2,3,4,6-F₄-4-CN | O | O |
| CH₂OCH₃ | H | CF₂CF₂CF₃ | 2,5-Cl₂-4-CF₃ | O | O |
| CH₂OCH₃ | H | CF₂CF₂CF₃ | 2,4,6-Cl₃ | O | O |
| CH₂OCH₃ | H | CF₂CF₂CF₃ | 2,6-Cl₂-4-CF₃ | O | O |
| CH₂OCH₃ | H | CF₂CF₂CF₃ | 2,6-Cl₂-4-NO₂ | O | O |
| CH₂OCH₃ | H | CF₂CF₂CF₃ | 2-Br-4-CF₃-6-Cl | O | O |
| CH₂OCH₃ | H | CF₂CF₂CF₃ | 2-Cl-4-CF₃-6-NO₂ | O | O |
| CH₂OCH₃ | H | CF₂CF₂CF₃ | 2,4-(NO₂)₂-6-CF₃ | O | O |
| CH₂OCH₃ | H | CF₂CF₂CF₃ | 2,6-(NO₂)₂-4-CF₃ | O | O |
| CH₂OCH₃ | H | CF₂CF₂CF₃ | 2,3,6-Cl₃-4-CF₃ | O | O |
| CH₂OCH₃ | H | CF₂CF₂CF₃ | 2,3,4,5,6-F₅ | O | O |
| CH₂OCH₃ | H | CF₂CF₂CF₃ | 2,3,4,6-F₄-4-CN | O | O |
| H | Cl | CF₂CF₂CF₃ | 2,5-Cl₂-4-CF₃ | O | O |
| H | Cl | CF₂CF₂CF₃ | 2,4,6-Cl₃ | O | O |
| H | Cl | CF₂CF₂CF₃ | 2,6-Cl₂-4-CF₃ | O | O |
| H | Cl | CF₂CF₂CF₃ | 2,6-Cl₂-4-NO₂ | O | O |
| H | Cl | CF₂CF₂CF₃ | 2-Br-4-CF₃-6-Cl | O | O |
| H | Cl | CF₂CF₂CF₃ | 2-Cl-4-CF₃-6-NO₂ | O | O |
| H | Cl | CF₂CF₂CF₃ | 2,4-(NO₂)₂-6-CF₃ | O | O |
| H | Cl | CF₂CF₂CF₃ | 2,6-(NO₂)₂-4-CF₃ | O | O |
| H | Cl | CF₂CF₂CF₃ | 2,3,6-Cl₃-4-CF₃ | O | O |
| H | Cl | CF₂CF₂CF₃ | 2,3,4,5,6-F₅ | O | O |
| H | Cl | CF₂CF₂CF₃ | 2,3,4,6-F₄-4-CN | O | O |
| H | NO₂ | CF₂CF₂CF₃ | 2,5-Cl₂-4-CF₃ | O | O |
| H | NO₂ | CF₂CF₂CF₃ | 2,4,6-Cl₃ | O | O |
| H | NO₂ | CF₂CF₂CF₃ | 2,6-Cl₂-4-CF₃ | O | O |
| H | NO₂ | CF₂CF₂CF₃ | 2,6-Cl₂-4-NO₂ | O | O |
| H | NO₂ | CF₂CF₂CF₃ | 2-Br-4-CF₃-6-Cl | O | O |
| H | NO₂ | CF₂CF₂CF₃ | 2-Cl-4-CF₃-6-NO₂ | O | O |
| H | NO₂ | CF₂CF₂CF₃ | 2,4-(NO₂)₂-6-CF₃ | O | O |
| H | NO₂ | CF₂CF₂CF₃ | 2,6-(NO₂)₂-4-CF₃ | O | O |
| H | NO₂ | CF₂CF₂CF₃ | 2,3,6-Cl₃-4-CF₃ | O | O |
| H | NO₂ | CF₂CF₂CF₃ | 2,3,4,5,6-F₅ | O | O |
| H | NO₂ | CF₂CF₂CF₃ | 2,3,4,6-F₄-4-CN | O | O |
| CH₂CH₃ | CH₃ | CF₃ | 2,5-Cl₂-4-CF₃ | O | O |
| CH₂CH₃ | CH₃ | CF₃ | 2,4,6-Cl₃ | O | O |
| CH₂CH₃ | CH₃ | CF₃ | 2,6-Cl₂-4-CF₃ | O | O |
| CH₂CH₃ | CH₃ | CF₃ | 2,6-Cl₂-4-NO₂ | O | O |
| CH₂CH₃ | CH₃ | CF₃ | 2-Br-4-CF₃-6-Cl | O | O |
| CH₂CH₃ | CH₃ | CF₃ | 2-Cl-4-CF₃-6-NO₂ | O | O |

| | | | -continued | | |
|---|---|---|---|---|---|
| CH$_2$CH$_3$ | CH$_3$ | CF$_3$ | 2,4-(NO$_2$)$_2$-6-CF$_3$ | O | O |
| CH$_2$CH$_3$ | CH$_3$ | CF$_3$ | 2,6-(NO$_2$)$_2$-4-CF$_3$ | O | O |
| CH$_2$CH$_3$ | CH$_3$ | CF$_3$ | 2,3,6-Cl$_3$-4-CF$_3$ | O | O |
| CH$_2$CH$_3$ | CH$_3$ | CF$_3$ | 2,3,4,5,6-F$_5$ | O | O |
| CH$_2$CH$_3$ | CH$_3$ | CF$_3$ | 2,3,4,6-F$_4$-4-CN | O | O |
| CH$_2$OCH$_3$ | Cl | CF$_3$ | 2,5-Cl$_2$-4-CF$_3$ | O | O |
| CH$_2$OCH$_3$ | Cl | CF$_3$ | 2,4,6-Cl$_3$ | O | O |
| CH$_2$OCH$_3$ | Cl | CF$_3$ | 2,6-Cl$_2$-4-CF$_3$ | O | O |
| CH$_2$OCH$_3$ | Cl | CF$_3$ | 2,6-Cl$_2$-4-NO$_2$ | O | O |
| CH$_2$OCH$_3$ | Cl | CF$_3$ | 2-Br-4-CF$_3$-6-Cl | O | O |
| CH$_2$OCH$_3$ | Cl | CF$_3$ | 2-Cl-4-CF$_3$-6-NO$_2$ | O | O |
| CH$_2$OCH$_3$ | Cl | CF$_3$ | 2,4-(NO$_2$)$_2$-6-CF$_3$ | O | O |
| CH$_2$OCH$_3$ | Cl | CF$_3$ | 2,6-(NO$_2$)$_2$-4-CF$_3$ | O | O |
| CH$_2$OCH$_3$ | Cl | CF$_3$ | 2,3,6-Cl$_3$-4-CF$_3$ | O | O |
| CH$_2$OCH$_3$ | Cl | CF$_3$ | 2,3,4,5,6-F$_5$ | O | O |
| CH$_2$OCH$_3$ | Cl | CF$_3$ | 2,3,4,6-F$_4$-4-CN | O | O |
| CO$_2$CH$_3$ | Br | CF$_3$ | 2,5-Cl$_2$-4-CF$_3$ | O | O |
| CO$_2$CH$_3$ | Br | CF$_3$ | 2,4,6-Cl$_3$ | O | O |
| CO$_2$CH$_3$ | Br | CF$_3$ | 2,6-Cl$_2$-4-CF$_3$ | O | O |
| CO$_2$CH$_3$ | Br | CF$_3$ | 2,6-Cl$_2$-4-NO$_2$ | O | O |
| CO$_2$CH$_3$ | Br | CF$_3$ | 2-Br-4-CF$_3$-6-Cl | O | O |
| CO$_2$CH$_3$ | Br | CF$_3$ | 2-Cl-4-CF$_3$-6-NO$_2$ | O | O |
| CO$_2$CH$_3$ | Br | CF$_3$ | 2,4-(NO$_2$)$_2$-6-CF$_3$ | O | O |
| CO$_2$CH$_3$ | Br | CF$_3$ | 2,6-(NO$_2$)$_2$-4-CF$_3$ | O | O |
| CO$_2$CH$_3$ | Br | CF$_3$ | 2,3,6-Cl$_3$-4-CF$_3$ | O | O |
| CO$_2$CH$_3$ | Br | CF$_3$ | 2,3,4,5,6-F$_5$ | O | O |
| CO$_2$CH$_3$ | Br | CF$_3$ | 2,3,4,6-F$_4$-4-CN | O | O |
| COCH$_3$ | NO$_2$ | CF$_3$ | 2,5-Cl$_2$-4-CF$_3$ | O | O |
| COCH$_3$ | NO$_2$ | CF$_3$ | 2,4,6-Cl$_3$ | O | O |
| COCH$_3$ | NO$_2$ | CF$_3$ | 2,6-Cl$_2$-4-CF$_3$ | O | O |
| COCH$_3$ | NO$_2$ | CF$_3$ | 2,6-Cl$_2$-4-NO$_2$ | O | O |
| COCH$_3$ | NO$_2$ | CF$_3$ | 2-Br-4-CF$_3$-6-Cl | O | O |
| COCH$_3$ | NO$_2$ | CF$_3$ | 2-Cl-4-CF$_3$-6-NO$_2$ | O | O |
| COCH$_3$ | NO$_2$ | CF$_3$ | 2,4-(NO$_2$)$_2$-6-CF$_3$ | O | O |
| COCH$_3$ | NO$_2$ | CF$_3$ | 2,6-(NO$_2$)$_2$-4-CF$_3$ | O | O |
| COCH$_3$ | NO$_2$ | CF$_3$ | 2,3,6-Cl$_3$-4-CF$_3$ | O | O |
| COCH$_3$ | NO$_2$ | CF$_3$ | 2,3,4,5,6-F$_5$ | O | O |
| COCH$_3$ | NO$_2$ | CF$_3$ | 2,3,4,6-F$_4$-4-CN | O | O |
| COCH$_3$ | CN | CF$_3$ | 2,5-Cl$_2$-4-CF$_3$ | O | O |
| CH$_2$OCH$_2$CH$_3$ | CN | CF$_3$ | 2,4,6-Cl$_3$ | O | O |
| CH$_2$OCH$_2$CH$_3$ | CN | CF$_3$ | 2,6-Cl$_2$-4-CF$_3$ | O | O |
| CH$_2$OCH$_2$CH$_3$ | CN | CF$_3$ | 2,6-Cl$_2$-4-NO$_2$ | O | O |
| CH$_2$OCH$_2$CH$_3$ | CN | CF$_3$ | 2-Br-4-CF$_3$-6-Cl | O | O |
| CH$_2$OCH$_2$CH$_3$ | CN | CF$_3$ | 2-Cl-4-CF$_3$-6-NO$_2$ | O | O |
| CH$_2$OCH$_2$CH$_3$ | CN | CF$_3$ | 2,4-(NO$_2$)$_2$-6-CF$_3$ | O | O |
| CH$_2$OCH$_2$CH$_3$ | CN | CF$_3$ | 2,6-(NO$_2$)$_2$-4-CF$_3$ | O | O |
| CH$_2$OCH$_2$CH$_3$ | CN | CF$_3$ | 2,3,6-Cl$_3$-4-CF$_3$ | O | O |
| CH$_2$OCH$_2$CH$_3$ | CN | CF$_3$ | 2,3,4,5,6-F$_5$ | O | O |
| CH$_2$OCH$_2$CH$_3$ | CN | CF$_3$ | 2,3,4,6-F$_4$-4-CN | O | O |
| CHF$_2$ | H | CF$_2$CF$_3$ | 2,5-Cl$_2$-4-CF$_3$ | O | O |
| CHF$_2$ | H | CF$_2$CF$_3$ | 2,4,6-Cl$_3$ | O | O |
| CHF$_2$ | H | CF$_2$CF$_3$ | 2,6-Cl$_2$-4-CF$_3$ | O | O |
| CHF$_2$ | H | CF$_2$CF$_3$ | 2,6-Cl$_2$-4-NO$_2$ | O | O |
| CHF$_2$ | H | CF$_2$CF$_3$ | 2-Br-4-CF$_3$-6-Cl | O | O |
| CHF$_2$ | H | CF$_2$CF$_3$ | 2-Cl-4-CF$_3$-6-NO$_2$ | O | O |
| CHF$_2$ | H | CF$_2$CF$_3$ | 2,4-(NO$_2$)$_2$-6-CF$_3$ | O | O |
| CHF$_2$ | H | CF$_2$CF$_3$ | 2,6-(NO$_2$)$_2$-4-CF$_3$ | O | O |
| CHF$_2$ | H | CF$_2$CF$_3$ | 2,3,6-Cl$_3$-4-CF$_3$ | O | O |
| CHF$_2$ | H | CF$_2$CF$_3$ | 2,3,4,5,6-F$_5$ | O | O |
| CHF$_2$ | H | CF$_2$CF$_3$ | 2,3,4,6-F$_4$-4-CN | O | O |
| CH$_3$ | Cl | CF$_2$CF$_3$ | 2,5-Cl$_2$-4-CF$_3$ | O | O |
| CH$_3$ | Cl | CF$_2$CF$_3$ | 2,4,6-Cl$_3$ | O | O |
| CH$_3$ | Cl | CF$_2$CF$_3$ | 2,6-Cl$_2$-4-CF$_3$ | O | O |
| CH$_3$ | Cl | CF$_2$CF$_3$ | 2,6-Cl$_2$-4-NO$_2$ | O | O |
| CH$_3$ | Cl | CF$_2$CF$_3$ | 2-Br-4-CF$_3$-6-Cl | O | O |
| CH$_3$ | Cl | CF$_2$CF$_3$ | 2-Cl-4-CF$_3$-6-NO$_2$ | O | O |
| CH$_3$ | Cl | CF$_2$CF$_3$ | 2,4-(NO$_2$)$_2$-6-CF$_3$ | O | O |
| CH$_3$ | Cl | CF$_2$CF$_3$ | 2,6-(NO$_2$)$_2$-4-CF$_3$ | O | O |
| CH$_3$ | Cl | CF$_2$CF$_3$ | 2,3,6-Cl$_3$-4-CF$_3$ | O | O |
| CH$_3$ | Cl | CF$_2$CF$_3$ | 2,3,4,5,6-F$_5$ | O | O |
| CH$_3$ | Cl | CF$_2$CF$_3$ | 2,3,4,6-F$_4$-4-CN | O | O |
| H | CN | CF$_2$CF$_3$ | 2,5-Cl$_2$-4-CF$_3$ | S | O |
| H | CN | CF$_2$CF$_3$ | 2,4,6-Cl$_3$ | S | O |
| H | CN | CF$_2$CF$_3$ | 2,6-Cl$_2$-4-CF$_3$ | S | O |
| H | CN | CF$_2$CF$_3$ | 2,6-Cl$_2$-4-NO$_2$ | S | O |
| H | CN | CF$_2$CF$_3$ | 2-Br-4-CF$_3$-6-Cl | S | O |
| H | CN | CF$_2$CF$_3$ | 2-Cl-4-CF$_3$-6-NO$_2$ | S | O |
| H | CN | CF$_2$CF$_3$ | 2,4-(NO$_2$)$_2$-6-CF$_3$ | S | O |
| H | CN | CF$_2$CF$_3$ | 2,6-(NO$_2$)$_2$-4-CF$_3$ | S | O |
| H | CN | CF$_2$CF$_3$ | 2,3,6-Cl$_3$-4-CF$_3$ | S | O |
| H | CN | CF$_2$CF$_3$ | 2,3,4,5,6-F$_5$ | S | O |
| H | CN | CF$_2$CF$_3$ | 2,3,4,6-F$_4$-4-CN | S | O |
| H | CN | CF$_3$ | 2,5-Cl$_2$-4-CF$_3$ | S | O |

-continued

| | | | | | |
|---|---|---|---|---|---|
| H | CN | CF₃ | 2,4,6-Cl₃ | S | O |
| H | CN | CF₃ | 2,6-Cl₂-4-CF₃ | S | O |
| H | CN | CF₃ | 2,6-Cl₂-4-NO₂ | S | O |
| H | CN | CF₃ | 2-Br-4-CF₃-6-Cl | S | O |
| H | CN | CF₃ | 2-Cl-4-CF₃-6-NO₂ | S | O |
| H | CN | CF₃ | 2,4-(NO₂)₂-6-CF₃ | S | O |
| H | CN | CF₃ | 2,6-(NO₂)₂-4-CF₃ | S | O |
| H | CN | CF₃ | 2,3,6-Cl₃-4-CF₃ | S | O |
| H | CN | CF₃ | 2,3,4,5,6-F₅ | S | O |
| H | CN | CF₃ | 2,3,4,6-F₄-4-CN | S | O |
| H | H | CF₃ | 2,3-F₂-4-Cl | O | O |
| H | H | CF₃ | 2,3-F₂-4-Br | O | O |
| H | H | CF₃ | 2,3-F₂-4-CF₃ | O | O |
| H | H | CF₃ | 2,4-F₂-3-Cl | O | O |
| H | H | CF₃ | 2-F-3,4-Cl₂ | O | O |
| H | H | CF₃ | 2,4-F₂-3-Br | O | O |
| H | H | CF₃ | 2,4-F₂-3-CN | O | O |
| H | H | CF₃ | 2,3,5-F₃ | O | O |
| H | H | CF₃ | 2,3,6-F₃ | O | O |
| H | H | CF₃ | 2,4-F₂-6-Br | O | O |
| H | H | CF₃ | 2,4-F₂-6-NO₂ | O | O |
| H | H | CF₃ | 2,6-F₂-4-Br | O | O |
| H | H | CF₃ | 2,6-F₂-4-Cl | O | O |
| H | H | CF₃ | 2,3,4-F₃-6-Br | O | O |
| H | H | CF₃ | 2,3,4-F₃-6-NO₂ | O | O |
| H | H | CF₃ | 2,3,5-F₃-4-Cl | O | O |
| H | H | CF₃ | 2,3,5,6-F₄ | O | O |
| H | H | CF₃ | 2,3,5-F₃-4,6-Cl₂ | O | O |
| H | H | CF₃ | 2,3,5,6-F₄-4-Br | O | O |
| H | H | CF₃ | 2,3,5,6-F₄-4-CH₃ | O | O |
| H | H | CF₃ | 2-Cl-3,4-F₂ | O | O |
| H | H | CF₃ | 2-Cl-3,6-(OCH₃)₂ | O | O |
| H | H | CF₃ | 2,4-Cl₂-6-Br | O | O |
| H | H | CF₃ | 2,4-Cl₂-6-CH₃ | O | O |
| H | H | CF₃ | 2,4-Cl₂-6-NO₂ | O | O |
| H | H | CF₃ | 2-Cl-4-Br-6-CH₃ | O | O |
| H | H | CF₃ | 2-Br-4-NO₂-6-Cl | O | O |
| H | H | CF₃ | 2-Cl-4-CN-6-F | O | O |
| H | H | CF₃ | 2,3-Cl₂-4,6-Br₂ | O | O |
| H | H | CF₃ | 2,4,6-Cl₃-3-NO₂ | O | O |
| H | H | CF₃ | 2,3,4,5-Cl₄-6-CO₂CH₃ | O | O |
| H | H | CF₃ | 2-Br-3,4-F₂ | O | O |
| H | H | CF₃ | 2,4,6-Br₃ | O | O |
| H | H | CF₃ | 2,6-Br₂-4-F | O | O |
| H | H | CF₃ | 2,6-Br₂-4-CH₂CH₂CH₃ | O | O |
| H | H | CF₃ | 2,4-Br₂-6-CO₂CH₃ | O | O |
| H | H | CF₃ | 2,4-(NO₂)₂-6-Br | O | O |
| H | H | CF₃ | 2-Br-4-NO₂-6-CN | O | O |
| H | H | CF₃ | 2-Br-4-CO₂CH₂CH₃-6-NO₂ | O | O |
| H | H | CF₃ | 2-Br-3,4,6-F₃ | O | O |
| H | H | CF₃ | 2,6-Br₂-3-Cl-4-F | O | O |
| H | H | CF₃ | 2,4-Br₂-3,6-Cl₂ | O | O |
| H | H | CF₃ | 2,4,6-Br₃-3-CH₃ | O | O |
| H | H | CF₃ | 2,6-Br₂-3,5-(CF₃)₂ | O | O |
| H | H | CF₃ | 2,6-I₂-4-NO₂ | O | O |
| H | H | CF₃ | 2,6-I₂-4-CO₂CH₂CH₃ | O | O |
| H | H | CF₃ | 2,3,4-(OCH₃)₃ | O | O |
| H | H | CF₃ | 2-OCH₃-3,5-Cl₂ | O | O |
| H | H | CF₃ | 2-OCH₂CH₃-4-F-6-NO₂ | O | O |
| H | H | CF₃ | 3,4,5-(OCH₃)₃ | O | O |
| H | H | CF₂CF₃ | 2,3-F₂-4-Cl | O | O |
| H | H | CF₂CF₃ | 2,3-F₂-4-Br | O | O |
| H | H | CF₂CF₃ | 2,3-F₂-4-CF₃ | O | O |
| H | H | CF₂CF₃ | 2,4-F₂-3-Cl | O | O |
| H | H | CF₂CF₃ | 2-F-3,4-Cl₂ | O | O |
| H | H | CF₂CF₃ | 2,4-F₂-3-Br | O | O |
| H | H | CF₂CF₃ | 2,4-F₂-3-CN | O | O |
| H | H | CF₂CF₃ | 2,3,5-F₃ | O | O |
| H | H | CF₂CF₃ | 2,3,6-F₃ | O | O |
| H | H | CF₂CF₃ | 2,4-F₂-6-Br | O | O |
| H | H | CF₂CF₃ | 2,4-F₂-6-NO₂ | O | O |
| H | H | CF₂CF₃ | 2,6-F₂-4-Br | O | O |
| H | H | CF₂CF₃ | 2,6-F₂-4-Cl | O | O |
| H | H | CF₂CF₃ | 2,3,4-F₃-6-Br | O | O |
| H | H | CF₂CF₃ | 2,3,4-F₃-6-NO₂ | O | O |
| H | H | CF₂CF₃ | 2,3,5-F₃-4-Cl | O | O |
| H | H | CF₂CF₃ | 2,3,5,6-F₄ | O | O |
| H | H | CF₂CF₃ | 2,3,5-F₃-4,6-Cl₂ | O | O |
| H | H | CF₂CF₃ | 2,3,5,6-F₄-4-Br | O | O |
| H | H | CF₂CF₃ | 2,3,5,6-F₄-4-CH₃ | O | O |
| H | H | CF₂CF₃ | 2-Cl-3,4-F₂ | O | O |
| H | H | CF₂CF₃ | 2-Cl-3,6-(OCH₃)₂ | O | O |
| H | H | CF₂CF₃ | 2,4-Cl₂-6-Br | O | O |

-continued

| | | | | | |
|---|---|---|---|---|---|
| H | H | CF$_2$CF$_3$ | 2,4-Cl$_2$-6-CH$_3$ | O | O |
| H | H | CF$_2$CF$_3$ | 2,4-Cl$_2$-6-NO$_2$ | O | O |
| H | H | CF$_2$CF$_3$ | 2-Cl-4-Br-6-CH$_3$ | O | O |
| H | H | CF$_2$CF$_3$ | 2-Br-4-NO$_2$-6-Cl | O | O |
| H | H | CF$_2$CF$_3$ | 2-Cl-4-CN-6-F | O | O |
| H | H | CF$_2$CF$_3$ | 2,3-Cl$_2$-4,6-Br$_2$ | O | O |
| H | H | CF$_2$CF$_3$ | 2,4,6-Cl$_3$-3-NO$_2$ | O | O |
| H | H | CF$_2$CF$_3$ | 2,3,4,5-Cl$_4$-6-CO$_2$CH$_3$ | O | O |
| H | H | CF$_2$CF$_3$ | 2-Br-3,4-F$_2$ | O | O |
| H | H | CF$_2$CF$_3$ | 2,4,6-Br$_3$ | O | O |
| H | H | CF$_2$CF$_3$ | 2,6-Br$_2$-4-F | O | O |
| H | H | CF$_2$CF$_3$ | 2,6-Br$_2$-4-CH$_2$CH$_2$CH$_3$ | O | O |
| H | H | CF$_2$CF$_3$ | 2,4-Br$_2$-6-CO$_2$CH$_3$ | O | O |
| H | H | CF$_2$CF$_3$ | 2,4-(NO$_2$)$_2$-6-Br | O | O |
| H | H | CF$_2$CF$_3$ | 2-Br-4-NO$_2$-6-CN | O | O |
| H | H | CF$_2$CF$_3$ | 2-Br-4-CO$_2$CH$_2$CH$_3$-6-NO$_2$ | O | O |
| H | H | CF$_2$CF$_3$ | 2-Br-3,4,6-F$_3$ | O | O |
| H | H | CF$_2$CF$_3$ | 2,6-Br$_2$-3-Cl-4-F | O | O |
| H | H | CF$_2$CF$_3$ | 2,4-Br$_2$-3,6-Cl$_2$ | O | O |
| H | H | CF$_2$CF$_3$ | 2,4,6-Br$_3$-3-CH$_3$ | O | O |
| H | H | CF$_2$CF$_3$ | 2,6-Br$_2$-3,5-(CF$_3$)$_2$ | O | O |
| H | H | CF$_2$CF$_3$ | 2,6-I$_2$-4-NO$_2$ | O | O |
| H | H | CF$_2$CF$_3$ | 2,6-I$_2$-4-CO$_2$CH$_2$CH$_3$ | O | O |
| H | H | CF$_2$CF$_3$ | 2,3,4-(OCH$_3$)$_3$ | O | O |
| H | H | CF$_2$CF$_3$ | 2-OCH$_3$-3,5-Cl$_2$ | O | O |
| H | H | CF$_2$CF$_3$ | 2-OCH$_2$CH$_3$-4-F-6-NO$_2$ | O | O |
| H | H | CF$_2$CF$_3$ | 3,4,5-(OCH$_3$)$_3$ | O | O |
| H | Cl | CF$_3$ | 2,3-F$_2$-4-Cl | O | O |
| H | Cl | CF$_3$ | 2,3-F$_2$-4-Br | O | O |
| H | Cl | CF$_3$ | 2,3-F$_2$-4-CF$_3$ | O | O |
| H | Cl | CF$_3$ | 2,4-F$_2$-3-Cl | O | O |
| H | Cl | CF$_3$ | 2-F-3,4-Cl$_2$ | O | O |
| H | Cl | CF$_3$ | 2,4-F$_2$-3-Br | O | O |
| H | Cl | CF$_3$ | 2,4-F$_2$-3-CN | O | O |
| H | Cl | CF$_3$ | 2,3,5-F$_3$ | O | O |
| H | Cl | CF$_3$ | 2,3,6-F$_3$ | O | O |
| H | Cl | CF$_3$ | 2,4-F$_2$-6-Br | O | O |
| H | Cl | CF$_3$ | 2,4-F$_2$-6-NO$_2$ | O | O |
| H | Cl | CF$_3$ | 2,6-F$_2$-4-Br | O | O |
| H | Cl | CF$_3$ | 2,6-F$_2$-4-Cl | O | O |
| H | Cl | CF$_3$ | 2,3,4-F$_3$-6-Br | O | O |
| H | Cl | CF$_3$ | 2,3,4-F$_3$-6-NO$_2$ | O | O |
| H | Cl | CF$_3$ | 2,3,5-F$_3$-4-Cl | O | O |
| H | Cl | CF$_3$ | 2,3,5,6-F$_4$ | O | O |
| H | Cl | CF$_3$ | 2,3,5-F$_3$-4,6-Cl$_2$ | O | O |
| H | Cl | CF$_3$ | 2,3,5,6-F$_4$-4-Br | O | O |
| H | Cl | CF$_3$ | 2,3,5,6-F$_4$-4-CH$_3$ | O | O |
| H | Cl | CF$_3$ | 2-Cl-3,4-F$_2$ | O | O |
| H | Cl | CF$_3$ | 2-Cl-3,6-(OCH$_3$)$_2$ | O | O |
| H | Cl | CF$_3$ | 2,4-Cl$_2$-6-Br | O | O |
| H | Cl | CF$_3$ | 2,4-Cl$_2$-6-CH$_3$ | O | O |
| H | Cl | CF$_3$ | 2,4-Cl$_2$-6-NO$_2$ | O | O |
| H | Cl | CF$_3$ | 2-Cl-4-Br-6-CH$_3$ | O | O |
| H | Cl | CF$_3$ | 2-Br-4-NO$_2$-6-Cl | O | O |
| H | Cl | CF$_3$ | 2-Cl-4-CN-6-F | O | O |
| H | Cl | CF$_3$ | 2,3-Cl$_2$-4,6-Br$_2$ | O | O |
| H | Cl | CF$_3$ | 2,4,6-Cl$_3$-3-NO$_2$ | O | O |
| H | Cl | CF$_3$ | 2,3,4,5-Cl$_4$-6-CO$_2$CH$_3$ | O | O |
| H | Cl | CF$_3$ | 2-Br-3,4-F$_2$ | O | O |
| H | Cl | CF$_3$ | 2,4,6-Br$_3$ | O | O |
| H | Cl | CF$_3$ | 2,6-Br$_2$-4-F | O | O |
| H | Cl | CF$_3$ | 2,6-Br$_2$-4-CH$_2$CH$_2$CH$_3$ | O | O |
| H | Cl | CF$_3$ | 2,4-Br$_2$-6-CO$_2$CH$_3$ | O | O |
| H | Cl | CF$_3$ | 2,4-(NO$_2$)$_2$-6-Br | O | O |
| H | Cl | CF$_3$ | 2-Br-4-NO$_2$-6-CN | O | O |
| H | Cl | CF$_3$ | 2-Br-4-CO$_2$CH$_2$CH$_3$-6-NO$_2$ | O | O |
| H | Cl | CF$_3$ | 2-Br-3,4,6-F$_3$ | O | O |
| H | Cl | CF$_3$ | 2,6-Br$_2$-3-Cl-4-F | O | O |
| H | Cl | CF$_3$ | 2,4-Br$_2$-3,6-Cl$_2$ | O | O |
| H | Cl | CF$_3$ | 2,4,6-Br$_3$-3-CH$_3$ | O | O |
| H | Cl | CF$_3$ | 2,6-Br$_2$-3,5-(CF$_3$)$_2$ | O | O |
| H | Cl | CF$_3$ | 2,6-I$_2$-4-NO$_2$ | O | O |
| H | Cl | CF$_3$ | 2,6-I$_2$-4-CO$_2$CH$_2$CH$_3$ | O | O |
| H | Cl | CF$_3$ | 2,3,4-(OCH$_3$)$_3$ | O | O |
| H | Cl | CF$_3$ | 2-OCH$_3$-3,5-Cl$_2$ | O | O |
| H | Cl | CF$_3$ | 2-OCH$_2$CH$_3$-4-F-6-NO$_2$ | O | O |
| H | Cl | CF$_3$ | 3,4,5-(OCH$_3$)$_3$ | O | O |
| H | Br | CF$_3$ | 2,3-F$_2$-4-Cl | O | O |
| H | Br | CF$_3$ | 2,3-F$_2$-4-Br | O | O |
| H | Br | CF$_3$ | 2,3-F$_2$-4-CF$_3$ | O | O |
| H | Br | CF$_3$ | 2,4-F$_2$-3-Cl | O | O |
| H | Br | CF$_3$ | 2-F-3,4-Cl$_2$ | O | O |
| H | Br | CF$_3$ | 2,4-F$_2$-3-Br | O | O |

| | | | -continued | | |
|---|---|---|---|---|---|
| H | Br | CF$_3$ | 2,4-F$_2$-3-CN | O | O |
| H | Br | CF$_3$ | 2,3,5-F$_3$ | O | O |
| H | Br | CF$_3$ | 2,3,6-F$_3$ | O | O |
| H | Br | CF$_3$ | 2,4-F$_2$-6-Br | O | O |
| H | Br | CF$_3$ | 2,4-F$_2$-6-NO$_2$ | O | O |
| H | Br | CF$_3$ | 2,6-F$_2$-4-Br | O | O |
| H | Br | CF$_3$ | 2,6-F$_2$-4-Cl | O | O |
| H | Br | CF$_3$ | 2,3,4-F$_3$-6-Br | O | O |
| H | Br | CF$_3$ | 2,3,4-F$_3$-6-NO$_2$ | O | O |
| H | Br | CF$_3$ | 2,3,5-F$_3$-4-Cl | O | O |
| H | Br | CF$_3$ | 2,3,5,6-F$_4$ | O | O |
| H | Br | CF$_3$ | 2,3,5-F$_3$-4,6-Cl$_2$ | O | O |
| H | Br | CF$_3$ | 2,3,5,6-F$_4$-4-Br | O | O |
| H | Br | CF$_3$ | 2,3,5,6-F$_4$-4-CH$_3$ | O | O |
| H | Br | CF$_3$ | 2-Cl-3,4-F$_2$ | O | O |
| H | Br | CF$_3$ | 2-Cl-3,6-(OCH$_3$)$_2$ | O | O |
| H | Br | CF$_3$ | 2,4-Cl$_2$-6-Br | O | O |
| H | Br | CF$_3$ | 2,4-Cl$_2$-6-CH$_3$ | O | O |
| H | Br | CF$_3$ | 2,4-Cl$_2$-6-NO$_2$ | O | O |
| H | Br | CF$_3$ | 2-Cl-4-Br-6-CH$_3$ | O | O |
| H | Br | CF$_3$ | 2-Br-4-NO$_2$-6-Cl | O | O |
| H | Br | CF$_3$ | 2-Cl-4-CN-6-F | O | O |
| H | Br | CF$_3$ | 2,3-Cl$_2$-4,6-Br$_2$ | O | O |
| H | Br | CF$_3$ | 2,4,6-Cl$_3$-3-NO$_2$ | O | O |
| H | Br | CF$_3$ | 2,3,4,5-Cl$_4$-6-CO$_2$CH$_3$ | O | O |
| H | Br | CF$_3$ | 2-Br-3,4-F$_2$ | O | O |
| H | Br | CF$_3$ | 2,4,6-Br$_3$ | O | O |
| H | Br | CF$_3$ | 2,6-Br$_2$-4-F | O | O |
| H | Br | CF$_3$ | 2,6-Br$_2$-4-CH$_2$CH$_2$CH$_3$ | O | O |
| H | Br | CF$_3$ | 2,4-Br$_2$-6-CO$_2$CH$_3$ | O | O |
| H | Br | CF$_3$ | 2,4-(NO$_2$)$_2$-6-Br | O | O |
| H | Br | CF$_3$ | 2-Br-4-NO$_2$-6-CN | O | O |
| H | Br | CF$_3$ | 2-Br-4-CO$_2$CH$_2$CH$_3$-6-NO$_2$ | O | O |
| H | Br | CF$_3$ | 2-Br-3,4,6-F$_3$ | O | O |
| H | Br | CF$_3$ | 2,6-Br$_2$-3-Cl-4-F | O | O |
| H | Br | CF$_3$ | 2,4-Br$_2$-3,6-Cl$_2$ | O | O |
| H | Br | CF$_3$ | 2,4,6-Br$_3$-3-CH$_3$ | O | O |
| H | Br | CF$_3$ | 2,6-Br$_2$-3,5-(CF$_3$)$_2$ | O | O |
| H | Br | CF$_3$ | 2,6-I$_2$-4-NO$_2$ | O | O |
| H | Br | CF$_3$ | 2,6-I$_2$-4-CO$_2$CH$_2$CH$_3$ | O | O |
| H | Br | CF$_3$ | 2,3,4-(OCH$_3$)$_3$ | O | O |
| H | Br | CF$_3$ | 2-OCH$_3$-3,5-Cl$_2$ | O | O |
| H | Br | CF$_3$ | 2-OCH$_2$CH$_3$-4-F-6-NO$_2$ | O | O |
| H | Br | CF$_3$ | 3,4,5-(OCH$_3$)$_3$ | O | O |
| H | SH | CF$_3$ | 2,4,6-Cl$_3$ | O | O |
| H | SH | CF$_3$ | 2,6-Cl$_2$-4-CF$_3$ | O | O |
| H | SCH$_3$ | CF$_3$ | 2,4,6-Cl$_3$ | O | O |
| H | SCH$_3$ | CF$_3$ | 2,6-Cl$_2$-4-CF$_3$ | O | O |
| H | SCH$_3$ | CF$_3$ | 2,4,6-Cl$_3$ | S | O |
| H | SCH$_3$ | CF$_3$ | 2,6-Cl$_2$-4-CF$_3$ | S | O |
| H | SCH$_3$ | CF$_2$Cl | 2,4,6-Cl$_3$ | O | O |
| H | SCH$_3$ | CF$_2$Cl | 2,6-Cl$_2$-4-CF$_3$ | O | O |
| H | SCH$_3$ | CF$_2$CF$_3$ | 2,4,6-Cl$_3$ | O | O |
| H | SCH$_3$ | CF$_2$CF$_3$ | 2,6-Cl$_2$-4-CF$_3$ | O | O |
| H | SOCH$_3$ | CF$_3$ | 2,4,6-Cl$_3$ | O | O |
| H | SOCH$_3$ | CF$_3$ | 2,6-Cl$_2$-4-CF$_3$ | O | O |
| H | SO$_2$CH$_3$ | CF$_3$ | 2,4,6-Cl$_3$ | O | O |
| H | SO$_2$CH$_3$ | CF$_3$ | 2,6-Cl$_2$-4-CF$_3$ | O | O |
| H | SCF$_3$ | CF$_3$ | 2,4,6-Cl$_3$ | O | O |
| H | SCF$_3$ | CF$_3$ | 2,6-Cl$_2$-4-CF$_3$ | O | O |
| H | SCF$_3$ | CF$_3$ | 2,4,6-Cl$_3$ | S | O |
| H | SCF$_3$ | CF$_3$ | 2,6-Cl$_2$-4-CF$_3$ | S | O |
| H | SCF$_3$ | CF$_2$Cl | 2,4,6-Cl$_3$ | O | O |
| H | SCF$_3$ | CF$_2$Cl | 2,6-Cl$_2$-4-CF$_3$ | O | O |
| H | SCF$_3$ | CF$_2$CF$_3$ | 2,4,6-Cl$_3$ | O | O |
| H | SCF$_3$ | CF$_2$CF$_3$ | 2,6-Cl$_2$-4-CF$_3$ | O | O |
| H | SOCF$_3$ | CF$_3$ | 2,4,6-Cl$_3$ | O | O |
| H | SOCF$_3$ | CF$_3$ | 2,6-Cl$_2$-4-CF$_3$ | O | O |
| H | SO$_2$CF$_3$ | CF$_3$ | 2,4,6-Cl$_3$ | O | O |
| H | SO$_2$CF$_3$ | CF$_3$ | 2,6-Cl$_2$-4-CF$_3$ | O | O |
| H | SCF$_2$Br | CF$_3$ | 2,4,6-Cl$_3$ | O | O |
| H | SCF$_2$Br | CF$_3$ | 2,6-Cl$_2$-4-CF$_3$ | O | O |
| H | OH | CF$_3$ | 2,4,6-Cl$_3$ | O | O |
| H | OH | CF$_3$ | 2,6-Cl$_2$-4-CF$_3$ | O | O |
| H | OCH$_3$ | CF$_3$ | 2,4,6-Cl$_3$ | O | O |
| H | OCH$_3$ | CF$_3$ | 2,6-Cl$_2$-4-CF$_3$ | O | O |
| H | OCH$_3$ | CF$_2$Cl | 2,4,6-Cl$_3$ | O | O |
| H | OCH$_3$ | CF$_2$Cl | 2,6-Cl$_2$-4-CF$_3$ | O | O |
| H | OCH$_3$ | CF$_2$CF$_3$ | 2,4,6-Cl$_3$ | O | O |
| H | OCH$_3$ | CF$_2$CF$_3$ | 2,6-Cl$_2$-4-CF$_3$ | O | O |
| H | OCHF$_2$ | CF$_3$ | 2,4,6-Cl$_3$ | O | O |
| H | OCHF$_2$ | CF$_3$ | 2,6-Cl$_2$-4-CF$_3$ | O | O |
| H | OCF$_2$Br | CF$_3$ | 2,4,6-Cl$_3$ | O | O |

-continued

| | | | | | |
|---|---|---|---|---|---|
| H | OCF$_2$Br | CF$_3$ | 2,6-Cl$_2$-4-CF$_3$ | O | O |
| H | OCF$_3$ | CF$_3$ | 2,4,6-Cl$_3$ | O | O |
| H | OCF$_3$ | CF$_3$ | 2,6-Cl$_2$-4-CF$_3$ | O | O |
| H | OCF$_3$ | CF$_3$ | 2,4,6-Cl$_3$ | S | O |
| H | OCF$_3$ | CF$_3$ | 2,6-Cl$_2$-4-CF$_3$ | S | O |
| H | OCF$_3$ | CF$_2$Cl | 2,4,6-Cl$_3$ | O | O |
| H | OCF$_3$ | CF$_2$Cl | 2,6-Cl$_2$-4-CF$_3$ | O | O |
| H | OCF$_3$ | CF$_2$CF$_3$ | 2,4,6-Cl$_3$ | O | O |
| H | OCF$_3$ | CF$_2$CF$_3$ | 2,6-Cl$_2$-4-CF$_3$ | O | O |
| H | CHO | CF$_3$ | 2,4,6-Cl$_3$ | O | O |
| H | CHO | CF$_3$ | 2,6-Cl$_2$-4-CF$_3$ | O | O |
| H | H | CF$_3$ | 2,4,6-Cl$_3$ | NH | O |
| H | H | CF$_3$ | 2,6-Cl$_2$-4-CF$_3$ | NH | O |
| H | H | CF$_2$Cl | 2,4,6-Cl$_3$ | NH | O |
| H | H | CF$_2$Cl | 2,6-Cl$_2$-4-CF$_3$ | NH | O |
| H | H | CF$_2$CF$_3$ | 2,4,6-Cl$_3$ | NH | O |
| H | H | CF$_2$CF$_3$ | 2,6-Cl$_2$-4-CF$_3$ | NH | O |
| H | CN | CF$_3$ | 2,4,6-Cl$_3$ | NH | O |
| H | CN | CF$_3$ | 2,6-Cl$_2$-4-CF$_3$ | NH | O |
| H | CN | CF$_2$Cl | 2,4,6-Cl$_3$ | NH | O |
| H | CN | CF$_2$Cl | 2,6-Cl$_2$-4-CF$_3$ | NH | O |
| H | CN | CF$_2$CF$_3$ | 2,4,6-Cl$_3$ | NH | O |
| H | CN | CF$_2$CF$_3$ | 2,6-Cl$_2$-4-CF$_3$ | NH | O |
| H | H | Cl | 2,4,6-Cl$_3$ | O | O |
| H | H | Cl | 2,6-Cl$_2$-4-CF$_3$ | O | O |
| H | H | Br | 2,4,6-Cl$_3$ | O | O |
| H | H | Br | 2,6-Cl$_2$-4-CF$_3$ | O | O |
| H | H | I | 2,4,6-Cl$_3$ | O | O |
| H | H | I | 2,6-Cl$_2$-4-CF$_3$ | O | O |
| H | H | NO$_2$ | 2,4,6-Cl$_3$ | O | O |
| H | H | NO$_2$ | 2,6-Cl$_2$-4-CF$_3$ | O | O |
| H | H | SOCH$_3$ | 2,4,6-Cl$_3$ | O | O |
| H | H | SOCH$_3$ | 2,6-Cl$_2$-4-CF$_3$ | O | O |
| H | H | SCHF$_2$ | 2,4,6-Cl$_3$ | O | O |
| H | H | SCHF$_2$ | 2,6-Cl$_2$-4-CF$_3$ | O | O |
| H | H | SCF$_2$Br | 2,4,6-Cl$_3$ | O | O |
| H | H | SCF$_2$Br | 2,6-Cl$_2$-4-CF$_3$ | O | O |
| H | H | SCF$_2$CHF$_2$ | 2,4,6-Cl$_3$ | O | O |
| H | H | SCF$_2$CHF$_2$ | 2,6-Cl$_2$-4-CF$_3$ | O | O |
| H | H | SOCF$_3$ | 2,4,6-Cl$_3$ | O | O |
| H | H | SOCF$_3$ | 2,6-Cl$_2$-4-CF$_3$ | O | O |
| H | H | OCH$_3$ | 2,4,6-Cl$_3$ | O | O |
| H | H | OCH$_3$ | 2,6-Cl$_2$-4-CF$_3$ | O | O |
| H | H | OCHF$_2$ | 2,4,6-Cl$_3$ | O | O |
| H | H | OCHF$_2$ | 2,6-Cl$_2$-4-CF$_3$ | O | O |
| H | H | OCF$_2$Br | 2,4,6-Cl$_3$ | O | O |
| H | H | OCF$_2$Br | 2,6-Cl$_2$-4-CF$_3$ | O | O |
| H | H | OCF$_3$ | 2,4,6-Cl$_3$ | O | O |
| H | H | OCF$_3$ | 2,6-Cl$_2$-4-CF$_3$ | O | O |
| H | H | CO$_2$CH$_3$ | 2,4,6-Cl$_3$ | O | O |
| H | H | CO$_2$CH$_3$ | 2,6-Cl$_2$-4-CF$_3$ | O | O |
| H | H | CN | 2,5-Cl$_2$-4-CF$_3$ | O | O |
| H | H | CN | 2,4,6-Cl$_3$ | O | O |
| H | H | CN | 2,6-Cl$_2$-4-CF$_3$ | O | O |
| H | H | CN | 2,6-Cl$_2$-4-NO$_2$ | O | O |
| H | H | CN | 2,6-Cl$_2$-4-OCF$_3$ | O | O |
| H | H | CN | 2,6-Cl$_2$-4-Br | O | O |
| H | H | CN | 2,6-F$_2$-4-CF$_3$ | O | O |
| H | H | CN | 2,6-(CH$_3$)$_2$-4-Br | O | O |
| H | H | CN | 2-Br-4-CF$_3$-6-Cl | O | O |
| H | H | CN | 2-Cl-4-CF$_3$-6-NO$_2$ | O | O |
| H | H | CN | 2,4-(NO$_2$)$_2$-6-CF$_3$ | O | O |
| H | H | CN | 2,3,6,-Cl$_3$-4-CF$_3$ | O | O |
| H | H | CN | 2,3,4,5,6-F$_5$ | O | O |
| H | H | CN | 2,3,4,6-F$_4$-4-CN | O | O |
| H | H | CN | 2,4,6-Cl$_3$ | S | O |
| H | H | CN | 2,6-Cl$_2$-4-CF$_3$ | S | O |
| H | H | CN | 2,6-Cl$_2$-4-NO$_2$ | S | O |
| H | H | CN | 2,6-Cl$_2$-4-OCF$_3$ | S | O |
| H | H | CN | 2,6-Cl$_2$-4-Br | S | O |
| H | H | CN | 2,6-F$_2$-4-CF$_3$ | S | O |
| H | H | CN | 2,6-(CH$_3$)$_2$-4-Br | S | O |
| H | H | CN | 2-Br-4-CF$_3$-6-Cl | S | O |
| H | SCF$_3$ | CN | 2,4,6-Cl$_3$ | O | O |
| H | SCF$_3$ | CN | 2,6-Cl$_2$-4-CF$_3$ | O | O |
| H | SCF$_3$ | CN | 2,6-Cl$_2$-4-NO$_2$ | O | O |
| H | SCF$_3$ | CN | 2,6-Cl$_2$-4-OCF$_3$ | O | O |
| H | SCF$_3$ | CN | 2,6-Cl$_2$-4-Br | O | O |
| H | SCF$_3$ | CN | 2,6-F$_2$-4-CF$_3$ | O | O |
| H | SCF$_3$ | CN | 2,6-(CH$_3$)$_2$-4-Br | O | O |
| H | SCF$_3$ | CN | 2-Br-4-CF$_3$-6-Cl | O | O |
| H | SCF$_2$Br | CN | 2,4,6-Cl$_3$ | O | O |
| H | SCF$_2$Br | CN | 2,6-Cl$_2$-4-CF$_3$ | O | O |

-continued

| | | | | | |
|---|---|---|---|---|---|
| H | SCF$_2$Br | CN | 2,6-Cl$_2$-4-NO$_2$ | O | O |
| H | SCF$_2$Br | CN | 2,6-Cl$_2$-4-OCF$_3$ | O | O |
| H | SCF$_2$Br | CN | 2,6-Cl$_2$-4-Br | O | O |
| H | SCF$_2$Br | CN | 2,6-F$_2$-4-CF$_3$ | O | O |
| H | SCF$_2$Br | CN | 2,6-(CH$_3$)$_2$-4-Br | O | O |
| H | SCF$_2$Br | CN | 2-Br-4-CF$_3$-6-Cl | O | O |
| H | H | SCH$_3$ | 2,5-Cl$_2$-4-CF$_3$ | O | O |
| H | H | SCH$_3$ | 2,4,6-Cl$_3$ | O | O |
| H | H | SCH$_3$ | 2,6-Cl$_2$-4-CF$_3$ | O | O |
| H | H | SCH$_3$ | 2,6-Cl$_2$-4-NO$_2$ | O | O |
| H | H | SCH$_3$ | 2,6-Cl$_2$-4-OCF$_3$ | O | O |
| H | H | SCH$_3$ | 2,6-Cl$_2$-4-Br | O | O |
| H | H | SCH$_3$ | 2,6-F$_2$-4-CF$_3$ | O | O |
| H | H | SCH$_3$ | 2,6-(CH$_3$)$_2$-4-Br | O | O |
| H | H | SCH$_3$ | 2-Br-4-CF$_3$-6-Cl | O | O |
| H | H | SCH$_3$ | 2-Cl-4-CF$_3$-6-NO$_2$ | O | O |
| H | H | SCH$_3$ | 2,4-(NO$_2$)$_2$-6-CF$_3$ | O | O |
| H | H | SCH$_3$ | 2,3,6,-Cl$_3$-4-CF$_3$ | O | O |
| H | H | SCH$_3$ | 2,3,4,5,6-F$_5$ | O | O |
| H | H | SCH$_3$ | 2,3,4,6-F$_4$-4-CN | O | O |
| H | H | SO$_2$CH$_3$ | 2,5-Cl$_2$-4-CF$_3$ | O | O |
| H | H | SO$_2$CH$_3$ | 2,4,6-Cl$_3$ | O | O |
| H | H | SO$_2$CH$_3$ | 2,6-Cl$_2$-4-CF$_3$ | O | O |
| H | H | SO$_2$CH$_3$ | 2,6-Cl$_2$-4-NO$_2$ | O | O |
| H | H | SO$_2$CH$_3$ | 2,6-Cl$_2$-4-OCF$_3$ | O | O |
| H | H | SO$_2$CH$_3$ | 2,6-Cl$_2$-4-Br | O | O |
| H | H | SO$_2$CH$_3$ | 2,6-F$_2$-4-CF$_3$ | O | O |
| H | H | SO$_2$CH$_3$ | 2,6-(CH$_3$)$_2$-4-Br | O | O |
| H | H | SO$_2$CH$_3$ | 2-Br-4-CF$_3$-6-Cl | O | O |
| H | H | SO$_2$CH$_3$ | 2-Cl-4-CF$_3$-6-NO$_2$ | O | O |
| H | H | SO$_2$CH$_3$ | 2,4-(NO$_2$)$_2$-6-CF$_3$ | O | O |
| H | H | SO$_2$CH$_3$ | 2,3,6,-Cl$_3$-4-CF$_3$ | O | O |
| H | H | SO$_2$CH$_3$ | 2,3,4,5,6-F$_5$ | O | O |
| H | H | SO$_2$CH$_3$ | 2,3,4,6-F$_4$-4-CN | O | O |
| H | CN | SO$_2$CH$_3$ | 2,4,6-Cl$_3$ | O | O |
| H | CN | SO$_2$CH$_3$ | 2,6-Cl$_2$-4-CF$_3$ | O | O |
| CH$_3$ | H | SO$_2$CH$_3$ | 2,4,6-Cl$_3$ | O | O |
| CH$_3$ | H | SO$_2$CH$_3$ | 2,6-Cl$_2$-4-CF$_3$ | O | O |
| H | H | SO$_2$CH$_3$ | 2,4,6-Cl$_3$ | S | O |
| H | H | SO$_2$CH$_3$ | 2,6-Cl$_2$-4-CF$_3$ | S | O |
| H | Br | SO$_2$CH$_3$ | 2,4,6-Cl$_3$ | O | O |
| H | Br | SO$_2$CH$_3$ | 2,6-Cl$_2$-4-CF$_3$ | O | O |
| H | I | SO$_2$CH$_3$ | 2,4,6-Cl$_3$ | O | O |
| H | I | SO$_2$CH$_3$ | 2,6-Cl$_2$-4-CF$_3$ | O | O |
| H | Cl | SO$_2$CH$_3$ | 2,4,6-Cl$_3$ | O | O |
| H | Cl | SO$_2$CH$_3$ | 2,6-Cl$_2$-4-CF$_3$ | O | O |
| CH$_2$OCH$_3$ | H | SO$_2$CH$_3$ | 2,4,6-Cl$_3$ | O | O |
| CH$_2$OCH$_3$ | H | SO$_2$CH$_3$ | 2,6-Cl$_2$-4-CF$_3$ | O | O |
| H | H | SCF$_3$ | 2,5-Cl$_2$-4-CF$_3$ | O | O |
| H | H | SCF$_3$ | 2,4,6-Cl$_3$ | O | O |
| H | H | SCF$_3$ | 2,6-Cl$_2$-4-CF$_3$ | O | O |
| H | H | SCF$_3$ | 2,6-Cl$_2$-4-NO$_2$ | O | O |
| H | H | SCF$_3$ | 2,6-Cl$_2$-4-OCF$_3$ | O | O |
| H | H | SCF$_3$ | 2,6-Cl$_2$-4-Br | O | O |
| H | H | SCF$_3$ | 2,6-F$_2$-4-CF$_3$ | O | O |
| H | H | SCF$_3$ | 2,6-(CH$_3$)$_2$-4-Br | O | O |
| H | H | SCF$_3$ | 2-Br-4-CF$_3$-6-Cl | O | O |
| H | H | SCF$_3$ | 2-Cl-4-CF$_3$-6-NO$_2$ | O | O |
| H | H | SCF$_3$ | 2,4-(NO$_2$)$_2$-6-CF$_3$ | O | O |
| H | H | SCF$_3$ | 2,3,6,-Cl$_3$-4-CF$_3$ | O | O |
| H | H | SCF$_3$ | 2,3,4,5,6-F$_5$ | O | O |
| H | H | SCF$_3$ | 2,3,4,6-F$_4$-4-CN | O | O |
| H | CN | SCF$_3$ | 2,4,6-Cl$_3$ | O | O |
| H | CN | SCF$_3$ | 2,6-Cl$_2$-4-CF$_3$ | O | O |
| H | CN | SCF$_3$ | 2,6-Cl$_2$-4-NO$_2$ | O | O |
| H | CN | SCF$_3$ | 2,6-Cl$_2$-4-OCF$_3$ | O | O |
| H | CN | SCF$_3$ | 2,6-Cl$_2$-4-Br | O | O |
| H | CN | SCF$_3$ | 2,6-F$_2$-4-CF$_3$ | O | O |
| H | CN | SCF$_3$ | 2,6-(CH$_3$)$_2$-4-Br | O | O |
| H | CN | SCF$_3$ | 2-Br-4-CF$_3$-6-Cl | O | O |
| H | H | SCF$_3$ | 2,4,6-Cl$_3$ | S | O |
| H | H | SCF$_3$ | 2,6-Cl$_2$-4-CF$_3$ | S | O |
| H | H | SCF$_3$ | 2,6-Cl$_2$-4-NO$_2$ | S | O |
| H | H | SCF$_3$ | 2,6-Cl$_2$-4-OCF$_3$ | S | O |
| H | H | SCF$_3$ | 2,6-Cl$_2$-4-Br | S | O |
| H | H | SCF$_3$ | 2,6-F$_2$-4-CF$_3$ | S | O |
| H | H | SCF$_3$ | 2,6-(CH$_3$)$_2$-4-Br | S | O |
| H | H | SCF$_3$ | 2-Br-4-CF$_3$-6-Cl | S | O |
| CH$_3$ | H | SCF$_3$ | 2,4,6-Cl$_3$ | O | O |
| CH$_3$ | H | SCF$_3$ | 2,6-Cl$_2$-4-CF$_3$ | O | O |
| CH$_3$ | H | SCF$_3$ | 2,6-Cl$_2$-4-NO$_2$ | O | O |
| CH$_3$ | H | SCF$_3$ | 2,6-Cl$_2$-4-OCF$_3$ | O | O |
| CH$_3$ | H | SCF$_3$ | 2,6-Cl$_2$-4-Br | O | O |

-continued

| | | | | | |
|---|---|---|---|---|---|
| CH₃ | H | SCF₃ | 2,6-F₂-4-CF₃ | O | O |
| CH₃ | H | SCF₃ | 2,6-(CH₃)₂-4-Br | O | O |
| CH₃ | H | SCF₃ | 2-Br-4-CF₃-6-Cl | O | O |
| H | SCF₃ | SCF₃ | 2,4,6-Cl₃ | O | O |
| H | SCF₃ | SCF₃ | 2,6-Cl₂-4-CF₃ | O | O |
| H | SCF₃ | SCF₃ | 2,6-Cl₂-4-NO₂ | O | O |
| H | SCF₃ | SCF₃ | 2,6-Cl₂-4-OCF₃ | O | O |
| H | SCF₃ | SCF₃ | 2,6-Cl₂-4-Br | O | O |
| H | SCF₃ | SCF₃ | 2,6-F₂-4-CF₃ | O | O |
| H | SCF₃ | SCF₃ | 2,6-(CH₃)₂-4-Br | O | O |
| H | SCF₃ | SCF₃ | 2-Br-4-CF₃-6-Cl | O | O |
| H | Br | SCF₃ | 2,4,6-Cl₃ | O | O |
| H | Br | SCF₃ | 2,6-Cl₂-4-CF₃ | O | O |
| H | Br | SCF₃ | 2,6-Cl₂-4-NO₂ | O | O |
| H | Br | SCF₃ | 2,6-Cl₂-4-OCF₃ | O | O |
| H | Br | SCF₃ | 2,6-Cl₂-4-Br | O | O |
| H | Br | SCF₃ | 2,6-F₂-4-CF₃ | O | O |
| H | Br | SCF₃ | 2,6-(CH₃)₂-4-Br | O | O |
| H | Br | SCF₃ | 2-Br-4-CF₃-6-Cl | O | O |
| H | Cl | SCF₃ | 2,4,6-Cl₃ | O | O |
| H | Cl | SCF₃ | 2,6-Cl₂-4-CF₃ | O | O |
| H | I | SCF₃ | 2,4,6-Cl₃ | O | O |
| H | I | SCF₃ | 2,6-Cl₂-4-CF₃ | O | O |
| H | NO₂ | SCF₃ | 2,4,6-Cl₃ | O | O |
| H | NO₂ | SCF₃ | 2,6-Cl₂-4-CF₃ | O | O |
| CH₂OCH₃ | H | SCF₃ | 2,4,6-Cl₃ | O | O |
| CH₂OCH₃ | H | SCF₃ | 2,6-Cl₂-4-CF₃ | O | O |
| H | H | SO₂CF₃ | 2,4,6-Cl₃ | O | O |
| H | H | SO₂CF₃ | 2,6-Cl₂-4-CF₃ | O | O |
| H | H | SO₂CF₃ | 2,6-Cl₂-4-NO₂ | O | O |
| H | H | SO₂CF₃ | 2,6-Cl₂-4-OCF₃ | O | O |
| H | H | SO₂CF₃ | 2,6-Cl₂-4-Br | O | O |
| H | H | SO₂CF₃ | 2,6-F₂-4-CF₃ | O | O |
| H | H | SO₂CF₃ | 2,6-(CH₃)₂-4-Br | O | O |
| H | H | SO₂CF₃ | 2-Br-4-CF₃-6-Cl | O | O |
| H | CN | CN | 2,4,6-Cl₃ | O | O |
| H | CN | CN | 2,6-Cl₂-4-CF₃ | O | O |
| H | CN | CN | 2,6-Cl₂-4-NO₂ | O | O |
| H | CN | CN | 2,6-Cl₂-4-OCF₃ | O | O |
| H | CN | CN | 2,6-Cl₂-4-Br | O | O |
| H | CN | CN | 2,6-F₂-4-CF₃ | O | O |
| H | CN | CN | 2,6-(CH₃)₂-4-Br | O | O |
| H | CN | CN | 2-Br-4-CF₃-6-Cl | O | O |
| H | Br | CN | 2,4,6-Cl₃ | O | O |
| H | Br | CN | 2,6-Cl₂-4-CF₃ | O | O |
| H | Br | CN | 2,6-Cl₂-4-NO₂ | O | O |
| H | Br | CN | 2,6-Cl₂-4-OCF₃ | O | O |
| H | Br | CN | 2,6-Cl₂-4-Br | O | O |
| H | Br | CN | 2,6-F₂-4-CF₃ | O | O |
| H | Br | CN | 2,6-(CH₃)₂-4-Br | O | O |
| H | Br | CN | 2-Br-4-CF₃-6-Cl | O | O |
| H | NO₂ | CN | 2,4,6-Cl₃ | O | O |
| H | NO₂ | CN | 2,6-Cl₂-4-CF₃ | O | O |
| H | NO₂ | CN | 2,6-Cl₂-4-NO₂ | O | O |
| H | NO₂ | CN | 2,6-Cl₂-4-OCF₃ | O | O |
| H | NO₂ | CN | 2,6-Cl₂-4-Br | O | O |
| H | NO₂ | CN | 2,6-F₂-4-CF₃ | O | O |
| H | NO₂ | CN | 2,6-(CH₃)₂-4-Br | O | O |
| H | NO₂ | CN | 2-Br-4-CF₃-6-Cl | O | O |
| H | CF₃ | CN | 2,4,6-Cl₃ | O | O |
| H | CF₃ | CN | 2,6-Cl₂-4-CF₃ | O | O |
| H | CF₃ | CN | 2,6-Cl₂-4-NO₂ | O | O |
| H | CF₃ | CN | 2,6-Cl₂-4-OCF₃ | O | O |
| H | CF₃ | CN | 2,6-Cl₂-4-Br | O | O |
| H | CF₃ | CN | 2,6-F₂-4-CF₃ | O | O |
| H | CF₃ | CN | 2,6-(CH₃)₂-4-Br | O | O |
| H | CF₃ | CN | 2-Br-4-CF₃-6-Cl | O | O |
| H | CF₃ | SCF₃ | 2,4,6-Cl₃ | O | O |
| H | CF₃ | SCF₃ | 2,6-Cl₂-4-CF₃ | O | O |
| H | CF₃ | SCF₃ | 2,6-Cl₂-4-Br | O | O |

TABLE 6

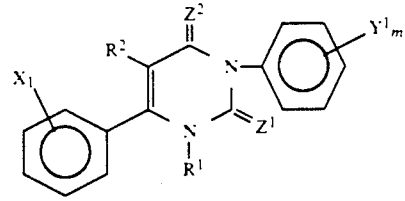

| No | R¹ | R² | X₁ | Y¹$_m$ | Z¹ | Z² | melting point (°C.) |
|---|---|---|---|---|---|---|---|
| 1.1 | H | H | 2-F | 4-OCF₃ | O | O | 263.0-264.0 |
| 1.2 | H | H | 2-F | 4-OCF₂CHF₂ | O | O | 265.0-266.0 |
| 1.3 | H | H | 2-F | 2-F-4-Cl | O | O | 186.0-190.0 |
| 1.4 | H | H | 2-Cl | H | O | O | 255.0-256.5 |
| 1.5 | H | H | 2-Cl | 2-Cl | O | O | 199.0-204.5 |
| 1.6 | H | H | 2-Cl | 3-Cl | O | O | 241.0-245.0 |
| 1.7 | H | H | 2-Cl | 4-Cl | O | O | 244.0-246.0 |
| 1.8 | H | H | 2-Cl | 4-F | O | O | 244.0-245.5 |
| 1.9 | H | H | 2-Cl | 4-Br | O | O | 243.5-245.0 |
| 1.10 | H | H | 2-Cl | 4-I | O | O | 288.0-291.0 |
| 1.11 | H | H | 2-Cl | 4-CH₃ | O | O | 241.0-243.0 |
| 1.12 | H | H | 2-Cl | 4-CF₃ | O | O | 267.0-268.0 |
| 1.13 | H | H | 2-Cl | 4-OCH₃ | O | O | 245.5-251.0 |
| 1.14 | H | H | 2-Cl | 4-OCF₃ | O | O | 254.0-256.0 |
| 1.15 | H | H | 2-Cl | 4-OCH₂CH₂CH₂CH₃ | O | O | 184.5-185.5 |
| 1.16 | H | H | 2-Cl | 4-OCF₂CHF₂ | O | O | 230.0-232.0 |
| 1.17 | H | H | 2-Cl | 4-SCH₃ | O | O | 255.5-259.0 |
| 1.18 | H | H | 2-Cl | 4-SO₂CH₃ | O | O | 296.0-300.5 |
| 1.19 | H | H | 2-Cl | 4-NO₂ | O | O | 274.0-277.0 |
| 1.20 | H | H | 2-Cl | 4-COCH₃ | O | O | >300.0 |
| 1.21 | H | H | 2-Cl | 2-F-4-Cl | O | O | 235.0-238.0 |
| 1.22 | H | H | 2-Cl | 2,4-Cl₂ | O | O | 243.5-247.0 |
| 1.23 | H | H | 2-Cl | 2,5-Cl₂ | O | O | 208.0-210.5 |
| 1.24 | H | H | 2-Cl | 2,6-Cl₂ | O | O | 268.0-270.0 |
| 1.25 | H | H | 2-Cl | 3,4-Cl₂ | O | O | 242.0-244.5 |
| 1.26 | H | H | 2-Cl | 3-Cl-4-F | O | O | 252.0-253.5 |
| 1.27 | H | H | 2-Cl | 3-CF₃-4-Cl | O | O | 246.5-249.0 |
| 1.28 | H | H | 2,4-Cl₂ | 4-OCF₃ | O | O | >300.0 |
| 1.29 | H | H | 2-Br | 4-OCF₃ | O | O | 265.0-267.0 |
| 1.30 | H | H | 2-CH₃ | 2-F-4-Cl | O | O | 191.0-195.0 |
| 1.31 | H | H | 2-OCH₃ | 4-OCF₃ | O | O | 225.0-227.0 |
| 1.32 | H | Cl | 2-Cl | 4-OCF₃ | O | O | 266.0-270.0 |
| 1.33 | H | Br | 2-Cl | 4-OCF₃ | O | O | 264.0-268.5 |
| 1.34 | CH₃ | H | 2-F | 4-OCF₃ | O | O | 180.0-181.0 |
| 1.35 | CH₃ | H | 2-F | 3-OCF₂CHF₂ | O | O | 167.0-168.0 |
| 1.36 | CH₃ | H | 2-F | 2-F-4-Cl | O | O | 199.0-200.0 |
| 1.37 | CH₃ | H | 2-Cl | 4-OCF₃ | O | O | 186.0-187.0 |
| 1.38 | CH₃ | H | 2-Cl | 4-OCF₂CHF₂ | O | O | 179.0-180.0 |
| 1.39 | CH₃ | H | 2-Cl | 2-F-4-Cl | O | O | 212.0-215.0 |
| 1.40 | CH₃ | H | 2-CH₃ | 2-F-4-Cl | O | O | 204.0-205.0 |
| 1.41 | CH₂OCH₂CH₃ | H | 2-Cl | 4-OCF₃ | O | O | 168.5-172.0 |
| 1.42 | COCH₃ | H | 2-Cl | 4-OCF₃ | O | O | 185.5-188.0 |
| 1.43 | H | H | 2-Cl | 4-Cl | S | O | 245.0-250.5 |
| 1.44 | H | H | 2-CF₃ | 4-OCF₃ | O | O | 240.0-242.0 |
| 1.45 | H | H | 2-CH₃ | 4-OCF₃ | O | O | 227.0-229.0 |
| 1.46 | H | H | 2-CH₃ | 4-OCF₂CHF₂ | O | O | 211.0-212.0 |
| 1.47 | H | H | 2-CF₃ | 2-F-4-Cl | O | O | 213.0-214.0 |
| 1.48 | H | H | 2-CF₃ | 4-OCF₂CHF₂ | O | O | 232.0-233.0 |
| 1.49 | H | H | 2-Cl | 3-OCH₂OCH₃ | O | O | 174.0-175.0 |
| 1.50 | H | H | 2-Cl | 3-OH | O | O | 286.0-288.0 |
| 1.51 | H | H | 2-Cl | 3,5-Cl₂-4-O(Q38-3-Cl-5-CF₃) | O | O | 253.0-254.0 |
| 1.52 | H | H | 2-Cl | 3-O(Q50-6-Cl) | O | O | >300.0 |
| 1.53 | H | H | 2,6-(OCH₃)₂ | 4-Cl | O | O | >300.0 |
| 1.54 | H | H | 2-Cl | 3,5-Cl₂-4-OCF₂CHF₂ | O | O | 203.0-205.5 |
| 1.55 | H | H | 2-F | 3,5-Cl₂-4-OCF₂CHF₂ | O | O | 231.0-234.5 |
| 1.56 | H | H | 2,6-(OCH₃)₂ | 4-OCF₃ | O | O | 245.0-247.0 |
| 1.57 | H | H | 2-F | 3,5-Cl₂-4-OH | O | O | 275.0-277.0 |
| 1.58 | H | H | 2-Cl | 4-OCH₂OCH₃ | O | O | 218.0-219.0 |
| 1.59 | H | H | 2-Cl | 4-OH | O | O | 288.0-290.0 |
| 1.60 | H | H | 2-Cl | 4-OCH₂(C₆H₄-4-CF₃) | O | O | 265.0-267.0 |
| 1.61 | H | H | 2-Cl | 4-O(Q50-6-CF₃) | O | O | 265.0-267.0 |
| 1.62 | H | H | 2-Cl | 2,4,6-Cl₃ | O | O | 263.0-265.0 |
| 1.63 | H | H | 2-Cl | 3,4,5-Cl₃ | O | O | 292.0-293.0 |
| 1.64 | H | H | 2-Cl | 2,4,5-Cl₃ | O | O | 270.0-272.0 |
| 1.65 | H | H | 2-Cl | 2,3,4-F₃ | O | O | 234.0-235.0 |
| 1.66 | H | H | 2-Cl | 4-O(Q38-3-Cl-5-CF₃) | O | O | 175.0-176.0 |
| 1.67 | H | H | 2-Cl | 4-CH₂ON=C(Q51)(C₆H₄-4-Cl) | O | O | 120.0-122.0 |
| 1.68 | H | H | 2-F | 4-CH₂ON=C(Q51)(C₆H₄-4-Cl) | O | O | 127.0-132.0 |
| 1.69 | H | H | 2-Cl | 2,4-F₂-3,5-Cl₂ | O | O | 233.0-235.0 |
| 1.70 | H | H | 2-F | 2,4-F₂-3,5-Cl₂ | O | O | 245.0-247.0 |

TABLE 6-continued

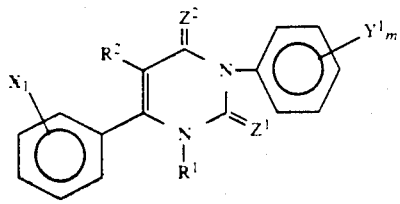

| No. | $R^1$ | $R^2$ | $X_1$ | $Y^1_m$ | $Z^1$ | $Z^2$ | melting point (°C.) |
|---|---|---|---|---|---|---|---|
| 1.71 | H | H | 2-Cl | 2-F-4-O($C_6H_5$-2-Cl-4-$CF_3$) | O | O | 151.0-153.0 |
| 1.72 | H | H | 2-F | 2-F-4-O($C_6H_5$-2-Cl-4-$CF_3$) | O | O | 146.0-148.0 |
| 1.73 | H | H | 2-Cl | 2,4,5-$F_3$ | O | O | 212.0-216.0 |
| 1.74 | H | $CH_3$ | 2-Cl | 4-$OCF_3$ | O | O | 229.0-233.0 |
| 1.75 | H | H | 2-Cl-6-F | 4-$OCF_3$ | O | O | 268.0-272.0 |
| 1.76 | H | H | 2-Cl-6-F | 4-Cl | O | O | 228.0-231.5 |
| 1.77 | H | H | 2-Cl | 2,3,4,5,6-$F_5$ | O | O | 186.0-188.0 |
| 1.78 | H | H | 2,6-$Cl_2$ | 4-Cl | O | O | 270.0-271.0 |
| 1.79 | H | H | 2,4-$Cl_2$ | 2-F-4-Cl | O | O | 261.0-266.0 |
| 1.80 | H | H | 2,6-$Cl_2$ | 4-$OCF_3$ | O | O | >300 |
| 1.81 | H | H | 2,6-$F_2$ | 4-Cl | O | O | 230.0-231.0 |
| 1.82 | H | H | 2,6-$F_2$ | 4-$OCF_3$ | O | O | 262.0-263.0 |
| 1.83 | H | H | 2,6-$F_2$ | 4-$CF_3$ | O | O | 268.0-270.0 |
| 1.84 | H | H | 2,6-$F_2$ | 4-$CH_3$ | O | O | 226.0-227.0 |
| 1.85 | H | H | 2,6-$F_2$ | 4-F | O | O | 271.0-273.0 |
| 1.86 | H | H | 2,6-$F_2$ | 4-Br | O | O | 229.0-231.0 |
| 1.87 | H | H | 2-Cl | 3,4-$F_2$ | O | O | 244.5-246.5 |
| 1.88 | H | H | 2-Cl | 3-F-4-$CH_3$ | O | O | 234.5-237.0 |
| 1.89 | H | H | 2-F | 3,4-$F_2$ | O | O | 238.5-242.0 |
| 1.90 | H | H | 2-F | 3-F-4-$CH_3$ | O | O | 192.0-194.5 |
| 1.91 | H | H | 2-Cl | 3,4-($CH_3)_2$ | O | O | 242.0-243.5 |
| 1.92 | H | H | 2-F | 4-F | O | O | 255.0-257.0 |
| 1.93 | H | H | 2-F | 4-Cl | O | O | 233.0-234.0 |
| 1.94 | H | H | 2-F | 4-Br | O | O | 241.0-242.0 |
| 1.95 | H | H | 2-F | 4-$CH_3$ | O | O | 223.0-224.0 |
| 1.96 | H | H | 2-F | 4-$OCH_3$ | O | O | 237.0-238.0 |
| 1.97 | H | H | 2-F | 4-$CF_3$ | O | O | 257.0-259.0 |
| 1.98 | H | H | 2-Cl-6-F | 4-Br | O | O | 265.0-267.0 |
| 1.99 | H | H | 2-Cl-6-F | 4-F | O | O | 246.0-249.0 |
| 1.100 | H | H | 2-Cl-6-F | 4-$CH_3$ | O | O | 252.0-256.0 |
| 1.101 | H | H | 2-Cl-6-F | 4-$CF_3$ | O | O | 276.0-278.0 |
| 1.102 | H | H | 2-Cl-6-F | 2-F-4-Cl | O | O | 237.0-238.0 |
| 1.103 | H | H | 2-Cl | 2,4,6-$F_3$ | O | O | 230.0-231.5 |
| 1.104 | H | H | 2-Cl | 2,4-$F_2$ | O | O | 242.0-243.0 |
| 1.105 | H | H | 2-Cl | 2-F-4-Br | O | O | 240.0-241.0 |
| 1.106 | H | H | 2-Cl | 2-F-4-$CH_3$ | O | O | 237.0-238.0 |
| 1.107 | H | H | 2-Cl | 2-Br-4-$OCF_3$ | O | O | 223.0-225.0 |
| 1.108 | H | H | 2-Cl | 4-C($CH_3)_3$ | O | O | 264.0-266.0 |
| 1.109 | H | H | 2-Cl | 4-($CH_2)_5CH_3$ | O | O | 160.0-161.0 |
| 1.110 | H | H | 2-Cl | 2-$CH_3$-4-Cl | O | O | 230.0-231.5 |
| 1.111 | H | H | 2-Cl | 3-Cl-4-$CH_3$ | O | O | 236.5-238.0 |
| 1.112 | H | H | 2-Cl | 2,5-$F_2$ | O | O | 217.0-218.5 |
| 1.113 | H | H | 2-Cl | 2-$CF_3$-4-Cl | O | O | 194.5-196.0 |
| 1.114 | H | H | 2,6-$F_2$ | 2,4-$F_2$ | O | O | 240.0-244.0 |
| 1.115 | H | H | 2,6-$F_2$ | 2-F-4-Cl | O | O | 208.0-209.0 |
| 1.116 | H | H | 2,6-$F_2$ | 2-F-4-Br | O | O | 202.0-205.0 |
| 1.117 | H | H | 2,6-$F_2$ | 2-F-4-$CH_3$ | O | O | 229.0-233.0 |
| 1.118 | H | H | 2,6-$F_2$ | 2-Br-4-$OCF_3$ | O | O | 248.0-252.0 |
| 1.119 | H | H | 2,6-$F_2$ | 4-C($CH_3)_3$ | O | O | 265.0-269.0 |
| 1.120 | H | H | 2,5-$F_2$ | 4-$OCF_3$ | O | O | 211.0-213.0 |
| 1.121 | H | H | 2,5-$F_2$ | 4-Cl | O | O | 237.0-238.0 |
| 1.122 | H | F | 2-Cl-4-F | 4-Cl | O | O | 254.0-256.0 |
| 1.123 | H | H | 2-Cl | 4-$OC_6H_5$ | O | O | 170.0-174.0 |
| 1.124 | H | H | 2-Cl | 4-$OCHF_2$ | O | O | 230.0-231.5 |
| 1.125 | H | H | 2-F | 4-$OCHF_2$ | O | O | 233.0-236.0 |
| 1.126 | H | H | 2-Cl-6-F | 4-$OCHF_2$ | O | O | 272.0-274.5 |
| 1.127 | H | H | 2,6-$F_2$ | 4-$OCHF_2$ | O | O | 263.0-266.5 |
| 1.128 | H | H | 2-Cl | 4-$OCF_2Br$ | O | O | 209.0-214.0 |
| 1.129 | H | H | 2-F | 4-$OCF_2Br$ | O | O | 231.0-235.5 |
| 1.130 | H | H | 2-Cl | 2,6-($CH_3)_2$-4-Br | O | O | 212.0-213.5 |
| 1.131 | H | H | 2-Cl | 4-$CH_2CH_3$ | O | O | 246.0-247.0 |
| 1.132 | H | H | 2-Cl | 3-Cl-4-Br | O | O | 243.0-244.0 |
| 1.133 | H | H | 2,6-$F_2$ | 4-$OCF_2Br$ | O | O | 243.5-247.5 |
| 1.134 | H | H | 2-Cl-6-F | 4-$OCF_2Br$ | O | O | 240.5-246.0 |
| 1.135 | H | H | 2-Cl | 4-$CO_2CH_2CH_3$ | O | O | 227.0-231.0 |
| 1.136 | H | H | 2-Cl | 4-CN | O | O | 264.0-266.0 |
| 1.137 | H | H | 2-Cl | 4-$CONH_2$ | O | O | 276.0-279.0 |
| 1.138 | H | H | 2-Cl | 3-F-4-Cl | O | O | 244.0-245.0 |
| 1.139 | H | H | 2-Cl | 4-$SCF_3$ | O | O | 243.5-246.0 |
| 1.140 | H | H | 2-F | 4-$SCF_3$ | O | O | 228.0-232.0 |

TABLE 6-continued

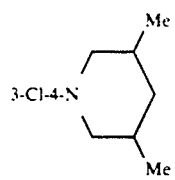

| No. | R¹ | R² | X₁ | Y¹ₘ | Z¹ | Z² | melting point (°C.) |
|---|---|---|---|---|---|---|---|
| 1.141 | H | H | 2-Cl | 2,4-(CH₃)₂ | O | O | 213.0-214.5 |
| 1.142 | H | H | 2-Cl | 4-OCH₂CH₃ | O | O | 238.5-239.5 |
| 1.143 | H | H | 2-Cl | 4-CO₂H | O | O | |
| 1.144 | H | H | 2-Cl | 3-Cl-4-N(piperidine with Me at 2,5) | O | O | 262.0-264.0 |
| 1.145 | H | H | 2-Cl | 4-O(CH₂)₅CH₃ | O | O | 210.0-211.0 |
| 1.146 | H | H | 2,6-F₂ | 4-O(CH₂)₅CH₃ | O | O | 214.0-215.0 |
| 1.147 | H | H | 2-Cl | 4-SCF₂Br | O | O | |
| 1.148 | H | H | 2,4-F₂ | 4-Cl | O | O | 207.0-214.0 |
| 1.149 | H | H | 2-Cl | 4-OCH₂CF₃ | O | O | 252.0-254.0 |
| 1.150 | H | H | 2,6-F₂ | 3,5-Cl₂-4-OCF₂CHF₂ | O | O | 208.0-209.0 |
| 1.151 | H | I | 2-Cl | 4-OCF₃ | O | O | 244.5-248.0 |
| 1.152 | H | Cl | 2-Cl | 4-SO₂CF₃ | O | O | |
| 1.153 | H | H | 2-Cl | 2,6-F₂-4-Br | O | O | 261.0-265.0 |
| 1.154 | H | H | 2-Cl | 2,4-F₂-6-Br | O | O | 234.0-235.5 |
| 1.155 | H | H | 2-Cl | 2-F-4-OCF₃ | O | O | 228.0-235.0 |
| 1.156 | H | H | 2,6-F₂ | 2,4-F₂-3,5-Cl₂ | O | O | 225.0-228.0 |
| 1.157 | H | H | 2,6-F₂ | 3,5-Cl₂-4-OH | O | O | >300 |
| 1.158 | H | H | 2-Cl | 4-SO₂CF₃ | O | O | 266.0-272.0 |
| 1.159 | H | H | 2,5-F₂ | 4-Br | O | O | 253.0-255.0 |
| 1.160 | H | H | 2,5-F₂ | 4-CF₃ | O | O | 284.0-286.0 |
| 1.161 | H | H | 2,6-F₂ | 2,3,4-F₃ | O | O | 147.0-152.0 |
| 1.162 | H | H | 2,6-F₂ | 2,4,5-F₃ | O | O | 164.0-168.0 |
| 1.163 | H | H | 2,6-F₂ | 2-CH₃-4-OCF₃ | O | O | 253.0-256.0 |
| 1.164 | H | H | 2-Cl | 4-N=N-C₆H₅ | O | O | 262.0-264.01 |
| 1.165 | H | H | 2-Cl | 3-OCH₂O-4 | O | O | 261.0-263.0 |
| 1.166 | H | H | 2,6-F₂ | 3,4-Cl₂ | O | O | 255.5-256.5 |
| 1.167 | H | H | 2,6-F₂ | 2-F-4-OCF₃ | O | O | 254.0-257.0 |
| 1.168 | H | H | 2-Cl | 4-OCOC₆H₅ | O | O | 240.0-243.0 |
| 1.169 | H | H | 2-Cl | 4-OSO₂C₆H₅ | O | O | 191.0-194.0 |
| 1.170 | H | H | 2-Cl | 2-Cl-4-OCF₃ | O | O | 214.0-216.0 |
| 1.171 | H | H | 2,6-F₂ | 2-Cl-4-OCF₃ | O | O | 236.0-240.0 |
| 1.172 | H | H | 2-Cl | 2,5-F₂-4-Cl | O | O | 227.0-229.0 |
| 1.173 | H | H | 2-F | 2,5-F₂-4-Cl | O | O | 221.0-223.0 |
| 1.174 | H | H | 2-Cl | 4-OCH₂(Q38) | O | O | 136.0-141.0 |
| 1.175 | CH₃ | H | 2-CF₃ | 4-OCF₃ | O | O | 174.0-176.0 |
| 1.176 | CH₃ | H | 2-CF₃ | 2-F-4-Cl | O | O | 187.0-188.0 |
| 1.177 | CH₃ | H | 2-CF₃ | 4-OCF₂CHF₂ | O | O | 166.0-167.0 |
| 1.178 | (CH₂)₃CH₃ | H | 2-Cl | 4-OCF₃ | O | O | 105.0-106.0 |
| 1.179 | CH₂C≡CH | H | 2-Cl | 4-OCF₃ | O | O | 191.0-192.0 |
| 1.180 | CH₂C₆H₅ | H | 2-Cl | 4-OCF₃ | O | O | 170.0-171.0 |
| 1.181 | CH₃ | H | 2-Cl | 3-O(Q50-6-Cl) | O | O | 191.0-192.0 |
| 1.182 | CH₃ | H | 2,6-(OCH₃)₂ | 4-Cl | O | O | 252.0-254.0 |
| 1.183 | CH₃ | H | 2,4-Cl₂ | 2-F-4-Cl | O | O | 240.0-247.0 |
| 1.184 | H | NO₂ | 2-Cl-4-NO₂ | 2-NO₂-4-OCF₃ | O | O | |
| 1.185 | H | H | 2-Cl | 4-O(C₆H₄-4-Cl) | O | O | 217.0-219.0 |
| 1.186 | H | H | 2-Cl | 4-O(C₆H₄-4-CH₃) | O | O | 212.0-213.0 |
| 1.187 | H | H | 2-Cl | 3-Cl-4-OC₆H₅ | O | O | 179.0-182.0 |
| 1.188 | H | H | 2-Cl | 4-O(Q38-5-Cl) | O | O | 230.0-230.5 |
| 1.189 | H | H | 2-Cl | 4-CH=CH(C₆H₄-4-OCH₃) | O | O | 244.0-247.0 |
| 1.190 | H | H | 2,6-F₂ | 4-OCF₂CHF₂ | O | O | 260.0-263.0 |
| 1.191 | H | H | 2-F | 4-OCF₃ | S | O | 220.0-222.0 |

TABLE 7

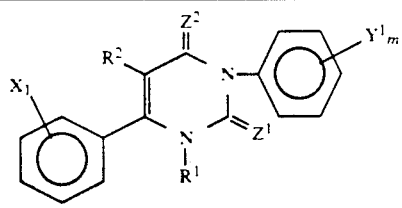

| No. | R¹ | R² | X₁ | Y¹ₘ | Z¹ | Z² | melting point (°C.) |
|---|---|---|---|---|---|---|---|
| 2.1 | H | H | H | 4-OCF₃ | O | O | >300.0 |
| 2.2 | H | Cl | H | 4-OCF₃ | O | O | 214.0–216.0 |
| 2.3 | H | Br | H | 4-OCF₃ | O | O | 293.0–295.0 |
| 2.4 | H | CH₃ | H | 4-OCF₃ | O | O | 240.0–245.0 |
| 2.5 | H | CN | H | 4-OCF₃ | O | O | 278.0–282.0 |
| 2.6 | H | CH₂CH₃ | H | 4-Cl | O | O | 235.5–238.0 |
| 2.7 | H | I | H | 4-OCF₃ | O | O | 294.0–298.0 |
| 2.8 | CH₃ | H | 3-CF₃ | H | O | O | 215.5–217.0 |
| 2.9 | CH₃ | H | 3-CF₃ | 2-Cl | O | O | 153.5–158.0 |
| 2.10 | CH₃ | H | 3-CF₃ | 3-Cl | O | O | 184.0–187.0 |
| 2.11 | CH₃ | H | 3-CF₃ | 4-Cl | O | O | 204.0–205.5 |
| 2.12 | CH₃ | H | 3-CF₃ | 4-OCF₃ | O | O | 205.5–208.5 |
| 2.13 | CH₃ | H | 3-CF₃ | 2,4-Cl₂ | O | O | 144.0–146.0 |
| 2.14 | CH₃ | H | 3-CF₃ | 2,5-Cl₂ | O | O | 150.0–151.0 |
| 2.15 | CH₃ | H | 3-CF₃ | 2,6-Cl₂ | O | O | 178.0–179.0 |
| 2.16 | CH₃ | H | 3-CF₃ | 3,4-Cl₂ | O | O | 182.0–183.0 |
| 2.17 | CH₃ | H | 3-CF₃ | 2,4,5-Cl₃ | O | O | 171.0–173.5 |
| 2.18 | CH₃ | H | 3-CF₃ | 2,4,6-Cl₃ | O | O | 155.0–157.0 |
| 2.19 | H | H | 3-CF₃ | H | O | O | 261.0–267.0 |
| 2.20 | H | H | 3-CF₃ | 2-Cl | O | O | 255.0–256.5 |
| 2.21 | H | H | 3-CF₃ | 3-Cl | O | O | 252.5–256.0 |
| 2.22 | H | H | 3-CF₃ | 4-Cl | O | O | 278.0–279.5 |
| 2.23 | H | H | 3-CF₃ | 4-OCF₃ | O | O | 250.0–256.0 |
| 2.24 | H | H | 3-CF₃ | 2,4-Cl₂ | O | O | 282.0–283.0 |
| 2.25 | H | H | 3-CF₃ | 2,5-Cl₂ | O | O | 270.0–272.0 |
| 2.26 | H | H | 3-CF₃ | 2,6-Cl₂ | O | O | 262.0–263.0 |
| 2.27 | H | H | 3-CF₃ | 3,4-Cl₂ | O | O | 220.0–223.0 |
| 2.28 | H | H | 3-CF₃ | 2,4,5-Cl₃ | O | O | 263.0–266.0 |
| 2.29 | H | H | 3-CF₃ | 2,4,6-Cl₃ | O | O | 261.0–264.0 |
| 2.30 | CH₃ | H | 3-CF₃ | 2,3-Cl₂ | O | O | 158.0–160.5 |
| 2.31 | CH₃ | H | 3-CF₃ | 3-Cl-4-F | O | O | 201.0–206.0 |
| 2.32 | CH₃ | H | 3-CF₃ | 3-CF₃-4-Cl | O | O | 149.5–150.5 |
| 2.33 | CH₃ | H | 3-CF₃ | 3,4,5-Cl₃ | O | O | 192.0–196.5 |
| 2.34 | H | H | 3-CF₃ | 2,3-Cl₂ | O | O | 255.0–258.0 |
| 2.35 | H | H | 3-CF₃ | 3-Cl-4-F | O | O | 253.0–254.0 |
| 2.36 | H | H | 3-CF₃ | 3-CF₃-4-Cl | O | O | 227.5–229.0 |
| 2.37 | H | H | 3-CF₃ | 3,4,5-Cl₃ | O | O | 255.0–257.0 |
| 2.38 | H | H | 3-CF₃ | 2,4-F₂-3,5-Cl₂ | O | O | 205.0–208.5 |
| 2.39 | CH₃ | H | 3-CF₃ | 2,4-F₂-3,5-Cl₂ | O | O | 145.0–148.0 |
| 2.40 | H | H | 3-CF₃ | 2-F-3,5-Cl₂-4-OCH₂CH₃ | O | O | 245.5–248.0 |
| 2.41 | CH₃ | H | 3-CF₃ | 2-F-3,5-Cl₂-4-OCH₂CH₃ | O | O | 181.5–185.0 |
| 2.42 | CH₂CH₃ | H | 3-CF₃ | 2-F-4-Cl | O | O | 133.0–135.5 |
| 2.43 | H | Br | 3-CF₃ | 2-F-4-Cl | O | O | 256.0–259.5 |
| 2.44 | CH₃ | Br | 3-CF₃ | 2-F-4-Cl | O | O | 174.0–175.5 |
| 2.45 | H | H | 3-CF₃ | 2,3,4-F₃ | O | O | 212.0–214.0 |
| 2.46 | CH₃ | H | 3-CF₃ | 2,3,4-F₃ | O | O | 162.5–165.0 |
| 2.47 | CH₃ | H | 3-Br | 2-F-4-Cl | O | O | 148.0–152.0 |
| 2.48 | CH₃ | H | 3,4-Cl₂ | 2-F-4-Cl | O | O | 231.0–234.5 |
| 2.49 | CH₃ | H | 3,5-(CF₃)₂ | 2-F-4-Cl | O | O | 175.0–179.0 |
| 2.50 | H | H | 3-Br | 2-F-4-Cl | O | O | 240.5–245.0 |
| 2.51 | H | H | 3,4-Cl₂ | 2-F-4-Cl | O | O | 273.0–277.0 |
| 2.52 | H | H | 3,5-(CF₃)₂ | 2-F-4-Cl | O | O | 257.0–263.0 |
| 2.53 | H | Br | 3-Cl | 4-OCF₃ | O | O | >300 |
| 2.54 | H | Br | 4-Cl | 4-OCF₃ | O | O | 292.0–293.0 |
| 2.55 | H | H | 4-Cl | 2-Cl | O | O | >300 |
| 2.56 | H | F | H | 4-OCF₃ | O | O | 295.0–303.0 |
| 2.57 | CH₃ | H | 3-CF₃ | 2-F-4-Cl | O | O | 139.0–142.0 |
| 2.58 | H | H | 3-CF₃ | 2-F-4-Cl | O | O | 233.0–235.0 |
| 2.59 | CH₃ | H | 3-F | 2-F-4-Cl | O | O | 180.0–181.0 |
| 2.60 | H | H | 3-F | 2-F-4-Cl | O | O | 269.0–271.0 |
| 2.61 | CH₃ | H | 3-Cl | 2-F-4-Cl | O | O | 128.0–131.0 |
| 2.62 | H | H | 3-Cl | 2-F-4-Cl | O | O | 248.0–253.0 |
| 2.63 | CH₃ | H | 4-CF₃ | 2-F-4-Cl | O | O | 250.0–253.0 |
| 2.64 | H | H | 4-CF₃ | 2-F-4-Cl | O | O | 295.0–298.0 |
| 2.65 | CH₃ | H | 4-Cl | 2-F-4-Cl | O | O | 160.0–162.0 |
| 2.66 | H | H | 4-Cl | 2-F-4-Cl | O | O | >300 |
| 2.67 | CH₃ | H | H | 2-F-4-Cl | O | O | 200.5–203.0 |
| 2.68 | H | H | H | 2-F-4-Cl | O | O | 242.0–243.0 |
| 2.69 | H | H | 3-Cl | 2-F-4-Cl | O | O | >300 |
| 2.70 | H | H | 4-Cl | 4-OCF₃ | O | O | >300 |

TABLE 7-continued

| No. | R¹ | R² | X₁ | Y¹ₘ | Z¹ | Z² | melting point (°C.) |
|---|---|---|---|---|---|---|---|
| 2.71 | H | H | 3,4-Cl₂ | 4-OCF₃ | O | O | >300 |
| 2.73 | H | H | H | 3,4-Cl₂ | O | O | >300 |
| 2.74 | H | Br | H | 3,4-Cl₂ | O | O | >300 |
| 2.75 | H | H | H | 3,5-Cl₂-4-OCF₂CHF₂ | O | O | 278.0–279.0 |
| 2.76 | H | Br | H | 3,5-Cl₂-4-OCF₂CHF₂ | O | O | >300 |

TABLE 8

| No. | R¹ | R² | A | Y¹ₘ | Z¹ | Z² | melting point (°C.) |
|---|---|---|---|---|---|---|---|
| 3.1 | H | H | Q38 | 4-Cl | O | O | >300 |
| 3.2 | H | H | Q38 | 4-OCF₃ | O | O | 280.0–286.0 |
| 3.3 | H | Br | Q38 | 4-OCF₃ | O | O | 185.0–187.0 |
| 3.4 | H | I | Q38 | 4-OCF₃ | O | O | 215.0–217.0 |
| 3.5 | H | H | Q6 | 2-F-4-Cl | O | O | 296.0–298.0 |
| 3.6 | CH₃ | H | Q6 | 2-F-4-Cl | O | O | 104.0–107.0 |

TABLE 9

| No | R¹ | R² | X₁ | B | Z¹ | Z² | melting point (°C.) |
|---|---|---|---|---|---|---|---|
| 4.1 | H | H | 2-Cl | Q39-2,6-Cl₂ | O | O | 122.0–123.0 |
| 4.2 | H | H | 2-Cl | Q39-6-Cl | O | O | 239.0–240.0 |
| 4.3 | H | H | 2-Cl | Q38-5-Cl | O | O | 251.0–254.0 |
| 4.4 | H | H | 2-Cl | Q38-5-CF₃ | O | O | 281.0–283.0 |
| 4.5 | H | H | 2-Cl | Q38-5-Br | O | O | 256.0–258.0 |
| 4.6 | H | H | H | Q43-4,6-(CH₃)₂ | O | O | >300 |
| 4.7 | CH₃ | H | H | Q43-4,6-(CH₃)₂ | O | O | 248.0–251.0 |
| 4.8 | H | H | 2-Cl | Q43-4,6-(CH₃)₂ | O | O | 277.0–279.0 |
| 4.9 | H | H | 2-Cl | Q17-5-CH₃ | O | O | 191.0–192.0 |
| 4.10 | H | H | 2-Cl | Q40-2-Cl | O | O | 231.0–233.0 |
| 4.11 | H | H | 2-Cl | Q49 | O | O | >300 |
| 4.12 | H | H | 2-Cl | Q7-2-CO₂CH₃ | O | O | 263.0–265.0 |
| 4.13 | H | H | 2-Cl | Q39-6-O(C₆H₄-3-CF₃) | O | O | 198.0–199.0 |

TABLE 10

| No. | R¹ | R² | A | Y²ᵣ | Z¹ | Z² | melting point (°C.) |
|---|---|---|---|---|---|---|---|
| 5.1 | H | H | CF₃ | 2,3,4-F₃ | O | O | 137.0–138.5 |
| 5.2 | H | H | CF₃ | 2,3,4-Cl₃ | O | O | 176.5–178.0 |
| 5.3 | H | H | CF₃ | 2,4,5-Cl₃ | O | O | 219.0–221.5 |
| 5.4 | H | H | CF₃ | 2,5-Cl₂-4-NO₂ | O | O | 173.0–176.0 |

TABLE 10-continued

| No. | R¹ | R² | A | Y²ᵣ | Z¹ | Z² | melting point (°C.) |
|---|---|---|---|---|---|---|---|
| 5.5 | H | H | $CF_3$ | 2-$CF_3$-4-$NO_2$-5-Cl | O | O | 198.5-201.0 |
| 5.6 | H | H | $CF_3$ | 2-$NO_2$-4,5-$Cl_2$ | O | O | 208.0-211.0 |
| 5.7 | H | H | $CF_3$ | 2,4,6-$Cl_3$ | O | O | 224.0-227.0 |
| 5.8 | H | H | $CF_3$ | 2,6-$Cl_2$-4-$CF_3$ | O | O | 248.0-250.0 |
| 5.9 | H | H | $CF_3$ | 2-Br-4-$CF_3$-6-Cl | O | O | 206.0-208.5 |
| 5.10 | H | H | $CF_3$ | 2,6-$Cl_2$-4-$NO_2$ | O | O | 221.0-224.0 |
| 5.11 | H | H | $CF_3$ | 2-Cl-4-$CF_3$-6-$NO_2$ | O | O | 172.0-174.0 |
| 5.12 | H | H | $CF_3$ | 3,4,5-$Cl_3$ | O | O | 249.0-253.0 |
| 5.13 | H | H | $CF_3$ | 2,3,4,5-$Cl_4$ | O | O | 235.0-239.0 |
| 5.14 | H | Cl | $CF_3$ | 2,4,6-$Cl_3$ | O | O | 238.0-239.5 |
| 5.15 | H | Br | $CF_3$ | 2,4,6-$Cl_3$ | O | O | 219.0-222.0 |
| 5.16 | $CH_3$ | H | $CF_3$ | 2,6-$Cl_2$-4-$CF_3$ | O | O | 145.0-148.0 |
| 5.17 | $CH_2CH_3$ | H | $CF_3$ | 2,4,6-$Cl_3$ | O | O | 136.0-137.5 |
| 5.18 | $CH_2CH=CH_2$ | H | $CF_3$ | 2,4,6-$Cl_3$ | O | O | 104.0-105.0 |
| 5.19 | $CH_2C\equiv CH$ | H | $CF_3$ | 2,4,6-$Cl_3$ | O | O | 131.0-132.0 |
| 5.20 | $CH_2OCH_2CH_3$ | H | $CF_3$ | 2,4,6-$Cl_3$ | O | O | oil |
| 5.21 | $COCH_3$ | H | $CF_3$ | 2,4,6-$Cl_3$ | O | O | 117.0-120.0 |
| 5.22 | H | H | $CF_2CF_3$ | 2,4,6-$Cl_3$ | O | O | 236.0-239.0 |
| 5.23 | H | H | $CF_2CF_3$ | 2,6-$Cl_2$-4-$CF_3$ | O | O | 207.0-209.0 |
| 5.24 | H | H | $CF_2CF_2CF_3$ | 2,4,6-$Cl_3$ | O | O | 203.0-207.0 |
| 5.25 | H | H | $CF_3$ | 3,5-$Cl_2$-4-$OCF_2CHF_2$ | O | O | 168.0-172.0 |
| 5.26 | $CH_2CH_2CH_3$ | H | $CF_3$ | 2,4,6-$Cl_3$ | O | O | oil |
| 5.27 | $(CH_2)_3CH_3$ | H | $CF_3$ | 2,4,6-$Cl_3$ | O | O | 106.0-107.0 |
| 5.28 | $CH_2C_6H_5$ | H | $CF_3$ | 2,4,6-$Cl_3$ | O | O | 127.0-129.0 |
| 5.29 | $CH_2CN$ | H | $CF_3$ | 2,4,6-$Cl_3$ | O | O | 173.0-175.0 |
| 5.30 | H | H | $CF_3$ | 2,4-$F_2$-3,5-$Cl_2$ | O | O | 224.0-227.0 |
| 5.31 | $CH_3$ | H | $CF_3$ | 2,3,4-$F_3$ | O | O | 138.0-141.0 |
| 5.32 | H | H | $CF_2CF_3$ | 2,3,4-$F_3$ | O | O | 159.0-160.5 |
| 5.33 | $CH_2OCH_3$ | H | $CF_3$ | 2,3,4-$F_3$ | O | O | 143.0-144.0 |
| 5.34 | H | H | $CF_3$ | 2,3,4,5,6-$F_5$ | O | O | 145.0-148.0 |
| 5.35 | H | H | $CF_3$ | 2,3,4,6-$F_4$ | O | O | 134.0-135.5 |
| 5.36 | H | H | $CF_3$ | 2,3,5,6-$F_4$ | O | O | 228.0-232.0 |
| 5.37 | H | $CH_3$ | $CF_3$ | 2,4,6-$Cl_3$ | O | O | 220.0-225.0 |
| 5.38 | H | H | $CF_3$ | 2,4,6-$F_3$ | O | O | 178.0-181.0 |
| 5.39 | H | H | $CF_3$ | 2,4,6-$Br_3$ | O | O | 240.0-241.0 |
| 5.40 | H | H | $CF_3$ | 2,4,6-$(CH_3)_3$ | O | O | 218.0-220.0 |
| 5.41 | H | H | $CF_2CF_3$ | 2,4,6-$F_3$ | O | O | 194.0-196.0 |
| 5.42 | H | H | $CF_3$ | 2,3,6-$F_3$ | O | O | 201.5-203.0 |
| 5.43 | H | H | $CF_3$ | 2,4-$F_2$-6-Br | O | O | 196.0-198.0 |
| 5.44 | H | Br | $CF_3$ | 2,3,4-$F_3$ | O | O | 153.0-155.5 |
| 5.45 | $CH_2OCH_2CH_3$ | H | $CF_3$ | 2,3,4-$F_3$ | O | O | oil |
| 5.46 | H | H | $CF_3$ | 2,6-$(CH_3)_2$-4-Br | O | O | 242.5-243.5 |
| 5.47 | H | H | $CF_3$ | 2,6-$Cl_2$-4-$OCF_3$ | O | O | 217.0-220.5 |
| 5.48 | H | H | $CF_3$ | 2,6-$Br_2$-4-F | O | O | 229.0-231.0 |
| 5.49 | H | H | $CF_3$ | 2-Br-4-F-6-Cl | O | O | 202.0-204.5 |
| 5.50 | H | H | $CF_3$ | 2,6-$Cl_2$-4-Br | O | O | 241.0-243.0 |
| 5.51 | H | H | $CF_3$ | 2,6-$Br_2$-4-(Q54) | O | O | 264.0-266.0 |
| 5.52 | H | H | $CF_2CF_3$ | 2,6-$(CH_3)_2$-4-Br | O | O | 225.0-228.0 |
| 5.53 | H | H | $CF_2CF_3$ | 2,4-$F_2$-6-Br | O | O | 189.0-192.0 |
| 5.54 | H | H | $CF_2CF_3$ | 2,6-$Br_2$-4-F | O | O | 217.0-219.0 |
| 5.55 | H | H | $CF_3$ | 2,4-$Cl_2$-6-$CH_3$ | O | O | 217.0-219.0 |
| 5.56 | H | H | $CF_2Cl$ | 2,4,6-$Cl_3$ | O | O | 268.0-270.0 |
| 5.57 | H | H | $CF_3$ | 2,6-$Br_2$-4-$OCF_3$ | O | O | 205.0-208.0 |
| 5.58 | H | H | $CF_2CF_3$ | 2,6-$Cl_2$-4-$OCF_3$ | O | O | 221.5-224.5 |
| 5.59 | H | H | $CF_2Cl$ | 2,6-$(CH_3)_2$-4-Br | O | O | 222.0-224.0 |
| 5.60 | H | H | $CF_2Cl$ | 2,6-$Cl_2$-4-$OCF_3$ | O | O | 232.0-233.5 |
| 5.61 | H | H | $CF_3$ | 2,6-$(CH(CH_3)_2)_2$-4-Br | O | O | 176.0-180.0 |
| 5.62 | H | H | $CF_3$ | 2,6-$(CH_2CH_3)_2$-4-Br | O | O | 179.5-181.0 |
| 5.63 | H | H | $CF_3$ | 2-$CH_3$-4-Br-6-$CH(CH_3)_2$ | O | O | 241.0-242.5 |
| 5.64 | H | H | $CF_2CF_3$ | 2,3,6-$F_3$ | O | O | 198.0-200.0 |
| 5.65 | H | H | $CF_3$ | 2,4-$(NO_2)_2$-6-$CF_3$ | O | O | 219.0-220.5 |
| 5.66 | H | H | $CF_3$ | 2-Cl-4-CN-6-$CH_3$ | O | O | 287.0-289.0 |
| 5.67 | H | H | $CF_3$ | 2-Cl-4-Br-6-$CH_3$ | O | O | 222.0-224.0 |
| 5.68 | H | H | $CF_3$ | 2,6-$(CH_3)_2$-4-CN | O | O | 273.0-276.0 |
| 5.69 | H | H | $CF_3$ | 2,6-$F_2$-4-Br | O | O | 213.0-215.5 |
| 5.70 | H | H | $CF_2Cl$ | 2,4,6-$F_3$ | O | O | 192.5-195.5 |
| 5.71 | H | H | $CF_2Cl$ | 2,3,4-$F_3$ | O | O | 145.5-146.5 |
| 5.72 | H | H | $CF_2Cl$ | 2,4-$F_2$-6-Br | O | O | 221.0-222.5 |
| 5.73 | H | H | $CF_3$ | 2,6-$(CH_3)_2$-4-I | O | O | 272.0-275.5 |
| 5.74 | H | H | $CF_3$ | 2,6-$(CH_3)_2$-4-$OCH_3$ | O | O | 183.0-185.0 |
| 5.75 | H | H | $CF_3$ | 2,4,6-$Cl_3$ | S | O | 208.0-214.0 |

TABLE 10-continued

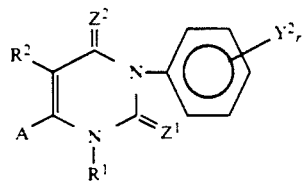

| No. | R¹ | R² | A | Y²ᵣ | Z¹ | Z² | melting point (°C.) |
|---|---|---|---|---|---|---|---|
| 5.76 | H | H | $CF_3$ | 2,6-$(CH_3)_2$-4-$OCF_3$ | O | O | 277.0-279.0 |
| 5.77 | H | H | $CF_3$ | 2,6-$(CH_3)_2$-4-$SCH_3$ | O | O | 273.0-276.0 |
| 5.78 | H | H | $CF_3$ | 2,6-$(CH_3)_2$-4-$SOCH_3$ | O | O | 262.0-264.0 |
| 5.79 | H | H | $CF_3$ | 2,6-$(CH_3)_2$-4-$SO_2CH_3$ | O | O | >300 |
| 5.80 | H | H | $CF_3$ | 2,6-$(CH_3)_2$-4-$CO_2CH_2CH_3$ | O | O | 264.0-268.0 |
| 5.81 | H | H | Br | 2,4,6-$Cl_3$ | O | O | 187.0-190.0 |
| 5.82 | H | H | $CF_2Cl$ | 2,6-$F_2$-4-Br | O | O | 232.0-233.5 |
| 5.83 | H | H | $CF_2Cl$ | 2,6-$Cl_2$-4-$CF_3$ | O | O | 236.0-239.0 |
| 5.84 | H | H | $CF_2Cl$ | 2,4,6-$Cl_3$ | S | O | 215.5-219.0 |
| 5.85 | H | H | Br | 2,6-$Cl_2$-4-$CF_3$ | O | O | 259.0-260.5 |
| 5.86 | H | H | $CF_3$ | 2,6-$Br_2$-4-$CH(CH_3)_2$ | O | O | 237.5-241.0 |
| 5.87 | H | H | $SCH_3$ | 2,6-$Cl_2$-4-$CF_3$ | O | O | 219.0-222.0 |
| 5.88 | H | $NO_2$ | $CF_3$ | 2,4,6-$Cl_3$-3-$NO_2$ | O | O | 252.0-253.0 |
| 5.89 | H | H | $CF_2CF_3$ | 2,6-$F_2$-4-Br | O | O | 195.0-196.0 |
| 5.90 | H | H | $CF_2CF_3$ | 2-Br-4-F-6-Cl | O | O | 221.0-222.5 |
| 5.91 | H | H | $CF_3$ | 2,6-$Br_2$-4-$CF_3$ | O | O | 220.0-223.0 |
| 5.92 | H | H | $CF_2Cl$ | 2,6-$Cl_2$-4-Br | O | O | 288.5-291.0 |
| 5.93 | H | H | $CF_3$ | 2,6-$Cl_2$-4-$CF_3$ | S | O | 205.5-209.0 |

In the following, examples of the pesticide containing a compound of the present invention as an active ingredient are shown. These examples are, of course, not limitative to the scope of the invention.

In the following descriptions of the Formulations, all "parts" are by weight unless otherwise noted.

| Formulation Example 1: Emulsifiable concentrates | |
|---|---|
| A compound of the present invention | 5 parts |
| Xylene | 70 parts |
| N,N-diemthylformamide | 20 parts |
| Sorpol 2680 (a mixture of a nonionic surfactant and an anionic surfactant, produced by Toho Chemicals Ind. Co., Ltd.) | 5 parts |

The above components are mixed uniformly to form an emulsifiable concentrate. In use of the emulsifiable concentrate, it is diluted 50 to 20,000 times and sprayed so that the active ingredient is applied at a rate of 0.05 to 50 kg per hectare.

| Formulation Example 2: Wettable powders | |
|---|---|
| A compound of the present invention | 25 parts |
| Zeeklite PFP (a mixture of kaolinite and sericite, produced by Zeeklite Mining Industries Co., Ltd.) | 66 parts |
| Sorpol 5039 (an anionic surfactant, produced by Toho Chemicals Ind. Co., Ltd.) | 4 parts |
| Carplex #80 (white carbon, produced by Shionogi & Co., Ltd.) | 3 parts |
| Calcium ligninesulfonate | 2 parts |

The above components are uniformly mixed and triturated to form a wettable powder. In use of this wettable powder, it is diluted 50 to 20,000 times and sprayed so that the active ingredient is applied at a rate of 0.005 to 50 kg per hectare.

| Formulation Example 3: Oil solutions | |
|---|---|
| A composition of the present invention | 10 parts |
| Methyl cellosolve | 90 parts |

The above components are mixed uniformly to form an oil solution. In use of this oil solution, it is sprayed so that the active ingredient is applied at a rate of 0.005 to 50 kg per hectare.

| Formulation Example 4: Dusts | |
|---|---|
| A compound of the present invention | 3.0 parts |
| Carplex #80 (white carbon, produced by Shionogi & Co., Ltd.) | 0.5 parts |
| Clay | 95 parts |
| Diisopropyl phosphate | 1.5 parts |

The above components are mixed and triturated uniformly to form a dust. In use, the dust is spread so that the active ingredient is applied at a rate of 0.005 to 50 kg per hectare.

| Preparation Example 5: Granules | |
|---|---|
| A compound of the present invention | 5 parts |
| Bentonite | 54 parts |
| Talc | 40 parts |
| Calcium ligninesulfonate | 1 part |

The above components are uniformly mixed and triturated, then kneaded by adding a small quantity of water, granulated by an extrusion-type granulator and dried to form granules.

In use, the granules are spread so that the active ingredient is applied at a rate of 0.005 to 50 kg per hectare.

| Preparation Example 6: Flowables | |
|---|---|
| A compound of the present invention | 35 parts |

-continued

| Preparation Example 6 Flowables | |
|---|---|
| Sorpol 3353 (a nonionic surfactant, produced by Toho Chemicals Co., Ltd.) | 10 parts |
| Lunox 1000C (an anionic surfactant, produced by Toho Chemicals Co., Ltd.) | 0.5 parts |
| 1% aqueous solution of xanthan gum (natural polymer) | 20 parts |
| Water | 34.5 parts |

The above components excepting the active ingredient (compound of the present invention) are dissolved uniformly, then the compound of the present invention is added, and the obtained mixture is stirred well and subjected to wet milling by a sand mill to form a flowable.

In use of this flowable, it is diluted 50 to 20,000 times and sprayed so that the active ingredient is applied at a rate of 0.005 to 50 kg per hectare.

The utility of the compounds of the present invention as a pesticide is described concretely below by showing the test examples.

Test Example 1: Insecticidal test on Green rice leafhopper (Nephotettix cincticeps)

5% emulsifiable concentrates (25% wettable powders in the case of certain compounds) containing the compounds of the present invention were diluted with water containing a spreader to prepare the samples of liquid insecticides with a concentration of 1,000 ppm.

Said samples of liquid insecticides were sprayed in an ample amount to the leaves and stems of rice plants-plant in the pots of 1/20,000 are. After air drying the leaves and stems, the second instar nymphae of green rice leafhopper (Nephotettix cincticeps), which are resistant to organophosphorous insecticides and carbamate insecticides, were released in the pots (10 insects per pot), and after the rice-plant thus treated was covered with a cylindrical wire gauze, the pots were kept in a thermostatic camber. The examination was made after the lapse of six days, and the percentage of mortality was calculated from the following formula. The tests were conducted twice of each compound.

$$\text{Mortality } (\%) = \frac{\text{number of insects killed}}{\text{number of insects released}} \times 100$$

In the test results, the compounds of the following Nos. of the present invention exhibited high effects of 100% mortality of insect pests. Compound Nos.: 1.1, 1.2, 1.3, 1.4, 1.7, 1.8, 1.9, 1.10, 1.11, 1.12, 1.13, 1.14, 1.16, 1.21, 1.41, 1.42, 1.60, 1.75, 1.76, 1.81, 1.82, 1.83, 1.84, 1.85, 1.86, 1.88, 1.93, 1.94, 1.95, 1.98, 1.99, 1.100, 1.114, 1.115, 1.116, 1.117, 1.118, 1.121, 1.122, 1.124, 1.125, 1.127, 1.129, 1.136, 1.138, 1.139, 1.140, 1.161, 1.163, 1.167, 1.171, 2.5, 4.2, 5.1, 5.2, 5.3, 5.6, 5.7, 5.8, 5.10, 5.11, 5.13, 5.20, 5.21, 5.22, 5.23, 5.24, 5.29, 5.31, 5.34, 5.38, 5.39, 5.41, 5.42, 5.43, 5.44, 5.46, 5.47, 5.48, 5.50, 5.52, 5.53, 5.54, 5.55, 5.56, 5.57, 5.58, 5.59, 5.60, 5.62, 5.64, 5.67, 5.69, 5.70, 5.71, 5.72, 5.75, 5.76, 5.82, 5.84.

Test Example 2: Insecticidal test on twenty eight-spotted lady beetle (Henosepilachna vigintioctopunctata)

5% emulsifiable concentrates (25% wettable powders in the case of certain compounds) containing the compounds of the present invention were diluted with water containing a spreader to prepare the samples of liquid insecticides with a concentration of 1,000 ppm. The leaves of tomato were immersed in each sample of liquid insecticides for about 10 seconds. Then, after air drying the leaves, they were placed in the laboratory dishes and the second instar nymphae of twenty eight-spotted lady beetle (Henosepilachna vigintioctopunctata) were released in the respective dishes (10 insects per dish). After covered, the dishes were kept in a 25° C. thermostatic chamber. The percentage of mortality after the lapse of 6 days was calculated from the following formula. The tests were conducted twice of each compound.

$$\text{Mortality } (\%) = \frac{\text{number of insects killed}}{\text{number of insects released}} \times 100$$

In the results, the compounds of the following Nos. of the present invention exhibited high effects of 100% mortality. Compound Nos.: 1.1, 1.2, 1.3, 1.7, 1.8, 1.9, 1.10, 1.12, 1.14, 1.16, 1.21, 1.23, 1.24, 1.25, 1.27, 1.28, 1.29, 1.41, 1.42, 1.46, 1.47, 1.53, 1.56, 1.66, 1.67, 1.68, 1.75, 1.76, 1.78, 1.79, 1.82, 1.83, 1.98, 1.101, 1.126, 1.127, 1.128, 1.131, 1.132, 1.134, 1.138, 1.140, 1.151, 1.155, 1.158, 1.167, 1.168, 1.172, 1.182, 2.11, 2.13, 2.16, 2.17, 2.31, 2.32, 5.1, 5.2, 5.3, 5.6, 5.7, 5.8, 5.11, 5.13, 5.20, 5.21, 5.22, 5.23, 5.24, 5.25, 5.26, 5.29, 5.30, 5.31, 5.32, 5.34, 5.35, 5.37, 5.38, 5.39, 5.41, 5.42, 5.43, 5.45, 5.46, 5.47, 5.50, 5.52, 5.53, 5.54, 5.55, 5.56, 5.57, 5.58, 5.59, 5.60, 5.61, 5.62, 5.64, 5.70, 5.73, 5.74, 5.76, 5.82.

Test Example 3: Insecticidal test on common cutworm (Spodoptera litura)

5% emulsifiable concentrates (25% wettable powders in the case of certain compounds) containing the compounds of the present invention were diluted with water containing a spreader to prepare the samples of liquid insecticides with a concentration of 1,000 ppm. The leaves of cabbage were immersed in each sample of liquid insecticides for about 10 seconds. After air drying, the leaves were placed in the laboratory disches and the second instar nymphae of common cutworm (Spodoptera litura) were released in the said dishes (10 insects per dish). The dishes were closed with a perforated cover and kept in a 25° C. thermostatic chamber. The percentage of mortality of the insects after the lapse of 6 days was calculated from the following formula. The tests were conducted twice of each compound.

$$\text{Mortality } (\%) = \frac{\text{number of insects killed}}{\text{number of insects released}} \times 100$$

In the result, the compounds of the present invention of the following Nos. exhibited high effects of 100% mortality of the insect. Compound Nos.: 1.1, 1.2, 1.3, 1.7, 1.8, 1.9, 1.10, 1.12, 1.14, 1.16, 1.21, 1.24, 1.25, 1.27, 1.28, 1.29, 1.45, 1.46, 1.51, 1.52, 1.54, 1.55, 1.63, 1.65, 1.66, 1.67, 1.70, 1.71, 1.72, 1.73, 1.74, 1.75, 1.76, 1.78, 1.81, 1.82, 1.83, 1.85, 1.86, 1.87, 1.89, 1.92, 1.97, 1.98, 1.101, 1.102, 1.104, 1.105, 1.110, 1.114, 1.115, 1.116, 1.120, 1.121, 1.122, 1.124, 1.125, 1.126, 1.127, 1.128, 1.129, 1.132, 1.133, 1.134, 1.138, 1.139, 1.140, 1.147, 1.149, 1.150, 1.151, 1.152, 1.153, 1.155, 1.156, 1.158, 1.159, 1.160, 1.161, 1.163, 1.164, 1.166, 1.167, 1.170, 1.171, 1.172, 2.7, 2.13, 2.14, 2.17, 2.32, 2.39, 2.42, 2.57, 3.3, 3.4, 4.4, 5.14, 5.31, 5.33, 5.88.

Test Example 4: Test on miticidal effect against two-spotted spider mite (Tetranychus urticae)

The leaves of kidney bean were cut into 3.0 cmφ circular pieces by a leaf punch and each circular leaf was placed on a wet filter paper on a 7 cmφ styrol cup. 10 nymphae of two-spotted spider mite (*Tetranychus urticae*) were released on each leaf. 5% emulsifiable concentrates (25% wettable powders in the case of certain compounds) containing the compounds of the present invention were diluted with water containing a spreader to prepare the samples of liquid insecticides with a concentration of 1,000 ppm and each sample was sprinkled over the styrol cups at a rate of 2 ml per cup by using a rotary sprinkler. After the above treatment, the styrol cups were kept in a 25° C. thermostatic chamber and the mortality of mites after the lapse of 96 hours was calculated from the following formula. The tests were conducted twice of each compound.

$$\text{Mortality} (\%) = \frac{\text{number of mites killed}}{\text{number of mites released}} \times 100$$

In the result, the compounds of the present invention of the following Nos. exhibited high effect of 100% mortality. Compound Nos.: 1.9, 1.11, 1.12, 1.17, 1.18, 1.19, 1.20, 1.21, 1.23, 1.25, 1.28, 1.29, 1.31, 1.32, 1.33, 1.42, 1.51, 1.63, 1.66, 1.68, 1.69, 1.70, 1.71, 1.72, 1.73, 1.75, 1.76, 1.81, 1.84, 1.85, 1.86, 1.87, 1.90, 1.92, 1.99, 1.112, 1.114, 1.115, 1.116, 1.122, 1.132, 1.138, 1.142, 1.156, 1.162, 1.166, 1.167, 1.170, 1.173, 1.184, 2.3, 2.7, 2.71, 2.72, 3.3, 3.4, 5.1, 5.3, 5.7, 5.11, 5.18, 5.19, 5.20, 5.22, 5.23, 5.24, 5.25, 5.26, 5.27, 5.30, 5.31, 5.32, 5.33, 5.34, 5.37, 5.38, 5.39, 5.41, 5.42, 5.43, 5.47, 5.49.

Comparative Test Example

A known compound: 3,6-diphenyluracil (in the formula (I) A=phenyl, B=phenyl, R¹=hydrogen atom, R²=hydrogen atom, Z¹=oxygen atom and Z²=oxygen atom) showed no insecticidal activity (mortality: 0) against any of the insect pests (green rice leafhopper (*Nephotettix cincitiseps*), twenty eight-spotted lady beetle (*Henosepilachna vigintioctopunctata*), common cutworm (*Spodoptera litura*), two-spotted spider mite (*Tetranychus urticae*)) in the same test as conducted in Test Examples 1~4 described above.

Test Example 5: Test on herbicidal effect in foliage treatment

Sterilized farmland soil was placed in a 30 cm×22 cm×6 cm plastic box and the seeds of *Abutilon avicennae, Xanthium strumarium, Amaranthus retroflexus, Lambsquarters, Persicaria blumei gross, Ipomoea* (morning glory), *Echinothloa, Digitaria adscendens, Setaria viridis, Sorghum bicolor*, and *Tripsacum* (corn) were sown spotwise and covered with soil by 1.5 cm.

When the above plants grew to a 2- to 3-foliage stage, a liquid herbicide containing a compound of the present invention as active ingredient was sprayed uniformly to the leaves and stems of said plants so that the active ingredient would be applied at a predetermined rate.

The liquid herbicide was produced by water-diluting a 25% wettable powder containing a compound of the present invention, and it was sprayed to the entirety of leaves and stems of each plant by a small-sized sprayer. 3 weeks after spray of the liquid herbicide, its herbicidal effect against the said plants was examined and rated according to the following criterion. The results are shown in Table 11.

Criterion for rating
5: perfect withering or more than 90% inhibition
4: 70~90% inhibition
3: 40~70% inhibition
2: 20~40% inhibition
1: 5~20% inhibition
0: less than 5% inhibition The degree of inhibition was determined by visual observation.

TABLE 11

| Compound No. | | 5.1 | |
|---|---|---|---|
| Dose kg/ha | 0.16 | 0.32 | 0.64 |
| Abutilon avidennae | 5 | 5 | 5 |
| Xanthium strumarium | 5 | 5 | 5 |
| Amaranthus retroflexus | 5 | 5 | 5 |
| Lambsquartess | 5 | 5 | 5 |
| Persocaroa blumei gross | 5 | 5 | 5 |
| Ipomoea | 5 | 5 | 5 |
| Echinothloa | 5 | 5 | 5 |
| Digitaria adscendens | 5 | 5 | 5 |
| Seteria viridis | 5 | 5 | 5 |
| Sorghum bicolor | 5 | 5 | 5 |
| Tripsacus | 0 | 0 | 0 |

What is claimed is:
1. Uracil derivatives represented by formula (I):

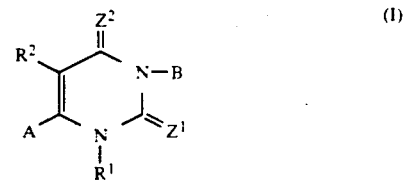

wherein R¹ represents hydrogen atom, $C_{1-4}$ alkyl group, $C_{2-4}$ alkenyl group, $C_{2-4}$ alkynyl group, $C_{1-4}$ haloalkyl group, $C_{2-4}$ alkoxyalkyl group, formyl group, $C_{2-6}$ alkylcarbonyl group, $C_{2-6}$ alkoxycarbonyl group, $C_{3-6}$ alkoxycarbonylalkyl group, $C_{2-6}$ cyanoalkyl group, benzyl group, phenyl group, —$SR^{12}$ group wherein $R^{12}$ is $C_{2-6}$ alkoxycarbonyl group, $C_{1-6}$ alkylsulfonyl group, —$NR^{13}R^{14}$ group wherein $R^{13}$ is $C_{1-6}$ alkyl group and $R^{14}$ is $C_{1-6}$ alkyl group, $C_{2-6}$ alkoxycarbonyl group $C_{3-9}$ alkoxycarbonylalkyl group, $C_{1-6}$ alkylsulfonyl group, $C_{2-6}$ alkylcarbonyl group, $C_{3-9}$ dialkylaminocarbonyl group and $C_{2-6}$ dialkylaminosulfonyl group or phenyl group which may be substituted or non-substituted,
the substituent is selected from halogen atom, cyano group, nitro group, $C_{1-4}$ alkyl group, $C_{1-4}$ haloalkyl group, $C_{1-4}$ alkoxy group, $C_{2-6}$ alkoxycarbonyl group, $C_{1-4}$ haloalkoxy group, $C_{2-6}$ haloalkoxycarbonyl group, $C_{2-6}$ alkylcarbonyl group, $C_{2-6}$ haloalkylcarbonyl group, $C_{1-4}$ alkylsulfonyl group or $C_{1-4}$ haloalkyl sulfonyl group, and when the number of the substituents is not less than 2, the substituents may be same or different, alkali metal or alkaline earth metal;
R² represents hydrogen atom, halogen atom, $C_{1-4}$ alkyl group, $C_{1-4}$ haloalkyl group, $C_{1-4}$ hydroxyalkyl group, $C_{2-4}$ alkoxyalkyl group, $C_{2-4}$ alkylthioalkyl group, thiol group, $C_{1-4}$ alkylthio group, $C_{1-4}$ alkylsulfinyl group, C$_{1-4}$ alkylsulfonyl group, C$_{1-4}$ haloalkylthio group, C$_{1-4}$ haloalkylsulfinyl group, C$_{1-4}$ haloalkylsulfonyl group, hydroxyl group, C$_{1-4}$ alkoxy group, C$_{1-4}$ haloalkoxy group, formyl group, cyano group, nitro group or thiocyanate group;

Z$^1$ and Z$^2$ represent independently oxygen atom, sulfur atom or imino group;

A represents

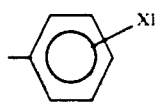

wherein X is halogen atom, C$_{1-4}$ alkyl group, C$_{1-4}$ alkoxy group, C$_{1-4}$ alkylthio group, C$_{1-4}$ haloalkyl group, C$_{1-4}$ haloalkoxy group, C$_{1-4}$ haloalkylthio group, amino group, cyano group or nitro group, and l is an integer of 0 to 5, and when l is an integer of 2 to 5 the substituents X may be same or different, naphthyl group furyl group, thienyl group, pyrrolyl group, pyrazolyl group, imidazolyl group, thiazolyl group, isothiazolyl group, oxazolyl group, isoxazolyl group, oxadiazolyl group, thiadiazolyl group, triazolyl group, pyridyl group, pyridazyl group, pyrimidyl group or pyrazyl group, any of which may be substituted or non-substituted, the substituent of the above aromatic groups is selected from halogen atom, C$_{1-4}$ alkyl group, C$_{1-4}$ alkoxy group, C$_{1-4}$ alkylthio group, C$_{1-4}$ haloalkyl group, C$_{1-4}$ haloalkoxy group, C$_{1-4}$ haloalkylthio group, amino group, cyano group and nitro group, and when the number of the substituents is not less than 2, these substituents may be same or different, C$_{1-6}$ haloalkyl group containing one or more fluorine atoms, halogen atom, cyano group, nitro group, C$_{1-6}$ alkylthio group, C$_{1-6}$ alkylsulfinyl group, C$_{1-6}$ alkylsulfonyl group, C$_{1-6}$ haloalkylthio group, C$_{1-6}$ haloalkylsulfinyl group, C$_{1-6}$ haloalkylsulfonyl group, C$_{1-6}$ alkoxy group, C$_{1-6}$ haloalkoxy group, or C$_{2-6}$ alkoxycarbonyl group; and when A is

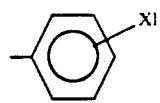

where X and l are as defined above, or a naphthyl group, furyl group, thienyl group, pyrrolyl group, pyrazolyl group, imidazolyl group, thiazolyl group, isothiazolyl group, oxazolyl group, isoxazolyl group, oxadiazolyl group, thiadiazolyl group, triazolyl group, pyridyl group, pyridazyl group, pyrimidyl group or pyrazyl group, any of which may be substituted as defined above, B is

wherein Y$^1$ is halogen atom, C$_{1-6}$ alkyl group, C$_{2-6}$ alkenyl group, C$_{2-6}$ alkynyl group, C$_{3-6}$ cycloalkyl group, C$_{1-6}$ haloalkyl group, C$_{2-6}$ haloalkenyl group, C$_{2-6}$ haloalkynyl group, C$_{3-6}$ halocycloalkyl group, C$_{2-6}$ cyanoalkyl group, C$_{1-6}$ hydroxyalkyl group, C$_{2-6}$ carboxyalkyl group, C$_{1-6}$ alkoxy group, C$_{2-6}$ alkenyloxy group, C$_{2-6}$ alkynyloxy group, C$_{3-6}$ cycloalkyloxy group, C$_{1-6}$ haloalkoxy group, C$_{2-6}$ haloalkenyloxy group, C$_{2-6}$ haloalkynyloxy group, C$_{3-6}$ halocycloalkoxy group, C$_{4-7}$ halocycloalkylalkoxy group, C$_{1-6}$ alkylthio group, C$_{2-6}$ alkenylthio group, C$_{2-6}$ alkynylthio group, C$_{3-6}$ cycloalkylthio group, C$_{1-6}$ haloalkylthio group, C$_{1-6}$ alkylsulfinyl group, C$_{2-6}$ alkenylsulfinyl group, C$_{2-6}$ alkynylsulfinyl group, C$_{3-6}$ cycloalkylsulfinyl group, C$_{1-6}$ haloalkylsulfinyl, C$_{1-6}$ alkylsulfonyl group, C$_{2-6}$ alkenylsulfonyl group, C$_{2-6}$ alkynylsulfonyl group, C$_{3-6}$ cycloalkylsulfonyl group, C$_{1-6}$ haloalkylsulfonyl group, C$_{2-6}$ alkoxyalkyl group, C$_{2-6}$ alkoxyalkoxy group, C$_{2-6}$ haloalkoxyalkyl group, C$_{2-6}$ haloalkoxyalkoxy group, C$_{2-6}$ alkylthioalkyl group, C$_{2-6}$ alkylthioalkoxy group, C$_{3-6}$ alkoxycarbonylalkyl group, C$_{3-6}$ alkylcarbonylalkyl group, C$_{2-6}$ alkoxycarbonyloxy group, C$_{2-6}$ alkylcarbonyl group, C$_{3-6}$ alkenylcarbonyl group, C$_{3-6}$ alkynylcarbonyl group, C$_{4-7}$ cycloalkylcarbonyl group, C$_{2-6}$ haloalkylcarbonyl group, C$_{2-6}$ alkoxycarbonyl group, C$_{2-6}$ haloalkoxycarbonyl group, C$_{3-6}$ alkoxycarbonylalkoxy group, nitro group, cyano group, hydroxyl group, carboxyl group, thiocyanate group, isothiocyanate group, C$_{2-6}$ thiocyanatealkyl group, C$_{1-6}$ alkylsulfonyloxy group, C$_{2-6}$ alkylthiocarbonyl group, amino group (—NR$^3$R$^4$), aminocarbonyl group (—CONR$^3$R$^4$), aminocarbonyloxy group (—OCONR$^3$R$^4$), amide group (—NR$^3$COR$^4$), alkoxycarbonylamino group (—NR$^3$CO$_2$R$^4$), aminosulfonyl group (—SO$_2$NR$^3$R$^4$), thioamide group (—NR$^3$CSR$^4$), methylenedioxy group, halomethylenedioxy group, ethylenedioxy group, haloethylenedioxy group, trimethylsilyl group of —W$_n$Ar group wherein W is

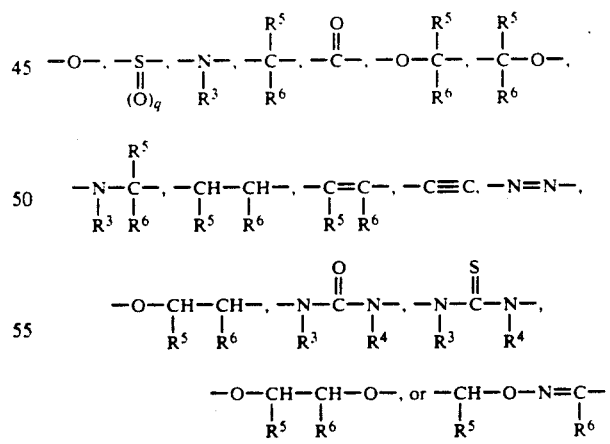

in which R$^3$ and R$^4$ represent independently hydrogen atom, C$_{1-6}$ alkyl group, C$_{2-6}$ alkenyl group, C$_{2-6}$ alkynyl group, C$_{1-6}$ haloalkyl group, C$_{2-6}$ haloalkenyl group, C$_{2-6}$ haloalkynyl group, C$_{2-6}$ alkylcarbonyl group, C$_{2-6}$ alkoxycarbonyl group, phenyl group or benzyl group; R$^5$ and R$^6$ represent independently hydrogen atom, halogen atom, C$_{1-6}$ alkyl group, C$_{3-6}$ cycloalkyl group, cyano group, or phenyl group; and q is an integer of 0 to 2;

n is an integer of 0 or 1; and Ar is phenyl group, naphthyl group, furyl group, thienyl group, pyrrolyl group, pyrazolyl group, imidazolyl group, thiazolyl group, isothiazolyl group, oxazolyl group, isoxazolyl group, oxadiazolyl group, thiadiazolyl group, triazolyl group, pyridyl group, pyridazyl group, pyrimidyl group, pyrazyl group, quinolyl group or quinoxalyl group, any of which may be substituted or non-substituted, the substituent of the above aromatic groups is selected from halogen atom, cyano group, nitro group, $C_{1-4}$ alkyl group, $C_{1-4}$ haloalkyl group, $C_{1-4}$ alkoxy group, $C_{1-4}$ haloalkoxy group, $C_{1-4}$ alkylthio group, $C_{1-4}$ haloalkylthio group, $C_{1-4}$ alkylsulfonyl group, $C_{1-4}$ haloalkylsulfonyl group, $C_{2-4}$ alkoxycarbonyl group, carboxyl group, amino group, $C_{1-4}$ monoalkylamino group, $C_{2-8}$ dialkylamino group, phenyl group, benzyl group, methylenedioxy group or halomethylenedioxy group, and when the number of the substituents is not less than 2, the substituents may be same or different;

and m is an integer of 0 to 5, and when it is 2 to 5, the substituents $Y^1$ may be same or different, naphthyl group, furyl group, thienyl group, pyrrolyl group, pyrazolyl group, imidazolyl group, thiazolyl group, isothiazolyl group, oxazolyl group, isoxazolyl group, thiadiazolyl group, oxadiazolyl group, triazolyl group, pyridyl group, pyridazyl group, pyrimizyl group, pyrazyl group, quinolyl group, quinoxalyl group, benzofuryl group, benzothienyl group, indolyl group, benzoxazolyl group or benzothiazolyl group, any of which may be substituted or non-substituted, the substituent of the above aromatic groups is selected from halogen atom, cyano group, nitro group, $C_{1-4}$ alkyl group, $C_{1-4}$ haloalkyl group, $C_{1-4}$ alkoxy group, $C_{1-4}$ haloalkoxy group, $C_{1-4}$ alkylthio group, $C_{1-4}$ haloalkylthio group, $C_{1-4}$ alkylsulfonyl group, $C_{1-4}$ haloalkylsulfonyl group, $C_{2-4}$ alkoxycarbonyl group, carboxyl group, amino group, $C_{1-4}$ monoalkylamino group, $C_{2-8}$ dialkylamino group, phenyl group, phenoxy group or benzyl group, and when the number of the substituents is 2 or more, the substituents may be same or different, and when A is $C_{1-6}$ haloalkyl group containing one or more fluorine atoms, halogen atom, cyano group, nitro group, $C_{1-6}$ alkylthio group, $C_{1-6}$ alkylsulfinyl group, $C_{1-6}$ alkylsulfonyl group, $C_{1-6}$ haloalkylthio group, $C_{1-6}$ haloalkylsulfinyl group, $C_{1-6}$ haloalkylsulfonyl group, $C_{1-6}$ alkoxy group, $C_{1-6}$ haloalkoxy group or $C_{2-6}$ alkoxycarbonyl group, B is

wherein $Y^2$ is halogen atom, $C_{1-4}$ alkyl group, $C_{1-4}$ alkoxy group, $C_{1-4}$ haloalkyl group, $C_{1-4}$ haloalkoxy group, $C_{1-4}$ alkylthio group, $C_{1-4}$ haloalkylthio group, $C_{1-4}$ alkylsulfinyl group, $C_{1-4}$ haloalkylsulfinyl group, $C_{1-4}$ alkylsulfonyl group, $C_{1-4}$ haloalkylsulfonyl group, sulfonamide group, $C_{2-4}$ alkenyl group, $C_{2-4}$ haloalkenyl group, amino group, $C_{1-4}$ monoalkylamino group, $C_{2-8}$ dialkylamino group, $C_{2-6}$ alkoxyalkoxy group, $C_{2-6}$ alkoxycarbonyl group, cyano group or nitro group, and r is an integer of 3 to 5, the substituents $Y^2$ may be same or different, and when r=3 with the substituents at the 2-, 4- and 5-positions, the substituent $Y^2$ at the 5-position is not $C_{1-4}$ alkoxy group, $C_{1-4}$ haloalkoxy group, $C_{2-6}$ alkoxyalkoxy group or $C_{2-6}$ alkoxycarbonyl group, provided that A is not a phenyl group or a 3-bromo-4-methoxyphenyl group when B is a phenyl group.

2. Uracil derivatives according to claim 1, wherein in formula (I), A is

or a naphthyl group, furyl group, thienyl group, pyrrolyl group, pyrazolyl group, imidazolyl group, thiazolyl group, isothiazolyl group, oxazolyl group, isoxazolyl group, oxadiazolyl group, thiadiazolyl group, triazolyl group, pyridyl group, pyridazyl group, pyrimidyl group or pyrazyl group, any of which may be substituted as defined in claim 1, and B is

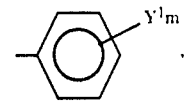

or a naphthyl group, furyl group, thienyl group, pyrrolyl group, pyrazolyl group, imidazolyl group, thiazolyl group, isothiazolyl group, oxazolyl group, isoxazolyl group, thiadiazolyl group, oxadiazolyl group, triazolyl group, pyridyl group, pyridazyl group, pyrimidyl group, pyrazyl group, quinolyl group, quinoxalyl group, benzofuryl group, benzothienyl group, indolyl group, benzoxazolyl group or benzothiazolyl group, any of which may be substituted as defined in claim 1, provided that A is not a phenyl group or a 3-bromo-4-methoxyphenyl group when B is phenyl group.

3. Uracil derivatives according to claim 2, wherein in formula (I),

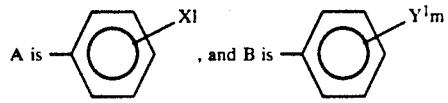

provided that A is not phenyl group and 3-bromo-4-methoxyphenyl group, when B is phenyl group.

4. Uracil derivatives according to claim 2, wherein in formula (I), A is naphthyl group, furyl group, thienyl group, pyrrolyl group, pyrazolyl group, imidazolyl group, thiazolyl group, isothiazolyl group, oxazolyl group, isoxazolyl group, oxadiazolyl group, thiadiazolyl group, triazolyl group, pyridyl group, pyridazyl group, pyrimidyl group or pyrazyl group, any of which may be substituted as defined in claim 2, and B

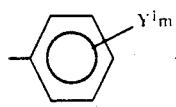

5. Uracil derivatives according to claim 1, wherein in formula (I), A is $C_{1-6}$ haloalkyl group containing at least one fluorine atom, halogen atoms, cyano group, nitro group, $C_{1-6}$ alkylthio group, $C_{1-6}$ alkylsulfinyl group, $C_{1-6}$ alkylsulfonyl group, $C_{1-6}$ haloalkylthio group, $C_{1-6}$ haloalkylsulfinyl group, $C_{1-6}$ haloalkylsulfonyl group, $C_{1-6}$ alkoxy group, $C_{1-6}$ haloalkoxy group, or $C_{2-6}$ alkoxycarbonyl group, and B is

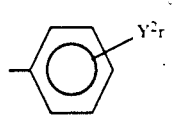

6. Uracil derivatives according to claim 3, wherein in formula (I), $R^1$ and $R^2$ represent hydrogen atom, $Z^1$ and $Z^2$ represent oxygen atom, A represents 2-fluorophenyl group, 2-chlorophenyl group, 2-chloro-6-fluorophenyl group or 2,6-difluorophenyl group, and B represents

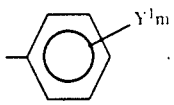

7. Uracil derivatives according to claim 5, wherein in formula (I), $R^1$ and $R^2$ represent hydrogen atom, $Z^1$ and $Z^2$ represent oxygen atom, A represents either a trifluoromethyl group, pentafluoroethyl group or chlorodifluoromethyl group, and B represents

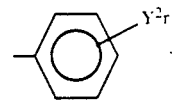

8. Pesticides comprising as an active ingredient a pesticidally effective amount of at least one of the uracil derivatives set forth in claim 1, and a pesticidally acceptable carrier or diluent therefor.

9. Insecticides and acaricides comprising as an active ingredient an insecticidally and acaricidally effective amount of at least one of the uracil derivatives set forth in claim 2, and an insecticidally and acaricidally acceptable carrier or diluent therefor.

10. Insecticides and acaricides comprising as an active ingredient an insecticidally and acaricidally effective amount of at least one of the uracil derivatives set forth in claim 3, and an insecticidally and acaricidally acceptable carrier or diluent therefor.

11. Insecticides and acaricides comprising as an active ingredient an insecticidally and acaricidally effective amount of at least one of the uracil derivatives set forth in claim 4, and an insecticidally and acaricidally acceptable carrier or diluent therefor.

12. Insecticides and acaricides comprising as an active ingredient an insecticidally and acaricidally effective amount of at least one of the uracil derivatives set forth in claim 5, and an insecticidally and acaricidally acceptable carrier or diluent therefor.

13. Herbicides comprising as an active ingredient a herbicidally effective amount of at least one of the uracil derivatives set forth in claim 5, and a herbicidally acceptable carrier on diluent therefor.

* * * * *